US010364278B2

(12) United States Patent
Mohammadi et al.

(10) Patent No.: US 10,364,278 B2
(45) Date of Patent: Jul. 30, 2019

(54) CHIMERIC FIBROBLAST GROWTH FACTOR 23 PROTEINS AND METHODS OF USE

(71) Applicant: New York University, New York, NY (US)

(72) Inventors: Moosa Mohammadi, Scarsdale, NY (US); Regina Goetz, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/598,420

(22) Filed: May 18, 2017

(65) Prior Publication Data

US 2017/0355738 A1 Dec. 14, 2017

Related U.S. Application Data

(62) Division of application No. 13/839,051, filed on Mar. 15, 2013, now Pat. No. 9,657,075.

(60) Provisional application No. 61/656,887, filed on Jun. 7, 2012, provisional application No. 61/664,097, filed on Jun. 25, 2012.

(51) Int. Cl.

| | |
|---|---|
| ***A61K 38/18*** | (2006.01) |
| ***C07K 14/50*** | (2006.01) |
| ***A61K 45/06*** | (2006.01) |

(52) U.S. Cl.

CPC .......... *C07K 14/50* (2013.01); *A61K 38/1825* (2013.01); *A61K 45/06* (2013.01); *C07K 14/501* (2013.01)

(58) Field of Classification Search

None

See application file for complete search history.

(56) References Cited

U.S. PATENT DOCUMENTS

| | | | |
|---|---|---|---|
| 5,132,408 | A | 7/1992 | Baird et al. |
| 5,478,804 | A | 12/1995 | Calabresi et al. |
| 5,648,260 | A | 7/1997 | Winter et al. |
| 5,656,458 | A | 8/1997 | Barr |
| 6,326,484 | B1 | 12/2001 | Gage et al. |
| 6,982,170 | B1 | 1/2006 | Maciag et al. |
| 7,223,563 | B2 | 5/2007 | Econs et al. |
| 7,314,618 | B2 | 1/2008 | Econs et al. |
| 7,491,697 | B2 | 2/2009 | Beals et al. |
| 7,582,607 | B2 | 9/2009 | Frye et al. |
| 7,622,445 | B2 | 11/2009 | Frye et al. |
| 7,655,627 | B2 | 2/2010 | Frye et al. |
| 7,745,406 | B2 | 6/2010 | Econs et al. |
| 7,947,810 | B2 | 5/2011 | Econs et al. |
| 7,956,033 | B2 | 6/2011 | Cheng et al. |
| 8,168,591 | B2 | 5/2012 | Takada et al. |
| 8,642,546 | B2 | 2/2014 | Belouski et al. |
| 8,889,426 | B2 | 11/2014 | Mohammadi et al. |
| 8,889,621 | B2 | 11/2014 | Mohammadi et al. |
| 8,906,854 | B2 | 12/2014 | Jonker et al. |
| 8,951,966 | B2 | 2/2015 | Ling et al. |
| 8,999,929 | B2 | 4/2015 | Mohammadi et al. |
| 9,072,708 | B2 | 7/2015 | Jonker et al. |
| 9,272,017 | B2 | 3/2016 | Mohammadi et al. |
| 9,464,126 | B2 | 10/2016 | Mohammadi et al. |
| 9,474,785 | B2 | 10/2016 | Mohammadi et al. |
| 9,475,856 | B2 | 10/2016 | Mohammadi et al. |
| 9,550,820 | B2 | 1/2017 | Mohammadi et al. |
| 9,657,075 | B2 | 5/2017 | Mohammadi et al. |
| 9,907,830 | B2 | 3/2018 | Mohammadi et al. |
| 9,926,355 | B2 | 3/2018 | Mohammadi et al. |
| 9,926,356 | B2 | 3/2018 | Mohammadi et al. |
| 2002/0082205 | A1 | 6/2002 | Itoh et al. |
| 2003/0105302 | A1 | 6/2003 | Itoh et al. |
| 2004/0043457 | A1 | 3/2004 | Schumacher et al. |
| 2004/0097414 | A1 | 5/2004 | Itoh et al. |
| 2004/0259780 | A1 | 12/2004 | Glasebrook et al. |
| 2006/0160181 | A1 | 7/2006 | Luethy et al. |
| 2006/0281679 | A1 | 12/2006 | Itoh et al. |
| 2007/0142278 | A1 | 6/2007 | Beals et al. |
| 2007/0237768 | A1 | 10/2007 | Glaesner et al. |

(Continued)

FOREIGN PATENT DOCUMENTS

| | | |
|---|---|---|
| EP | 0645451 B1 | 8/2001 |
| JP | 2008/0117661 A | 4/2008 |

(Continued)

OTHER PUBLICATIONS

Pellegrini et al., "Crystal Structure of Fibroblast Growth Factor Receptor Ectodomain Bound to Ligand and Heparin," *Nature* 407:1029-1034 (2000).

Pellegrini et al., Protein Data Bank, 1E0O, "Crystal Structure of a Ternary FGF1-FGFR2-Heparin Complex," (Released Oct. 23, 2000).

Office Action in Chinese Patent Application No. 201380039848.9 (dated Oct. 8, 2016).

Abraham et al., "Human Basic Fibroblast Growth Factor: Nucleotide Sequence and Genomic Organization," *EMBO J.* 5(10):2523-2528 (1986).

Esch et al., "Primary Structure of Bovine Pituitary Basic Fibroblast Growth Factor (FGF) and Comparison with the Amino-Terminal Sequence of Bovine Brain Acidic FGF," *PNAS* 82:6507-6511 (1985).

(Continued)

*Primary Examiner* — Marianne P Allen

(74) *Attorney, Agent, or Firm* — Pepper Hamilton LLP

(57) ABSTRACT

The present invention relates to a chimeric protein that includes an N-terminus coupled to a C-terminus, where the N-terminus includes a portion of a paracrine fibroblast growth factor ("FGF") and the C-terminus includes a C-terminal portion of an FGF23 molecule. The portion of the paracrine FGF is modified to decrease binding affinity for heparin and/or heparan sulfate compared to the portion without the modification. The present invention also relates to pharmaceutical compositions including chimeric proteins according to the present invention, methods for treating a subject suffering from a disorder, and methods of screening for compounds with enhanced binding affinity for the αKlotho-FGF receptor complex involving the use of chimeric proteins of the present invention.

30 Claims, 11 Drawing Sheets

Specification includes a Sequence Listing.

(56) References Cited

U.S. PATENT DOCUMENTS

| | | | |
|---|---|---|---|
| 2007/0265200 | A1 | 11/2007 | Glaesner et al. |
| 2007/0293430 | A1 | 12/2007 | Frye et al. |
| 2007/0299007 | A1 | 12/2007 | Frye et al. |
| 2008/0103096 | A1 | 5/2008 | Frye et al. |
| 2008/0255045 | A1 | 10/2008 | Cujec et al. |
| 2008/0261875 | A1 | 10/2008 | Etgen et al. |
| 2009/0111742 | A1 | 4/2009 | Kharitonenkov et al. |
| 2009/0118190 | A1 | 5/2009 | Beals et al. |
| 2009/0192087 | A1 | 7/2009 | Glass et al. |
| 2009/0305986 | A1 | 12/2009 | Belouski et al. |
| 2010/0062984 | A1 | 3/2010 | Kumar et al. |
| 2010/0158914 | A1 | 6/2010 | Desnoyers |
| 2010/0184665 | A1 | 7/2010 | Suzuki et al. |
| 2010/0216715 | A1 | 8/2010 | Tagmose et al. |
| 2010/0285131 | A1 | 11/2010 | Belouski et al. |
| 2010/0286042 | A1 | 11/2010 | Imamura et al. |
| 2010/0323954 | A1 | 12/2010 | Li et al. |
| 2011/0053841 | A1 | 3/2011 | Yayon et al. |
| 2011/0104152 | A1 | 5/2011 | Sonoda |
| 2011/0150901 | A1 | 6/2011 | Smith et al. |
| 2011/0171218 | A1 | 7/2011 | Seehra et al. |
| 2011/0172401 | A1 | 7/2011 | Cujec et al. |
| 2011/0190207 | A1 | 8/2011 | Mohammadi et al. |
| 2011/0195077 | A1 | 8/2011 | Gass et al. |
| 2012/0052069 | A1 | 3/2012 | Belouski et al. |
| 2012/0288886 | A1 | 11/2012 | Mohammadi et al. |
| 2013/0023474 | A1 | 1/2013 | Ling et al. |
| 2013/0058896 | A1 | 3/2013 | Takada et al. |
| 2013/0116171 | A1 | 5/2013 | Jonker et al. |
| 2013/0172275 | A1 | 7/2013 | Mohammadi et al. |
| 2013/0184211 | A1 | 7/2013 | Mohammadi et al. |
| 2013/0231277 | A1 | 9/2013 | Mohammadi et al. |
| 2013/0331316 | A1 | 12/2013 | Mohammadi et al. |
| 2013/0331317 | A1 | 12/2013 | Mohammadi et al. |
| 2014/0094406 | A1 | 4/2014 | Mohammadi et al. |
| 2014/0107022 | A1 | 4/2014 | Mohammadi et al. |
| 2014/0155316 | A1 | 6/2014 | Mohammadi et al. |
| 2014/0171361 | A1 | 6/2014 | Jonker et al. |
| 2014/0243260 | A1 | 8/2014 | Mohammadi et al. |
| 2015/0111821 | A1 | 4/2015 | Suh et al. |
| 2015/0343022 | A1 | 12/2015 | Jonker et al. |
| 2016/0206695 | A1 | 7/2016 | Suh et al. |
| 2017/0029480 | A1 | 2/2017 | Mohammadi et al. |
| 2017/0096462 | A1 | 4/2017 | Mohammadi et al. |
| 2017/0101449 | A1 | 4/2017 | Mohammadi et al. |
| 2017/0226172 | A1 | 8/2017 | Mohammadi et al. |
| 2018/0186849 | A1 | 7/2018 | Mohammadi et al. |
| 2018/0186850 | A1 | 7/2018 | Mohammadi et al. |

FOREIGN PATENT DOCUMENTS

| | | | |
|---|---|---|---|
| WO | WO 2013/184958 | A1 | 8/2001 |
| WO | WO 01/66595 | A2 | 9/2001 |
| WO | WO 01/66596 | A2 | 9/2001 |
| WO | WO 2009/095372 | | 8/2009 |
| WO | WO 2009/133905 | A1 | 11/2009 |
| WO | WO 2011/047267 | A1 | 4/2011 |
| WO | WO 2011/130729 | A2 | 10/2011 |
| WO | WO 2013/027191 | A1 | 2/2013 |
| WO | WO 2013/184960 | A2 | 12/2013 |
| WO | WO 2013/184962 | A1 | 12/2013 |
| WO | WO 2015/149069 | A1 | 10/2015 |

OTHER PUBLICATIONS

Kurosu et al., "The Klotho Gene Family as a Regulator of Endocrine Fibroblast Growth Factors," *Mol. Cel. Endocrin.* 299:72-78 (2009).

Ono et al., "Novel Regulation of Fibroblast Growth Factor 2 (FGF2)-Mediated Cell Growth by Polysialic Acid," *J. Biol. Chem.* 287(6):3710-3722 (2012).

Schlessinger et al., "Crystal Structure of a Ternary FGF-FGFR-Heparin Complex Reveals a Dual Role for Heparin in FGFR Binding and Dimerization," *Molecular Cell* 6:743-750 (2000).

Thompson et al., "Energetic Characterization of the Basic Fibroblast Growth Factor-Heparin Interaction: Identification of the Heparin Binding Domains,"*Biochemistry* 33:3831-3840 (1994).

Suh et al., "Endocrinization of FGF1 Produces a Neomorphic and Potent Insulin Sensitizer," Author Manuscript, *Nature*513(7518): 436-439 (2014).

Shalhoub et al. "FGF23 Neutralization Improves Chronic Kidney Disease-Associated Hyperparathyroidism yet Increases Mortality," *J. Clin. Invest.* 122(7):2543-2553 (2012).

Nallamsetty et al., "Gateway Vectors for the Production of Combinatorially-Tagged His6-MBP Fusion Proteins in the Cytoplasm and Periplasm of *Escherichia coli*," *Protein Sci.* 14:2964-2971 (2005).

Isakova et al., "Fibroblast Growth Factor 23 is Elevated Before Parathyroid Hormone and Phosphate in Chronic Kidney Disease," *Kidney International* 79:1370-1378 (2011).

Faul et al., "FGF23 Induces Left Ventricular Hypertrophy," *J. Clin. Invest.* 121:4393-4408 (2011).

Andrukhova et al., "FGF23 Drives Progression of Chronic Kidney Disease in Mice," Abstract No. TH-OR105, Kidney Week, Nov. 2015, San Diego, CA.

Fliser et al., "Fibroblast Growth Factor 23 (FGF23) Predicts Progression of Chronic Kidney Disease: The Mild to Moderate Kidney Disease (MMKD) Study," *J. Am. Soc. Nephrol.* 18(9):2600-2608 (2007).

Gutierrez et al., "Fibroblast Growth Factor-23 Mitigates Hyperphosphatemia but Accentuates Calcitriol Deficiency in Chronic Kidney Disease," *J. Am. Soc. Nephrol.* 16(7):2205-2215 (2005).

Gutierrez et al., "Fibroblast Growth Factor 23 and Mortality Among Patients Undergoing Hemodialysis," *N. Engl. J. Med.* 359(6):584-592 (2008).

Gutierrez et al., "Fibroblast Growth Factor 23 and Left Ventricular Hypertrophy in Chronic Kidney Disease," *Circulation* 119(19):2545-2552 (2009).

Hasegawa et al., "Direct Evidence for a Causative Role of FGF23 in the Abnormal Renal Phosphate Handling and Vitamin D Metabolism in Rats with Early-Stage Chronic Kidney Disease," *Kidney International* 78:975-980 (2010).

Hsu HJ and Wu MS, "Fibroblast Growth Factor 23: A Possible Cause of Left Ventricular Hypertrophy in Hemodialysis Patients," *Am. J. Med. Sci.* 337(2):116-122 (2009).

Jean et al., "High Levels of Serum Fibroblast Growth Factor (FGF)-23 are Associated with Increased Mortality in Long Haemodialysis Patients," *Nephrol. Dial. Transplant* 24(9):2792-2796 (2009).

Larsson et al., "Circulating Concentration of FGF-23 Increases as Renal Function Declines in Patients with Chronic Kidney Disease, but does not Change in Response to Variation in Phosphate Intake in Healthy Volunteers," Kidney Int 64(6):2272-2279 (2003).

Mirza et al., "Circulating Fibroblast Growth Factor-23 is Associated with Vascular Dysfunction in the Community," *Atherosclerosis* 205(2):385-390 (2009).

Mirza et al., "Serum Intact FGF23 Associate with Left Ventricular Mass, Hypertrophy and Geometry in an Elderly Population," *Atherosclerosis* 207(2):546-551 (2009).

Mirza et al., "Circulating Fibroblast Growth Factor-23 is Associated with Fat Mass and Dyslipidemia in Two Independent Cohorts of Elderly Individuals," *Arterioscler. Thromb. Vasc. Biol.* 31:219-227 (2011).

Nakanishi et al., "Serum Fibroblast Growth Factor-23 Levels Predict the Future Refractory Hyperparathyroidism in Dialysis Patients," *Kidney Int.* 67(3):1171-1178 (2005).

Nasrallah et al., "Fibroblast Growth Factor-23 (FGF-23) is Independently Correlated to Aortic Calcification in Haemodialysis Patients," *Nephrol. Dial. Transplant* 25(8):2679-2685 (2010).

Shigematsu et al., "Possible Involvement of Circulating Fibroblast Growth Factor 23 in the Development of Secondary Hyperparathyroidism Associated with Renal Insufficiency," *Am. J. Kidney Dis.* 44(2):250-256 (2004).

Westerberg et al., "Regulation of Fibroblast Growth Factor-23 in Chronic Kidney Disease," *Nephrol. Dial. Transplant* 22(11):3202-3207 (2007).

Beenken et al., "The FGF Family: Biology, Pathophysiology and Therapy," *Nat. Rev. Drug Discov.* 8(3):235-53 (Mar. 2009).

(56) References Cited

OTHER PUBLICATIONS

Perwad et al., "Fibroblast Growth Factor 23 Impairs Phosphorus and Vitamin D Metabolism in vivo and Suppresses 25-Hydroxyvitamin D-1α-Hydroxylase Expression in vitro," *Am. J. Of Phys. Renal Phys.* 293(5):F1577-F1583 (2007).
Aono et al., "Therapeutic Effects of Anti-FGF23 Antibodies in Hypophosphatemic Rickets/Osteomalacia," J. *Bone Miner. Res.* 24(11):1879-1888 (available online May 4, 2009).
Aono et al., "The Neutralization of FGF-23 Ameliorates Hypophosphatemia and Rickets in Hyp Mice," Abstract, Oral Presentation, No. 1056, 25th American Society for Bone and Mineral Research Meeting, Sep. 19-23, 2003, Minneapolis, Minnesota, *J. Bone Miner. Res.* 18 (Suppl. S1): S15 (2003).
Shimada et al., "Mutant FGF-23 Responsible for Autosomal Dominant Hypophosphatemic Rickets Is Resistant to Proteolytic Cleavage and Causes Hypophosphatemia in Vivo," *Endocrinology* 143(8):3179-82 (2002).
Shimada et al., "Neutralization of Intrinsic FGF-23 Action by Antibodies Reveals the Essential Role of FGF-23 in Physiological Phosphate and Vitamin D Metabolism," Abstract, Poster Presentation, Nos. SA414 and F414, 25th American Society for Bone and Mineral Research Meeting, Sep. 19-23, 2003, Minneapolis, Minnesota, *J. Bone Miner. Res.* 18 (Suppl. S1): S93, S164 (2003).
Yamazaki et al., "Anti-FGF23 Neutralizing Antibodies Show the Physiological Role and Structural Features of FGF23," *J. Bone Miner. Res.* 23(9):1509-1518 (available online Apr. 1, 2008).
Berndt et al., "Biological Activity of FGF-23 Fragments," *Eur. J. Physiol.* 454:615-623 (2007).
Hu et al., "C-terminal Fragments of Fibroblast Growth Factor (FGF) 23 Inhibit Renal Phosphate (Pi) Excretion as an FGF23 Antagonist by Displacing FGF23 from its Receptor," Abstract SA-FC345, *J. Am. Soc. Nephrol.* 19:78A (2008).
Hu et al., "C-terminal Fragment of Fibroblast Growth Factor (FGF) 23 Inhibits Renal Phosphate (Pi) Excretion as an FGF23 Antagonist by Displacing FGF23 from its Receptor," Oral Presentation at the 41st Annual Meeting of the American Society of.Nephrology (Renal Week 2008) Philadelphia, PA, Nov. 4-9, 2008.
Shimada, "Possible Roles of Fibroblast Growth Factor 23 in Developing X-Linked Hypophosphatemia," Clin. Pediatr. Endocrinol. 14(Suppl 23):33-37 (2005).
Kurosu et al. "Regulation of Fibroblast Growth Factor-23 Signaling by Klotho," *J. Biol. Chem.* 281(10): 6120-6123 (2006).
Kurosu et al., "Tissue-specific Expression of βKlotho and Fibroblast Growth Factor (FGF) Receptor Isoforms Determines Metabolic Activity of FGF19 and FGF21," *J. Biol. Chem.* 282(37):26687-26695 (2007).
Micanovic et al., "Different Roles of N- and C- Termini in the Functional Activity of FGF21," *J. Cell. Physiol.* 219:227-234 (2009).
Kharitonenkov et al.,"FGF-21/FGF-21 Receptor Interaction and Activation is Determined by βKlotho," *J. Cell. Physiol.* 215:1-7 (2008).
Neyra et al., "Fibroblast Growth Factor 23 and Acute Kidney Injury," *Pediatr Nephrol.* 30(11):1909-18 (2015).
Hu et al., "Fibroblast Growth Factor 23 and Klotho: Physiology and Pathophysiology of an Endocrine Network of Mineral Metabolism," *Annu Rev Physiol.* 75:503-33 (2013).
Yao et al., "Expression and Pharmacological Evaluation of Fusion Protein FGF21-L-Fc," *Acta Pharmaceutica Sinica* 46(7):787-92 (2011) (Abstract in English).
Presta et al., "Structure-Function Relationship of Basic Fibroblast Growth Factor: Site-Directed Mutagenesis of a Putative Heparin-Binding and Receptor-Binding Region," *Biochem. Biophys. Res. Commun.* 185(3):1098-1107 (1992).
Zakrzewska et al., "Increased Protein Stability of FGF1 Can Compensate for Its Reduced Affinity for Heparin," *J. Biol. Chem.* 284(37):25388-403 (2009).
Motomura et al., "An FGF1:FGF2 Chimeric Growth Factor Exhibits Universal FGF Receptor Specificity, Enhanced Stability and Augmented Activity Useful for Epithelial Proliferation and Radioprotection," *Biochim. Biophys. Acta* 1780(12):1432-40 (2008).
Nakayama et al., "Post Treatment With an FGF Chimeric Growth Factor Enhances Epithelial Cell Proliferation to Improve Recovery From Radiation-Induced Intestinal Damage," *Int. J. Radiat. Oncol. Biol. Phys.* 78(3):860-7 (2010).
Kharitonenkov et al., "The Metabolic State of Diabetic Monkeys is Regulated by Fibroblast Growth Factor-21," *Endocrinology* 148(2):774-81 (2007).
Igarashi et al., "Characterization of Recombinant Human Fibroblast Growth Factor (FGF)-10 Reveals Functional Similarities With Keratinocyte Growth Factor (FGF-7)," *J. Biol. Chem.* 273(21):13230-5 (1998).
International Search Report and Written Opinion for PCT/US13/44589 (dated Nov. 13, 2013).
Goetz et al., "Molecular Insights Into the Klotho-Dependent, Endocrine Mode of Action of Fibroblast Growth Factor 19 Subfamily Members," *Mol. Cell. Biol.* 27(9):3417-3428 (2007).
Beenken, "Structural and Biochemical Studies of FGF-FGFR Complexes," Thesis (Sep. 2011).
Ge et al., "Characterization of a FGF19 Variant With Altered Receptor Specificity Revealed a Central Role for FGFR1c in the Regulation of Glucose Metabolism," *PLoS One*, 7(3):e33603 (Epub Mar. 23, 2012).
Wu et al., "FGF19 Regulates Cell Proliferation, Glucose and Bile Acid Metabolism Via FGFR4-Dependent and Independent Pathways," *PLoS One* 6(3):e17868 (Mar. 8, 2011).
Wu et al., "Selective Activation of FGFR4 by an FGF19 Variant Does Not Improve Glucose Metabolism in OB/OB Mice," *Proc. Nat'l. Acad. Sci U.S.A.* 106(34):14379-84 (2009).
Mohammadi et al., "Structural Basis for Fibroblast Growth Factor Receptor Activation," *Cytokine & Growth Factor Reviews* 16:107-137 (2005).
Hutley et al., "Fibroblast Growth Factor 1: A Key Regulator of Human Adipogenesis," *Diabetes* 53:3097-3106 (2004).
International Search Report and Written Opinion for PCT/US13/44594 (dated Nov. 13, 2013).
Imamura et al., "Recovery of Mitogenic Activity of a Growth Factor Mutant with Nuclear Translocation Sequence," *Science* 249:1567-1570 (Sep. 28, 1990).
International Search Report and Written Opinion for corresponding PCT/US13/44592 (dated Jan. 17, 2014).
Restriction Requirement for U.S. Appl. No. 13/838,350 (dated Jan. 30, 2014).
Office Action in U.S. Appl. No. 13/641,451 (dated Dec. 16, 2013).
Goetz et al., "Isolated C-Terminal tail of FGF23 Alleviates Hypophosphatemia by Inhibiting FGF23-FGFR-Klotho Complex Formation," *PNAS* 107(1):407-412 (Epub Dec. 4, 2009).
International Search Report and Written Opinion for PCT/US2013/028888 (dated Jul. 23, 2013).
International Search Report and Written Opinion for PCT/US14/17367 (dated Jun. 18, 2014).
Razzaque, "The FGF23-Klotho Axis: Endocrine Regulation of Phosphate Homeostasis," *Nat. Rev. Endocrinol.* 5(11):611-19 (2009).
Office Action in U.S. Appl. No. 14/176,992 (dated Jun. 26, 2014).
Restriction Requirement in U.S. Appl. No. 14/176,992 (dated Mar. 7, 2014).
Yie et al., "FGF21 N- and C-Termini Play Different Roles in Receptor Interaction and Activation," *FEBS Lett.* 583:19-24 (2009).
Andrukhova et al., "FGF23 Acts Directly on Renal Proximal Tubules to Induce Phosphaturia Through Activation of the ERK1/2-SKG1 Signaling Pathway," *Bone* 51(3):621-8 (Jun. 12, 2012).
Beenken et al., "Plasticity in Interactions of Fibroblast Growth Factor 1 (FGF1) N Terminus With FGF Receptors Underlies Promiscuity of FGF1," *J. Biol. Chem.* 287(5):3067-3078 (Nov. 4, 2011).
Jonker et al., "A PPARgamma-FGF1 Axis is Required for Adaptive Adipose Remodelling and Metabolic Homeostasis," *Nature* 485(7398):391-394 (Apr. 22, 2012).
Wu et al., "A Unique FGF23 With the Ability to Activate FGFR Signaling Through Both alphaKlotho and betaKlotho," *J. Mol. Biol.* 418:82-89 (2012).

(56) References Cited

OTHER PUBLICATIONS

Beenken & Mohammadi, "The Structural Biology of the FGF19 Subfamily," *Adv. Exp. Med. Biol.* 728:1-24 (2012).
Wu et al., "C-Terminal Tail of FGF19 Determines Its Specificity Toward Klotho Co-Receptors," *J. Biol. Chem.* 283(48):33304-33309 (2008).
Goetz et al., "Conversion of a Paracrine Fibroblast Growth Factor Into an Endocrine Fibrobalst Growth Factor," *J. Biol. Chem.* 287(34):29134-29146 (Jun. 25, 2012).
Goetz et al., "Klotho Coreceptors Inhibit Signaling by Paracrine Fibroblast Growth Factor 8 Subfamily Ligands," *Mol. Cell. Biol.* 32(10):1944-1954 (Mar. 26, 2012).
Olsen et al., "Insights Into the Molecular Basis for Fibroblast Growth Factor Receptor Autoinhibition and Ligand-Binding Promiscuity," *Proc. Nat'l. Acad. Sci. USA* 101(4):935-940 (2004).
Wei et al., "Fibroblast Growth Factor 21 Promotes Bone Loss by Potentiating the.Effects of Peroxisome Proliferator-Activated Receptor Gamma," *Proc. Nat'l. Acad. Sci. USA* 109(8):3143-3148 (Feb. 21, 2012).
Wu et al., "Separating Mitogenic and Metabolic Activities of Fibroblast Growth Factor 19 (FGF19)," *Proc. Nat'l. Acad. Sci. USA* 107(32):14158-14163 (2010).
Wu et al., "FGF19-Induced Hepatocyte Proliferation is Mediated Through FGFR4 Activation," *J. Biol. Chem.* 285(8):5165-5170 (2009).
Zhang et al., "Receptor Specificity of the Fibroblast Growth Factor Family," *J. Biol. Chem.* 281(23):15694-15700 (2006).
Restriction Requirement in U.S. Appl. No. 13/784,289 (dated Sep. 3, 2014).
Restriction Requirement in U.S. Appl. No. 13/837,880 (dated Sep. 3, 2014).
Office Action in U.S. Appl. No. 13/838,350 (dated Jul. 17, 2014).
Restriction Requirement in U.S. Appl. No. 14/097,056 (dated Aug. 14, 2014).
Office Action in U.S. Appl. No. 13/838,350 (dated Dec. 11, 2014).
Office Action in U.S. Appl. No. 13/784,289 (dated Mar. 4, 2015).
Office Action in U.S. Appl. No. 13/837,880 (dated Dec. 11, 2014).
Office Action in U.S. Appl. No. 13/837,880 (dated Aug. 4, 2015).
Office Action in U.S. Appl. No. 13/838,350 (dated Aug. 3, 2015).
Restriction Requirement in U.S. Appl. No. 14/097,116 (dated Dec. 11, 2014).
Restriction Requirement in U.S. Appl. No. 14/185,366 (dated Jun. 4, 2015).
Office Action in U.S. Appl. No. 14/185,366 (dated Jan. 15, 2016).
Office Action in U.S. Appl. No. 13/784,289 (dated Nov. 5, 2015).
Extended European Search Report for European Application No. 13799858.9 (dated May 3, 2016).
Restriction Requirement in U.S. Appl. No. 13/839,051 (dated Sep. 3, 2014).
Office Action in U.S. Appl. No. 13/839,051 (dated Dec. 11, 2014).
Office Action in U.S. Appl. No. 13/839,051 (dated Aug. 6, 2015).
Office Action in U.S. Appl. No. 13/839,051 (dated May 25, 2016).
Patent Examination Report in Australian Patent Application No. 2014274604 (dated Oct. 16, 2015).
Second Office Action for Chinese Patent Application No. 201380039848.9 (dated Jun. 8, 2017).
Office Action in U.S. Appl. No. 15/289,447 (dated Jun. 16, 2017).
DiGabriele et al., "Structure of a Heparin-Linked Biologically Active Dimer of Fibroblast Growth Factor," *Nature* 393(6687):812-7 (1998).
Office Action in U.S. Appl. No. 15/289,544 (dated May 30, 2017).
Isakova et al., "Fibroblast Growth Factor 23 and Adverse Clinical Outcomes in Chronic Kidney Disease," NIH Public Access, Author Manuscript (available May 1, 2013), published in final edited Form in Curr. Opin. Neprhol. Hypertens. 21(3):334-340 (2012).
Razzaque et al., "Therapeutic Potential of KlothoFGF23 Fusion Polypeptides:W02009095372," *Expert Opin. Ther. Pat.* 20(7):981-5 (2010).
Czajkowsky et al., "Fc-Fusion Proteins: New Developments and Future Perspectives," *EMBO Mol. Med.* 4(10):1015-1028 (2012).
Creative Biomart, Specification Sheet, "Recombinant Human Fibroblast Growth Factor 23, Fc Chimera," http://www.creativebiomart.net/pdf/FGF23-416H,FGF23,Fc Chimera.pdf, Rev 092708A.
Creative Biomart, Specification Sheet, "Recombinant Mouse Fibroblast Growth Factor 23, Fc Chimera," http://www.creativebiomart.net/pdf/FGF23-417M,FGF23,Fc Chimera.pdf, Rev 092708A.
Liu et al., "SUMO Fusion System Facilitates Soluble Expression and High Production of Bioactive Human Fibroblast Growth Factor 23 (FGF23)," *Appl. Micro. Biotech.* 96(1):103-111 (2012).
Crumley et al., Genbank Accession No. 1605206A, acidic fibroblast growth factor (1996).
Restriction Requirement for U.S. Appl. No. 15/283,862 dated Feb. 22, 2018.
Office Action for U.S. Appl. No. 15/300,048 dated Nov. 30, 2018.

```
FGF19 (169) LPMV PEEPEDLRGH LESDMFSSPL ETDSMDPFGL VTGLEAVRSP SFEK------
FGF21 (168) PGLP PALPE----- PPGILAPQPP DVGSSDPLSM V-GPSQGRSP SYAS------
FGF23 (163) --EI PLI--HFNTP IPRRHTRSAE DDSERDPLN- VLKPRARMTP APASCSQELP

FGF19       ---------- ---------- ---------- ----------
FGF21       ---------- ---------- ---------- ----------
FGF23 (212) SAEDNSPMAS DPLGVVRGGR VNTHAGGTGP EGCRPFAKFI
```

*FIG. 11*

CHIMERIC FIBROBLAST GROWTH FACTOR 23 PROTEINS AND METHODS OF USE

This application is a divisional of Ser. No. 13/839,051, filed Mar. 15, 2013, which claims priority benefit of U.S. Provisional Patent Application No. 61/656,887, filed Jun. 7, 2012, and U.S. Provisional Patent Application No. 61/664,097, filed Jun. 25, 2012, each of which is hereby incorporated by reference in its entirety.

This invention was made with government support under grant numbers DE13686, DK077276, AG019712, DK091392, and DK067158 awarded by the U.S. National Institutes of Health. The government has certain rights in this invention.

FIELD OF THE INVENTION

The present invention relates to chimeric fibroblast growth factor ("FGF") proteins and uses thereof.

BACKGROUND OF THE INVENTION

Fibroblast growth factor (FGF) 23, is an endocrine regulator of phosphate homeostasis and vitamin D metabolism, and was originally identified as the mutated gene in patients with the phosphate wasting disorder "autosomal dominant hypophosphatemic rickets" (ADHR) (Anonymous, "Autosomal Dominant Hypophosphataemic Rickets is Associated with Mutations in FGF23," *Nat Genet* 26(3):345-348 (2000)). FGF23 inhibits reabsorption of phosphate in the renal proximal tubule by decreasing the abundance of the type II sodium-dependent phosphate transporters $NaP_i$-2A and $NaP_i$-2C in the apical brush border membrane (Baum et al., "Effect of Fibroblast Growth Factor-23 on Phosphate Transport in Proximal Tubules," *Kidney Int* 68(3):1148-1153 (2005); Perwad et al., "Fibroblast Growth Factor 23 Impairs Phosphorus and Vitamin D Metabolism In Vivo and Suppresses 25-hydroxyvitamin D-1alpha-hydroxylase Expression In Vitro," *Am J Physiol Renal Physiol* 293(5):F1577-1583 (2007); Larsson et al., "Transgenic Mice Expressing Fibroblast Growth Factor 23 under the Control of the Alpha1(I) Collagen Promoter Exhibit Growth Retardation, Osteomalacia, and Disturbed Phosphate Homeostasis," *Endocrinology* 145(7):3087-3094 (2004)). The phosphaturic activity of FGF23 is down-regulated by proteolytic cleavage at the $^{176}$RXXR$^{179}$ (SEQ ID NO: 233) motif, where "XX" is defined as "HT", corresponding to positions 177 and 178, respectively, of the FGF23 amino acid sequence, producing an inactive N-terminal fragment (Y25 to R179) and a C-terminal fragment (S180 to I251) (Goetz et al., "Molecular Insights into the Klotho-dependent, Endocrine Mode of Action of Fibroblast Growth Factor 19 Subfamily Members," *Mol Cell Biol* 27(9):3417-3428 (2007)). αKlotho, a protein first described as an aging suppressor (Kuro-o et al., "Mutation of the Mouse Klotho Gene Leads to a Syndrome Resembling Aging," *Nature* 390(6655):45-51 (1997)), is required by FGF23 in its target tissue in order to exert its phosphaturic activity (Kurosu et al., "Regulation of Fibroblast Growth Factor-23 Signaling by Klotho," *J Biol Chem* 281(10):6120-6123 (2006); Urakawa et al., "Klotho Converts Canonical FGF Receptor into a Specific Receptor for FGF23," *Nature* 444(7120):770-774 (2006)). αKlotho constitutively binds the cognate FGFRs of FGF23, and the binary FGFR-αKlotho complexes exhibit enhanced binding affinity for FGF23 ((Kurosu et al., "Regulation of Fibroblast Growth Factor-23 Signaling by Klotho," *J Biol Chem* 281 (10):6120-6123 (2006); Urakawa et al., "Klotho Converts Canonical FGF Receptor into a Specific Receptor for FGF23," *Nature* 444(7120):770-774 (2006)). In co-immunoprecipitation studies, it was demonstrated that the mature, full-length form of FGF23 (Y25 to I251) but not the inactive N-terminal fragment of proteolytic cleavage (Y25 to R179) binds to binary FGFR-αKlotho complexes (Goetz et al., "Molecular Insights into the Klotho-dependent, Endocrine Mode of Action of Fibroblast Growth Factor 19 Subfamily Members," *Mol Cell Biol* 27(9):3417-3428 (2007)).

It was further shown that the mature, full-length form of FGF23 (Y25 to I251) forms a stable ternary complex with the ectodomain of αKlotho and the ligand-binding domain of FGFR1c in solution (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). The ligand interacts with a de novo binding site generated at the composite receptor-coreceptor interface in the binary αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). The region on FGF23 that binds to this de novo site was mapped to the 72 amino acid long C-terminal tail, which follows the β-trefoil core domain (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). Thus, the N-terminal fragment of proteolytic cleavage (Y25 to R179) is metabolically inactive because it lacks the binding site for the αKlotho-FGFR complex. The C-terminal proteolytic fragment (S180 to I251), however, can compete with full-length FGF23 for binding to the αKlotho-FGFR complex to antagonize the metabolic activity of FGF23, because this fragment contains the binding site for the αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010)). These findings suggest a dual mechanism by which proteolytic cleavage at the RXXR motif inactivates FGF23: the cleavage removes the binding site for the αKlotho-FGFR complex from FGF23 and concomitantly generates an endogenous inhibitor of FGF23. Inhibition of this proteolytic cleavage by missense mutations at the RXXR motif in FGF23 leads to accumulation of full-length, bioactive FGF23, causing renal phosphate wasting disease in humans (Shimada et al., "Mutant FGF-23 Responsible for Autosomal Dominant Hypophosphatemic Rickets is Resistant to Proteolytic Cleavage and Causes Hypophosphatemia in vivo," *Endocrinology* 143:3179-3182 (2002); White et al., "Autosomal-dominant Hypophosphatemic Rickets (ADHR) Mutations Stabilize FGF-23," *Kidney Int* 60:2079-2086 (2001); White et al., "Autosomal Dominant Hypophosphataemic Rickets is Associated with Mutations in FGF23," *Nature Genet* 26:345-348 (2000)).

Conversely, enhanced FGF23 cleavage due to impaired O-glycosylation of FGF23 leads to a deficit in full-length FGF23, which manifests as hyperphosphatemia and soft tissue calcification in humans (Frishberg Y et al., "Hyperostosis-hyperphosphatemia Syndrome: a Congenital Disorder of O-glycosylation Associated with Augmented Processing of Fibroblast Growth Factor 23," *J Bone Miner Res* 22:235-242 (2007); Kato et al., "Polypeptide GalNAc-transferase T3 and Familial Tumoral Calcinosis. Secretion of Fibroblast Growth Factor 23 Requires O-glycosylation," *J Biol Chem* 281:18370-18377 (2006)). Familial tumoral calcinosis is an autosomal recessive metabolic disorder associated with hyperphosphatemia and soft tissue calcification. Missense mutations in either the UDP-N-acetyl-α-D-galactosamine: polypeptide N-acetylglactosaminyltransferase 3 (GALNT3) gene (Garringer et al., "Two Novel GALNT3 Mutations in Familial Tumoral Calcinosis," *Am J Med Genet A* 143A: 2390-2396 (2007)) or the FGF23 gene (Garringer et al., "Molecular Genetic and Biochemical Analyses of FGF23 Mutations in Familial Tumoral Calcinosis," *Am J Physiol Endocrinol Metab* 295:E929-E937 (2008); Araya et al., "A Novel Mutation in Fibroblast Growth Factor 23 Gene as a Cause of Tumoral Calcinosis," *J Clin Endocrinol Metab* 90:5523-5527 (2005)) have been associated with familial tumoral calcinosis. There is a great need for suitable treatments for such patients.

The present invention is directed to overcoming these and other deficiencies in the art.

SUMMARY OF THE INVENTION

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF23 molecule. The portion of the paracrine FGF is modified to decrease binding affinity for heparin and/or heparan sulfate compared to the portion without the modification.

Another aspect of the present invention relates to a method for treating a subject suffering from a disorder. This method involves selecting a subject suffering from the disorder. The method also involves providing a chimeric FGF protein, where the chimeric FGF protein includes an N-terminus coupled to a C-terminus. The N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a C-terminal portion of FGF23 that includes an α-Klotho-FGFR complex binding domain to the modified FGF protein's C-terminus.

Yet another aspect of the present invention relates to a method of facilitating fibroblast growth factor receptor ("FGFR")-α-Klotho co-receptor complex formation. This method involves providing a cell that includes a α-Klotho co-receptor and an FGFR and providing a chimeric FGF protein. The chimeric FGF protein includes a C-terminal portion of FGF23 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-αKlotho co-receptor complex formation.

Yet a further aspect of the present invention relates to a method of screening for agents capable of facilitating fibroblast growth factor receptor ("FGFR")-αKlotho co-receptor complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves providing a binary αKlotho-FGFR complex and providing one or more candidate agents. This method further involves combining the chimeric FGF, the binary αKlotho-FGFR complex, and the one or more candidate agents under conditions permitting the formation of a ternary complex between the chimeric FGF and the binary αKlotho-FGFR complex in the absence of the one or more candidate agents. This method also involves identifying the one or more candidate agents that decrease ternary complex formation between the chimeric FGF and the binary αKlotho-FGFR compared to the ternary complex formation in the absence of the one or more candidate agents as suitable for treating the disorder.

Yet another aspect of the present invention relates to a modified FGF23 protein. The modified FGF23 protein includes an FGF23 protein that includes a modification to decrease binding affinity for heparin and/or heparan sulfate compared to an FGF23 protein without the modification.

Another aspect of the present invention relates to a method for treating a subject suffering from a disorder. This method involves selecting a subject suffering from the disorder and administering to the selected subject a therapeutically effective amount of a modified FGF23 protein that includes a modification to decrease binding affinity for heparin and/or heparan sulfate compared to an FGF23 protein without the modification.

Fibroblast growth factors (FGFs) 19, 21, and 23 are hormones that regulate in a Klotho co-receptor-dependent fashion major metabolic processes such as glucose and lipid metabolism (FGF21) and phosphate and vitamin D homeostasis (FGF23). The role of heparan sulfate glycosaminoglycan in the formation of the cell surface signaling complex of endocrine FGFs has remained unclear. To decipher the role of HS in endocrine FGF signaling, we generated FGF19 and FGF23 mutant ligands devoid of HS binding and compared their signaling capacity with that of wild-type ligands. The data presented herein show that the mutated ligands retain full metabolic activity demonstrating that HS does not participate in the formation of the endocrine FGF signaling complex. Here it is shown that heparan sulfate is not a component of the signal transduction unit of FGF19 and FGF23. A paracrine FGF is converted into an endocrine ligand by diminishing heparan sulfate binding affinity of the paracrine FGF and substituting its C-terminal tail for that of an endocrine FGF containing the Klotho co-receptor binding site in order to home the ligand into the target tissue. The ligand conversion provides a novel strategy for engineering endocrine FGF-like molecules for the treatment of metabolic disorders, including global epidemics such as type 2 diabetes and obesity.

BRIEF DESCRIPTION OF THE DRAWINGS

FIG. 1A shows interactions of FGF2 (schematic representation) with a heparin hexasaccharide (shown as sticks) as observed in the crystal structure of the 2:2 FGF2-FGFR1c dimer (PDB ID: 1FQ9; (Schlessinger et al., *Mol. Cell* 6:743-750 (2000), which is hereby incorporated by reference in its entirety)). The heparin hexasaccharide consists of three disaccharide units of 1→4 linked N-sulfated-6-O-sulfated D-glucosamine and 2-O-sulfated L-iduronic acid. Note that the heparin hexasaccharide interacts with both side chain and backbone atoms of residues in the HS-binding site of FGF2. Dashed lines denote hydrogen bonds. K128, R129, and K134, which make the majority of hydrogen bonds with the heparin hexasaccharide, are boxed. The β-strand nomenclature follows the original FGF1 and FGF2 crystal structures (Ago et al., *J Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety). Please note that compared to the prototypical β-trefoil fold seen in soybean trypsin inhibitor (PDB ID: 1TIE; (Onesti et al., *J. Mol. Biol.* 217:153-176 (1991), which is hereby incorporated by reference in its entirety)) and interleukin 113 (PDB ID: 1I1B; (Finzel et al., *J Mol. Biol.* 209:779-791 (1989), which is hereby incorporated by reference in its entirety)), the β10-β11 strand pairing in FGF2 and other paracrine FGFs is less well defined. FIGS. 1B and 1C show cartoon representation of the crystal structures of FGF19 (PDB ID: 2P23; (Goetz et al., *Mol. Cell Biol.* 27:3417-3428 (2007), which is hereby incorporated by reference in its entirety)) (FIG. 1B) and FGF23 (PDB ID: 2P39; (Goetz et al., *Mol. Cell Biol.* 27:3417-3428 (2007), which is hereby incorporated by reference in its entirety)) (FIG. 1C) shown in the same orientation as the FGF2 structure in FIG. 1A. Side chains of residues that map to the corresponding HS-binding sites of these ligands are shown as sticks. Residues selected for mutagenesis to knock out residual HS binding in FGF19 and FGF23 are boxed. NT and CT indicate N- and C-termini of the FGFs. FIG. 1D is a schematic of two working models for the endocrine FGF-FGFR-Klotho coreceptor signal transduction unit. A recent study on the ternary complex formation between FGF21, FGFR1c, and βKlotho supports the 1:2:1 model rather than the 2:2:2 model (Ming et al., *J Biol. Chem.* 287:19997-20006 (2012), which is hereby incorporated by reference in its entirety). For comparison, a schematic of the paracrine FGF-FGFR-HS signaling unit is shown, which was made based on the crystal structure of the 2:2:2 FGF2-FGFR1c-HS complex (PDB ID: 1FQ9; (Schlessinger et al., *Mol. Cell* 6:743-750 (2000), which is hereby incorporated by reference in its entirety)). HS engages both paracrine FGF and receptor to enhance binding of FGF to its primary and secondary receptors thus promoting receptor dimerization. A question mark denotes whether or not HS is also a component of the endocrine FGF signaling complex.

FIG. 3A shows an overlay of SPR sensorgrams illustrating heparin binding of FGF2, FGF19, FGF21, and FGF23 (left panel) and an exploded view of the binding responses for FGF19-, FGF21-, and FGF23-heparin interactions (right panel). Heparin was immobilized on a biosensor chip, and 400 nM of FGF2, FGF19, FGF21, or FGF23 were passed over the chip. Note that FGF19, FGF21, and FGF23 exhibit measurable, residual heparin binding and that differences in heparin binding exist between these three endocrine FGFs. FIGS. 3B-3D show overlays of SPR sensorgrams illustrating binding of FGF19 to heparin (FIG. 3B) and lack of interaction between the FGF19$^{K149A}$ mutant and heparin (FIG. 3C) and between the FGF19$^{K149A,\ R157A}$ mutant and heparin (FIG. 3D). Heparin was immobilized on a biosensor chip, and increasing concentrations of FGF19 were passed over the chip. Thereafter, FGF19$^{K149A}$ or FGF19$^{K149A,\ R157A}$ was injected over the heparin chip at the highest concentration tested for the wild-type ligand. FIGS. 3E-3G show overlays of SPR sensorgrams illustrating binding of FGF23 to heparin (FIG. 3E), poor interaction between the FGF23$^{R48A,\ N49A}$ mutant and heparin (FIG. 3F), and lack of interaction between the FGF23$^{R140A,\ R143A}$ mutant and heparin (FIG. 3G). Heparin was immobilized on a biosensor chip, and increasing concentrations of FGF23 were passed over the chip. FGF23$^{R48A,\ N49A}$ or FGF23$^{R140A,\ R143A}$ was then injected over the heparin chip at the highest concentration tested for the wild-type ligand.

FIG. 4A shows results of an immunoblot analysis of phosphorylation of FRS2α (pFRS2α) and 44/42 MAP kinase (p44/42 MAPK) in H4IIE hepatoma cells following stimulation with the FGF19$^{K149A}$ mutant, the FGF19$^{K149A,\ R157A}$ mutant, or wild-type FGF19. Numbers above the lanes give the amounts of protein added in ng ml$^{-1}$. Total 44/42 MAPK protein expression was used as a loading control. FIG. 4B shows results of an immunoblot analysis of phosphorylation of FRS2a (pFRS2a) and 44/42 MAP kinase (p44/42 MAPK) in a HEK293-αKlotho cell line following stimulation with the FGF23$^{R48A,\ N49A}$ mutant, the FGF23$^{R140A,\ R143A}$ mutant, or wild-type FGF23. Numbers above the lanes give the amounts of protein added in ng ml$^{-1}$. Total 44/42 MAPK and αKlotho protein expression were used as loading controls. FIG. 4C shows graphical results of a quantitative analysis of CYP7A1 and CYP8B1 mRNA expression in liver tissue from mice treated with FGF19K149A, FGF19$^{K149A,\ R157A}$ FGF19, or vehicle. 1 mg of protein per kg of body weight was given. Data are presented as mean±SEM; *, P<0.001 by Student's t test. FIG. 4**D shows graphical results of analysis of serum phosphate concentrations (serum $P_i$) in mice before and 8 h after intraperitoneal injection of FGF23$^{R48A,\ N49A}$ FGF23$^{R140A,\ R143A}$ FGF23, or vehicle. Wild-type mice were given a single dose of protein (0.29 mg kg body weight$^{-1}$), whereas Fgf23 knockout mice received two doses of 0.71 mg kg body weight$^{-1}$ each. Data are presented as mean±SEM; *, P<0.05, and **, P<0.01 by ANOVA.

FIG. 5A is a schematic of human FGF2, FGF19, FGF21, FGF23, and engineered FGF2-FGF19, FGF2-FGF21, and FGF2-FGF23 chimeras. Amino acid boundaries of each ligand and of each component of the chimeras are labeled with residue letter and number. The β-trefoil core domain for the known ligand crystal structures is shaded gray. HS-binding residues mutated in the FGF2 portion of chimeras are labeled with residue letter and number. Also labeled are the arginine residues of the proteolytic cleavage site in the C-terminal region of FGF23 that were mutated to glutamine in both FGF23 and the FGF2-FGF23 chimeras. FIGS. 5B and 5C show overlays of SPR sensorgrams illustrating binding of FGF2$^{WTcore}$-FGF21$^{C\text{-}tail}$ (FIG. 5B) and FGF2$^{\Delta HBScore}$-FGF21$^{C\text{-}tail}$ (FIG. 5C) to heparin, and fitted saturation binding curves. Heparin was immobilized on a biosensor chip, and increasing concentrations of FGF2$^{WTcore}$-FGF21$^{C\text{-}tail}$ or FGF2$^{\Delta HBScore}$-FGF21$^{C\text{-}tail}$ were passed over the chip. Dissociation constants ($K_D$s) were derived from the saturation binding curves. FIGS. 5D and 5E show overlays of SPR sensorgrams illustrating binding of FGF2$^{WTcore}$-FGF23$^{C\text{-}tail}$ (FIG. 5D) and FGF2$^{\Delta HBScore}$-FGF23$^{C\text{-}tail}$ (FIG. 5E) to heparin. Increasing concentrations of FGF2$^{WTcore}$-FGF23$^{C\text{-}tail}$ or FGF2$^{\Delta HBScore}$-FGF23$^{C\text{-}tail}$ were passed over a chip containing immobilized heparin. FIGS. 5F and 5G show results of immunoblot analysis for Egr1 expression in HEK293 cells following stimulation with chimeras or native FGFs as denoted. Numbers above the lanes give the amounts of protein added in nanomolar. GAPDH protein expression was used as a loading control.

FIGS. 7A and 7B show overlays of SPR sensorgrams illustrating inhibition by FGF2$^{\Delta HBScore}$-FGF23$^{C\text{-}tail}$ (FIG. 7A) or FGF23 (FIG. 7B) of αKlotho-FGFR1c binding to FGF23 immobilized on a biosensor chip. Increasing concentrations of FGF2$^{\Delta HBScore}$-FGF23$^{C\text{-}tail}$ or FGF23 were mixed with a fixed concentration of αKlotho-FGFR1c complex, and the mixtures were passed over a FGF23 chip. FIG. 7C shows an overlay of SPR sensorgrams illustrating failure of FGF2 to inhibit αKlotho-FGFR1c binding to FGF23. FGF2 and αKlotho-FGFR1c complex were mixed at a molar ratio of 15:1, and the mixture was passed over a biosensor chip containing immobilized FGF23. FIGS. 7D and 7E show overlays of SPR sensorgrams illustrating no inhibition by FGF2$^{\Delta HBScore}$-FGF23$^{C\text{-}tail}$ (FIG. 7D) or FGF23 (FIG. 7E) of βKlotho-FGFR1c binding to FGF21. FGF2$^{\Delta HBScore}$-FGF23$^{C\text{-}tail}$ or FGF23 were mixed with βKlotho-FGFR1c complex at a molar ratio of 10:1, and the mixtures were passed over a biosensor chip containing immobilized FGF21. FIG. 7F shows analysis of serum phosphate concentrations (serum $P_i$) in mice before and 8 h after intraperitoneal injection of FGF2$^{\Delta HBScore}$-FGF23$^{C\text{-}tail}$, FGF2$^{WTcore}$-FGF23$^{C\text{-}tail}$, FGF23, or vehicle. Wild-type mice and αKlotho knockout mice were given 0.21 mg and 0.51 mg of protein, respectively, per kg of body weight. Data are presented as mean±SEM; , P<0.01; *, P<0.001 by ANOVA. FIG. 7G shows quantitative analysis of CYP27B1 mRNA expression in renal tissue from mice injected with FGF2$^{\Delta HBScore}$-FGF23$^{C\text{-}tail}$, FGF2$^{WTcore}$-FGF23$^{C\text{-}tail}$, FGF23, or vehicle. 0.21 mg of protein per kg of body weight were injected. Data are presented as mean±SEM; ***, P<0.001 by ANOVA.

FIGS. 8A-8B show overlays of SPR sensorgrams illustrating inhibition by FGF2$^{\Delta HBScore}$-FGF21$^{C\text{-}tail}$ (FIG. 8A) or FGF21 (FIG. 8B) of βKlotho-FGFR1c binding to FGF21 immobilized on a biosensor chip. Increasing concentrations of FGF2$^{\Delta HBScore}$-FGF21$^{C\text{-}tail}$ or FGF21 were mixed with a fixed concentration of βKlotho-FGFR1c complex, and the mixtures were passed over a FGF21 chip. FIG. 8C shows an overlay of SPR sensorgrams illustrating failure of FGF2 to inhibit βKlotho-FGFR1c binding to FGF21. FGF2 and βKlotho-FGFR1c complex were mixed at a molar ratio of 15:1, and the mixture was passed over a biosensor chip containing immobilized FGF21. FIGS. 8D-8E show overlays of SPR sensorgrams illustrating no inhibition by FGF2$^{\Delta HBScore}$-FGF21 (FIG. 8D) or FGF21 (FIG. 8E) of αKlotho-FGFR1c binding to FGF23. FGF2$^{\Delta HBScore}$-FGF21$^{C\text{-}tail}$ or FGF21 were mixed with αKlotho-FGFR1c complex at a molar ratio of 10:1, and the mixtures were passed over a biosensor chip containing immobilized FGF23. FIG. 8F shows results of immunoblot analysis for Egr1 expression in HEK293-βKlotho cells stimulated with FGF2$^{\Delta HBScore}$-FGF21$^{C\text{-}tail}$ or FGF21. Numbers above the lanes give the amounts of protein added in ng ml$^{-1}$. GAPDH protein expression was used as a loading control. Note that the FGF2$^{\Delta HBScore}$-FGF21$^{C\text{-}tail}$ chimera is more potent than native FGF21 at inducing Egr1 expression suggesting that the chimera has agonistic property. This is expected since the core domain of FGF2 has inherently greater binding affinity for FGFR than the core domain of FGF21 (see FIGS. 10A and 10C). FIG. 8G shows graphical results of analysis of blood glucose concentrations in mice before and at the indicated time points after intraperitoneal injection of insulin alone, insulin plus FGF2$^{\Delta HBScore}$-FGF21$^{C\text{-}tail}$ chimera, insulin plus FGF21, or vehicle alone. 0.5 units of insulin per kg of body weight and 0.3 mg of FGF21 ligand per kg of body weight were injected. Blood glucose concentrations are expressed as percent of pre-injection values. Data are presented as mean±SEM.

FIG. 9A shows graphical results of analysis of blood glucose concentrations in ob/ob mice before and at the indicated time points after subcutaneous injection of FGF1 or FGF21. FIG. 9B shows graphical results of analysis of blood glucose concentrations in ob/ob mice before and at the indicated time points after subcutaneous injection of FGF1, FGF1$^{\Delta NT}$, or FGF1$^{\Delta HBS}$. FIG. 9C shows graphical results of analysis of blood glucose concentrations in ob/ob mice before and at the indicated time points after subcutaneous injection of FGF1 or FGF1$^{\Delta HBScore}$-FGF21$^{C\text{-}tail}$ chimera. For the experiments shown in FIGS. 9A-9C, ob/ob mice were injected with a bolus of 0.5 mg of FGF protein per kg of body weight. Data are presented as mean±SD.

FIGS. 10A-10D show overlays of SPR sensorgrams illustrating binding of FGFR1c to FGF2 (FIG. 10A), FGF19 (FIG. 10B), FGF21 (FIG. 10C), and FGF23 (FIG. 10D), and fitted saturation binding curves. Increasing concentrations of FGFR1c ligand-binding domain were passed over a biosensor chip containing immobilized FGF2, FGF19, FGF21, or FGF23. FIG. 10E shows an overlay of SPR sensorgrams illustrating binding of αKlotho-FGFR1c complex to FGF23. Increasing concentrations of αKlotho-FGFR1c complex were passed over a biosensor chip containing immobilized FGF23. FIG. 10F shows an overlay of SPR sensorgrams showing lack of interaction between the C-terminal tail peptide of FGF23 and FGFR1c. $FGF23^{C\text{-}tail}$ was immobilized on a biosensor chip and increasing concentrations of FGFR1c ligand-binding domain were passed over the chip. Dissociation constants ($K_D$s) given in FIGS. 10A-10E were derived from the saturation binding curves.

FIG. 11 shows an alignment of the C-terminal tail sequences of human FGF19 (GenBank Accession No. NP_005108, which is hereby incorporated by reference in its entirety), FGF21 (GenBank Accession No. NP_061986, which is hereby incorporated by reference in its entirety), and FGF23 (GenBank accession no. AAG09917, which is hereby incorporated by reference in its entirety). Residue numbers are in parenthesis to the left of the alignment. Gaps (dashes) were introduced to optimize the alignment. Residues that are identical between FGF19 and FGF21 are shaded gray. Note that 40% of these residues map the most C-terminal sequence.

DETAILED DESCRIPTION OF THE INVENTION

Figures 1A, 1B, 1C, 1D:
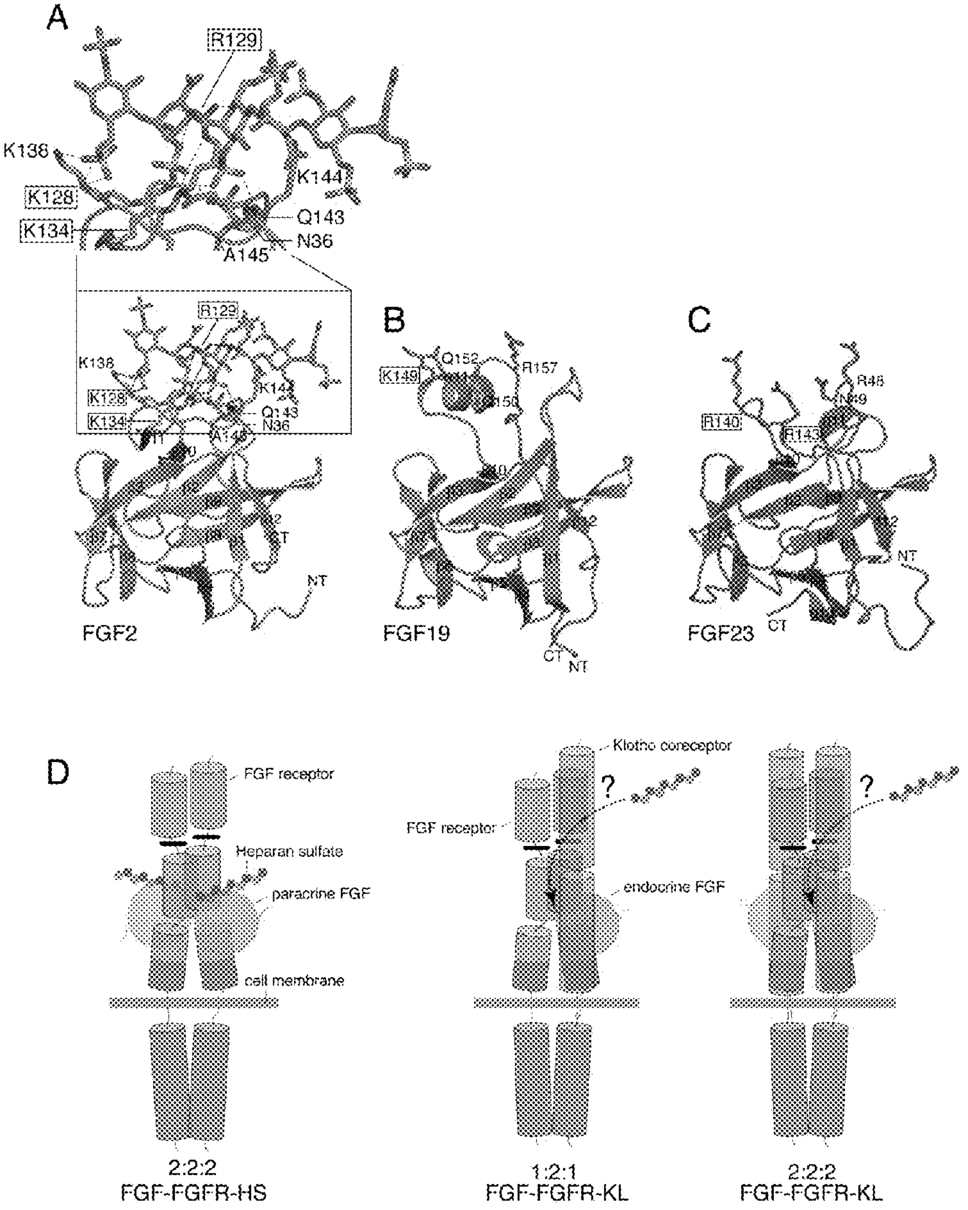
FIGS. 1A-1D are schematic diagrams showing side-by-side comparison of the HS-binding site of FGF2, FGF19, and FGF23, and working model of the endocrine FGF signaling complex.

One aspect of the present invention relates to a chimeric protein. The chimeric protein includes an N-terminus coupled to a C-terminus, where the N-terminus includes a portion of a paracrine fibroblast growth factor ("FGF") and the C-terminus includes a C-terminal portion of an FGF23 molecule. The portion of the paracrine FGF is modified to decrease binding affinity for heparin and/or heparan sulfate compared to the portion without the modification.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryogenesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells and FGFRc-interacting FGFs are produced by mesenchymal cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of specific paracrine FGF signaling loops between the epithelium and the mesenchyme, which is essential for proper organogenesis and patterning during embryonic development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J. Biochem.* 149:121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149:121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signalling in Mouse Beta-cells Leads to Diabetes," *Nature* 408:864-868 (2000); Jonker et al., "A PPARγ-FGF1 Axis is Required for Adaptive Adipose Remodelling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331: 1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF-21 as a Novel Metabolic Regulator," *J. Clin. Invest.* 115: 1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

FGFs share a core homology region of about one hundred and twenty amino acids that fold into a β-trefoil (Ago et al., *J. Biochem.* 110:360-363 (1991); Eriksson et al., *Proc. Nat'l. Acad. Sci. U.S.A.* 88:3441-3445 (1991); Zhang et al., *Proc. Nat'l. Acad. Sci. U.S.A.* 88:3446-3450 (1991); Zhu et al., *Science* 251:90-93 (1991), which are hereby incorporated by reference in their entirety) consisting of twelve β strands in paracrine FGFs (β1-(β12) and eleven β strands in endocrine FGFs (β1-β10 and β12) (Mohammadi et al., "Structural Basis for Fibroblast Growth Factor Receptor Activation," *Cytokine Growth Factor Rev.* 16:107-137 (2005); Goetz et al., *Mol. Cell Biol.* 27:3417-3428 (2007), which are hereby incorporated by reference in their entirety). The conserved core region is flanked by divergent N- and C-termini, which play a critical role in conferring distinct biological activity on FGFs (Mohammadi et al., "Structural Basis for Fibroblast Growth Factor Receptor Activation," *Cytokine Growth Factor Rev.* 16:107-137 (2005); Olsen et al., *Genes Dev.* 20:185-198 (2006), which are hereby incorporated by reference in their entirety).

All FGFs interact with pericellular heparan sulfate (HS) glycosaminoglycans albeit with different affinities (Asada et al., *Biochim. Biophys. Acta.* 1790:40-48 (2009), which is hereby incorporated by reference in its entirety). The HS-binding site of FGFs is comprised of the β1-β2 loop and the region between β10 and β12 strands (Mohammadi et al., "Structural Basis for Fibroblast Growth Factor Receptor Activation," *Cytokine Growth Factor Rev.* 16:107-137 (2005), which is hereby incorporated by reference in its entirety). HS interacts with both side chain and main chain atoms of the HS-binding site in paracrine FGFs (Schlessinger et al., *Mol. Cell* 6:743-750 (2000), which is hereby incorporated by reference in its entirety). The HS-binding site of endocrine FGFs deviates from the common conformation adopted by paracrine FGFs such that interaction of HS with backbone atoms of the HS-binding site is precluded (Goetz et al., *Mol. Cell Biol.* 27:3417-3428 (2007), which is hereby incorporated by reference in its entirety). As a result, compared to paracrine FGFs, endocrine FGFs exhibit poor affinity for HS (Beenken and Mohammadi, "The FGF Family: Biology, Pathophysiology and Therapy," *Nat. Rev. Drug Discov.* 8:235-253 (2009); Asada et al., *Biochim. Biophys. Acta.* 1790:40-48 (2009), which are hereby incorporated by reference in their entirety). The poor HS affinity enables these ligands to diffuse freely away from the site of their secretion and enter the blood circulation to reach their distant target organs (Goetz et al., *Mol. Cell Biol.* 27:3417-3428 (2007); Asada et al., *Biochim. Biophys. Acta.* 1790: 40-48 (2009), which are hereby incorporated by reference in their entirety).

By contrast, owing to their high HS affinity (Asada et al., *Biochim. Biophys. Acta.* 1790:40-48 (2009), which is hereby incorporated by reference in its entirety), paracrine FGFs are mostly immobilized in the vicinity of the cells secreting these ligands, and hence can only act within the same organ. There is emerging evidence that differences in HS-binding affinity among paracrine FGFs translate into the formation of ligand-specific gradients in the pericellular matrix (Kalinina et al., *Mol. Cell Biol.* 29:4663-4678 (2009); Makarenkova et al., *Sci. Signal* 2:ra55 (2009), which are hereby incorporated by reference in their entirety), which contribute to the distinct functions of these ligands (Beenken and Mohammadi, "The FGF Family: Biology, Pathophysiology and Therapy," *Nat. Rev. Drug* Discov. 8:235-253 (2009); Itoh and Ornitz, "Fibroblast Growth Factors: From Molecular Evolution to Roles in Development, Metabolism and Disease," *J. Biochem.* 149:121-130 (2011), which are hereby incorporated by reference in their entirety).

Besides controlling ligand diffusion in the extracellular space, HS promotes the formation of the 2:2 paracrine FGF-FGFR signal transduction unit (Schlessinger et al., *Mol. Cell* 6:743-750 (2000); Mohammadi et al., *Curr. Opin. Struct. Biol.* 15:506-516 (2005), which are hereby incorporated by reference in their entirety). HS engages both ligand and receptor to enhance the binding affinity of FGF for receptor and promote dimerization of ligand-bound receptors. Owing to their poor HS-binding affinity, endocrine FGFs rely on Klotho co-receptors to bind their cognate FGFR (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444:770-774 (2006), which are hereby incorporated by reference in their entirety). Klotho co-receptors are single-pass transmembrane proteins with an extracellular domain composed of two type I β-glycosidase domains (Ito et al., *Mech. Dev.* 98:115-119 (2000); Kuro-o et al., *Nature* 390:45-51 (1997), which are hereby incorporated by reference in their entirety). Klotho co-receptors constitutively associate with FGFRs to enhance the binding affinity of endocrine FGFs for their cognate FGFRs in target tissues (Kurosu et al., *J. Biol. Chem.* 282:26687-26695 (2007); Kurosu et al., *J. Biol. Chem.* 281:6120-6123 (2006); Ogawa et al., *Proc. Nat'l. Acad. Sci. U.S.A.* 104:7432-7437 (2007); Urakawa et al., *Nature* 444: 770-774 (2006), which are hereby incorporated by reference in their entirety). αKlotho is the co-receptor for FGF23 (Kurosu et al., *J. Biol. Chem.* 281:6120-6123 (2006); Urakawa et al., *Nature* 444:770-774 (2006), which are hereby incorporated by reference in their entirety), and βKlotho is the co-receptor for both FGF19 and FGF21 (Kurosu et al., *J. Biol. Chem.* 282:26687-26695 (2007); Ogawa et al., *Proc. Nat'l. Acad. Sci. U.S.A.* 104:7432-7437 (2007), which are hereby incorporated by reference in their entirety). The C-terminal region of endocrine FGFs mediates binding of these ligands to the FGFR-α/βKlotho co-receptor complex (Goetz et al., *Mol. Cell Biol.* 27:3417-3428 (2007); Goetz et al., *Proc. Nat'l. Acad. Sci. U.S.A* 107:407-412 (2010); Micanovic et al., *J. Cell Physiol.* 219:227-234 (2009); Wu et al., *J. Biol. Chem.* 283:33304-33309 (2008); Yie et al., *FEBS Lett,* 583:19-24 (2009); Goetz et al., *Mol. Cell Biol.* 32:1944-1954 (2012), which are hereby incorporated by reference in their entirety).

FGF23 interacts with a de novo binding site generated at the composite receptor-coreceptor interface in the binary αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010), which is hereby incorporated by reference in its entirety). The region on FGF23 that binds to this de novo site was mapped to the 72 amino acid long C-terminal tail, which follows the β-trefoil core domain (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010), which is hereby incorporated by reference in its entirety). Thus, the N-terminal fragment of proteolytic cleavage of FGF23 (Y25 to R179) is metabolically inactive because it lacks the binding site for the αKlotho-FGFR complex. The C-terminal proteolytic fragment (S180 to 1251), however, can compete with full-length FGF23 for binding to the αKlotho-FGFR complex to antagonize the metabolic activity of FGF23, because this fragment contains the binding site for the αKlotho-FGFR complex (Goetz et al., "Isolated C-terminal Tail of FGF23 Alleviates Hypophosphatemia by Inhibiting FGF23-FGFR-Klotho Complex Formation," *Proc Natl Acad Sci USA* 107:407-412 (2010), which is hereby incorporated by reference in its entirety).

Endocrine FGFs still possess residual HS-binding affinity, and moreover, there are differences in this residual binding affinity among the endocrine FGFs (Goetz et al., *Mol. Cell Biol.* 27:3417-3428 (2007), which is hereby incorporated by reference in its entirety). These observations raise the possibility that HS may play a role in endocrine FGF signaling. Indeed, there are several reports showing that HS can promote endocrine FGF signaling in the presence as well as in the absence of Klotho co-receptor. It has been shown that HS augments the mitogenic signal elicited by endocrine FGFs in BaF3 cells over-expressing FGFR and Klotho co-receptor by at least two-fold (Suzuki et al., *Mol. Endocrinol.* 22:1006-1014 (2008), which is hereby incorporated by reference in its entirety). In addition, even in the absence of Klotho co-receptor, HS enables endocrine FGFs to induce proliferation of BaF3 cells over-expressing FGFR (Yu et al., *Endocrinology* 146:4647-4656 (2005); Zhang et al., *J. Biol. Chem.* 281:15694-15700 (2006), which are hereby incorporated by reference in their entirety). Compared to paracrine FGFs, however, significantly higher concentrations of both ligand and HS are needed, and the proliferative response of cells to endocrine FGFs still lags behind that of paracrine FGFs by about one order of magnitude (Zhang et al., *J. Biol. Chem.* 281:15694-15700 (2006), which is hereby incorporated by reference in its entirety).

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, where the first and second polypeptides are different polypeptides. A chimeric polypeptide also encompasses polypeptides that include two or more non-contiguous portions derived from the same polypeptide. A chimeric polypeptide or protein also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

As noted above, a chimeric protein according to the present invention may include an N-terminus coupled to a C-terminus. N-terminus and C-terminus are used herein to refer to the N-terminal region or portion and the C-terminal region or portion, respectively, of the chimeric protein of the present invention. In some embodiments of the present invention, the C-terminal portion and the N-terminal portion of the chimeric protein of the present invention are contiguously joined. In alternative embodiments, the C-terminal portion and the N-terminal portion of the chimeric protein of the present invention are coupled by an intervening spacer. In one embodiment, the spacer may be a polypeptide sequence of 1, 2, 3, 4, 5, 6, 7, 8, 9, 10, or more amino acid residues. In some embodiments, the C-terminal portion and/or the N-terminal portion of the chimeric protein of the present invention may include additional portion(s) coupled to the C-terminal residue and/or the N-terminal residue of the chimeric protein of the present invention, respectively. In some embodiments, the additional portion(s) may be a polypeptide sequence of 1, 2, 3, 4, 5, 6, 7, 8, 9, 10, or more amino acid residues. In some embodiments, the N-terminal portion and/or the C-terminal portion having such additional portion(s) will maintain the activity of the corresponding naturally occurring N-terminal portion and/or C-terminal portion, respectively. In some embodiments, the N-terminal portion and/or the C-terminal portion having such additional portion(s) will have enhanced and/or prolonged activity compared to the corresponding naturally occurring N-terminal portion and/or C-terminal portion, respectively. In other embodiments, the C-terminal portion and/or the N-terminal portion of the chimeric protein of the present invention do not include any additional portion(s) coupled to the C-terminal residue and/or the N-terminal residue of the chimeric protein of the present invention, respectively.

The portion of the paracrine FGF may be derived from any suitable paracrine FGF. Suitable paracrine FGFs in accordance with the present invention include FGF1, FGF2, and ligands of the FGF4 and FGF9 subfamilies. Certain embodiments of the present invention may include a full-length amino acid sequence of a paracrine FGF, rather than a portion of a paracrine FGF.

In one embodiment, the portion of the paracrine FGF is derived from a mammalian FGF. In one embodiment, the portion of the paracrine FGF is derived from a vertebrate FGF. In one embodiment, the portion of the paracrine FGF is derived from a human FGF. In one embodiment, the paracrine FGF is derived from a non-human mammalian FGF. In one embodiment, the portion of the paracrine FGF is derived from a non-human vertebrate FGF. In one embodiment, the paracrine FGF is derived from an ortholog of human FGF, or a polypeptide or protein obtained from one species that is the functional counterpart of a polypeptide or protein from a different species.

In one embodiment according to the present invention, the portion of the paracrine FGF of the chimeric protein includes an N-terminal portion of the paracrine FGF.

In one embodiment, the paracrine FGF is FGF1. In one embodiment, the portion of the FGF1 is from human FGF1 having the following amino acid sequence (GenBank Accession No. AAH32697, which is hereby incorporated by reference in its entirety) (SEQ ID NO: 1):

```
  1  MAEGEITTFT ALTEKFNLPP GNYKKPKLLY CSNGGHFLRI LPDGTVDGTR DRSDQHIQLQ

 61  LSAESVGEVY IKSTETGQYL AMDTDGLLYG SQTPNEECLF LERLEENHYN TYISKKHAEK

121  NWFVGLKKNG SCKRGPRTHY GQKAILFLPL PVSSD
```

In one embodiment, the portion of the paracrine FGF includes an amino acid sequence beginning at any one of residues 1 to 25 and ending at any one of residues 150 to 155 of SEQ ID NO: 1 (human FGF1). In one embodiment, the portion of the paracrine FGF includes amino acid residues 1-150, 1-151, 1-152, 1-153, 1-154, 1-155, 2-150, 2-151, 2-152, 2-153, 2-154, 2-155, 3-150, 3-151, 3-152, 3-153, 3-154, 3-155, 4-150, 4-151, 4-152, 4-153, 4-154, 4-155, 5-150, 5-151, 5-152, 5-153, 5-154, 5-155, 6-150, 6-151, 6-152, 6-153, 6-154, 6-155, 7-150, 7-151, 7-152, 7-153, 7-154, 7-155, 8-150, 8-151, 8-152, 8-153, 8-154, 8-155, 9-150, 9-151, 9-152, 9-153, 9-154, 9-155, 10-150, 10-151, 10-152, 10-153, 10-154, 10-155, 11-150, 11-151, 11-152, 11-153, 11-154, 11-155, 12-150, 12-151, 12-152, 12-153, 12-154, 12-155, 13-150, 13-151, 13-152, 13-153, 13-154, 13-155, 14-150, 14-151, 14-152, 14-153, 14-154, 14-155, 15-150, 15-151, 15-152, 15-153, 15-154, 15-155, 16-150, 16-151, 16-152, 16-153, 16-154, 16-155, 17-150, 17-151, 17-152, 17-153, 17-154, 17-155, 18-150, 18-151, 18-152, 18-153, 18-154, 18-155, 19-150, 19-151, 19-152, 19-153, 19-154, 19-155, 20-150, 20-151, 20-152, 20-153, 20-154, 20-155, 21-150, 21-151, 21-152, 21-153, 21-154, 21-155, 22-150, 22-151, 22-152, 22-153, 22-154, 22-155, 23-150, 23-151, 23-152, 23-153, 23-154, 23-155, 24-150, 24-151, 24-152, 24-153, 24-154, 24-155, 25-150, 25-151, 25-152, 25-153, 25-154, or 25-155 of FGF1 (SEQ ID NO: 1). In one embodiment, the portion of the paracrine FGF includes amino acid residues 1-150 or 25-150 of SEQ ID NO: 1.

In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 150 to 155 of SEQ ID NO: 1 (human FGF1). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 150 to 155 of SEQ ID NO: 1 (human FGF1).

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In one embodiment of the present invention, the portion of the paracrine FGF of the chimeric protein is derived from an ortholog of human FGF1. In one embodiment, the portion of FGF1 is derived from *Papio Anubis, Pongo abelii, Callithrix jacchus, Equus caballus, Pan troglodytes, Loxodonta Africana, Canis lupus familiaris, Ailuropoda mela-*

*noleuca, Saimiri boliviensis boliviensis, Sus scrofa, Otolemur garnettii, Rhinolophus ferrumequinum, Sorex araneus, Oryctolagus cuniculus, Cricetulus griseus, Sarcophilus harrisii, Mus musculus, Cavia porcellus, Monodelphis domestica, Desmodus rotundus, Bos taurus, Ornithorhynchus anatinus, Taeniopygia guttata, Dasypus novemcinctus, Xenopus Silurana tropicalis, Heterocephalus glaber, Pteropus alecto, Tupaia chinensis, Columba livia, Ovis aries, Gallus gallus, Vicugna pacos, Anolis carolinensis, Otolemur garnettii, Felis catus, Pelodiscus sinensis, Latimeria chalumnae, Tursiops truncates, Mustela putorius furo, Nomascus leucogenys, Gorilla gorilla, Erinaceus europaeus, Procavia capensis, Dipodomys ordii, Petromyzon marinus, Echinops telfairi, Macaca mulatta, Pteropus vampyrus, Myotis lucifugus, Microcebus murinus, Ochotona princeps, Rattus norvegicus, Choloepus hoffmanni, Ictidomys tridecemlineatus, Tarsius syrichta, Tupaia belangeri, Meleagris gallopavo, Macropus eugenii*, or *Danio rerio*. The portions of an ortholog of human paracrine FGF1 include portions corresponding to the above-identified amino acid sequences of human FGF1. Corresponding portions may be determined by, for example, sequence analysis and structural analysis.

In one embodiment, the portion of the FGF1 of the chimeric protein of the present invention is derived from an ortholog of human FGF1 having the amino acid sequence shown in Table 1.

TABLE 1

```
Amino acid sequence of human FGF1 (SEQ ID NO: 1)(GenBank accession no.
AAH32697, which is hereby incorporated by reference in its entirety):
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYISKKHAEK
121    NWFVGLKKNG SCKRGPRTHY GQKAILFLPL PVSSD

Amino acid sequence of Papio anubis (olive baboon) FGF1(SEQ ID NO: 2)
(GenBank accession no. NP_001162557, which is hereby incorporated by
reference in its entirety):
  1    MAEGEITTFT ALTEKFNLPP ANYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYISKKHAEK
121    NWFVGLKKNG SCKRGPRTHY GQKAILFLPL PVSSD

Amino acid sequence of Pongo abelii (Sumatran orangutan) FGF1(SEQ ID
NO: 3) (GenBank accession no. NP_001127073, which is hereby
incorporated by reference in its entirety)
 60                                                                M
 61    AEGEITTFTA LTEKFNLPPG NYKKPKLLYC SNGGHFLRIL PDGTVDGTRD RSDQHIQLQL
121    SAESVGEVYI KSTETGQYLA MDTDGLLYGS QTPNEECLFL ERLEENHYNT YISKKHAEKN
181    WFVGLKKNGS CKRGPRTHYG QKAILFLPLP VSSD

Amino acid sequence of Callithrix jacchus (white-tufted-ear marmoset)
FGF1(SEQ ID NO: 4) (GenBank accession no. XP_002744341, which is hereby
incorporated by reference in its entirety):
  1    MAEGEITTFT ALTEKFDLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYISKKHAEK
121    NWFVGLKKNG SCKRGPRTHY GQKAILFLPL PVSSD

Amino acid sequence of Equus caballus (horse) FGF1(SEQ ID NO: 5)
(GenBank accession no. NP_001157358, which is hereby incorporated by
reference in its entirety):
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYTSKKHAEK
121    NWFVGLKKNG SCKRGPRTHY GQKAILFLPL PVSSD

Amino acid sequence of Pan troglodytes (chimpanzee) FGF1(SEQ ID NO: 6)
(GenBank accession no. JAA29511, which is hereby incorporated by
reference in its entirety):
  1    MAEGEITTFT ALTEKFNLPS GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYISKKHAEK
121    NWFVGLKKNG SCKRGPRTHY GQKAILFLPL PVSSD

Amino acid sequence of Loxodonta africana (elephant) FGF1(SEQ ID NO: 7)
(GenBank accession no. XP_003404621, which is hereby incorporated by
reference in its entirety):
  1    MAEGEITTFT ALTEKFNLPP GNYKKPKLLY CSNGGHFLRI LPDGTVDGTR DRSDQHIQLQ
 61    LSAESVGEVY IKGTETGQYL AMDTDGLLYG SQTPNEECLF LERLEENHYN TYTSKKHAEK
121    NWFVGLKKNG SCKRGPRTHY GQKAILFLPL PVSSD

Amino acid sequence of Canis lupus familiaris (dog) FGF1(SEQ ID NO: 8)
(GenBank accession no. XP_849274, which is hereby incorporated by
reference in its entirety):
  1    MAEGEITTFT ALTEKFNLPP GNYMKPKLLY CSNGGHFLRI LPDGTVDGTR DRSDQHIQLQ
 61    LSAESVGEVY IKSTETGQYL AMDTDGLLYG SQTPNEECLF LERLEENHYN TYTSKKHAEK
121    NWFVGLKKNG SCKRGPRTHY GQKAILFLPL PVSSD

Amino acid sequence of Ailuropoda melanoleuca (giant panda) FGF1(SEQ
ID NO: 9) (GenBank accession no. XP_002912581, which is hereby
incorporated by reference in its entirety):
  1    MAEGEITTFT ALTEKFNLPA GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYTSKKHAEK
121    NWFVGLKKNG SCKRGPRTHY GQKAILFLPL PVSSD
```

TABLE 1-continued

Amino acid sequence of *Saimiri boliviensis boliviensis* (Bolivian squirrel monkey) FGF1(SEQ ID NO: 10) (GenBank accession no. XP_003920596, which is hereby incorporated by reference in its entirety):

```
  1  MAEGEITTFT ALTEKFDLPP GNYKKPKLLY CSNGGHFLRI LPDGTVDGTR DRSDLHIQLQ
 61  LSAESVGEVY IKSTETGQYL AMDTDGLLYG SQTPNEECLF LERLEENHYN TYISKKHAEK
121  NWFVGLKKNG SCKRGPRTHY GQKAILFLPL PVSSD
```

Amino acid sequence of *Sus scrofa* (pig) FGF1(SEQ ID NO: 11) (GenBank accession no. XP_003124058, which is hereby incorporated by reference in its entirety):

```
  1  MAEGEITTFT ALTEKFNLPP GNYKKPKLLY CSNGGHFLRI LPDGTVDGTR DRSDQHIQLQ
 61  LSAESVGEVY IKSTETGQYL AMDTSGLLYG SQTPSEECLF LERLEENHYN TYTSKKHAEK
121  NWFVGLKKNG SCKRGPRTHY GQKAILFLPL PVSSD
```

Amino acid sequence of *Otolemur garnettii* (small-eared galago) FGF1(SEQ ID NO: 12) (GenBank accession no. XP_003782135, which is hereby incorporated by reference in its entirety):

```
  1  MAEGEITTFT ALTEKFNLPL GNYKKPKLLY CSNGGHFLRI LPDGTVDGTQ DRSDQHIQLQ
 61  LSAESVGEVY IKSTQTGQYL AMDSDGLLYG SQTPNEECLF LERLEENHYN TYVSKKHAEK
121  NWFVGLKKNG SCKRGPRTHY GQKAILFLPL PVSSD
```

Amino acid sequence of *Rhinolophus ferrumequinum* (greater horseshoe bat) FGF1(SEQ ID NO: 13) (GenBank accession no. ACC62496, which is hereby incorporated by reference in its entirety):

```
  1  MAEGEVTTFT ALTEKFNLPT GNYKKPKLLY CSNGGHFLRI LPDGTVDGTR DKSDQHIQLQ
 61  LSAESVGEVY IKSTESGQYL AMDSDGLLYG SQTPNEECLF LERLEENHYN TYTSKKHAEK
121  NWFVGLKKNG SCKRGPRTHY GQKAILFLPL PVSSD
```

Amino acid sequence of *Sorex araneus* (European shrew) FGF1(SEQ ID NO: 14) (GenBank accession no. ACE75805, which is hereby incorporated by reference in its entirety):

```
  1  MAEGEITTFG ALMEKFNLPP GNYKKPKLLY CSNGGHFLRI LPDGTVDGTR DRSDQHIQLQ
 61  LSAESVGEVY IKSTETGHYL AMDTDGLLYG SQTPNEECLF LERLEENHYN TYTSKKHAEK
121  NWFVGLKKNG SCKRGPRTHY GQKAILFLPL PVSSD
```

Amino acid sequence of *Oryctolagus cuniculus* (rabbit) FGF1(SEQ ID NO: 15) (GenBank accession no. NP_001164959, which is hereby incorporated by reference in its entirety):

```
  1  MAEGEVTTFT ALTEKFNLPA GNYKLPKLLY CSNGGHFLRI LPDGTVDGTR DRSDQHIQLQ
 61  LSAESVGEVY IKSTETGQYL AMDTDGLLYG SQTPSEECLF LERLEENHYN TYTSKKHAEK
121  NWFVGLKKNG SCKRGPRTHY GQKAILFLPL PVSSD
```

Amino acid sequence of *Cricetulus griseus* (Chinese hamster) FGF1(SEQ ID NO: 16) (GenBank accession no. XP_003502469, which is hereby incorporated by reference in its entirety):

```
  1  MAEGEITTFS ALTERFNLPP GNYKKPKLLY CSNGGHFLRI LPDGTVDGTR DRSDQHIQLQ
 61  LSAESAGEVY IKGTETGQYR NMDTDGLLYG SQTPNEECLF LERLEENHYN TYTSKKHAEK
121  NWFVGLKKNG SCKRGPRTHY GQKAILFLPL PVSSD
```

Amino acid sequence of *Sarcophilus harrisii* (Tasmanian devil) FGF1(SEQ ID NO: 17) (GenBank accession no. XP_003756738, which is hereby incorporated by reference in its entirety):

```
  1  MAEGEITTFT ALTERFNLPL GNYKKPKLLY CSNGGHFLRI LPDGKVDGTR DRNDQHIQLQ
 61  LSAESVGEVY IKSTESGQYL AMDTDGLLYG SQTPTEECLF LERLEENHYN TYISKKHAEK
121  NWFVGLKKNG SCKRGPRTHY GQKAILFLPL PVSSE
```

Amino acid sequence of *Mus musculus* (house mouse) FGF1(SEQ ID NO: 18) (GenBank accession no. NP_034327, which is hereby incorporated by reference in its entirety):

```
  1  MAEGEITTFA ALTERFNLPL GNYKKPKLLY CSNGGHFLRI LPDGTVDGTR DRSDQHIQLQ
 61  LSAESAGEVY IKGTETGQYL AMDTEGLLYG SQTPNEECLF LERLEENHYN TYTSKKHAEK
121  NWFVGLKKNG SCKRGPRTHY GQKAILFLPL PVSSD
```

Amino acid sequence of *Cavia porcellus* (domestic guinea pig) FGF1(SEQ ID NO: 19) (GenBank accession no. XP_003477242, which is hereby incorporated by reference in its entirety):

```
  1  MAEGEITTFA ALTEKFNLPP GNYKKPKLLY CSNGGHFLRI LPDGTVDGTR DRSDQHIQLQ
 61  LSAEGVGEVY IQSTETGQYL AMDTDGLLYG SQTPSEECLF LERLEENHYN TYTSKKHVEK
121  NWFVGLKKNG SCKRGPRTHY GQKAILFLPL PVSD
```

Amino acid sequence of *Monodelphis domestica* (gray short-tailed opossum) FGF1(SEQ ID NO: 20) (GenBank accession no. XP_001368921, which is hereby incorporated by reference in its entirety):

```
  1  MAEGEITTFT ALTERFNLPL GNYKKPKLLY CSNGGHFLRI LPDGKVDGTR DRNDQHIQLQ
 61  LSTESVGEVY IKSTESGQYL AMDTDGLLYG SQTPSEECLF LERLEENHYN TYTSKKHAEK
121  NWFVGLKKNG SCKKGPRTHY GQKAILFLPL PVSSE
```

TABLE 1-continued

Amino acid sequence of *Desmodus rotundus* (common vampire bat) FGF1(SEQ ID NO: 21) (GenBank accession no. JAA45191, which is hereby incorporated by reference in its entirety):

```
  1    MAEGEVTTFT ALTEKFNLPL ESYKKPKLLY CSNGGHFLRI LPDGTVDGTR DKSDQHIQLQ
 61    LSAESVGEVY IKSTGSGQYL AMDSAGLLYG SQTPNEECLF LERLEENHYN TYTSKKHAEK
121    NWFVGLKKNG SCKRGPRTHY GQKAILFLPL PVNSD
```

Amino acid sequence of *Bos taurus* (cattle) FGF1(SEQ ID NO: 22) (GenBank accession no. NP_776480, which is hereby incorporated by reference in its entirety):

```
  1    MAEGETTTFT ALTEKFNLPL GNYKKPKLLY CSNGGYFLRI LPDGTVDGTK DRSDQHIQLQ
 61    LCAESIGEVY IKSTETGQFL AMDTDGLLYG SQTPNEECLF LERLEENHYN TYISKKHAEK
121    HWFVGLKKNG RSKLGPRTHF GQKAILFLPL PVSSD
```

Amino acid sequence of *Ornithorhynchus anatinus* (platypus) FGF1(SEQ ID NO: 23) (GenBank accession no. XP_001514861, which is hereby incorporated by reference in its entirety):

```
  1    MAEGEITTFT ALMEKFDLPL GNYKKPRLLY CSNGGYFLRI QPDGKVDGTR DRSDQHIQLQ
 61    LSAESVGEVY IKSTESGHYL AMDTEGLLYG SQAPSEDCLF LERLEENHYN TYVSKKHAEK
121    NWFVGLKKNG SCKRGPRTHY GQKAILFLPL PVASD
```

Amino acid sequence of *Taeniopygia guttata* (zebra finch) FGF1(SEQ ID NO: 24) (GenBank accession no. XP_002193287, which is hereby incorporated by reference in its entirety):

```
  1    MAEGEITTFS ALTEKFNLPP GNYKKPKLLY CSNGGHFLRI LPDGTVDGTR DRSDQHIQLQ
 61    LSAESVGVVH IQSTQSGQYL AMDTNGLLYG SQLPPGECLF LERLEENHYN TYVSKMHADK
121    NWFVGLKKNG TSKLGPRTHY GQKAILFLPL PVAAD
```

Amino acid sequence of *Dasypus novemcinctus* (nine-banded armadillo) FGF1(SEQ ID NO: 25) (GenBank accession no. AC006224, which is hereby incorporated by reference in its entirety):

```
  1    MAEGEITTFM ALMEKFNLPL ENYKHPRLLY CRNGGHFLRI LPDGTVDGTR DRSDQHIQLQ
 61    LSAESVGEVY IKSAETGQYL AMDTDGLLYG SETPSEECLF MEKLEENNYN TYISKKHAEK
121    KWFVGLKKDG SSKRGPQTHY GQKAILFLPL PVSSD
```

Amino acid sequence of *Xenopus Silurana tropicalis* (western clawed frog) FGF1(SEQ ID NO: 26) (GenBank accession no. ACJ50585, which is hereby incorporated by reference in its entirety):

```
  1    MAEGDITTFN PIAESFSLPI GNYKKPKLLY CNNGGYFLRI LPDGVVDGTR DRDDLYITLK
 61    LSAQSQGEVH IKSTETGSYL AMDSSGQLYG TLTPNEESLF LETLEENHYN TYKSKKYAEN
121    NWFVGIKKNG ASKKGSRTHY GQKAILFLPL PASPD
```

Amino acid sequence of *Heterocephalus glaber* (naked mole-rat) FGF1(SEQ ID NO: 27) (GenBank accession no. EHA99379, which is hereby incorporated by reference in its entirety):

```
  1    MAEGEITTFT ALTEKFNLPP GNYKKPKLLY CSNGGHFLRI LPDGKVDGTR DRSDQHIQLQ
 61    LSAEGVGEVY IKSTETGQYL AMDTDGLLYG SQTASEECLF LERLEENHYN TYISKKHAEK
121    NWFVGLKKNG SCKRGPRTHY GQKAILFLPL PVSSD
```

Amino acid sequence of *Pteropus alecto* (black flying fox) FGF1(SEQ ID NO: 28) (GenBank accession no. ELK02961, which is hereby incorporated by reference in its entirety):

```
  1    MAEGEVTTFT ALTERFNLPP GNYKKPKLLY CSNGGHFLRI LPDGTVDGTR DKSDQHIQLQ
 61    LSAESVGEVY IKSTESGQYL AMDSDGLLYG SQTPDEDCLF LERLEENHYN TYTSKKHAEK
121    NWFVGLKKNG SCKRGPRTHY GQKAILFLPL PVSSD
```

Amino acid sequence of *Tupaia chinensis* (Chinese tree shrew) FGF1(SEQ ID NO: 29) (GenBank accession no. ELW69091, which is hereby incorporated by reference in its entirety):

```
  1    MAEGEITTFA ALTEKFDLPP GNYKKPKLLY CSNGGHFLRI LPDGTVDGTR DRSDQHIQLQ
 61    LTAENVGEVY IKSTETGQYL AMDADGLLYG SQTPNEECLF LERLEENHYN TYISKKHAEK
121    NWFVALKKNG SCKLGPRTHY GQKAILFLPL PVSSD
```

Amino acid sequence of *Columba livia* (rock pigeon) FGF1(SEQ ID NO: 30) (GenBank accession no. EMC79997, which is hereby incorporated by reference in its entirety):

```
  1    MAEGEITTFT ALTEKFNLPP GNYKKPKLLY CSNGGHFLRI LPDGKVDGTR DRSDQHIQLQ
 61    LSAESVGEVY IKSTQSGQYL AMDPTGLLYG SQLLGEECLF LERIEENHYN TYVSKKHADK
121    NWFVGLKKNG NSKLGPRTHY GQKAILFLPL PVSAD
```

Amino acid sequence of *Ovis aries* (sheep) FGF1(SEQ ID NO: 31) (GenBank accession no. XP_004008958, which is hereby incorporated by reference in its entirety):

```
  1    MAEGETTTFR ALTEKFNLPL GNYKKPKLLY CSNGGYFLRI LPDGRVDGTK DRSDQHIQLQ
 61    LYAESIGEVY IKSTETGQFL AMDTNGLLYG SQTPSEECLF LERLEENHYN TYISKKHAEK
121    NWFIGLKKNG SSKLGPRTHF GQKAILFLPL PVSSD
```

TABLE 1-continued

Amino acid sequence of *Gallus gallus* (chicken) FGF1(SEQ ID NO: 32) (GenBank accession no. NP_990511, which is hereby incorporated by reference in its entirety):

```
  1    MAEGEITTFT ALTERFGLPL GNYKKPKLLY CSNGGHFLRI LPDGKVDGTR DRSDQHIQLQ
 61    LSAEDVGEVY IKSTASGQYL AMDTNGLLYG SQLPGEECLF LERLEENHYN TYISKKHADK
121    NWFVGLKKNG NSKLGPRTHY GQKAILFLPL PVSAD
```

Amino acid sequence of *Vicugna pacos* (alpaca) FGF1(SEQ ID NO: 33) (Ensembl accession no. ENSVPAP00000007810; partial sequence corresponding to human FGF1 residues 58 to 155, which is hereby incorporated by reference in its entirety):

```
 1     QLQLSAESVG EVYIKSTETG QYLAMDTDGL LHGSQTPNEE CLFLERLEEN HYNTYTSKKH
61     AEKNWFVGLK KNGSCKRGPR THYGQKAILF LPLPVSSD
```

Amino acid sequence of *Anolis carolinensis* (anole lizard) FGF1(SEQ ID NO: 34) (Ensembl accession no. ENSACAP00000013203, which is hereby incorporated by reference in its entirety):

```
  1    MAEGEITTFT ALTERFALPM ENYKKPKLLY CSNGGHFLRI LPDGKVDGTM DRNDSYIQLL
 61    LTAEDVGVVY IKGTETGQYL AMDANGHLYG SQLPTEECLF VETLEENHYN TYTSKMHGDK
121    KWYVGLKKNG KGKLGPRTHR GQKAILFLPL PVSPD
```

Amino acid sequence of *Otolemur garnettii* (bushbaby) FGF1(SEQ ID NO: 35) (Ensembl accession no. ENSOGAP00000004540, which is hereby incorporated by reference in its entirety):

```
  1    MAEGEITTFT ALTEKFNLPL GNYKKPKLLY CSNGGHFLRI LPDGTVDGTQ DRSDQHIQLQ
 61    LSAESVGEVY IKSTQTGQYL AMDSDGLLYG SQTPNEECLF LERLEENHYN TYVSKKHAEK
121    NWFVGLKKNG SCKRGPRTHY GQKAILFLPL PVSSD
```

Amino acid sequence of *Felis catus* (cat) FGF1(SEQ ID NO: 36) (Ensembl accession no. ENSFCAP00000008457, which is hereby incorporated by reference in its entirety):

```
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYTSKKHAEK
121    NWFVGLKKNG SCKRGPRTHY GQKAILFLPL PVSSD
```

Amino acid sequence of *Pelodiscus sinensis* (Chinese softshell turtle) FGF1(SEQ ID NO: 37) (Ensembl accession no. ENSPSIP00000016356, which is hereby incorporated by reference in its entirety):

```
  1    MAEGEITTFT ALTEKFNLPL GNYKNPKLLY CSNGGYFLRI HPDGKVDGTR DRSDQHIQLQ
 61    LSAESVGEVY IKSTESGQFL AMDANGLLYG SLSPSEECLF LERMEENHYN TYISKKHADK
121    NWFVGLKKNG SCKLGPRTHY GQKAVLFLPL PVSAD
```

Amino acid sequence of *Latimeria chalumnae* (coelacanth) FGF1(SEQ ID NO: 38) (Ensembl accession no. ENSLACP00000015106, which is hereby incorporated by reference in its entirety):

```
  1    MAEDKITTLK ALAEKFNLPM GNYKKAKLLY CSNGGYFLRI PPDGKVEGIR ERSDKYIQLQ
 61    MNAESLGMVS IKGVEAGQYL AMNTNGLLYG SQSLTEECLF MEKMEENHYN TYRSKTHADK
121    NWYVGIRKNG SIKPGPRTHI GQKAVLFLPL PASSD
```

Amino acid sequence of *Tursiops truncatus* (dolphin) FGF1(SEQ ID NO: 39) (Ensembl accession no. ENSTTRP00000004470, which is hereby incorporated by reference in its entirety):

```
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYASKKHAEK
121    NWFVGLKKNG SCKRGPRTHY GQKAILFLPL PVSSD
```

Amino acid sequence of *Mustela putorius furo* (ferret) FGF1(SEQ ID NO: 40) (Ensembl accession no. ENSMPUP00000007888, which is hereby incorporated by reference in its entirety):

```
  1    MAEGEITTFT ALMEKFNLPA GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYTSKKHAEK
121    NWFVGLKKNG SCKRGPRTHY GQKAILFLPL PVSSD
```

Amino acid sequence of *Nomascus leucogenys* (gibbon) FGF1(SEQ ID NO: 41) (Ensembl accession no. ENSNLEP00000011873, which is hereby incorporated by reference in its entirety):

```
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYISKKHAEK
121    NWFVGLKKNG SCKRGPRTHY GQKAILFLPL PVSSD
```

Amino acid sequence of *Gorilla gorilla* (gorilla) FGF1(SEQ ID NO: 42) (Ensembl accession no. ENSGGOP00000017663, which is hereby incorporated by reference in its entirety):

```
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYISKKHAEK
121    NWFVGLKKNG SCKRGPRTHY GQKAILFLPL PVSSD
```

TABLE 1-continued

Amino acid sequence of *Erinaceus europaeus* (hedgehog) FGF1(SEQ ID NO: 43) (Ensembl accession no. ENSEEUP00000005318, which is hereby incorporated by reference in its entirety):

```
  1   MAEGEITTFT ALTEKFNLPL GNYKKPKLLY CSNGGHFLRI LPDGTVDGTR DRSDQHIQLQ
 61   LSAESVGEVY IKSTETGQYL AMDTDGLLYG SQTPNEECLF LERLEENHYN TYTSKKHAEK
121   NWFVGLKKNG SCKRGPRTHY GQKAILFLPL PVSSD
```

Amino acid sequence of *Procavia capensis* (hyrax) FGF1(SEQ ID NO: 44) (Ensembl accession no. ENSPCAP00000010969, which is hereby incorporated by reference in its entirety)(partial sequence corresponding to human FGF1 residues 1 to 91):

```
 1    MAEGEITTFT ALTEKFNLPL ENYKKPKLLY CSNGGHFLRI LPDGTVDGTR DRSDQHIQLQ
61    LSAESVGEVY IKGTETGQYL AMDTDGLLYG S
```

Amino acid sequence of *Dipodomys ordii* (kangaroo rat) FGF1(SEQ ID NO: 45) (Ensembl accession no. ENSDORP00000006889, which is hereby incorporated by reference in its entirety) (partial sequence corresponding to human FGF1 residues 1 to 16 and 58 to 155):

```
  1   MAEGEITTFT ALTERF---- ---------- ---------- ---------- -------QLQ
 61   LSAESVGEVY IKSTETGQYL AMDADGLLYG SQTPDEECLF LERLEENHYN TYIAKKHAEK
121   NWFVGLKKNG SCKRGPRTHY GQKAILFLPL PVSSD
```

Amino acid sequence of *Petromyzon marinus* (lamprey) FGF1(SEQ ID NO: 46) (Ensembl accession no. ENSPMAP00000010683, which is hereby incorporated by reference in its entirety)(partial sequence corresponding to human FGF1 residues 1 to 93):

```
 1    MEVGHIGTLP VVPAGPVFPG SFKEPRRLYC RSAGHHLQIL GDGTVSGTQD ENEPHAVLQL
61    QAVRRGVVTI RGLCAERFLA MSTEGHLYGA VR
```

Amino acid sequence of *Echinops telfairi* (lesser hedgehog tenrec) FGF1(SEQ ID NO: 47) (Ensembl accession no. ENSETEP00000014504, which is hereby incorporated by reference in its entirety)(partial sequence corresponding to human FGF1 residues 58 to 155)

```
1     QLKLVAESVG VVYIKSIKTG QYLAMNPDGL LYGSETPEEE CLFLETLEEN HYTTFKSKKH
61    VEKNWFVGLR KNGRVKIGPR THQGQKAILF LPLPVSSD
```

Amino acid sequence of *Macaca mulatta* (rhesus monkey) FGF1(SEQ ID NO: 48) (Ensembl accession no. ENSMMUP00000030943, which is hereby incorporated by reference in its entirety):

```
  1   MAEGEITTFT ALTEKFNLPP GNYKKPKLLY CSNGGHFLRI LPDGTVDGTR DRSDQHIQLQ
 61   LSAESVGEVY IKSTETGQYL AMDTDGLLYG SQTPNEECLF LERLEENHYN TYTSKKHAEK
121   NWFVGLKKNG SCKRGPRTHY GQKAILFLPL PVSSD
```

Amino acid sequence of *Pteropus vampyrus* (megabat) FGF1(SEQ ID NO: 49) (Ensembl accession no. ENSPVAP00000004349, which is hereby incorporated by reference in its entirety):

```
  1   MAEGEVTTFT ALTERFNLPP GNYKKPKLLY CSNGGHFLRI LPDGTVDGTR DKSDQHIQLQ
 61   LSAESVGEVY IKSTESGQYL AMDSDGLLYG SQTPDEDCLF LERLEENHYN TYTSKKHAEK
121   NWFVGLKKNG SCKRGPRTHY GQKAILFLPL PVSSD
```

Amino acid sequence of *Myotis lucifugus* (microbat) FGF1(SEQ ID NO: 50) (Ensembl accession no. ENSMLUP00000006481, which is hereby incorporated by reference in its entirety):

```
  1   MAEGEVTTFT ALTERFNLPL ENYKKPKLLY CSNGGHFLRI LPDGTVDGTR DRSDQHIQLQ
 61   LSAESVGEVY IKSTESGQYL AMDSDGLLYG SQTPNEECLF LERLEENHYN TYTSKKHAEK
121   NWFVGLKKNG SCKRGPRTHY GQKAILFLPL PVSSD
```

Amino acid sequence of *Microcebus murinus* (mouse lemur) FGF1(SEQ ID NO: 51) (Ensembl accession no. ENSMICP00000008602, which is hereby incorporated by reference in its entirety):

```
  1   MAEGEITTFT ALTEKFNLPP GNYKKPKLLY CSNGGHFLRI LPDGTVDGTR DRSDQHIQLQ
 61   LSAESAGEVY IKSTQTGRYL AMDADGLLYG SQTPNEECLF LERLEENHYN TYVSKKHAEK
121   NWFVGLKKNG SCKRGPRTHY GQKAILFLPL PVSSD
```

Amino acid sequence of *Ochotona princeps* (pika) FGF1(SEQ ID NO: 52) (Ensembl accession no. ENSOPRP00000011739, which is hereby incorporated by reference in its entirety):

```
  1   MAEGEVTTFS ALTEKFNLPG GNYKLPKLLY CSNGGHFLRI LPDGTVDGTR DRSDLH----
 61   -------EVF IKSTETGQYL AMDTDGLLYG SQTPSEECLF LERLEENHYN TYTSKKHAEK
121   NWFVGIKKNG SCKRGPRTHY GQKAILFLPL PVSSD
```

Amino acid sequence of *Rattus norvegicus* (rat) FGF1(SEQ ID NO: 53) (Ensembl accession no. ENSRNOP00000018577, which is hereby incorporated by reference in its entirety):

```
  1   MAEGEITTFA ALTERFNLPL GNYKKPKLLY CSNGGHFLRI LPDGTVDGTR DRSDQHIQLQ
 61   LSAESAGEVY IKGTETGQYL AMDTEGLLYG SQTPNEECLF LERLEENHYN TYTSKKHAEK
121   NWFVGLKKNG SCKRGPRTHY GQKAILFLPL PVSSD
```

TABLE 1-continued

```
Amino acid sequence of Choloepus hoffmanni (sloth) FGF1(SEQ ID NO: 54)
(Ensembl accession no. ENSCHOP00000010964, which is hereby
incorporated by reference in its entirety):
  1    MAEGEITTFT ALMEKFNLPP GNYMKPKLLY CSNGGHFLRI LPDGTVDGTR DRSDLHIQLQ
 61    LSAESVGEVY IKSAETGQYL AMDTGGLLYG SQTPSEECLF LERLEENHYN TYVSKKHAEK
121    NWFVGLKKNG SSKRGPRTHY GQKAILFLPL PVSSD

Amino acid sequence of Ictidomys tridecemlineatus (squirrel) FGF1(SEQ
ID NO: 55) (Ensembl accession no. ENSSTOP00000021782, which is hereby
incorporated by reference in its entirety):
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYTSKKHAEK
121    NWFVGLKKNG SCKRGPRTHY GQKAILFLPL PVSSD

Amino acid sequence of Tarsius syrichta (tarsier) FGF1(SEQ ID NO: 56)
(Ensembl accession no. ENSTSYP00000006804, which is hereby
incorporated by reference in its entirety):
  1    MAEGEITTFT ALTEKFNLPP GNYKKPKLLY CSNGGHFLRI LPDGTVDGTR DRSDQHIQLQ
 61    LSAESVGEVY IKSTETGQYL AMDTDGLLYG SQTPNEECLF LERLEENHYN TYVSKKHAEK
121    NWFVGLKKNG SCKRGPRTHY GQKAILFLPL PVSSD

Amino acid sequence of Tupaia belangeri (tree shrew) FGF1(SEQ ID
NO: 57) (Ensembl accession no. ENSTBEP00000010264, which is hereby
incorporated by reference in its entirety):
  1    MAEGEITTFA ALTEKFDLPP GNYKKPKLLY CSNGGHFLRI LPDGTVDGTR DRSDQHIQLQ
 61    LTAENVGEVY IKSTETGQYL AMDADGLLYG SQTPNEECLF LERLEENHYN TYISKKHAEK
121    NWFVALKKNG SCKLGPRTHY GQKAILFLPL PVSSD

Amino acid sequence of Meleagris gallopavo (turkey) FGF1(SEQ ID NO: 58)
(Ensembl accession no. ENSMGAP00000016398; partial sequence
corresponding to human FGF1 residues 1 to 56, which is hereby
incorporated by reference in its entirety):
1      MAEGEITTFT ALTERFGLPL GNYKKPKLLY CSNGGHFLRI LPDGKVDGTR DRSDQH

Amino acid sequence of Macropus eugenii (wallaby) FGF1(SEQ ID NO: 59)
(Ensembl accession no. ENSMEUP00000015084, which is hereby
incorporated by reference in its entirety):
  1    MAEGEITTFT ALTERFNLPL GNYKKPKLLY CSNGGHFLRI LPDGKVDGTR DRNDQHIQLQ
 61    LSAESVGEVY IKSTESGQYL AMDTNGLLYG SQTPSEECLF LERLEENHYN TYISKKHAEK
121    NWFVGLKKNG SCKRGPRTHY GQKAILFLPL PVSSE

Amino acid sequence of Danio rerio (zebrafish) FGF1(SEQ ID NO: 60)
(Ensembl accession no. ENSDARP00000008825, which is hereby
incorporated by reference in its entirety):
  1    MTEADIAVKS SPRDYKKLTR LYCMNGGFHL QILADGTVAG AADENTYSIL RIKATSPGVV
 61    VIEGSETGLY LSMNEHGKLY ASSLVTDESY FLEKMEENHY NTYQSQKHGE NWYVGIKKNG
121    KMKRGPRTHI GQKAIFFLPR QVEQEED
```

As noted above, the portion of the paracrine FGF may be modified to decrease binding affinity for heparin and/or heparan sulfate compared to the portion without the modification. In one embodiment, the modified portion of the paracrine FGF includes one or more substitutions, additions, or deletions.

In one embodiment, the one or more substitutions are located at one or more amino acid residues of SEQ ID NO: 1 selected from N33, K127, K128, N129, K133, R134, R137, Q142, K143, and combinations thereof. In one embodiment, the one or more substitutions are selected from N33T, K127D, K128Q, N129T, K133V, R134L, R137H, Q142M, K143T/L/I, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. In one embodiment, the modification is one or more substitutions which are located at one or more amino acid residues corresponding to residues of SEQ ID NO: 1 selected from N33, K127, K128, N129, K133, R134, R137, Q142, K143, and combinations thereof. Amino acid residues corresponding to those of SEQ ID NO:1 may be determined by, for example, sequence analysis and structural analysis.

Also encompassed within the present invention are portions of paracrine FGFs other than FGF1 (e.g., FGF2, FGF4, FGF5, FGF6, FGF9, FGF16, and FGF20). The portions derived from paracrine FGFs other than FGF1 include portions corresponding to the above-identified amino acid sequences of FGF1. Corresponding portions may be determined by, for example, sequence analysis and structural analysis.

It will be understood that the portion of the paracrine FGF according to the present invention may be derived from a nucleotide sequence that encodes a paracrine FGF protein. For example, in one embodiment, the nucleotide sequence is the nucleotide sequence that encodes human FGF1 (GenBank Accession No. BC032697, which is hereby incorporated by reference in its entirety) (SEQ ID NO: 61), as follows:

```
 91                                  ATGGCTGAAG GGGAAATCAC CACCTTCACA
121   GCCCTGACCG AGAAGTTTAA TCTGCCTCCA GGGAATTACA AGAAGCCCAA ACTCCTCTAC
181   TGTAGCAACG GGGGCCACTT CCTGAGGATC CTTCCGGATG GCACAGTGGA TGGGACAAGG
241   GACAGGAGCG ACCAGCACAT TCAGCTGCAG CTCAGTGCGG AAAGCGTGGG GGAGGTGTAT
301   ATAAAGAGTA CCGAGACTGG CCAGTACTTG GCCATGGACA CCGACGGGCT TTTATACGGC
361   TCACAGACAC CAAATGAGGA ATGTTTGTTC CTGGAAAGGC TGGAGGAGAA CCATTACAAC
421   ACCTATATAT CCAAGAAGCA TGCAGAGAAG AATTGGTTTG TTGGCCTCAA GAAGAATGGG
481   AGCTGCAAAC GCGGTCCTCG GACTCACTAT GGCCAGAAAG CAATCTTGTT TCTCCCCCTG
541   CCAGTCTCTT CTGATTAA
```

In another embodiment of the present invention, the portion of the paracrine FGF of the chimeric protein may be derived from a nucleotide sequence that encodes an ortholog of human FGF1. Nucleotide sequences that encode FGF1 orthologs are shown in Table 2.

TABLE 2

Olive Baboon FGF1 gene coding sequence (1-155) (SEQ ID NO: 62) (GenBank accession no. NM_001169086, which is hereby incorporated by reference in its entirety):

```
  1 ATGGCTGAAG GGGAAATCAC CACGTTCACA GCCCTGACCG AGAAGTTTAA TCTGCCTCCA
 61 GCGAATTACA AGAAGCCCAA ACTGCTCTAC TGTAGCAACG GGGGACACTT CTTGAGGATC
121 CTTCCGGATG GCACAGTGGA TGGGACAAGG GACAGGAGCG ACCAGCACAT TCAGCTGCAG
181 CTCAGTGCGG AAAGCGTGGG GGAGGTGTAT ATAAAGAGTA CCGAGACTGG CCAGTACTTG
241 GCCATGGACA CCGACGGGCT TTTATACGGC TCACAGACAC CAAATGAGGA ATGTTTGTTC
301 CTGGAAAGGC TGGAGGAGAA CCATTACAAC ACCTACATAT CCAAGAAGCA CGCAGAGAAG
361 AATTGGTTTG TTGGCCTCAA GAAGAATGGA AGCTGCAAAC GTGGTCCTCG GACTCACTAT
421 GGCCAGAAAG CAATCTTGTT TCTTCCCCTG CCAGTCTCTT CTGATTAA
```

Sumatran orangutan FGF1 gene coding sequence (60-214) (SEQ ID NO: 63) (GenBank accession no. NM_001133601, which is hereby incorporated by reference in its entirety):

```
211                                 ATGGCTGAAG GGGAAATCAC CACCTTCACA
241 GCCCTGACCG AGAAGTTTAA TCTGCCTCCA GGGAATTACA AGAAGCCCAA ACTCCTCTAC
301 TGTAGCAACG GGGGCCACTT CTTGAGGATC CTTCCGGATG GCACAGTGGA TGGGACAAGG
361 GACAGGAGCG ACCAGCACAT TCAGCTGCAG CTCAGTGCGG AAAGCGTGGG GGAGGTGTAT
421 ATAAAGAGTA CCGAGACTGG CCAGTACTTG GCCATGGACA CCGACGGGCT TTTATACGGC
481 TCACAGACAC CAAATGAGGA ATGTTTGTTC CTGGAAAGGC TGGAGGAGAA CCATTACAAC
541 ACCTATATAT CCAAGAAGCA TGCAGAGAAG AATTGGTTTG TTGGCCTCAA GAAGAATGGA
601 AGCTGCAAAC GCGGTCCTCG GACTCACTAT GGCCAGAAAG CAATCTTGTT TCTCCCCCTG
661 CCAGTCTCTT CCGATTAA
```

White-tufted-ear marmoset FGF1 gene coding sequence (1-155) (SEQ ID NO: 64) (GenBank accession no. XM_002744295, which is hereby incorporated by reference in its entirety):

```
130          A TGGCTGAAGG GGAAATCACC ACCTTCACAG CCCTGACCGA GAAGTTTGAT
181 CTGCCTCCAG GGAATTACAA GAAGCCCAAA CTCCTCTACT GTAGCAATGG GGGCCACTTC
241 TTGAGGATCC TTCCGGATGG CACAGTGGAT GGGACAAGGG ACAGGAGCGA CCAGCACATT
301 CAGCTGCAGC TCAGTGCGGA AAGCGTGGGG GAGGTGTATA TAAAGAGTAC CGAGACTGGC
```

TABLE 2-continued

```
361 CAGTACTTGG CCATGGACAC CGACGGGCTT TTATACGGCT CACAGACACC AAATGAGGAA
421 TGTTTGTTCC TGGAGAGGCT GGAGGAGAAC CATTACAACA CCTATATATC CAAGAAACAT
481 GCAGAGAAGA ATTGGTTTGT CGGCCTCAAG AAGAATGGAA GCTGTAAACG TGGTCCTCGG
541 ACTCACTATG GTCAGAAAGC GATCTTGTTT CTCCCCCTGC CAGTTTCTTC TGATTAA
```

Horse FGF1 gene coding sequence (1-155) (SEQ ID NO: 65) (GenBank accession no. NM_001163886, which is hereby incorporated by reference in its entirety):

```
34                                  ATGGCTG AAGGAGAAAT CACAACCTTC
61 ACGGCCCTGA CCGAGAAGTT TAATCTGCCT CCAGGGAATT ACAAGAAGCC CAAACTCCTC
121 TACTGTAGCA ATGGGGGCCA CTTCCTGAGG ATCCTTCCAG ATGGCACAGT GGATGGGACA
181 AGGGACAGGA GCGACCAGCA CATTCAGCTG CAGCTCAGTG CGGAAAGCGT GGGGGAGGTG
241 TATATAAAGA GTACCGAGAC TGGCCAGTAC TTGGCCATGG ACACCGACGG GCTGTTGTAC
301 GGCTCACAGA CACCAAACGA GGAATGTTTG TTCCTGGAAA GGCTGGAGGA AAACCATTAC
361 AACACCTACA CATCCAAGAA GCATGCAGAG AAGAACTGGT TCGTTGGTCT CAAGAAGAAT
421 GGGAGCTGCA AACGCGGTCC TCGGACTCAC TATGGGCAGA AAGCAATCTT GTTTCTTCCC
481 CTGCCCGTCT CCTCTGACTA A
```

Chimpanzee FGF1 gene coding sequence (1-155) (SEQ ID NO: 66) (GenBank accession no. GABD01003589, which is hereby incorporated by reference in its entirety):

```
80                      A TGGCTGAAGG GGAAATCACC ACCTTCACAG CCCTGACCGA
121 GAAGTTTAAT CTGCCTTCAG GGAATTACAA GAAGCCCAAA CTCCTCTACT GTAGCAACGG
181 GGGCCACTTC CTGAGGATCC TTCCGGATGG CACAGTGGAT GGGACAAGGG ACAGGAGCGA
241 CCAGCACATT CAGCTGCAGC TCAGTGCGGA AAGCGTGGGG GAGGTGTATA TAAAGAGTAC
301 CGAGACTGGC CAGTACTTGG CCATGGACAC CGACGGGCTT TTATACGGCT CACAGACACC
361 AAATGAGGAA TGTTTGTTCC TGGAACGGCT GGAGGAGAAC CATTACAACA CCTATATATC
421 CAAGAAGCAT GCAGAGAAGA ATTGGTTTGT TGGCCTCAAG AAGAATGGAA GCTGCAAACG
481 CGGTCCTCGG ACTCACTATG GCCAGAAAGC AATCTTGTTT CTCCCCCTGC CAGTCTCTTC
541 CGATTAA
```

Elephant FGF1 gene coding sequence (1-155) (SEQ ID NO: 67) (GenBank accession no. XM_003404573, which is hereby incorporated by reference in its entirety):

```
1 ATGGCCGAAG GGGAAATCAC AACTTTCACA GCCCTGACAG AGAAGTTCAA CCTGCCTCCA
61 GGGAATTACA AGAAGCCCAA ACTCCTCTAC TGTAGCAATG GAGGTCACTT CTTAAGGATC
121 CTTCCAGATG GCACAGTGGA TGGCACCAGG GACAGGAGTG ACCAGCACAT TCAGCTGCAG
181 CTCAGTGCGG AAAGCGTGGG GGAGGTGTAT ATAAAGGGCA CCGAGACTGG CCAGTACTTG
241 GCCATGGACA CCGACGGGCT TTTATACGGC TCACAGACAC CAAATGAGGA ATGTTTGTTC
301 CTGGAAAGGC TGGAGGAAAA CCATTACAAC ACCTACACAT CCAAGAAGCA CGCAGAGAAG
361 AATTGGTTCG TTGGTCTCAA GAAGAATGGA AGCTGCAAAC GCGGTCCTCG GACTCACTAT
421 GGCCAGAAAG CAATCTTGTT TCTCCCCCTG CCAGTCTCCT CTGATTAA
```

TABLE 2-continued

Dog FGF1 gene coding sequence (1-155) (SEQ ID NO: 68) (GenBank accession no. XM_844181, which is hereby incorporated by reference in its entirety):

```
164                                                ATGGCTG AAGGGGAAAT
181 CACAACCTTC ACTGCCCTGA CGGAGAAGTT TAATCTGCCT CCGGGGAATT ACATGAAGCC
241 CAAACTCCTC TACTGTAGCA ACGGGGGCCA CTTCCTGAGG ATCCTTCCAG ATGGCACAGT
301 GGATGGGACA AGGGACAGGA GCGACCAGCA CATTCAGCTG CAGCTCAGCG CGGAAAGCGT
361 GGGGGAGGTG TATATAAAGA GCACCGAGAC TGGCCAGTAC TTGGCCATGG ACACCGATGG
421 GCTTCTGTAC GGCTCACAGA CACCGAATGA GGAATGTTTG TTCCTGGAAA GGCTGGAGGA
481 AAACCATTAC AACACCTACA CATCCAAGAA GCATGCAGAA AAAAATTGGT TTGTTGGTCT
541 CAAGAAGAAT GGAAGCTGCA AACGCGGTCC TCGGACTCAC TATGGTCAAA AAGCAATTTT
601 GTTTCTCCCC CTGCCAGTGT CCTCTGATTA A
```

Giant panda FGF1 gene coding sequence (1-155) (SEQ ID NO: 69) (GenBank accession no. XM_002912535, which is hereby incorporated by reference in its entirety):

```
146                              ATGGC TGAAGGGGAG ATCACAACCT TCACCGCCCT
181 GACGGAGAAG TTTAATCTGC CTGCGGGGAA TTACAAGAAG CCCAAACTCC TCTACTGTAG
241 CAACGGGGGC CACTTCCTGA GGATCCTTCC AGATGGCACA GTGGACGGGA CGAGGGACAG
301 GAGCGACCAG CACATTCAAC TGCAGCTCAG CGCGGAAAGC GTAGGGGAGG TGTACATAAA
361 GAGCACCGAG ACCGGCCAGT ACTTGGCCAT GGACACCGAT GGGCTTCTGT ACGGCTCACA
421 GACACCAAAT GAGGAATGTT TGTTCCTGGA AAGGCTGGAG GAAAACCATT ACAACACCTA
481 CACATCCAAG AAGCACGCGG AGAAGAATTG GTTTGTTGGT CTCAAGAAGA ATGGAAGCTG
541 CAAACGTGGT CCTCGGACTC ACTATGGCCA GAAAGCAATT CTGTTTCTCC CCCTGCCAGT
601 CTCCTCTGAT TAA
```

Bolivian squirrel monkey FGF1 gene coding sequence (1-155) (SEQ ID NO: 70) (GenBank accession no. XM_003920547, which is hereby incorporated by reference in its entirety):

```
130          A TGGCTGAAGG GGAAATCACC ACCTTTACAG CCCTGACCGA GAAGTTTGAT
181 CTGCCTCCAG GGAATTACAA GAAGCCCAAA CTCCTCTACT GTAGCAACGG GGGCCACTTC
241 TTGAGGATCC TTCCGGATGG CACAGTGGAT GGGACCAGGG ACAGGAGCGA TCTTCACATT
301 CAGCTGCAGC TCAGTGCGGA AAGCGTGGGG GAGGTGTATA TAAAGAGTAC CGAGACTGGC
361 CAGTACTTGG CCATGGACAC CGACGGGCTT TTATACGGCT CACAGACACC AAATGAGGAA
421 TGTTTGTTCC TGGAAAGGCT GGAGGAGAAC CATTACAACA CCTATATATC CAAGAAACAC
481 GCAGAGAAGA ATTGGTTTGT TGGCCTCAAG AAGAATGGAA GCTGCAAGCG CGGTCCTCGG
541 ACTCACTATG GCCAGAAAGC AATCTTGTTT CTCCCCCTGC CAGTCTCTTC TGATTAA
```

Pig FGF1 gene coding sequence (1-155) (SEQ ID NO: 71) (GenBank accession no. XM_003124010, which is hereby incorporated by reference in its entirety):

```
 35                                     ATGGCT GAAGGCGAAA TCACAACCTT
 61 CACGGCCCTG ACCGAGAAGT TTAATCTGCC TCCAGGAAAT TACAAGAAGC CCAAGCTCCT
121 CTACTGCAGC AACGGGGGCC ATTTCCTCAG GATCCTTCCA GATGGCACAG TGGATGGGAC
181 CAGGGACAGG AGCGACCAGC ACATTCAGCT GCAGCTCAGT GCGGAAAGCG TGGGGGAGGT
241 GTATATAAAG AGTACGGAGA CTGGCCAGTA CTTGGCCATG GACACCAGCG GGCTTTTGTA
301 CGGCTCACAG ACACCCAGTG AGGAGTGTTT GTTCCTGGAG AGGCTGGAGG AAAACCATTA
```

TABLE 2-continued

```
361 CAATACCTAC ACATCCAAGA AGCACGCAGA GAAGAACTGG TTCGTTGGCC TCAAGAAGAA

421 TGGAAGCTGC AAACGCGGTC CTCGGACTCA CTATGGCCAG AAAGCCATCC TGTTTCTCCC

481 CCTGCCAGTA TCCTCGGATT AA
```

Small-eared galago FGF1 gene coding sequence (1-155) (SEQ ID NO: 72) (GenBank accession no. XM_003782087, which is hereby incorporated by reference in its entirety):

```
 28                               ATG GCTGAAGGGG AAATCACAAC CTTCACAGCC

 61 CTCACAGAGA AGTTTAATCT GCCTCTAGGA AATTACAAGA AGCCCAAGCT CCTCTACTGT

121 AGCAACGGGG GTCACTTTCT GAGGATCCTG CCGGATGGCA CCGTGGATGG GACACAAGAC

181 AGGAGCGACC AGCACATTCA GCTGCAGCTC AGTGCGGAAA GCGTGGGGGA GGTGTATATA

241 AAGAGTACCC AGACTGGCCA GTACTTGGCC ATGGACTCCG ACGGGCTTTT ATACGGCTCA

301 CAAACACCAA ATGAGGAATG CCTGTTCCTG GAACGGCTGG AGGAAAACCA TTACAACACC

361 TATGTGTCCA AGAAGCACGC CGAGAAGAAT TGGTTTGTCG GTCTCAAGAA GAACGGAAGT

421 TGCAAACGTG GTCCTCGGAC TCACTACGGC CAGAAAGCAA TCTTGTTTCT CCCCCTGCCA

481 GTCTCCTCTG ATTAA
```

Greater horseshoe bat FGF1 gene coding sequence (1-155) (SEQ ID NO: 73) (GenBank accession no. DP000705, which is hereby incorporated by reference in its entirety):

```
190120                                          T TAATCAGAGG AGACTGGCAG

190141 GGGGAGAAAC AGGATTGCTT TCTGGCCATA GTGAGTCCGA GGACCGCGCT TGCAGCTTCC

190201 ATTCTTCTTG AGCCCAACGA ACCAATTCTT TTCTGCGTGC TTCTTGGACG TGTAGGTGTT

190261 GTAATGGTTT TCCTCCAGCC TTTCCAGGAA CAGACATTCC TCATTTGGTG TCTG

194466      TGAGC CGTACAAAAG CCCGTCGGAG TCCATGGCCA AGTACTGGCC ACTCTCGGTG

194521 CTCTTTATAT ACACCTCCCC CACGCTTTCC GCACTGAGCT GCAGCTGAA

208114                                   TGTGCTG GTCACTCTTG TCCCTTGTCC

208141 CATCCACTGT GCCATCTGGA AGGATCCTCA GGAAGTGGCC CCCGTTGCTG CAGTAGAGAA

208201 GTTTGGGTTT CTTGTAATTC CCTGTAGGCA GATTAAACTT CTCAGTAAGG GCTGTGAACG

208261 TGGTGACTTC CCCTTCGGCC AT
```

European shrew FGF1 gene coding sequence (1-155) (SEQ ID NO: 74) (GenBank accession no. DP000767, which is hereby incorporated by reference in its entirety):

```
138344                                              CTAGTCG GAGGAGACGG

138361 GCAGGGGGAG AAACAAGATC GCTTTCTGGC CGTAGTGAGT CCGGGGACCA CGCTTGCAGC

138421 TTCCGTTCTT CTTCAGACCA ACAAACCAAT TCTTCTCGGC ATGCTTCTTG GAGGTATAGG

138481 TGTTGTAATG GTTTTCCTCC AGCCTTTCCA GAAACAGACA TTCCTCATTC GGTGTTTG

143512                                                        TGAGCCGTA

143521 TAAAAGCCCG TCGGTGTCCA TGGCCAAGTA ATGGCCAGTC TCCGTGCTCT TTATATACAC

143581 CTCCCCCACG CTTTCCGCAC TGAGCTGCAG CTGAA

157009                                                    TG TGCTGGTCGC

157021 TGCGGTCCCT GGTCCCATCC ACTGTGCCGT CCGGGAGGAT GCGCAGGAAG TGGCCCCCGT

157081 TGCTGCAGTA CAGGAGTTTG GGCTTCTTGT AGTTCCCTGG TGGCAGGTTA AACTTCTCCA

157141 TGAGGGCCCC AAAGGTGGTG ATCTCCCCCT CGGCCAT
```

TABLE 2-continued

Rabbit FGF1 gene coding sequence (1-155) (SEQ ID NO: 75) (GenBank accession no. NM_001171488, which is hereby incorporated by reference in its entirety):

```
  1 ATGGCTGAGG GGGAGGTCAC CACCTTCACA GCCCTGACCG AGAAGTTCAA CCTGCCTGCA
 61 GGGAACTACA AGTTGCCCAA ACTCCTCTAC TGCAGCAACG GGGGCCACTT CCTGAGGATC
121 CTGCCGGACG GCACTGTGGA CGGCACAAGG GACAGGAGCG ACCAGCACAT TCAGCTGCAG
181 CTGAGTGCGG AAAGCGTGGG GGAGGTGTAT ATAAAGAGTA CGGAGACCGG CCAGTACTTG
241 GCCATGGACA CCGACGGCCT TTTATACGGC TCGCAAACGC CCAGTGAGGA GTGTTTGTTC
301 CTGGAACGGC TGGAGGAGAA CCACTACAAC ACCTACACGT CCAAGAAGCA CGCCGAGAAG
361 AACTGGTTCG TGGGGCTGAA GAAAAACGGG AGCTGCAAGC GCGGTCCTCG GACTCACTAC
421 GGCCAGAAAG CCATCTTGTT CCTCCCCCTG CCGGTCTCCT CCGACTAA
```

Chinese hamster FGF1 gene coding sequence (1-155) (SEQ ID NO: 76) (GenBank accession no. XM_003502421, which is hereby incorporated by reference in its entirety):

```
  1 ATGGCTGAAG GAGAAATCAC CACCTTCTCA GCCCTGACAG AGAGATTTAA TCTGCCTCCA
 61 GGAAACTACA AGAAGCCCAA ACTGCTCTAC TGCAGCAACG GGGGCCACTT CTTGAGGATC
121 CTTCCAGATG GCACAGTGGA TGGGACAAGG GACAGGAGTG ACCAGCACAT TCAGCTGCAG
181 CTGAGTGCGG AAAGCGCGGG CGAAGTGTAT ATAAAGGGTA CAGAGACAGG CCAGTACAGG
241 AACATGGACA CGGATGGCCT TTTATACGGC TCACAGACAC CAAATGAAGA ATGCCTGTTC
301 CTGGAAAGGC TGGAAGAAAA CCATTACAAC ACTTATACAT CCAAGAAGCA CGCAGAGAAG
361 AACTGGTTTG TGGGCCTCAA GAAAAACGGG AGCTGCAAGC GTGGTCCTCG GACTCACTAT
421 GGCCAGAAAG CAATCTTGTT TCTCCCCCTG CCTGTATCTT CTGACTAG
```

Tasmanian devil FGF1 gene coding sequence (1-155) (SEQ ID NO: 77) (GenBank accession no. XM_003756690, which is hereby incorporated by reference in its entirety):

```
 24                             ATGGCCG AAGGGGAGAT CACAACCTTC ACAGCCCTGA
 61 CCGAAAGATT TAATCTGCCA CTGGGGAATT ACAAGAAGCC CAAGCTTCTC TACTGTAGCA
121 ATGGGGGCCA CTTTTTGAGG ATTCTTCCTG ATGGTAAAGT GGATGGGACA AGGGACAGAA
181 ATGATCAACA CATTCAACTG CAACTAAGCG CGGAAAGCGT GGGTGAGGTG TATATAAAGA
241 GCACTGAGTC TGGCCAGTAT TTGGCTATGG ACACCGATGG ACTTTTATAC GGCTCACAGA
301 CACCCACTGA AGAATGCTTG TTCCTGGAGA GATTGGAGGA GAATCATTAC AACACCTACA
361 TATCAAAGAA GCATGCGGAG AAAAATTGGT TTGTGGGCCT CAAGAAAAAT GGAAGCTGCA
421 AAAGAGGTCC CAGGACTCAC TATGGCCAGA AAGCCATCCT CTTCCTTCCC CTCCCTGTGT
481 CCTCTGAGTA A
```

House mouse FGF1 gene coding sequence (1-155) (SEQ ID NO: 78) (GenBank accession no. NM_010197, which is hereby incorporated by reference in its entirety):

```
188        ATG GCTGAAGGGG AGATCACAAC CTTCGCAGCC CTGACCGAGA GGTTCAACCT
241 GCCTCTAGGA AACTACAAAA AGCCCAAACT GCTCTACTGC AGCAACGGGG GCCACTTCTT
301 GAGGATCCTT CCTGATGGCA CCGTGGATGG GACAAGGGAC AGGAGCGACC AGCACATTCA
361 GCTGCAGCTC AGTGCGGAAA GTGCGGGCGA AGTGTATATA AAGGGTACGG AGACCGGCCA
421 GTACTTGGCC ATGGACACCG AAGGGCTTTT ATACGGCTCG CAGACACCAA ATGAGGAATG
481 TCTGTTCCTG GAAAGGCTGG AAGAAAACCA TTATAACACT TACACCTCCA AGAAGCATGC
```

TABLE 2-continued

```
 541 GGAGAAGAAC TGGTTTGTGG GCCTCAAGAA GAACGGGAGC TGTAAGCGCG GTCCTCGGAC

 601 TCACTATGGC CAGAAAGCCA TCTTGTTTCT GCCCCTCCCG GTGTCTTCTG ACTAG
```

Domestic guinea pig FGF1 gene coding sequence (1-154) (SEQ ID NO: 79) (GenBank accession no. XM_003477194, which is hereby incorporated by reference in its entirety):

```
   1 ATGGCTGAAG GAGAAATCAC AACTTTTGCA GCCCTGACTG AGAAGTTTAA TCTGCCTCCA

  61 GGGAATTATA AGAAGCCCAA ACTGCTCTAC TGCAGCAATG GGGGCCACTT CCTGAGGATC

 121 CTTCCAGACG GCACAGTGGA CGGCACAAGA GACAGGAGCG ACCAGCACAT TCAGCTGCAG

 181 CTCAGTGCGG AAGGCGTGGG GGAGGTGTAT ATACAGAGCA CCGAGACCGG CCAGTACTTG

 241 GCCATGGACA CCGACGGGCT TTTATACGGC TCACAGACAC CAAGTGAGGA ATGCTTGTTC

 301 CTGGAAAGGC TGGAGGAAAA CCATTACAAC ACCTACACAT CCAAGAAGCA TGTGGAGAAG

 361 AATTGGTTTG TTGGCCTCAA GAAGAACGGA AGCTGCAAGC GTGGTCCTCG GACTCACTAT

 421 GGCCAGAAAG CAATCTTGTT CCTCCCCTTG CCAGTCTCTG ATTAG
```

Gray short-tailed opossum FGF1 gene coding sequence (1-155) (SEQ ID NO: 80) (GenBank accession no. XM_001368884, which is hereby incorporated by reference in its entirety):

```
   1 ATGGCCGAAG GGGAGATCAC AACCTTCACA GCCCTGACTG AAAGATTTAA CCTGCCACTG

  61 GGGAATTACA AGAAACCCAA GCTTCTCTAC TGTAGCAATG GGGGCCATTT CTTGAGGATC

 121 CTTCCTGATG GCAAAGTGGA TGGGACACGG GACAGAAATG ATCAACACAT TCAACTGCAG

 181 CTGAGCACGG AAAGTGTGGG TGAGGTGTAT ATAAAGAGCA CTGAGTCTGG CCAGTATTTG

 241 GCTATGGACA CCGATGGACT TTTATATGGC TCACAGACAC CCAGTGAAGA ATGCTTGTTT

 301 CTGGAGAGGT TGGAGGAGAA TCATTACAAC ACCTACACAT CGAAGAAGCA TGCAGAGAAA

 361 AATTGGTTTG TTGGTCTCAA GAAGAATGGA AGCTGCAAAA AGGGTCCCAG GACTCACTAC

 421 GGCCAGAAAG CCATCCTGTT CCTTCCCCTC CCTGTGTCCT CTGAGTAA
```

Common vampire bat FGF1 gene coding sequence (1-155) (SEQ ID NO: 81) (GenBank accession no. GABZ01008334, which is hereby incorporated by reference in its entirety):

```
   1 ATGGCTGAAG GGGAAGTCAC CACGTTCACA GCTCTGACTG AGAAGTTTAA TCTGCCTCTG

  61 GAGAGTTACA AGAAGCCCAA ACTTCTCTAC TGCAGCAACG GTGGCCACTT CCTGAGGATC

 121 CTTCCAGATG GTACAGTGGA TGGGACAAGG GACAAGAGCG ACCAGCACAT TCAGCTGCAG

 181 CTCAGTGCGG AAAGCGTGGG GGAGGTGTAC ATAAAGAGCA CCGGGAGTGG CCAGTACTTG

 241 GCCATGGACT CCGCCGGGCT TTTGTATGGC TCACAGACAC CAAATGAGGA ATGTTTGTTC

 301 CTGGAAAGGC TGGAGGAAAA CCATTACAAC ACCTACACAT CCAAGAAGCA TGCAGAAAAG

 361 AATTGGTTCG TGGGGCTCAA GAAGAATGGA AGCTGCAAGC GTGGCCCCCG GACTCATTAT

 421 GGCCAGAAAG CAATCTTGTT TCTCCCCCTG CCAGTCAACT CTGATTAA
```

Cattle FGF1 gene coding sequence (1-155) (SEQ ID NO: 82) (GenBank accession no. NM_174055, which is hereby incorporated by reference in its entirety):

```
 918                  ATG GCTGAAGGAG AAACCACGAC CTTCACGGCC CTGACTGAGA

 961 AGTTTAACCT GCCTCTAGGC AATTACAAGA AGCCCAAGCT CCTCTACTGC AGCAACGGGG

1021 GCTACTTCCT GAGAATCCTC CCAGATGGCA CAGTGGATGG GACGAAGGAC AGGAGCGACC

1081 AGCACATTCA GCTGCAGCTC TGTGCGGAAA GCATAGGGGA GGTGTATATT AAGAGTACGG

1141 AGACTGGCCA GTTCTTGGCC ATGGACACCG ACGGGCTTTT GTACGGCTCA CAGACACCCA

1201 ATGAGGAATG TTTGTTCCTG GAAAGGTTGG AGGAAAACCA TTACAACACC TACATATCCA
```

TABLE 2-continued

```
1261 AGAAGCATGC AGAGAAGCAT TGGTTCGTTG GTCTCAAGAA GAACGGAAGG TCTAAACTCG

1321 GTCCTCGGAC TCACTTCGGC CAGAAAGCCA TCTTGTTTCT CCCCCTGCCA GTCTCCTCTG

1381 ATTAA
```

Platypus FGF1 gene coding sequence (1-155) (SEQ ID NO: 83) (GenBank accession no. XM_001514811, which is hereby incorporated by reference in its entirety):

```
  1 ATGGCGGAGG GTGAAATCAC CACGTTCACA GCCCTGATGG AGAAGTTCGA CCTACCCCTG

 61 GGCAACTACA AAAAGCCTAG GCTGCTCTAC TGCAGCAATG GCGGCTACTT CCTGCGCATC

121 CAGCCAGACG GTAAAGTGGA CGGGACCAGG GATCGGAGCG ATCAGCACAT TCAACTGCAG

181 CTAAGCGCGG AAAGCGTGGG CGAGGTGTAT ATAAAGAGCA CCGAGTCTGG CCACTATTTG

241 GCTATGGACA CCGAAGGACT TTTATATGGC TCACAGGCAC CCAGTGAAGA CTGCTTGTTC

301 CTGGAGCGGC TGGAGGAGAA CCACTATAAC ACGTACGTGT CCAAGAAGCA CGCTGAGAAG

361 AATTGGTTTG TCGGTCTCAA GAAGAACGGG AGCTGCAAAC GAGGTCCCCG GACTCACTAC

421 GGCCAGAAAG CCATCCTCTT CCTCCCGCTC CCCGTGGCAT CCGACTAG
```

Zebra finch FGF1 gene coding sequence (1-155) (SEQ ID NO: 84) (GenBank accession no. XM_002193251, which is hereby incorporated by reference in its entirety):

```
  1 ATGGCCGAGG GGGAGATCAC CACCTTCAGC GCCCTGACGG AGAAGTTCAA CCTGCCCCCG

 61 GGGAACTACA AGAAGCCCAA ACTGCTGTAC TGCAGCAACG GGGGGCATTT CCTGCGCATC

121 CTCCCGGACG GCACCGTGGA TGGCACCAGG GACCGCAGCG ACCAGCACAT TCAGCTCCAG

181 CTGAGTGCAG AGAGCGTGGG GGTGGTGCAC ATCCAGAGCA CCCAGTCGGG GCAGTACCTG

241 GCCATGGACA CCAACGGGCT GCTCTACGGC TCGCAGCTGC CACCCGGTGA GTGTCTGTTC

301 CTGGAAAGGC TGGAGGAGAA CCATTACAAC ACCTACGTCT CCAAAATGCA CGCGGACAAG

361 AACTGGTTTG TGGGGCTGAA GAAGAACGGG ACAAGCAAGC TGGGCCCGCG GACTCACTAC

421 GGCCAGAAGG CGATCCTGTT CCTGCCGCTG CCCGTGGCGG CCGACTGA
```

Nine-banded armadillo FGF1 gene coding sequence (1-155) (SEQ ID NO: 85) (GenBank accession no. DP001080, which is hereby incorporated by reference in its entirety):

```
178389         TT AATCAGAGGA GACTGGCAGG GGAAGAAACA AGATAGCTTT CTGGCCATAG

178441 TGAGTCTGAG GACCACGTTT GCTGCTTCCG TCCTTCTTGA GACCAACAAA CCATTTCTTC

178501 TCTGCATGCT TCTTGGATAT GTAGGTGTTG TAATTGTTTT CTTCCAGCTT TTCCATGAAC

178561 AAGCATTCCT CACTTGGTGT CTC

182873                                                     TGAGCCAT

182881 ATAAAAGCCC GTCGGTGTCC ATGGCTAAGT ACTGGCCGGT CTCTGCACTC TTTATATACA

182941 CCTCCCCCAC GCTTTCCGCA CTGAGCTGCA GCTGAA

197786                            TGTGT TGGTCGCTCC TGTCCCTTGT CCCATCCACC

197821 GTGCCATCTG GAAGGATCCT CAAGAAGTGG CCCCCGTTTC TGCAGTAGAG GAGTCTGGGG

197881 TGCTTGTAAT TTTCTAGGGG CAGGTTGAAC TTCTCCATCA GGGCCATGAA GGTTGTGATC

197941 TCCCCTTCAG CCAT
```

Xenopus Silurana tropicalis FGF1 gene coding sequence (1-155) (SEQ ID NO: 86) (GenBank accession no. FJ428265, which is hereby incorporated by reference in its entirety):

```
  1 ATGGCAGAGG GAGACATCAC AACATTCAAC CCCATTGCAG AGTCCTTCAG TCTTCCAATT

 61 GGCAACTACA AGAAACCAAA ACTTCTGTAC TGTAATAATG GAGGGTATTT TTTGCGCATC
```

TABLE 2-continued

```
121 CTCCCAGATG GGGTTGTGGA TGGAACAAGA GACAGAGATG ACCTTTACAT TACACTGAAG

181 TTAAGCGCAC AAAGCCAAGG GGAGGTGCAT ATCAAAAGCA CAGAGACAGG GAGTTACTTA

241 GCCATGGACT CCAGTGGACA GTTGTATGGA ACTCTCACAC CAAATGAAGA AAGCCTGTTT

301 CTGGAGACAT TAGAAGAGAA TCACTATAAC ACATACAAGT CAAAGAAGTA TGCAGAAAAT

361 AACTGGTTTG TGGGGATAAA GAAGAACGGG GCAAGCAAAA AGGGATCAAG GACTCACTAT

421 GGACAAAAAG CCATCCTTTT TCTGCCGCTG CCAGCATCAC CTGACTAG
```

Heterocephalus glaber FGF1 gene coding sequence (1-155) (SEQ ID NO: 87) (generated using SMS Reverse Translate tool on the ExPASy Bioinformatics Resource website (www.expasy.org):

```
  1 ATGGCGGAAG GCGAAATTAC CACCTTTACC GCGCTGACCG AAAAATTTAA CCTGCCGCCG

 61 GGCAACTATA AAAAACCGAA ACTGCTGTAT TGCAGCAACG GCGGCCATTT TCTGCGCATT

121 CTGCCGGATG GCAAAGTGGA TGGCACCCGC GATCGCAGCG ATCAGCATAT TCAGCTGCAG

181 CTGAGCGCGG AAGGCGTGGG CGAAGTGTAT ATTAAAAGCA CCGAAACCGG CCAGTATCTG

241 GCGATGGATA CCGATGGCCT GCTGTATGGC AGCCAGACCG CGAGCGAAGA ATGCCTGTTT

301 CTGGAACGCC TGGAAGAAAA CCATTATAAC ACCTATATTA GCAAAAAACA TGCGGAAAAA

361 AACTGGTTTG TGGGCCTGAA AAAAAACGGC AGCTGCAAAC GCGGCCCGCG CACCCATTAT

421 GGCCAGAAAG CGATTCTGTT TCTGCCGCTG CCGGTGAGCA GCGAT
```

Black flying fox FGF1 gene coding sequence (1-155) (SEQ ID NO: 88) (generated using SMS Reverse Translate tool on the ExPASy Bioinformatics Resource website (www.expasy.org):

```
  1 ATGGCGGAAG GCGAAGTGAC CACCTTTACC GCGCTGACCG AACGCTTTAA CCTGCCGCCG

 61 GGCAACTATA AAAAACCGAA ACTGCTGTAT TGCAGCAACG GCGGCCATTT TCTGCGCATT

121 CTGCCGGATG GCACCGTGGA TGGCACCCGC GATAAAAGCG ATCAGCATAT TCAGCTGCAG

181 CTGAGCGCGG AAAGCGTGGG CGAAGTGTAT ATTAAAAGCA CCGAAAGCGG CCAGTATCTG

241 GCGATGGATA GCGATGGCCT GCTGTATGGC AGCCAGACCC CGGATGAAGA TTGCCTGTTT

301 CTGGAACGCC TGGAAGAAAA CCATTATAAC ACCTATACCA GCAAAAAACA TGCGGAAAAA

361 AACTGGTTTG TGGGCCTGAA AAAAAACGGC AGCTGCAAAC GCGGCCCGCG CACCCATTAT

421 GGCCAGAAAG CGATTCTGTT TCTGCCGCTG CCGGTGAGCA GCGAT
```

Chinese tree shrew FGF1 gene coding sequence (1-155) (SEQ ID NO: 89) (generated using SMS Reverse Translate tool on the ExPASy Bioinformatics Resource website (www.expasy.org):

```
  1 ATGGCGGAAG GCGAAATTAC CACCTTTGCG GCGCTGACCG AAAAATTTGA TCTGCCGCCG

 61 GGCAACTATA AAAAACCGAA ACTGCTGTAT TGCAGCAACG GCGGCCATTT TCTGCGCATT

121 CTGCCGGATG GCACCGTGGA TGGCACCCGC GATCGCAGCG ATCAGCATAT TCAGCTGCAG

181 CTGACCGCGG AAAACGTGGG CGAAGTGTAT ATTAAAAGCA CCGAAACCGG CCAGTATCTG

241 GCGATGGATG CGGATGGCCT GCTGTATGGC AGCCAGACCC CGAACGAAGA ATGCCTGTTT

301 CTGGAACGCC TGGAAGAAAA CCATTATAAC ACCTATATTA GCAAAAAACA TGCGGAAAAA

361 AACTGGTTTG TGGCGCTGAA AAAAAACGGC AGCTGCAAAC TGGGCCCGCG CACCCATTAT

421 GGCCAGAAAG CGATTCTGTT TCTGCCGCTG CCGGTGAGCA GCGAT
```

Rock pigeon FGF1 gene coding sequence (1-155) (SEQ ID NO: 90) (generated using SMS Reverse Translate tool on the ExPASy Bioinformatics Resource website (www.expasy.org):

```
  1 ATGGCGGAAG GCGAAATTAC CACCTTTACC GCGCTGACCG AAAAATTTAA CCTGCCGCCG

 61 GGCAACTATA AAAAACCGAA ACTGCTGTAT TGCAGCAACG GCGGCCATTT TCTGCGCATT
```

TABLE 2-continued

```
121 CTGCCGGATG GCAAAGTGGA TGGCACCCGC GATCGCAGCG ATCAGCATAT TCAGCTGCAG

181 CTGAGCGCGG AAAGCGTGGG CGAAGTGTAT ATTAAAAGCA CCCAGAGCGG CCAGTATCTG

241 GCGATGGATC CGACCGGCCT GCTGTATGGC AGCCAGCTGC TGGGCGAAGA ATGCCTGTTT

301 CTGGAACGCA TTGAAGAAAA CCATTATAAC ACCTATGTGA GCAAAAAACA TGCGGATAAA

361 AACTGGTTTG TGGGCCTGAA AAAAAACGGC AACAGCAAAC TGGGCCCGCG CACCCATTAT

421 GGCCAGAAAG CGATTCTGTT TCTGCCGCTG CCGGTGAGCG CGGAT
```

Sheep FGF1 gene coding sequence (1-155) (SEQ ID NO: 91) (GenBank accession no. XM_004008909, which is hereby incorporated by reference in its entirety):

```
361 ATGGCTGAAG GAGAAACCAC AACCTTCAGG GCCCTGACTG AGAAGTTTAA CCTGCCTCTA

421 GGCAATTACA AGAAGCCCAA GCTCCTCTAT TGCAGCAACG GGGGCTACTT CCTGAGAATC

481 CTCCCAGATG GCAGAGTGGA TGGGACGAAG GACAGGAGCG ACCAGCACAT TCAGCTGCAG

541 CTCTATGCGG AAAGCATAGG GGAGGTGTAT ATTAAGAGTA CGGAGACTGG CCAGTTCTTG

601 GCCATGGACA CCAACGGGCT TTTGTACGGC TCACAAACAC CCAGTGAGGA ATGTTTGTTC

661 CTGGAAAGGC TGGAGGAAAA CCATTATAAC ACCTACATAT CCAAGAAGCA TGCAGAGAAG

721 AATTGGTTCA TTGGTCTCAA GAAGAACGGA AGCTCCAAAC TCGGTCCTCG GACTCACTTC

781 GGCCAGAAAG CCATCTTGTT TCTCCCCCTG CCAGTTTCCT CTGATTAA
```

Chicken FGF1 gene coding sequence (1-155) (SEQ ID NO: 92) (GenBank accession no. NM_205180, which is hereby incorporated by reference in its entirety):

```
 52                                                      ATGGCCGAG

 61 GGGGAGATAA CCACCTTCAC CGCCCTGACC GAGCGCTTCG GCCTGCCGCT GGGCAACTAC

121 AAGAAGCCCA AACTCCTGTA CTGCAGCAAC GGGGGCCACT TCCTACGGAT CCTGCCGGAC

181 GGCAAGGTGG ACGGGACGCG GGACCGGAGT GACCAGCACA TTCAGCTGCA GCTCAGCGCG

241 GAAGATGTGG GCGAGGTCTA TATAAAGAGC ACAGCGTCGG GGCAGTACCT GGCAATGGAC

301 ACCAACGGGC TCCTGTATGG CTCGCAGCTA CCAGGCGAGG AGTGCTTGTT CCTTGAGAGG

361 CTCGAGGAGA ACCATTACAA CACATACATC TCCAAAAAGC ACGCAGACAA GAACTGGTTC

421 GTCGGGCTGA AGAAAAACGG GAACAGCAAG CTGGGGCCGC GGACTCACTA TGGGCAAAAG

481 GCGATCCTCT TCCTCCCATT GCCGGTGTCG GCTGACTGA
```

Alpaca FGF1 gene coding sequence (1-155, excluding 1-57) (SEQ ID NO: 93) (Ensembl accession no. ENSVPAT00000008395, which is hereby incorporated by reference in its entirety):

```
  1 CAGCTGCAGC TCAGTGCGGA AAGCGTGGGG GAGGTGTATA TAAAGAGTAC CGAGACTGGC

 61 CAGTACTTGG CCATGGACAC CGACGGGCTT TTGCACGGCT CACAGACACC AAATGAGGAA

121 TGTTTGTTCC TGGAAAGGCT GGAGGAGAAC CATTACAACA CCTACACGTC CAAGAAGCAC

181 GCCGAAAAGA ATTGGTTTGT TGGTCTCAAG AAGAATGGAA GCTGCAAACG CGGTCCTCGG

241 ACTCACTACG GCCAGAAGGC GATCTTGTTT CTCCCCTTGC CAGTCTCCTC TGATTAA
```

Anole lizard FGF1 gene coding sequence (1-155) (SEQ ID NO: 94) (Ensembl accession no. ENSACAT00000013467, which is hereby incorporated by reference in its entirety):

```
  1 ATGGCTGAAG GTGAAATAAC AACATTCACA GCCTTGACCG AGAGGTTTGC TCTCCCAATG

 61 GAGAATTACA AGAAGCCCAA ACTCCTGTAT TGCAGCAATG GAGGCCACTT CCTGAGGATC

121 CTTCCAGATG GAAAAGTGGA TGGCACCATG GACCGGAATG ACAGCTATAT TCAGTTGCTG

181 TTAACAGCAG AAGATGTGGG TGTGGTATAT ATAAAAGGCA CTGAGACCGG GCAGTACTTG
```

TABLE 2-continued

241 GCCATGGATG CCAATGGACA TTTATATGGC TCGCAGTTGC CAACAGAAGA GTGTTTATTT

301 GTGGAAACGC TGGAAGAAAA CCATTACAAT ACATATACCT CAAAGATGCA TGGCGATAAG

361 AAGTGGTATG TTGGCTTGAA AAAGAATGGG AAAGGCAAAC TGGGGCCACG GACTCATCGC

421 GGCCAAAAGG CAATACTTTT CCTTCCACTG CCAGTATCAC CTGATTAG

Bushbaby FGF1 gene coding sequence (1-155) (SEQ ID NO: 95) (Ensembl accession no. ENSOGAT00000005081, which is hereby incorporated by reference in its entirety):

1 ATGGCTGAAG GGGAAATCAC AACCTTCACA GCCCTCACAG AGAAGTTTAA TCTGCCTCTA

61 GGAAATTACA AGAAGCCCAA GCTCCTCTAC TGTAGCAACG GGGGTCACTT TCTGAGGATC

121 CTGCCGGATG GCACCGTGGA TGGGACACAA GACAGGAGCG ACCAGCACAT TCAGCTGCAG

181 CTCAGTGCGG AAAGCGTGGG GGAGGTGTAT ATAAAGAGTA CCCAGACTGG CCAGTACTTG

241 GCCATGGACT CCGACGGGCT TTTATACGGC TCACAAACAC CAAATGAGGA ATGCCTGTTC

301 CTGGAACGGC TGGAGGAAAA CCATTACAAC ACCTATGTGT CCAAGAAGCA CGCCGAGAAG

361 AATTGGTTTG TCGGTCTCAA GAAGAACGGA AGTTGCAAAC GTGGTCCTCG GACTCACTAC

421 GGCCAGAAAG CAATCTTGTT TCTCCCCCTG CCAGTCTCCT CTGATTAA

Cat FGF1 gene coding sequence (1-155) (SEQ ID NO: 96) (Ensembl accession no. ENSFCAT00000009123, which is hereby incorporated by reference in its entirety):

1 ATGGCTGAAG GGGAAATCAC AACCTTCACG GCCCTGACGG AGAAGTTCAA TCTGCCTCCA

61 GGGAATTACA AGAAACCCAA ACTCCTCTAC TGTAGCAACG GGGGCCACTT CCTGAGGATC

121 CTTCCAGATG GCACAGTGGA TGGGACGAGG GACAGGAGCG ACCAGCACAT TCAGCTGCAG

181 CTCAGTGCGG AAAGCGTGGG GGAGGTGTAT ATAAAGAGTA CCGAGACTGG CCAGTACTTG

241 GCCATGGACA CCGACGGGCT TTTGTACGGC TCACAGACAC CAAATGAGGA ATGCTTGTTC

301 CTGGAAAGGC TGGAAGAAAA CCATTACAAC ACCTACACAT CCAAGAAGCA CGCAGAAAAG

361 AATTGGTTTG TGGGTCTCAA GAAGAATGGA AGCTGCAAAC GCGGTCCCCG GACTCACTAT

421 GGCCAGAAGG CAATTTTGTT TCTCCCCCTG CCAGTCTCCT CTGATTAA

Chinese softshell turtle FGF1 gene coding sequence (1-155) (SEQ ID NO: 97) (Ensembl accession no. ENSPSIT00000016432, which is hereby incorporated by reference in its entirety):

131 ATGGCTGAAG GGGAAATAAC AACGTTCACC GCCCTGACCG AAAAATTCAA

181 CCTTCCCCTG GGGAATTACA AGAATCCCAA ACTCTTATAT TGCAGCAATG GAGGCTACTT

241 CTTGAGGATA CATCCAGATG GCAAAGTAGA TGGGACAAGG GACCGAAGTG ACCAACACAT

301 TCAGCTGCAG CTAAGTGCGG AAAGCGTGGG TGAGGTATAT ATAAAGAGCA CTGAGTCTGG

361 ACAGTTTTTG GCTATGGACG CCAATGGACT TTTATATGGA TCACTGTCAC CGAGTGAGGA

291 ATGCTTATTC TTGGAAAGAA TGGAAGAAAA TCATTATAAC ACCTACATCT CCAAGAAGCA

351 TGCAGACAAG AACTGGTTCG TTGGCTTAAA GAAGAATGGA AGCTGCAAAC TGGGACCGCG

411 GACGCACTAC GGCCAAAAGG CCGTCCTTTT CCTTCCACTG CCAGTGTCAG CTGATTAA

Coelacanth FGF1 gene coding sequence (1-155) (SEQ ID NO: 98) (Ensembl accession no. ENSLACT00000015212, which is hereby incorporated by reference in its entirety):

1 ATGGCTGAAG ACAAAATAAC AACACTGAAG GCCTTGGCTG AAAAATTTAA CCTTCCTATG

61 GGAAATTACA AGAAAGCAAA ACTCCTCTAC TGCAGCAACG GAGGGTATTT CCTGCGAATA

121 CCCCCAGACG GGAAAGTGGA AGGAATTAGA GAACGAAGCG ACAAGTACAT TCAGCTGCAA

181 ATGAATGCAG AAAGTTTAGG CATGGTGTCT ATAAAGGGTG TGGAGGCAGG GCAATACCTA

TABLE 2-continued

```
241 GCTATGAATA CAAATGGACT CCTGTATGGA TCTCAGTCTC TAACTGAAGA ATGCCTTTTC
301 ATGGAAAAGA TGGAAGAAAA CCACTACAAC ACATACAGGT CTAAGACACA TGCAGATAAA
361 AACTGGTATG TTGGCATTAG AAAGAACGGT AGCATCAAAC CAGGACCAAG GACTCACATT
421 GGCCAAAAGG CTGTTCTTTT TCTCCCTCTG CCTGCCTCGA GTGATTAG
```

Dolphin FGF1 gene coding sequence (1-155) (SEQ ID NO: 99) (Ensembl accession no. ENSTTRT00000004742, which is hereby incorporated by reference in its entirety):

```
  1 ATGGCTGAAG GGGAAATCAC AACCTTCACA GCCCTGACCG AGAAGTTTAA TCTGCCTCCA
 61 GGGAATTACA AGAAGCCCAA ACTCCTCTAC TGTAGCAACG GGGGCCACTT CCTGAGGATC
121 CTTCCAGATG GCACAGTGGA TGGGACAAGG GACAGGAGTG ACCAGCACAT TCAGCTGCAG
181 CTCAGTGCGG AAAGCGTGGG GGAGGTGTAT ATAAAGAGTA CGGAGACTGG CCAGTACTTG
241 GCCATGGACA CCGACGGGCT TTTGTACGGC TCACAGACAC CCAATGAGGA ATGTTTGTTC
301 CTGGAAAGGT TGGAGGAAAA CCATTACAAC ACCTACGCAT CCAAGAAGCA TGCAGAAAAG
361 AATTGGTTCG TTGGTCTCAA GAAGAACGGA AGCTGCAAAC GCGGTCCTCG GACTCACTAC
421 GGCCAGAAAG CAATCTTGTT TCTCCCCCTG CCAGTCTCCT CCGATTAA
```

Ferret FGF1 gene coding sequence (1-155) (SEQ ID NO: 100) (Ensembl accession no. ENSMPUT00000008013, which is hereby incorporated by reference in its entirety):

```
  1                                      ATGGCT GAAGGGGAAA TCACAACCTT
 61 CACAGCCCTG ATGGAGAAGT TTAATCTGCC TGCGGGGAAT TACAAGAAGC CCAAACTCCT
121 CTACTGTAGC AATGGGGGCC ACTTCCTGAG GATCCTTCCA GATGGCACAG TGGACGGCAC
181 AAGGGACAGG AGCGACCAGC ACATTCAGCT GCAGCTCAGT GCGGAAAGCG TGGGGGAGGT
241 GTACATAAAG AGTACCGAGA CTGGCCAGTA CTTGGCCATG GACACCGATG GGCTTTTGTA
301 CGGCTCACAA ACACCAAATG AGGAATGTCT GTTCCTGGAA AGGCTGGAGG AAAACCATTA
361 CAACACCTAC ACATCCAAGA AGCACGCTGA GAAGAATTGG TTTGTAGGTC TCAAGAAGAA
421 CGGAAGCTGC AAACGCGGTC CTCGGACTCA CTATGGCCAG AAAGCAATTC TGTTTCTCCC
481 CCTGCCAGTC TCCTCTGATT AA
```

Gibbon FGF1 gene coding sequence (1-155) (SEQ ID NO: 101) (Ensembl accession no. ENSNLET00000012455, which is hereby incorporated by reference in its entirety):

```
241                                                 ATGG CCGAAGGGGA
301 AATCACCACC TTCACAGCCC TGACCGAGAA GTTTAATCTG CCTCCAGGGA ATTACAAGAA
361 GCCCAAACTC CTCTACTGTA GCAACGGGGG CCACTTCTTG AGGATCCTTC CGGATGGCAC
421 AGTGGATGGG ACAAGGGACA GGAGCGACCA GCACATTCAG CTGCAGCTCA GTGCGGAAAG
481 CGTGGGGGAG GTGTATATAA AGAGTACCGA GACTGGCCAG TACTTGGCCA TGGACACCGA
541 CGGGCTTTTA TACGGCTCAC AGACACCAAA TGAGGAATGT TTGTTCCTGG AAAGGCTGGA
601 GGAGAACCAT TACAACACCT ATATATCCAA GAAGCATGCA GAGAAGAATT GGTTTGTTGG
661 CCTCAAGAAG AATGGAAGCT GCAAACGCGG TCCTCGGACT CACTATGGCC AGAAAGCAAT
721 CTTGTTTCTC CCCCTGCCAG TCTCTTCTGA TTAA
```

TABLE 2-continued

Gorilla FGF1 gene coding sequence (1-155) (SEQ ID NO: 102) (Ensembl accession no. ENSGGOT00000025344, which is hereby incorporated by reference in its entirety):

```
121                                                 ATGG CTGAAGGGGA
181 AATCACCACC TTCACAGCCC TGACCGAGAA GTTTAATCTG CCTCCAGGGA ATTACAAGAA
241 GCCCAAACTC CTCTACTGTA GCAATGGGGG CCACTTCTTG AGGATCCTTC CGGATGGCAC
301 AGTGGATGGG ACAAGGGACA GGAGCGACCA GCACATTCAG CTGCAGCTCA GTGCGGAAAG
361 CGTGGGGGAG GTGTATATAA AGAGTACCGA GACTGGCCAG TACTTGGCCA TGGACACCGA
421 CGGGCTTTTA TACGGCTCAC AGACACCAAA TGAGGAATGT TTGTTCCTGG AAAGGCTGGA
481 GGAGAACCAT TACAACACCT ATATATCCAA GAAGCATGCA GAGAAGAATT GGTTTGTTGG
541 CCTCAAGAAG AATGGAAGCT GCAAACGCGG TCCTCGGACT CACTATGGCC AGAAAGCAAT
601 CTTGTTTCTC CCCCTGCCAG TCTCTTCCGA TTAA
```

Hedgehog FGF1 gene coding sequence (1-155) (SEQ ID NO: 103) (Ensembl accession no. ENSEEUT00000005832, which is hereby incorporated by reference in its entirety):

```
  1 ATGGCTGAAG GAGAAATCAC CACCTTCACG GCCCTGACTG AGAAGTTTAA TCTGCCACTA
 61 GGGAATTACA AGAAGCCCAA GCTCCTCTAC TGTAGCAACG GGGGCCACTT CCTGAGGATC
121 CTTCCAGATG GCACCGTGGA TGGGACAAGG GACAGGAGCG ACCAGCATAT TCAGCTGCAG
181 CTCAGTGCGG AAAGCGTGGG GGAGGTGTAT ATAAAGAGTA CGGAGACTGG CCAGTACTTG
241 GCCATGGACA CCGACGGGCT TTTATACGGC TCACAAACAC CAAATGAGGA ATGTCTGTTC
301 CTTGAAAGGC TGGAAGAGAA CCATTACAAT ACCTACACAT CCAAGAAGCA TGCCGAGAAG
361 AACTGGTTTG TTGGCCTCAA GAAGAATGGA AGCTGCAAGC GTGGTCCTCG GACTCATTAT
421 GGCCAGAAAG CTATTTTGTT TCTCCCCCTG CCAGTTTCCT CTGATTAA
```

Hyrax FGF1 gene coding sequence (1-155, excluding 1-90) (SEQ ID NO: 104) (Ensembl accession no. ENSPCAT00000011746, which is hereby incorporated by reference in its entirety):

```
  1 ATGGCTGAAG GCGAAATCAC AACCTTCACA GCCCTGACTG AGAAGTTTAA CCTGCCACTA
 61 GAGAATTACA AGAAGCCCAA ACTCCTCTAC TGTAGCAACG GAGGCCACTT CCTGAGGATC
121 CTTCCGGACG GCACAGTGGA TGGCACCAGG GACAGGAGTG ACCAGCACAT TCAGCTGCAG
181 CTCAGTGCGG AAAGCGTGGG GGAGGTGTAT ATAAAGGGCA CCGAGACTGG CCAGTACTTG
241 GCCATGGACA CCGACGGGCT TTTATATGGC TCA
```

Kangaroo rat FGF1 gene coding sequence (1-155, excluding 1-16 and 58-155) (SEQ ID NO: 105) (Ensembl accession no. ENSDORT00000007345, which is hereby incorporated by reference in its entirety):

```
  1 ATGGCTGAAG GGGAAATCAC AACCTTCACA GCCCTGACGG AAAGGTTTAA ----------
    ---------- ---------- ---------- ---------- ---------- ----------
 51 ---------- ---------- ---------- ---------- ---------T TCAGCTGCAA
 62 CTGAGTGCGG AAAGCGTGGG GGAGGTCTAT ATAAAGAGCA CCGAGACTGG CCAATACTTG
122 GCCATGGATG CCGACGGGCT TTTATACGGC TCACAGACAC CTGATGAAGA ATGCTTGTTC
182 CTGGAGAGGC TGGAAGAAAA TCATTATAAC ACCTACATAG CCAAGAAACA TGCTGAAAAG
242 AATTGGTTTG TCGGCCTCAA AAAGAATGGA AGCTGCAAGC GTGGTCCTCG GACTCACTAT
302 GGCCAGAAAG CAATCCTGTT CCTCCCCTTG CCTGTCTCCT CTGATTAG
```

TABLE 2-continued

Lamprey FGF1 gene coding sequence (1-155, excluding 94-155) (SEQ ID NO: 106) (Ensembl accession no. ENSPMAT00000010729, which is hereby incorporated by reference in its entirety):

```
  1 ATGGAGGTGG GCCACATCGG CACGCTGCCC GTGGTCCCCG CGGGGCCCGT GTTCCCCGGC
 61 AGTTTCAAGG AGCCACGGCG CCTCTACTGC CGCAGCGCGG GCCACCACCT CCAGATCCTG
121 GGGGACGGCA CCGTGAGTGG CACCCAGGAC GAGAACGAGC CCCACGCCGT TCTGCAGCTG
181 CAGGCGGTGC GCCGCGGGGT GGTGACGATC CGTGGGCTCT GCGCCGAGAG GTTCCTCGCC
241 ATGAGCACGG AGGGACACCT GTACGGGGCG GTGAGG
```

Lesser hedgehog tenrec FGF1 gene coding sequence (1-155, excluding 1-57) (SEQ ID NO: 107) (Ensembl accession no. ENSETET00000017851, which is hereby incorporated by reference in its entirety):

```
  1 CAGCTGAAGC TCGTTGCCGA AAGCGTGGGG GTGGTGTATA TAAAGAGCAT CAAGACCGGC
 61 CAGTACTTGG CCATGAACCC CGACGGGCTT TTATACGGCT CCGAGACCCC AGAGGAAGAA
121 TGCTTGTTCC TGGAAACGCT GGAGGAAAAC CACTACACCA CCTTCAAATC TAAGAAGCAC
181 GTAGAGAAGA ATTGGTTCGT TGGTCTCCGG AAGAATGGAA GGGTCAAGAT CGGGCCTCGG
241 ACTCACCAAG GCCAGAAAGC AATCTTGTTC CTGCCCCTCC CGGTGTCCTC TGATTAA
```

Rhesus monkey FGF1 gene coding sequence (1-155) (SEQ ID NO: 108) (Ensembl accession no. ENSMMUT00000033070, which is hereby incorporated by reference in its entirety):

```
 36                                      ATGGC TGAAGGGGAA ATCACCACGT
 61 TCACAGCCCT GACCGAGAAG TTTAATCTGC CTCCAGGGAA TTACAAGAAG CCCAAACTGC
121 TCTACTGTAG CAATGGGGGC CACTTCTTGA GGATCCTTCC GGATGGCACA GTGGATGGGA
181 CAAGGGACAG GAGCGACCAG CACATTCAGC TGCAGCTCAG TGCGGAAAGC GTGGGGGAGG
241 TGTATATAAA GAGTACCGAG ACTGGCCAGT ACTTGGCCAT GGACACCGAC GGGCTTTTAT
301 ACGGCTCACA GACACCAAAT GAGGAATGTT TGTTCCTGGA AAGGCTGGAG GAGAACCATT
361 ACAACACCTA TACATCCAAG AAGCACGCAG AGAAGAATTG GTTTGTTGGC CTCAAGAAGA
421 ATGGAAGCTG CAAACGTGGT CCTCGGACTC ACTATGGCCA GAAAGCAATC TTGTTTCTTC
481 CCCTGCCAGT CTCTTCTGAT TAA
```

Megabat FGF1 gene coding sequence (1-155) (SEQ ID NO: 109) (Ensembl accession no. ENSPVAT00000004596, which is hereby incorporated by reference in its entirety):

```
  1 ATGGCCGAGG GGGAAGTCAC GACGTTCACG GCCCTGACCG AGAGGTTTAA CCTGCCTCCA
 61 GGGAATTACA AGAAGCCCAA ACTTCTCTAC TGCAGCAACG GGGGCCACTT CCTGAGGATC
121 CTCCCAGATG GCACAGTGGA TGGGACAAGG GACAAGAGCG ACCAGCACAT TCAGCTGCAG
181 CTCAGTGCGG AAAGTGTGGG GGAGGTGTAT ATAAAGAGCA CCGAGAGTGG CCAGTACTTG
241 GCCATGGACT CCGACGGGCT TTTGTACGGC TCACAGACAC CAGATGAGGA CTGTTTGTTC
301 CTGGAAAGGC TGGAGGAAAA CCATTACAAC ACCTACACAT CCAAGAAGCA CGCAGAGAAG
361 AATTGGTTTG TTGGGCTCAA GAAGAATGGA AGCTGCAAGC GCGGTCCCCG GACTCACTAC
421 GGCCAGAAAG CGATCCTGTT TCTCCCCCTG CCAGTCTCCT CTGATTAG
```

Microbat FGF1 gene coding sequence (1-155) (SEQ ID NO: 110) (Ensembl accession no. ENSMLUT00000007098, which is hereby incorporated by reference in its entirety):

```
 66      ATGGC TGAGGGGGAA GTCACCACAT TCACGGCCCT GACCGAGAGG TTCAATCTGC
121 CTCTGGAGAA CTACAAGAAG CCCAAGCTTC TCTACTGCAG CAACGGGGGC CACTTCCTGC
181 GGATCCTCCC AGACGGCACC GTGGACGGGA CGAGGGACAG GAGCGACCAG CACATTCAGC
```

TABLE 2-continued

241 TGCAGCTCAG TGCGGAAAGC GTGGGGGAGG TGTATATAAA GAGCACCGAG AGTGGCCAGT

301 ACTTGGCCAT GGACTCCGAC GGGCTTTTGT ACGGCTCACA AACACCCAAT GAGGAATGTT

361 TGTTCCTGGA AAGGCTGGAG GAGAACCACT ACAACACCTA CACGTCCAAG AAGCACGCAG

421 AAAAGAATTG GTTCGTTGGG CTCAAGAAGA ACGGAAGCTG CAAGCGTGGT CCTCGGACGC

481 ATTATGGCCA GAAAGCAATC TTGTTTCTCC CCCTGCCAGT CTCCTCCGAT TAA

Mouse lemur FGF1 gene coding sequence (1-155) (SEQ ID NO: 111) (Ensembl accession no. ENSMICT00000009454, which is hereby incorporated by reference in its entirety):

1 ATGGCCGAAG GGGAGATCAC AACCTTCACG GCCCTCACCG AGAAGTTTAA CCTGCCTCCG

61 GGGAACTACA AGAAGCCCAA GCTCCTCTAC TGCAGCAACG GCGGCCACTT CCTGCGCATC

121 CTTCCCGACG GCACCGTGGA TGGCACGAGA GACAGGAGCG ACCAGCACAT TCAGCTGCAG

181 CTCAGTGCGG AAAGCGCGGG GGAGGTGTAT ATAAAGAGCA CCCAGACTGG CCGGTACTTG

241 GCCATGGACG CCGACGGGCT TTTATACGGC TCACAAACAC CAAATGAGGA ATGTTTGTTC

301 CTGGAAAGGC TGGAGGAAAA CCATTACAAC ACCTACGTAT CCAAGAAGCA CGCAGAGAAG

361 AATTGGTTTG TTGGCCTCAA GAAGAATGGA AGTTGCAAAC GCGGCCCCCG GACTCACTAT

421 GGCCAGAAAG CAATCTTGTT TCTGCCCCTG CCAGTCTCCT CTGATTAA

Pika FGF1 gene coding sequence (1-155, excluding 57-67) (SEQ ID NO: 112) (Ensembl accession no. ENSOPRT00000012854, which is hereby incorporated by reference in its entirety):

1 ATGGCCGAGG GAGAAGTCAC CACCTTCTCA GCCCTGACGG AGAAGTTCAA TCTGCCTGGA

61 GGAAACTACA AGTTGCCCAA GCTCCTTTAC TGTAGCAACG GAGGCCACTT CCTGAGGATC

121 CTTCCAGATG GCACAGTGGA TGGGACCAGG GACAGGAGCG ACCTGCACA- ----------

170 ---------- ---------- -GAGGTGTTT ATAAAGAGTA CGGAGACTGG CCAGTACTTG

209 GCTATGGACA CCGATGGCCT TTTATATGGC TCGCAGACAC CCAGTGAGGA GTGTTTGTTC

269 CTGGAGCGGC TGGAGGAGAA CCACTACAAC ACCTACACAT CCAAGAAGCA TGCCGAGAAG

329 AACTGGTTTG TGGGCATCAA GAAGAATGGA AGCTGCAAGC GTGGTCCTCG GACTCACTAC

389 GGCCAGAAAG CCATCTTGTT TCTCCCTCTG CCAGTCTCTT CTGACTAA

Rat FGF1 gene coding sequence (1-155) (SEQ ID NO: 113) (Ensembl accession no. ENSRNOT00000018577, which is hereby incorporated by reference in its entirety):

268 ATG GCCGAAGGGG AGATCACAAC CTTTGCAGCC

301 CTGACCGAGA GGTTCAATCT GCCTCTAGGG AACTACAAAA AACCCAAACT GCTCTACTGC

361 AGCAACGGGG GCCACTTCTT GAGGATTCTT CCCGATGGCA CCGTGGATGG GACCAGGGAC

421 AGGAGCGACC AGCACATTCA GCTGCAGCTC AGTGCGGAAA GCGCGGGCGA AGTGTATATA

481 AAGGGTACAG AGACTGGCCA GTACTTGGCC ATGGACACCG AAGGGCTTTT ATACGGCTCG

541 CAGACACCAA ATGAAGAATG CCTATTCCTG GAAAGGCTAG AAGAAAACCA TTATAACACT

601 TACACATCCA AGAAGCACGC GGAGAAGAAC TGGTTTGTGG GCCTCAAGAA GAACGGGAGT

661 TGTAAGCGCG GTCCTCGGAC TCACTACGGC CAGAAAGCCA TCTTGTTTCT CCCCCTCCCG

721 GTATCTTCTG ACTAA

Sloth FGF1 gene coding sequence (1-155) (SEQ ID NO: 114) (Ensembl accession no. ENSCHOT00000012416, which is hereby incorporated by reference in its entirety):

1 ATGGCTGAAG GGGAAATCAC AACCTTCACA GCTCTGATGG AGAAGTTTAA CCTGCCACCA

61 GGGAATTACA TGAAGCCCAA ACTCCTCTAC TGTAGCAACG GGGGCCACTT CTTGAGGATC

TABLE 2-continued

```
121 CTTCCAGACG GCACAGTGGA TGGGACAAGG GACAGGAGCG ACCTGCACAT TCAGCTGCAG

181 CTCAGTGCGG AAAGCGTGGG GGAGGTGTAT ATAAAGAGTG CGGAGACCGG CCAGTACTTA

241 GCCATGGACA CCGGCGGGCT TTTATACGGC TCACAGACAC CAAGTGAGGA ATGCCTGTTC

301 CTAGAAAGGC TGGAGGAAAA CCATTACAAC ACCTACGTAT CCAAGAAGCA TGCGGAGAAG

361 AACTGGTTCG TTGGCCTAAA GAAGAATGGA AGCAGCAAAC GCGGCCCCCG GACTCACTAT

421 GGCCAGAAAG CCATCTTGTT TCTTCCCCTG CCAGTCTCCT CTGATTAA
```

Squirrel FGF1 gene coding sequence (1-155) (SEQ ID NO: 115) (Ensembl accession no. ENSSTOT00000029249, which is hereby incorporated by reference in its entirety):

```
  1                                                        ATGG

  5 CTGAAGGGGA AATCACAACC TTCACAGCCC TGACCGAGAA GTTCAATCTG CCTCCAGGGA

 65 ACTACAAGAA GCCCAAACTG CTCTACTGTA GCAACGGAGG CCACTTCTTG AGGATCCTTC

125 CTGATGGCAC AGTGGATGGG ACAAGAGACA GGAGCGACCA ACACATTCAG CTGCAGCTCA

185 GTGCGGAAAG CGTGGGGGAG GTGTATATAA AGAGTACCGA GACCGGCCAG TACTTGGCCA

245 TGGACACCGA CGGGCTTTTA TATGGCTCAC AGACCCCAAA TGAGGAATGC TTATTCCTGG

305 AAAGGCTGGA GGAAAACCAT TACAACACGT ACACATCCAA GAAGCATGCA GAGAAGAATT

365 GGTTTGTTGG CCTCAAGAAG AACGGAAGCT GCAAGCGCGG TCCCCGGACT CACTATGGCC

425 AGAAAGCGAT CTTGTTTCTC CCACTGCCTG TCTCCTCTGA TTAG
```

Tarsier FGF1 gene coding sequence (1-155) (SEQ ID NO: 116) (Ensembl accession no. ENSTSYT00000007425, which is hereby incorporated by reference in its entirety):

```
  1 ATGGCCGAAG GGGAAATCAC AACCTTCACA GCCCTGACCG AGAAGTTCAA CCTGCCCCCG

 61 GGGAATTACA AGAAGCCCAA ACTCCTCTAC TGCAGCAACG GGGGCCACTT CTTGAGGATC

121 CTTCCGGATG GCACTGTGGA TGGAACGAGG GACAGGAGCG ACCAGCACAT TCAGCTGCAG

181 CTCAGCGCGG AAAGCGTGGG GGAGGTGTAT ATAAAGAGTA CCGAGACCGG CCAGTACTTG

241 GCCATGGACA CCGACGGGCT TTTGTACGGC TCACAGACAC CAAATGAGGA GTGTCTGTTC

301 CTGGAAAGGC TGGAAGAGAA TCATTACAAT ACCTACGTGT CCAAGAAGCA TGCGGAGAAG

361 AATTGGTTTG TCGGCCTCAA GAAGAATGGA AGCTGCAAAC GCGGTCCTCG GACTCACTAT

421 GGCCAGAAAG CAATCTTGTT TCTCCCCCTG CCAGTTTCCT CTGATTAA
```

Tree shrew FGF1 gene coding sequence (1-155) (SEQ ID NO: 117) (Ensembl accession no. ENSTBET00000011861, which is hereby incorporated by reference in its entirety):

```
  1 ATGGCTGAAG GGGAAATCAC GACCTTCGCA GCCCTGACCG AGAAGTTTGA TCTGCCTCCA

 61 GGGAATTACA AGAAGCCCAA ACTTCTCTAC TGTAGCAACG GGGGCCATTT CTTGAGGATT

121 CTTCCAGATG GCACCGTGGA TGGGACAAGA GACAGGAGCG ACCAGCACAT TCAGCTGCAG

181 CTCACTGCGG AAAACGTGGG GGAGGTGTAC ATAAAGAGTA CGGAGACTGG CCAGTACTTG

241 GCCATGGACG CCGACGGGCT TTTATATGGC TCACAGACAC CAAACGAGGA ATGTTTGTTC

301 CTGGAAAGGC TGGAGGAGAA CCATTACAAC ACCTACATAT CCAAGAAGCA CGCAGAGAAG

361 AATTGGTTTG TTGCCCTCAA GAAGAACGGA AGCTGCAAAC TCGGTCCTCG GACTCACTAT

421 GGCCAGAAAG CAATCTTGTT TCTCCCCCTG CCAGTCTCCT CTGATTAA
```

TABLE 2-continued

Turkey FGF1 gene coding sequence (1-155, excluding 57-155) (SEQ ID NO: 118) (Ensembl accession no. ENSMGAT00000017372, which is hereby incorporated by reference in its entirety):

```
  1 ATGGCCGAGG GGGAGATAAC CACCTTCACA GCCCTGACCG AGCGCTTCGG CCTGCCGCTG
 61 GGCAACTACA AGAAGCCCAA ACTCCTGTAC TGCAGCAACG GGGGCCACTT CCTACGGATC
121 CTGCCGGACG GCAAGGTGGA CGGGACGCGG GACCGGAGCG ACCAGCAC
```

Wallaby FGF1 gene coding sequence (1-155) (SEQ ID NO: 119) (Ensembl accession no. ENSMEUT00000016544, which is hereby incorporated by reference in its entirety):

```
  1 ATGGCCGAAG GGGAGATCAC AACCTTCACA GCCCTGACCG AAAGATTTAA CCTGCCACTG
 61 GGGAATTACA AGAAGCCCAA GCTTCTCTAC TGTAGCAATG GGGGCCACTT TTTGAGGATC
121 CTTCCTGATG GCAAAGTGGA TGGGACAAGG GACAGAAATG ATCAACACAT TCAACTGCAA
181 CTAAGCGCGG AAAGCGTGGG TGAGGTGTAT ATAAAGAGCA CTGAGTCTGG GCAGTATTTG
241 GCCATGGACA CCAATGGACT TTTATATGGC TCACAGACCC CCAGCGAAGA ATGCTTATTC
301 CTGGAGAGGT TGGAGGAGAA TCATTACAAC ACCTACATAT CAAAGAAGCA TGCGGAGAAA
361 AATTGGTTTG TTGGCCTCAA GAAGAACGGA AGTTGCAAAA GAGGTCCCAG GACTCACTAT
421 GGCCAGAAAG CCATCCTATT CCTTCCCCTC CCTGTGTCCT CTGAGTAA
```

Zebrafish FGF1 gene coding sequence (1-147) (SEQ ID NO: 120) (Ensembl accession no. ENSDART00000005842, which is hereby incorporated by reference in its entirety):

```
178                                                          ATG
181 ACCGAGGCCG ATATTGCGGT AAAGTCCAGC CCGCGCGACT ATAAAAAACT GACGCGGCTG
241 TACTGTATGA ATGGAGGATT TCACCTTCAG ATCCTGGCGG ACGGGACAGT GGCTGGAGCA
124 GCAGACGAAA ACACATACAG CATACTGCGC ATAAAAGCAA CAAGTCCAGG AGTGGTGGTG
184 ATCGAAGGAT CAGAAACAGG TCTTTACCTC TCGATGAATG AACATGGCAA GCTGTACGCT
244 TCATCATTAG TGACGGATGA AAGTTATTTC CTGGAGAAGA TGGAGGAAAA CCACTACAAC
304 ACATATCAGT CTCAAAAGCA CGGTGAAAAC TGGTACGTCG GAATAAAAAA GAACGGGAAA
364 ATGAAACGGG GCCCAAGAAC TCACATCGGA CAAAAGGCCA TTTTCTTTCT TCCACGACAG
424 GTGGAGCAGG AAGAGGACTG A
```

As noted above, also encompassed within the present invention are portions of paracrine FGFs other than FGF1 (e.g., FGF2, FGF4, FGF5, FGF6, FGF9, FGF16, and FGF20). The portions derived from paracrine FGF2 include portions corresponding to the above-identified amino acid sequences of FGF1. Corresponding portions may be determined by, for example, sequence analysis and structural analysis.

In one embodiment, the paracrine FGF is FGF2. In one embodiment, the portion of the FGF2 is derived from human FGF2 having the amino acid sequence of SEQ ID NO: 121 (GenBank Accession No. EAX05222, which is hereby incorporated by reference in its entirety), as follows:

In one embodiment, the portion of the paracrine FGF includes an amino acid sequence beginning at any one of residues 1 to 25 and ending at any one of residues 151 to 155 of SEQ ID NO: 121. In one embodiment, the portion of the paracrine FGF includes amino acid residues 1-151, 1-152, 1-153, 1-154, 1-155, 2-151, 2-152, 2-153, 2-154, 2-155, 3-151, 3-152, 3-153, 3-154, 3-155, 4-151, 4-152, 4-153, 4-154, 4-155, 5-151, 5-152, 5-153, 5-154, 5-155, 6-151, 6-152, 6-153, 6-154, 6-155, 7-151, 7-152, 7-153, 7-154, 7-155, 8-151, 8-152, 8-153, 8-154, 8-155, 9-151, 9-152, 9-153, 9-154, 9-155, 10-151, 10-152, 10-153, 10-154, 10-155, 11-151, 11-152, 11-153, 11-154, 11-155, 12-151, 12-152, 12-153, 12-154, 12-155, 13-151, 13-152, 13-153, 13-154, 13-155, 14-151, 14-152, 14-153, 14-154, 14-155,

```
  1 MAAGSITTLP ALPEDGGSGA FPPGHFKDPK RLYCKNGGFF LRIHPDGRVD GVREKSDPHI
 61 KLQLQAEERG VVSIKGVCAN RYLAMKEDGR LLASKCVTDE CFFFERLESN NYNTYRSRKY
121 TSWYVALKRT GQYKLGSKTG PGQKAILFLP MSAKS
```

15-151, 15-152, 15-153, 15-154, 15-155, 16-151, 16-152, 16-153, 16-154, 16-155, 17-151, 17-152, 17-153, 17-154, 17-155, 18-151, 18-152, 18-153, 18-154, 18-155, 19-151, 19-152, 19-153, 19-154, 19-155, 20-151, 20-152, 20-153, 20-154, 21-155, 21-151, 21-152, 21-153, 21-154, 21-155, 22-151, 22-152, 22-153, 22-154, 22-155, 23-151, 23-152, 23-153, 23-154, 23-155, 24-151, 24-152, 24-153, 24-154, 24-155, 25-151, 25-152, 25-153, 25-154, or 25-155 of FGF2 (SEQ ID NO: 121). In one embodiment, the portion of the paracrine FGF includes amino acid residues 1-151 or 1-152 of SEQ ID NO: 121.

In one embodiment, the portion of the paracrine FGF of the chimeric protein includes an amino acid sequence that has at least 80%, at least 85%, at least 90%, at least 95%, at least 97% or at least 99% amino acid sequence identity to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence identity to an amino acid sequence beginning at any one of residues 1 to 25 and ending at any one of residues 151 to 155 of SEQ ID NO: 121. In one embodiment, the portion of the paracrine FGF includes an amino acid sequence that has at least 80%, at least 85%, at least 90%, at least 95%, at least 97% or at least 99% amino acid sequence homology to the corresponding amino acid sequence of native paracrine FGF (e.g., SEQ ID NO: 121). In one embodiment, the portion of the paracrine FGF includes an amino acid sequence that has at least 80%, at least 85%, at least 90%, at least 95%, at least 97% or at least 99% amino acid sequence homology to an amino acid sequence beginning at any one of residues 1 to 25 and ending at any one of residues 151 to 155 of SEQ ID NO: 121.

Also encompassed within the present invention are portions of paracrine FGFs other than FGF2 (e.g., FGF1, FGF4, FGF5, FGF6, FGF9, FGF16, and FGF20). The portions derived from paracrine FGFs other than FGF2 include portions corresponding to the above-identified amino acid sequences of FGF2. Corresponding portions may be determined by, for example, sequence analysis and structural analysis.

In one embodiment of the present invention, the portion of the paracrine FGF is derived from an ortholog of a human paracrine FGF. In one embodiment of the present invention, the portion of the paracrine FGF of the chimeric protein is derived from an ortholog of human FGF2. In one embodiment, the portion of the FGF2 is derived from *Gorilla, Pongo abelii, Macaca mulatta, Pan troglodytes, Pan paniscus, Saimiri boliviensis, Nomascus leucogenys, Equus caballus, Bos taurus, Papio Anubis, Vicugna pacos, Ovis aries, Capreolus, Loxodonta Africana, Sus scrofa, Ailuropoda melanoleuca, Choloepus hoffmanni, Bubalus bubalis, Canis lupus familiaris, Rattus norvegicus, Heterocephalus glaber, Otolemur garnettii, Mus musculus, Ictidomys tridecemlineatus, Felis catus, Cavia porcellus, Sarcophilus harrisii, Monodelphis domestica, Oryctolagus cuniculus, Meleagris gallopavo, Gallus gallus, Taeniopygia guttata, Cynops pyrrhogaster, Xenopus laevis, Didelphis albiventris, Myotis lucifugus, Anolis carolinensis, Dasypus novemcinctus, Tupaia belangeri, Xenopus silurana tropicalis, Latimeria chalumnae, Tetraodon nigroviridis, Gasterosteus aculeatus, Takifugu rubripes, Oncorhynchus mykiss, Salmo salar, Danio rerio, Oreochromis niloticus*, or *Oryzias latipes*. The portions of an ortholog of human paracrine FGF include portions corresponding to the above-identified amino acid sequences of FGF2. Corresponding portions may be determined by, for example, sequence analysis and structural analysis.

In one embodiment, the portion of the FGF2 of the chimeric protein of the present invention is derived from an ortholog of human FGF2 having the amino acid sequence shown in Table 3.

TABLE 3

Amino acid sequence of Gorilla gorilla (gorilla) FGF2 (SEQ ID NO: 122) (Ensembl accession no. ENSGGOP00000004720, which is hereby incorporated by reference in its entirety):

```
104                                                   MAAGSI TTLPALPEDG

120  GSGAFPPGHF KDPKRLYCKN GGFFLRIHPD GRVDGVREKS DPHIKLQLQA EERGVVSIKG

180  VCANRYLAMK EDGRLLASKC VTDECFFFER LESNNYNTYR SRKYTSWYVA LKRTGQYKLG

240  SKTGPGQKAI LFLPMSAKS
```

Amino acid sequence of *Pongo abelii* (sumatran orangutan) FGF2 (SEQ ID NO: 123) (GenBank accession no. XP_002815172, which is hereby incorporated by reference in its entirety):

```
168                                                       MAA GSITTLPALP

181  EDGGSGAFPP GHFKDPKRLY CKNGGFFLRI HPDGRVDGVR EKSDPHIKLQ LQAEERGVVS

241  IKGVCANRYL AMKEDGRLLA SKCVTDECFF FERLESNNYN TYRSRKYTSW YVALKRTGQY

301  KLGSKTGPGQ KAILFLPMSA KS
```

Amino acid sequence of *Macaca mulatta* (rhesus monkey) FGF2 (SEQ ID NO: 124) (GenBank accession no. XP_001099284, which is hereby incorporated by reference in its entirety):

```
83                              MAAGSITT LPALPEDGGS GAFPPGHFKD PKRLYCKNGG

121  FFLRIHPDGR VDGVREKSDP HIKLQLQAEE RGVVSIKGVC ANRYLAMKED GRLLASKCVT

181  DECFFFERLE SNNYNTYRSR KYTSWYVALK RTGQYKLGSK TGPGQKAILF LPMSAKS
```

TABLE 3-continued

Amino acid sequence of *Pan troglodytes* (chimpanzee) FGF2 (SEQ ID NO: 125) (GenBank accession no. NP_001103711, which is hereby incorporated by reference in its entirety):

134 MAAGSIT TLPALPEDGG SGAFPPGHFK DPKRLYCKNG GFFLRIHPDG

181 RVDGVREKSD PHIKLQLQAE ERGVVSIKGV CANRYLAMKE DGRLLASKCV TDECFFFERL

241 ESNNYNTYRS RKYTSWYVAL KRTGQYKLGS KTGPGQKAIL FLPMSAKS

Amino acid sequence of *Pan paniscus* (Pygmy chimpanzee) FGF2 (SEQ ID NO: 126) (GenBank accession no. XP_003816481, which is hereby incorporated by reference in its entirety):

112 MAAGSITTL

121 PALPEDGGSG AFPPGHFKDP KRLYCKNGGF FLRIHPDGRV DGVREKSDPH IKLQLQAEER

181 GVVSIKGVCA NRYLAMKEDG RLLASKCVTD ECFFFERLES NNYNTYRSRK YTSWYVALKR

241 TGQYKLGSKT GPGQKAILFL PMSAKS

Amino acid sequence of *Saimiri boliviensis boliviensis* (Bolivian squirrel monkey) FGF2 (SEQ ID NO: 127) (GenBank accession no. XP_003936290, which is hereby incorporated by reference in its entirety):

1 MAAGSITTLP ALPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESN NYNTYRSRKY

121 TSWYVALKRT GQYKLGSKTG PGQKAILFLP MSAKS

Amino acid sequence of *Nomascus leucogenys* (Northern white-cheeked gibbon) FGF2 (SEQ ID NO: 128) (GenBank accession no. XP_003271404, which is hereby incorporated by reference in its entirety):

1 MAAGSITTLP ALPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESN NYNTYRSRKY

121 TSWYVALKRT GQYKLGSKTG PGQKAILFLP MSAKS

Amino acid sequence of *Equus caballus* (horse) FGF2 (SEQ ID NO: 129) (GenBank accession no. NP_001182150, which is hereby incorporated by reference in its entirety):

1 MAAGSITTLP ALPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESN NYNTYRSRKY

121 SSWYVALKRT GQYKLGPKTG PGQKAILFLP MSAKS

Amino acid sequence of *Bos taurus* (cattle) FGF2 (SEQ ID NO: 130) (GenBank accession no. NP_776481, which is hereby incorporated by reference in its entirety):

1 MAAGSITTLP ALPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESN NYNTYRSRKY

121 SSWYVALKRT GQYKLGPKTG PGQKAILFLP MASKS

Amino acid sequence of *Papio anubis* (Olive baboon) FGF2 (SEQ ID NO: 131) (GenBank accession no. XP_003899210, which is hereby incorporated by reference in its entirety):

1 MAAGSITTLP ALPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESN NYNTYRSRKY

121 TSWYVALKRT GQYKLGSKTG PGQKAILFLP MSAKS

TABLE 3-continued

Amino acid sequence of *Vicugna pacos* (alpaca) FGF2 (SEQ ID NO: 132) (Ensembl accession no. ENSVPAP00000009804, which is hereby incorporated by reference in its entirety):

```
111                                                        MAAGSITTLP
121  ALPEDGGSGA FPPGHFKDPK RLYCKNGGFF LRIHPDGRVD GVREKSDPHI KLQLQAEERG
181  VVSIKGVCAN RYLAMKEDGR LLASKCVTDE CFFFERLESN NYNTYRSRKY SSWYVALKRT
241  GQYKLGPKTG PGQKAILFLP MSAKS
```

Amino acid sequence of Ovis aries (sheep) FGF2 (SEQ ID NO: 133) (GenBank accession no. NP_001009769, which is hereby incorporated by reference in its entirety):

```
  1  MAAGSITTLP ALPEDGGSSA FPPGHFKDPK RLYCKNGGFF LRIHPDGRVD GVREKSDPHI
 61  KLQLQAEERG VVSIKGVCAN RYLAMKEDGR LLASKCVTDE CFFFERLESN NYNTYRSRKY
121  SSWYVALKRT GQYKLGPKTG PGQKAILFLP MSAKS
```

Amino acid sequence of *Capreolus capreolus* (Western roe deer) FGF2 (partial amino acid sequence corresponding to human FGF2 residues 42 to 149) (SEQ ID NO: 134) (GenBank accession no. AAF73226, which is hereby incorporated by reference in its entirety):

```
  1  RIHPDGRVDG VREKSDPHIK LQLQAEERGV VSIKGVCANR YLAMKEDGRL LASKCVTDEC
 61  FFFERLESNN YNTYRSRKYS SWYVALKRTG QYKLGPKTGP GQKAILFL
```

Amino acid sequence of *Loxodonta africana* (elephant) FGF2 (partial amino acid sequence corresponding to human FGF2 residues 60 to 155) (SEQ ID NO: 135) (Ensembl accession no. ENSLAFP00000008249, which is hereby incorporated by reference in its entirety):

```
  1  VKLQLQAEER GVVSIKGVCA NRYLAMKEDG RLLASRCVTD ECFFFERLES NNYNTYRSRK
 61  YTSWYVALKR TGQYKLGSKT GPGQKAILFL PMSAKS
```

Amino acid sequence of *Sus scrofa* (pig) FGF2 (partial amino acid sequence corresponding to human FGF2 residues 36 to 155) (SEQ ID NO: 136) (GenBank accession no. CAE11791 and Ensembl accession no. ENSSSCP00000009695, which is hereby incorporated by reference in its entirety):

```
 1   NGGFFLRIHP DGRVDGVREK SDPHIKLQLQ AEERGVVSIK GVCANRYLAM KEDGRLLASK
 61  CVTDECFFFE RLESNNYNTY RSRKYSSWYV ALKRTGQYKL GPKTGPGQKA ILFLPMSAKS
```

Amino acid sequence of *Ailuropoda melanoleuca* (panda) FGF2 (partial amino acid sequence corresponding to human FGF2 residues 60 to 155) (SEQ ID NO: 137) (Ensembl accession no. ENSAMEP00000018489, which is hereby incorporated by reference in its entirety):

```
  1  VKLQLQAEER GVVSIKGVCA NRYLAMKEDG RLLASKCVTD ECFFFERLES NNYNTYRSRK
 61  YSSWYVALKR TGQYKLGPKT GPGQKAILFL PMSAKS
```

Amino acid sequence of *Choloepus hoffmanni* (sloth) FGF2 (SEQ ID NO: 138) (Ensembl accession no. ENSCHOP00000010051, which is hereby incorporated by reference in its entirety):

```
 14                                                           MAAGSIT
 21  TLPALPEDGG SGALPPGHFK DPKRLYCKNG GFFLRIHPDG RVDGVREKSD PHIKLQLQAE
 81  ERGVVSIKGV CANRYLAMKE DGRLQASKCV TDECFFFERL ESNNYNTYRS RKYSSWYVAL
141  KRTGQYKLGP KTGPGQKAIL FLPMSAKS
```

TABLE 3-continued

Amino acid sequence of *Bubalus bubalis* (water buffalo) FGF2 (SEQ ID NO: 139) (GenBank accession no. AFH66795, which is hereby incorporated by reference in its entirety):

1 MAAGSITTLP PLPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESS NYNTYRSRKY

121 SSWYVALKRT GQYKLGPKTG PGQKAILFLP MSAKS

Amino acid sequence of *Canis lupus familiaris* (dog) FGF2 (SEQ ID NO: 140) (GenBank accession no. XP_003432529, which is hereby incorporated by reference in its entirety):

40 M AAGSITTLPA LPEDGGSGAF

61 PPGHFKDPKR LYCKKGGFFL RIHPDGRVDG VREKSDPHVK LQLQAEERGV VSIKGVCANR

121 YLAMKEDGRL LASKCVTDEC FFFERLESNN YNTYRSRKYS SWYVALKRTG QYKLGPKTGP

181 GQKAILFLPM SAKS

Amino acid sequence of *Rattus norvegicus* (Norway rat) FGF2 (SEQ ID NO: 141) (GenBank accession no. NP_062178, which is hereby incorporated by reference in its entirety):

1 MAAGSITSLP ALPEDGGGAF PPGHFKDPKR LYCKNGGFFL RIHPDGRVDG VREKSDPHVK

61 LQLQAEERGV VSIKGVCANR YLAMKEDGRL LASKCVTEEC FFFERLESNN YNTYRSRKYS

121 SWYVALKRTG QYKLGSKTGP GQKAILFLPM SAKS

Amino acid sequence of *Heterocephalus glaber* (naked mole-rat) FGF2 (partial amino acid sequence corresponding to human FGF2 residues 22 to 155) (SEQ ID NO: 142) (GenBank accession no. EHB17407, which is hereby incorporated by reference in its entirety):

1 ppghfkdpkr lyckngffl rihpdgrvdg vreksdphvk lqlqaeergv vsikgvcanr 61 ylamkedgrl laskcvtdec ffferlesnn yntyrsrkys swyvalkrtg qyklgsktgp 121 gqkailflpm saks Amino acid sequence of *Otolemur garnettii* (bushbaby) FGF2 (SEQ ID NO: 143) (Ensembl accession no. ENSOGAP00000021960, which is hereby incorporated by reference in its entirety):

52 MAAGSITTL

61 PSLPEDGGSD AFPPGHFKDP KRLYCKNGGF FLRIHPDGRV DGVREKSDPY IKLQLQAEER

121 GVVSIKGVCA NRYLAMKEDG RLLASKLITD ECFFFERLES NNYNTYRSRK YSSWYVALKR

181 TGQYKLGSKT GPGQKAILFL PMSAKS

Amino acid sequence of *Mus musculus* (house mouse) FGF2 (SEQ ID NO: 144) (GenBank accession no. NP_032032, which is hereby incorporated by reference in its entirety):

1 MAASGITSLP ALPEDGGAAF PPGHFKDPKR LYCKNGGFFL RIHPDGRVDG VREKSDPHVK

61 LQLQAEERGV VSIKGVCANR YLAMKEDGRL LASKCVTEEC FFFERLESNN YNTYRSRKYS

121 SWYVALKRTG QYKLGSKTGP GQKAILFLPM SAKS

Amino acid sequence of *Ictidomys tridecemlineatus* (squirrel) FGF2 (partial amino acid sequence corresponding to human FGF2 residues 12 to 155) (SEQ ID NO: 145) (Ensembl accession no. ENSSTOP00000015653, which is hereby incorporated by reference in its entirety):

1 LPEDGGGAF PPGHFKDPKR LYCKNGGFFL RIHPDGRVDG VREKSDPHIK LQLQAEDRGV

61 VSIKGVCANR YLAMKEDGRL LASKCVTDEC FFFERLESNN YNTYRSRKYS SWYVALKRTG

121 QYKLGSKTGP GQKAILFLPM SAKS

TABLE 3-continued

Amino acid sequence of *Felis catus* (domestic cat) FGF2 (partial amino acid sequence corresponding to human FGF2 residues 25 to 130) (SEQ ID NO: 146) (GenBank accession no. ABY47638, which is hereby incorporated by reference in its entirety):

1 HFKDPKRLYC KNGGFFLRIH PDGRVDGVRE KSDPHIKLQL QAEERGVVSI KGVCANRYLA

61 MKEDGRLLAS KCVTDECFFF ERLESNNYNT YRSRKYSSWY VALKRT

Amino acid sequence of *Cavia porcellus* (guinea pig) FGF2 (partial amino acid sequence corresponding to human FGF2 residues 60 to 155) (SEQ ID NO: 147) (Ensembl accession no. ENSCPOP00000004847, which is hereby incorporated by reference in its entirety):

1 VKLQLQAEDR GVVSIKGVCA NRYLAMKEDG RLLASKCVTD ECFFFERLES NNYNTYRSRK

61 YSSWYVALKR TGQYKLGSKT GPGQKAILFL PMSAKS

Amino acid sequence of *Sarcophilus harrisii* (Tasmanian devil) FGF2 (SEQ ID NO: 148) (Ensembl accession no. ENSSHAP00000012215, which is hereby incorporated by reference in its entirety):

48 MAA GSITTLPALA

61 GDGASGGAFP PGHFQDPKRL YCKNGGFFLR IHPDGHVDGI REKSDPHIKL QLQAEERGVV

121 SIKGVCANRY LAMKEDGRLL ALKCVTEECF FFERLESNNY NTYRSRKYSN WYVALKRTGQ

181 YKLGSKTGPG QKAILFLPMS AKS

Amino acid sequence of *Monodelphis domestica* (gray short-tailed opossum) FGF2 (SEQ ID NO: 149) (GenBank accession no. NP_001029148, which is hereby incorporated by reference in its entirety):

1 MAAGSITTLP ALSGDGGGGG AFPPGHFKDP KRLYCKNGGF FLRIHPDGRV DGIREKSDPN

61 IKLQLQAEER GVVSIKGVCA NRYLAMKEDG RLLALKYVTE ECFFFERLES NNYNTYRSRK

121 YSNWYVALKR TGQYKLGSKT GPGQKAILFL PMSAKS

Amino acid sequence of *Oryctolagus cuniculus* (rabbit) FGF2 (SEQ ID NO: 150) (GenBank accession no. XP_002717284, which is hereby incorporated by reference in its entirety):

1 MAAESITTLP ALPEDGGSGA FPPGHFKDPK RLYCKNGGFF LRIHPDGRVD GVREKSDPHI

61 KLQLQAEERG VVSIKGVCAN RYLAMKEDGR LLASKCVTDE CFFFERLESN NYNTYRSRKY

121 SSWYVALKRT GQYKLGSKTG PGQKAILFLP MSAKS

Amino acid sequence of *Meleagris gallopavo* (turkey) FGF2 (partial amino acid sequence corresponding to human FGF2 residues 31 to 155) (SEQ ID NO: 151) (Ensembl accession no. ENSMGAP00000010977, which is hereby incorporated by reference in its entirety):

1 RLYCKNGGFF LRINPDGRVD GVREKSDPHI KLQLQAEERG VVSIKGVSAN RFLAMKEDGR

61 LLALKCATEE CFFFERLESN NYNTYRSRKY SDWYVALKRT GQYKPGPKTG PGQKAILFLP

121 MSAKS

Amino acid sequence of *Gallus gallus* (chicken) FGF2 (SEQ ID NO: 152) (GenBank accession no. NP_990764

1 maagaagsit tlpalpddgg ggafppghfk dpkrlyckng gfflrinpdg rvdgvreksd

61 PHIKLQLQAE ERGVVSIKGV SANRFLAMKE DGRLLALKCA TEECFFFERL ESNNYNTYRS

121 RKYSDWYVAL KRTGQYKPGP KTGPGQKAIL FLPMSAKS

Amino acid sequence of *Taeniopygia guttata* (zebra finch) FGF2 (SEQ ID NO: 153) (GenBank accession no. XP_002188397, which is hereby incorporated by reference in its entirety):

1 MAAAGGIATL PDDGGSGAFP PGHFKDPKRL YCKNGGFFLR INPDGKVDGV REKSDPHIKL

61 QLQAEERGVV SIKGVSANRF LAMKEDGRLL ALKYATEECF FFERLESNNY NTYRSRKYSD

121 WYVALKRTGQ YKPGPKTGPG QKAILFLPMS AKS

TABLE 3-continued

Amino acid sequence of *Cynops pyrrhogaster* (Japanese firebelly newt) FGF2 (SEQ ID NO: 154) (GenBank accession no. BAB63249, which is hereby incorporated by reference in its entirety):

1 MAAGSITSLP ALPEDGNGGT FTPGGFKEPK RLYCKNGGFF LRINSDGKVD GAREKSDSYI

61 KLQLQAEERG VVSIKGVCAN RYLAMKDDGR LMALKWITDE CFFFERLESN NYNTYRSRKY

121 SDWYVALKRT GQYKNGSKTG AGQKAILFLP MSAKS

Amino acid sequence of *Xenopus laevis* (African clawed frog) FGF2 (SEQ ID NO: 155) (GenBank accession no. NP_001093341, which is hereby incorporated by reference in its entirety):

1 MAAGSITTLP TESEDGGNTP FSPGSFKDPK RLYCKNGGFF LRINSDGRVD GSRDKSDSHI

61 KLQLQAVERG VVSIKGITAN RYLAMKEDGR LTSLRCITDE CFFFERLEAN NYNTYRSRKY

121 SSWYVALKRT GQYKNGSSTG PGQKAILFLP MSAKS

Amino acid sequence of *Didelphis albiventris* (white-eared opossum) FGF2 (SEQ ID NO: 156) (GenBank accession no. ABL77404, which is hereby incorporated by reference in its entirety):

1 MAAGSITTLP ALSGDGGGGG AFPPGHFKDP KRLYCKNGGF FLRIHPDGRV DGIREKSDPN

61 IKLQLQAEER GVVSIKGVCA NRYLAMKEDG RLLALKYVTE ECFFFERLES NNYNTYRSRK

121 YSNWYVALKR TGQYKLGSKT GPGQKAILFS PCLLRC

Amino acid sequence of *Myotis lucifugus* (microbat) FGF2 (partial amino acid sequence corresponding to human FGF2 residues 60 to 155) (SEQ ID NO: 157) (Ensembl accession no. ENSMLUP00000017859, which is hereby incorporated by reference in its entirety):

1 VKLQLQAEER GVVSIKGVCA NRYLAMKEDG RLQASKCVTD ECFFFERLES NNYNTYRSRK

61 YSSWYVALKR NGQYKLGPKT GPGQKAILFL PMSAKS

Amino acid sequence of *Anolis carolinensis* (anole lizard) FGF2 (partial amino acid sequence corresponding to human FGF2 residues 16 to 155) (SEQ ID NO: 158) (Ensembl accession no. ENSACAP00000011657, which is hereby incorporated by reference in its entirety):

1 AAAASFPPGP FKDPKRLYCK NGGFFLRINP DGGVDGVREK SDPNIKLLLQ AEERGVVSIK

61 GVCANRFLAM NEDGRLLALK YVTDECFFFE RLESNNYNTY RSRKYRDWYI ALKRTGQYKL

121 GPKTGRGQKA ILFLPMSAKS

Amino acid sequence of *Dasypus novemcinctus* (armadillo) FGF2 (partial amino acid sequence corresponding to human FGF2 residues 1 to 94) (SEQ ID NO: 159) (Ensembl accession no. ENSDNOP00000011351, which is hereby incorporated by reference in its entirety):

124 MAAGSIT TLPALPEDGG SGAFPPGHFK DPKRLYCKNG GFFLRIHPDG RVDGVREKSD

181 PNIKLQLQAE ERGVVSIKGV CANRYLAMRE DGRLQAS

Amino acid sequence of *Tupaia belangeri* (tree shrew) FGF2 (SEQ ID NO: 160) (Ensembl accession no. ENSTBEP00000000985, which is hereby incorporated by reference in its entirety):

1 AGVRAEREEA PGSGDSRGTD PAARSLIRRP DAAAREALLG ARSRVQGSST SWPASSRTGI

61 KLPDDSGQGM GGYPLDRPSR STGRGLGGAP DPAVKLQLQA EERGVVSIKG VCANRYLAMK

121 EDGRLLASKC VTDECFFFER LESNNYNTYR SRKYSSWYVA LKRTGQYKLG SKTGPGQKAI

181 LFLPMSAKS

TABLE 3-continued

Amino acid sequence of *Xenopus silurana tropicalis* (western clawed frog) FGF2 (SEQ ID NO: 161) (GenBank accession no. NP_001017333, which is hereby incorporated by reference in its entirety):

1 MAAGSITTLP TESEDGNTPF PPGNFKDPKR LYCKNGGYFL RINSDGRVDG SRDKSDLHIK

61 LQLQAVERGV VSIKGITANR YLAMKEDGRL TSLKCITDEC FFYERLEANN YNTYRSRKNN

121 SWYVALKRTG QYKNGSTTGP GQKAILFLPM SAKS

Amino acid sequence of *Latimeria chalumnae* (coelacanth) FGF2 (SEQ ID NO: 162) (Ensembl accession no. ENSLACP00000019200, which is hereby incorporated by reference in its entirety):

1 MAAGGITTLP AVPEDGGSST FPPGNFKEPK RLYCKNGGYF LRINPDGRVD GTREKNDPYI

61 KLQLQAESIG VVSIKGVCSN RYLAMNEDCR LFGLKYPTDE CFFHERLESN NYNTYRSKKY

121 SDWYVALKRT GQYKPGPKTG LGQKAILFLP MSAKS

Amino acid sequence of *Tetraodon nigroviridis* (spotted green pufferfish) FGF2 (SEQ ID NO: 163) (GenBank accession no. CAG04681, which is hereby incorporated by reference in its entirety):

34 MATGGIT TLPSTPEDGG SSGFPPGSFK

61 DPKRLYCKNG GFFLRIKSDG VVDGIREKSD PHIKLQLQAT SVGEVVIKGV CANRYLAMNR

121 DGRLFGTKRA TDECHFLERL ESNNYNTYRS RKYPTMFVGL TRTGQYKSGS KTGPGQKAIL

181 FLPMSAKC

Amino acid sequence of *Gasterosteus aculeatus* (stickleback) FGF2 (SEQ ID NO: 164) (Ensembl accession no. ENSGACP00000022078, which is hereby incorporated by reference in its entirety):

1 MATAGFATLP STPEDGGSGG FTPGGFKDPK RLYCKNGGFF LRIRSDGGVD GIREKSDAHI

61 KLQIQATSVG EVVIKGVCAN RYLAMNRDGR LFGVRRATDE CYFLERLESN NYNTYRSRKY

121 PGMYVALKRT GQYKSGSKTG PGQKAILFLP MSAKC

Amino acid sequence of *Takifugu rubripes* (fugu rubripes) FGF2 (SEQ ID NO: 165) (GenBank accession no. CAD19830, which is hereby incorporated by reference in its entirety):

1 MATGGITTLP STPEDGGSGG FPPGSFKDPK RLYCKNGGFF LRIRSDGAVD GTREKTDPHI

61 KLQLQATSVG EVVIKGVCAN RYLAMNRDGR LFGMKRATDE CHFLERLESN NYNTYRSRKY

121 PNMFVGLTRT GNYKSGTKTG PCQKAILFLP MSAKY

Amino acid sequence of *Oncorhynchus mykiss* (rainbow trout) FGF2 (SEQ ID NO: 166) (GenBank accession no. NP_001118008, which is hereby incorporated by reference in its entirety):

1 MATGEITTLP ATPEDGGSGG FLPGNFKEPK RLYCKNGGYF LRINSNGSVD GIRDKNDPHN

61 KLQLQATSVG EVVIKGVSAN RYLAMNADGR LFGPRRTTDE CYFMERLESN NYNTYRSRKY

121 PEMYVALKRT GQYKSGSKTG PGQKAILFLP MSARR

Amino acid sequence of *Salmo salar* (salmon) FGF2 (SEQ ID NO: 167) (GenBank accession no. ACJ02099, which is hereby incorporated by reference in its entirety):

1 MATGEITTLP ATPEDGGSGG FPPGNFKDPK RLYCKNGGYF LRINSNGSVD GIREKNDPHK

61 QPQFVRAWTL QGVKRSTGML AHVDSNASHN CVKVAGCSLG EFGSMSNRPH NRRPRVATPA

121 QDLHIRLLHL RDRLKPATRT ADKTEEYFCL

TABLE 3-continued

Amino acid sequence of *Danio rerio* (zebrafish) FGF2 (SEQ ID NO: 168) (GenBank accession no. AAP32155, which is hereby incorporated by reference in its entirety):

```
  1  MATGGITTLP AAPDAENSSF PAGSFRDPKR LYCKNGGFFL RINADGRVDG ARDKSDPHIR

 61  LQLQATAVGE VLIKGICTNR FLAMNADGRL FGTKRTTDEC YFLERLESNN YNTYRSRKYP

121  DWYVALKRTG QYKSGSKTSP GQKAILFLPM SAKC
```

Amino acid sequence of *Oreochromis niloticus* (Nile tilapia) FGF2 (SEQ ID NO: 169) (GenBank accession no. XP_003443412, which is hereby incorporated by reference in its entirety):

```
  1  MATGGITTLP ATPEDGGSSG FPPGNFKDPK RLYCKNGGFF LRIKSDGGVD GIREKNDPHI

 61  KLQLQATSVG EVVIKGICAN RYLAMNRDGR LFGARRATDE CYFLERLESN NYNTYRSRKY

121  PNMYVALKRT GQYKSGSKTG PGQKAILFLP MSAKC
```

Amino acid sequence of *Oryzias latipes* (medaka) FGF2 (SEQ ID NO: 170) (Ensembl accession no. ENSORLP00000025834, which is hereby incorporated by reference in its entirety):

```
  1  MATGEITTLP SPAENSRSDG FPPGNYKDPK RLYCKNGGLF LRIKPDGGVD GIREKKDPHV

 61  KLRLQATSAG EVVIKGVCSN RYLAMHGDGR LFGVRQATEE CYFLERLESN NYNTYRSKKY

121  PNMYVALKRT GQYKPGNKTG PGQKAILFLP MSAKY
```

As noted above, the portion of the paracrine FGF may be modified to decrease binding affinity for heparin and/or heparan sulfate compared to the portion without the modification. In one embodiment, the modification of the paracrine FGF includes one or more substitutions, additions, or deletions.

In one embodiment, the modification is one or more substitutions located at one or more amino acid residues of SEQ ID NO: 121 selected from N36, K128, R129, K134, K138, Q143, K144, C78, C96, and combinations thereof. In one embodiment, the one or more substitutions are selected from N36T, K128D, R129Q, K134V, K138H, Q143M, K144T/L/I, C78S, C96S, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. In one embodiment, the modification is one or more substitutions which are located at one or more amino acid residues corresponding to residues of SEQ ID NO: 121 selected from N36, K128, R129, K134, K138, Q143, K144, C78, C96, and combinations thereof. Amino acid residues corresponding to those of SEQ ID NO: 121 may be determined by, for example, sequence analysis and structural analysis.

It will be understood that the portion of the paracrine FGF according to the present invention may be derived from a nucleotide sequence that encodes a paracrine FGF protein. For example, in one embodiment, nucleotide sequence is the nucleotide sequence that encodes human FGF2 (GenBank Accession No. NM 002006, which is hereby incorporated by reference in its entirety)(SEQ ID NO: 171), as follows:

```
468                                             ATG GCAGCCGGGA

481 GCATCACCAC GCTGCCCGCC TTGCCCGAGG ATGGCGGCAG CGGCGCCTTC CCGCCCGGCC

541 ACTTCAAGGA CCCCAAGCGG CTGTACTGCA AAAACGGGGG CTTCTTCCTG CGCATCCACC

601 CCGACGGCCG AGTTGACGGG GTCCGGGAGA AGAGCGACCC TCACATCAAG CTACAACTTC

661 AAGCAGAAGA GAGAGGAGTT GTGTCTATCA AAGGAGTGTG TGCTAACCGT TACCTGGCTA

721 TGAAGGAAGA TGGAAGATTA CTGGCTTCTA AATGTGTTAC GGATGAGTGT TTCTTTTTTG

781 AACGATTGGA ATCTAATAAC TACAATACTT ACCGGTCAAG GAAATACACC AGTTGGTATG

841 TGGCACTGAA ACGAACTGGG CAGTATAAAC TTGGATCCAA AACAGGACCT GGGCAGAAAG

901 CTATACTTTT TCTTCCAATG TCTGCTAAGA GCTGA
```

In another embodiment of the present invention, the portion of the paracrine FGF of the chimeric protein may be derived from a nucleotide sequence that encodes an ortholog of human FGF2. Nucleotide sequences that encode FGF2 orthologs are shown in Table 4.

TABLE 4

Gorilla FGF2 gene coding sequence (amino acids ("aa") 104-258) (SEQ ID NO: 172) (Ensembl accession no. ENSGGOT00000004842, which is hereby incorporated by reference in its entirety):

```
310            ATGGCAGCC GGGAGCATCA CCACGCTGCC CGCCTTGCCC GAGGATGGCG
359 GCAGCGGCGC CTTCCCGCCC GGCCACTTCA AGGACCCCAA GCGGCTGTAC TGCAAAAACG
419 GGGGCTTCTT CCTGCGCATC CACCCCGACG GCCGAGTTGA CGGGGTCCGG GAGAAGAGCG
479 ACCCTCACAT CAAGCTACAA CTTCAAGCAG AAGAGAGAGG AGTTGTGTCT ATCAAAGGAG
539 TGTGTGCTAA CCGTTACCTT GCTATGAAGG AAGATGGAAG ATTACTGGCT TCTAAATGTG
599 TTACGGATGA GTGTTTCTTT TTTGAACGAT TGGAATCTAA TAACTACAAT ACTTACCGGT
659 CAAGGAAATA CACCAGTTGG TATGTGGCAC TGAAACGAAC TGGGCAGTAT AAACTTGGAT
719 CCAAAACAGG ACCTGGGCAG AAAGCTATAC TTTTTCTTCC AATGTCTGCT AAGAGCTGA
```

Sumatran orangutan FGF2 gene coding sequence (aa 168-322) (SEQ ID NO: 173) (GenBank accession no. XM_002815126, which is hereby incorporated by reference in its entirety):

```
504                         ATGGCAG CCGGGAGCAT CACCACGCTG CCCGCCTTGC
541 CCGAGGATGG CGGCAGCGGC GCCTTCCCGC CGGGCCACTT CAAGGACCCC AAGCGGCTGT
601 ACTGCAAAAA CGGGGGCTTC TTCCTGCGCA TCCACCCCGA CGGCCGAGTT GACGGGGTCC
661 GAGAGAAGAG CGACCCTCAC ATCAAACTAC AACTTCAAGC AGAAGAAAGA GGAGTTGTGT
721 CTATCAAAGG AGTGTGTGCT AACCGCTACC TTGCTATGAA GGAAGATGGA AGATTACTGG
781 CTTCTAAATG TGTTACGGAT GAGTGTTTCT TTTTTGAACG ATTGGAATCT AATAACTACA
841 ATACTTACCG GTCAAGGAAA TACACCAGTT GGTATGTGGC ACTGAAACGA ACTGGGCAGT
901 ATAAACTTGG ATCCAAAACA GGACCTGGGC AGAAAGCTAT ACTTTTTCTT CCAATGTCTG
961 CTAAGAGCTG A
```

Rhesus monkey FGF2 gene coding sequence (aa 83-237) (SEQ ID NO: 174) (GenBank accession no. XM_001099284, which is hereby incorporated by reference in its entirety):

```
247       ATGG CAGCCGGGAG CATCACCACG CTGCCCGCCT TGCCCGAGGA TGGCGGCAGC
301 GGCGCCTTCC CGCCTGGCCA CTTCAAGGAC CCCAAGCGGC TGTACTGCAA AAACGGGGGC
361 TTCTTCCTGC GCATTCACCC CGACGGCCGA GTTGACGGGG TCCGGGAGAA GAGCGACCCT
421 CACATCAAAT TACAACTTCA AGCAGAAGAG AGAGGAGTTG TGTCTATCAA AGGAGTGTGT
481 GCTAACCGTT ACCTTGCTAT GAAGGAAGAT GGAAGATTAC TGGCTTCTAA ATGTGTTACA
541 GATGAGTGTT TCTTTTTTGA ACGATTGGAA TCTAATAACT ACAATACTTA CCGGTCAAGG
601 AAATACACCA GTTGGTATGT GGCACTGAAA CGAACTGGGC AATATAAACT TGGATCCAAA
661 ACAGGACCTG GGCAGAAAGC TATACTTTTT CTTCCAATGT CTGCTAAGAG CTGA
```

Chimpanzee FGF2 gene coding sequence (aa 134-288) (SEQ ID NO: 175) (GenBank accession no. NM_001110241, which is hereby incorporated by reference in its entirety):

```
400                                        A TGGCAGCCGG GAGCATCACC
421 ACGCTGCCCG CCTTGCCCGA GGATGGCGGC AGCGGCGCCT TCCCGCCCGG CCACTTCAAG
481 GACCCCAAGC GGCTGTACTG CAAAAACGGG GGCTTCTTCC TGCGCATCCA CCCCGACGGC
541 CGAGTTGACG GGGTCCGGGA GAAGAGCGAC CCTCACATCA AGCTACAACT TCAAGCAGAA
601 GAGAGAGGAG TTGTGTCTAT CAAAGGAGTG TGTGCTAACC GTTACCTTGC TATGAAGGAA
661 GATGGAAGAT TACTGGCTTC TAAATGTGTT ACGGATGAGT GTTTCTTTTT TGAACGATTG
721 GAATCTAATA ACTACAATAC TTACCGGTCA AGGAAATACA CCAGTTGGTA TGTGGCACTG
```

TABLE 4-continued

```
781 AAACGAACTG GGCAGTATAA ACTTGGATCC AAAACAGGAC CTGGGCAGAA AGCTATACTT

841 TTTCTTCCAA TGTCTGCTAA GAGCTGA
```

Pygmy chimpanzee FGF2 gene coding sequence (112-266) (SEQ ID NO: 176) (GenBank accession no. XM_003816433, which is hereby incorporated by reference in its entirety):

```
334                                ATGGCAG CCGGGAGCAT CACCACGCTG

361 CCCGCCTTGC CCGAGGATGG CGGCAGCGGC GCCTTCCCGC CCGGCCACTT CAAGGACCCC

421 AAGCGGCTGT ACTGCAAAAA CGGGGGCTTC TTCCTGCGCA TCCACCCCGA CGGCCGAGTT

481 GACGGGGTCC GGGAGAAGAG CGACCCTCAC ATCAAGCTAC AACTTCAAGC AGAAGAGAGA

541 GGAGTTGTGT CTATCAAAGG AGTGTGTGCT AACCGTTACC TTGCTATGAA GGAAGATGGA

601 AGATTACTGG CTTCTAAATG TGTTACGGAT GAGTGTTTCT TTTTTGAACG ATTGGAATCT

661 AATAACTACA ATACTTACCG GTCAAGGAAA TACACCAGTT GGTATGTGGC ACTGAAACGA

721 ACTGGGCAGT ATAAACTTGG ATCCAAAACA GGACCTGGGC AGAAAGCTAT ACTTTTTCTT

781 CCAATGTCTG CTAAGAGCTG A
```

Bolivian squirrel monkey FGF2 gene coding sequence (1-155) (SEQ ID NO: 177) (GenBank accession no. XM_003936241, which is hereby incorporated by reference in its entirety):

```
 23                     ATGGCAGC CGGGAGCATC ACCACGCTGC CCGCCCTGCC

 61 CGAAGACGGC GGCAGCGGCG CCTTCCCGCC CGGCCACTTC AAAGACCCCA AGCGGCTGTA

121 CTGCAAAAAC GGGGGCTTCT TCCTGCGAAT CCACCCCGAC GGCCGAGTGG ACGGGGTCCG

181 GGAGAAGAGC GACCCTCACA TCAAACTACA ACTTCAAGCA GAAGAGAGAG GAGTTGTATC

241 TATCAAAGGA GTGTGTGCTA ACCGTTACCT TGCTATGAAG GAAGATGGAA GATTACTGGC

301 TTCTAAATGT GTTACGGACG AGTGTTTCTT TTTTGAACGA TTGGAATCTA ATAACTACAA

361 TACTTACCGA TCAAGGAAAT ACACCAGTTG GTATGTGGCA CTGAAACGAA CTGGGCAGTA

421 TAAACTTGGA TCCAAAACAG GACCTGGGCA GAAAGCTATA CTTTTTCTTC CAATGTCTGC

481 TAAGAGCT GA
```

Northern white-cheeked gibbon FGF2 gene coding sequence (aa 1-155) (SEQ ID NO: 178) (GenBank accession no. XM_003271356, which is hereby incorporated by reference in its entirety):

```
435                                              ATG GCAGCCGGGA

481 GCATCACCAC GCTGCCCGCC TTGCCGGAGG ATGGCGGCAG CGGCGCCTTC CCGCCCGGCC

541 ACTTCAAGGA CCCCAAGCGG CTGTACTGCA AAAACGGGGG TTTCTTCCTG CGCATCCACC

601 CCGACGGTCG AGTTGACGGG GTCCGGGAGA AGAGCGACCC TCACATCAAA CTACAACTTC

661 AAGCAGAAGA GAGAGGAGTT GTGTCTATCA AAGGAGTGTG TGCTAACCGT TACCTTGCTA

721 TGAAGGAAGA TGGAAGATTA CTGGCTTCTA AATGTGTTAC GGATGAGTGT TTCTTTTTTG

781 AACGATTGGA ATCTAATAAC TACAATACTT ACCGGTCAAG GAAATACACC AGTTGGTATG

841 TGGCACTGAA ACGAACTGGG CAGTATAAAC TTGGATCCAA AACAGGACCT GGGCAGAAAG

901 CTATACTTTT TCTTCCAATG TCTGCTAAGA GCTGA
```

Horse FGF2 gene coding sequence (aa 1-155) (SEQ ID NO: 179) (GenBank accession no. NM_001195221, which is hereby incorporated by reference in its entirety):

```
 54                                                     ATGGCAG

 61 CCGGGAGCAT CACCACGCTG CCCGCCCTGC CCGAGGACGG CGGCAGCGGC GCCTTCCCGC

121 CCGGCCACTT CAAGGACCCC AAGCGGCTCT ACTGCAAAAA CGGGGGCTTC TTCCTGCGCA
```

TABLE 4-continued

```
181 TCCACCCCGA CGGCCGAGTG GACGGGGTCC GGGAGAAGAG CGACCCTCAC ATCAAACTAC
241 AACTTCAAGC AGAAGAGAGA GGGGTTGTGT CTATCAAAGG AGTGTGTGCG AACCGTTATC
301 TTGCTATGAA GGAAGATGGA AGGTTACTGG CTTCTAAATG TGTTACGGAC GAGTGTTTCT
361 TTTTTGAACG ATTGGAATCT AATAACTACA ATACTTACCG GTCAAGGAAA TACTCCAGTT
421 GGTATGTGGC CCTGAAACGA ACGGGGCAGT ATAAACTTGG ACCCAAAACA GGACCTGGAC
481 AGAAAGCTAT ACTTTTTCTT CCAATGTCTG CTAAGAGCTG A
```

Cattle FGF2 gene coding sequence (aa 1-155) (SEQ ID NO: 180) (GenBank accession no. NM_174056, which is hereby incorporated by reference in its entirety):

```
104                                                    ATGGCCG CCGGGAGCAT
121 CACCACGCTG CCAGCCCTGC CGGAGGACGG CGGCAGCGGC GCTTTCCCGC CGGGCCACTT
181 CAAGGACCCC AAGCGGCTGT ACTGCAAGAA CGGGGGCTTC TTCCTGCGCA TCCACCCCGA
241 CGGCCGAGTG GACGGGGTCC GCGAGAAGAG CGACCCACAC ATCAAACTAC AACTTCAAGC
301 AGAAGAGAGA GGGGTTGTGT CTATCAAAGG AGTGTGTGCA AACCGTTACC TTGCTATGAA
361 AGAAGATGGA AGATTACTAG CTTCTAAATG TGTTACAGAC GAGTGTTTCT TTTTTGAACG
421 ATTGGAGTCT AATAACTACA ATACTTACCG GTCAAGGAAA TACTCCAGTT GGTATGTGGC
481 ACTGAAACGA ACTGGGCAGT ATAAACTTGG ACCCAAAACA GGACCTGGGC AGAAAGCTAT
541 ACTTTTTCTT CCAATGTCTG CTAAGAGCTG A
```

Olive baboon FGF2 gene coding sequence (1-155) (SEQ ID NO: 181) (GenBank accession no. XM_003899161, which is hereby incorporated by reference in its entirety):

```
467                                                       ATGG CAGCCGGGAG
481 CATCACCACG CTGCCCGCCT TGCCCGAGGA TGGCGGCAGC GGCGCCTTCC CGCCCGGCCA
541 CTTCAAGGAC CCCAAGCGGC TGTACTGCAA AAACGGGGGC TTCTTCCTGC GCATTCACCC
601 CGACGGCCGA GTTGACGGGG TCCGGGAGAA GAGCGACCCT CACATCAAAT TACAACTTCA
661 AGCAGAAGAG AGAGGAGTTG TGTCTATCAA AGGAGTGTGT GCTAACCGTT ACCTTGCTAT
721 GAAGGAAGAT GGAAGATTAC TGGCTTCTAA ATGTGTTACG GATGAGTGTT TCTTTTTTGA
781 ACGATTGGAA TCTAATAACT ACAATACTTA CCGGTCAAGG AAATACACCA GTTGGTATGT
841 GGCACTGAAA CGAACTGGGC AGTATAAACT TGGATCCAAA ACAGGACCTG GGCAGAAAGC
901 TATACTTTTT CTTCCAATGT CTGCTAAGAG CTGA
```

Alpaca FGF2 gene coding sequence (aa 111-265) (SEQ ID NO: 182) (Ensembl accession no. ENSVPAT00000010536, which is hereby incorporated by reference in its entirety):

```
341                                 ATGGCAGCTG GGAGCATCAC CACGCTGCCC
361 GCCCTGCCGG AGGACGGCGG CAGCGGCGCC TTCCCGCCCG GCCACTTCAA GGACCCCAAG
421 CGGTTGTACT GCAAAAACGG GGGCTTCTTC CTGCGCATCC ACCCCGACGG CCGAGTGGAC
481 GGGGTCCGGG AGAAGAGCGA CCCTCACATC AAACTACAAC TTCAAGCAGA AGAGAGAGGG
541 GTCGTGTCTA TCAAAGGAGT GTGTGCAAAC CGTTACCTTG CTATGAAGGA AGATGGAAGA
601 TTACTGGCTT CTAAATGTGT CACAGACGAG TGTTTCTTTT TTGAACGATT GGAATCTAAT
661 AACTACAATA CTTACCGGTC AAGGAAATAC TCCAGTTGGT ATGTGGCACT GAAACGAACT
721 GGGCAGTACA AACTTGGACC CAAAACAGGA CCTGGGCAGA AAGCTATACT TTTCCTTCCA
781 ATGTCTGCTA AGAGCTGA
```

TABLE 4-continued

Sheep FGF2 gene coding sequence (aa 1-155) (SEQ ID NO: 183) (GenBank accession no. NM_001009769, which is hereby incorporated by reference in its entirety):

```
  1 ATGGCCGCCG GGAGCATCAC CACGCTGCCA GCCCTGCCGG AGGACGGCGG CAGCAGCGCT
 61 TTCCCGCCCG GCCACTTTAA GGACCCCAAG CGGCTGTACT GCAAGAACGG GGGCTTCTTC
121 CTGCGCATCC ACCCCGACGG CCGAGTGGAC GGGGTCCGCG AGAAGAGCGA CCCTCACATC
181 AAACTACAAC TTCAAGCAGA AGAGAGAGGG GTTGTGTCTA TCAAAGGAGT GTGTGCAAAC
241 CGTTACCTTG CTATGAAAGA AGATGGAAGA TTACTAGCTT CTAAATGTGT TACAGACGAG
301 TGTTTCTTTT TTGAACGATT GGAGTCTAAT AACTACAATA CTTACCGGTC AAGGAAATAC
361 TCCAGTTGGT ATGTGGCACT GAAACGAACT GGGCAGTATA AACTTGGACC CAAAACAGGA
421 CCTGGGCAGA AAGCTATACT TTTTCTTCCA ATGTCTGCTA AGAGCTGA
```

Western roe deer FGF2 gene coding sequence (1-108; partial amino acid sequence corresponding to human FGF2 residues 42 to 149) (SEQ ID NO: 184) (GenBank accession no. AF152587, which is hereby incorporated by reference in its entirety):

```
  1 GCGCATCCAC CCCGACGGCC GAGTGGACGG GGTCCGCGAG AAGAGTGACC CTCACATCAA
 61 ACTACAACTT CAAGCAGAAG AGAGAGGGGT TGTGTCTATC AAAGGAGTGT GTGCGAACCG
121 TTATCTTGCT ATGAAAGAAG ACGGAAGATT ATTGGCTTCA AAATGTGTTA CAGACGAATG
181 TTTCTTTTTT GAACGATTGG AGTCTAATAA CTACAATACT TACCGGTCAA GGAAATACTC
241 CAGTTGGTAT GTGGCACTGA AACGAACTGG GCAGTATAAA CTTGGACCCA AAACAGGACC
301 TGGGCAGAAA GCTATACTTT TTCTT
```

Elephant FGF2 gene coding sequence (1-96; partial amino acid sequence corresponding to human FGF2 residues 60 to 155) (SEQ ID NO: 185) (Ensembl accession no. ENSLAFT00000008249, which is hereby incorporated by reference in its entirety):

```
  1 GTTAAACTAC AGCTTCAAGC AGAAGAGAGA GGTGTTGTGT CTATCAAAGG AGTGTGTGCC
 61 AACCGTTATC TGGCTATGAA GGAAGATGGA AGATTGCTGG CTTCTAGATG TGTGACAGAT
121 GAATGTTTCT TCTTTGAACG ACTGGAATCT AATAACTACA ATACTTACCG GTCAAGGAAA
181 TACACCAGTT GGTATGTGGC ACTGAAACGA ACGGGGCAGT ATAAACTTGG ATCCAAAACA
241 GGACCTGGAC AGAAAGCTAT ACTTTTTCTT CCCATGTCTG CTAAGAGC
```

Pig FGF2 gene coding sequence (1-120; partial amino acid sequence corresponding to human FGF2 residues 36 to 155) (SEQ ID NO: 186) (GenBank accession no. AJ577089 and Ensembl accession no. ENSSSCT00000009952, which is hereby incorporated by reference in its entirety):

```
  1 GAACGGGGGC TTCTTCCTGC GCATCCACCC CGACGGCCGA GTGGATGGGG TCCGGGAGAA
 61 GAGCGACCCT CACATCAAAC TACAACTTCA AGCAGAAGAG AGAGGGGTTG TGTCTATCAA
121 AGGAGTGTGT GCAAACCGTT ATCTTGCTAT GAAGGAAGAT GGAAGATTAC TGGCTTCTAA
181 ATGTGTTACA GACGAGTGTT TCTTTTTTGA ACGACTGGAA TCTAATAACT ACAATACTTA
241 CCGGTCGAGG AAATACTCCA GTTGGTATGT GGCACTGAAA CGAACTGGGC AGTATAAACT
301 TGGACCCAAA ACAGGACCTG GGCAGAAAGC TATACTTTTT CTTCCAATGT CTGCTAAGAG
361 C
```

TABLE 4-continued

Panda FGF2 gene coding sequence (1-96; partial amino acid sequence corresponding to human FGF2 residues 60 to 155) (SEQ ID NO: 187) (Ensembl accession no ENSAMET00000019232, which is hereby incorporated by reference in its entirety):

```
  1 GTCAAACTGC AACTTCAAGC GGAAGAGAGA GGGGTTGTAT CCATCAAAGG AGTATGTGCA

 61 AATCGCTATC TTGCCATGAA GGAAGATGGA AGATTACTGG CTTCTAAATG TGTTACCGAT

121 GAGTGTTTCT TTTTTGAGCG ACTGGAATCT AATAACTACA ATACTTACCG GTCAAGGAAA

181 TACTCCAGTT GGTATGTGGC ACTGAAACGA ACTGGGCAGT ATAAACTTGG ACCCAAAACA

241 GGACCTGGGC AGAAAGCTAT ACTTTTTCTT CCAATGTCTG CTAAGAGC
```

Sloth FGF2 gene coding sequence (aa 14-168) (SEQ ID NO: 188) (Ensembl accession no. ENSCHOT00000011394, which is hereby incorporated by reference in its entirety):

```
 40                                             A TGGCAGCCGG GAGCATCACC

 61 ACGCTGCCCG CCCTGCCCGA GGACGGAGGC AGCGGCGCCT TACCGCCCGG CCACTTCAAA

121 GATCCCAAGC GGCTCTACTG CAAAAACGGG GGCTTCTTCC TGCGTATCCA TCCCGACGGC

181 AGAGTGGACG GGGTCCGGGA GAAGAGCGAC CCCCACATCA AACTACAACT TCAAGCAGAA

241 GAGAGAGGGG TTGTGTCTAT CAAAGGTGTG TGTGCAAACC GATATCTTGC TATGAAGGAA

301 GATGGAAGAT TACAGGCTTC TAAATGTGTA ACGGACGAGT GTTTCTTTTT TGAACGATTG

361 GAATCTAATA ACTACAATAC GTACCGATCA AGGAAATACT CCAGTTGGTA TGTGGCACTG

421 AAACGAACTG GGCAATATAA ACTTGGACCC AAAACAGGAC CTGGGCAGAA AGCCATACTT

481 TTTCTTCCAA TGTCTGCTAA GAGCTGA
```

Water buffalo FGF2 gene coding sequence (aa 1-155) (SEQ ID NO: 189) (GenBank accession no. JQ326277, which is hereby incorporated by reference in its entirety):

```
  1 ATGGCCGCCG GGAGCATCAC CACGCTGCCA CCCCTGCCGG AGGACGGCGG CAGCGGCGCT

 61 TTCCCGCCCG GCCACTTCAA GGACCCCAAG CGGCTGTACT GCAAGAACGG GGGCTTCTTC

121 CTGCGCATCC ACCCCGACGG CCGAGTGGAC GGGGTCCGCG AGAAGAGCGA CCCACACATC

181 AAACTACAAC TTCAAGCAGA AGAGAGAGGG GTTGTGTCTA TCAAAGGAGT GTGTGCAAAC

241 CGTTACCTTG CTATGAAAGA AGATGGAAGA TTACTAGCTT CCAAATGTGT TACAGACGAG

301 TGTTTCTTTT TTGAACGATT GGAGTCTAGT AACTACAATA CTTACCGGTC AAGGAAATAC

361 TCCAGTTGGT ATGTGGCACT GAAACGAACT GGGCAGTATA AACTTGGACC CAAAACAGGA

421 CCTGGGCAGA AAGCTATACT TTTTCTTCCA ATGTCTGCTA AGAGCTGA
```

Dog FGF2 gene coding sequence (aa 40-194) (SEQ ID NO: 190) (GenBank accession no. XM_003432481, which is hereby incorporated by reference in its entirety):

```
118                                                               ATG

121 GCAGCCGGGA GCATCACCAC GCTGCCCGCC CTGCCGGAGG ACGGCGGCAG CGGCGCCTTC

181 CCGCCCGGCC ACTTCAAGGA CCCCAAGAGG CTGTACTGCA AAAAAGGGGG CTTCTTCCTG

241 CGGATCCACC CCGACGGCCG GGTGGACGGG GTCCGGGAGA AGAGCGATCC CCACGTCAAA

301 TTGCAACTTC AAGCAGAAGA GAGAGGCGTT GTGTCCATCA AAGGAGTATG TGCAAATCGC

361 TATCTTGCTA TGAAGGAAGA TGGAAGATTA CTGGCTTCTA AATGTGTTAC TGACGAGTGC

421 TTCTTTTTTG AACGATTGGA ATCTAATAAC TACAATACTT ACCGGTCAAG GAAATACTCC

481 AGTTGGTATG TGGCACTGAA ACGAACTGGG CAGTATAAAC TTGGACCAAA AACAGGACCT

541 GGGCAGAAAG CTATACTTTT TCTTCCAATG TCTGCTAAGA GCTGA
```

TABLE 4-continued

Norway rat FGF2 gene coding sequence (aa 1-154) (SEQ ID NO: 191) (GenBank accession no. NM_019305, which is hereby incorporated by reference in its entirety):

```
533                                                      ATGGCTGC
541 CGGCAGCATC ACTTCGCTTC CCGCACTGCC GGAGGACGGC GGCGGCGCCT TCCCACCCGG
601 CCACTTCAAG GATCCCAAGC GGCTCTACTG CAAGAACGGC GGCTTCTTCC TGCGCATCCA
661 TCCAGACGGC CGCGTGGACG GCGTCCGGGA GAAGAGCGAC CCACACGTCA AACTACAGCT
721 CCAAGCAGAA GAGAGAGGAG TTGTGTCCAT CAAGGGAGTG TGTGCGAACC GGTACCTGGC
781 TATGAAGGAA GATGGACGGC TGCTGGCTTC TAAGTGTGTT ACAGAAGAGT GTTTCTTCTT
841 TGAACGCCTG GAGTCCAATA ACTACAACAC TTACCGGTCA CGGAAATACT CCAGTTGGTA
901 TGTGGCACTG AAACGAACTG GGCAGTATAA ACTCGGATCC AAAACGGGGC CTGGACAGAA
961 GGCCATACTG TTTCTTCCAA TGTCTGCTAA GAGCTGA
```

Naked mole-rat FGF2 gene coding sequence (1-134; partial amino acid sequence corresponding to human FGF2 residues 22 to 155) (SEQ ID NO: 192) (GenBank accession no. JH173674, which is hereby incorporated by reference in its entirety):

```
378500                     C CACCCGGCCA CTTCAAGGAC CCAAAGCGGC
378531 TGTACTGCAA AAACGGGGGC TTCTTCCTGC GCATCCACCC CGACGGCCGC
378581 GTGGACGGGG TCCGGGAGAA GAGCGACCCT CACG
418784    TCAAACT ACAACTTCAA GCAGAAGAGA GAGGAGTTGT GTCTATTAAG
418831 GGAGTGTGTG CGAACCGTTA CCTTGCTATG AAGGAAGATG GAAGATTACT
418881 GGCTTCT
433983   AAATGTGT TACAGATGAG TGTTTCTTTT TTGAACGATT GGAATCTAAT
434031 AACTACAATA CTTATCGGTC AAGGAAATAC TCCAGTTGGT ATGTGGCACT
434081 GAAACGAACT GGACAATATA AACTTGGATC CAAAACAGGA CCGGGGCAGA
434131 AAGCTATACT TTTTCTTCCA ATGTCTGCTA AGAGCTGA
```

Bushbaby FGF2 gene coding sequence (aa 52-206) (SEQ ID NO: 193) (Ensembl accession no. ENSOGAT00000025228, which is hereby incorporated by reference in its entirety):

```
154                                 ATGGCAG CCGGGAGCAT CACCACGCTG
181 CCCTCCCTGC CCGAGGACGG CGGCAGCGAC GCCTTTCCGC CCGGCCACTT CAAGGACCCC
241 AAGCGACTGT ACTGCAAAAA CGGGGGCTTC TTCCTGCGCA TCCACCCCGA CGGCCGAGTG
301 GACGGGGTCC GGGAGAAGAG CGACCCTTAC ATCAAACTAC AACTTCAAGC AGAAGAGAGA
361 GGAGTTGTGT CTATCAAAGG AGTGTGTGCG AACCGTTACC TTGCTATGAA GGAAGACGGA
421 AGATTGCTGG CTTCTAAATT GATTACAGAC GAGTGCTTCT TTTTTGAACG ACTGGAATCT
481 AATAACTACA ATACTTACCG GTCAAGAAAA TACTCCAGTT GGTATGTGGC ACTGAAACGA
541 ACTGGACAGT ATAAACTTGG ATCCAAAACA GGACCTGGGC AGAAAGCTAT ACTTTTTCTT
601 CCAATGTCTG CTAAGAGCTG A
```

House mouse FGF2 gene coding sequence (aa 1-154) (SEQ ID NO: 194) (GenBank accession no. NM_008006, which is hereby incorporated by reference in its entirety):

```
198                        ATG GCTGCCAGCG GCATCACCTC GCTTCCCGCA CTGCCGGAGG
241 ACGGCGGCGC CGCCTTCCCA CCAGGCCACT TCAAGGACCC CAAGCGGCTC TACTGCAAGA
301 ACGGCGGCTT CTTCCTGCGC ATCCATCCCG ACGGCCGCGT GGATGGCGTC CGCGAGAAGA
361 GCGACCCACA CGTCAAACTA CAACTCCAAG CAGAAGAGAG AGGAGTTGTG TCTATCAAGG
```

TABLE 4-continued

```
421 GAGTGTGTGC CAACCGGTAC CTTGCTATGA AGGAAGATGG ACGGCTGCTG GCTTCTAAGT

481 GTGTTACAGA AGAGTGTTTC TTCTTTGAAC GACTGGAATC TAATAACTAC AATACTTACC

541 GGTCACGGAA ATACTCCAGT TGGTATGTGG CACTGAAACG AACTGGGCAG TATAAACTCG

601 GATCCAAAAC GGGACCTGGA CAGAAGGCCA TACTGTTTCT TCCAATGTCT GCTAAGAGCT

661 GA
```

Squirrel FGF2 gene coding sequence (1-144; partial amino acid sequence corresponding to human FGF2 residues 12 to 155) (SEQ ID NO: 195) (Ensembl accession no. ENSSTOT00000022105, which is hereby incorporated by reference in its entirety):

```
  1 CTGCCCGAGG ACGGCGGCGG CGGCGCCTTC CCGCCCGGCC ACTTTAAGGA CCCCAAGCGG

 61 CTCTACTGCA AAAACGGAGG CTTCTTCCTG CGCATCCACC CCGACGGCCG AGTGGACGGG

121 GTCCGGGAGA AGAGCGACCC CCACATCAAG CTCCAGCTTC AAGCCGAAGA CCGAGGGGTT

181 GTGTCCATCA AGGGAGTGTG TGCAAACCGA TACCTGGCCA TGAAGGAGGA CGGGAGGCTC

241 CTGGCTTCTA AATGTGTTAC GGACGAGTGT TTCTTTTTTG AACGACTGGA ATCAAATAAC

301 TACAATACTT ACCGGTCAAG GAAATACTCC AGTTGGTATG TGGCCCTGAA ACGAACAGGG

361 CAGTATAAAC TTGGATCCAA AACAGGACCT GGGCAGAAAG CTATACTTTT TCTTCCAATG

421 TCTGCTAAGA GC
```

Domestic cat FGF2 gene coding sequence (1-106; partial amino acid sequence corresponding to human FGF2 residues 25 to 130) (SEQ ID NO: 196) (GenBank accession no. EU314952, which is hereby incorporated by reference in its entirety):

```
  1 CCACTTCAAG GACCCCAAGC GTCTGTACTG CAAAAACGGG GGCTTCTTCC TGCGCATCCA

 61 CCCCGACGGC CGAGTGGATG GGGTCCGGGA GAAGAGCGAC CCTCACATCA AACTGCAACT

121 TCAGGCAGAA GAGAGAGGGG TTGTGTCCAT CAAAGGAGTC TGTGCAAACC GCTATCTTGC

181 CATGAAGGAA GATGGAAGAT TACTGGCTTC TAAATGTGTT ACGGACGAGT GTTTCTTTTT

241 TGAACGATTG GAATCTAATA ACTACAATAC TTATCGGTCA AGGAAATACT CCAGCTGGTA

301 TGTGGCACTG AAACGAAC
```

Guinea pig FGF2 gene coding sequence (1-96; partial amino acid sequence corresponding to human FGF2 residues 60 to 155) (SEQ ID NO: 197) (Ensembl accession no. ENSCPOT00000005443, which is hereby incorporated by reference in its entirety):

```
  1 GTTAAACTAC AACTTCAAGC CGAAGACAGA GGAGTTGTGT CTATCAAGGG AGTCTGTGCG

 61 AACCGTTACC TTGCTATGAA GGAAGACGGA AGATTATTGG CTTCCAAATG TGTTACAGAT

121 GAATGTTTCT TTTTTGAACG ACTGGAATCT AATAACTACA ACACTTACCG GTCAAGGAAA

181 TACTCCAGTT GGTATGTGGC ACTGAAACGA ACTGGACAAT ATAAACTTGG GTCCAAAACA

241 GGACCAGGGC AGAAAGCCAT ACTTTTTCTT CCAATGTCTG CGAAGAGC
```

Tasmanian devil FGF2 gene coding sequence (aa 48-203) (SEQ ID NO: 198) (Ensembl accession no. ENSSHAP00000012215, which is hereby incorporated by reference in its entirety):

```
142                            ATGGCCGCG GGCAGCATCA CCACGTTGCC GGCCCTGGCC

181 GGGGATGGAG CCAGCGGGGG CGCCTTTCCC CCGGGCCACT TCCAGGACCC CAAGCGGCTG

241 TACTGCAAGA ACGGAGGCTT CTTCTTGCGC ATCCATCCCG ACGGTCACGT GGACGGCATC

301 CGCGAGAAGA GCGATCCGCA CATTAAACTT CAGCTTCAGG CAGAAGAGAG AGGAGTAGTG

361 TCTATTAAAG GAGTTTGTGC CAACCGCTAT CTTGCCATGA AAGAGGATGG CAGATTACTG

421 GCTCTGAAAT GTGTGACTGA AGAGTGTTTC TTCTTTGAAC GTCTAGAGTC CAACAATTAC
```

TABLE 4-continued

481 AACACTTATC GCTCAAGGAA ATACTCCAAT TGGTATGTGG CATTGAAACG CACAGGCCAG

541 TATAAGCTTG GATCCAAGAC TGGACCAGGG CAGAAAGCCA TCCTTTTCCT TCCCATGTCT

601 GCTAAGAGCT GA

Gray short-tailed opossum FGF2 gene coding sequence (aa 1-155) (SEQ ID NO: 199) (GenBank accession no. NM_001033976, which is hereby incorporated by reference in its entirety):

29 AT GGCCGCAGGC AGCATCACCA CGCTGCCAGC

61 CCTGTCCGGG GACGGAGGCG GCGGGGGCGC CTTTCCCCCG GGCCACTTCA AGGACCCCAA

121 GCGGCTGTAC TGCAAGAACG GAGGCTTCTT CCTGCGCATC CACCCCGACG GCCGTGTGGA

181 CGGCATCCGC GAGAAGAGCG ACCCGAACAT TAAACTACAA CTTCAGGCAG AAGAGAGAGG

241 AGTGGTGTCT ATTAAAGGAG TATGTGCCAA TCGCTATCTT GCCATGAAGG AAGATGGAAG

301 ATTATTGGCT TTGAAATATG TGACCGAAGA GTGTTTCTTT TTCGAACGCT TGGAGTCCAA

361 CAACTACAAC ACTTATCGCT CGAGGAAATA TTCCAATTGG TACGTGGCAC TGAAACGAAC

421 GGGGCAGTAC AAGCTTGGAT CCAAGACTGG CCCGGGGCAG AAAGCCATCC TTTTCCTCCC

481 CATGTCTGCT AAGAGCTGA

Rabbit FGF2 gene coding sequence (aa 1-155) (SEQ ID NO: 200) (GenBank accession no. XM_002717238, which is hereby incorporated by reference in its entirety):

1 ATGGCAGCCG AGAGCATCAC CACGCTGCCC GCCCTGCCGG AGGATGGAGG CAGCGGCGCC

61 TTCCCGCCCG GCCACTTCAA GGACCCCAAG CGGCTGTACT GCAAAAACGG GGGTTTCTTC

121 CTGCGTATCC ACCCCGACGG CCGCGTGGAC GGGGTCCGGG AGAAGAGCGA CCCACACATC

181 AAATTACAAC TTCAAGCAGA AGAGAGAGGA GTTGTATCCA TCAAAGGTGT GTGTGCAAAC

241 CGTTACCTTG CTATGAAGGA AGATGGAAGA CTGCTGGCTT CTAAATGTGT TACAGACGAG

301 TGCTTCTTTT TTGAACGACT GGAGTCTAAT AACTACAATA CTTACCGGTC AAGGAAATAT

361 TCCAGCTGGT ATGTGGCACT GAAACGAACT GGGCAGTATA AACTTGGATC CAAAACAGGA

421 CCTGGGCAGA AGGCTATACT TTTTCTTCCA ATGTCTGCTA AGAGCTGA

Turkey FGF2 gene coding sequence (1-125; partial amino acid sequence corresponding to human FGF2 residues 31 to 155) (SEQ ID NO: 201) (Ensembl accession no. ENSMGAT00000011845, which is hereby incorporated by reference in its entirety):

1 CGGCTCTACT GTAAGAACGG CGGCTTCTTC CTGCGCATCA ATCCCGACGG CAGAGTGGAC

61 GGCGTCCGCG AGAAGAGCGA TCCGCACATC AAACTGCAGC TTCAGGCAGA AGAAAGAGGA

121 GTGGTATCAA TCAAAGGTGT AAGTGCAAAC CGCTTTCTGG CTATGAAGGA GGATGGCAGA

181 TTGCTGGCAC TGAAATGTGC AACAGAAGAA TGTTTCTTTT TTGAGCGTTT GGAATCTAAT

241 AATTATAACA CTTACCGGTC ACGGAAGTAC TCTGATTGGT ATGTGGCACT GAAAAGAACT

301 GGACAGTACA AGCCCGGACC AAAAACTGGA CCTGGACAGA AAGCTATCCT TTTTCTTCCA

361 ATGTCTGCTA AAAGC

Gallus gallus FGF2 gene coding sequence (aa 1-158) (SEQ ID NO: 202) (GenBank accession no. NM_205433, which is hereby incorporated by reference in its entirety):

98 ATG GCGGCGGGGG CGGCGGGGAG

121 CATCACCACG CTGCCGGCGC TGCCCGACGA CGGGGGCGGC GGCGCTTTTC CCCCCGGGCA

181 CTTCAAGGAC CCCAAGCGGC TCTACTGCAA GAACGGCGGC TTCTTCCTGC GCATCAACCC

241 CGACGGCAGG GTGGACGGCG TCCGCGAGAA GAGCGATCCG CACATCAAAC TGCAGCTTCA

301 AGCAGAAGAA AGAGGAGTAG TATCAATCAA AGGCGTAAGT GCAAACCGCT TTCTGGCTAT

TABLE 4-continued

```
361 GAAGGAGGAT GGCAGATTGC TGGCACTGAA ATGTGCAACA GAGGAATGTT TCTTTTTCGA

421 GCGCTTGGAA TCTAATAACT ATAACACTTA CCGGTCACGG AAGTACTCTG ATTGGTATGT

481 GGCACTGAAA AGGACTGGAC AGTACAAGCC CGGACCAAAA ACTGGACCTG GACAGAAAGC

541 TATCCTTTTT CTTCCAATGT CTGCTAAAAG CTGA
```

Zebra finch FGF2 gene coding sequence (aa 1-153) (SEQ ID NO: 203) (GenBank accession no. XM_002188361, which is hereby incorporated by reference in its entirety):

```
  1 ATGGCGGCGG CGGGGGGCAT CGCTACGCTG CCCGACGACG GCGGCAGCGG CGCCTTTCCC

 61 CCGGGGCACT TCAAGGACCC CAAGCGCCTG TACTGCAAGA ACGGCGGCTT CTTCCTGCGC

121 ATCAACCCCG ACGGGAAGGT GGACGGCGTC CGCGAGAAGA GCGACCCGCA CATCAAGCTG

181 CAGCTTCAGG CGGAGGAACG AGGAGTGGTG TCCATCAAAG GTGTCAGTGC CAATCGCTTC

241 CTGGCCATGA AAGAGGATGG CAGATTGCTG GCCTTGAAAT ATGCAACAGA AGAATGTTTC

301 TTTTTTGAAC GTTTGGAATC CAATAACTAT AACACTTACC GGTCACGGAA ATACTCGGAT

361 TGGTATGTGG CACTGAAAAG AACTGGACAG TACAAACCTG GACCAAAAAC TGGACCTGGA

421 CAGAAAGCTA TCCTTTTCCT TCCTATGTCT GCTAAAAGCT GA
```

Japanese firebelly newt FGF2 gene coding sequence (aa 1-155) (SEQ ID NO: 204) (GenBank accession no. AB064664, which is hereby incorporated by reference in its entirety):

```
384                         ATGGCTG CTGGGAGCAT CACCAGTCTC CCTGCCCTAC

421 CCGAGGACGG GAATGGCGGC ACCTTCACAC CCGGCGGATT CAAAGAGCCG AAGAGGCTGT

481 ACTGCAAGAA CGGGGGCTTC TTTCTCCGGA TCAACTCCGA CGGCAAGGTG GACGGAGCCC

541 GGGAGAAGAG CGACTCCTAC ATTAAACTGC AGCTTCAAGC AGAAGAGCGC GGTGTGGTGT

601 CCATCAAGGG AGTATGTGCA AACCGCTATC TCGCTATGAA GGATGATGGC AGGCTGATGG

661 CGCTGAAATG GATAACCGAT GAATGCTTCT TTTTCGAGCG ACTGGAGTCC AACAACTATA

721 ACACGTATCG ATCACGGAAA TATTCCGATT GGTATGTGGC GCTGAAAAGA ACTGGGCAAT

781 ACAAAAATGG ATCAAAAACC GGAGCAGGAC AGAAAGCAAT CCTTTTTCTA CCCATGTCGG

841 CCAAGAGTTG A
```

African clawed frog FGF2 gene coding sequence (aa 1-155) (SEQ ID NO: 205) (GenBank accession no. NM_001099871, which is hereby incorporated by reference in its entirety):

```
335                                    ATGGCG GCAGGGAGCA TCACAACTCT

361 GCCAACTGAA TCCGAGGATG GGGGAAACAC TCCTTTTTCA CCAGGGAGTT TTAAAGACCC

421 CAAGAGGCTC TACTGCAAGA ACGGGGGCTT CTTCCTCAGG ATAAACTCAG ACGGGAGAGT

481 GGACGGGTCA AGGGACAAAA GTGACTCGCA CATAAAATTA CAGCTACAAG CTGTAGAGCG

541 GGGAGTGGTA TCAATAAAGG GAATCACTGC AAATCGCTAC CTTGCCATGA AGGAAGATGG

601 GAGATTAACA TCGCTGAGGT GTATAACAGA TGAATGCTTC TTTTTTGAAC GACTGGAAGC

661 TAATAACTAC AACACTTACC GGTCTCGGAA ATACAGCAGC TGGTATGTGG CACTAAAGCG

721 AACCGGGCAG TACAAAAATG GATCGAGCAC TGGACCGGGA CAAAAAGCTA TTTTATTTCT

781 CCCAATGTCC GCAAAGAGCT GA
```

White-eared opossum FGF2 gene coding sequence (aa 1-156) (SEQ ID NO: 206) (GenBank accession no. EF057322, which is hereby incorporated by reference in its entirety):

```
  1 ATGGCAGCAG GCAGCATCAC CACATTGCCG GCCCTGTCCG GGGACGGAGG CGGCGGGGGA

 61 GCCTTTCCTC CAGGCCACTT CAAGGACCCC AAGCGGCTGT ACTGCAAGAA CGGAGGCTTC
```

TABLE 4-continued

121 TTCCTGCGCA TCCACCCCGA CGGCCGCGTG GACGGCATCC GCGAGAAGAG CGACCCGAAC

181 ATTAAACTAC AACTTCAGGC AGAAGAGAGA GGAGTAGTGT CTATTAAAGG AGTATGTGCC

241 AACCGATATC TTGCCATGAA GGAGGATGGC AGATTATTGG CTTTGAAATA TGTGACCGAA

301 GAGTGTTTCT TTTTTGAACG TTTGGAGTCC AACAACTACA ACACTTATCG CTCAAGAAAA

361 TATTCCAATT GGTATGTGGC ACTGAAACGA ACGGGGCAGT ATAAGCTTGG ATCCAAGACT

421 GGCCCGGGGC AGAAAGCCAT CCTTTTCTCC CCATGTCTGC TAAGATGCTG A

Microbat FGF2 gene coding sequence (1-96; partial amino acid sequence corresponding to human FGF2 residues 60 to 155) (SEQ ID NO: 207) (Ensembl accession no. ENSMLUT00000027717, which is hereby incorporated by reference in its entirety):

1 GTCAAACTCC AACTTCAAGC AGAAGAGAGA GGGGTCGTGT CTATCAAAGG AGTGTGTGCC

61 AACCGCTATC TCGCTATGAA GGAGGACGGC CGGTTACAGG CTTCTAAATG TGTTACGGAT

121 GAGTGTTTCT TTTTTGAACG GTTGGAATCC AATAACTACA ACACTTACCG GTCAAGAAAG

181 TACTCCAGTT GGTATGTGGC ATTGAAGCGG AATGGGCAGT ATAAACTTGG ACCCAAAACA

241 GGACCTGGCC AGAAAGCCAT ACTTTTTCTT CCCATGTCTG CTAAGAGC

Anole lizard FGF2 gene coding sequence (1-140; partial amino acid sequence corresponding to human FGF2 residues 16 to 155) (SEQ ID NO: 208) (Ensembl accession no. ENSACAT00000011897, which is hereby incorporated by reference in its entirety):

1 GCGGCGGCGG CCTCTTTCCC CCCGGGCCCC TTCAAGGACC CCAAGCGCCT CTACTGCAAG

61 AACGGGGGCT TCTTCCTGCG GATCAACCCC GACGGCGGCG TGGACGGCGT CCGAGAGAAG

121 AGCGACCCCA ACATCAAATT GCTGCTCCAG GCAGAGGAGA GAGGTGTAGT GTCCATCAAA

181 GGTGTATGCG CAAACCGTTT CCTGGCTATG AATGAAGACG GTCGATTGTT AGCACTGAAA

241 TACGTAACAG ATGAATGCTT CTTTTTTGAA CGCTTGGAAT CTAATAATTA CAATACTTAT

301 CGGTCTCGTA AATACCGTGA TTGGTACATT GCACTGAAAC GAACTGGTCA GTACAAACTT

361 GGACCAAAAA CTGGACGAGG CCAGAAAGCT ATCCTTTTCC TTCCAATGTC TGCCAAAAGT

Armadillo FGF2 gene coding sequence (124-217; partial amino acid sequence corresponding to human FGF2 residues 1 to 94) (SEQ ID NO: 209) (Ensembl accession no. ENSDNOT00000014647, which is hereby incorporated by reference in its entirety):

361 A TGGCAGCCGG GAGCATCACC ACGCTGCCCG CTCTGCCCGA GGACGGCGGC

421 AGCGGCGCCT TCCCGCCGGG CCACTTCAAG GACCCCAAGC GGCTGTACTG CAAAAACGGG

481 GGCTTCTTCC TGCGCATCCA TCCCGACGGC CGAGTGGACG GGGTCCGGGA GAAGAGCGAC

541 CCTAACATCA AACTACAACT TCAAGCAGAA GAGAGAGGGG TCGTGTCTAT CAAAGGCGTG

601 TGTGCGAACC GTTACCTTGC TATGCGGGAA GACGGAAGAC TCCAGGCGTC T

Tree shrew FGF2 gene coding sequence (1-189) (SEQ ID NO: 210) (Ensembl accession no. ENSTBET00000001143, which is hereby incorporated by reference in its entirety):

1 GCGGGGGTTA GAGCTGAGAG GGAGGAGGCA CCGGGGAGCG GTGACAGCCG GGGGACCGAT

61 CCCGCCGCGC GTTCGCTCAT CAGGAGGCCG GATGCTGCAG CGCGAGAGGC GCTTCTTGGA

121 GCCAGGAGCC GGGTTCAGGG CAGCTCCACC TCCTGGCCAG CCTCGTCACG AACCGGGATC

181 AAGTTGCCGG ACGACTCAGG TCAAGGAATG GGCGGCTATC CTCTGGACCG CCCGAGCCGG

241 AGCACAGGGC GAGGGCTGGG CGGTGCCCCG GACCCTGCCG TAAAACTACA GCTTCAAGCG

301 GAAGAGAGAG GGGTCGTGTC TATCAAAGGA GTGTGTGCAA ACCGTTACCT GGCCATGAAG

361 GAGGATGGGC GACTGCTGGC TTCTAAATGT GTTACAGATG AGTGTTTCTT TTTTGAACGA

TABLE 4-continued

```
421 CTGGAATCTA ATAACTACAA TACTTACCGG TCCCGAAAGT ACTCCAGCTG GTATGTGGCA

481 CTGAAACGAA CTGGGCAGTA TAAACTTGGA TCCAAAACAG GACCTGGGCA GAAAGCTATA

541 CTTTTTCTTC CAATGTCTGC TAAAAGC
```

Western clawed frog FGF2 gene coding sequence (aa 1-154) (SEQ ID NO: 211) (GenBank accession no. NM_001017333, which is hereby incorporated by reference in its entirety):

```
171                                                         ATGGCAGCAG

181 GAAGCATCAC AACCCTACCA ACCGAATCTG AGGATGGAAA CACTCCTTTC CCACCGGGGA

241 ACTTTAAGGA CCCCAAGAGG CTCTACTGCA AGAATGGGGG CTACTTCCTC AGGATTAACT

301 CAGACGGGAG AGTGGACGGA TCAAGGGATA AAAGTGACTT ACACATAAAA TTACAGCTAC

361 AAGCAGTAGA GCGGGGAGTG GTATCAATAA AGGGAATCAC TGCAAATCGC TACCTTGCCA

421 TGAAGGAAGA TGGGAGATTA ACATCGCTGA AGTGTATAAC AGATGAATGC TTCTTTTATG

481 AACGATTGGA AGCTAATAAC TACAACACTT ACCGGTCTCG GAAAAACAAC AGCTGGTATG

541 TGGCACTAAA GCGAACTGGG CAGTATAAAA ATGGATCGAC CACTGGACCA GGACAAAAAG

601 CTATTTTGTT TCTCCCAATG TCAGCAAAAA GCTGA
```

Coelacanth FGF2 gene coding sequence (aa 1-155) (SEQ ID NO: 212) (Ensembl accession no. ENSLACT00000019333, which is hereby incorporated by reference in its entirety):

```
  1                        ATGGCTGCGG GAGGAATCAC TACCCTGCCG GCGGTACCTG

 41 AGGATGGAGG CAGCAGCACC TTCCCTCCAG GAAACTTCAA GGAGCCCAAG AGACTTTACT

101 GTAAGAATGG AGGCTATTTC TTAAGGATAA ACCCCGATGG AAGAGTGGAT GGAACAAGGG

161 AGAAAAATGA TCCTTATATA AAATTACAAC TGCAAGCTGA ATCTATAGGA GTGGTGTCGA

221 TAAAGGGAGT TTGTTCAAAC CGTTACCTAG CGATGAATGA AGACTGTAGA CTTTTTGGAT

281 TGAAATATCC AACGGATGAA TGTTTCTTCC ATGAGAGGCT GGAGTCCAAC AACTACAATA

341 CTTATCGTTC AAAGAAGTAT TCGGATTGGT ATGTGGCGCT GAAACGGACT GGTCAGTACA

401 AACCTGGGCC AAAAACTGGA CTGGGACAAA AAGCAATCCT TTTCCTTCCG ATGTCTGCCA

461 AGAGTTGA
```

Spotted green pufferfish FGF2 gene coding sequence (aa 34-188) (SEQ ID NO: 213) (Ensembl accession no. ENSTNIT00000016254, which is hereby incorporated by reference in its entirety):

```
  1 ATGGCCACGG GAGGGATCAC GACGCTTCCA TCCACACCTG AAGACGGCGG CAGCAGCGGC

 61 TTTCCTCCCG GCAGCTTCAA GGATCCCAAA AGGCTCTACT GTAAAAACGG AGGTTTCTTC

121 CTGAGGATCA AGTCCGACGG GGTCGTGGAC GGAATCCGGG AGAAGAGTGA CCCCCACATA

181 AAGCTTCAGC TCCAGGCGAC CTCTGTGGGG GAGGTGGTCA TCAAGGGGGT GTGCGCTAAC

241 CGCTATCTGG CCATGAACAG AGATGGACGG CTGTTCGGAA CGAAACGAGC CACGGACGAA

301 TGCCATTTCT TAGAGCGGCT TGAGAGCAAC AACTACAACA CTTACCGCTC CAGGAAGTAC

361 CCAACCATGT TTGTGGGACT GACGCGGACG GGCCAGTACA AGTCTGGGAG CAAAACTGGA

421 CCGGGCCAAA AGGCCATCCT TTTTCTTCCG ATGTCCGCCA AATGCTAA
```

Stickleback FGF2 gene coding sequence (aa 1-155) (SEQ ID NO: 214) (Ensembl accession no. ENSGACT00000022120, which is hereby incorporated by reference in its entirety):

```
  1                     AT GGCCACGGCA GGCTTCGCGA CGCTTCCCTC CACGCCCGAA

 43 GACGGCGGCA GCGGCGGCTT CACCCCCGGG GGATTCAAGG ATCCCAAGAG GCTGTACTGC

103 AAAAACGGGG GCTTCTTCTT GAGGATCAGG TCCGACGGAG GTGTAGATGG AATCAGGGAG
```

TABLE 4-continued

```
163 AAGAGCGACG CCCACATAAA GCTCCAAATC CAGGCGACGT CGGTGGGGGA GGTGGTCATC

223 AAAGGAGTCT GTGCCAACCG CTATCTGGCC ATGAACAGAG ACGGCCGGCT GTTCGGAGTG

283 AGACGGGCGA CGGACGAATG CTACTTCCTG GAGCGGCTGG AGAGTAACAA CTACAACACC

343 TACCGCTCCA GGAAGTACCC CGGCATGTAC GTGGCTCTGA AGCGGACCGG CCAGTACAAG

403 TCCGGGAGCA AAACCGGACC CGGTCAAAAG GCCATTCTGT TCCTCCCCAT GTCGGCTAAG

463 TGCTAA
```

Fugu rubripes FGF2 gene coding sequence (aa 1-155) (SEQ ID NO: 215) (Ensembl accession no. ENSTRUT00000022363, which is hereby incorporated by reference in its entirety):

```
127       ATGG CCACGGGAGG GATCACAACA CTTCCATCCA CACCTGAAGA CGGCGGCAGC

181 GGCGGTTTTC CTCCCGGGAG CTTCAAGGAT CCCAAAAGGC TGTACTGTAA AAACGGCGGC

241 TTCTTCCTGA GGATCAGGTC CGACGGGGCC GTGGACGGAA CCCGGGAGAA GACTGACCCC

301 CACATAAAGC TTCAGCTCCA GGCGACCTCT GTGGGGGAGG TGGTCATCAA GGGGGTTTGT

361 GCTAATCGTT ATCTGGCCAT GAACAGAGAT GGACGACTGT TTGGAATGAA ACGAGCGACG

421 GATGAATGCC ACTTCTTAGA GCGGCTCGAG AGCAACAACT ACAACACCTA CCGCTCCAGG

481 AAGTACCCCA ACATGTTTGT GGGACTGACG CGAACTGGCA ACTACAAGTC TGGGACTAAA

541 ACTGGACCGG GCCAAAAGGC CATCCTCTTT CTTCCGATGT CGGCCAAATA CTAA
```

Rainbow trout FGF2 gene coding sequence (aa 1-155) (SEQ ID NO: 216) (GenBank accession no. NM_001124536, which is hereby incorporated by reference in its entirety):

```
390                            A TGGCCACAGG AGAAATCACC ACTCTACCCG

421 CCACACCTGA AGATGGAGGC AGTGGCGGCT TCCTTCCAGG AAACTTTAAG GAGCCCAAGA

481 GGTTGTACTG TAAAAATGGA GGCTACTTCT TGAGGATAAA CTCTAACGGA AGCGTGGACG

541 GGATCAGAGA TAAGAACGAC CCCCACAATA AGCTTCAACT CCAGGCGACC TCAGTGGGGG

601 AAGTAGTAAT CAAAGGGGTC TCAGCCAACC GCTATCTGGC CATGAATGCA GATGGAAGAC

661 TGTTTGGACC GAGACGGACA ACAGATGAAT GCTACTTCAT GGAGAGGCTG GAGAGTAACA

721 ACTACAACAC CTACCGCTCT CGAAAGTACC CTGAAATGTA TGTGGCACTG AAAAGGACTG

781 GCCAGTACAA GTCAGGATCC AAAACTGGAC CCGGCCAAAA AGCCATCCTC TTCCTCCCCA

841 TGTCAGCCAG ACGCTGA
```

Salmon FGF2 gene coding sequence (1-150) (SEQ ID NO: 217) (GenBank accession no. EU816603, which is hereby incorporated by reference in its entirety):

```
 99402                                        ATGGCCACA GGAGAAATCA

 99421 CCACTCTACC CGCCACACCT GAAGATGGAG GCAGTGGCGG CTTCCCTCCA GGAAACTTTA

 99481 AGGATCCCAA GAGGCTGTAC TGTAAAAACG GGGGCTACTT CTTGAGAATA AACTCTAATG

 99541 GAAGCGTGGA CGGGATCCGA GAGAAGAACG ACCCCCACA

100968                                               AAC AGCCTCAATT

100981 TGTCAGGGCA TGGACTCTTC AAGGTGTCAA ACGTTCCACA GGGATGCTGG CCCATGTTGA

101041 CTCCAACGCT TCCCACAATT GTGTCAAGGT GGCTGGATGT TCTTTGGGAG

101845                          AATTTG GCAGTATGTC CAACCGGCCT CATAACCGCA

101881 GACCACGTGT AGCTACACCA GCCCAGGACC TCCACATCCG GCTTCTTCAT CTACGGGATC

101941 GTCTGAAACC AGCCACCCGA ACAGCTGATA AAACTGAGGA GTATTTCTGT CTGTAA
```

TABLE 4-continued

| |
|---|
| Zebrafish FGF2 gene coding sequence (aa 1-154) (SEQ ID NO: 218) (GenBank accession no. AY269790, which is hereby incorporated by reference in its entirety): |
| 43 ATGGCCAC CGGAGGGATC |
| 61 ACCACACTCC CGGCCGCTCC GGACGCCGAA AACAGCAGCT TTCCCGCGGG CAGCTTCAGG |
| 121 GATCCCAAGC GCCTGTACTG CAAAAACGGA GGATTCTTCC TGCGGATCAA CGCGGACGGC |
| 181 CGAGTGGACG GAGCCCGAGA CAAGAGCGAC CCGCACATTC GTCTGCAGCT GCAGGCGACG |
| 241 GCAGTGGGTG AAGTACTCAT TAAAGGCATC TGTACCAACC GTTTCCTTGC CATGAACGCA |
| 301 GACGGACGAC TGTTCGGGAC GAAAAGGACC ACAGATGAAT GTTATTTCCT GGAGCGCCTG |
| 361 GAGTCCAACA ACTACAACAC ATACAGATCC CGCAAGTATC CCGACTGGTA CGTGGCTCTG |
| 421 AAGAGAACCG GCCAGTATAA AAGCGGCTCT AAAACCAGCC CGGGACAGAA GGCCATCCTG |
| 481 TTTCTGCCCA TGTCGGCCAA ATGCTGA |
| Nile tilapia FGF2 gene coding sequence (aa 1-155) (SEQ ID NO: 219) (GenBank accession no. XM_003443364, which is hereby incorporated by reference in its entirety): |
| 1 ATGGCCACGG GAGGAATCAC AACACTTCCC GCTACACCTG AAGACGGCGG CAGCAGCGGC |
| 61 TTTCCTCCTG GGAACTTCAA GGACCCTAAA AGGCTGTACT GTAAAAATGG TGGCTTCTTC |
| 121 TTGAGGATAA AATCTGATGG AGGAGTGGAT GGAATACGAG AGAAAAACGA CCCCCACATA |
| 181 AAGCTTCAAC TCCAGGCGAC CTCAGTGGGA GAAGTGGTCA TCAAAGGGAT TTGTGCAAAC |
| 241 CGATATCTGG CAATGAACAG AGATGGACGA CTGTTTGGAG CGAGAAGAGC AACAGATGAG |
| 301 TGCTACTTCT TAGAGCGGCT CGAGAGCAAC AACTACAACA CCTACCGCTC CAGGAAGTAC |
| 361 CCAAACATGT ACGTGGCGCT GAAGCGGACT GGCCAGTACA AGTCTGGAAG CAAAACTGGA |
| 421 CCGGGTCAAA AGGCAATTCT CTTTCTCCCA ATGTCTGCTA AATGCTAA |
| Medaka FGF2 gene coding sequence (aa 1-155) (SEQ ID NO: 220) (Ensembl accession no. ENSORLT00000025835, which is hereby incorporated by reference in its entirety): |
| 1 ATGGCTACGG GAGAAATCAC AACACTTCCC TCCCCAGCTG AAAACAGCAG AAGCGATGGC |
| 61 TTTCCTCCAG GGAACTACAA GGATCCTAAG AGGCTCTACT GTAAAAATGG AGGTTTGTTT |
| 121 TTGAGGATTA AACCTGATGG AGGAGTGGAT GGAATCCGGG AAAAAAAAGA TCCCCACGTT |
| 181 AAGCTTCGCC TTCAGGCTAC CTCAGCGGGA GAGGTGGTGA TCAAAGGAGT TTGTTCAAAC |
| 241 AGATATCTGG CGATGCATGG AGATGGACGT CTATTTGGAG TGAGACAAGC AACAGAGGAA |
| 301 TGCTACTTCT TGGAGCGACT AGAGAGCAAC AACTATAACA CCTATCGCTC TAAAAAGTAC |
| 361 CCAAACATGT ACGTGGCACT GAAGCGGACA GGCCAGTACA AACCTGGAAA CAAAACTGGA |
| 421 CCAGGTCAAA AGGCCATTCT CTTTCTGCCT ATGTCTGCCA AGTACTAA |

As noted above, also encompassed within the present invention are portions of paracrine FGFs other than FGF1 and/or FGF2 (e.g., FGF4, FGF5, FGF6, FGF9, FGF16, and FGF20). The portion of the paracrine FGF may be from human FGF4, FGF5, FGF6, FGF9, FGF16, and/or FGF20 having the amino acid sequences shown in Table 5, or orthologs thereof.

TABLE 5

| |
|---|
| Amino acid sequence of human FGF4 (SEQ ID NO: 221) (GenBank accession no. NP_001998, which is hereby incorporated by reference in its entirety): |
| 1 MSGPGTAAVA LLPAVLLALL APWAGRGGAA APTAPNGTLE AELERRWESL VALSLARLPV |
| 61 AAQPKEAAVQ SGAGDYLLGI KRLRRLYCNV GIGFHLQALP DGRIGGAHAD TRDSLLELSP |

TABLE 5-continued

| | |
|---|---|
| 121 | VERGVVSIFG VASRFFVAMS SKGKLYGSPF FTDECTFKEI LLPNNYNAYE SYKYPGMFIA |
| 181 | LSKNGKTKKG NRVSPTMKVT HFLPRL |

Amino acid sequence of human FGF5 (SEQ ID NO: 222) (GenBank Accession No. NP_004455, which is hereby incorporated by reference in its entirety):

| | |
|---|---|
| 1 | MSLSFLLLLF FSHLILSAWA HGEKRLAPKG QPGPAATDRN PRGSSSRQSS SSAMSSSSAS |
| 61 | SSPAASLGSQ GSGLEQSSFQ WSPSGRRTGS LYCRVGIGFH LQIYPDGKVN GSHEANMLSV |
| 121 | LEIFAVSQGI VGIRGVFSNK FLAMSKKGKL HASAKFTDDC KFRERFQENS YNTYASAIHR |
| 181 | TEKTGREWYV ALNKRGKAKR GCSPRVKPQH ISTHFLPRFK QSEQPELSFT VTVPEKKKPP |
| 241 | SPIKPKIPLS APRKNTNSVK YRLKFRFG |

Amino acid sequence of human FGF6 (SEQ ID NO: 223) (NP_066276, which is hereby incorporated by reference in its entirety):

| | |
|---|---|
| 1 | MALGQKLFIT MSRGAGRLQG TLWALVFLGI LVGMVVPSPA GTRANNTLLD SRGWGTLLSR |
| 61 | SRAGLAGEIA GVNWESGYLV GIKRQRRLYC NVGIGFHLQV LPDGRISGTH EENPYSLLEI |
| 121 | STVERGVVSL FGVRSALFVA MNSKGRLYAT PSFQEECKFR ETLLPNNYNA YESDLYQGTY |
| 181 | IALSKYGRVK RGSKVSPIMT VTHFLPRI |

Amino acid sequence of human FGF9 (SEQ ID NO: 224) (GenBank accession no. NP_002001, which is hereby incorporated by reference in its entirety):

| | |
|---|---|
| 1 | MAPLGEVGNY FGVQDAVPFG NVPVLPVDSP VLLSDHLGQS EAGGLPRGPA VTDLDHLKGI |
| 61 | LRRRQLYCRT GFHLEIFPNG TIQGTRKDHS RFGILEFISI AVGLVSIRGV DSGLYLGMNE |
| 121 | KGELYGSEKL TQECVFREQF EENWYNTYSS NLYKHVDTGR RYYVALNKDG TPREGTRTKR |
| 181 | HQKFTHFLPR PVDPDKVPEL YKDILSQS |

Amino acid sequence of human FGF16 (SEQ ID NO: 225) (GenBank accession no. NP_003859, which is hereby incorporated by reference in its entirety):

| | |
|---|---|
| 1 | MAEVGGVFAS LDWDLHGFSS SLGNVPLADS PGFLNERLGQ IEGKLQRGSP TDFAHLKGIL |
| 61 | RRRQLYCRTG FHLEIFPNGT VHGTRHDHSR FGILEFISLA VGLISIRGVD SGLYLGMNER |
| 121 | GELYGSKKLT RECVFREQFE ENWYNTYAST LYKHSDSERQ YYVALNKDGS PREGYRTKRH |
| 181 | QKFTHFLPRP VDPSKLPSMS RDLFHYR |

Amino acid sequence of human FGF20 (SEQ ID NO: 226) (GenBank accession no. NP_062825, which is hereby incorporated by reference in its entirety):

| | |
|---|---|
| 1 | MAPLAEVGGF LGGLEGLGQQ VGSHFLLPPA GERPPLLGER RSAAERSARG GPGAAQLAHL |
| 61 | HGILRRRQLY CRTGFHLQIL PDGSVQGTRQ DHSLFGILEF ISVAVGLVSI RGVDSGLYLG |
| 121 | MNDKGELYGS EKLTSECIFR EQFEENWYNT YSSNIYKHGD TGRRYFVALN KDGTPRDGAR |
| 181 | SKRHQKFTHF LPRPVDPERV PELYKDLLMY T |

It will be understood that the portion of the paracrine FGF according to the present invention may be derived from a nucleotide sequence that encodes human FGF4, FGF5, FGF6, FGF9, FGF16, and/or FGF20 having the nucleotide sequences shown in Table 6, or orthologs thereof.

TABLE 6

Human FGF4 gene coding sequence (1-206) (SEQ ID NO: 227) (GenBank accession no. NM_002007, which is hereby incorporated by reference in its entirety):

```
320                         A TGTCGGGGCC CGGGACGGCC GCGGTAGCGC TGCTCCCGGC
361 GGTCCTGCTG GCCTTGCTGG CGCCCTGGGC GGGCCGAGGG GGCGCCGCCG CACCCACTGC
421 ACCCAACGGC ACGCTGGAGG CCGAGCTGGA GCGCCGCTGG GAGAGCCTGG TGGCGCTCTC
481 GTTGGCGCGC CTGCCGGTGG CAGCGCAGCC CAAGGAGGCG GCCGTCCAGA GCGGCGCCGG
541 CGACTACCTG CTGGGCATCA AGCGGCTGCG GCGGCTCTAC TGCAACGTGG GCATCGGCTT
601 CCACCTCCAG GCGCTCCCCG ACGGCCGCAT CGGCGGCGCG CACGCGGACA CCCGCGACAG
661 CCTGCTGGAG CTCTCGCCCG TGGAGCGGGG CGTGGTGAGC ATCTTCGGCG TGGCCAGCCG
721 GTTCTTCGTG GCCATGAGCA GCAAGGGCAA GCTCTATGGC TCGCCCTTCT TCACCGATGA
781 GTGCACGTTC AAGGAGATTC TCCTTCCCAA CAACTACAAC GCCTACGAGT CCTACAAGTA
841 CCCCGGCATG TTCATCGCCC TGAGCAAGAA TGGGAAGACC AAGAAGGGGA ACCGAGTGTC
901 GCCCACCATG AAGGTCACCC ACTTCCTCCC CAGGCTGTGA
```

Human FGF5 gene coding sequence (1-268) (SEQ ID NO: 228) (GenBank Accession No. NM_004464, which is hereby incorporated by reference in its entirety):

```
238                                                             ATG
241 AGCTTGTCCT TCCTCCTCCT CCTCTTCTTC AGCCACCTGA TCCTCAGCGC CTGGGCTCAC
301 GGGGAGAAGC GTCTCGCCCC CAAAGGGCAA CCCGGACCCG CTGCCACTGA TAGGAACCCT
361 AGAGGCTCCA GCAGCAGACA GAGCAGCAGT AGCGCTATGT CTTCCTCTTC TGCCTCCTCC
421 TCCCCCGCAG CTTCTCTGGG CAGCCAAGGA AGTGGCTTGG AGCAGAGCAG TTTCCAGTGG
481 AGCCCCTCGG GGCGCCGGAC CGGCAGCCTC TACTGCAGAG TGGGCATCGG TTTCCATCTG
541 CAGATCTACC CGGATGGCAA AGTCAATGGA TCCCACGAAG CCAATATGTT AAGTGTTTTG
601 GAAATATTTG CTGTGTCTCA GGGGATTGTA GGAATACGAG GAGTTTTCAG CAACAAATTT
661 TTAGCGATGT CAAAAAAAGG AAAACTCCAT GCAAGTGCCA AGTTCACAGA TGACTGCAAG
721 TTCAGGGAGC GTTTTCAAGA AAATAGCTAT AATACCTATG CCTCAGCAAT ACATAGAACT
781 GAAAAAACAG GGCGGGAGTG GTATGTGGCC CTGAATAAAA GAGGAAAAGC CAAACGAGGG
841 TGCAGCCCCC GGGTTAAACC CCAGCATATC TCTACCCATT TTCTGCCAAG ATTCAAGCAG
901 TCGGAGCAGC CAGAACTTTC TTTCACGGTT ACTGTTCCTG AAAAGAAAAA GCCACCTAGC
961 CCTATCAAGC CAAAGATTCC CCTTTCTGCA CCTCGGAAAA ATACCAACTC AGTGAAATAC
1021 AGACTCAAGT TTCGCTTTGG ATAA
```

Human FGF6 gene coding sequence (1-208) (SEQ ID NO: 229) (NM_020996, which is hereby incorporated by reference in its entirety):

```
45                                                   ATGGCC CTGGGACAGA
61 AACTGTTCAT CACTATGTCC CGGGGAGCAG GACGTCTGCA GGGCACGCTG TGGGCTCTCG
121 TCTTCCTAGG CATCCTAGTG GGCATGGTGG TGCCCTCGCC TGCAGGCACC CGTGCCAACA
181 ACACGCTGCT GGACTCGAGG GGCTGGGGCA CCCTGCTGTC CAGGTCTCGC GCGGGGCTAG
241 CTGGAGAGAT TGCCGGGGTG AACTGGGAAA GTGGCTATTT GGTGGGGATC AAGCGGCAGC
301 GGAGGCTCTA CTGCAACGTG GGCATCGGCT TTCACCTCCA GGTGCTCCCC GACGGCCGGA
361 TCAGCGGGAC CCACGAGGAG AACCCCTACA GCCTGCTGGA AATTTCCACT GTGGAGCGAG
421 GCGTGGTGAG TCTCTTTGGA GTGAGAAGTG CCCTCTTCGT TGCCATGAAC AGTAAAGGAA
481 GATTGTACGC AACGCCCAGC TTCCAAGAAG AATGCAAGTT CAGAGAAACC CTCCTGCCCA
```

TABLE 6-continued

```
541 ACAATTACAA TGCCTACGAG TCAGACTTGT ACCAAGGGAC CTACATTGCC CTGAGCAAAT

601 ACGGACGGGT AAAGCGGGGC AGCAAGGTGT CCCCGATCAT GACTGTCACT CATTTCCTTC

661 CCAGGATCTA A
```

Human FGF9 gene coding sequence (1-208) (SEQ ID NO: 230) (GenBank accession no. NM_002010, which is hereby incorporated by reference in its entirety):

```
838                                                            ATG

841 GCTCCCTTAG GTGAAGTTGG GAACTATTTC GGTGTGCAGG ATGCGGTACC GTTTGGGAAT

901 GTGCCCGTGT TGCCGGTGGA CAGCCCGGTT TTGTTAAGTG ACCACCTGGG TCAGTCCGAA

961 GCAGGGGGGC TCCCCAGGGG ACCCGCAGTC ACGGACTTGG ATCATTTAAA GGGGATTCTC

1021 AGGCGGAGGC AGCTATACTG CAGGACTGGA TTTCACTTAG AAATCTTCCC CAATGGTACT

1081 ATCCAGGGAA CCAGGAAAGA CCACAGCCGA TTTGGCATTC TGGAATTTAT CAGTATAGCA

1141 GTGGGCCTGG TCAGCATTCG AGGCGTGGAC AGTGGACTCT ACCTCGGGAT GAATGAGAAG

1201 GGGGAGCTGT ATGGATCAGA AAAACTAACC CAAGAGTGTG TATTCAGAGA ACAGTTCGAA

1261 GAAAACTGGT ATAATACGTA CTCATCAAAC CTATATAAGC ACGTGGACAC TGGAAGGCGA

1321 TACTATGTTG CATTAAATAA AGATGGGACC CCGAGAGAAG GGACTAGGAC TAAACGGCAC

1381 CAGAAATTCA CACATTTTTT ACCTAGACCA GTGGACCCCG ACAAAGTACC TGAACTGTAT

1441 AAGGATATTC TAAGCCAAAG TTGA
```

Human FGF16 gene coding sequence (1-207) (SEQ ID NO: 231) (GenBank accession no. NM_003868, which is hereby incorporated by reference in its entirety):

```
1 ATGGCAGAGG TGGGGGGCGT CTTCGCCTCC TTGGACTGGG ATCTACACGG CTTCTCCTCG

61 TCTCTGGGGA ACGTGCCCTT AGCTGACTCC CCAGGTTTCC TGAACGAGCG CCTGGGCCAA

121 ATCGAGGGGA AGCTGCAGCG TGGCTCACCC ACAGACTTCG CCCACCTGAA GGGGATCCTG

181 CGGCGCCGCC AGCTCTACTG CCGCACCGGC TTCCACCTGG AGATCTTCCC CAACGGCACG

241 GTGCACGGGA CCCGCCACGA CCACAGCCGC TTCGGAATCC TGGAGTTTAT CAGCCTGGCT

301 GTGGGGCTGA TCAGCATCCG GGGAGTGGAC TCTGGCCTGT ACCTAGGAAT GAATGAGCGA

361 GGAGAACTCT ATGGGTCGAA GAAACTCACA CGTGAATGTG TTTTCCGGGA ACAGTTTGAA

421 GAAAACTGGT ACAACACCTA TGCCTCAACC TTGTACAAAC ATTCGGACTC AGAGAGACAG

481 TATTACGTGG CCCTGAACAA AGATGGCTCA CCCCGGGAGG GATACAGGAC TAAACGACAC

541 CAGAAATTCA CTCACTTTTT ACCCAGGCCT GTAGATCCTT CTAAGTTGCC CTCCATGTCC

601 AGAGACCTCT TTCACTATAG GTAA
```

Human FGF20 gene coding sequence (1-211) (SEQ ID NO: 232) (GenBank accession no. NM_019851, which is hereby incorporated by reference in its entirety):

```
134             ATGGCTC CCTTAGCCGA AGTCGGGGGC TTTCTGGGCG GCCTGGAGGG

181 CTTGGGCCAG CAGGTGGGTT CGCATTTCCT GTTGCCTCCT GCCGGGGAGC GGCCGCCGCT

241 GCTGGGCGAG CGCAGGAGCG CGGCGGAGCG GAGCGCGCGC GGCGGGCCGG GGGCTGCGCA

301 GCTGGCGCAC CTGCACGGCA TCCTGCGCCG CCGGCAGCTC TATTGCCGCA CCGGCTTCCA

361 CCTGCAGATC CTGCCCGACG GCAGCGTGCA GGGCACCCGG CAGGACCACA GCCTCTTCGG

421 TATCTTGGAA TTCATCAGTG TGGCAGTGGG ACTGGTCAGT ATTAGAGGTG TGGACAGTGG

481 TCTCTATCTT GGAATGAATG ACAAAGGAGA ACTCTATGGA TCAGAGAAAC TTACTTCCGA

541 ATGCATCTTT AGGGAGCAGT TTGAAGAGAA CTGGTATAAC ACCTATTCAT CTAACATATA
```

TABLE 6-continued

```
601 TAAACATGGA GACACTGGCC GCAGGTATTT TGTGGCACTT AACAAAGACG GAACTCCAAG

661 AGATGGCGCC AGGTCCAAGA GGCATCAGAA ATTTACACAT TTCTTACCTA GACCAGTGGA

721 TCCAGAAAGA GTTCCAGAAT TGTACAAGGA CCTACTGATG TACACTTGA
```

As noted above, the chimeric protein includes a portion of a paracrine FGF coupled to a C-terminal region derived from an FGF23. FGF23 is an endocrine FGF that was cloned by Itoh et al. at Kyoto University (WO 01/66596 to Itoh et al., which is hereby incorporated by reference in its entirety). FGF23 mRNA is expressed mainly in the brain, preferentially in the ventrolateral thalamic nucleus. It is also expressed in the thymus at low levels (Yamashita et al., "Identification of a Novel Fibroblast Growth Factor, FGF-23, Preferentially Expressed in the Ventrolateral Thalamic Nucleus of the Brain," *Biochem Biophys Res Comm* 277(2): 494-498 (2000), which is hereby incorporated by reference in its entirety). The tissue with the highest level of FGF23 expression is bone (osteocytes and osteoblasts), where it is highly expressed during phases of active bone remodeling (Riminucci et al., "FGF-23 in Fibrous Dysplasia of Bone and its Relationship to Renal Phosphate Wasting," *J Clin Invest* 112:683-692 (2003), which is hereby incorporated by reference in its entirety). Expression of FGF23 in dendritic cells has also been reported (Katoh et al., "Comparative Genomics on Mammalian Fgf6-Fgf23 Locus.," *Int J Mol Med* 16(2):355-358 (2005), which is hereby incorporated by reference in its entirety). See also Zhang et al., "Receptor Specificity of the Fibroblast Growth Factor Family," *J Biol Chem* 281(23):15694-15700; Yu et al., "Analysis of the Biochemical Mechanisms for the Endocrine Actions of Fibroblast Growth Factor-23," *Endocrinology* 146(11): 4647-4656, which are hereby incorporated by reference in their entirety.

In one embodiment the C-terminal region of the FGF23 molecule includes an α-Klotho-FGFR complex binding domain. In one embodiment, the C-terminal region is from human FGF23 having the amino acid sequence of SEQ ID NO: 233 (GenBank accession no. AAG09917, which is hereby incorporated by reference in its entirety), as follows:

```
  1 MLGARLRLWV CALCSVCSMS VLRAYPNASP LLGSSWGGLI HLYTATARNS YHLQIHKNGH

 61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTRS

181 AEDDSERDPL NVLKPRARMT PAPASCSQEL PSAEDNSPMA SDPLGVVRGG RVNTHAGGTG

241 PEGCRPFAKF I
```

In one embodiment, the C-terminal portion from FGF23 of the chimeric protein according to the present invention includes an amino acid sequence beginning at any of amino acid residues 161-180 and ending at any of amino acid residues 200-251 of SEQ ID NO: 233. In one embodiment, the C-terminal portion from FGF23 of the chimeric protein according to the present invention comprises amino acid residues 161-200, 162-200, 163-200, 164-200, 165-200, 166-200, 167-200, 168-200, 169-200, 170-200, 171-200, 172-200, 173-200, 174-200, 175-200, 176-200, 177-200, 178-200, 179-200, 180-200, 161-205, 162-205, 163-205, 164-205, 165-205, 166-205, 167-205, 168-205, 169-205, 170-205, 171-205, 172-205, 173-205, 174-205, 175-205, 176-205, 177-205, 178-205, 179-205, 180-205, 161-251, 162-251, 163-251, 164-251, 165-251, 166-251, 167-251, 168-251, 169-251, 170-251, 171-251, 172-251, 173-251, 174-251, 175-251, 176-251, 177-251, 178-251, 179-251, or 180-251 of SEQ ID NO: 233.

In one embodiment, the C-terminal portion from FGF23 of the chimeric protein according to the present invention includes one or more deletions or substitutions while retaining the ability to bind the binary α-Klotho-FGFR complex. In one embodiment, the C-terminal portion from FGF23 of the chimeric protein according to the present invention includes a substitution at amino acid residues (or amino acid residues corresponding to) R176 and/or R179 of SEQ ID NO:233. In one embodiment, the R176 substitution is a R176Q/W substitution and/or the R179 substitution is a R179Q/W substitution. In one embodiment, the C-terminal portion from FGF23 of the chimeric protein according to the present invention includes amino acid residues 161-200, 162-200, 163-200, 164-200, 165-200, 166-200, 167-200, 168-200, 169-200, 170-200, 171-200, 172-200, 173-200, 174-200, 175-200, 176-200, 177-200, 178-200, 179-200, 180-200, 161-205, 162-205, 163-205, 164-205, 165-205, 166-205, 167-205, 168-205, 169-205, 170-205, 171-205, 172-205, 173-205, 174-205, 175-205, 176-205, 177-205, 178-205, 179-205, 180-205, 161-251, 162-251, 163-251, 164-251, 165-251, 166-251, 167-251, 168-251, 169-251, 170-251, 171-251, 172-251, 173-251, 174-251, 175-251, 176-251, 177-251, 178-251, 179-251, or 180-251 of SEQ ID NO: 233, where one or both of R176 and R179 are substituted. In one embodiment, the R176 substitution is a R176Q/W substitution and/or the R179 substitution is a R179Q/W substitution.

In one embodiment, the FGF23 according to the present invention is from a mammal. In one embodiment, the FGF23 according to the present invention is from a vertebrate. It will be understood that this includes orthologs of human FGF23, or a polypeptide or protein obtained from one species that is the functional counterpart of a polypeptide or protein from a different species. In one embodiment of the present invention, the FGF23 according to the present invention is from *Gorilla gorilla, Nomascus leucogenys, Macaca mulatta, Macaca fascicularis, Pan troglodytes, Callithrix jacchus, Loxodonta Africana, Erinaceus telfairi, Erinaceus europaeus, Otolemur garnettii, Oryctolagus cuniculus, Equus caballus, Ailuropoda melanoleuca, Ochotona princeps, Bos taurus, Sus scrofa, Canis lupus familiaris, Cavia porcellus, Cricetulus griseus, Tupaia belangeri, Rattus norvegicus, Mus musculus, Pteropus vampyrus, Myotis*

*lucifugus, Sarcophilus harrisii, Monodelphis domestica, Dasypus novemcinctus, Macropus eugenii, Taeniopygia guttata, Gallus gallus, Meleagris gallopavo, Anolis carolinensis, Latimeria chalumnae, Xenopus silurana tropicalis, Felis catus, Pelodiscus sinensis, Mustela putorius furo, Microcebus murinus, Pongo abelii, Sorex araneus, Tetraodon nigroviridis, Oreochromis niloticus*, or *Danio rerio*. In one embodiment, FGF23 according to the present invention is from a non-human FGF23 (or an FGF23 ortholog) having an amino acid sequence as shown in Table 7. The portions of an ortholog of human FGF23 of a chimeric protein according to the present invention include portions corresponding to the above-identified amino acid sequences of human FGF23. Corresponding portions may be determined by, for example, sequence analysis and structural analysis.

TABLE 7

Amino acid sequence of Gorilla gorilla (gorilla) FGF23 (SEQ ID NO: 234) (Ensembl accession no. ENSGGOP00000002917, which is hereby incorporated by reference in its entirety):

```
  1 MLGARLRLWV CALCSVCSLS VLRAYPNASP LLGSSWGGLI HLYTATARNS YHLQIHKNGH
 61 VDGAPHQTIY SALMIRSEDA GFVVITGVMS RRYLCMDFRG NIFGSHYFDP ENCRFQHQTL
121 ENGYDVYHSP QYHFLVSLGR AKRAFLPGMN PPPYSQFLSR RNEIPLIHFN TPIPRRHTRS
181 AEDDSERDPL NVLKPRARMT PAPASCSQEL PSAEDNSPMA SDPLGVVRGG RVNTYAGGTG
241 PEGCRPFPKF I
```

Amino acid sequence of *Nomascus leucogenys* (Northern white-cheeked gibbon) FGF23 (SEQ ID NO: 235) (GenBank accession no. XP_003273749, which is hereby incorporated by reference in its entirety):

```
  1 MLGARLRLWV CALCSVCSMS VLRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFQHQTL
121 ENGYDVYHSP QHHFLVSLGR AKRAFLPGMN PPPYSQFLSR RNEIPLLHFN TPTPRRHTRS
181 AEDDSERDPL NVLKPRARMT PAPASCSQEL LSSEDNSPMA SDPLGVVRGG RVNTHAGGTG
241 PEGCRPFPKF I
```

Amino acid sequence of *Macaca mulatta* (rhesus monkey) FGF23 (SEQ ID NO: 236) (GenBank accession no. NP_001181066, which is hereby incorporated by reference in its entirety):

```
  1 MLGARLRLWV CALCSVCSMS VIRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFRHWTL
121 ENGYDVYHSP QHHFLVSLGR AKRAFLPGMN PPPYSQFLSR RNEIPLIHFN TPRPRRHTRS
181 AEDDSERDPL NVLKPRARMT PAPASCSQEL PSAEDNSPVA SDPLGVVRGG RVNTHAGGTG
241 PEACRPFPKF I
```

Amino acid sequence of *Macaca fascicularis* (crab-eating macaque) FGF23 (SEQ ID NO: 237) (GenBank accession no. EHH66001, which is hereby incorporated by reference in its entirety):

```
  1 MLGARLRLWV CALCSVCSMS VIRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFRHWTL
121 ENGYDVYHSP QHHFLVSLGR AKRAFLPGMN PPPYSQFLSR RNEIPLIHFN TPRPRRHTRS
181 AEDDSERDPL NVLKPRARMT PAPASCSQEL PSAEDNSPVA SDPLGVVRAG RVNTHAGGTG
241 PEACRPFPKF I
```

Amino acid sequence of *Pan troglodytes* (chimpanzee) FGF23 (SEQ ID NO: 238) (GenBank accession no. XP_001157070, which is hereby incorporated by reference in its entirety):

```
  1 MLGARLRLWV CALCSVCSVS VLRAYPNASP LLGSSWGGLI HLYTATARNS YHLQIHKNGH
 61 VDGAPHQTIY SALMIRSEDA GFVVITGVMS RRYLCMDFRG NIFGSHYFNP ENCRFQHQTL
121 ENGYDVYYSP QYHFLVSLGR AKRAFLPSMN PPPYSQFLSR RNEIPLIHFN TPIPRRHTRS
181 AEDDSERDPL NVLKPRARMT PAPASCSQEL PSAEDNSPMA SDPLGVVRGG RVNTHAGGTG
241 PEGCRPFPKF I
```

TABLE 7-continued

Amino acid sequence of *Callithrix jacchus* (white-tufted-ear marmoset) FGF23 (SEQ ID NO: 239) (GenBank accession no. XP_002752281, which is hereby incorporated by reference in its entirety):

1 MLGARLRLWV CALCSVCSMS VLRAYPNASP LLASSWGGLI HLYTATARNS YHLQIHKNGH

61 VDGAPHQTIY SALLIRSEDA GFVVITGVMS RRYLCMDFRG NIFGSHYFNP ENCRFRPQRL

121 ENGYDVYQSP QHHFLVSLGR AKRAFLPGMN PPPYSQFLSR RNEIPLIHFN TPKPRRHTRS

181 AEDDPELDPL NVLKSRVRMT PAPASCSQEL LSAEDNSPVG SDPLGMVRGG RVNSHAEGTG

241 PEGCSPFPKL I

Amino acid sequence of *Loxodonta africana* (elephant) FGF23 (SEQ ID NO: 240) (GenBank accession no. XP_003410677, which is hereby incorporated by reference in its entirety):

1 MLGARLRLWV CTLCSACSMC SVRAYPNASP LLHSSWGGLT HLYTATARNS YHLQIHKDGH

61 VDGTPDQTIY SALIIRSEEA GFVVITGVMS RRYLCMDFRG NIFGSHYFNP ENCRFKHWTL

121 ENGYDVYHSP QHHFLVSLGR VKKAFLPGMN PPPYSQFLSR RNEIPLIYFN TPKPRRHTRS

181 AEDDSERDPL NVLKPRPRMT PAPASCSQEL LSAEDNSVVA NDPLGVVRSN RVNTHAGGIG

241 VERCRPFPKF I

Amino acid sequence of *Erinaceus telfairi* (lesser hedgehog tenrec) FGF23 (SEQ ID NO: 241) (Ensembl accession no. ENSETEP00000001298, which is hereby incorporated by reference in its entirety):

1 MLGAHLRLWV CALCSVSAMY HVRAYPNASP LLGTSWAGLT HLYTATARNS FHLQIHKDGH

61 VDGTPHQTIY SALMIRSEDS GFVVITGVMS RRYLCMDFRG NIFGSHYFTA DSCRFRQRTL

121 ENGYDVYHSP QHHFLISLGR AKRVFLPGMN PPPYSQFLSR RNEIPLIHFN TPRPRRHTRS

181 AEEEVEQDPL NVLKPRPRMT PAPASCSQEL PSAEDNSALA SDPLGVVRGK KLNTHAVGMG

241 AERCRPFPKF

Amino acid sequence of *Erinaceus europaeus* (hedgehog) FGF23 (SEQ ID NO: 242) (Ensembl accession no. ENSEEUP00000007211, which is hereby incorporated by reference in its entirety):

1 MLGAHLGLVV CALVSRAYPN ASPLLGFSWG GLTHLYTATA RNSYHLQIHK DGHVDGSPQQ

61 TIY------- --AGFVMITG VMSRRYLCMD FRSNIFGSHH FAPESCRFRH RTLENGYDVY

121 HSPQHHFLVS LGRAKRAFLP GTNPPPYSQF LSRRNEVPLI HFNTPRPRRH TRSAEDNSEL

181 DPLNVLKPRP RMTPAPASCS QELPSAEDNS MVASDPLGVV RANRVNTHAG GLGVDKCRPF

241 PKFI

Amino acid sequence of *Otolemur garnettii* (bushbaby) FGF23 (SEQ ID NO: 243) (Ensembl accession no. ENSOGAP00000004657, which is hereby incorporated by reference in its entirety):

1 MLGTCLRLWV CALCSVCSVS IVRAYPNASP LLSSSWGGLT HLYTASARNS YHLQIHKDGH

61 VDGTPHQTIY SALMIRSEDA GFVVITGVMS RRYLCMDFKG NIFGSHSFHP ESCRFRHRTL

121 ENGYDVYLSP QHHFLVSLGR SKRPFLPGMN PPPFSQFLSR RNDIPLIHFN TPRPRRHTRS

181 AEDNDSELDP LNVLKPRPRA TPGPASCSQE LPSAEDNSLV ASDPLGVVRG NRVNAHAGRA

241 GLDRCRPFPR YF

Amino acid sequence of *Oryctolagus cuniculus* (rabbit) FGF23 (SEQ ID NO: 244) (GenBank accession no. XP_002712872, which is hereby incorporated by reference in its entirety):

1 MLGARLLRLL VCALGSVCSW CVVRAYPDTS PLLSSSWAGL THLYTATARN SYHLQIHKDG

61 QVDGTPHQTI YSALMIRSED AGFVVITGVM SRRYLCMDFR GNIFGSHYFD PQNCRFRHRT

TABLE 7-continued

```
121 LENGYDVYHS PEHHFLVSLG RAKRPFLPGM NPPPYSQFLS RRNEIPLIHF NTPRPRRHTR

181 SAEDAWEQDP LNVLKPRFRL TPAPASCSQE APSAEDNGLV ASDPFGVLRG NRVNMHGDRM

241 GPERCHHFPK FI
```

Amino acid sequence of *Equus caballus* (horse) FGF23 (SEQ ID NO: 245) (GenBank accession no. XP_001491469, which is hereby incorporated by reference in its entirety):

```
  1 MSGPCLGLLV YVLCSAVKAY PNASPLLDSS WGSLTHLYTA TARNSYHLQI HKDGHVDGTP

 61 HQTIYSALMI RSEDAGFVVI TGVMSRRYLC MDFRGNIFGS HHFSPESCSF RQRTLENGYD

121 VYHSPQHRFL VSLGRAKRAF LPGTNPPPYS QFLSRRNEIP LVHFNTPRPR RHTRSAEDNS

181 ERDPLNVLKP RPRMTPAPAS CSQELPSAED NSVLASDPLG VVRGNRVNTH AGGAGVERCR

241 PFPKFF
```

Amino acid sequence of *Ailuropoda melanoleuca* (giant panda) FGF23 (SEQ ID NO: 246) (GenBank accession no. XP_002920496, which is hereby incorporated by reference in its entirety):

```
  1 MSGTRLGLLV SVLCWVGRAY PNTSPLLGSS WGGLTHLYTA SARNSYHLQI HKDGHVDGTP

 61 HQTIYSALMI RSEDAGFVVI TGVMSRRYLC MDLRGNIFGS HLFSPESCRF RQRTLENGYD

121 VYHSPQHRFL VSLGQAKRTF LPGTNPPPYS QFLSRRNEIP LIHFNTPRPR RHTRSAEDTE

181 RDPLNVLKPR PRMTPAPASC SQELPSAEDN SVVASDPLGV LRGNRVNAHA GGMGVDRCRP

241 FPKFI
```

Amino acid sequence of *Ochotona princeps* (pika) FGF23 (SEQ ID NO: 247) (Ensembl accession no. ENSOPRP00000006546, which is hereby incorporated by reference in its entirety):

```
  1 MLGGLGLWVC VLGSVCSWRG VRAYPDTSPL LGSSWTGLTH LYTATARNSF HLQIHKDGHV

 61 DGTPQQTIYS ALMIRSEDAG FVVITGVMSR RYLCMDFRGN IFGSHYFEPQ NCRFQQRTLE

121 NGYDIYHSPQ HDFLVSLGRA KRPFLPGMNP PPYSQFLSRR NEIPLILFNT PRPRRHTRSA

181 EEGWERDPLN VLKSRPRMTP APASCSREAP SAEDDGLLAS DPMGVLRGHR VDVHGGGTGR

241 DRCRPFPRFI
```

Amino acid sequence of *Bos taurus* (cattle) FGF23 (SEQ ID NO: 248) (GenBank accession no. XP_002687926, which is hereby incorporated by reference in its entirety):

```
  1 MLGARLGLWV CTLSCVVQAY PNSSPLLGSS WGGLTHLYTA TARNSYHLQI HGDGHVDGSP

 61 QQTVYSALMI RSEDAGFVVI TGVMSRRYLC MDFTGNIFGS HHFSPESCRF RQRTLENGYD

121 VYHSPQHRFL VSLGRAKRAF LPGTNPPPYA QFLSRRNEIP LPHFAATARP RRHTRSAHDS

181 GDPLSVLKPR ARATPVPAAC SQELPSAEDS GPAASDPLGV LRGHRLDVRA GSAGAERCRP

241 FPGFA
```

Amino acid sequence of *Sus scrofa* (pig) FGF23 (SEQ ID NO: 249) (GenBank accession no. XP_001926560, which is hereby incorporated by reference in its entirety):

```
  1 MLGARLGLWV CTLCCAARAY PDTSPLLSSG WGGLTHLYTA TARNSYHLQI HKDGHVDGSP

 61 QQTIYSALMI RSEDAGFVVI TGVMSRRYLC MDLRGNIFGS LHFSPESCRF RQRTLENGYD

121 VYHSPHYRFL VSLGRAKRAF LPGTNPPPYA QFLSRRNEIP LLHFATARPR RHTRSAHDGG

181 DPLSVLKPRA RATPAPVSCS RELPSAEDGG PAASDPLGVL RGQRLDARAG VGGAERCRPF

241 PSFA
```

TABLE 7-continued

Amino acid sequence of *Canis lupus* familiaris (dog) FGF23 (SEQ ID NO: 250) (GenBank accession no. XP_854580, which is hereby incorporated by reference in its entirety):

1 MWTVEFFLFD VTGPPFKSLR EKRRESSLGL SRKIPTKKRR KRPVRHSRGI KEAVSGFKLQ

61 PAIQRAVMSG TRLGFLVSVL CWVVRAYSNT SPLLGSSWGS LTHLYTATAR NSYHLQIHKD

121 GHVDGTPHQT IYSALMIRSE DAGFVVITGV MSRRYLCMDF RGNIFGSHLF SPESCRFRQR

181 TLENGYDVYH SPQHRFLVSL GQAKRAFLPG TNPPPYSQFL SRRNEIPLVH FHTPRPRRHT

241 RSAEAPERDP LNVLKPRPRL APAPASCSQE LPSAEDPGAP ASDPLGVLRG HRANARAGGV

301 GVDRCRAFPT PI

Amino acid sequence of *Cavia porcellus* (domestic guinea pig) FGF23 (SEQ ID NO: 251) (GenBank accession no. XP_003463346, which is hereby incorporated by reference in its entirety):

1 MLGTCLGLLA CTVSLVGAYP DASPLLTSSW GGLIHLYTAT ARNSYHLQIH KDGHIDGAPY

61 PTIYSALMIR SEDAGFVVIT GVTSRRFLCM DFRGNIFGSH HFNPQDCRFQ HRTLENGYDV

121 YLSPEHHFLI SLGRTKKFFL PGTNPPPYSQ FLSRRNELPL ARFVTPGPRR HTRSAEEDQG

181 RDPLSVLKLR PRATPAPASC SQELPSAEDA AQASDPLGVL RGARVHAHGG PRPARCRPGP

241 GAK

Amino acid sequence of *Cricetulus griseus* (Chinese hamster) FGF23 (SEQ ID NO: 252) (GenBank accession no. XP_003496132, which is hereby incorporated by reference in its entirety):

1 MLGTCLRLLV GVLCSACSLG TVRAYPDTSP LLGSNWGSLT HLYTATARNS YHLQIHKDGR

61 VDGTPHQTIY SALMIRSEDA GFVIITGAVT RRFLCMDLRG NIFGSHHFSP ENCRFRQRTL

121 ENGYDVYLSP QHHYLVSLGR AKRPFEPGTN PPPFSQFLAR RNEVPLLRFH TARPRRHTRS

181 AEDPPEWDPL NVLKPRPRAT PVPVSCSREL PSAEEGDLAA SDPLGVLRRG RGDARGGAGG

241 VDRCRPFPRF A

Amino acid sequence of *Tupaia belangeri* (tree shrew) FGF23 (SEQ ID NO: 253) (Ensembl accession no. ENSTBEP00000014220, which is hereby incorporated by reference in its entirety):

1 ALLIRPEEAG FAVITGVMSR RYLCMDFRGN IFGSHLFSPE SCRFRQRALE NGYDVYHHPQ

61 HHFLVSLGRP KRAFVPGTNP PPYSQFLARK NEIPLIHFNT PKPRRHTRSA EDNSGRDPLN

121 VLKPRPRMTP APASCSQELP SAEDNSVVAS DPLGVLRGNR VNTHAGGWGV DRCRPFPRFI

Amino acid sequence of *Rattus norvegicus* (Norway rat) FGF23 (SEQ ID NO: 254) (GenBank accession no. NP_570110, which is hereby incorporated by reference in its entirety):

1 MLGACLRLLV GALCTVCSLG TARAYSDTSP LLGSNWGSLT HLYTATARNS YHLQIHRDGH

61 VDGTPHQTIY SALMITSEDA GSVVIIGAMT RRFLCMDLRG NIFGSYHFSP ENCRFRQWTL

121 ENGYDVYLSP KHHYLVSLGR SKRIFQPGTN PPPFSQFLAR RNEVPLLHFY TARPRRHTRS

181 AEDPPERDPL NVLKPRPRAT PIPVSCSREL PSAEEGGPAA SDPLGVLRRG RGDARRGAGG

241 TDRCRPFPRF V

Amino acid sequence of *Mus musculus* (house mouse) FGF23 (SEQ ID NO: 255) (GenBank accession no. AAI20606, which is hereby incorporated by reference in its entirety):

1 MLGTCLRLLV GALCTVCSLG TARAYPDTSP LLGSNWGSLT HLYTATARTS YHLQIHRDGH

61 VDGTPHQTIY SALMITSEDA GSVVITGAMT RRFLCMDLHG NIFGSLHFSP ENCKFRQWTL

121 ENGYDVYLSQ KHHYLVSLGR AKRIFQPGTN PPPFSQFLAR RNEVPLLHFY TVRPRRHTRS

TABLE 7-continued

181 AEDPPERDPL NVLKPRPRAT PVPVSCSREL PSAEEGGPAA SDPLGVLRRG RGDARGGAGG

241 ADRCRPFPRF V

Amino acid sequence of *Pteropus vampyrus* (megabat) FGF23 (SEQ ID NO: 256) (Ensembl accession no. ENSPVAP00000000222, which is hereby incorporated by reference in its entirety):

1 MPRGSLGLLV CILCCRAYPD ASPLLSSSLG GLIHLYTATA RNGYHLQIHK DGHVDGTPHQ

61 TIYSALMIRS EDSGFVVIIG VMSRRYLCMD FKGNIFGSHH FSPESCKFRQ RTLENGYDVY

121 HSPQHHFFVS LGRAKRAFLP GTNPPPYSQF LSRRNEIPLF QFNTPRPRRH TRSVEDYKDY

181 DLDPDPLKVL RPRPRWVPAL PSCSQELPSA EDNSVVANDP LGVLRPSRVN IYRERMGKGR

241 CRPHPEFV

Amino acid sequence of *Myotis lucifugus* (microbat) FGF23 (SEQ ID NO: 257) (Ensembl accession no. ENSMLUP00000017312, which is hereby incorporated by reference in its entirety):

1 MPGARLGLLV CVLALRCVVR AYPNASPLLG SSWGGLTHLY TASARNSYHL QIHKDGHVDG

61 TPHQTIYSAL MIRSEDAGFV VITGVMSRRY LCMDFRGNIF GSLFFSPSNF SFLEWKKESG

121 MDHWISRQTH FLVSPGPSQE GLPAGHNPPP YSQFLSRNEI PLFHFNTPAP RRHTRSAEEN

181 SAADPLVVLK PVPRLTPPPA SCSRELSSAE DNSVAAHDPL GVLRSSNRVN SHAPPPGPPR

241 TRQGMLLV

Amino acid sequence of *Sarcophilus harrisii* (Tasmanian devil) FGF23 (SEQ ID NO: 258) (Ensembl accession no. ENSSHAP00000010151, which is hereby incorporated by reference in its entirety):

1 MSGGCLRLLF CALCSLRAIQ AFPNASPLLS LGWGGLTHLY TATARNSYHL QIHKDGHVDG

61 SPHQTIYSAL MIRSEDAGLV IITGVMSRRY LCMDIRGNIF GSHFFSPDNC RFKHRTLENG

121 YDIYHSPQNN FLISLGKAKR AFLPGMNPPP YSQFLSRRNE IPIIHFNTPE PHRHTRSAEN

181 SPDLDPMNVL KLRPRITPCS QELHSAEENS VVDDDPLEVL RNSNRLKPYP GRMSLERCLH

241 VPKAA

Amino acid sequence of *Monodelphis domestica* (gray short-tailed opossum) FGF23 (SEQ ID NO: 259) (GenBank accession no. XP_001372436, which is hereby incorporated by reference in its entirety):

1 MANCREKELE MYICALMIRS EDAGLVIITG VMSRRYLCMD IRGNIFGSHF FNPDNCKFKH

61 RTLENGYDIY HSPQNNFLIS LGKAKRAFLP GMNPPPYSQF LSRKNEIPII HFNTPEPHRH

121 TRSAENSPDL DPMNVLKPRP RMTPCSQELY SAEENSVVDD DPLEVLRNSN RLKPFPGRLG

181 LERCHHVPKT D

Amino acid sequence of *Dasypus novemcinctus* (armadillo) FGF23 (SEQ ID NO: 260) (Ensembl accession no. ENSDNOP00000004491, which is hereby incorporated by reference in its entirety):

1 ALMISSEDAG FVVITGVMSR RYLCMDFRGN IFGSHDFTPD SCRFRQRTLE NGYDVYHSPQ

61 HHFLVSLGRA KRAFQPGSNP PPYSQFLSRR NEIPLMRFST PRPRRHTRSA QDHADPDPLR

121 VLKPRLRLTP APASCSQELP SDEDDGAVAS DPLRVVLGRR PHARAAGAGG ERCRPGPQLS

Amino acid sequence of *Macropus eugenii* (wallaby) FGF23 (SEQ ID NO: 261) (Ensembl accession no. ENSMEUP00000003725, which is hereby incorporated by reference in its entirety):

1 ALMIRSEDAG LVIISGVMSR RYLCMDLRGN IFGSHFFSPD NCRFKHRTLE NGYDIYHSPQ

61 NNLLISLGKA KRAFLPGMNP PPYSQFLSRR NEIPIIHFNT PEPRRHTRSA ENSPDLDPMN

121 VLKPRPRVTP CSQELRSAEE NSVVDDDPLE VLRNSNRLKP YPGRMSLERC LQVPKAA

TABLE 7-continued

Amino acid sequence of *Taeniopygia guttata* (zebra finch) FGF23 (SEQ ID NO: 262) (GenBank accession no. XP_002190520

1 MEWRATLQGI PCSSLLLLLC SLKASLAFPN SSPLLSPSWG NGDRLMHLYT DTERSSFHLQ

61 INADGYIDGA PHQTIYSALM IKSEGAGSVI ITGVKSGRYL CMDMKGNIFG SHYFSQEDCM

121 FNHRTLENGY DVYQSPKHHF LVSLGRVKQV FSPGMNPPPY SQFLSRKNEI PLFRFNTPEP

181 HRHTRSADVD PVDPHQILVP QRKTPVFGSL QQQPADFPHM PREPMRINQN DVVNPDDPHA

241 MMEARRYPSP RFYITR

Amino acid sequence of *Gallus gallus* (chicken) FGF23 (SEQ ID NO: 263) (GenBank accession no. XP_425663, which is hereby incorporated by reference in its entirety):

1 MPHTSPCSCL EYMLLVLCIL KAAVAFPNSS PLLNPSWGNG DQLMHLYTST ERNSFHLQIN

61 ADGHINGVPH QTIYSALMIK SEGAGCVIIT GVKSGRYLCM DMKGDIFGSY YFSQEDCVFN

121 QRTLENGYDV YQSPKHNFLV SLGRTKQVFF PGMNPPPYSQ FLSRRNEIPL FRFNTPEPHR

181 NTRSADVDPL DPHQILVPQR KVSALGSQLQ LQMDFSHVPR EPMRVNQNDV VNPDDPHAMM

241 DARRYASPRF YITR

Amino acid sequence of *Meleagris gallopavo* (turkey) FGF23 (SEQ ID NO: 264) (GenBank accession no. XP_003202623, which is hereby incorporated by reference in its entirety):

1 MPHTSPCSCL EYMLLVLCIL KAAVSFPNSS PLLNPSWGNG DQLMHLYTST ERNSFHLQIN

61 ADGHISGVPY QTIYSALMIK SEGAGSVIIT GVKSGRYLCM DMKGDIFGSH YFSQEDCVFN

121 QRTLENGYDV YQSPKHNFLV SLGRTKQVFF PGMNPPPYSQ FLSRRNEIPL FRFNTPEPHR

181 NTRSADVDPM DPHQILVPQR KVSAIESQLQ LQMDFSHVPR EPMRVNQNDV VNPDDPHAMM

241 DARRYASPRF YITR

Amino acid sequence of *Anolis carolinensis* (green anole) FGF23 (SEQ ID NO: 265) (GenBank accession no. XP_003221411, which is hereby incorporated by reference in its entirety):

1 MVQATLYSFL KYMLLATCSW KAIAAFPNAS PLLSLNWGNS DSLLHLYTST ARNSFHLQIH

61 SNGYVDGSPY QTIYSALMIK SEVAGYVIIN GVKSGRFLCM DMNGNIFGSH FFSYEDCTFK

121 HWVLENGYDV YQSPKYNYLV SLGKAKQPLF PNMNPPPYSQ FLSRRNEIPL VQFNTPKPHR

181 HTRSANADPC GSIISSGNIA KENLQLQPLM YNTKMNSNSE DEDPNSAIIN RRFLSPRTDV

241 RS

Amino acid sequence of *Latimeria chalumnae* (coelacanth) FGF23 (SEQ ID NO: 266) (Ensembl accession no. ENSLACP00000020506, which is hereby incorporated by reference in its entirety):

1 LESALLAFSM AIFYSFKAVS SFPNSSPLLN PVWGNTDNLI HLYTASETNS FHLQINSDGH

61 VDGTPHQTAY SALLIKSEEA GSVVILGVKS GRYLCMDIKG NIIGLHHFSK EDCTFKQEGL

121 ENGFDVLRSP KHNILVSLDK TKRSYIPGMN LPPYSQFLSR QNEVALINFI NTPDIHRHSR

181 NVDVDPSDPH GMIIQPDVGV SFRKSSSLFS DLPRDSMRTS HNGMDMVDPA DPHGMLDSRR

241 RPSPRFFAR

Amino acid sequence of *Xenopus silurana tropicalis* (western clawed frog) FGF23 (SEQ ID NO: 267) (GenBank accession no. XP_002940351, which is hereby incorporated by reference in its entirety):

1 MTKQQTRLGL VLTVLASIKV ISAFPNSSPI ISGGWGVPDR LMHLYTASDW NSFHLQINHD

61 GSIDGTPTQT IYSAIMIKSE SAGHVVITGV KTNRYLCMDK SGNIFGYHDF NHDDCVFKHE

121 TLENNFDVYH SPKHNFVISL KEPKHHFRLG MDLPPYSQFL SLENEIPITR FNAPEPEMRI

TABLE 7-continued

```
181 PEGNFADPSD IIKNPRNWDF SQSIHNPFQD VWLPFPSGSL PIIRASLPII HNNVINTDDP

241 EEIVKMKRYR YFKR
```

Amino acid sequence of *Felis catus* (cat) FGF23 (SEQ ID NO: 268) (Ensembl accession no. ENSFCAP00000000128, which is hereby incorporated by reference in its entirety):

```
  1 MSGTRLGLLV SVLCWVVRAY PNTSPLLGSS WGGLTHLYTA TARNSYHLQI HKDGHVDGTP

 61 HQTIYSALMI RSEDAGFVVI TGVMSQRYLC MDFRGNIFGS HLFSPESCRF RQRTLENGYD

121 VYHSPQHRFL VSLGPAKRAF LPGTNRMTPA PASCSQELPS AEDSGVVASD PLGVLRGNRV

181 NAHAGGMGVE RCRPFPKFN
```

Amino acid sequence of *Pelodiscus sinensis* (Chinese softshell turtle) FGF23 (SEQ ID NO: 269) (Ensembl accession no. ENSPSIP00000012755, which is hereby incorporated by reference in its entirety):

```
  1 MSQPSQCSCL NFMLFVLCSF KAIAAFPFFS SLLNPSWGET DSLIHLYTAT EKNSFHLQIN

 61 PDGYVDGTPH QTIYSALMIK SEDAGYVVIS GVKSGRYLCM DIKGNIFGSH YFSQEDCMFK

121 HRTLENGYDV YQSPKHNFLV SLGRNKQAFF PGMNLPPYSQ FLPRRNEIPL IRFNTPEPHR

181 HTRNADVDPL QILIPRGEAF DTGPQRLQTH FDHLPREPMR INPNDVVSPD DPLAMMDVRR

241 NASPRLYITR
```

Amino acid sequence of *Mustela putorius furo* (Ferret) FGF23 (SEQ ID NO: 270) (Ensembl accession no. ENSMPUP00000009243, which is hereby incorporated by reference in its entirety):

```
  1 MSVTRLGLLV SVLCWVVRAY PNASPLLGSS WGGLTHLYTA TARNSYHLQI HKDGHVDGTP

 61 HQTIYSALMI RSEDAGFVVI TGVMSRRYLC MDFRGNIFGS HLFSPESCRF RQRTLENGYD

121 VYHSPQHRFL VSLGQAKRAF LPGTNPPPYS QFLSRRNEIP LIHFNTPRPR RHTRSAEDME

181 HDPLNVLKPR PRMTPAPASC SQELPSAEDN SVVASDPLGV LRGNRVNVHA GGMGVDRCRP

241 LPKFI
```

Amino acid sequence of *Microcebus murinus* (Mouse lemur) FGF23 (SEQ ID NO: 271) (Ensembl accession no. ENSMICP00000004444, which is hereby incorporated by reference in its entirety):

```
  1 MLGACLRLWV CALCSVCGVS VVRAYPNASP LLASSWGGLI HLYTATARNS YHLQIHKDGH

 61 VDGTPHQTIY SALMIRSEDA GFVVITGVMS RRYLCMDFRG NIFGSHVFSA ESCRFRQRTL

121 ENGFDVYQSP QHHFLVSLGR AKGAFPAGAK PPPFPQFLPR GNEAPGRKTR GPEEKGAPHP

181 LRGVESGGRK GGAPPLCLER LSRARE
```

Amino acid sequence of *Pongo abelii* (Orangutan) FGF23 (SEQ ID NO: 272) (Ensembl accession no. ENSPPYP00000005881, which is hereby incorporated by reference in its entirety) (partial sequence corresponding to human FGF23 residues 23 to 37 and 72 to 251):

```
  1 M--------- ---------- --RN--ESLP CLVFSIG--- ---------- ----------

 61 ---------- -ALMIRSEDA GFVVITGVMS RRYLCMDFRG NIFGSHYFNP ENCRFQHQTL

121 ENGYDVYHSP QHHFLVSLGR VKRAFLPGM- PPPYSQFLSR RNEIPLIHFN TPVPRRHTRS

181 AEDDTERDPL KVLKPRARMT PAPASCSQEL PSSEDNSPMA SDPLGVVRGG RVNTHAGGTG

241 PEGCRPFPKF I
```

TABLE 7-continued

Amino acid sequence of *Sorex araneus* (Shrew) FGF23 (SEQ ID NO: 273) (Ensembl accession no. ENSSARP00000007042, which is hereby incorporated by reference in its entirety) (partial sequence corresponding to human FGF23 residues 1 to 18, 28 to 70, 106 to 197, and 201 to 235):

```
  1 MWGLRLGLLV GLLGCVDR-- -------ASP MLASSWGGLT HLYTATARNS YHLQIHKDGL
 61 VDGSPQQTVY ---------- ---------- ---------- -----HHFSP ESCRFQQRTL
121 ENGYDVYQSP QHRFLVSLGR PKRAFQPGAN PPPYAQFLAR RNEVPLARFH TPAPRRHTRS
181 AHDNGDADPL NVLAPRA--- AAAASCSHEL PSAEDNSVVA SDPLGVIRSN RFRTH
```

Amino acid sequence of *Tetraodon nigroviridis* (Tetraodon) FGF23 (SEQ ID NO: 274) (Ensembl accession no. ENSTNIP00000014355, which is hereby incorporated by reference in its entirety):

```
  1 MDVNRRIGVK DALLALLLAL LQGCPLGETA PNASPLVGSN WGNPRRYVHL QTSTDMSNFY
 61 LEIRLDGTVR KSTARTSYSV ILLKADTRER IAILGVKSNR YLCMDLEGSP FSSPTCIRDD
121 CLFNHSLLEN NRDVYYSSRT GILFNLEGSR QVFVVGQNVP QTSLFLPRTN TVPLERLLLH
181 RDKRNQVVDP SDPHRVAVGR AEEGSDSRAL QEDDADLEVE TEVEVGDDGR NASRERLQAP
241 SDHDPWGVFS SNPGSPRSSG TVG
```

Amino acid sequence of *Oreochromis niloticus* (Tilapia) FGF23 (SEQ ID NO: 275) (Ensembl accession no. ENSONIP00000000020, which is hereby incorporated by reference in its entirety):

```
  1 MDVNRRMGMR DTVLALFLAV LQGFPLGDTV PNPSPLAGSN WGNPRRYVHL QTSTDLNNFY
 61 LEIRLDGSVR KTTSRSTYSV ILLKSEARDR VAILGVKSSR YLCMDLEGNP FSSPVCLRDD
121 CLFNHKLLEN NRDVYYSSRT GILFNLEGSR QVYSVGQNLP QTSLFLPRKN TVPLERLLLH
181 REKRNRGQTE EGSDSRAVPE ELEEREVEME TEIETEVGDD GRNVSREKLA APSSHDPWNV
241 HFSNPASPRS TGTVG
```

Amino acid sequence of *Danio rerio* (Zebrafish) FGF23 (SEQ ID NO: 276) (Ensembl accession no. ENSDARP00000067387, which is hereby incorporated by reference in its entirety):

```
  1 MRCALSNLHM LHSSVLALWF TALQGLRPAD AAPNPSPLLG SNWGNPRRYI HLQTTSDLNN
 61 YYLEISPSGH VRKTTNRGSY SVILLKTESR DRLAIFGVKS NRFLCMDTGG TLFTSTICNK
121 EDCLFHHKLL ENHRDVYYST KHSILLNLDG DKQAFIAGQN LPQSSLFLSE KNTVPLERLQ
181 HRERRNRQVN PTDPLNALRY AEESDSRAAQ EDDGDMDFEP SEGQNISRET LVSPSDDDPW
241 DLLHDTSPGS PRIAAIVG
```

In certain embodiments according to the present invention, the C-terminal portion of FGF23 of the chimeric protein of the present invention includes a polypeptide sequence that has at least 80%, at least 85%, at least 90%, at least 95%, at least 97%, or at least 99% amino acid sequence identity to the amino acid sequence of SEQ ID NO: 233.

It will be understood that the FGF23 according to the present invention may be from a nucleotide sequence that encodes an FGF23 protein (e.g., those encoding orthologs) from a mammal or even a non-mammalian species. For example, a nucleotide sequence encoding a mammalian or non-mammalian FGF23 protein according to the present invention may include, but is not limited to, those FGF-encoding nucleotide sequences shown in Table 8.

TABLE 8

Human FGF23 gene coding sequence (1-251) (SEQ ID NO: 277) (GenBank accession no. AF263537, which is hereby incorporated by reference in its entirety)

```
147                            ATGT TGGGGGCCCG CCTCAGGCTC TGGGTCTGTG

181 CCTTGTGCAG CGTCTGCAGC ATGAGCGTCC TCAGAGCCTA TCCCAATGCC TCCCCACTGC

241 TCGGCTCCAG CTGGGGTGGC CTGATCCACC TGTACACAGC CACAGCCAGG AACAGCTACC

301 ACCTGCAGAT CCACAAGAAT GGCCATGTGG ATGGCGCACC CCATCAGACC ATCTACAGTG

361 CCCTGATGAT CAGATCAGAG GATGCTGGCT TTGTGGTGAT TACAGGTGTG ATGAGCAGAA

421 GATACCTCTG CATGGATTTC AGAGGCAACA TTTTTGGATC ACACTATTTC GACCCGGAGA

481 ACTGCAGGTT CCAACACCAG ACGCTGGAAA ACGGGTACGA CGTCTACCAC TCTCCTCAGT

541 ATCACTTCCT GGTCAGTCTG GGCCGGGCGA AGAGAGCCTT CCTGCCAGGC ATGAACCCAC

601 CCCCGTACTC CCAGTTCCTG TCCCGGAGGA ACGAGATCCC CCTAATTCAC TTCAACACCC

661 CCATACCACG GCGGCACACC CGGAGCGCCG AGGACGACTC GGAGCGGGAC CCCCTGAACG

721 TGCTGAAGCC CCGGGCCCGG ATGACCCCGG CCCCGGCCTC CTGTTCACAG GAGCTCCCGA

781 GCGCCGAGGA CAACAGCCCG ATGGCCAGTG ACCCATTAGG GGTGGTCAGG GGCGGTCGAG

841 TGAACACGCA CGCTGGGGGA ACGGGCCCGG AAGGCTGCCG CCCCTTCGCC AAGTTCATCT

901 AG
```

Gorilla FGF23 gene coding sequence (1-251) (SEQ ID NO: 278) (Ensembl accession no. ENSGGOT00000002983, which is hereby incorporated by reference in its entirety)

```
  1                            ATGT TGGGGGCCCG CCTCAGGCTC TGGGTCTGTG

 35 CCTTGTGCAG CGTCTGCAGC TTGAGCGTCC TCAGAGCCTA TCCCAATGCC TCCCCACTGC

 95 TCGGCTCCAG CTGGGGTGGC CTGATCCACC TGTACACAGC CACAGCCAGG AACAGCTACC

155 ACCTGCAGAT CCACAAGAAT GGCCATGTGG ATGGCGCACC CCATCAGACC ATCTACAGTG

215 CCCTGATGAT CAGATCAGAG GATGCTGGCT TTGTGGTGAT TACAGGTGTG ATGAGCAGAA

275 GATACCTCTG CATGGATTTC AGAGGCAACA TTTTTGGATC ACACTATTTC GACCCGGAGA

335 ACTGCAGGTT CCAACACCAG ACGCTGGAAA ACGGGTACGA CGTCTACCAC TCTCCTCAGT

395 ATCACTTCCT GGTCAGTCTG GGCCGGGCGA AGAGAGCCTT CCTGCCAGGC ATGAACCCAC

455 CCCCGTACTC CCAGTTCCTG TCCCGGAGGA ACGAGATCCC CCTCATTCAC TTCAACACCC

515 CCATACCACG GCGGCACACC CGGAGCGCCG AGGACGACTC GGAGCGGGAC CCCCTGAACG

575 TGCTGAAGCC CCGGGCCCGG ATGACCCCGG CCCCGGCCTC CTGTTCACAG GAGCTCCCGA

635 GCGCCGAGGA CAACAGCCCG ATGGCCAGTG ACCCATTAGG GGTGGTCAGG GGCGGTCGAG

695 TGAACACGTA CGCTGGGGGA ACGGGCCCGG AAGGCTGCCG CCCCTTCCCC AAGTTCATCT

755 AG
```

Northern white-cheeked gibbon FGF23 gene coding sequence (1-251) (SEQ ID NO: 279) (GenBank accession no. XM_003273701, which is hereby incorporated by reference in its entirety)

```
140                       A TGTTGGGGGC CCGCCTCAGG CTCTGGGTCT GTGCCTTGTG

181 CAGCGTCTGC AGCATGAGCG TCCTCAGAGC CTATCCCAAT GCCTCCCCAC TGCTCGGCTC

241 CAGCTGGGGT GGCCTGATCC ACCTGTACAC AGCCACAGCC AGGAACAGCT ACCACCTGCA

301 GATCCACAAG AATGGCCATG TGGATGGCGC ACCCCATCAG ACCATCTACA GTGCCCTGAT

361 GATCAGATCA GAGGATGCTG GCTTTGTGGT GATTACAGGT GTGATGAGCA GAAGATACCT

421 CTGCATGGAT TTCAGAGGCA ACATTTTTGG ATCACACTAT TTCAACCCGG AGAACTGCAG
```

TABLE 8-continued

| |
|---|
| 481 GTTCCAACAC CAGACGCTGG AAAACGGGTA CGACGTCTAC CACTCTCCTC AGCATCACTT |
| 541 CCTGGTCAGT CTGGGCCGGG CCAAGAGAGC CTTCCTGCCG GGCATGAACC CACCCCCGTA |
| 601 CTCCCAGTTC CTGTCCCGGA GGAACGAGAT CCCCCTACTT CACTTCAACA CCCCCACACC |
| 661 ACGGCGGCAC ACCCGGAGCG CCGAGGACGA CTCGGAGCGG GACCCCCTGA ACGTGCTGAA |
| 721 ACCCCGGGCC CGGATGACCC CGGCCCCGGC CTCCTGCTCA CAGGAGCTCC TGAGCTCCGA |
| 781 GGACAACAGC CCGATGGCCA GCGACCCATT AGGGGTGGTC AGGGGCGGTC GAGTGAACAC |
| 841 GCACGCTGGG GGAACGGGCC CGGAAGGCTG CCGCCCCTTC CCCAAGTTCA TCTAG |

| Rhesus monkey FGF23 gene coding sequence (1-251) (SEQ ID NO: 280) (GenBank accession no. NM_001194137, which is hereby incorporated by reference in its entirety) |
|---|
| 69 AT GTTGGGGGCC CGCCTCAGGC TCTGGGTCTG TGCCTTGTGC AGCGTCTGCA |
| 121 GCATGAGCGT CATCAGAGCC TATCCCAATG CCTCCCCATT GCTCGGCTCC AGCTGGGGTG |
| 181 GCCTGATCCA CCTGTACACA GCCACAGCCA GGAACAGCTA CCACCTGCAG ATCCACAAGA |
| 241 ATGGCCACGT GGATGGCGCA CCCCATCAGA CCATCTACAG TGCCCTGATG ATCAGATCAG |
| 301 AGGATGCTGG CTTTGTGGTG ATTACAGGTG TGATGAGCAG AAGATACCTC TGCATGGATT |
| 361 TCAGAGGCAA CATTTTTGGA TCACACTATT TCAACCCGGA GAACTGCAGG TTCCGACACT |
| 421 GGACGCTGGA GAACGGCTAC GACGTCTACC ACTCTCCTCA GCATCACTTT CTGGTCAGTC |
| 481 TGGGCCGGGC GAAGAGGGCC TTCCTGCCAG GCATGAACCC ACCCCCCTAC TCCCAGTTCC |
| 541 TGTCCCGGAG GAACGAGATC CCCCTCATCC ACTTCAACAC CCCCAGACCA CGGCGGCACA |
| 601 CCCGGAGCGC CGAGGACGAC TCGGAGCGGG ACCCCCTGAA CGTGCTGAAG CCCCGGGCCC |
| 661 GGATGACCCC GGCCCCGGCC TCCTGCTCAC AGGAGCTCCC GAGCGCCGAG GACAACAGCC |
| 721 CGGTGGCCAG CGACCCGTTA GGGGTGGTCA GGGGCGGTCG GGTGAACACG CACGCTGGGG |
| 781 GAACGGGCCC GGAAGCCTGC CGCCCCTTCC CCAAGTTCAT CTAG |

| Crab-eating macaque FGF23 gene coding sequence (1-251) (SEQ ID NO: 281) (GenBank accession no. ENSMMUT00000020999, which is hereby incorporated by reference in its entirety) |
|---|
| 1 ATGTTG GGGGCCCGCC TCAGGCTCTG GGTCTGTGCC TTGTGCAGCG |
| 47 TCTGCAGCAT GAGCGTCATC AGAGCCTATC CCAATGCCTC CCCATTGCTC GGCTCCAGCT |
| 107 GGGGTGGCCT GATCCACCTG TACACAGCCA CAGCCAGGAA CAGCTACCAC CTGCAGATCC |
| 167 ACAAGAATGG CCACGTGGAT GGCGCACCCC ATCAGACCAT CTACAGTGCC CTGATGATCA |
| 227 GATCAGAGGA TGCTGGCTTT GTGGTGATTA CAGGTGTGAT GAGCAGAAGA TACCTCTGCA |
| 287 TGGATTTCAG AGGCAACATT TTTGGATCAC ACTATTTCAA CCCGGAGAAC TGCAGGTTCC |
| 347 GACACTGGAC GCTGGAGAAC GGCTACGACG TCTACCACTC TCCTCAGCAT CACTTTCTGG |
| 407 TCAGTCTGGG CCGGGCGAAG AGGGCCTTCC TGCCAGGCAT GAACCCACCC CCCTACTCCC |
| 467 AGTTCCTGTC CCGGAGGAAC GAGATCCCCC TCATCCACTT CAACACCCCC AGACCACGGC |
| 527 GGCACACCCG GAGCGCCGAG GACGACTCGG AGCGGGACCC CCTGAACGTG CTGAAGCCCC |
| 587 GGGCCCGGAT GACCCCGGCC CCGGCCTCCT GCTCACAGGA GCTCCCGAGC GCCGAGGACA |
| 647 ACAGCCCGGT GGCCAGCGAC CCGTTAGGGG TGGTCAGGGG CGGTCGGGTG AACACGCACG |
| 707 CTGGGGGAAC GGGCCCGGAA GCCTGCCGCC CCTTCCCCAA GTTCATCTAG |

TABLE 8-continued

Chimpanzee FGF23 gene coding sequence (1-251) (SEQ ID NO: 282) (GenBank accession no. XM_001157070, which is hereby incorporated by reference in its entirety)

```
141                       ATGTTGGGGG CCCGCCTCAG GCTCTGGGTC TGTGCCTTGT
181 GCAGTGTCTG CAGCGTGAGC GTCCTCAGAG CCTACCCCAA TGCCTCCCCA CTGCTCGGCT
241 CCAGCTGGGG TGGCCTGATC CACCTGTACA CAGCCACAGC CAGGAACAGC TACCACCTGC
301 AGATCCACAA GAATGGCCAT GTGGATGGCG CACCCCATCA GACCATCTAC AGTGCCCTGA
361 TGATCAGATC AGAGGATGCT GGCTTTGTGG TGATTACAGG TGTGATGAGC AGAAGATACC
421 TCTGCATGGA TTTCAGAGGC AACATTTTTG GATCACACTA TTTCAACCCG GAGAACTGCA
481 GGTTCCAACA CCAGACGCTG GAAAACGGGT ACGACGTCTA CTACTCTCCT CAGTATCACT
541 TCCTGGTCAG TCTGGGCCGG GCGAAGAGAG CCTTCCTGCC AAGCATGAAC CCACCCCCGT
601 ACTCCCAGTT CCTGTCCCGG AGGAACGAGA TCCCCCTAAT TCACTTCAAC ACCCCCATAC
661 CACGGCGGCA CACCCGGAGC GCCGAGGACG ACTCGGAGCG GGACCCCCTG AACGTGCTGA
721 AGCCCCGGGC CCGGATGACC CCGGCCCCGG CCTCCTGTTC ACAGGAGCTC CCGAGCGCCG
781 AGGACAACAG CCCGATGGCC AGTGACCCAT TAGGGGTGGT CAGGGGCGGT CGAGTGAACA
841 CGCACGCTGG GGGAACGGGC CCGGAAGGCT GCCGCCCCTT CCCCAAGTTC ATCTAG
```

White-tufted-ear marmoset FGF23 gene coding sequence (1-251) (SEQ ID NO: 283) (GenBank accession no. XM_002752235, which is hereby incorporated by reference in its entirety)

```
  1 ATGTTGGGGG CCCGCCTCAG GCTCTGGGTC TGTGCCTTGT GCAGCGTCTG CAGCATGAGC
 61 GTCCTCAGAG CCTATCCCAA TGCCTCCCCA CTGCTTGCCT CCAGCTGGGG TGGCCTGATC
121 CACCTGTACA CAGCCACAGC CAGGAACAGC TACCACCTGC AGATCCACAA GAATGGCCAT
181 GTGGATGGCG CACCCCATCA GACCATCTAC AGTGCCCTGC TGATCAGATC AGAGGATGCT
241 GGCTTTGTGG TGATTACAGG TGTGATGAGC AGAAGATACC TCTGCATGGA TTTCAGAGGC
301 AACATTTTTG GATCACACTA TTTCAACCCG GAGAACTGCA GGTTCCGACC CCAGAGGCTG
361 GAGAACGGGT ACGACGTCTA CCAGTCTCCT CAGCATCACT TCCTGGTCAG TCTGGGCCGG
421 GCGAAGAGGG CCTTCCTGCC AGGCATGAAC CCACCCCCGT ACTCCCAGTT CCTGTCCCGG
481 AGGAACGAGA TCCCCCTCAT TCACTTCAAC ACCCCCAAAC CGCGGCGGCA CACCCGGAGC
541 GCCGAGGACG ACCCGGAGCT AGACCCCCTG AACGTGCTGA AGTCCCGGGT CCGGATGACC
601 CCGGCCCCGG CCTCCTGCTC GCAGGAGCTC CTGAGCGCCG AGGACAACAG CCCGGTGGGC
661 AGCGACCCCT TAGGGATGGT CCGGGGTGGT CGGGTGAACA GCCACGCTGA GGGAACAGGC
721 CCAGAAGGCT GCAGCCCCTT CCCCAAGCTC ATCTAG
```

Elephant FGF23 gene coding sequence (1-251) (SEQ ID NO: 284) (GenBank accession no. XM_003410629, which is hereby incorporated by reference in its entirety)

```
  1 ATGTTGGGGG CCCGCCTCAG GCTCTGGGTC TGCACCCTGT GCAGTGCCTG CAGCATGTGC
 61 AGTGTCAGAG CCTATCCCAA TGCCTCCCCG CTGCTCCACT CCAGCTGGGG TGGCCTGACC
121 CACCTGTACA CAGCCACCGC CAGGAACAGC TACCACCTGC AGATCCACAA GGACGGCCAT
181 GTGGATGGTA CGCCGGACCA GACCATCTAC AGTGCCCTGA TAATCAGATC AGAGGAGGCC
241 GGCTTCGTGG TGATTACAGG GGTGATGAGT AGGAGATACC TCTGTATGGA TTTCAGAGGC
301 AACATTTTTG GATCGCATTA CTTCAACCCA GAGAACTGCA GGTTCAAACA CTGGACGCTG
361 GAAAATGGAT ATGACGTCTA TCACTCTCCT CAGCATCATT TCCTGGTCAG TCTGGGTCGC
421 GTGAAGAAGG CCTTCCTGCC AGGCATGAAC CCACCACCTT ACTCTCAGTT CCTGTCCCGG
```

TABLE 8-continued

481 AGGAATGAGA TCCCCTTGAT TTACTTCAAC ACCCCCAAGC CCCGGCGGCA CACCCGGAGT

541 GCCGAGGATG ACTCTGAACG GGACCCACTG AATGTGCTGA AGCCCCGGCC CCGTATGACA

601 CCTGCTCCAG CTTCTTGCTC CCAGGAACTC CTGAGTGCTG AAGACAACAG CGTGGTGGCC

661 AATGACCCTT TAGGAGTGGT CAGAAGCAAT AGGGTCAACA CACATGCTGG TGGGATAGGT

721 GTGGAAAGGT GCCGCCCCTT CCCCAAGTTC ATCTAG

Lesser hedgehog tenrec FGF23 gene coding sequence (1-250) (SEQ ID NO: 285) (Ensembl accession no. ENSETET00000001609, which is hereby incorporated by reference in its entirety)

1 ATGTTGGGGG CCCACCTCAG ACTCTGGGTC TGTGCCTTGT GCAGTGTGAG CGCCATGTAC

61 CACGTCAGAG CCTACCCCAA CGCCTCCCCG CTCCTGGGTA CCAGCTGGGC TGGCCTGACC

121 CACCTGTACA CGGCGACAGC CAGGAACAGC TTCCACCTGC AGATCCACAA GGATGGCCAC

181 GTGGACGGCA CCCCCCACCA GACCATCTAC AGTGCCCTGA TGATCCGATC AGAGGACTCT

241 GGCTTCGTGG TGATCACAGG GGTGATGAGC AGGAGATACC TGTGTATGGA TTTCAGAGGC

301 AACATTTTTG GATCGCACTA CTTCACTGCG GACAGCTGCA GGTTCAGACA GCGGACGCTG

361 GAGAACGGCT ATGACGTCTA CCACTCTCCT CAGCATCATT TCCTGATCAG CCTGGGCCGG

421 GCCAAGAGGG TCTTCCTGCC CGGCATGAAC CCGCCGCCTT ACTCCCAGTT CCTGTCCCGA

481 AGGAATGAGA TCCCCCTGAT TCACTTCAAC ACCCCCAGGC CCCGGCGGCA CACACGGAGT

541 GCCGAGGAGG AAGTGGAGCA GGATCCGCTG AACGTGCTGA AGCCCAGGCC CCGGATGACG

601 CCGGCTCCAG CCTCCTGCTC CCAGGAGCTG CCCAGTGCCG AAGACAACAG CGCCCTGGCC

661 AGCGACCCGC TGGGAGTGGT CAGAGGCAAA AAGCTCAACA CCCATGCTGT GGGCATGGGC

721 GCGGAAAGAT GCCGCCCCTT TCCCAAGTTC

Hedgehog FGF23 gene coding sequence (1-63 and 73-244) (SEQ ID NO: 286) (Ensembl accession no. ENSEEUT00000007917, which is hereby incorporated by reference in its entirety)

1 ATGTTGGGGG CCCACCTGGG TCTGGTGGTC TGCGCCCTGG TCAGCAGAGC CTATCCCAAT

61 GCCTCGCCAC TGCTGGGCTT CAGCTGGGGG GGCCTGACAC ATCTGTACAC GGCCACAGCC

121 AGGAACAGCT ACCACCTGCA GATCCACAAG GACGGCCACG TGGACGGCTC GCCTCAGCAG

181 ACCATCTACA ---------- ---------- -----TGCTG GTTTCGTGAT GATCACAGGC

241 GTGATGAGTA GGCGCTACCT CTGCATGGAC TTCAGGAGCA ACATCTTTGG ATCGCATCAC

301 TTCGCCCCTG AGAGCTGCAG GTTCAGACAT CGGACACTGG AAAACGGCTA TGACGTCTAC

361 CACTCCCCCC AGCACCATTT CCTGGTCAGC CTGGGCCGGG CCAAGCGGGC CTTCCTGCCG

421 GGCACCAACC CCCCACCATA CTCCCAGTTT TTGTCCCGGA GGAACGAGGT TCCCCTCATC

481 CACTTCAACA CCCCCAGGCC CAGGCGTCAC ACCCGCAGCG CCGAGGACAA CTCAGAGCTG

541 GATCCCCTGA ACGTGCTGAA GCCCAGGCCC CGCATGACCC CCGCCCCAGC CTCCTGCTCC

601 CAGGAGCTTC CGAGCGCTGA GGACAACAGC ATGGTGGCCA GTGACCCACT GGGTGTGGTC

661 AGAGCCAACA GAGTGAACAC ACACGCAGGG GGCCTGGGTG TGGACAAGTG CCGCCCCTTC

721 CCCAAGTTTA TCTAG

Bushbaby FGF23 gene coding sequence (1-252) (SEQ ID NO: 287) (Ensembl accession no. ENSOGAT00000005213, which is hereby incorporated by reference in its entirety)

1 ATGCTGGGGA CCTGCCTCAG GCTCTGGGTC TGTGCCCTGT GCAGTGTTTG CAGCGTGAGC

61 ATTGTCAGAG CCTATCCCAA CGCCTCCCCA CTGCTCAGCT CCAGCTGGGG TGGCCTGACC

121 CACCTGTACA CGGCCTCGGC CAGAAACAGC TACCACCTGC AGATCCACAA GGATGGCCAT

TABLE 8-continued

```
181 GTGGACGGCA CACCCCACCA GACCATCTAC AGCGCCCTAA TGATCAGGTC AGAGGATGCT

241 GGCTTCGTGG TGATTACAGG CGTGATGAGC AGAAGATACC TCTGTATGGA TTTCAAAGGC

301 AACATTTTTG GATCACACTC CTTCCACCCC GAGAGCTGCA GGTTCAGACA CCGGACTCTG

361 GAGAACGGCT ATGACGTCTA CCTCTCGCCG CAGCATCACT TCTTGGTCAG CCTGGGCCGC

421 TCCAAGAGGC CCTTCCTGCC GGGCATGAAC CCGCCCCCCT TCTCCCAGTT CCTGTCGCGG

481 AGGAACGACA TCCCGCTCAT TCACTTCAAC ACCCCCCGCC CGCGGAGACA CACCCGCAGC

541 GCCGAGGACA ACGACTCGGA GCTCGACCCC CTGAACGTGC TGAAGCCGCG GCCCCGGGCC

601 ACCCCGGGCC CCGCCTCCTG CTCGCAGGAG CTCCCCAGCG CCGAGGACAA CAGCCTGGTG

661 GCCAGCGACC CTTTAGGGGT GGTCCGGGGC AACAGGGTGA ACGCTCACGC CGGGAGGGCC

721 GGCCTGGACA GGTGCCGCCC CTTCCCCAGG TATTTCTAG
```

Rabbit FGF23 gene coding sequence (1-252) (SEQ ID NO: 288) (GenBank accession no. XM_002712826, which is hereby incorporated by reference in its entirety)

```
  1 ATGTTAGGGG CCCGGCTCCT CCGGCTCTTG GTCTGTGCCC TGGGCAGTGT GTGCAGCTGG

 61 TGTGTGGTCC GAGCCTACCC TGACACCTCC CCGCTGCTCA GCTCCAGCTG GGCTGGCCTG

121 ACCCACCTGT ACACGGCCAC CGCCAGAAAC AGCTACCACC TGCAGATCCA CAAGGACGGC

181 CAAGTGGATG GCACACCTCA TCAGACCATC TACAGTGCCC TGATGATCAG ATCGGAGGAT

241 GCTGGCTTCG TGGTGATAAC AGGTGTCATG AGCAGGAGGT ACCTCTGTAT GGATTTCAGA

301 GGCAACATTT TTGGATCGCA TTACTTCGAC CCCCAGAACT GCAGGTTCAG ACACAGGACG

361 CTGGAAAACG GGTACGACGT CTACCACTCT CCGGAGCATC ACTTCCTGGT CAGCCTGGGC

421 CGGGCCAAGA GGCCCTTCCT GCCAGGCATG AACCCGCCAC CCTATTCCCA GTTCCTGTCC

481 CGGAGGAACG AGATCCCCCT GATCCACTTC AACACGCCGA GGCCGCGAAG GCACACCCGG

541 AGCGCCGAGG ACGCCTGGGA GCAGGACCCG CTGAACGTGC TGAAGCCCAG GTTCCGGCTG

601 ACCCCGGCCC CAGCCTCCTG CTCACAGGAG GCCCCAAGTG CTGAAGACAA TGGCCTGGTG

661 GCCAGCGACC CCTTCGGAGT GCTCCGGGGC AATAGGGTGA ACATGCACGG GGACAGGATG

721 GGCCCGGAAA GGTGCCACCA TTTCCCCAAG TTCATCTAG
```

Horse FGF23 gene coding sequence (1-246) (SEQ ID NO: 289) (GenBank accession no. XM_001491419, which is hereby incorporated by reference in its entirety)

```
  1 ATGTCAGGGC CCTGCCTTGG GCTCCTGGTC TACGTCCTGT GCTCCGCAGT GAAAGCCTAT

 61 CCCAACGCCT CCCCGCTGCT AGACTCCAGC TGGGGCAGCC TGACCCACCT GTACACGGCC

121 ACAGCCAGGA ACAGCTACCA CCTGCAGATC CACAAGGATG GCCACGTGGA TGGCACACCC

181 CATCAGACCA TCTACAGTGC CCTGATGATC AGATCAGAGG ATGCTGGCTT TGTGGTGATA

241 ACAGGTGTGA TGAGCAGGAG ATACCTCTGC ATGGACTTCA GAGGAAACAT TTTTGGATCA

301 CATCACTTCA GCCCCGAGAG CTGCAGCTTC CGACAGCGGA CGCTGGAGAA CGGCTACGAC

361 GTGTACCACT CGCCGCAGCA TCGCTTCCTC GTCAGCCTGG GCCGCGCCAA GAGGGCCTTC

421 CTGCCCGGCA CGAACCCCCC GCCCTACTCG CAGTTCCTGT CCCGGAGGAA CGAGATCCCC

481 CTGGTCCACT TCAACACCCC GCGGCCGCGG CGGCACACGC GCAGCGCCGA GGACAACTCG

541 GAGCGCGACC CGCTGAACGT GCTGAAGCCC CGGCCCCGCA TGACCCCCGC GCCGGCCTCC

601 TGCTCCCAGG AGCTCCCGAG CGCCGAGGAC AACAGCGTGC TGGCCAGCGA CCCCTTAGGG

661 GTGGTCCGTG GCAACAGGGT GAACACGCAC GCGGGGGGCG CGGGCGTGGA GCGCTGCCGC

721 CCCTTCCCCA AGTTCTTCTA G
```

TABLE 8-continued

Giant panda FGF23 gene coding sequence (1-245) (SEQ ID NO: 290) (GenBank accession no. XM_002920450, which is hereby incorporated by reference in its entirety)

```
  1 ATGTCAGGGA CCCGCCTTGG GCTGCTGGTC TCTGTCCTGT GCTGGGTAGG CAGAGCCTAT
 61 CCCAACACCT CCCCACTGCT CGGCTCCAGC TGGGGTGGCC TGACCCACCT GTACACAGCC
121 AGCGCCAGGA ACAGCTACCA CCTGCAGATC CACAAGGACG GCCATGTGGA TGGCACACCC
181 CATCAGACCA TCTACAGTGC CCTGATGATC AGGTCAGAGG ATGCCGGCTT TGTGGTGATA
241 ACAGGTGTGA TGAGTAGGCG ATACCTCTGT ATGGACCTCA GAGGCAACAT CTTTGGATCC
301 CACCTCTTCA GCCCGGAGAG CTGCAGGTTC CGACAGCGGA CGCTGGAAAA CGGCTACGAC
361 GTGTACCACT CGCCGCAGCA CCGCTTCCTC GTCAGCCTGG GCCAGGCCAA GAGGACCTTC
421 CTGCCGGGGA CCAACCCGCC GCCCTACTCC CAGTTCCTGT CCCGGAGGAA CGAGATCCCC
481 CTCATCCACT TCAACACCCC CAGGCCAAGG CGGCACACGC GCAGCGCCGA GGACACGGAG
541 CGCGACCCGT TGAACGTGCT GAAGCCCAGG CCCCGCATGA CCCCCGCCCC GGCCTCCTGC
601 TCCCAGGAGC TCCCGAGCGC CGAGGACAAC AGTGTGGTGG CCAGCGACCC GTTAGGGGTG
661 CTCAGAGGCA ACCGGGTGAA CGCGCACGCC GGGGGGATGG GCGTGGACAG GTGCCGCCCC
721 TTCCCCAAGT TCATCTAG
```

Pika FGF23 gene coding sequence (1-250) (SEQ ID NO: 291) (Ensembl accession no. ENSOPRT00000007149, which is hereby incorporated by reference in its entirety)

```
  1 ATGCTGGGGG GGCTGGGGCT GTGGGTCTGT GTCCTGGGCA GTGTGTGCAG CTGGCGTGGG
 61 GTCCGTGCCT ATCCCGACAC CTCCCCGCTG CTCGGCTCCA GCTGGACTGG CCTGACCCAC
121 CTGTACACGG CCACCGCCAG GAACAGCTTC CACCTGCAGA TCCACAAGGA TGGCCATGTG
181 GATGGCACAC CCCAGCAGAC CATCTATAGT GCCCTGATGA TCAGATCAGA GGATGCCGGC
241 TTCGTGGTGA TAACAGGTGT CATGAGCAGG AGGTACCTCT GTATGGATTT CAGAGGCAAC
301 ATCTTCGGAT CGCATTACTT CGAGCCACAG AACTGCAGGT TCCAGCAGAG GACGCTGGAG
361 AACGGCTACG ACATCTACCA CTCTCCGCAG CACGACTTCC TGGTCAGCCT AGGTCGGGCC
421 AAGAGGCCGT TCCTGCCAGG CATGAACCCG CCACCCTACT CCCAGTTCCT GTCTCGGAGG
481 AACGAGATTC CGCTGATCCT CTTCAACACG CCCAGGCCTC GGAGGCACAC CCGCAGCGCG
541 GAGGAGGGCT GGGAGCGGGA CCCTCTGAAT GTGCTGAAGT CCAGGCCCCG AATGACCCCG
601 GCCCCAGCCT CCTGCTCGCG GGAGGCCCCC AGTGCCGAAG ACGACGGCCT GCTGGCCAGT
661 GACCCCATGG GAGTGCTCAG AGGCCATAGG GTGGATGTGC ACGGGGGTGG GACGGGTAGG
721 GACAGGTGCC GCCCGTTCCC CAGGTTCATC TAG
```

Cattle FGF23 gene coding sequence (1-245) (SEQ ID NO: 292) (GenBank accession no. XM_002687880, which is hereby incorporated by reference in its entirety)

```
  1 ATGCTGGGGG CCCGCCTGGG GCTCTGGGTC TGCACCCTGA GCTGTGTGGT CCAAGCCTAT
 61 CCCAACAGCT CCCCGCTGCT GGGCTCCAGC TGGGGCGGCC TGACCCACCT GTACACGGCC
121 ACGGCCAGGA ACAGCTACCA CCTGCAGATC CACGGAGACG GGCACGTAGA TGGCTCCCCG
181 CAGCAGACTG TCTACAGCGC CCTGATGATC AGGTCGGAGG ATGCCGGCTT CGTGGTGATA
241 ACAGGTGTGA TGAGCAGGCG GTACCTCTGC ATGGACTTCA CAGGCAACAT TTTTGGATCC
301 CATCACTTCA GTCCGGAGAG CTGCCGGTTC CGGCAGCGGA CACTGGAGAA CGGCTACGAC
361 GTGTACCACT CGCCGCAGCA CCGCTTCCTC GTCAGCCTGG GCCGGGCCAA GCGCGCCTTC
421 CTGCCGGGCA CCAACCCGCC CCCATACGCG CAGTTCCTGT CGCGCAGGAA CGAGATCCCG
```

TABLE 8-continued

```
481 CTGCCGCACT TCGCCGCCAC CGCGCGGCCC CGGCGCCACA CGCGCAGCGC ACACGACAGC
541 GGGGACCCGC TCAGCGTGCT CAAGCCGCGC GCCCGCGCCA CGCCCGTGCC CGCCGCCTGC
601 TCCCAGGAGC TGCCCAGCGC CGAGGACTCC GGCCCTGCCG CCAGCGACCC GCTCGGGGTG
661 CTCCGCGGAC ACCGCCTGGA CGTGCGCGCC GGCTCCGCGG GCGCCGAGCG CTGCCGGCCC
721 TTCCCCGGCT TCGCCTAG
```

Pig FGF23 gene coding sequence (1-244) (SEQ ID NO: 293) (GenBank accession no. XM_001926525, which is hereby incorporated by reference in its entirety)

```
  1 ATGCTGGGGG CCCGCCTCGG GCTCTGGGTC TGCACCCTGT GCTGTGCGGC CAGAGCCTAT
 61 CCCGACACCT CCCCGCTGCT GAGCTCTGGC TGGGGCGGCC TGACCCACCT GTACACGGCC
121 ACGGCCAGGA ACAGCTACCA CCTGCAGATC CACAAGGATG GCCACGTGGA TGGCTCACCC
181 CAACAGACCA TCTACAGTGC CCTAATGATC AGGTCGGAGG ACGCAGGCTT CGTGGTCATA
241 ACAGGCGTGA TGAGCAGGAG ATACCTCTGC ATGGACTTAA GGGGCAACAT TTTTGGATCG
301 CTGCACTTCA GCCCCGAGAG CTGCAGGTTC CGGCAGCGGA CGCTGGAGAA CGGCTACGAC
361 GTGTACCACT CGCCGCACTA CCGCTTCCTC GTCAGCCTGG GCCGGGCCAA GCGGGCCTTC
421 CTGCCGGGTA CCAACCCGCC CCCGTACGCG CAGTTCTTGT CGCGCAGGAA CGAGATCCCG
481 CTGCTGCACT TCGCCACCGC GCGGCCCCGG CGCCACACGC GCAGCGCGCA CGACGGCGGG
541 GACCCGCTGA GCGTCCTGAA GCCGCGCGCG CGCGCCACGC CCGCGCCCGT CTCCTGCTCC
601 CGCGAGCTGC CCAGCGCCGA GGACGGCGGC CCCGCGGCCA GCGACCCGCT CGGGGTGCTC
661 CGGGGCCAGC GGCTGGACGC GCGCGCTGGG GTGGGGGGCG CCGAGCGCTG CCGGCCCTTC
721 CCCAGCTTCG CCTAG
```

Dog FGF23 gene coding sequence (1-312) (SEQ ID NO: 294) (GenBank accession no. XM_849487, which is hereby incorporated by reference in its entirety)

```
  1 ATGTGGACAG TGGAGTTTTT CCTGTTTGAT GTCACAGGGC CACCCTTTAA AAGTCTGAGG
 61 GAAAAAAGGA GGGAATCTAG CCTGGGACTT TCACGCAAGA TACCCACAAA GAAGAGGAGA
121 AAAAGGCCTG TGAGGCACAG CCGGGGGAATC AAGGAGGCAG TGTCAGGTTT CAAACTCCAG
181 CCAGCCATTC AGAGAGCTGT GATGTCTGGC ACCCGCCTTG GATTCCTGGT CTCTGTCCTG
241 TGCTGGGTAG TCAGAGCCTA TTCCAACACC TCCCCGCTGC TCGGCTCCAG CTGGGGTAGC
301 CTAACCCACC TGTATACGGC CACAGCCAGG AACAGCTACC ACCTGCAGAT CCACAAGGAC
361 GGCCATGTGG ATGGCACACC TCATCAGACC ATCTACAGTG CCTTGATGAT CCGGTCAGAG
421 GATGCCGGCT TTGTGGTGAT AACAGGTGTG ATGAGTAGGA GGTACCTCTG TATGGACTTC
481 AGAGGCAACA TCTTTGGATC ACACCTCTTC AGCCCGGAGA GCTGCCGGTT CCGACAGCGG
541 ACGCTGGAGA ACGGCTACGA CGTGTACCAC TCCCCGCAGC ACCGCTTCCT CGTCAGCCTG
601 GGCCAGGCCA AGAGGGCCTT CCTGCCCGGC ACCAACCCGC CGCCCTACTC GCAGTTCCTG
661 TCCCGGAGGA ACGAGATCCC CCTCGTGCAC TTCCACACGC CCAGGCCGCG GCGGCACACG
721 CGCAGCGCCG AGGCCCCGGA GCGCGACCCG CTGAACGTGC TGAAGCCCAG GCCGCGCTTG
781 GCCCCCGCCC CGGCCTCCTG CTCGCAGGAG CTCCCGAGCG CCGAGGACCC CGGCGCGCCG
841 GCCAGCGACC CGCTCGGGGT GCTCAGGGGC CACAGGGCCA ACGCGCGCGC CGGCGGGGTG
901 GGCGTGGACA GGTGCCGCGC CTTCCCCACG CCCATCTAG
```

TABLE 8-continued

| Domestic guinea pig FGF23 gene coding sequence (1-243) (SEQ ID NO: 295) (GenBank accession no. XM_003463298, which is hereby incorporated by reference in its entirety) |
|---|
| 1 ATGCTGGGGA CCTGCCTTGG GCTCCTGGCC TGCACCGTGA GCTTAGTAGG AGCCTATCCT |
| 61 GATGCCTCCC CATTGCTCAC CTCCAGCTGG GGTGGCCTGA TCCATCTGTA CACGGCCACA |
| 121 GCCAGAAACA GCTACCATCT GCAGATCCAC AAAGATGGCC ACATAGATGG TGCACCCTAT |
| 181 CCGACCATCT ACAGTGCCCT GATGATCAGA TCAGAAGATG CTGGGTTCGT CGTGATAACA |
| 241 GGGGTCACAA GCAGGAGATT CCTCTGCATG GATTTCAGAG GCAACATTTT TGGATCTCAC |
| 301 CACTTCAATC CCCAAGACTG CCGATTCCAA CACCGCACGC TGGAAAACGG TTACGACGTC |
| 361 TACCTCTCTC CCGAGCACCA CTTTCTGATC AGCCTGGGCA GGACCAAGAA GTTCTTCCTG |
| 421 CCGGGCACCA ACCCACCGCC CTACTCCCAG TTCCTGTCGC GCAGGAACGA GCTGCCCCTG |
| 481 GCCCGCTTCG TCACGCCCGG GCCGCGGCGA CACACGCGCA GCGCGGAGGA GGACCAGGGC |
| 541 CGCGACCCGC TGAGCGTGCT CAAGCTTCGG CCCCGCGCCA CGCCCGCGCC CGCCTCGTGC |
| 601 TCGCAGGAGC TGCCCAGCGC GGAGGACGCG GCCCAGGCCA GCGACCCCCT GGGCGTGCTG |
| 661 CGGGGCGCCA GGGTGCACGC GCACGGCGGG CCGCGCCCCG CGAGGTGCCG CCCGGGACCC |
| 721 GGGGCCAAGT AA |

| Chinese hamster FGF23 gene coding sequence (1-251) (SEQ ID NO: 296) (GenBank accession no. XM_003496084, which is hereby incorporated by reference in its entirety) |
|---|
| 1 ATGCTGGGGA CCTGCCTCAG ACTCCTGGTG GGTGTTCTGT GTAGTGCCTG CAGCCTGGGC |
| 61 ACTGTTAGAG CCTATCCTGA CACCTCCCCA CTGCTCGGCT CCAATTGGGG CAGCCTGACC |
| 121 CACCTGTACA CAGCTACAGC CAGGAACAGT TATCACCTAC AGATCCACAA GGATGGCCGT |
| 181 GTAGATGGCA CACCCCATCA GACCATCTAC AGTGCCCTGA TGATTAGATC AGAGGATGCT |
| 241 GGCTTCGTGA TCATAACAGG AGCTGTGACT AGAAGGTTCC TTTGTATGGA TCTCAGGGGC |
| 301 AACATTTTTG GATCGCATCA CTTCAGCCCG GAGAACTGCA GGTTCCGCCA GCGGACTCTG |
| 361 GAGAATGGCT ATGACGTCTA CCTGTCGCCA CAGCATCACT ACCTGGTGAG CCTGGGCCGC |
| 421 GCCAAGCGCC CCTTCGAGCC CGGCACCAAC CCGCCTCCCT TCTCGCAGTT CCTGGCGCGC |
| 481 AGGAACGAGG TCCCGCTGCT GCGCTTCCAT ACCGCACGGC CACGGCGCCA CACGCGCAGC |
| 541 GCCGAGGACC CTCCCGAGTG GGACCCACTG AACGTGCTCA AGCCGCGGCC CCGTGCCACG |
| 601 CCCGTGCCCG TGTCCTGCTC GCGGGAGCTG CCGAGCGCCG AGGAAGGTGA CCTCGCGGCC |
| 661 AGTGACCCAC TGGGCGTCCT GCGCAGAGGC CGCGGGGATG CTCGCGGGGG CGCAGGAGGC |
| 721 GTGGACCGGT GCCGTCCCTT TCCCAGATTC GCCTAG |

| Tree shrew FGF23 gene coding sequence (1-180) (SEQ ID NO: 297) (Ensembl accession no. ENSTBET00000016365, which is hereby incorporated by reference in its entirety) |
|---|
| 1 GCCCTGCTGA TCAGGCCGGA GGAGGCTGGC TTCGCGGTGA TCACGGGCGT GATGAGCAGG |
| 61 AGATACCTCT GCATGGATTT CAGGGGCAAC ATTTTCGGAT CACACCTCTT CAGCCCGGAG |
| 121 AGCTGCAGGT TCCGGCAGCG CGCCCTGGAG AACGGCTACG ACGTCTACCA CCACCCGCAG |
| 181 CACCACTTCC TGGTCAGCCT GGGCCGGCCC AAGAGGGCCT TCGTGCCAGG CACGAACCCG |
| 241 CCCCCCTACT CCCAGTTCCT GGCCCGGAAG AACGAGATCC CGCTCATCCA CTTCAACACC |
| 301 CCGAAGCCGC GGCGGCACAC CCGCAGCGCA GAGGACAACT CGGGGCGCGA CCCGCTGAAC |
| 361 GTGCTGAAGC CCCGGCCGCG CATGACCCCG GCGCCCGCCT CCTGCTCGCA GGAGCTCCCG |
| 421 AGTGCCGAGG ACAACAGCGT GGTGGCCAGC GACCCCCTGG GAGTGCTCAG GGGCAACAGG |

TABLE 8-continued

```
481 GTGAACACGC ACGCGGGGGG CTGGGGCGTG GACCGCTGCC GCCCCTTCCC CAGGTTTATC

541 TAG
```

Norway rat FGF23 gene coding sequence (1-251) (SEQ ID NO: 298) (GenBank accession no. NM_130754, which is hereby incorporated by reference in its entirety)

```
  1 ATGCTGGGGG CCTGCCTCAG ACTCCTGGTG GGCGCTCTGT GCACCGTCTG CAGCTTGGGC

 61 ACTGCTAGAG CCTATTCAGA CACTTCCCCA CTGCTTGGCT CCAACTGGGG GAGCCTGACC

121 CACCTGTACA CAGCTACAGC CAGGAACAGC TATCACCTAC AGATCCATAG GGATGGCCAT

181 GTAGACGGAA CACCCCATCA GACTATCTAC AGTGCCCTGA TGATCACATC AGAGGATGCT

241 GGCTCCGTAG TGATAATAGG GGCCATGACC AGAAGGTTCC TTTGTATGGA TCTCCGCGGC

301 AACATTTTTG GATCGTATCA CTTCAGCCCG GAGAACTGCA GATTCCGCCA GTGGACGCTA

361 GAGAACGGCT ACGACGTCTA CCTGTCACCG AAGCATCACT ACCTGGTGAG CTTGGGCCGC

421 TCCAAGCGCA TCTTCCAGCC CGGTACCAAC CCGCCGCCCT TCTCGCAGTT CCTGGCGCGC

481 AGGAACGAGG TCCCGCTGCT GCACTTCTAC ACCGCGCGCC CACGGCGCCA CACGCGCAGC

541 GCCGAGGACC CGCCCGAGCG CGACCCGCTG AATGTGCTCA AGCCGCGGCC CCGCGCTACT

601 CCCATACCGG TATCCTGCTC GCGAGAGCTA CCGAGTGCAG AGGAAGGTGG CCCCGCGGCC

661 AGCGACCCCC TGGGAGTGCT GCGCAGAGGC CGCGGGGATG CTCGCCGGGG CGCGGGAGGC

721 ACGGATCGGT GTCGCCCCTT TCCCAGGTTC GTCTAG
```

House mouse FGF23 gene coding sequence (1-251) (SEQ ID NO: 299) (GenBank accession no. BC120605, which is hereby incorporated by reference in its entirety)

```
 24                              ATGCTAG GGACCTGCCT TAGACTCCTG GTGGGCGCGC

 61 TCTGCACTGT CTGCAGCTTG GGCACTGCTA GAGCCTATCC AGACACTTCC CCATTGCTTG

121 GCTCCAACTG GGGAAGCCTG ACCCACCTGT ACACGGCTAC AGCCAGGACC AGCTATCACC

181 TACAGATCCA TAGGGATGGT CATGTAGATG GCACCCCCCA TCAGACCATC TACAGTGCCC

241 TGATGATTAC ATCAGAGGAC GCCGGCTCTG TGGTGATAAC AGGAGCCATG ACTCGAAGGT

301 TCCTTTGTAT GGATCTCCAC GGCAACATTT TTGGATCGCT TCACTTCAGC CCAGAGAATT

361 GCAAGTTCCG CCAGTGGACG CTGGAGAATG GCTATGACGT CTACTTGTCG CAGAAGCATC

421 ACTACCTGGT GAGCCTGGGC CGCGCCAAGC GCATCTTCCA GCCGGGCACC AACCCGCCGC

481 CCTTCTCCCA GTTCCTGGCG CGCAGGAACG AGGTCCCGCT GCTGCACTTC TACACTGTTC

541 GCCCACGGCG CCACACGCGC AGCGCCGAGG ACCCACCCGA GCGCGACCCA CTGAACGTGC

601 TCAAGCCGCG GCCCCGCGCC ACGCCTGTGC CTGTATCCTG CTCTCGCGAG CTGCCGAGCG

661 CAGAGGAAGG TGGCCCCGCA GCCAGCGATC CTCTGGGGGT GCTGCGCAGA GGCCGTGGAG

721 ATGCTCGCGG GGGCGCGGGA GGCGCGGATA GGTGTCGCCC CTTTCCCAGG TTCGTCTAG
```

Megabat FGF23 gene coding sequence (1-248) (SEQ ID NO: 300) (Ensembl accession no. ENSPVAT00000000244, which is hereby incorporated by reference in its entirety)

```
  1 ATGCCGAGGG GCAGCCTAGG GCTCCTGGTC TGCATCCTGT GCTGCAGAGC CTATCCCGAT

 61 GCCTCTCCGC TGCTTAGCTC CAGCTTGGGG GGCCTGATCC ACCTCTACAC AGCCACAGCC

121 AGGAACGGCT ACCACCTGCA GATCCACAAG GATGGCCATG TGGATGGCAC ACCCCATCAG

181 ACCATCTACA GTGCCCTGAT GATAAGATCA GAGGACAGTG GCTTTGTGGT GATAATAGGT

241 GTGATGAGTA GAAGATACCT CTGCATGGAC TTCAAAGGCA ACATTTTTGG ATCACATCAC

301 TTCAGCCCCG AGAGCTGCAA GTTCCGCCAG CGAACGCTGG AGAATGGCTA CGACGTGTAT
```

TABLE 8-continued

```
361 CACTCGCCCC AGCATCACTT CTTCGTCAGC CTGGGCCGAG CTAAGAGGGC CTTCCTGCCG

421 GGCACGAACC CCCCACCTTA CTCCCAGTTC CTGTCCCGAA GGAATGAGAT CCCCCTGTTC

481 CAGTTCAACA CCCCGCGGCC GCGGCGGCAC ACGCGCAGCG TGGAGGACTA CAAAGACTAC

541 GATTTGGACC CCGACCCGCT GAAAGTTCTG AGGCCCCGTC CCCGGTGGGT CCCCGCCCTG

601 CCCTCCTGCT CCCAGGAGCT CCCGAGTGCC GAGGACAACA GCGTGGTAGC CAACGACCCG

661 TTAGGGGTGC TCAGGCCCAG CAGGGTAAAC ATATACCGTG AGAGAATGGG CAAGGGGAGG

721 TGCCGTCCCC ACCCTGAGTT TGTCTAG
```

Microbat FGF23 gene coding sequence (1-248) (SEQ ID NO: 301) (Ensembl accession no. ENSMLUT00000031180, which is hereby incorporated by reference in its entirety)

```
  1 ATGCCAGGGG CCCGCCTTGG GTTGCTGGTC TGCGTCCTGG CCCTGCGCTG TGTGGTCAGA

 61 GCCTATCCCA ACGCCTCCCC ACTGCTCGGC TCCAGCTGGG GTGGCCTGAC CCACCTGTAC

121 ACGGCCTCAG CCAGGAACAG CTACCACCTG CAGATCCACA AGGACGGCCA TGTGGACGGC

181 ACACCCCATC AGACCATCTA CAGTGCCCTG ATGATCAGAT CAGAGGACGC TGGCTTTGTG

241 GTGATAACTG GAGTGATGAG TAGGAGATAC CTCTGCATGG ACTTTAGAGG CAACATTTTT

301 GGATCCCTTT TTTTCAGTCC AAGTAATTTC AGTTTCCTTG AATGGAAAAA GGAAAGTGGG

361 ATGGACCATT GGATAAGCAG ACAGACGCAC TTCCTCGTCA GCCCTGGGCC GAGCCAAGAG

421 GGCCTTCCTG CCGGGCACAA CCCGCCGCCC TACTCGCAGT TCCTGTCGCG AAACGAGATC

481 CCGCTCTTCC ACTTCAACAC GCCCGCGCCG CGCCGGCACA CGCGCAGCGC CGAGGAGAAC

541 TCGGCGGCCG ACCCGCTGGT CGTGCTGAAG CCCGTGCCGC GCCTGACGCC CCCGCCCGCC

601 TCCTGCTCCC GGGAGCTGAG CAGCGCCGAG GACAACAGCG TGGCGGCCCA CGACCCGCTC

661 GGGGTGCTGC GGAGCAGCAA CAGGGTGAAC TCGCACGCGC CGCCCCCAGG TCCACCTAGG

721 ACCCGCCAAG GAATGCTTCT CGTA
```

Tasmanian devil FGF23 gene coding sequence (1-245) (SEQ ID NO: 302) (Ensembl accession no. ENSSHAT00000010240, which is hereby incorporated by reference in its entirety)

```
  1 ATGTCAGGGG GTTGCCTCAG GCTCCTATTC TGTGCCCTGT GCAGCTTAAG GGCCATCCAA

 61 GCCTTCCCCA ATGCTTCCCC CCTGCTCAGC CTTGGCTGGG GGGGTCTGAC TCACCTCTAT

121 ACGGCCACAG CCAGGAACAG CTACCACCTG CAGATCCACA AAGATGGCCA CGTGGATGGG

181 TCTCCTCATC AAACCATCTA TAGTGCCTTG ATGATCAGAT CAGAGGATGC TGGGCTAGTC

241 ATAATAACTG GTGTGATGAG CAGGAGATAT CTCTGTATGG ACATTAGGGG CAACATCTTC

301 GGATCGCATT TCTTCAGCCC AGACAACTGC AGGTTCAAAC ACCGGACATT AGAAAATGGG

361 TATGACATCT ATCACTCTCC CCAGAACAAC TTCCTGATCA GCCTTGGCAA GGCAAAGAGG

421 GCCTTCCTAC CAGGGATGAA CCCACCTCCT TACTCCCAAT TCCTGTCTCG GAGAAATGAA

481 ATCCCCATAA TACACTTCAA TACACCTGAA CCCCACCGGC ATACCAGGAG TGCTGAGAAC

541 AGTCCTGACT TGGACCCAAT GAATGTGCTG AAACTCCGAC CAAGGATAAC TCCCTGCTCC

601 CAGGAACTTC ACAGTGCTGA AGAGAACAGT GTAGTGGATG ATGACCCTTT GGAAGTACTC

661 AGAAATAGCA ATAGATTGAA GCCCTATCCT GGCAGGATGA GTTTGGAAAG ATGCCTCCAT

721 GTCCCCAAGG CAGCTTAA
```

TABLE 8-continued

Gray short-tailed opossum FGF23 gene coding sequence (1-191) (SEQ ID NO: 303) (GenBank accession no. XM_001372399, which is hereby incorporated by reference in its entirety)

```
  1 ATGGCAAATT GTAGAGAAAA GGAGCTGGAG ATGTACATTT GTGCCTTGAT GATCAGATCA
 61 GAGGATGCTG GGCTAGTCAT AATAACTGGT GTGATGAGCA GGAGATATCT CTGTATGGAC
121 ATCAGGGGCA ACATCTTTGG TTCGCATTTC TTCAACCCGG ACAACTGCAA GTTCAAGCAC
181 CGGACACTAG AAAATGGGTA TGACATCTAT CATTCTCCCC AGAACAACTT CCTGATCAGC
241 CTTGGCAAGG CAAAGAGGGC CTTTCTGCCA GGCATGAATC CACCTCCGTA CTCTCAATTC
301 CTGTCTCGGA AGAATGAGAT CCCCATAATC CACTTCAACA CACCTGAACC CCACCGGCAC
361 ACCAGGAGTG CTGAAAACAG TCCTGACTTG GACCCAATGA ATGTGCTGAA ACCCCGACCA
421 AGGATGACTC CCTGCTCTCA GGAACTCTAC AGTGCTGAAG AGAACAGTGT AGTGGATGAT
481 GACCCTTTGG AAGTACTTAG AAATAGCAAT CGACTGAAGC CCTTCCCTGG TAGGCTGGGT
541 TTAGAAAGGT GCCACCATGT TCCCAAGACT GATTAA
```

Armadillo FGF23 gene coding sequence (1-180) (SEQ ID NO: 304) (Ensembl accession no. ENSDNOT00000005805, which is hereby incorporated by reference in its entirety)

```
  1 GCCCTGATGA TCAGCTCTGA AGATGCTGGC TTTGTGGTGA TAACAGGTGT GATGAGCAGG
 61 AGGTACCTCT GTATGGATTT CAGAGGCAAC ATTTTTGGAT CGCACGACTT CACCCCGGAC
121 AGCTGCAGGT TCCGCCAGCG CACGCTGGAG AACGGCTACG ACGTCTACCA CTCGCCGCAG
181 CACCACTTCC TCGTCAGCCT GGGGCGGGCC AAGCGGGCCT TCCAGCCGGG CTCCAACCCG
241 CCGCCCTACT CCCAGTTCCT GTCCCGCAGG AACGAGATCC CGCTGATGCG CTTCAGCACC
301 CCGCGGCCGC GGCGGCACAC GCGCAGCGCC CAGGACCACG CGGACCCCGA CCCGCTGAGG
361 GTGCTCAAGC CCCGGCTCCG GCTGACCCCG GCCCCCGCCT CCTGCTCCCA GGAGCTGCCG
421 AGCGACGAGG ACGACGGCGC GGTGGCCAGC GACCCCCTGC GCGTGGTCCT CGGCCGCCGG
481 CCCCACGCGC GGGCCGCGGG CGCGGGCGGG GAGCGGTGCC GCCCCGGCCC GCAGCTCAGC
541 TAG
```

Wallaby FGF23 gene coding sequence (1-177) (SEQ ID NO: 305) (Ensembl accession no. ENSMEUT00000004101, which is hereby incorporated by reference in its entirety)

```
  1 GCCTTGATGA TCAGATCAGA GGACGCTGGG CTAGTCATAA TAAGTGGTGT GATGAGCAGG
 61 AGGTATCTCT GTATGGACCT CAGAGGCAAC ATCTTCGGAT CGCATTTCTT CAGCCCAGAC
121 AACTGCAGGT TCAAACACCG GACACTAGAA AATGGGTATG ACATCTATCA CTCTCCACAG
181 AACAACCTCC TGATCAGCCT TGGCAAGGCA AAAAGGGCCT TCCTGCCAGG CATGAACCCA
241 CCTCCTTACT CCCAGTTCCT ATCTCGGAGG AATGAGATCC CCATAATCCA CTTCAATACA
301 CCTGAACCCC GCCGGCACAC CAGGAGCGCA GAGAACAGTC CTGACTTGGA CCCAATGAAT
361 GTGCTGAAAC CCCGACCAAG GGTGACTCCC TGCTCCCAGG AACTCCGCAG TGCTGAAGAG
421 AACAGTGTAG TAGATGATGA CCCTTTGGAA GTACTCAGAA ATAGTAATCG CCTGAAGCCC
481 TACCCTGGTA GAATGAGTTT GGAAAGATGC CTCCAAGTCC CCAAAGCTGC TTAA
```

Zebra finch FGF23 gene coding sequence (1-256) (SEQ ID NO: 306) (GenBank accession no. XM_002190484, which is hereby incorporated by reference in its entirety)

```
  1 ATGGAGTGGA GAGCCACTCT CCAGGGCATT CCCTGCAGCT CCCTGCTCCT GCTGCTCTGC
 61 AGCCTAAAGG CTTCCCTTGC CTTTCCCAAC TCCTCTCCAC TGCTGAGTCC CAGCTGGGGC
121 AATGGAGATC GCCTGATGCA CCTCTACACC GACACCGAGA GGAGCAGCTT CCACCTCCAG
```

TABLE 8-continued

```
181 ATCAACGCTG ATGGCTACAT CGATGGCGCT CCTCACCAAA CCATCTACAG TGCCCTAATG

241 ATCAAGTCTG AGGGTGCTGG CTCAGTAATA ATCACAGGTG TGAAGAGTGG ACGCTACCTG

301 TGTATGGACA TGAAAGGAAA TATATTTGGC TCGCATTACT TCAGCCAAGA GGACTGCATG

361 TTCAACCACA GGACGCTGGA AAATGGGTAC GATGTGTACC AATCCCCCAA ACACCACTTC

421 TTGGTGAGCT TAGGCAGAGT TAAACAAGTC TTCTCCCCTG GTATGAATCC ACCACCATAC

481 TCCCAGTTTC TGTCCAGGAA GAATGAGATC CCTCTGTTCC GATTCAACAC CCCCGAGCCC

541 CACAGGCACA CCAGGAGTGC AGATGTTGAT CCCGTAGATC CTCACCAGAT CCTGGTCCCG

601 CAGAGGAAGA CCCCAGTGTT TGGCTCCCTG CAGCAGCAGC CAGCAGACTT TCCCCACATG

661 CCCAGGGAGC CCATGAGGAT CAACCAGAAC GACGTGGTGA ACCCCGATGA TCCCCACGCA

721 ATGATGGAGG CCAGGAGGTA CCCAAGCCCC CGCTTCTACA TCACGAGATA A
```

Chicken FGF23 gene coding sequence (1-254) (SEQ ID NO: 307)
(GenBank accession no. XM_425663, which is hereby incorporated by reference in its entirety)

```
  1 ATGCCACACA CCAGTCCCTG CAGCTGCCTG GAGTACATGC TGCTTGTGCT CTGTATCCTG

 61 AAGGCTGCAG TCGCCTTCCC CAACTCCTCT CCGCTGCTGA ATCCCAGCTG GGGGAATGGA

121 GATCAGCTGA TGCACTTGTA CACTTCTACA GAGAGGAACA GCTTCCATCT CCAAATCAAT

181 GCTGATGGAC ACATCAATGG TGTTCCTCAC CAAACCATTT ACAGTGCCTT AATGATCAAG

241 TCTGAGGGTG CTGGCTGTGT AATAATCACA GGTGTGAAGA GTGGACGCTA CCTATGCATG

301 GACATGAAAG GAGACATTTT TGGATCGTAT TATTTCAGCC AAGAGGACTG TGTGTTCAAC

361 CAAAGGACAC TGGAAAATGG ATATGATGTG TACCAATCTC CCAAGCACAA TTTTCTGGTT

421 AGCTTGGGCA GAACTAAGCA AGTTTTCTTC CCTGGTATGA ATCCACCACC ATACTCCCAG

481 TTTTTGTCCA GGAGAAACGA AATCCCTTTG TTTCGATTCA ACACACCTGA ACCCCACAGA

541 AACACTAGAA GTGCAGATGT CGATCCACTG GATCCTCACC AAATCCTGGT CCCACAGAGA

601 AAGGTCTCTG CATTAGGGTC TCAGCTGCAG CTGCAAATGG ACTTTTCCCA TGTGCCCAGA

661 GAACCCATGA GAGTCAATCA GAATGATGTG GTCAATCCAG ATGACCCACA TGCTATGATG

721 GATGCTAGGA GGTATGCTAG TCCTCGCTTT TACATTACAA GATAA
```

Turkey FGF23 gene coding sequence (1-254) (SEQ ID NO: 308)
(GenBank accession no. XM_003202575, which is hereby incorporated by reference in its entirety)

```
  1 ATGCCGCACA CCAGTCCCTG CAGCTGCCTG GAGTACATGC TGCTTGTGCT CTGTATCCTG

 61 AAGGCTGCAG TCAGCTTCCC CAACTCCTCT CCACTGCTGA ATCCCAGCTG GGGGAACGGA

121 GATCAGCTGA TGCACTTGTA TACTTCTACA GAGAGGAACA GCTTCCATCT TCAAATCAAT

181 GCTGATGGCC ACATCAGTGG TGTTCCTTAC CAAACCATTT ACAGTGCCCT AATGATCAAG

241 TCTGAGGGTG CTGGCAGCGT TATAATCACA GGTGTGAAGA GTGGACGCTA CCTATGCATG

301 GACATGAAAG GAGACATTTT TGGATCGCAT TATTTCAGCC AAGAGGACTG CGTGTTCAAC

361 CAAAGAACAC TGGAAAATGG ATATGATGTG TATCAATCTC CCAAGCACAA TTTTCTGGTT

421 AGCTTAGGCA GAACTAAGCA AGTTTTCTTC CCTGGTATGA ATCCACCACC GTACTCCCAG

481 TTTTTGTCCA GGAGAAACGA AATCCCGTTG TTTCGATTCA ACACACCTGA ACCCCACAGA

541 AACACTAGAA GTGCAGATGT TGATCCAATG GATCCTCACC AGATCCTGGT CCCACAGAGA

601 AAGGTCTCTG CAATAGAGTC TCAGCTGCAA CTGCAAATGG ACTTTTCCCA TGTGCCCAGA

661 GAACCCATGA GAGTCAATCA GAACGATGTG GTCAACCCAG ATGACCCACA CGCTATGATG

721 GATGCCAGGA GATATGCTAG TCCTCGCTTT TACATTACAA GATAA
```

TABLE 8-continued

Green anole FGF23 gene coding sequence (1-242) (SEQ ID NO: 309) (GenBank accession no. XM_003221363, which is hereby incorporated by reference in its entirety)

```
  1 ATGGTCCAGG CTACTCTATA CAGCTTCCTC AAATATATGC TGCTTGCAAC ATGTAGCTGG
 61 AAAGCAATTG CTGCTTTCCC CAACGCATCA CCTTTGCTCA GCCTCAACTG GGGAAATTCA
121 GACAGCCTGC TACACTTGTA CACTTCCACA GCAAGAAACA GCTTCCACCT GCAAATCCAC
181 TCCAATGGCT ACGTGGATGG AAGTCCGTAT CAAACAATTT ACAGTGCCTT GATGATCAAA
241 TCTGAAGTTG CTGGTTATGT TATAATAAAT GGTGTGAAAA GTGGACGTTT TCTTTGTATG
301 GATATGAATG GGAACATCTT TGGATCGCAT TTCTTCAGTT ATGAGGACTG CACTTTCAAA
361 CACTGGGTCC TGGAAAATGG TTATGATGTT TATCAGTCTC CCAAATACAA CTACCTTGTC
421 AGCTTAGGAA AAGCAAAGCA ACCATTGTTC CCCAATATGA ATCCACCACC TTACTCCCAG
481 TTCTTGTCCA GGAGAAATGA AATTCCTTTA GTCCAGTTCA ACACACCGAA ACCTCACAGA
541 CATACCAGAA GTGCCAACGC GGATCCCTGC GGCAGCATCA TATCATCAGG AAATATTGCG
601 AAAGAAAACC TACAGTTACA GCCACTAATG TATAACACTA AAATGAATTC AAACAGTGAA
661 GATGAAGACC CAAACAGTGC AATAATCAAT AGAAGATTTT TGAGTCCTAG AACAGATGTC
721 AGGAGCTGA
```

Coelacanth FGF23 gene coding sequence (1-249) (SEQ ID NO: 310) (Ensembl accession no. ENSLACT00000020646, which is hereby incorporated by reference in its entirety)

```
  1 CTAGAGTCCG CTCTTCTTGC GTTTTCTATG GCTATATTCT ATAGCTTTAA AGCTGTGAGC
 61 TCTTTTCCAA ATTCTTCGCC ACTGCTTAAC CCAGTCTGGG GAAACACTGA CAACCTGATA
121 CACCTGTATA CAGCTTCTGA GACGAACAGC TTCCACTTGC AGATCAACTC CGATGGACAT
181 GTGGATGGTA CTCCACACCA AACCGCTTAC AGTGCACTGC TGATCAAGTC CGAGGAGGCT
241 GGTTCTGTAG TTATCCTGGG GGTGAAGAGT GGACGTTACC TCTGTATGGA TATCAAGGGC
301 AATATTATTG GACTGCATCA CTTCAGCAAG GAAGACTGTA CATTCAAACA AGAGGGCTTG
361 GAAAATGGAT TTGATGTGCT GCGCTCACCT AAGCACAACA TTTTGGTCAG CCTTGACAAG
421 ACTAAACGCT CCTACATCCC GGGTATGAAC CTGCCACCTT ACTCACAGTT TTTATCCCGA
481 CAGAATGAAG TAGCTCTGAT CAACTTCATT AACACACCTG ACATACACAG ACATAGTCGA
541 AATGTTGATG TTGATCCTTC AGACCCCCAT GGGATGATAA TTCAGCCTGA TGTGGGTGTT
601 TCATTTCGTA AGTCTTCATC TCTGTTTTCA GATCTGCCCA GAGACTCCAT GAGAACTAGC
661 CATAATGGTA TGGATATGGT TGATCCTGCT GACCCACATG GAATGTTAGA TTCCAGGAGA
721 AGACCAAGTC CAAGGTTCTT TGCAAGATAG
```

Western clawed frog FGF23 gene coding sequence (1-254) (SEQ ID NO: 311) (GenBank accession no. XM_002940305, which is hereby incorporated by reference in its entirety)

```
 25                             ATGACC AAGCAGCAAA CTAGACTAGG ACTGGTGCTC
 61 ACTGTTCTTG CCAGTATAAA GGTTATATCT GCCTTCCCCA ACTCTTCTCC AATAATCAGT
121 GGCGGCTGGG GGGTCCCTGA CAGACTGATG CACCTATATA CGGCCAGTGA CTGGAACAGC
181 TTCCACCTAC AGATCAACCA TGATGGAAGC ATTGATGGAA CCCCTACCCA AACCATTTAC
241 AGTGCAATAA TGATCAAATC AGAATCCGCT GGGCACGTGG TTATTACTGG GGTGAAGACT
301 AATCGGTACC TGTGCATGGA TAAAAGTGGG AACATTTTTG GATATCACGA CTTCAACCAC
361 GACGACTGCG TTTTTAAGCA CGAGACTCTG GAGAACAACT TTGACGTTTA CCATTCTCCA
421 AAACACAACT TTGTGATCAG CCTCAAGGAG CCCAAGCATC ATTTCCGCCT CGGCATGGAC
```

TABLE 8-continued

```
481 CTGCCCCCTT ACTCCCAATT CCTGTCCTTG GAGAATGAAA TCCCCATAAC CAGATTCAAT

541 GCTCCAGAGC CGGAAATGAG AATCCCAGAG GGCAACTTTG CTGACCCCAG CGACATCATA

601 AAGAACCCCA GGAACTGGGA CTTTTCGCAG TCTATTCATA ATCCATTTCA GGATGTGTGG

661 TTGCCGTTCC CCAGCGGTTC ATTACCAATC ATTAGAGCTT CCTTGCCAAT TATTCATAAC

721 AATGTGATTA ATACAGATGA CCCTGAAGAA ATTGTAAAAA TGAAGAGATA CAGATATTTC

781 AAGAGGTAG
```

Cat FGF23 gene coding sequence (1-199) (SEQ ID NO: 312) (Ensembl accession no. ENSFCAT00000000141, which is hereby incorporated by reference in its entirety)

```
  1 ATGTCAGGGA CCCGCCTTGG GCTCCTGGTC TCTGTCCTGT GCTGGGTAGT CAGAGCCTAT

 61 CCTAACACCT CCCCGCTGCT GGGCTCCAGC TGGGGTGGCC TGACCCACCT GTACACGGCC

121 ACAGCCAGGA ACAGCTACCA CCTGCAGATA CACAAGGACG GCCATGTGGA TGGCACACCC

181 CATCAGACCA TCTACAGTGC CCTGATGATC AGATCGGAGG ATGCCGGCTT TGTGGTGATA

241 ACAGGTGTGA TGAGTCAGAG GTACCTCTGT ATGGACTTCA GAGGCAATAT CTTCGGATCG

301 CACCTCTTCA GCCCCGAGAG CTGCAGGTTC CGACAGCGGA CGCTGGAAAA CGGCTACGAC

361 GTGTACCACT CCCCGCAGCA CCGCTTCCTA GTCAGCCTGG GCCCGGCCAA GAGGGCCTTC

421 CTGCCGGGCA CCAACCGCAT GACCCCCGCG CCGGCCTCCT GCTCCCAGGA GCTCCCAAGC

481 GCCGAGGACA GCGGCGTGGT GGCCAGCGAC CCGTTAGGGG TGCTCAGGGG CAACAGGGTG

541 AACGCGCACG CCGGGGGGAT GGGCGTGGAG AGGTGCCGCC CCTTCCCCAA GTTCAACTAG
```

Chinese softshell turtle FGF23 gene coding sequence (1-250) (SEQ ID NO: 313) (Ensembl accession no. ENSPSIT00000012816, which is hereby incorporated by reference in its entirety)

```
 98                                         ATG TCACAGCCCA GCCAGTGCAG

121 CTGCCTGAAC TTCATGCTGT TCGTGCTATG TAGCTTCAAA GCTATTGCTG CCTTTCCCTT

181 CTTCTCTTCA CTGCTGAATC CCAGCTGGGG GGAAACGGAT AGTTTGATAC ACCTGTACAC

241 AGCTACTGAG AAGAACAGCT TCCATCTGCA GATCAACCCT GATGGTTATG TTGACGGCAC

301 ACCTCACCAA ACCATTTACA GTGCTCTAAT GATCAAATCT GAGGATGCTG GCTATGTGGT

361 GATAAGTGGT GTAAAGAGTG GGCGCTACCT ATGTATGGAC ATTAAAGGAA ATATCTTTGG

421 ATCGCATTAC TTCAGTCAAG AGGACTGCAT GTTTAAACAC AGAACACTGG AAAATGGATA

481 TGATGTGTAC CAGTCTCCCA AGCACAACTT CCTGGTCAGC CTGGGCAGGA ATAAACAAGC

541 TTTCTTCCCT GGTATGAATC TGCCACCATA CTCCCAGTTT TTGCCCAGGA GAAATGAAAT

601 CCCTCTGATC CGATTCAACA CACCCGAACC CCACAGGCAC ACTAGGAATG CAGATGTTGA

661 TCCCCTCCAG ATTTTGATCC CTCGGGGAGA GGCTTTTGAC ACAGGACCTC AGAGGTTGCA

721 GACTCACTTT GATCACCTGC CTAGAGAACC CATGAGAATC AATCCAAATG ATGTAGTCAG

781 CCCGGATGAC CCACTCGCCA TGATGGATGT CAGAAGGAAT GCAAGTCCAC GCCTTTACAT

841 TACAAGA
```

Ferret FGF23 gene coding sequence (1-245) (SEQ ID NO: 314) (Ensembl accession no. ENSMPUT00000009396, which is hereby incorporated by reference in its entirety)

```
186      ATGTC AGTGACCCGT CTTGGGCTCC TGGTCTCTGT CCTGTGCTGG GTAGTCAGAG

241 CCTATCCCAA CGCCTCCCCG CTGCTCGGCT CCAGCTGGGG TGGCCTGACC CACCTGTACA

301 CGGCCACTGC CAGGAACAGC TACCACCTGC AGATCCACAA GGATGGCCAT GTGGATGGCA

361 CACCCCACCA GACCATCTAC AGCGCCCTGA TGATCAGATC AGAGGATGCC GGCTTTGTGG
```

TABLE 8-continued

```
421 TGATCACAGG TGTGATGAGC AGGCGGTACC TGTGTATGGA CTTCCGAGGC AACATCTTTG
481 GATCCCACCT CTTCAGCCCC GAGAGCTGCA GGTTCCGACA GCGGACACTG GAAAACGGCT
541 ACGACGTGTA CCACTCCCCG CAGCACCGCT TCCTCGTCAG CCTGGGCCAA GCCAAGAGGG
601 CCTTCCTGCC GGGCACCAAC CCGCCGCCCT ACTCCCAGTT TCTGTCCCGG AGGAATGAGA
661 TCCCCCTCAT CCACTTCAAC ACCCCCAGGC CGCGGCGTCA CACGCGCAGC GCCGAGGACA
721 TGGAGCACGA CCCGTTGAAC GTGCTGAAGC CCCGGCCCCG CATGACCCCG GCCCCGGCCT
781 CCTGCTCCCA GGAGCTCCCG AGCGCCGAGG ACAACAGTGT GGTGGCCAGC GACCCGTTAG
841 GGGTGCTCAG AGGCAACCGG GTGAACGTGC ACGCGGGGGG GATGGGCGTG GACAGGTGCC
901 GCCCCCTCCC CAAGTTCATC TAG
```

Mouse lemur FGF23 gene coding sequence (1-206) (SEQ ID NO: 315) (Ensembl accession no. ENSMICT00000004875, which is hereby incorporated by reference in its entirety)

```
  1 ATGCTGGGGG CCTGCCTCAG GCTCTGGGTC TGTGCCCTGT GCAGTGTCTG CGGCGTGAGC
 61 GTCGTCAGAG CCTATCCCAA CGCCTCCCCG CTGCTCGCCT CCAGCTGGGG TGGCCTGATC
121 CACCTGTACA CGGCCACGGC CAGGAACAGC TACCACCTGC AGATCCACAA GGACGGCCAT
181 GTGGACGGCA CACCCCACCA GACCATCTAC AGTGCCTTGA TGATCAGGTC AGAGGATGCT
241 GGCTTTGTGG TGATCACAGG TGTGATGAGC AGAAGATACC TCTGCATGGA TTTCAGAGGC
301 AACATTTTTG GATCACATGT CTTCAGCGCG GAGAGCTGCA GGTTCAGACA GCGGACGCTG
361 GAGAACGGCT TCGACGTGTA CCAGTCCCCT CAGCACCACT TCCTGGTCAG CCTGGGCCGC
421 GCCAAAGGGG CCTTTCCGGC CGGGGCGAAA CCGCCCCCCT TCCCCCAGTT CCTGCCGCGG
481 GGGAACGAGG CTCCCGGGCG CAAAACGCGG GGGCCCGAGG AAAAAGGGGC CCCACACCCT
541 CTCCGCGGGG TGGAAAGCGG GGGCCGGAAA GGCGGGGCCC CGCCTCTCTG TTTGGAGAGG
601 CTCTCCAGAG CCCGAGAG
```

Orangutan FGF23 gene coding sequence (1-251, excluding 2-22 and 38-71) (SEQ ID NO: 316) (Ensembl accession no. ENSPPYT00000006110, which is hereby incorporated by reference in its entirety)

```
  1 ATG------- ---------- ---------- ---------- ---------- ----------
 61 ------CGCA AT------GA GTCTTTGCCC TGCCTGGTTT TCTCCATAGG T---------
121 ---------- ---------- ---------- ---------- ---------- ----------
181 ---------- ---------- ---------- GCCCTGATGA TCAGATCAGA GGATGCTGGC
241 TTTGTGGTGA TTACAGGTGT GATGAGCAGA AGATACCTCT GCATGGATTT CAGAGGCAAC
301 ATTTTTGGAT CACACTATTT CAACCCGGAG AACTGCAGGT TCCAACACCA GACGCTGGAA
361 AACGGGTATG ACGTCTACCA CTCTCCTCAG CATCACTTCC TGGTCAGTCT GGGCCGGGTG
421 AAGAGAGCCT TCCTGCCAGG CATG---CCA CCCCCGTACT CCCAGTTCCT GTCCCGGAGG
481 AACGAGATCC CCCTAATTCA CTTCAACACC CCCGTACCAC GGCGGCACAC CCGGAGCGCC
541 GAGGATGACA CGGAGCGGGA CCCCCTGAAA GTGCTGAAGC CCCGGGCCCG GATGACCCCG
601 GCCCCGGCCT CCTGCTCACA GGAGCTCCCG AGCTCCGAGG ACAACAGCCC GATGGCCAGC
661 GACCCATTAG GGGTGGTCAG GGGCGGTCGA GTGAACACGC ACGCTGGGGG AACGGGCCCG
721 GAAGGCTGCC GCCCCTTCCC CAAGTTCATC
```

TABLE 8-continued

Shrew FGF23 gene coding sequence (1-251, excluding 19-27, 71-105, 198-200, and 236-251) (SEQ ID NO: 317) (Ensembl accession no. ENSSART00000007775, which is hereby incorporated by reference in its entirety)

```
  1 ATGTGGGGAC TCCGCCTGGG TCTCTTGGTC GGCCTCCTGG GCTGCGTGGA CAGA------
 61 GCCTCCCCGA TGCTGGCGTC CAGCTGGGGC GGCCTGACGC ACCTGTACAC GGCCACGGCC
121 AGGAACAGCT ACCACCTCCA GATCCACAAG GACGGCCTGG TCGACGGCTC CCCGCAGCAG
181 ACCGTCTAC- ---------- ---------- ---------- ---------- ----------
241 ---------- ---------- ---------- ---------- ---------- ----CACCAT
301 TTCAGCCCGG AGAGCTGCCG CTTCCAGCAG CGCACGCTGG AGAACGGCTA CGACGTGTAC
361 CAGTCCCCGC AGCACCGCTT CCTCGTGAGC CTGGGCCGGC CCAAGCGCGC CTTCCAGCCG
421 GGCGCCAACC CGCCGCCCTA CGCGCAGTTC CTGGCGCGCC GCAACGAGGT GCCCCTGGCG
481 CGCTTCCACA CGCCCGCGCC GCGCCGCCAC ACGCGCAGCG CGCACGACAA CGGCGACGCC
541 GACCCGCTCA ACGTGCTGGC GCCTCGGGCC ---------G CCGCCGCCGC CTCCTGCTCG
601 CACGAGCTGC CCAGCGCCGA GGACAACAGC GTGGTGGCCA GCGACCCGCT GGGCGTCATC
661 CGCAGCAACC GCTTCCGCAC GCAC
```

Tetraodon FGF23 gene coding sequence (1-263) (SEQ ID NO: 318) (Ensembl accession no. ENSTNIT00000014553, which is hereby incorporated by reference in its entirety)

```
  1 ATGGACGTAA ACAGAAGGAT CGGGGTGAAG GACGCCTTGC TGGCGCTCCT GCTCGCCCTT
 61 CTCCAGGGAT GCCCCCTGGG GGAAACGGCT CCCAACGCGT CACCGCTGGT CGGTTCCAAC
121 TGGGGGAACC CGAGGAGGTA CGTTCACCTT CAGACATCCA CAGACATGAG CAACTTCTAC
181 TTGGAGATCA GACTGGATGG AACCGTGCGC AAAAGCACAG CCCGGACTTC ATACAGTGTG
241 ATTTTACTGA AAGCCGACAC GAGGGAGCGC ATCGCCATCC TGGGCGTCAA GAGCAACCGT
301 TACCTGTGTA TGGACCTCGA GGGGAGCCCA TTTAGCTCTC CCACCTGCAT CAGGGACGAC
361 TGCTTGTTCA ACCACAGTCT TCTGGAGAAC AACCGGGACG TCTACTACTC CAGCCGGACC
421 GGCATTCTCT TCAACCTTGA GGGCTCCCGC CAGGTGTTCG TGGTGGGCCA GAACGTCCCG
481 CAGACCTCCC TCTTCCTGCC CAGGACGAAC ACGGTGCCGC TGGAGCGACT CCTTCTGCAC
541 AGGGACAAGC GGAACCAGGT GGTGGACCCC TCTGACCCGC ACCGCGTCGC CGTGGGTCGC
601 GCCGAGGAGG GCTCGGACTC CCGGGCCTTG CAGGAGGACG ACGCCGACCT GGAGGTGGAG
661 ACAGAGGTTG AGGTCGGGGA CGACGGACGC AACGCGTCCC GGGAGCGGCT GCAGGCTCCG
721 TCCGATCACG ACCCCTGGGG CGTGTTCTCC TCCAACCCCG GGAGCCCCCG CAGCAGCGGC
781 ACGGTGGGCT GA
```

Tilapia FGF23 gene coding sequence (1-255) (SEQ ID NO: 319) (Ensembl accession no. ENSONIT00000000020, which is hereby incorporated by reference in its entirety)

```
472                                                        ATGGACGTC
481 AACAGGCGAA TGGGGATGAG AGACACCGTG CTGGCGCTCT TTCTCGCTGT CTTGCAGGGA
541 TTTCCTCTCG GGGATACGGT CCCGAACCCA TCACCTCTGG CTGGATCCAA CTGGGGGAAC
601 CCAAGGAGAT ACGTCCACCT GCAGACATCC ACAGACCTCA ATAACTTCTA CTTGGAGATC
661 AGATTAGATG GGAGTGTGCG CAAAACTACG TCCAGGAGCA CCTATAGTGT GATTCTACTG
721 AAATCTGAAG CAAGAGATCG CGTCGCCATC CTCGGCGTCA AAAGCAGCCG TTACCTATGC
781 ATGGACCTGG AGGGCAACCC GTTCAGCTCT CCTGTCTGCC TTCGGGATGA CTGTCTGTTC
```

TABLE 8-continued

| | |
|---|---|
| 841 | AACCACAAGC TCCTGGAGAA CAACCGGGAC GTGTACTACT CCAGCCGGAC AGGCATCTTG |
| 901 | TTCAACCTGG AGGGCTCCCG ACAGGTGTAC TCGGTGGGCC AGAACCTGCC GCAGACCTCC |
| 961 | CTCTTCTTGC CCAGGAAAAA CACCGTACCA CTGGAGCGCC TCCTGCTGCA CAGGGAGAAG |
| 1021 | AGAAACCGGG GGCAGACAGA AGAGGGTTCG GACTCCCGGG CCGTGCCGGA GGAGCTGGAG |
| 1081 | GAAAGGGAGG TGGAAATGGA GACGGAAATA GAAACAGAGG TCGGGGATGA CGGACGCAAC |
| 1141 | GTGTCCCGGG AGAAACTCGC GGCTCCATCC AGCCACGACC CCTGGAACGT GCACTTCTCC |
| 1201 | AACCCGGCCA GCCCCCGGAG CACCGGGACA GTGGGCTGA |

Zebrafish FGF23 gene coding sequence (1-258) (SEQ ID NO: 320) (Ensembl accession no. ENSDART00000067388, which is hereby incorporated by reference in its entirety)

| | |
|---|---|
| 79 | AT GCGTTGCGCA CTTTCCAACC TGCACATGCT GCATTCATCC |
| 121 | GTCCTCGCGC TGTGGTTCAC GGCTCTCCAG GGACTCAGAC CTGCAGATGC GGCCCCCAAT |
| 103 | CCTTCTCCGC TGCTGGGCTC CAACTGGGGG AACCCGCGGA GATACATCCA CCTTCAGACC |
| 163 | ACTTCAGACT TAAACAACTA CTACCTGGAG ATCAGCCCGA GTGGACACGT GCGCAAAACT |
| 223 | ACAAATCGGG GCTCATACAG TGTAATCTTA TTGAAAACAG AAAGCAGAGA CCGTCTGGCG |
| 283 | ATATTTGGAG TGAAAAGTAA CCGGTTTTTG TGCATGGATA CAGGAGGAAC CCTTTTCACA |
| 343 | TCTACGATCT GCAATAAGGA AGACTGTCTT TTCCACCACA AACTGTTGGA AAACCATCGT |
| 403 | GATGTGTATT ACTCCACTAA ACACAGCATA CTGCTTAATC TGGACGGGGA CAAACAGGCG |
| 463 | TTTATAGCGG GACAAAACCT CCCTCAGTCG TCTCTCTTCT TGTCGGAGAA GAACACGGTT |
| 523 | CCGCTGGAGC GCCTGCAGCA TCGGGAGCGC AGGAACCGGC AGGTGAACCC AACAGACCCG |
| 583 | CTGAACGCGC TCCGGTACGC GGAGGAGTCT GATTCCAGAG CCGCGCAGGA GGATGATGGA |
| 643 | GACATGGATT TTGAGCCCTC AGAAGGTCAA AACATCTCTA GAGAAACCCT TGTTTCCCCT |
| 703 | TCCGATGATG ATCCATGGGA TCTTCTGCAC GACACGAGCC CTGGAAGTCC TCGGATTGCA |
| 763 | GCAATTGTCG GATAA |

Chimeric proteins according to the present invention may be isolated proteins or polypeptides. The isolated chimeric proteins of the present invention may be prepared for use in the above described methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

In one embodiment, the chimeric protein of the present invention includes the amino acid sequence of SEQ ID NO: 321, SEQ ID NO: 322, SEQ ID NO: 323, or SEQ ID NO: 324, as shown in Table 9.

TABLE 9

| Description of Chimeric Protein | Sequence |
|---|---|
| Amino acid sequence of a FGF1/FGF23 chimera composed of residues M1 to L150 of human FGF1 harboring K127D/K128Q/K133V triple mutation (bold) and residues R161 to I251 of human FGF23 (bold) harboring R176Q/R179Q double mutation (bold italic) | SEQ ID NO: 321<br>MAEGEITTFT ALTEKFNLPP GNYKKPKLLY<br>CSNGGHFLRI LPDGTVDGTR DRSDQHIQLQ<br>LSAESVGEVY IKSTETGQYL AMDTDGLLYG<br>SQTPNEECLF LERLEENHYN TYISKKHAEK<br>NWFVGL**DQ**NG SC**V**RGPRTHY GQKAILFLPL<br>**RNEIPLIHFN TPIPR*Q*HT*Q*S AEDDSERDPL**<br>**NVLKPRARMT PAPASCSQEL PSAEDNSPMA**<br>**SDPLGVVRGG RVNTHAGGTG PEGCRPFAKF I** |
| Amino acid sequence of a FGF1/FGF23 chimera composed of residues K25 to L150 of human FGF1 harboring K127D/K128Q/K133V triple | SEQ ID NO: 322<br>KPKLLY<br>CSNGGHFLRI LPDGTVDGTR DRSDQHIQLQ<br>LSAESVGEVY IKSTETGQYL AMDTDGLLYG<br>SQTPNEECLF LERLEENHYN TYISKKHAEK |

TABLE 9-continued

| Description of Chimeric Protein | Sequence |
|---|---|
| mutation (bold) and residues R161 to I251 of human FGF23 (bold) harboring R176Q/R179Q double mutation (bold italic) | NWFVGL**DQ**NG SCVRGPRTHY GQKAILFLPL<br>**RNEIPLIHFN TPIPR*Q*HT*Q*S AEDDSERDPL**<br>**NVLKPRARMT PAPASCSQEL PSAEDNSPMA**<br>**SDPLGVVRGG RVNTHAGGTG PEGCRPFAKF I** |
| Amino acid sequence of a FGF2/FGF23 chimera composed of residues M1 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 323<br>MAAGSITTLP ALPEDGGSGA FPPGHFKDPK<br>RLYCKNGGFF LRIHPDGRVD GVREKSDPHI<br>KLQLQAEERG VVSIKGVCAN RYLAMKEDGR<br>LLASKCVTDE CFFFERLESN NYNTYRSRKY<br>TSWYVAL**DQT** GQY**V**LGSKTG PGQKAILFLP<br>M**RNEIPLIHF NTPIPR*Q*HT*Q* SAEDDSERDP**<br>**LNVLKPRARM TPAPASCSQE LPSAEDNSPM**<br>**ASDPLGVVRG GRVNTHAGGT GPEGCRPFAK**<br>**FI** |
| Amino acid sequence of a FGF2/FGF23 chimera composed of residues H25 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 324<br>HFKDPK<br>RLYCKNGGFF LRIHPDGRVD GVREKSDPHI<br>KLQLQAEERG VVSIKGVCAN RYLAMKEDGR<br>LLASKCVTDE CFFFERLESN NYNTYRSRKY<br>TSWYVAL**DQT** GQY**V**LGSKTG PGQKAILFLP<br>M**RNEIPLIHF NTPIPR*Q*HT*Q* SAEDDSERDP**<br>**LNVLKPRARM TPAPASCSQE LPSAEDNSPM**<br>**ASDPLGVVRG GRVNTHAGGT GPEGCRPFAK**<br>**FI** |

Chimeric proteins according to the present invention may be isolated proteins or polypeptides. The isolated chimeric proteins of the present invention may be prepared for use in accordance with the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule comprises the nucleotide sequence of SEQ ID NO: 325, SEQ ID NO: 326, SEQ ID NO: 327, or SEQ ID NO: 328 (as shown in Table 10).

TABLE 10

| Description of Chimeric Protein | Sequence |
|---|---|
| Nucleotide sequence of a FGF1/FGF23 chimera composed of residues M1 to L150 of human FGF1 harboring K127D/K128Q/K133V triple mutation (bold) and residues R161 to I251 of human FGF23 (bold) harboring R176Q/R179Q double mutation (bold italic) | SEQ ID NO: 325<br>ATGGCTGAAG GGGAAATCAC CACCTTCACA<br>GCCCTGACCG AGAAGTTTAA TCTGCCTCCA<br>GGGAATTACA AGAAGCCCAA ACTCCTCTAC<br>TGTAGCAACG GGGGCCACTT CCTGAGGATC<br>CTTCCGGATG GCACAGTGGA TGGGACAAGG<br>GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTC**GA TCAG**AATGGG<br>AGCTGC**GTT**C GCGGTCCTCG GACTCACTAT<br>GGCCAGAAAG CAATCTTGTT TCTCCCCCTG<br>**AGGAACGAGA TCCCCCTAAT TCACTTCAAC**<br>**ACCCCCATAC CACGG*CAG*CA CACC*CAG*AGC**<br>**GCCGAGGACG ACTCGGAGCG GGACCCCCTG**<br>**AACGTGCTGA AGCCCCGGGC CCGGATGACC**<br>**CCGGCCCCGG CCTCCTGTTC ACAGGAGCTC**<br>**CCGAGCGCCG AGGACAACAG CCCGATGGCC**<br>**AGTGACCCAT TAGGGGTGGT CAGGGGCGGT**<br>**CGAGTGAACA CGCACGCTGG GGGAACGGGC**<br>**CCGGAAGGCT GCCGCCCCTT CGCCAAGTTC**<br>**ATC** |
| Nucleotide sequence of a FGF1/FGF23 chimera composed of residues K25 to L150 of human FGF1 harboring | SEQ ID NO: 326<br>AAGCCCAA ACTCCTCTAC<br>TGTAGCAACG GGGGCCACTT CCTGAGGATC<br>CTTCCGGATG GCACAGTGGA TGGGACAAGG |

TABLE 10-continued

| Description of Chimeric Protein | Sequence |
|---|---|
| K127D/K128Q/K133V triple mutation (bold) and residues R161 to I251 of human FGF23 (bold) harboring R176Q/R179Q double mutation (bold italic) | GACAGGAGCG ACCAGCACAT TCAGCTGCAG<br>CTCAGTGCGG AAAGCGTGGG GGAGGTGTAT<br>ATAAAGAGTA CCGAGACTGG CCAGTACTTG<br>GCCATGGACA CCGACGGGCT TTTATACGGC<br>TCACAGACAC CAAATGAGGA ATGTTTGTTC<br>CTGGAAAGGC TGGAGGAGAA CCATTACAAC<br>ACCTATATAT CCAAGAAGCA TGCAGAGAAG<br>AATTGGTTTG TTGGCCTC**GA TCAG**AATGGG<br>AGCTGC**GTTC** GCGGTCCTCG GACTCACTAT<br>GGCCAGAAAG CAATCTTGTT TCTCCCCCTG<br>**AGGAACGAGA TCCCCCTAAT TCACTTCAAC**<br>**ACCCCCATAC CACGG*CAG*CA CACC*CAG*AGC**<br>**GCCGAGGACG ACTCGGAGCG GGACCCCCTG**<br>**AACGTGCTGA AGCCCCGGGC CCGGATGACC**<br>**CCGGCCCCGG CCTCCTGTTC ACAGGAGCTC**<br>**CCGAGCGCCG AGGACAACAG CCCGATGGCC**<br>**AGTGACCCAT TAGGGGTGGT CAGGGGCGGT**<br>**CGAGTGAACA CGCACGCTGG GGGAACGGGC**<br>**CCGGAAGGCT GCCGCCCCTT CGCCAAGTTC**<br>**ATC** |
| Nucleotide sequence of a FGF2/FGF23 chimera composed of residues M1 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 327<br>ATG GCAGCCGGGA<br>GCATCACCAC GCTGCCCGCC TTGCCCGAGG<br>ATGGCGGCAG CGGCGCCTTC CCGCCCGGCC<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTG**GA TCAG**ACTGGG CAGTAT**GTTC**<br>TTGGATCCAA AACAGGACCT GGGCAGAAAG<br>CTATACTTTT TCTTCCAATG **AGGAACGAGA**<br>**TCCCCCTAAT TCACTTCAAC ACCCCCATAC**<br>**CACGG*CAG*CA CACC*CAG*AGC GCCGAGGACG**<br>**ACTCGGAGCG GGACCCCCTG AACGTGCTGA**<br>**AGCCCCGGGC CCGGATGACC CCGGCCCCGG**<br>**CCTCCTGTTC ACAGGAGCTC CCGAGCGCCG**<br>**AGGACAACAG CCCGATGGCC AGTGACCCAT**<br>**TAGGGGTGGT CAGGGGCGGT CGAGTGAACA**<br>**CGCACGCTGG GGGAACGGGC CCGGAAGGCT**<br>**GCCGCCCCTT CGCCAAGTTC ATC** |
| Nucleotide sequence of a FGF2/FGF23 chimera composed of residues H25 to M151 of human FGF2 harboring K128D/R129Q/K134V triple mutation (bold) and residues R161 to I251 of human FGF23 (bold) harboring R176Q/R179Q double mutation (bold italic) | SEQ ID NO: 328<br>C<br>ACTTCAAGGA CCCCAAGCGG CTGTACTGCA<br>AAAACGGGGG CTTCTTCCTG CGCATCCACC<br>CCGACGGCCG AGTTGACGGG GTCCGGGAGA<br>AGAGCGACCC TCACATCAAG CTACAACTTC<br>AAGCAGAAGA GAGAGGAGTT GTGTCTATCA<br>AAGGAGTGTG TGCTAACCGT TACCTGGCTA<br>TGAAGGAAGA TGGAAGATTA CTGGCTTCTA<br>AATGTGTTAC GGATGAGTGT TTCTTTTTTG<br>AACGATTGGA ATCTAATAAC TACAATACTT<br>ACCGGTCAAG GAAATACACC AGTTGGTATG<br>TGGCACTG**GA TCAG**ACTGGG CAGTAT**GTTC**<br>TTGGATCCAA AACAGGACCT GGGCAGAAAG<br>CTATACTTTT TCTTCCAATG **AGGAACGAGA**<br>**TCCCCCTAAT TCACTTCAAC ACCCCCATAC**<br>**CACGG*CAG*CA CACC*CAG*AGC GCCGAGGACG**<br>**ACTCGGAGCG GGACCCCCTG AACGTGCTGA**<br>**AGCCCCGGGC CCGGATGACC CCGGCCCCGG**<br>**CCTCCTGTTC ACAGGAGCTC CCGAGCGCCG**<br>**AGGACAACAG CCCGATGGCC AGTGACCCAT**<br>**TAGGGGTGGT CAGGGGCGGT CGAGTGAACA**<br>**CGCACGCTGG GGGAACGGGC CCGGAAGGCT**<br>**GCCGCCCCTT CGCCAAGTTC ATC** |

Another aspect of the present invention relates to a nucleic acid construct including a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

Also encompassed are vectors or expression vectors including such nucleic acid molecules and host cells including such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., Molecular Cloning: a Laboratory Manual (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., Molecular Cloning: a Laboratory Manual (Cold Springs Harbor 1989); Frederick M. Ausubel, Short Protocols in Molecular Biology (Wiley 1999); and U.S. Pat. No. 4,237,224 to Cohen and Boyer, which are hereby incorporated by reference in their entirety.

Once the nucleic acid molecule encoding the protein has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by Joseph Sambrook et al., Molecular Cloning: a Laboratory Manual (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Another aspect of the present invention relates to a pharmaceutical composition that includes a chimeric protein according to the present invention and a pharmaceutically acceptable carrier.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution.

Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the pharmaceutical composition includes an organotropic targeting agent. In one embodiment, the targeting agent is covalently linked to the chimeric protein via a linker that is cleaved under physiological conditions.

Chimeric and/or modified proteins according to the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the chimeric and/or modified proteins may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The chimeric and/or modified proteins may also be fused to a macromolecule other than protein that confers a longer half-life to the protein upon in vivo administration. Suitable macromolecules include, without limitation, polyethylene glycols (PEGs). Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., which are hereby incorporated by reference in their entirety.

The pharmaceutical composition according to the present invention can be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The formulations may conveniently be presented in unit dosage form and may be prepared by any of the methods well known in the art of pharmacy.

In one particular embodiment of the present invention, the pharmaceutical composition according to the present invention is administered with another hypophosphatemic agent, a phosphate binder, a vitamin D antagonist, an analgesic, and/or an anti-inflammatory agent.

The pharmaceutical composition according to the present invention can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. The formulations may conveniently be presented in unit dosage form and may be prepared by any of the methods well known in the art of pharmacy.

Another aspect of the present invention relates to a method for treating a subject suffering from a disorder. This method involves selecting a subject suffering from the disorder and administering the pharmaceutical composition according to the present invention to the selected subject under conditions effective to treat the disorder. In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification.

Accordingly, another aspect of the present invention relates to a method for treating a subject suffering from a disorder. This method involves selecting a subject suffering from the disorder. The method also involves providing a chimeric FGF protein, where the chimeric FGF protein includes an N-terminus coupled to a C-terminus. The N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves administering a therapeutically effective amount of the chimeric FGF protein to the selected subject under conditions effective to treat the disorder.

Suitable chimeric proteins for use in accordance with this aspect of the present invention are described above and throughout the present application.

In one embodiment, the selected subject is a mammal. In one embodiment, the selected subject is a human. In another embodiment, the selected subject is a rodent.

In one embodiment, the chimeric FGF protein is effective for treating disorders associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the chimeric FGF protein is effective for treating disorders associated with soft tissue calcification. In one embodiment, the chimeric FGF protein normalizes vitamin D metabolism and/or phosphate metabolism. In one embodiment, the chimeric FGF protein ameliorates soft tissue calcification.

The chimeric protein of the present invention or pharmaceutical composition thereof can be used to treat a number of conditions. In one embodiment, the condition is one which the therapeutic outcome includes a decrease in circulating phosphate levels. In one embodiment, the condition is one which the therapeutic outcome includes a decrease in circulating levels of bioactive vitamin D. Each of these parameters can be measured by standard methods, for example, by performing blood tests for phosphate and vitamin D.

In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification. In one embodiment, the disorder is tumoral calcinosis (also referred to as hyperphosphatemic familial tumoral calcinosis, Online Mendelian Inheritance in Man, ID 211900 (purl.bioontology.org/ontology/OMIM/211900), which is hereby incorporated by reference in its entirety). In one embodiment, the disorder is associated with hyperostosis, diaphysitis, arterial aneurysms, dental abnormalities, and/or angioid streaks of the retina.

Familial tumoral calcinosis is an autosomal recessive metabolic disorder associated with hyperphosphatemia and soft tissue calcification. Missense mutations in either the UDP-N-acetyl-α-D-galactosamine:polypeptide N-acetylglactosaminyltransferase 3 (GALNT3) gene (Garringer et al., "Two Novel GALNT3 Mutations in Familial Tumoral Calcinosis," *Am J Med Genet A* 143A:2390-2396 (2007)) or the FGF23 gene (Garringer et al., "Molecular Genetic and Biochemical Analyses of FGF23 Mutations in Familial Tumoral Calcinosis," *Am J Physiol Endocrinol Metab* 295: E929-E937 (2008); Araya et al., "A Novel Mutation in Fibroblast Growth Factor 23 Gene as a Cause of Tumoral Calcinosis," *J Clin Endocrinol Metab* 90:5523-5527 (2005), each of which is hereby incorporated by reference in its entirety) have been associated with familial tumoral calcinosis. All patients with familial tumoral calcinosis have abnormally high plasma levels of the C-terminal proteolytic fragment of FGF23 but abnormally low plasma levels of intact, full-length FGF23. The excess C-terminal FGF23 fragment may aggravate hyperphosphatemia, and the resulting soft tissue calcification, by antagonizing the action of any residual, functional FGF23 ligand in these patients. Thus, the chimeric and modified proteins according to the present invention are FGF23 agonists that provide a causative form of treatment for these patients.

In one embodiment, the the chimeric protein of the present invention or pharmaceutical composition thereof is administered with a pharmaceutically-acceptable carrier.

The chimeric protein according to the present invention or pharmaceutical composition thereof can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. Formulations including chimeric proteins according to the present invention may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions including the chimeric protein according to the present invention, as determined by good medical practice and the clinical condition of the individual patient.

When in vivo administration of a chimeric protein of the present invention or is employed, normal dosage amounts may vary from, for example, about 10 ng/kg to up to 100 mg/kg of mammal body weight or more per day. In one embodiment, the dosage may be from about 1 μg/kg/day to 10 mg/kg/day, depending upon the route of administration. In one embodiment, the chimeric protein according to the present invention is administered at a dose of about 0.1 to 10 mg/kg once or twice daily. In one embodiment, the chimeric protein according to the present invention is administered at a dose of about 1 to 9, 1 to 8, 1 to 7, 1 to 6, 1 to 5, 1 to 4, 1 to 3, or 1 to 2 mg/kg. Guidance as to particular dosages and methods of delivery of proteins is provided in the literature; see, for example, U.S. Pat. Nos. 4,657,760; 5,206,344; or 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated. Microencapsulation of recombinant proteins for sustained release has been successfully performed with human growth hormone (rhGH), interferon-(rhIFN-), interleukin-2, and MN rgp120. Johnson et al., "Preparation and Characterization of Poly(D,L-lactide-co-glycolide) Microspheres for Controlled Release of Human Growth Hormone," *Nat. Med.* 2:795-799 (1996); Yasuda, "Sustained Release Formulation of Interferon," *Biomed. Ther.* 27:1221-1223 (1993); Hora et al., "Controlled Release of Interleukin-2 from Biodegradable Microspheres," *Nat. Biotechnol.* 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The chimeric protein of the present invention or pharmaceutical composition thereof may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

In some embodiments, the chimeric protein of the present invention or a pharmaceutical composition thereof is administered in a therapeutically effective amount in combination with a therapeutically effective amount of a second agent. In one embodiment, the chimeric protein of the present invention or pharmaceutical composition thereof is administered in conjunction with the second agent, i.e., the respective periods of administration are part of a single administrative regimen. In one embodiment, the chimeric protein of the present invention or pharmaceutical composition thereof and the second agent are administered concurrently, i.e., the respective periods of administration overlap each other. In one embodiment, the chimeric protein of the present invention or pharmaceutical composition thereof and the second agent are administered non-concurrently, i.e., the respective periods of administration do not overlap each other. In one embodiment, the chimeric protein of the present invention or pharmaceutical composition thereof and the second agent are administered sequentially, i.e., the chimeric protein of the present invention or pharmaceutical composition thereof is administered prior to and/or after the administration of the second agent. In one embodiment, the chimeric protein of the present invention or pharmaceutical composition thereof and the second agent are administered simultaneously as separate compositions. In one embodiment, the chimeric protein of the present invention or pharmaceutical composition thereof and the second agent are administered simultaneously as part of the same compositions.

In one embodiment, the second agent is a hypophosphatemic agent, a phosphate binder, a vitamin D antagonist, an analgesic, and/or an anti-inflammatory agent.

Another aspect of the present invention relates to a method of making a chimeric FGF protein possessing enhanced endocrine activity. This method involves introducing one or more modifications to an FGF protein, where the modification decreases the affinity of the FGF protein for heparin and/or heparan sulfate and coupling a C-terminal portion of FGF23 that includes a α-Klotho-FGFR complex binding domain to the modified FGF protein's C-terminus, whereby a chimeric FGF protein possessing enhanced endocrine activity is made.

Suitable C-terminal portions of FGF23 are described above. In one embodiment, the C-terminal region from FGF23 is derived from a mammalian FGF23. In one embodiment, the C-terminal region derived from FGF23 is from a vertebrate FGF23.

In one embodiment, the chimeric FGF protein has greater binding affinity for FGFR than native FGF23. In one embodiment the chimeric FGF protein possesses enhanced endocrine activity compared to the chimeric FGF protein in the absence of the modification or the α-Klotho-FGFR complex binding domain. In one embodiment, the native endocrine FGF ligand having the α-Klotho co-receptor-FGFR binding domain is native FGF23. In one embodiment, the FGFR is FGFR1c, FGFR3c, or FGFR4.

In one embodiment, the chimeric FGF protein has greater stability than a native endocrine FGF ligand possessing the α-Klotho-FGFR complex binding domain. In one embodiment, increasing the stability includes an increase in thermal stability of the protein as compared to either wild type protein or native endocrine FGF ligand. In one embodiment, increasing the stability includes increasing the half-life of the protein in the blood circulation as compared to wild type or native protein or native endocrine FGF ligand.

In one embodiment, the FGF is derived from a mammalian FGF. In one embodiment, the FGF is derived from a vertebrate FGF. In one embodiment, the FGF protein is a paracrine FGF molecule. In one embodiment the FGF molecule is FGF1 or FGF2. In one embodiment, the FGF protein is an FGF protein that possesses intrinsically greater binding affinity for FGF receptor than a native endocrine FGF ligand. In one embodiment, the FGF protein is an FGF protein that possesses intrinsically greater thermal stability than a native endocrine FGF ligand. In one embodiment, the method involves introducing one or more modifications to the FGF protein, where the modification alters receptor-binding specificity and/or receptor-binding affinity of the FGF protein. In one embodiment, the method involves introducing one or more modifications to the FGF protein, where the modification alters the stability of the FGF protein. For example, receptor-binding specificity of FGF1, which by nature binds to all the seven principal FGFRs, may be altered to, for example, reduce any risk for adverse effects (e.g., mitogenicity). Paracrine FGFs, portions of paracrine FGFs, and modifications thereto are described above.

In one embodiment, the chimeric FGF protein normalizes vitamin D metabolism and/or phosphate metabolism.

Suitable methods of generating chimeric proteins according to the present invention include standard methods of synthesis known in the art, as described above.

Yet another aspect of the present invention relates to a method of facilitating fibroblast growth factor receptor ("FGFR")-α-Klotho co-receptor complex formation. This method involves providing a cell that includes a α-Klotho co-receptor and an FGFR and providing a chimeric FGF protein. The chimeric FGF protein includes a C-terminal portion of FGF23 and a portion of a paracrine FGF, where the portion of the paracrine FGF is modified to decrease binding affinity for heparin and/or heparan sulfate compared to the portion without the modification. This method also involves contacting the cell and the chimeric FGF protein under conditions effective to cause FGFR-αKlotho co-receptor complex formation.

The portion of the paracrine FGF may also be modified to alter receptor-binding specificity and/or receptor-binding affinity of the FGF, as noted above. Suitable portions of the paracrine FGFs for use in accordance with the present invention, as well as modifications to receptor-binding specificity and/or receptor-binding affinity of the FGF are described above. Suitable modifications to the paracrine FGFs for use in accordance with the present invention are also described above. Suitable C-terminal portions from FGF23 are described above and throughout the present application.

In one embodiment according to the present invention, α-Klotho is mammalian αKlotho. In one embodiment, α-Klotho is human or mouse α-Klotho. In one particular embodiment of the present invention, α-Klotho is human or mouse αKlotho having the amino acid sequence of SEQ ID NO: 329 (i.e., GenBank Accession No. NP_004786, which is hereby incorporated by reference in its entirety) or SEQ ID NO: 331 (i.e., GenBank Accession No. NP_038851, which is hereby incorporated by reference in its entirety), respectively, as follows:

```
SEQ ID NO: 329:
  1 MPASAPPRRP RPPPPSLSLL LVLLGLGGRR LRAEPGDGAQ TWARFSRPPA PEAAGLFQGT

 61 FPDGFLWAVG SAAYQTEGGW QQHGKGASIW DTFTHHPLAP PGDSRNASLP LGAPSPLQPA

121 TGDVASDSYN NVFRDTEALR ELGVTHYRFS ISWARVLPNG SAGVPNREGL RYYRRLLERL
```

-continued

```
181 RELGVQPVVT LYHWDLPQRL QDAYGGWANR ALADHFRDYA ELCFRHFGGQ VKYWITIDNP
241 YVVAWHGYAT GRLAPGIRGS PRLGYLVAHN LLLAHAKVWH LYNTSFRPTQ GGQVSIALSS
301 HWINPRRMTD HSIKECQKSL DFVLGWFAKP VFIDGDYPES MKNNLSSILP DFTESEKKFI
361 KGTADFFALC FGPTLSFQLL DPHMKFRQLE SPNLRQLLSW IDLEFNHPQI FIVENGWFVS
421 GTTKRDDAKY MYYLKKFIME TLKAIKLDGV DVIGYTAWSL MDGFEWHRGY SIRRGLFYVD
481 FLSQDKMLLP KSSALFYQKL IEKNGFPPLP ENQPLEGTFP CDFAWGVVDN YIQVDTTLSQ
541 FTDLNVYLWD VHHSKRLIKV DGVVTKKRKS YCVDFAAIQP QIALLQEMHV THFRFSLDWA
601 LILPLGNQSQ VNHTILQYYR CMASELVRVN ITPVVALWQP MAPNQGLPRL LARQGAWENP
661 YTALAFAEYA RLCFQELGHH VKLWITMNEP YTRNMTYSAG HNLLKAHALA WHVYNEKFRH
721 AQNGKISIAL QADWIEPACP FSQKDKEVAE RVLEFDIGWL AEPIFGSGDY PWVMRDWLNQ
781 RNNFLLPYFT EDEKKLIQGT FDFLALSHYT TILVDSEKED PIKYNDYLEV QEMTDITWLN
841 SPSQVAVVPW GLRKVLNWLK FKYGDLPMYI ISNGIDDGLH AEDDQLRVYY MQNYINEALK
901 AHILDGINLC GYFAYSFNDR TAPRFGLYRY AADQFEPKAS MKHYRKIIDS NGFPGPETLE
961 RFCPEEFTVC TECSFFHTRK SLLAFIAFLF FASIISLSLI FYYSKKGRRS YK
```

SEQ ID NO: 331:

```
  1 MLARAPPRRP PRLVLLRLLL LHLLLLALRA RCLSAEPGQG AQTWARFARA PAPEAAGLLH
 61 DTFPDGFLWA VGSAAYQTEG GWRQHGKGAS IWDTFTHHSG AAPSDSPIVV APSGAPSPPL
121 SSTGDVASDS YNNVYRDTEG LRELGVTHYR FSISWARVLP NGTAGTPNRE GLRYYRRLLE
181 RLRELGVQPV VTLYHWDLPQ RLQDTYGGWA NRALADHFRD YAELCFRHFG GQVKYWITID
241 NPYVVAWHGY ATGRLAPGVR GSSRLGYLVA HNLLLAHAKV WHLYNTSFRP TQGGRVSIAL
301 SSHWINPRRM TDYNIRECQK SLDFVLGWFA KPIFIDGDYP ESMKNNLSSL LPDFTESEKR
361 LIRGTADFFA LSFGPTLSFQ LLDPNMKFRQ LESPNLRQLL SWIDLEYNHP PIFIVENGWF
421 VSGTTKRDDA KYMYYLKKFI METLKAIRLD GVDVIGYTAW SLMDGFEWHR GYSIRRGLFY
481 VDFLSQDKEL LPKSSALFYQ KLIEDNGFPP LPENQPLEGT FPCDFAWGVV DNYVQVDTTL
541 SQFTDPNVYL WDVHHSKRLI KVDGVVAKKR KPYCVDFSAI RPQITLLREM RVTHFRFSLD
601 WALILPLGNQ TQVNHTVLHF YRCMISELVH ANITPVVALW QPAAPHQGLP HALAKHGAWE
661 NPHTALAFAD YANLCFKELG HWVNLWITMN EPNTRNMTYR AGHHLLRAHA LAWHLYDDKF
721 RAAQKGKISI ALQADWIEPA CPFSQNDKEV AERVLEFDIG WLAEPIFGSG DYPRVMRDWL
781 NQKNNFLLPY FTEDEKKLVR GSFDFLAVSH YTTILVDWEK EDPMKYNDYL EVQEMTDITW
841 LNSPSQVAVV PWGLRKVLNW LRFKYGDLPM YVTANGIDDD PHAEQDSLRI YYIKNYVNEA
901 LKAYVLDDIN LCGYFAYSLS DRSAPKSGFY RYAANQFEPK PSMKHYRKII DSNGFLGSGT
961 LGRFCPEEYT VCTECGFFQT RKSLLVFISF LVFTFIISLA LIFHYSKKGQ RSYK
```

In one particular embodiment of the present invention, α-Klotho is human or mouse α-Klotho encoded by a nucleotide sequence having the nucleotide sequences of SEQ ID NO: 330 (GenBank Accession No. NM_04795, which is hereby incorporated by reference in its entirety) and SEQ ID NO: 332 (GenBank Accession No. NM_013823, which is hereby incorporated by reference in its entirety), as follows:

SEQ ID NO: 330 (human αKlotho gene coding sequence):

```
  9         AT GCCCGCCAGC GCCCCGCCGC GCCGCCCGCG GCCGCCGCCG CCGTCGCTGT
 61 CGCTGCTGCT GGTGCTGCTG GGCCTGGGCG GCCGCCGCCT GCGTGCGGAG CCGGGCGACG
121 GCGCGCAGAC CTGGGCCCGT TTCTCGCGGC CTCCTGCCCC CGAGGCCGCG GGCCTCTTCC
181 AGGGCACCTT CCCCGACGGC TTCCTCTGGG CCGTGGGCAG CGCCGCCTAC CAGACCGAGG
241 GCGGCTGGCA GCAGCACGGC AAGGGTGCGT CCATCTGGGA TACGTTCACC CACCACCCCC
```

-continued

```
 301 TGGCACCCCC GGGAGACTCC CGGAACGCCA GTCTGCCGTT GGGCGCCCCG TCGCCGCTGC
 361 AGCCCGCCAC CGGGGACGTA GCCAGCGACA GCTACAACAA CGTCTTCCGC GACACGGAGG
 421 CGCTGCGCGA GCTCGGGGTC ACTCACTACC GCTTCTCCAT CTCGTGGGCG CGAGTGCTCC
 481 CCAATGGCAG CGCGGGCGTC CCCAACCGCG AGGGGCTGCG CTACTACCGG CGCCTGCTGG
 541 AGCGGCTGCG GGAGCTGGGC GTGCAGCCCG TGGTCACCCT GTACCACTGG GACCTGCCCC
 601 AGCGCCTGCA GGACGCCTAC GGCGGCTGGG CCAACCGCGC CCTGGCCGAC CACTTCAGGG
 661 ATTACGCGGA GCTCTGCTTC CGCCACTTCG GCGGTCAGGT CAAGTACTGG ATCACCATCG
 721 ACAACCCCTA CGTGGTGGCC TGGCACGGCT ACGCCACCGG GCGCCTGGCC CCCGGCATCC
 781 GGGGCAGCCC GCGGCTCGGG TACCTGGTGG CGCACAACCT CCTCCTGGCT CATGCCAAAG
 841 TCTGGCATCT CTACAATACT TCTTTCCGTC CCACTCAGGG AGGTCAGGTG TCCATTGCCC
 901 TAAGCTCTCA CTGGATCAAT CCTCGAAGAA TGACCGACCA CAGCATCAAA GAATGTCAAA
 961 AATCTCTGGA CTTTGTACTA GGTTGGTTTG CCAAACCCGT ATTTATTGAT GGTGACTATC
1021 CCGAGAGCAT GAAGAATAAC CTTTCATCTA TTCTGCCTGA TTTTACTGAA TCTGAGAAAA
1081 AGTTCATCAA AGGAACTGCT GACTTTTTTG CTCTTTGCTT TGGACCCACC TTGAGTTTTC
1141 AACTTTTGGA CCCTCACATG AAGTTCCGCC AATTGGAATC TCCCAACCTG AGGCAACTGC
1201 TTTCCTGGAT TGACCTTGAA TTTAACCATC CTCAAATATT TATTGTGGAA AATGGCTGGT
1261 TTGTCTCAGG GACCACCAAG AGAGATGATG CCAAATATAT GTATTACCTC AAAAAGTTCA
1321 TCATGGAAAC CTTAAAAGCC ATCAAGCTGG ATGGGGTGGA TGTCATCGGG TATACCGCAT
1381 GGTCCCTCAT GGATGGTTTC GAGTGGCACA GAGGTTACAG CATCAGGCGT GGACTCTTCT
1441 ATGTTGACTT TCTAAGCCAG GACAAGATGT TGTTGCCAAA GTCTTCAGCC TTGTTCTACC
1501 AAAAGCTGAT AGAGAAAAAT GGCTTCCCTC CTTTACCTGA AAATCAGCCC CTAGAAGGGA
1561 CATTTCCCTG TGACTTTGCT TGGGGAGTTG TTGACAACTA CATTCAAGTA GATACCACTC
1621 TGTCTCAGTT TACCGACCTG AATGTTTACC TGTGGGATGT CCACCACAGT AAAAGGCTTA
1681 TTAAAGTGGA TGGGGTTGTG ACCAAGAAGA GGAAATCCTA CTGTGTTGAC TTTGCTGCCA
1741 TCCAGCCCCA GATCGCTTTA CTCCAGGAAA TGCACGTTAC ACATTTTCGC TTCTCCCTGG
1801 ACTGGGCCCT GATTCTCCCT CTGGGTAACC AGTCCCAGGT GAACCACACC ATCCTGCAGT
1861 ACTATCGCTG CATGGCCAGC GAGCTTGTCC GTGTCAACAT CACCCCAGTG GTGGCCCTGT
1921 GGCAGCCTAT GGCCCCGAAC CAAGGACTGC CGCGCCTCCT GGCCAGGCAG GGCGCCTGGG
1981 AGAACCCCTA CACTGCCCTG GCCTTTGCAG AGTATGCCCG ACTGTGCTTT CAAGAGCTCG
2041 GCCATCACGT CAAGCTTTGG ATAACGATGA ATGAGCCGTA TACAAGGAAT ATGACATACA
2101 GTGCTGGCCA CAACCTTCTG AAGGCCCATG CCCTGGCTTG GCATGTGTAC AATGAAAAGT
2161 TTAGGCATGC TCAGAATGGG AAAATATCCA TAGCCTTGCA GGCTGATTGG ATAGAACCTG
2221 CCTGCCCTTT CTCCCAAAAG GACAAAGAGG TGGCTGAGAG AGTTTTGGAA TTTGACATTG
2281 GCTGGCTGGC TGAGCCCATT TTCGGCTCTG GAGATTATCC ATGGGTGATG AGGGACTGGC
2341 TGAACCAAAG AAACAATTTT CTTCTTCCTT ATTTCACTGA AGATGAAAAA AAGCTAATCC
2401 AGGGTACCTT TGACTTTTTG GCTTTAAGCC ATTATACCAC CATCCTTGTA GACTCAGAAA
2461 AAGAAGATCC AATAAAATAC AATGATTACC TAGAAGTGCA AGAAATGACC GACATCACGT
2521 GGCTCAACTC CCCCAGTCAG GTGGCGGTAG TGCCCTGGGG GTTGCGCAAA GTGCTGAACT
2581 GGCTGAAGTT CAAGTACGGA GACCTCCCCA TGTACATAAT ATCCAATGGA ATCGATGACG
2641 GGCTGCATGC TGAGGACGAC CAGCTGAGGG TGTATTATAT GCAGAATTAC ATAAACGAAG
```

-continued

2701 CTCTCAAAGC CCACATACTG GATGGTATCA ATCTTTGCGG ATACTTTGCT TATTCGTTTA

2761 ACGACCGCAC AGCTCCGAGG TTTGGCCTCT ATCGTTATGC TGCAGATCAG TTTGAGCCCA

2821 AGGCATCCAT GAAACATTAC AGGAAAATTA TTGACAGCAA TGGTTTCCCG GGCCCAGAAA

2881 CTCTGGAAAG ATTTTGTCCA GAAGAATTCA CCGTGTGTAC TGAGTGCAGT TTTTTTCACA

2941 CCCGAAAGTC TTTACTGGCT TTCATAGCTT TTCTATTTTT TGCTTCTATT ATTTCTCTCT

3001 CCCTTATATT TTACTACTCG AAGAAAGGCA GAAGAAGTTA CAAATAG

SEQ ID NO: 332 (murine αKlotho gene coding sequence):

111 ATGCTAGCCC

121 GCGCCCCTCC TCGCCGCCCG CCGCGGCTGG TGCTGCTCCG TTTGCTGTTG CTGCATCTGC

181 TGCTGCTCGC CCTGCGCGCC CGCTGCCTGA GCGCTGAGCC GGGTCAGGGC GCGCAGACCT

241 GGGCTCGCTT CGCGCGCGCT CCTGCCCCAG AGGCCGCTGG CCTCCTCCAC GACACCTTCC

301 CCGACGGTTT CCTCTGGGCG GTAGGCAGCG CCGCCTATCA GACCGAGGGC GGCTGGCGAC

361 AGCACGGCAA AGGCGCGTCC ATCTGGGACA CTTTCACCCA TCACTCTGGG GCGGCCCCGT

421 CCGACTCCCC GATCGTCGTG GCGCCGTCGG GTGCCCCGTC GCCTCCCCTG TCCTCCACTG

481 GAGATGTGGC CAGCGATAGT TACAACAACG TCTACCGCGA CACAGAGGGG CTGCGCGAAC

541 TGGGGGTCAC CCACTACCGC TTCTCCATAT CGTGGGCGCG GGTGCTCCCC AATGGCACCG

601 CGGGCACTCC CAACCGCGAG GGGCTGCGCT ACTACCGGCG GCTGCTGGAG CGGCTGCGGG

661 AGCTGGGCGT GCAGCCGGTG GTTACCCTGT ACCATTGGGA CCTGCCACAG CGCCTGCAGG

721 ACACCTATGG CGGATGGGCC AATCGCGCCC TGGCCGACCA TTTCAGGGAT TATGCCGAGC

781 TCTGCTTCCG CCACTTCGGT GGTCAGGTCA AGTACTGGAT CACCATTGAC AACCCCTACG

841 TGGTGGCCTG GCACGGGTAT GCCACCGGGC GCCTGGCCCC GGGCGTGAGG GGCAGCTCCA

901 GGCTCGGGTA CCTGGTTGCC CACAACCTAC TTTTGGCTCA TGCCAAAGTC TGGCATCTCT

961 ACAACACCTC TTTCCGCCCC ACACAGGGAG GCCGGGTGTC TATCGCCTTA AGCTCCCATT

1021 GGATCAATCC TCGAAGAATG ACTGACTATA ATATCAGAGA ATGCCAGAAG TCTCTTGACT

1081 TTGTGCTAGG CTGGTTTGCC AAACCCATAT TTATTGATGG CGACTACCCA GAGAGTATGA

1141 AGAACAACCT CTCGTCTCTT CTGCCTGATT TTACTGAATC TGAGAAGAGG CTCATCAGAG

1201 GAACTGCTGA CTTTTTTGCT CTCTCCTTCG GACCAACCTT GAGCTTTCAG CTATTGGACC

1261 CTAACATGAA GTTCCGCCAA TTGGAGTCTC CCAACCTGAG GCAGCTTCTG TCTTGGATAG

1321 ATCTGGAATA TAACCACCCT CCAATATTTA TTGTGGAAAA TGGCTGGTTT GTCTCGGGAA

1381 CCACCAAAAG GGATGATGCC AAATATATGT ATTATCTCAA GAAGTTCATA ATGGAAACCT

1441 TAAAAGCAAT CAGACTGGAT GGGGTCGACG TCATTGGGTA CACCGCGTGG TCGCTCATGG

1501 ACGGTTTCGA GTGGCATAGG GGCTACAGCA TCCGGCGAGG ACTCTTCTAC GTTGACTTTC

1561 TGAGTCAGGA CAAGGAGCTG TTGCCAAAGT CTTCGGCCTT GTTCTACCAA AAGCTGATAG

1621 AGGACAATGG CTTTCCTCCT TTACCTGAAA ACCAGCCCCT TGAAGGGACA TTTCCCTGTG

1681 ACTTTGCTTG GGGAGTTGTT GACAACTACG TTCAAGTGGA CACTACTCTC TCTCAGTTTA

1741 CTGACCCGAA TGTCTATCTG TGGGATGTGC ATCACAGTAA GAGGCTTATT AAAGTAGACG

1801 GGGTTGTAGC CAAGAAGAGA AAACCTTACT GTGTTGATTT CTCTGCCATC CGGCCTCAGA

1861 TAACCTTACT TCGAGAAATG CGGGTCACCC ACTTTCGCTT CTCCCTGGAC TGGGCCCTGA

1921 TCTTGCCTCT GGGTAACCAG ACCCAAGTGA ACCACACGGT TCTGCACTTC TACCGCTGCA

1981 TGATCAGCGA GCTGGTGCAC GCCAACATCA CTCCAGTGGT GGCCCTGTGG CAGCCAGCAG

2041 CCCCGCACCA AGGCCTGCCA CATGCCCTTG CAAAACATGG GGCCTGGGAG AACCCGCACA

-continued

```
2101 CTGCTCTGGC GTTTGCAGAC TACGCAAACC TGTGTTTTAA AGAGTTGGGT CACTGGGTCA

2161 ATCTCTGGAT CACCATGAAC GAGCCAAACA CACGGAACAT GACCTATCGT GCCGGGCACC

2221 ACCTCCTGAG AGCCCATGCC TTGGCTTGGC ATCTGTACGA TGACAAGTTT AGGGCGGCTC

2281 AGAAAGGCAA AATATCCATC GCCTTGCAGG CTGACTGGAT AGAACCGGCC TGCCCTTTCT

2341 CTCAAAATGA CAAAGAAGTG GCCGAGAGAG TTTTGGAATT TGATATAGGC TGGCTGGCAG

2401 AGCCTATTTT TGGTTCCGGA GATTATCCAC GTGTGATGAG GGACTGGCTG AACCAAAAAA

2461 ACAATTTTCT TTTGCCCTAT TTCACCGAAG ATGAAAAAAA GCTAGTCCGG GGTTCCTTTG

2521 ACTTCCTGGC GGTGAGTCAT TACACCACCA TTCTGGTAGA CTGGGAAAAG GAGGATCCGA

2581 TGAAATACAA CGATTACTTG GAGGTACAGG AGATGACTGA CATCACATGG CTCAACTCTC

2641 CCAGTCAGGT GGCAGTGGTG CCTTGGGGGC TGCGCAAAGT GCTCAACTGG CTAAGGTTCA

2701 AGTACGGAGA CCTCCCGATG TATGTGACAG CCAATGGAAT CGATGATGAC CCCCACGCCG

2761 AGCAAGACTC ACTGAGGATC TATTATATTA AGAATTATGT GAATGAGGCT CTGAAAGCCT

2821 ACGTGTTGGA CGACATCAAC CTTTGTGGCT ACTTTGCGTA TTCACTTAGT GATCGCTCAG

2881 CTCCCAAGTC TGGCTTTTAT CGATATGCTG CGAATCAGTT TGAGCCCAAA CCATCTATGA

2941 AACATTACAG GAAAATTATT GACAGCAATG GCTTCCTGGG TTCTGGAACA CTGGGAAGGT

3001 TTTGTCCAGA AGAATACACT GTGTGCACCG AATGTGGATT TTTTCAAACC CGGAAGTCTT

3061 TGCTGGTCTT CATCTCGTTT CTTGTTTTTA CTTTTATTAT TTCTCTTGCT CTCATTTTTC

3121 ACTACTCCAA GAAAGGCCAG AGAAGTTATA AGTAA
```

In one embodiment, the FGFR is FGFR1c, FGFR3c, or FGFR4. In one embodiment of the present invention, the FGF receptor is FGFR1c receptor. In one particular embodiment, the FGFR1c receptor is the human FGFR1c receptor (GenBank Accession No. NP_075598, which is hereby incorporated by reference in its entirety). In another embodiment, the FGF receptor is FGFR3c receptor. In one particular embodiment, the FGFR3c receptor is the human FGFR3c receptor (GenBank Accession No. NP_000133, which is hereby incorporated by reference in its entirety). In another embodiment, the FGF receptor is FGFR4 receptor. In one particular embodiment, the FGFR4 receptor is the human FGFR4 receptor (GenBank Accession No. NP_002002, which is hereby incorporated by reference in its entirety).

In one embodiment, the method of facilitating FGFR-αKlotho co-receptor complex formation is carried out in vitro. In one embodiment, the method is carried out in a cell ectopically expressing αKlotho co-receptor and one or more of the cognate FGFRs of FGF23, which are FGFR1c, FGFR3c, and FGFR4. In one particular embodiment, the interleukin-3-dependent murine pro-B BaF3 cell line is used for ectopic expression of αKlotho co-receptor and one or more of the cognate FGFRs of FGF23. In one embodiment, the method is carried out in a cell endogenously expressing αKlotho co-receptor and one or more of the cognate FGFRs of FGF23. In one embodiment, the method is carried out in a renal cell, a parathyroid cell, a blood cell, a thymus cell, a pituitary cell, a hypothalamus-derived cell, a cell derived from the corpus striatum, and/or a cell derived from the cerebrum. In one particular embodiment, the method is carried out in a renal proximal tubule epithelial cell.

In one embodiment, the method of facilitating FGFR-αKlotho co-receptor complex formation is carried out in vivo. In one embodiment, the method is carried out in a mammal. In one particular embodiment, the mammal is a mouse. In one embodiment, the mouse is an fgf23-gene knockout mouse. In one embodiment, serum concentration of phosphate is used as readout for the method. In one embodiment, renal excretion of phosphate is used as readout for the method. In one embodiment, serum concentration of bioactive vitamin D is used as readout for the method. In one embodiment, renal expression of 1α-hydroxylase (CYP27B1) is used as readout for the method. In one embodiment, renal expression of $NaP_i$-2A and/or $NaP_i$-2C is used as readout for the method.

Yet a further aspect of the present invention relates to a method of screening for agents capable of facilitating fibroblast growth factor receptor ("FGFR")-αKlotho co-receptor complex formation in the treatment of a disorder. This method involves providing a chimeric FGF that includes an N-terminus coupled to a C-terminus, where the N-terminus includes a portion of a paracrine FGF and the C-terminus includes a C-terminal portion of FGF23. The portion of the paracrine FGF is modified to decrease binding affinity for heparin and/or heparan sulfate compared to the portion without the modification. This method also involves providing a binary αKlotho-FGFR complex and providing one or more candidate agents. This method further involves combining the chimeric FGF, the binary αKlotho-FGFR complex, and the one or more candidate agents under conditions permitting the formation of a ternary complex between the chimeric FGF and the binary αKlotho-FGFR complex in the absence of the one or more candidate agents. This method also involves identifying the one or more candidate agents that decrease ternary complex formation between the chimeric FGF and the binary αKlotho-FGFR compared to the ternary complex formation in the absence of the one or more candidate agents as suitable for treating the disorder.

In one embodiment the FGF molecule is FGF1 or FGF2. In one embodiment, the FGF protein is an FGF protein that possesses intrinsically greater binding affinity for FGF receptor than a native endocrine FGF ligand. In one embodiment, the FGF protein is an FGF protein that possesses intrinsically greater thermal stability than a native endocrine FGF ligand. In one embodiment, the method involves introducing one or more modifications to the FGF protein, where the modification alters receptor-binding specificity and/or receptor-binding affinity of the FGF protein. In one embodiment, the method involves introducing one or more modifications to the FGF protein, where the modification alters the stability of the FGF protein. For example, receptor-binding specificity of FGF1, which by nature binds to all the seven principal FGFRs, may be altered to, for example, reduce any risk for adverse effects (e.g., mitogenicity). Paracrine FGFs, portions of paracrine FGFs, and modifications thereto are described above.

Suitable chimeric proteins for use in accordance with this aspect of the present invention are described above and throughout the present application. Suitable paracrine FGFs, as well as suitable modifications to decrease binding affinity for heparin and/or heparan sulfate, to alter receptor-binding specificity and/or to alter receptor-binding affinity compared to the portion without the modification, are also described above.

In one embodiment, the modulation is a competitive interaction between the chimeric FGF molecule and the one or more candidate agents for binding to the binary αKlotho-FGFR complex.

In one embodiment, the FGFR is FGFR1c, FGFR3c, or FGFR4.

In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification.

In one embodiment of the screening aspects of the present invention, a plurality of compounds or agents is tested. Candidate agents may include small molecule compounds or larger molecules (e.g., proteins or fragments thereof). In one embodiment, the candidate compounds are biomolecules. In one embodiment, the biomolecules are proteins. In one embodiment, the biomolecules are peptides. In one embodiment, the candidates are peptides or peptide mimetics having similar structural features to native FGF ligand. In one embodiment, the candidate agent is a second chimeric FGF molecule. In one particular embodiment, the peptides are synthetic peptides. In one embodiment, the compounds are small organic molecules.

In one embodiment of the screening aspects of the present invention, the method is carried out using a cell-based assay. In one embodiment, the identifying is carried out using a cell-based assay.

In one embodiment of the screening aspects of the present invention, the method is carried out using a binding assay. In one embodiment, the binding assay is a direct binding assay. In one embodiment, the binding assay is a competition-binding assay. In one embodiment, the modulation stabilizes the ternary complex between the chimeric FGF molecule and the binary αKlotho-FGFR complex. In one embodiment, the stabilization is compared to the native ternary complex.

In one embodiment, the modulation is an allosteric or kinetic modulation. In one embodiment, the allosteric or kinetic modulation is compared to the native ternary complex. Such stabilization or allosteric or kinetic modulation can be measured modulation determined according to methods known in the art (e.g., by use of surface plasmon resonance (SPR) spectroscopy experiments as described in the Examples infra).

In one embodiment, the binding assay is carried out using surface plasmon resonance spectroscopy. In one embodiment, the identifying is carried out using a binding assay. In one embodiment, the identifying is carried out using surface plasmon resonance spectroscopy.

In one embodiment of the screening aspects of the present invention, the cell-based assay is carried out with renal cells. In one particular embodiment, the renal cells are proximal tubule epithelial cells. In one embodiment, the cell-based assay is carried out with parathyroid cells. In one embodiment, the cell-based assay is carried out with blood cells. In one embodiment, the cell-based assay is carried out with thymus cells. In one embodiment, the cell-based assay is carried out with pituitary cells. In one embodiment, the cell-based assay is carried out with cells derived from the hypothalamus. In one embodiment, the cell-based assay is carried out with cells derived from the corpus striatum. In one embodiment, the cell-based assay is carried out with cells derived from the cerebrum. In one embodiment, inhibition of phosphate uptake by the cells is the assay readout. In one embodiment, repression of the $NaP_i$-2A gene and/or the $NaP_i$-2C gene is the assay readout. In one embodiment, reduction of NaPi-2A and/or $NaP_i$-2C protein expression is the assay readout. In one embodiment, reduction of NaPi-2A and/or $NaP_i$-2C protein in the cell membrane is the assay readout. In one embodiment, repression of the CYP27B1 gene is the assay readout. In one embodiment, a dose-response curve is generated for inhibition of phosphate uptake (repression of the $NaP_i$-2A gene and/or the $NaP_i$-2C gene, reduction of NaPi-2A and/or $NaP_i$-2C protein expression, reduction of NaPi-2A and/or $NaP_i$-2C protein in the cell membrane, repression of the CYP27B1 gene) by a candidate compound to determine potency and efficacy of the candidate compound. For example, if the dose-response curve is shifted to the left compared to that obtained for the chimeric FGF protein, the candidate compound is more potent than the chimeric FGF protein and/or native FGF23. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF23.

In one embodiment of the screening aspects of the present invention, the cell-based assay is carried out with mammalian cells ectopically expressing αKlotho. In one particular embodiment, the cells are HEK293 cells. In one embodiment, activation of FGF receptor is the assay readout. In one embodiment, tyrosine phosphorylation of an FGF receptor substrate is used as readout for FGF receptor activation. In one particular embodiment, the FGF receptor substrate is FGF receptor substrate 2a. In one embodiment, activation of downstream mediators of FGF signaling is used as readout for (or an indicator of) FGF receptor activation. In one particular embodiment, the downstream mediator of FGF signaling is 44/42 mitogen-activated protein kinase. In one embodiment, the downstream mediator of FGF signaling is a transcription factor. In one particular embodiment, the transcription factor is early growth response 1. In one embodiment, a dose-response curve is generated for αKlotho-dependent activation of FGF receptor by a candidate compound to determine potency and efficacy of the candidate compound. For example, if the dose-response curve is shifted to the left compared to that obtained for the chimeric FGF protein, the candidate compound is more potent than the chimeric FGF protein and/or native FGF23. In one embodiment, an $IC_{50}$ value is derived from the dose-response curve of a candidate compound to determine potency of the candidate compound. An $IC_{50}$ value smaller than that obtained for the chimeric FGF protein identifies a candidate compound as more potent than the chimeric FGF protein and/or native FGF23.

In one embodiment of the screening aspects of the present invention, the surface plasmon resonance spectroscopy-based assay is carried out using the chimeric FGF protein as ligand coupled to a biosensor chip. In one embodiment, mixtures of the binary complex of FGFR ligand-binding domain and αKlotho ectodomain with increasing concentrations of a candidate compound are passed over a biosensor chip containing chimeric FGF protein. In one particular embodiment, the FGFR ligand-binding domain is the FGFR1c ligand-binding domain. In one embodiment, an inhibition-binding curve is plotted for a candidate compound to determine potency of the candidate compound. For example, if the inhibition-binding curve is shifted to the left compared to that obtained for the chimeric FGF protein, the candidate compound has greater potency than the chimeric FGF protein and/or native FGF23. In one embodiment, an $IC_{50}$ value is derived from the inhibition-binding curve of a candidate compound to determine potency of the candidate compound. An $IC_{50}$ value smaller than that obtained for containing chimeric FGF protein identifies a candidate compound as more potent than the chimeric FGF protein and/or native FGF23. In one embodiment, the inhibition constant $K_i$ is determined for a candidate compound to determine potency of the candidate compound. A $K_i$ value smaller than that obtained for native FGF23 identifies a candidate compound as more potent than the chimeric FGF protein and/or native FGF23.

Yet another aspect of the present invention relates to a modified FGF23 protein. The modified FGF23 protein includes an FGF23 protein that includes a modification to decrease binding affinity for heparin and/or heparan sulfate compared to an FGF23 protein without the modification.

FGF23 proteins suitable for use in accordance with this aspect of the present invention include those described above (i.e., human FGF23 and orthologs thereof). In one embodiment, the modified FGF23 is derived from a mammalian FGF23. In one embodiment, the modified FGF23 protein includes an FGF protein that includes the amino acid sequence of SEQ ID NO: 233, where the modification includes a substitution at amino acid residues selected from R48, N49, R140, R143, and combinations thereof. In one embodiment, the modification includes one or more substitutions selected from R48A/G/S, N49A/G/S, R140A/G/S, R143A/G/S, and combinations thereof. In one embodiment, the modified FGF23 protein has an amino acid sequence that has at least 80%, at least 85%, at least 90%, at least 95%, at least 97% or at least 99% amino acid sequence identity or homology to the amino acid sequence of SEQ ID NO: 233. In one embodiment, the modified FGF23 protein has an amino acid sequence that has at least 80%, at least 85%, at least 90%, at least 95%, at least 97% or at least 99% amino acid sequence identity or homology to an ortholog of human FGF23 (SEQ ID NO:233). In one embodiment, the modified FGF23 includes a modification to decrease binding affinity for heparin and/or heparan sulfate compared to an FGF23 protein without the modification and retains biological activity of native FGF23. In one embodiment, the modified FGF23 includes a modification to decrease binding affinity for heparin and/or heparan sulfate compared to an FGF23 protein without the modification and retains the ability to bind a binary αKlotho-FGFR complex.

In one embodiment, the modification includes a substitution at amino acid residues corresponding to positions of SEQ ID NO: 233 selected from R48, N49, R140, R143, and combinations thereof. In one embodiment, the modification includes one or more substitutions selected from R48A/G/S, N49A/G/S, R140A/G/S, R143A/G/S, and combinations thereof.

Another aspect of the present invention relates to a pharmaceutical composition including the modified FGF23 protein according to the present invention and a pharmaceutically-acceptable carrier. Suitable pharmaceutical compositions, dosages, carriers and the like are described above.

In one embodiment, the pharmaceutical composition further includes a hypophosphatemic agent, a phosphate binder, a vitamin D antagonist, an analgesic, and/or an anti-inflammatory agent.

In one embodiment, the pharmaceutical composition further includes an organotropic targeting agent. In one embodiment, the targeting agent is covalently linked to the chimeric protein via a linker that is cleaved under physiological conditions.

As noted above, chimeric and/or modified proteins according to the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the chimeric and/or modified proteins may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The chimeric and/or modified proteins may also be fused to a macromolecule other than protein that confers a longer half-life to the protein upon in vivo administration. Suitable macromolecules include, without limitation, polyethylene glycols (PEGs).

In one embodiment, the modified FGF23 is fused at its N-terminus to an agent that increases the half-life of the modified FGF23 protein in circulation. In one embodiment, the agent that increases the half-life is a PEG molecule. In one embodiment, the agent that increases the half-life is an antibody fragment.

Another aspect of the present invention relates to a method for treating a subject suffering from a disorder. This method involves selecting a subject suffering from the disorder and administering to the selected subject a therapeutically effective amount of a modified FGF23 protein including a modification to decrease binding affinity for heparin and/or heparan sulfate compared to an FGF23 protein without the modification.

In one embodiment, the disorder is associated with hyperphosphatemia, abnormally high renal phosphate reabsorption, abnormally low blood levels of full-length, bioactive FGF23, inappropriately normal blood levels of bioactive vitamin D, and/or elevated blood levels of bioactive vitamin D. In one embodiment, the disorder is associated with soft tissue calcification. Such disorders and methods for evaluating those disorders are described above and will be known to those of skill in the art. Suitable modes of administration are also described above.

In one embodiment, the modified FGF23 protein is administered with a pharmaceutically-acceptable carrier.

In one embodiment, the selected subject is a mammal. In one embodiment, the selected subject is a human.

In one embodiment, the modified FGF23 protein is co-administered with a hypophosphatemic agent, a phosphate binder, a vitamin D antagonist, an analgesic, and/or an anti-inflammatory agent.

EXAMPLES

Example 1

Purification of FGF, FGFR, and Klotho Proteins

Figures 5A, 5B, 5C, 5D, 5E, 5F, 5G:
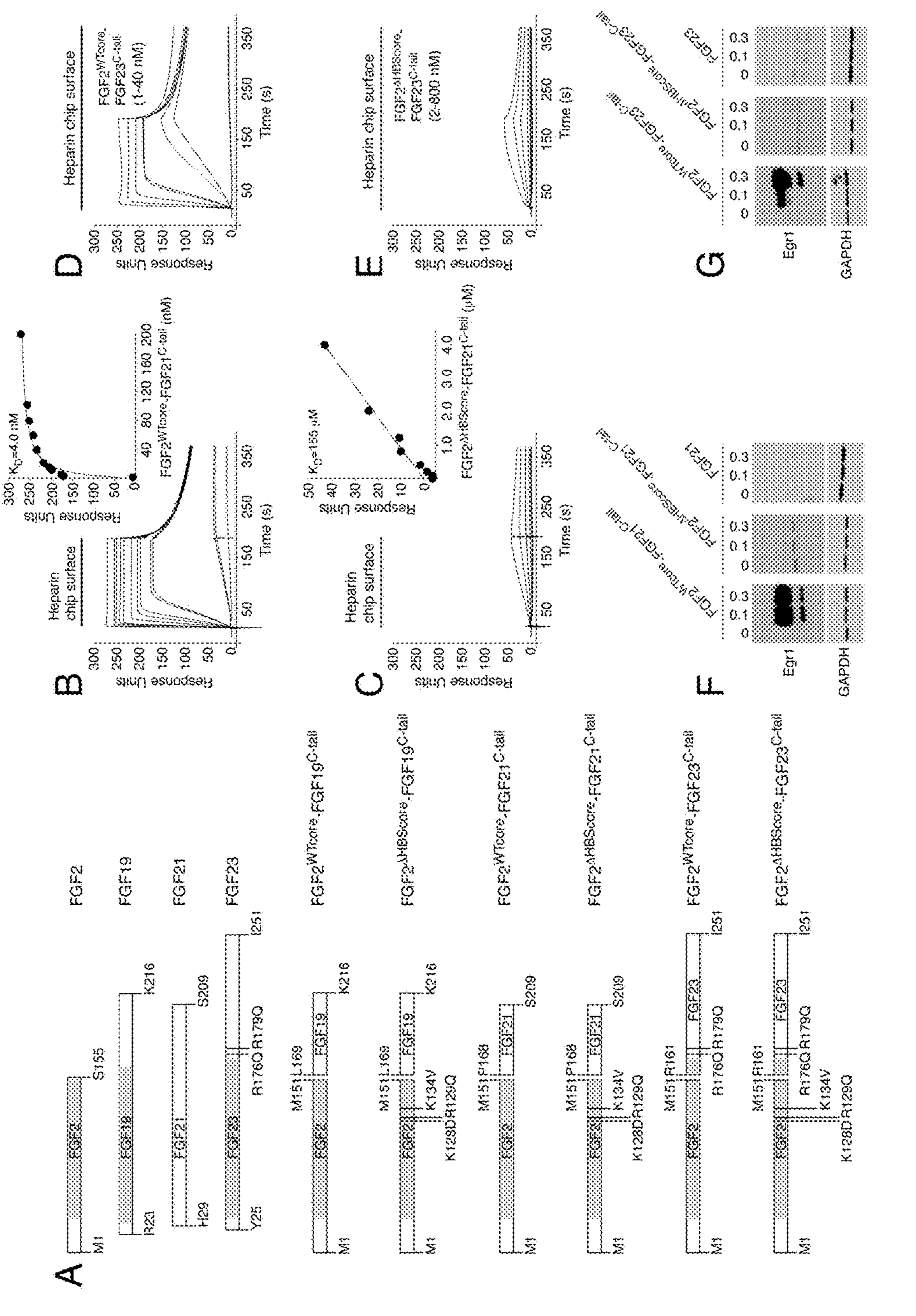
FIGS. 5A-5G show design and results relating to the conversion of FGF2 into an endocrine ligand.

The N-terminally hexahistidine-tagged, mature form of human FGF19 (SEQ ID NO: 333) (R23 to K216), human FGF21 (SEQ ID NO: 334) (H29 to S209; FIG. 5A), and human FGF23 (Y25 to I251; FIG. 5A) was refolded in vitro from bacterial inclusion bodies, and purified by published protocols (Ibrahimi et al., *Hum. Mol. Genet.* 13:2313-2324 (2004); Plotnikov et al., *Cell* 101:413-424 (2000), which is hereby incorporated by reference in its entirety). The amino acid sequence of human FGF19 (SEQ ID NO:333) (GenBank Accession No. NP_005108, which is hereby incorporated by reference in its entirety) is as follows:

```
  1 MRSGCVVVHV WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

The amino acid sequence of human FGF21 (SEQ ID NO: 334) (GenBank Accession No. NP_061986, which is hereby incorporated by reference in its entirety), as follows:

```
  1 MDSDETGFEH SGLWVSVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG PARFLPLPGL PPALPEPPGI
181 LAPQPPDVGS SDPLSMVGPS QGRSPSYAS.
```

FIG. 11 shows an alignment of the C-terminal tail sequences of human FGF19, FGF21, and FGF23.

Figure 6:
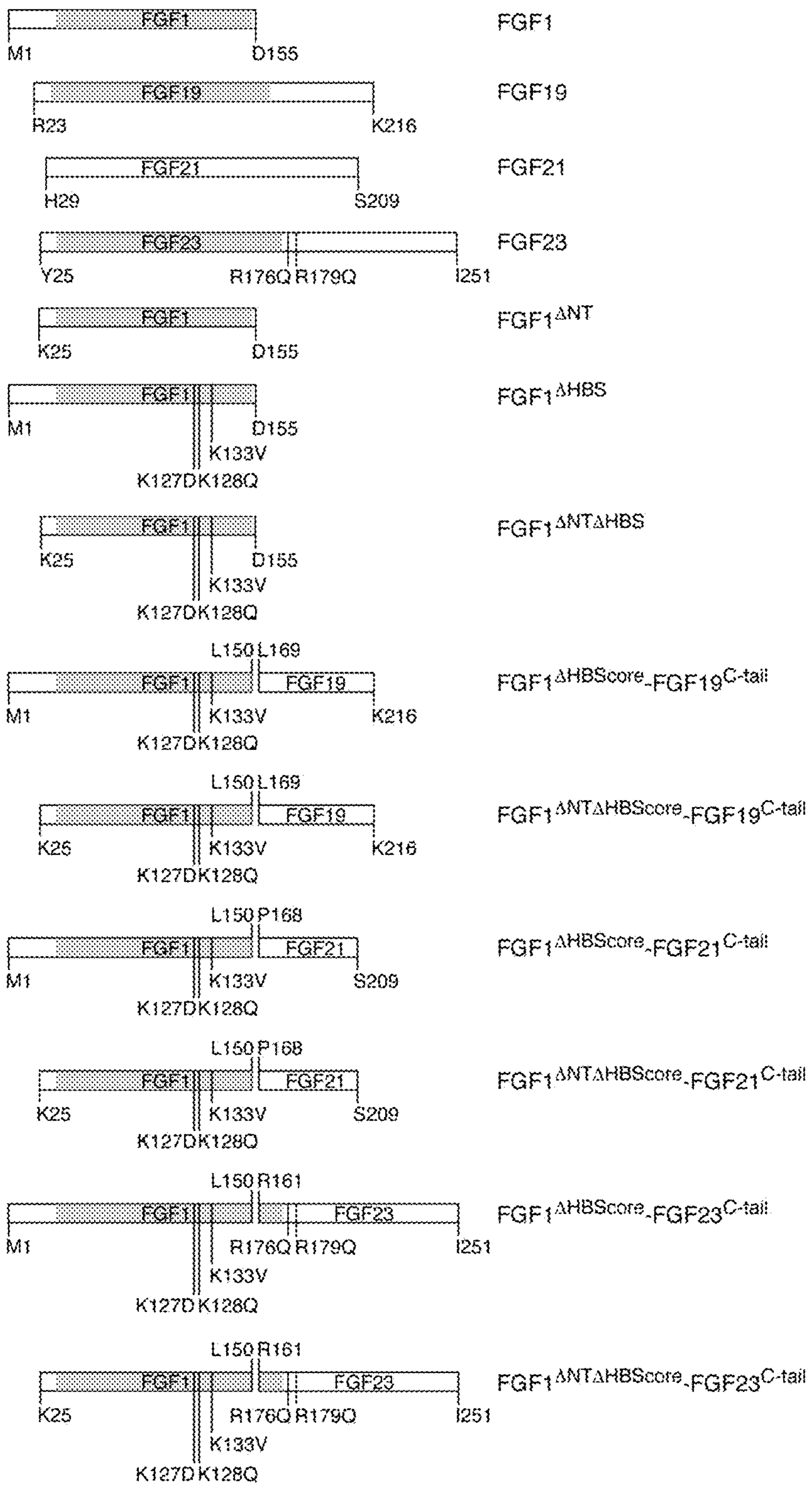
FIG. 6 is a schematic illustrating the conversion of FGF1 into an endocrine ligand. Shown are schematic drawings of human FGF1, FGF19, FGF21, FGF23, and exemplary FGF1-FGF19, FGF1-FGF21, and FGF1-FGF23 chimeras according to the present invention. Amino acid boundaries of each ligand and of each component of the chimeras are labeled with residue letter and number. The β-trefoil core domain for the known ligand crystal structures is shaded gray. HS-binding residues mutated in the FGF1 portion of chimeras are labeled with residue letter and number. Also labeled are the arginine residues of the proteolytic cleavage site in the C-terminal region of FGF23 that were mutated to glutamine in both FGF23 and the FGF1-FGF23 chimeras.

HS-binding site mutants of FGF19 (K149A) and FGF23 (R140A/R143A) were purified from bacterial inclusion bodies by similar protocols as the wild-type proteins. In order to minimize proteolysis of FGF23 wild-type and mutant proteins, arginine residues 176 and 179 of the proteolytic cleavage site $^{176}$RXXR$^{179}$ were replaced with glutamine as it occurs in the phosphate wasting disorder "autosomal dominant hypophosphatemic rickets" (ADHR) (White et al., *Nat. Genet.* 26:345-348 (2000); White et al., *Kidney Int.* 60:2079-2086 (2001), which are hereby incorporated by reference in their entirety). Human FGF1 (SEQ ID NO: 1) (M1 to D155; FIG. 6), N-terminally truncated human FGF1 (K25 to D155, termed FGF1$^{\Delta NT}$; FIG. 6), human FGF2 (SEQ ID NO: 121) (M1 to S155; FIG. 5A), and human FGF homologous factor 1B (FHF1B; M1 to T181) were purified by published protocols (Plotnikov et al., *Cell* 101:413-424 (2000); Olsen et al., *J. Biol. Chem.* 278:34226-34236 (2003), which are hereby incorporated by reference in their entirety).

Chimeras composed of the core domain of FGF2 (M1 to M151) and the C-terminal region of either FGF21 (P168 to 5209) or FGF23 (R161 to 1251) (termed FGF2$^{WTcore}$-FGF21$^{C\text{-}tail}$ and FGF2$^{WTcore}$-FGF23$^{C\text{-}tail}$, respectively; FIG. 5A) were purified by the same protocol as that for native FGF2 (Plotnikov et al., *Cell* 101:413-424 (2000), which is hereby incorporated by reference in its entirety). Analogous chimeras containing three mutations in the HS-binding site of the FGF2 core (K128D/R129Q/K134V) (termed FGF2$^{\Delta HBScore}$-FGF21$^{C\text{-}tail}$ and FGF2$^{\Delta HBScore}$-FGF23$^{C\text{-}tail}$, respectively, FIG. 5A) were purified from the soluble bacterial cell lysate fraction by ion-exchange and size-exclusion chromatographies. In order to minimize proteolysis of the chimeras containing the C-terminal sequence from R161 to 1251 of FGF23, arginine residues 176 and 179 of the proteolytic cleavage site $^{176}$RXXR$^{179}$ located within this sequence were replaced with glutamine as it occurs in ADHR (White et al., *Nat. Genet.* 26:345-348 (2000); White et al., *Kidney Int.* 60:2079-2086 (2001), which are hereby incorporated by reference in their entirety). In addition, in order to prevent disulfide-mediated dimerization of FGF2 and chimeric FGF2 proteins, cysteine residues 78 and 96 were mutated to serine. An HS-binding site mutant of FGF1 (K127D/K128Q/K133V) (termed FGF1$^{\Delta HBScore}$; FIG. 6) and chimeras composed of the core domain of the HS-binding site mutant of FGF1 (M1 to L150, K127D/K128Q/K133V) and the C-terminal region of either FGF19 (L169 to K216) or FGF21 (P168 to 5209) (termed FGF1$^{\Delta HBScore}$-FGF19$^{C\text{-}tail}$ and FGF1$^{\Delta HBScore}$-FGF21$^{C\text{-}tail}$, respectively; FIG. 6) were purified from the soluble bacterial cell lysate fraction by ion-exchange and size-exclusion chromatographies. The N-terminally hexahistidine-tagged C-terminal tail peptide of FGF23 (S180 to I251, termed FGF23$^{C\text{-}tail}$) was purified by a published protocol (Goetz et al., *Proc. Nat'l. Acad. Sci. U.S.A* 107:407-412 (2010), which is hereby incorporated by reference in its entirety). The ligand-binding domain of human FGFR1c (D142 to R365) was refolded in vitro from bacterial inclusion bodies, and purified by published protocols (Ibrahimi et al., *Hum. Mol. Genet.* 13:2313-2324 (2004); Plotnikov et al., *Cell* 101:413-424 (2000), which are hereby incorporated by reference in their entirety). The ectodomain of murine αKlotho (A35 to K982) and the ectodomain of murine βKlotho (F53 to L995) were expressed in HEK293 cells as fusion proteins with a C-terminal FLAG tag (Kurosu et al., *J. Biol. Chem.* 281:6120-6123 (2006); Kurosu et al., *Science* 309:1829-1833 (2005), which are hereby incorporated by reference in their entirety). The binary complex of FGFR1c ligand-binding domain with αKlotho ectodomain (referred to as αKlotho-FGFR1c complex) was prepared by a published protocol (Goetz et al., *Proc. Nat'l. Acad. Sci. U.S.A* 107:407-412 (2010), which is hereby incorporated by reference in its entirety). The binary complex of FGFR1c ligand-binding domain with βKlotho ectodomain (referred to as βKlotho-FGFR1c complex) was prepared in the same fashion as the αKlotho-FGFR1c complex.

Example 2

Analysis of FGF-heparin and FGF-FGFR-α/βKlotho Interactions by Surface Plasmon Resonance Spectroscopy Surface plasmon resonance (SPR) experiments were performed on a Biacore 2000 instrument (Biacore AB), and the interactions were studied at 25° C. in HBS-EP buffer (10 mM HEPES-NaOH, pH 7.4, 150 mM NaCl, 3 mM EDTA, 0.005% (v/v) polysorbate 20). To study endocrine FGF-heparin interactions, a heparin chip was prepared by immobilizing biotinylated heparin (Sigma-Aldrich) on flow channels of a research-grade streptavidin chip (Biacore AB). The coupling density was ~5 fmol mm$^{-2}$ of flow channel. To measure binding of chimeric FGF2 proteins to heparin, biotinylated heparin was coupled to a streptavidin chip at an approximately 4-fold lower density as judged based on the binding responses obtained for FGF1. To study FGF-FGFR-α/βKlotho interactions, FGF chips were prepared by covalent coupling of FGF proteins through their free amino groups on flow channels of research grade CMS chips (Biacore AB). Proteins were injected over a chip at a flow rate of 50 μl min$^{-1}$, and at the end of each protein injection (180 and 300 s, respectively), HBS-EP buffer (50 μl min$^{-1}$) was flowed over the chip to monitor dissociation for 180 or 240 s. The heparin chip surface was regenerated by injecting 50 μl of 2.0 M NaCl in 10 mM sodium acetate, pH 4.5. For FGF chips, regeneration was achieved by injecting 2.0 M NaCl in 10 mM sodium/potassium phosphate, pH 6.5. To control for nonspecific binding in experiments where an FGF ligand was immobilized on the chip, FHF1B, which shares structural similarity with FGFs but does not exhibit any FGFR binding (Olsen et al., *J. Biol. Chem.* 278:34226-34236 (2003), which is hereby incorporated by reference in its entirety), was coupled to the control flow channel of the chip (~15-30 fmol mm$^{-2}$). In experiments where heparin was immobilized on the chip, the control flow channel was left blank. The data were processed with BiaEvaluation software (Biacore AB). For each protein injection over the heparin chip, the nonspecific responses from the control flow channel were subtracted from the responses recorded for the heparin flow channel. Similarly, for each protein injection over a FGF chip, the nonspecific responses from the FHF1B control flow channel were subtracted from the responses recorded for the FGF flow channel. Where possible, equilibrium dissociation constants ($K_D$s) were calculated from fitted saturation binding curves. Fitted binding curves were judged to be accurate based on the distribution of the residuals (even and near zero) and $\chi^2$ (<10% of $R_{max}$).

To examine whether the K149A mutation abrogates residual heparin binding of FGF19, increasing concentrations of wild-type FGF19 were passed over a heparin chip. Thereafter, the FGF19$^{K149A}$ mutant was injected over the heparin chip at the highest concentration tested for the wild-type ligand. The effect of the R140A/R143A double mutation in the HS-binding site of FGF23 on residual heparin binding of FGF23 was examined in the same fashion as was the effect of the HS-binding site mutation in FGF19.

To verify that the K128D/R129Q/K134V triple mutation in the HS-binding site of the FGF2 core domain diminishes heparin-binding affinity of the FGF2 core, increasing concentrations of FGF2$^{ΔHBScore}$-FGF21$^{C-tail}$ and FGF2$^{ΔHBScore}$-FGF23$^{C-tail}$ were passed over a heparin chip. As a control, binding of FGF2$^{WTcore}$-FGF21$^{C-tail}$ and FGF2$^{WTcore}$-FGF23$^{C-tail}$ to heparin was studied.

To examine whether the FGF2$^{ΔHBScore}$-FGF23$^{C-tail}$ chimera can compete with FGF23 for binding to the αKlotho-FGFR1c complex, FGF23 was immobilized on a chip (~16 fmol mm$^{-2}$ of flow channel). Increasing concentrations of FGF2$^{ΔHBScore}$-FGF23$^{C-tail}$ were mixed with a fixed concentration of αKlotho-FGFR1c complex in HBS-EP buffer, and the mixtures were injected over the FGF23 chip. As controls, the binding competition was carried out with FGF23 or FGF2 as the competitor in solution. As an additional specificity control, competition of the FGF2$^{ΔHBScore}$-FGF23$^{C-tail}$ chimera with FGF21 for binding to the αKlotho-FGFR1c complex was studied. αKlotho-FGFR1c complex was mixed with FGF2$^{ΔHBScore}$-FGF23$^{C-tail}$ or FGF23 at a molar ratio of 1:10, and the mixture was injected over a chip containing immobilized FGF21 (~12 fmol mm$^{-2}$ of flow channel).

To test whether the FGF2$^{ΔHBScore}$-FGF21$^{C-tail}$ chimera can compete with FGF21 for binding to the βKlotho-FGFR1c complex, increasing concentrations of FGF2$^{ΔHBScore}$-FGF21$^{C-tail}$ were mixed with a fixed concentration of βKlotho-FGFR1c complex in HBS-EP buffer, and the mixtures were passed over a chip containing immobilized FGF21 (~19 fmol mm$^{-2}$ of flow channel). As controls, the binding competition was carried out with FGF21 or FGF2 as the competitor in solution. As an additional specificity control, competition of the FGF2$^{ΔHBScore}$-FGF21$^{C-tail}$ chimera with FGF23 for binding to the αKlotho-FGFR1c complex was studied. αKlotho-FGFR1c complex was mixed with FGF2$^{ΔHBScore}$-FGF21$^{C-tail}$ or FGF21 at a molar ratio of 1:10, and the mixture was injected over a chip containing immobilized FGF23 (~12 fmol mm$^{-2}$ of flow channel).

To measure binding of FGFR1c to each of the three endocrine FGFs, increasing concentrations of FGFR1c ligand-binding domain were injected over a chip containing immobilized FGF19, FGF21, and FGF23 (~30 fmol mm$^{-2}$ of flow channel). As a control, binding of FGFR1c to FGF2 immobilized on a chip was studied. As additional controls, binding of the αKlotho-FGFR1c complex to FGF23 and binding of FGFR1c to the C-terminal tail peptide of FGF23 was measured.

Example 3

Analysis of Phosphorylation of FRS2α and 44/42 MAP Kinase in Hepatoma and Epithelial Cell Lines To examine whether the FGF19$^{K149A}$ and FGF23$^{R140-143A}$ mutants can activate FGFR in a α/βKlotho-dependent fashion, induction of tyrosine phosphorylation of FGFR substrate 2a (FRS2a) and downstream activation of MAP kinase cascade was used as readout for FGFR activation. Subconfluent cells of the H4IIE rat hepatoma cell line, which endogenously expresses βKlotho (Kurosu et al., *J. Biol. Chem.* 282:26687-26695 (2007), which is hereby incorporated by reference in its entirety), were serum starved for 16 h and then stimulated for 10 min with the FGF19$^{K149A}$ mutant or wild-type FGF19 (0.2 ng $ml^{-1}$ to 2.0 μg $ml^{-1}$). Similarly, subconfluent cells of a HEK293 cell line ectopically expressing the transmembrane isoform of murine αKlotho (Kurosu et al., *J. Biol. Chem.* 281:6120-6123 (2006), which is hereby incorporated by reference in its entirety) were treated with the $FGF23^{R140A/R143A}$ mutant or wild-type FGF23 (0.1 to 100 ng $ml^{-1}$). After stimulation, the cells were lysed (Kurosu et al., *Science* 309:1829-1833 (2005), which is hereby incorporated by reference in its entirety), and cellular proteins were resolved on SDS-polyacrylamide gels and transferred to nitrocellulose membranes. The protein blots were probed with antibodies to phosphorylated FRS2α, phosphorylated 44/42 MAP kinase, total (phosphorylated and nonphosphorylated) 44/42 MAP kinase, and αKlotho. Except for the anti-αKlotho antibody (KM2119) (Kato et al., *Biochem. Biophys. Res. Commun.* 267:597-602 (2000), which is hereby incorporated by reference in its entirety), all antibodies were from Cell Signaling Technology.

Example 4

Analysis of Egr1 Protein Expression in an Epithelial Cell Line

To examine whether the $FGF2^{\Delta HBScore}$-$FGF21^{C\text{-}tail}$ and $FGF2^{\Delta HBScore}$-$FGF23^{C\text{-}tail}$ chimeras can activate FGFR in a HS-dependent fashion, induction of protein expression of the transcription factor early growth response 1 (Egr1), a known downstream mediator of FGF signaling, was used as readout for FGFR activation. HEK293 cells were serum starved overnight and then stimulated for 90 min with $FGF2^{\Delta HBScore}$-$FGF21^{C\text{-}tail}$ or $FGF2^{\Delta HBScore}$-$FGF23^{C\text{-}tail}$ (0.1 and 0.3 nM). Cell stimulation with $FGF2^{WTcore}$-$FGF21^{C\text{-}tail}$, $FGF2^{WTcore}$-$FGF23^{C\text{-}tail}$, FGF21, and FGF23 served as controls. To test whether the $FGF2^{\Delta HBScore}$-$FGF21^{C\text{-}tail}$ chimera can activate FGFR in a βKlotho-dependent fashion, HEK293 cells transfected with murine βKlotho were serum starved overnight and then stimulated for 90 min with $FGF2^{\Delta HBScore}$-$FGF21^{C\text{-}tail}$ or FGF21 (3 to 300 ng $ml^{-1}$). After stimulation, the cells were lysed (Kurosu et al., *Science* 309:1829-1833 (2005), which is hereby incorporated by reference in its entirety), and cellular proteins were resolved on SDS-polyacrylamide gels and transferred to nitrocellulose membranes. The protein blots were probed with antibodies to Egr1 and glyceraldehyde 3-phosphate dehydrogenase (GAPDH). The anti-Egr1 antibody was from Cell Signaling Technology and the anti-GAPDH antibody was from Abcam.

Example 5

Analysis of CYP7A1 and CYP8B1 mRNA Expression in Murine Liver Tissue

To examine the metabolic activity of the $FGF19^{K149A}$ mutant in vivo, 6- to 8-week old C57BL/6 mice were fasted overnight and then given intraperitoneally a single dose (1 mg kg body $weight^{-1}$) of $FGF19^{K149A}$ or FGF19 as a control. 6 h after the injection, the mice were sacrificed, and liver tissue was excised and frozen. Total RNA was isolated from liver tissue, and mRNA levels of cholesterol 7α-hydroxylase (CYP7A1) and sterol 12α-hydroxylase (CYP8B1) were measured using quantitative real time RT-PCR as described previously (Inagaki et al., *Cell Metab.* 2:217-225 (2005); Kim et al., *J. Lipid Res.* 48:2664-2672 (2007), which are hereby incorporated by reference in their entirety). The Institutional Animal Care and Use Committee at the University of Texas Southwestern Medical Center at Dallas had approved the experiments.

Example 6

Measurement of Serum Phosphate in Mice

The metabolic activity of the $FGF23^{R140/143A}$ mutant was examined both in normal mice and in Fgf23 knockout mice. 4- to 5-week old C57BL/6 mice were given intraperitoneally a single dose (0.29 mg kg body $weight^{-1}$) of $FGF23^{R140/143A}$ or FGF23 as a control. Before the injection and 8 h after the injection, blood was drawn from the cheek pouch and spun at 3,000×g for 10 min to obtain serum. Phosphate concentration in serum was measured using the Phosphorus Liqui-UV Test (Stanbio Laboratory). 6- to 8-week old Fgf23 knockout mice (Sitara et al., *Matrix Biol.* 23:421-432 (2004), which is hereby incorporated by reference in its entirety) (56) were given two injections of $FGF23^{R140/143A}$ or FGF23 at 8 h intervals (0.71 mg kg body $weight^{-1}$ each), and blood samples were collected for phosphate analysis before the first injection and 8 h after the second injection.

To test whether the $FGF2^{\Delta HBScore}$-$FGF23^{C\text{-}tail}$ chimera exhibits FGF23-like metabolic activity, 5- to 6-week old C57BL/6 mice were given a single injection of $FGF2^{\Delta HBScore}$-FGF23c-tail (0.21 mg kg body $weight^{-1}$). As controls, mice were injected with $FGF2^{WTcore}$-$FGF23^{C\text{-}tail}$ or FGF23. Before the injection and 8 h after the injection, blood samples were collected for measurement of serum phosphate. To confirm that αKlotho is required for the metabolic activity of the $FGF2^{\Delta HBScore}$-$FGF23^{C\text{-}tail}$ chimera, 7- to 8-week old αKlotho knockout mice (Lexicon Genetics) were injected once with $FGF2^{\Delta HBScore}$-$FGF23^{C\text{-}tail}$ or FGF23 as a control (0.51 mg kg body weight'). Before the injection and 8 h after the injection, blood samples were collected for phosphate analysis. The Harvard University Animal Care and Research committee board had approved all the experiments.

Example 7

Analysis of CYP27B1 mRNA Expression in Murine Renal Tissue

The ability of the $FGF2^{\Delta HBScore}$-$FGF23^{C\text{-}tail}$ chimera to reduce renal expression of 25-hydroxyvitamin $D_3$ 1α-hydroxylase (CYP27B1) was used as another readout for FGF23-like metabolic activity. C57BL/6 mice injected with $FGF2^{\Delta HBScore}$-$FGF23^{C\text{-}tail}$, $FGF2^{WTcore}$-$FGF23^{C\text{-}tail}$, or FGF23 were sacrificed 8 h after the protein injection, and renal tissue was excised and frozen. CYP27B1 mRNA levels in total renal tissue RNA were measured using real time quantitative PCR as described previously (Nakatani et al., *FASEB J.* 23:3702-3711 (2009); Ohnishi et al., *Kidney Int.* 75:1166-1172 (2009), which are hereby incorporated by reference in their entirety). The Harvard University Animal Care and Research committee board had approved the experiments.

Example 8

Insulin Tolerance Test in Mice

The ability of the $FGF2^{\Delta HBScore}$-$FGF21^{C\text{-}tail}$ chimera to potentiate the hypoglycemic effect of insulin was used as readout for FGF21-like metabolic activity (Ohnishi et al.,

*FASEB J.* 25:2031-2039 (2011), which is hereby incorporated by reference in its entirety). 8- to 12-week old C57BL/6 mice were kept on normal chow. On the day of the insulin tolerance test, mice were fasted for 4 h and then bled from the cheek pouch for measuring fasting blood glucose levels. Thereafter, mice were administered intraperitoneally insulin (0.5 units kg body weight$^{-1}$) alone or insulin (0.5 units·kg body weight$^{-1}$) plus FGF2$^{\Delta HBScore}$-FGF21$^{C\text{-}tail}$ chimera (0.3 mg kg body weight$^{-1}$). As a control, mice were co-injected with insulin plus FGF21. At the indicated time points after the injection (FIG. 7G), blood was drawn from the tail vein. Glucose concentrations in the blood samples were determined using Bayer Contour® blood glucose test strips (Bayer Corp.). The Harvard University Animal Care and Research committee board had approved the experiments.

Example 9

Analysis of Blood Glucose in Ob/Ob Mice ob/ob mice were injected subcutaneously with FGF1$^{\Delta NT}$, FGF1$^{\Delta HBS}$, or FGF1$^{\Delta HBScore}$-FGF21$^{C\text{-}tail}$ chimera. Injection of native FGF1 or native FGF21 served as controls. A single bolus of 0.5 mg of protein per kg of body weight was injected. This dose was chosen on the basis that maximal efficacy of the hypoglycemic effect of native FGF1 is seen at this dose. Before the protein injection and at the indicated time points after the injection (FIGS. 9A-9C), blood glucose concentrations were measured using an OneTouch Ultra glucometer (Lifescan). The Institutional Animal Care and Use Committee at the Salk Institute for Biological Sciences at La Jolla had approved the experiments.

Example 10

Statistical Analysis

Data are expressed as mean±SEM. A Student's t test or analysis of variance (ANOVA) was used as appropriate to make statistical comparisons. A value of $P<0.05$ was considered significant.

Example 11

HS is Dispensable for the Metabolic Activity of FGF19 and FGF23

Figure 2:
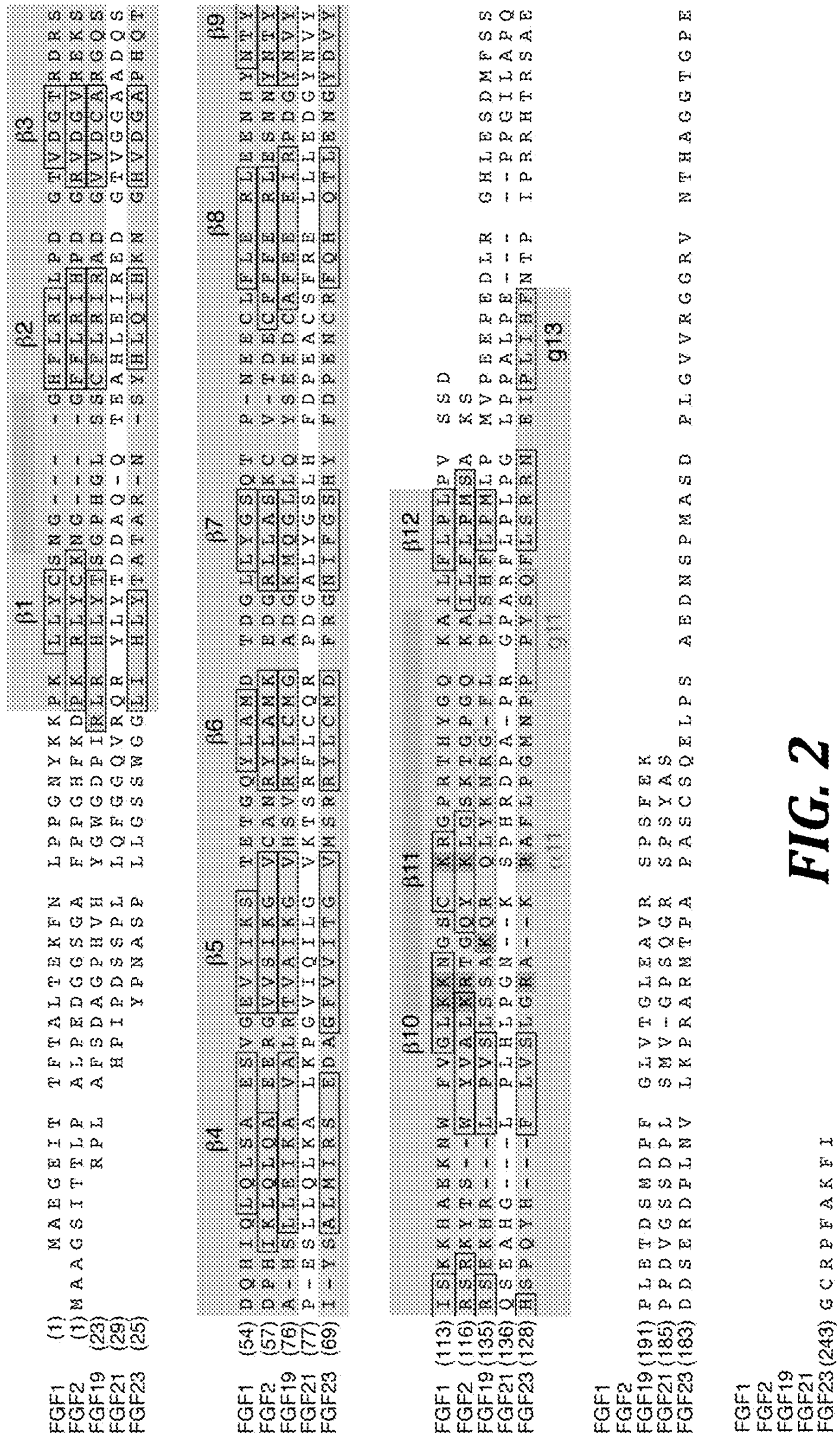
FIG. 2 shows a sequence alignment of the endocrine FGFs, FGF1, and FGF2. The amino acid sequences of the mature human FGF19, FGF21, and FGF23 ligands are aligned. Also included in the alignment are the human sequences of FGF1 and FGF2, prototypical paracrine FGFs, which were used in the experiments described herein, in which FGF1 and FGF2 were converted into endocrine FGF ligands. Residue numbers corresponding to the human sequence of FGF1 (SEQ ID NO: 1) (GenBank Accession No. AAH32697, which is hereby incorporated by reference in its entirety), FGF2 (SEQ ID NO: 121) (GenBank Accession No. EAX05222, which is hereby incorporated by reference in its entirety), FGF19 (SEQ ID NO: 333) (GenBank Accession No. NP_005108, which is hereby incorporated by reference in its entirety), FGF21 (SEQ ID NO: 334) (GenBank Accession No. NP_061986, which is hereby incorporated by reference in its entirety), and FGF23 (SEQ ID NO: 233) (GenBank accession no. AAG09917, which is hereby incorporated by reference in its entirety) are in parenthesis to the left of the alignment. Secondary structure elements are labeled, and residues containing these elements for known secondary structures are boxed. Gaps (dashes) were introduced to optimize the sequence alignment. The β-trefoil core domain for known FGF crystal structures is shaded gray. Blue bars on top of the alignment indicate the location of the HS-binding regions. HS-binding residues selected for mutagenesis are shaded blue.
Figures 3A, 3B, 3C, 3D, 3E, 3F, 3G:
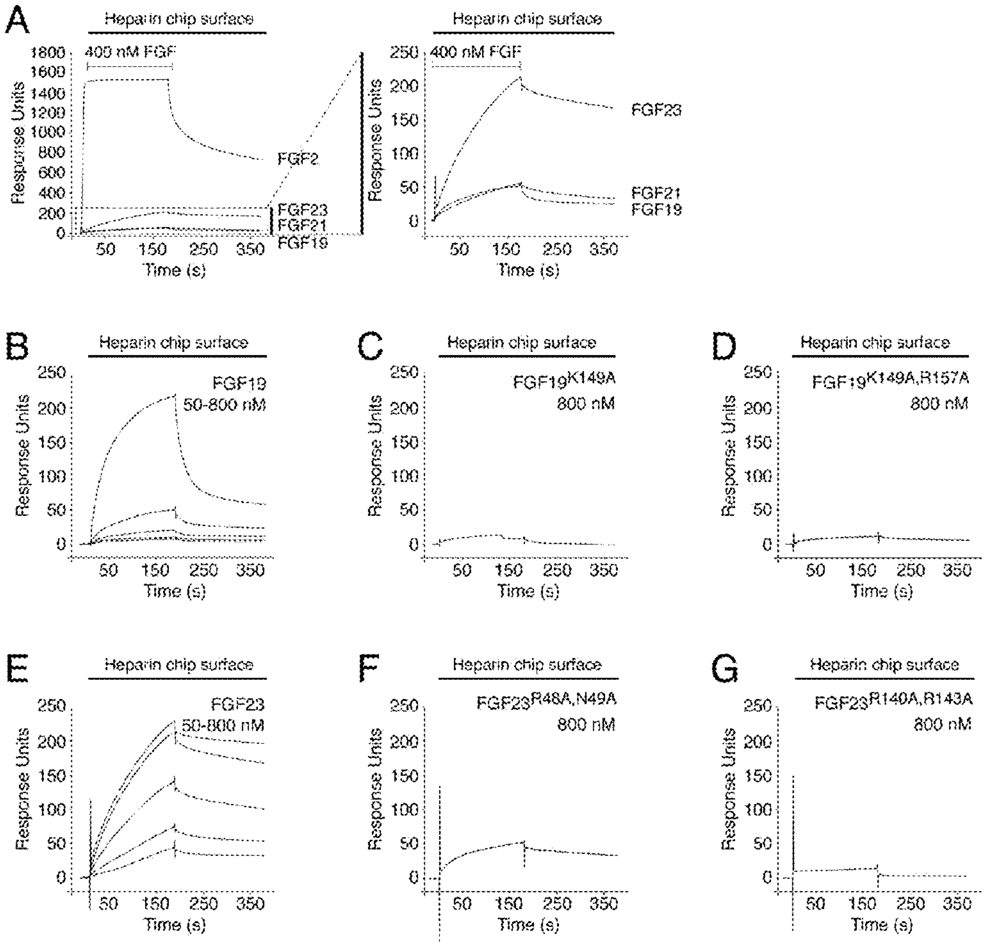
FIGS. 3A-3G show Surface plasmon resonance ("SPR") results relating to knockout of residual heparin binding in FGF19 and FGF23 by site-directed mutagenesis.

In order to engineer endocrine FGFs devoid of HS binding, the FGF19 crystal structure (PDB ID: 2P23; (Goetz et al., *Mol. Cell Biol.* 27:3417-3428 (2007), which is hereby incorporated by reference in its entirety) was compared with that of FGF2 bound to a heparin hexasaccharide (PDB ID: 1FQ9; (Schlessinger et al., *Mol. Cell* 6:743-750 (2000), which is hereby incorporated by reference in its entirety)). This analysis shows that solvent-exposed residues K149, Q150, Q152, and R157 of FGF19 lie at the corresponding HS-binding site of this ligand, and hence could account for the residual HS binding of FGF19 (FIGS. 1A, 1B, and 2). Likewise, comparative analysis of the FGF23 crystal structure (PDB ID: 2P39; (Goetz et al., *Mol. Cell Biol.* 27:3417-3428 (2007), which is hereby incorporated by reference in its entirety)) with that of heparin-bound FGF2 (PDB ID: 1FQ9; (Schlessinger et al., *Mol. Cell* 6:743-750 (2000), which is hereby incorporated by reference in its entirety)) points to R48, N49, R140, and R143 as candidates mediating the residual HS binding of this ligand (FIGS. 1A, 1C, and 2). In agreement with the structural predictions, replacement of K149 alone in FGF19 with alanine and combined substitution of R140 and R143 in FGF23 for alanine were sufficient to abolish residual HS binding of these ligands (FIGS. 3B-3G).

Figures 4A, 4B, 4C, 4D:
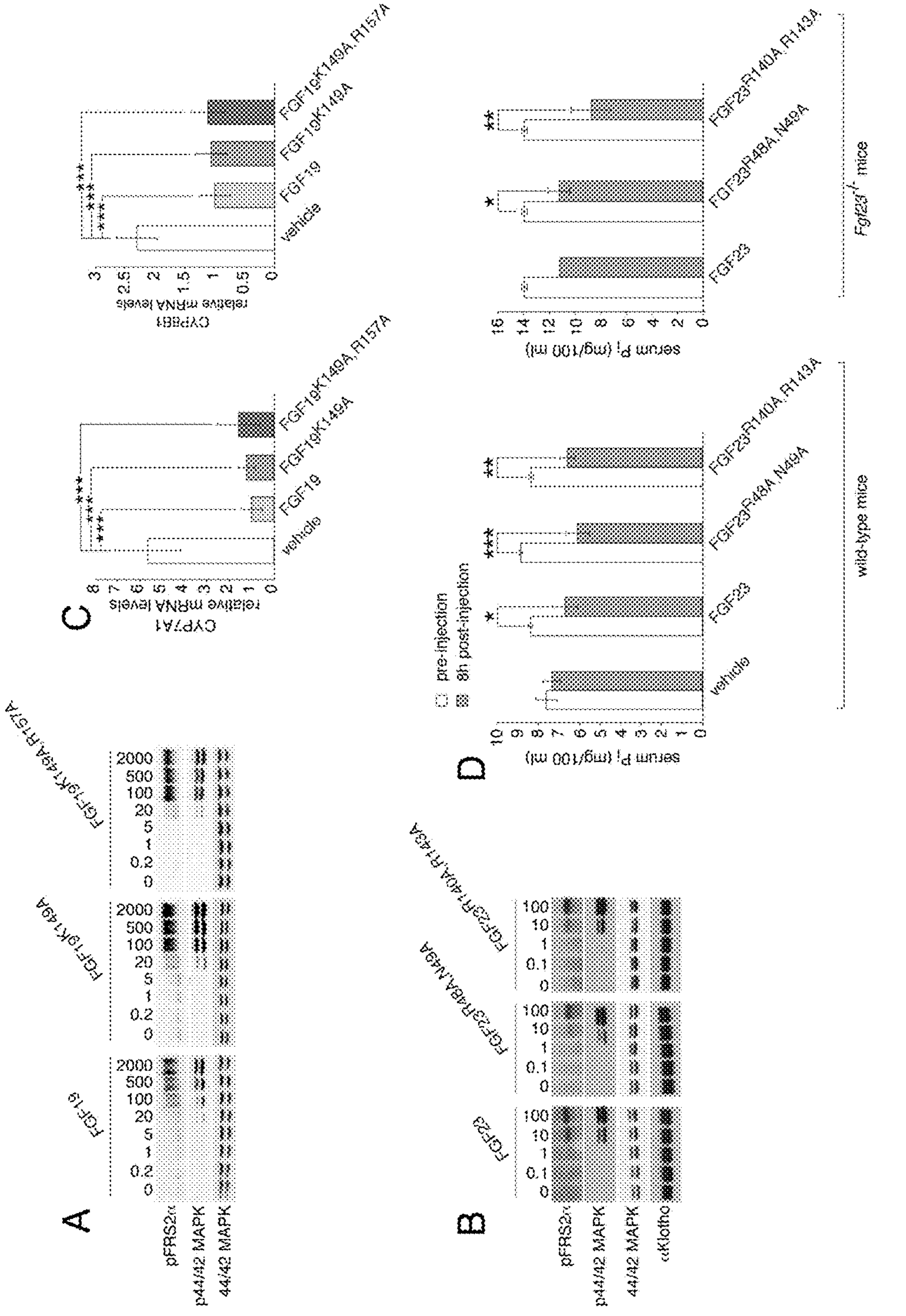
FIGS. 4A-4D show results demonstrating that HS is dispensable for the metabolic activity of FGF19 and FGF23.

To test the impact of knocking out residual HS binding of FGF19 on the signaling by this ligand, H4IIE hepatoma cells were stimulated with the FGF19$^{K149A}$ mutant or wild-type FGF19. H4IIE cells endogenously express FGFR4 and βKlotho (Kurosu et al., *J. Biol. Chem.* 282:26687-26695 (2007), which is hereby incorporated by reference in its entirety), the cognate receptor and co-receptor, respectively, for FGF19. The FGF19$^{K149A}$ mutant was as effective as wild-type FGF19 in inducing tyrosine phosphorylation of FRS2a and downstream activation of MAP kinase cascade (FIG. 4A). These data show that elimination of residual HS binding has no impact on the ability of FGF19 to signal in cultured cells. To test whether the same holds true for FGF23 signaling, HEK293 cells, which naturally express two of the three cognate receptors of FGF23, namely FGFR1c and FGFR3c (Kurosu et al., *J. Biol. Chem.* 281:6120-6123 (2006), which is hereby incorporated by reference in its entirety) were transfected with the transmembrane isoform of αKlotho, the co-receptor of FGF23. These cells were treated with the FGF23$^{R140/143A}$ double mutant or wild-type FGF23. The FGF23$^{R140A/R143A}$ mutant had the same capacity as wild-type FGF23 in inducing phosphorylation of FRS2a and downstream activation of MAP kinase cascade (FIG. 4B). These data show that similar to FGF19, FGF23 does not need to bind HS in order to activate FGFR in cultured cells.

To substantiate the findings in cells, the metabolic activity of wild-type and mutated ligands in vivo were compared. Mice were injected with the FGF19$^{K149A}$ mutant or wild-type FGF19 and liver gene expression of CYP7A1 and CYP8B1, which are key enzymes in the major bile acid biosynthetic pathway (Russell, D. W., *Annu. Rev. Biochem.* 72:137-174 (2003), which is hereby incorporated by reference in its entirety), was analyzed. Like wild-type FGF19, the FGF19$^{K149A}$ mutant markedly decreased CYP7A1 and CYP8B1 mRNA levels (FIG. 4C), demonstrating that knockout of residual HS binding does not affect the metabolic activity of FGF19. To examine whether residual HS binding is also dispensable for the metabolic activity of FGF23, mice were injected with the FGF23$^{R140/143A}$ mutant or wild-type FGF23 and serum phosphate concentrations were measured. The FGF23$^{R140A/R143A}$ mutant reduced serum phosphate as effectively as wild-type FGF23 (FIG. 4D). Moreover, when injected into Fgf23 knockout mice, the FGF23$^{R140A/R143A}$ mutant exhibited as much of phosphate-lowering activity as wild-type FGF23 (FIG. 4D). These data show that, as in the case of FGF19, abolishment of residual HS binding does not impact the metabolic activity of FGF23 leading to the conclusion that HS is not a component of the endocrine FGF signal transduction unit (FIG. 1D).

Example 12

Conversion of a Paracrine FGF into an Endocrine Ligand Confirms that HS is Dispensable for the Metabolic Activity of Endocrine FGFs If HS is dispensable for the metabolic activity of endocrine FGFs, then it should be feasible to convert a paracrine FGF into an endocrine FGF by eliminating HS-binding affinity of the paracrine FGF and substituting its C-terminal tail for that of an endocrine FGF containing the Klotho co-receptor binding site. Reducing HS-binding affinity will allow the ligand to freely diffuse and enter the blood circulation while attaching the C-terminal tail of an endocrine FGF will home the ligand into its target tissues. FGF2, a prototypical paracrine FGF, was chosen for conversion into FGF23-like and FGF21-like ligands, respectively. FGF2 was selected as paracrine ligand for this protein engineering exercise because it preferentially binds to the "c" isoform of FGFR1, the principal receptor mediating the metabolic activity of FGF23 (Gattineni et al., *Am. J. Physiol. Renal Physiol.* 297:F282-291 (2009); Liu et al., *J. Am. Soc. Nephrol.* 19:2342-2350 (2008), which are hereby incorporated by reference in their entirety) and FGF21 (Kurosu et al., *J. Biol. Chem.* 282:26687-26695 (2007), which is hereby incorporated by reference in its entirety), respectively. In the crystal structure of heparin-bound FGF2 (PDB ID: 1FQ9; (Schlessinger et al., *Mol. Cell* 6:743-750 (2000), which is hereby incorporated by reference in its entirety)), K128, R129, and K134 mediate the majority of hydrogen bonds with heparin and hence mutation of these residues was predicted to cause a major reduction in HS-binding affinity of FGF2 (FIGS. 1A, 2, and 5A). Accordingly, these three residues were mutated and then the short C-terminal tail of the mutated FGF2 was replaced with the C-terminal tail of FGF23 (R161 to 1251) or the C-terminal tail of FGF21 (P168 to S209) (FIG. 5A). The resulting chimeras were termed $FGF2^{\Delta HBScore}$-$FGF23^{C\text{-}tail}$ and $FGF2^{\Delta HBScore}$-$FGF21^{C\text{-}tail}$ (FIG. 5A). To demonstrate that reduction in HS-binding affinity is required for converting FGF2 into an endocrine ligand, two control chimeras were made in which the HS-binding site of the FGF2 core was left intact ($FGF2^{WTcore}$-$FGF23^{C\text{-}tail}$ and $FGF2^{WTcore}$-$FGF21^{C\text{-}tail}$; FIG. 5A).

Consistent with the structural prediction, $FGF2^{\Delta HBScore}$-$FGF23^{C\text{-}tail}$ and $FGF2^{\Delta HBScore}$-$FGF21^{C\text{-}tail}$ exhibited poor binding affinity for HS compared to the corresponding control chimeras with intact HS-binding site (FIGS. 5B-5E). Since HS is an cofactor in paracrine FGF signaling, the $FGF2^{\Delta HBScore}$-$FGF23^{C\text{-}tail}$ and $FGF2^{\Delta HBScore}$-$FGF21^{C\text{-}tail}$ chimeras were predicted to lose the ability to activate FGFR1c in an HS-dependent fashion. To test this, HEK293 cells, which endogenously express FGFR1c, were stimulated with $FGF2^{\Delta HBScore}$-FGF23 or $FGF2^{WTcore}$-$FGF23^{C\text{-}tail}$. Induction of protein expression of the transcription factor Egr1, a known downstream mediator of FGF signaling, was used as readout for FGFR activation. As shown in FIG. 5G, the $FGF2^{\Delta HBScore}$-$FGF23^{C\text{-}tail}$ chimera, like native FGF23, was ineffective in inducing Egr1 expression at concentrations at which the $FGF2^{WTcore}$-$FGF23^{C\text{-}tail}$ chimera elicited a near maximal effect. The same observations were made for the $FGF2^{\Delta HBScore}$-$FGF21^{C\text{-}tail}$ chimera (FIG. 5F). These data show that, similar to native FGF23 and FGF21, the $FGF2^{\Delta HBScore}$-$FGF23^{C\text{-}tail}$ and $FGF2^{\Delta HBScore}$-$FGF21^{C\text{-}tail}$ chimeras lost the ability to activate FGFR in an HS-dependent, paracrine fashion.

Figures 7A, 7B, 7C, 7D, 7E, 7F, 7G:
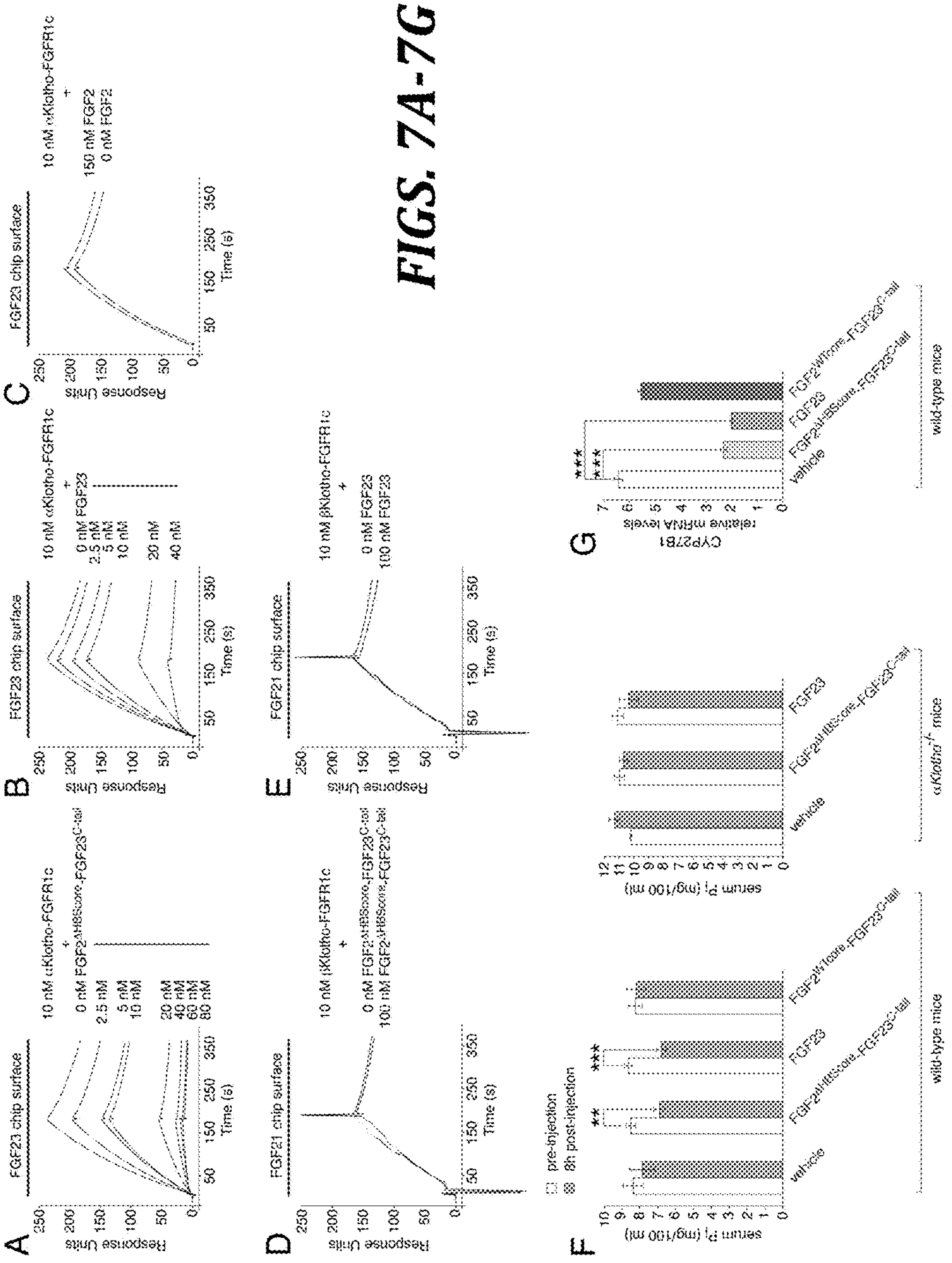
FIGS. 7A-7G show results demonstrating that the FGF2$^{\Delta HBScore}$-FGF23$^{C\text{-}tail}$ chimera exhibits FGF23-like activity.
Figures 8A, 8B, 8C, 8D, 8E, 8F, 8G:
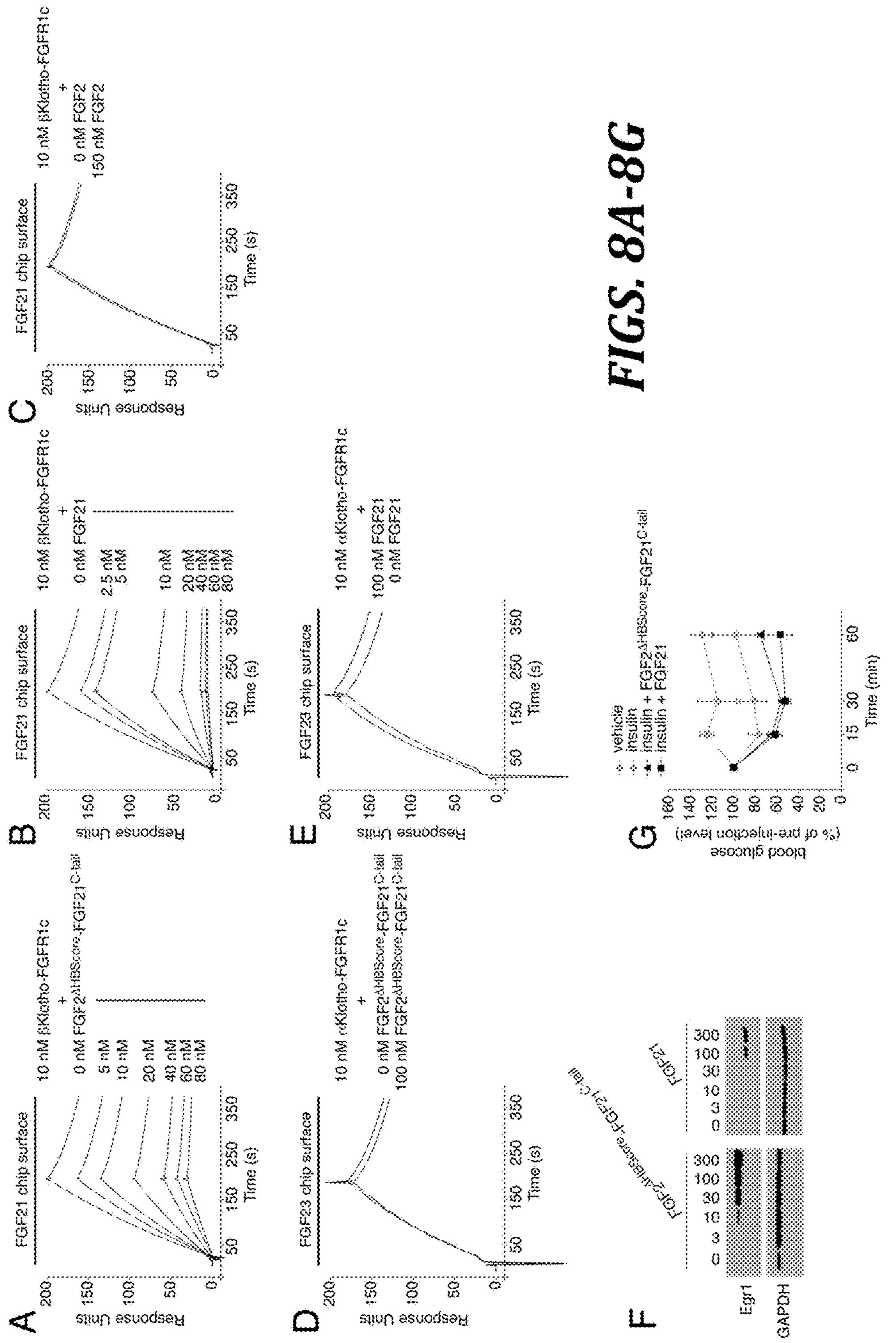
FIGS. 8A-8G show results demonstrating that the FGF2$^{\Delta HBScore}$-FGF21$^{C\text{-}tail}$ chimera exhibits FGF21-like activity.

To determine whether the $FGF2^{\Delta HBScore}$-$FGF23^{C\text{-}tail}$ and $FGF2^{\Delta HBScore}$-$FGF21^{C\text{-}tail}$ chimeras gained the ability to signal in a Klotho co-receptor-dependent, endocrine fashion, it was first analyzed whether these chimeras can form ternary complexes with FGFR1c and Klotho co-receptor. To this end, a SPR-based binding competition assay was employed. FGF23 was immobilized onto a SPR biosensor chip, and mixtures of a fixed concentration of binary αKlotho-FGFR1c complex with increasing concentrations of $FGF2^{\Delta HBScore}$-$FGF23^{C\text{-}tail}$ chimera were passed over the chip. $FGF2^{\Delta HBScore}$-$FGF23^{C\text{-}tail}$ competed, in a dose-dependent fashion, with immobilized FGF23 for binding to the αKlotho-FGFR1c complex (FIG. 7A), demonstrating that the chimera, like native FGF23 (FIG. 7B), is able to form a ternary complex with FGFR1c and αKlotho. To test whether the $FGF2^{\Delta HBScore}$-$FGF21^{C\text{-}tail}$ chimera can likewise form a ternary complex with FGFR1c and βKlotho, FGF21 was coupled to a SPR biosensor chip, and mixtures of the binary βKlotho-FGFR1c complex with $FGF2^{\Delta HBScore}$-$FGF21^{C\text{-}tail}$ were passed over the chip. $FGF2^{\Delta HBScore}$-$FGF21^{C\text{-}tail}$ effectively competed with immobilized FGF21 for binding to the βKlotho-FGFR1c complex (FIG. 8A), demonstrating that the chimera, like native FGF21 (FIG. 8B), is capable of binding to the binary complex of FGFR1c and βKlotho. Notably, native FGF2 failed to compete with FGF23 for binding to the αKlotho-FGFR1c complex (FIG. 7C), and with FGF21 for binding to the βKlotho-FGFR1c complex (FIG. 8C) since it lacks the Klotho co-receptor binding domain. To further confirm the binding specificity of the $FGF2^{\Delta HBScore}$-$FGF23^{C\text{-}tail}$ chimera for the αKlotho-FGFR1c complex, $FGF2^{\Delta HBScore}$-$FGF23^{C\text{-}tail}$ and βKlotho-FGFR1c complex were mixed at a molar ratio of 10:1, and the mixture was injected over a chip containing immobilized FGF21. $FGF2^{\Delta HBScore}$-$FGF23^{C\text{-}tail}$, like native FGF23, failed to compete with FGF21 for binding to the βKlotho-FGFR1c complex (FIGS. 7D and 7E). Similarly, the $FGF2^{\Delta HBScore}$-$FGF21^{C\text{-}tail}$ chimera, like native FGF21, failed to compete with FGF23 for binding to the αKlotho-FGFR1c complex (FIGS. 8D and 8E). For the $FGF2^{\Delta HBScore}$-$FGF21^{C\text{-}tail}$ chimera, we investigated whether it is able to activate FGFR1c in a βKlotho-dependent fashion in cells. HEK293 cells were transfected with βKlotho and then stimulated with $FGF2^{\Delta HBScore}$-$FGF21^{C\text{-}tail}$ or FGF21. Similar to native FGF21, the $FGF2^{\Delta HBScore}$ $FGF21^{C\text{-}tail}$ chimera induced Egr1 protein expression in HEK293-βKlotho cells (FIG. 8F), indicating that the chimera is capable of activating FGFR1c in the presence of βKlotho.

To provide definite proof for the ligand conversion, the metabolic activity of the chimeras in vivo was tested. Specifically, the ability of the $FGF2^{\Delta HBScore}$-$FGF23^{C\text{-}tail}$ chimera to lower serum phosphate and to reduce renal gene expression of CYP27B1, which catalyzes the conversion of vitamin D into its bioactive form, was examined. Mice were injected with $FGF2^{\Delta HBScore}$ $FGF23^{C\text{-}tail}$ or as controls, FGF23 or $FGF2^{WTcore}$-$FGF23^{C\text{-}tail}$, and serum phosphate concentrations and renal CYP27B1 mRNA levels were measured. Similar to native FGF23, the $FGF2^{\Delta HBScore}$-$FGF23^{C\text{-}tail}$ chimera caused a decrease in serum phosphate in wild-type mice (FIG. 7F). The chimera also induced a marked decrease in CYP27B1 mRNA levels, just like the native FGF23 ligand (FIG. 7G). These data show that the $FGF2^{\Delta HBScore}$-$FGF23^{C\text{-}tail}$ chimera acts as an FGF23-like hormone. Importantly, the $FGF2^{WTcore}$-$FGF23^{C\text{-}tail}$ chimera failed to decrease serum phosphate or CYP27B1 mRNA levels (FIGS. 7F and 7G). This is expected because, owing to its high affinity for HS, this chimera should be trapped in the vicinity of the injection site and hence not be able to enter the blood circulation. Moreover, these data show that adding the Klotho co-receptor binding site is not sufficient to convert a paracrine FGF into an endocrine ligand. To confirm that the metabolic activity of the $FGF2^{\Delta HBScore}$ $FGF23^{C\text{-}tail}$ chimera is dependent on αKlotho, αKlotho knockout mice were injected with $FGF2^{\Delta HBScore}$-$FGF23^{C\text{-}tail}$ or FGF23 as a control, and serum concentrations of phosphate were measured. As shown in FIG. 7F, $FGF2^{\Delta HBScore}$-$FGF23^{C\text{-}tail}$ failed to lower serum phosphate, demonstrating that the chimera, like native FGF23 (FIG. 7F), requires αKlotho for metabolic activity.

To determine whether the FGF2$^{\Delta HBScore}$-FGF21$^{C\text{-}tail}$ chimera exhibits FGF21-like metabolic activity, its ability to potentiate the hypoglycemic effect of insulin was examined (Ohnishi et al., *FASEB J.* 25:2031-2039 (2011), which is hereby incorporated by reference in its entirety). Mice were injected with insulin plus FGF2$^{\Delta HBScore}$-FGF21$^{C\text{-}tail}$, insulin plus FGF21, or insulin alone, and blood glucose concentrations were monitored for up to one hour after the injection. Similar to FGF21, the FGF2$^{\Delta HBScore}$-FGF21$^{C\text{-}tail}$ chimera enhanced the hypoglycemic effect of insulin (FIG. 8G), demonstrating that the chimera acts as an FGF21-like hormone.

Figures 9A, 9B, 9C:
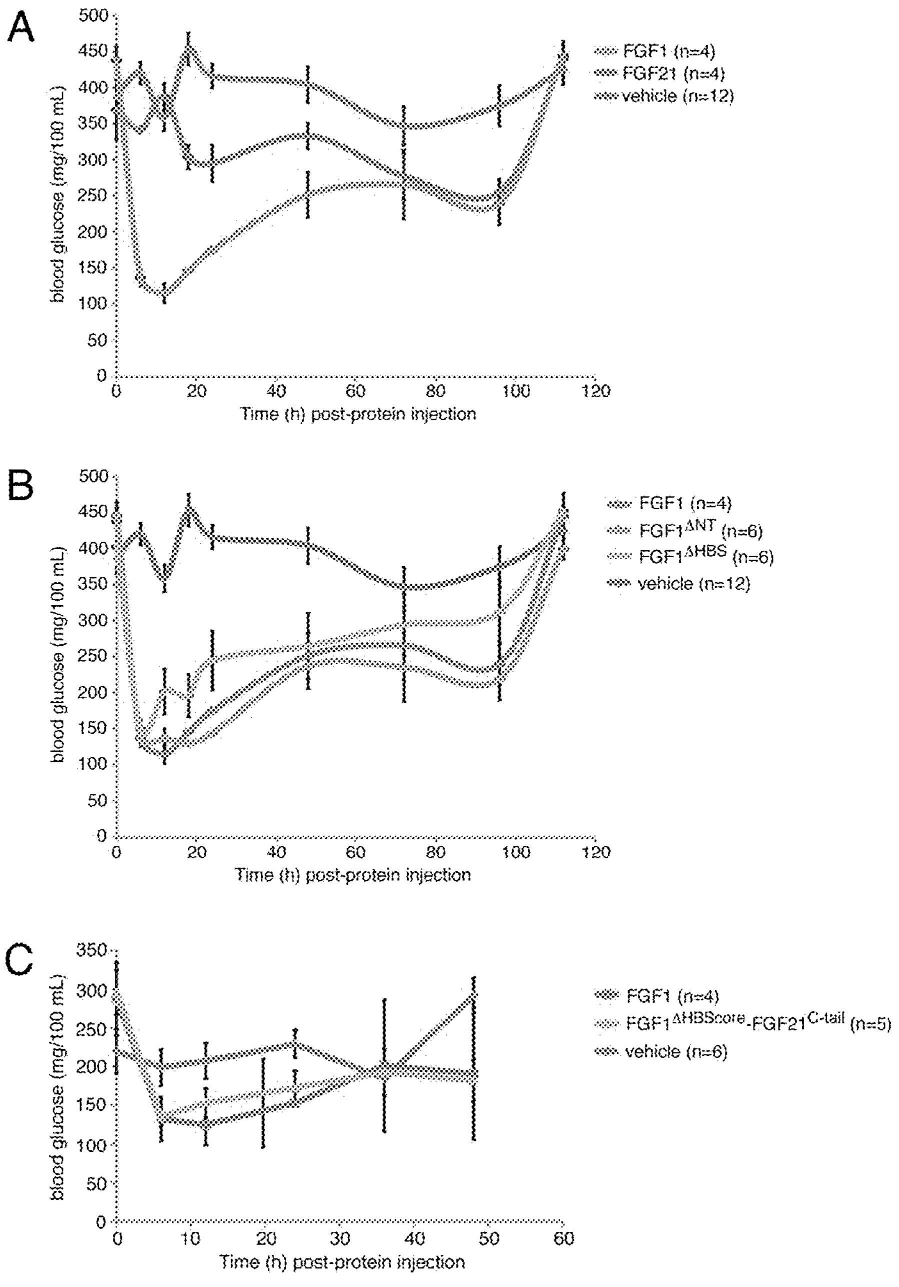
FIGS. 9A-9C show the glucose-lowering effects in ob/ob mice of FGF1 variants according to the present invention.

To substantiate further the concept of FGF ligand conversion, another FGF21-like ligand was engineered using FGF1 as paracrine FGF, and the metabolic activity of the engineered protein was tested in vivo in a mouse model of diabetes and obesity. Besides serving as an additional proof-of-concept, the use of FGF1 for this particular ligand conversion was appealing because FGF1 on its own plays an essential role in glucose metabolism (Jonker et al., "A PPARγ-FGF1 Axis is Required for Adaptive Adipose Remodelling and Metabolic Homeostasis," *Nature* 485:391-394 (2012), which is hereby incorporated by reference in its entirety). Notably, similar to FGF21, FGF1 is induced postprandially in gonadal white adipose tissue by the nuclear hormone receptor PPARγ (peroxisome proliferator activated receptor-γ) (Jonker et al., "A PPARγ-FGF1 Axis is Required for Adaptive Adipose Remodelling and Metabolic Homeostasis," *Nature* 485:391-394 (2012); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). FGF1 is required for the remodeling of adipose tissue to adjust to fluctuations in nutrient availability (Jonker et al., "A PPARγ-FGF1 Axis is Required for Adaptive Adipose Remodelling and Metabolic Homeostasis," *Nature* 485:391-394 (2012), which is hereby incorporated by reference in its entirety), and this process is influenced by FGF21 (Hotta et al., "Fibroblast Growth Factor 21 Regulates Lipolysis in White Adipose Tissue But is Not Required for Ketogenesis and Triglyceride Clearance in Liver," *Endocrinology* 150:4625-4633 (2009); Dutchak et al., "Fibroblast Growth Factor-21 Regulates PPARγ Activity and the Antidiabetic Actions of Thiazolidinediones," *Cell* 148:556-567 (2012), which are hereby incorporated by reference in their entirety). As part of a positive feedback loop, FGF21 stimulates PPARγ activity in adipocytes (Dutchak et al., "Fibroblast Growth Factor-21 Regulates PPARγ Activity and the Antidiabetic Actions of Thiazolidinediones," *Cell* 148:556-567 (2012), which is hereby incorporated by reference in its entirety), raising the intriguing possibility that FGF21 regulates FGF1 signaling in adipose tissue through PPARγ. An FGF1$^{\Delta HBScore}$-FGF21$^{C\text{-}tail}$ chimera was generated in the same manner as the FGF2$^{\Delta HBScore}$-FGF21$^{C\text{-}tail}$ chimera (FIGS. 5 and 6). Specifically, K127, K128, and K133 of FGF1, which correspond to the key HS-binding residues identified in the crystal structure of heparin-bound FGF2 (PDB ID: 1FQ9; (Schlessinger et al., *Mol. Cell* 6:743-750 (2000), which is hereby incorporated by reference in its entirety)), were mutated and then the short C-terminal tail of the mutated FGF1 was replaced with the C-terminal tail of FGF21 (P168 to S209) (FIG. 6). A full-length FGF1 protein harboring the HS-binding site mutations was used as a control (FIG. 6). Consistent with the structural prediction, this protein exhibited poor binding affinity for HS compared to wild-type FGF1 as evidenced by the fact that, unlike the wild-type ligand, the mutant protein did not bind to a Heparin sepharose column. A subcutaneous bolus injection of the FGF1$^{\Delta HBScore}$-FGF21$^{C\text{-}tail}$ chimera elicited a hypoglycemic effect in ob/ob mice (FIG. 9C), demonstrating that the chimera has metabolic activity. The effect was of similar magnitude as that observed for native FGF1 (FIG. 9C), which itself has a much greater hypoglycemic effect in ob/ob mice than native FGF21 (FIG. 9A). The HS-binding site mutant of FGF1, which was included as a control in these experiments, showed a similar hypoglycemic effect as the wild-type ligand (FIG. 9B), indicating that the loss in HS-binding affinity had no impact on the metabolic activity of FGF1. To alter the receptor-binding specificity of FGF1 such that FGF1 selectively binds to the "c" splice isoform of FGFR1, the principal receptor mediating the metabolic activity of FGF21, an N-terminally truncated FGF1 protein was made (FIG. 6). The truncated FGF1 ligand lacked twenty four residues from the N-terminus including the nine residues that are critical for the promiscuous binding of FGF1 to both splice isoforms of FGFR1-3 (Beenken et al., "Plasticity in Interactions of Fibroblast Growth Factor 1 (FGF1) N Terminus with FGF Receptors Underlies Promiscuity of FGF1," *J Biol Chem* 287(5):3067-3078 (2012), which is hereby incorporated by reference in its entirety). Based on the crystal structures of FGF1-FGFR complexes, the truncation was also predicted to reduce the receptor-binding affinity of FGF1, and hence the ligand's mitogenicity. The truncated FGF1 protein induced a similar hypoglycemic effect in ob/ob mice as native FGF1 did (FIG. 9B), indicating that the metabolic activity of FGF1 is mediated through the "c" splice isoform of FGFR. Together, these findings provide a starting point for engineering FGF1 ligands that have no mitogenicity but the same or enhanced metabolic activity compared to native FGF1.

The demonstrated ability to convert a paracrine FGF into an endocrine ligand by means of reducing HS-binding affinity of the paracrine FGF and adding the Klotho co-receptor binding site substantiates that HS does not participate in the formation of the endocrine FGF signal transduction unit. The dispensability of HS for the metabolic activity of endocrine FGFs has an intriguing implication as to how these FGFs have evolved to become hormones. It appears that these ligands have lost the requirement to bind HS in order to signal, while acquiring the ability to bind Klotho co-receptors, which is necessary to direct these ligands to their target organs.

Figures 10A, 10B, 10C, 10D, 10E, 10F:
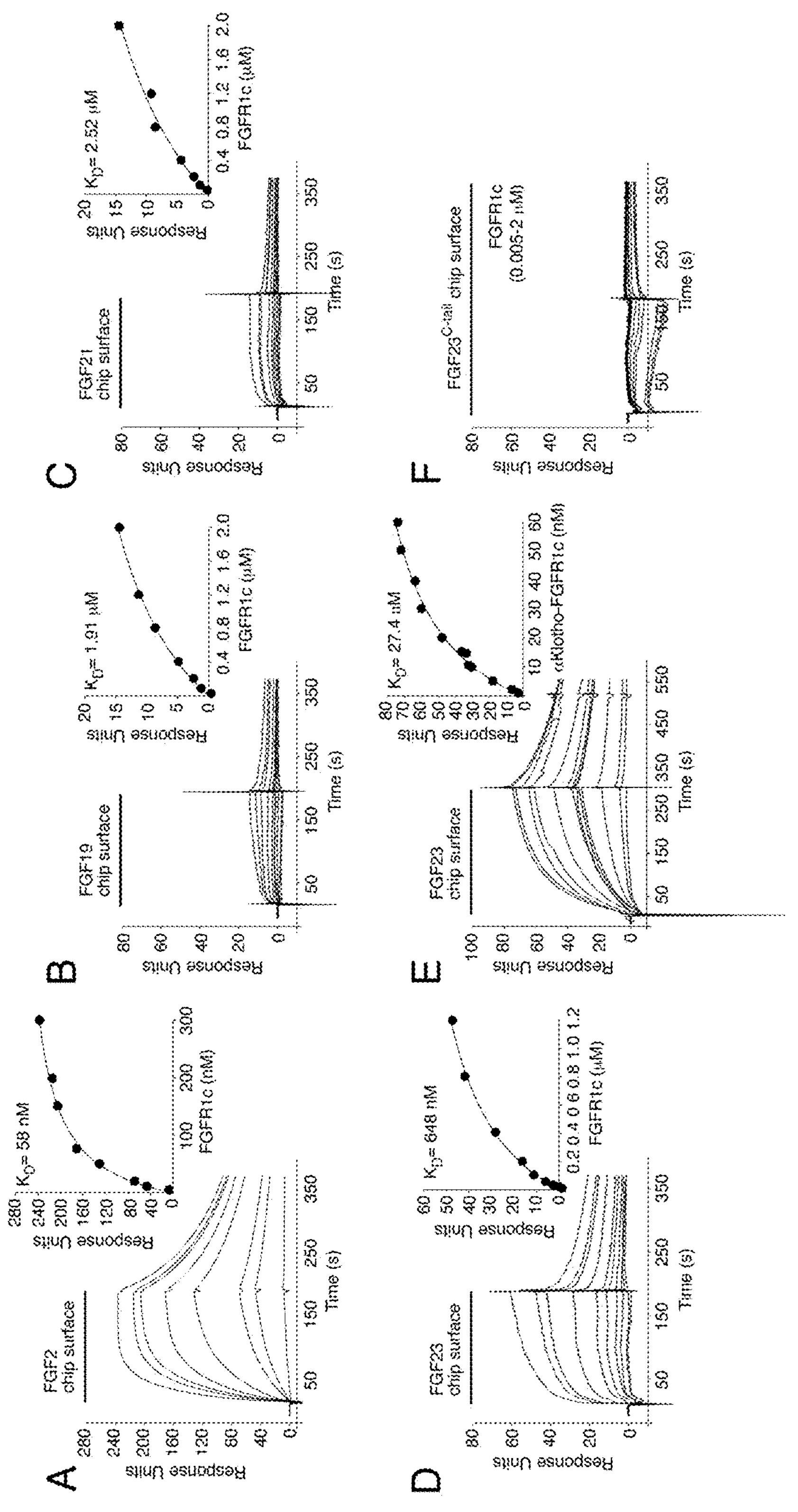
FIGS. 10A-10F show results demonstrating that endocrine FGFs have low binding affinity for FGFR1c compared to FGF2.

In the target tissue, Klotho co-receptors constitutively associate with cognate receptors of endocrine FGFs to offset the inherently low receptor-binding affinity of endocrine FGFs (FIGS. 10B-10D; Kurosu et al., J Biol. Chem. 282: 26687-26695 (2007); Kurosu et al., *J. Biol. Chem.* 281: 6120-6123 (2006); Ogawa et al., *Proc. Nat'l. Acad. Sci. U.S.A.* 104:7432-7437 (2007); Urakawa et al., *Nature* 444: 770-774 (2006), which are hereby incorporated by reference in their entirety). This low binding affinity is due to the fact that key receptor-binding residues in the β-trefoil core of endocrine FGFs are replaced by residues that are suboptimal for receptor binding (Goetz et al., *Mol. Cell Biol.* 27:3417-3428 (2007), which is hereby incorporated by reference in its entirety). To measure the degree to which Klotho co-receptors enhance the receptor-binding affinity of endocrine FGFs, SPR experiments were conducted using FGF23 and FGFR1c and αKlotho co-receptor as an example (see FIGS. 10A-10F). The SPR data show that αKlotho enhances the affinity of FGF23 for FGFR1c by over 20-fold (FIGS. 10D and 10E). The affinity of FGF23 for FGFR1c in the presence of αKlotho is comparable to that of FGF2 for FGFR1c in the absence of its HS cofactor (FIGS. 10A and 10E). It should be noted, however, that HS further increases the binding affinity of FGF2 for FGFR1c by at least an order of magnitude (Pantoliano et al., *Biochemistry* 33:10229-10248 (1994); Roghani et al., *J. Biol. Chem.* 269:3976-3984 (1994), which are hereby incorporated by reference in their entirety). Hence, the receptor-binding affinity of FGF23 in the presence of αKlotho co-receptor still is lower than that of FGF2 in the presence of HS cofactor. These observations imply that the signaling capacity of the endocrine FGF signal transduction unit should be weaker than that of the paracrine FGF signaling unit. Indeed, cell-based studies show that even in the presence of their Klotho co-receptor, endocrine FGFs are inferior to paracrine FGFs at activating FGFR-induced intracellular signaling pathways (Kurosu et al., *J. Biol. Chem.* 282:26687-26695 (2007); Urakawa et al., *Nature* 444:770-774 (2006), which are hereby incorporated by reference in their entirety).

The finding that endocrine FGFs do not need to rely on HS for signaling has another important implication in regard to the role of Klotho co-receptors. Since FGFR dimerization is a prerequisite for FGF signaling in general, it is proposed that Klotho co-receptors not only enhance the binding affinity of endocrine ligand for receptor but also promote receptor dimerization upon ligand binding. In other words, Klotho co-receptors must fulfill the same dual role that HS plays in signaling by paracrine FGFs (FIG. 1D). The ligand conversion also provides the framework for the rational design of endocrine FGF-like molecules for the treatment of metabolic disorders. An FGF23-like molecule, for example, will be useful for the treatment of inherited or acquired hyperphosphatemia, and an FGF21-like molecule, for example, for the treatment of type 2 diabetes, obesity, and related metabolic disorders.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A chimeric protein comprising:

an N-terminus coupled to a C-terminus, wherein the N-terminus comprises an FGF1 portion beginning at any one of residues 1 to 25 and ending at any one of residues 150 to 155 of SEQ ID NO: 1, wherein the FGF1 amino acid positions corresponding to those selected from the group consisting of N33, K127, K128, N129, K133, R134, R137, Q142, K143, and combinations thereof are substituted to decrease binding affinity for heparin and/or heparan sulfate compared to FGF1 without substitution, and wherein the C-terminus comprises a C-terminal portion of an FGF23 comprising amino acid residues 161-251 of SEQ ID NO: 233.

2. The chimeric protein according to claim 1, wherein the FGF1 portion is amino acid residues 1-150 of SEQ ID NO: 1.

3. The chimeric protein according to claim 1, wherein the FGF1 portion is amino acid residues 1-151, 1-152, 1-153, 1-154, 1-155, 2-150, 2-151, 2-152, 2-153, 2-154, 2-155, 3-150, 3-151, 3-152, 3-153, 3-154, 3-155, 4-150, 4-151, 4-152, 4-153, 4-154, 4-155, 5-150, 5-151, 5-152, 5-153, 5-154, 5-155, 6-150, 6-151, 6-152, 6-153, 6-154, 6-155, 7-150, 7-151, 7-152, 7-153, 7-154, 7-155, 8-150, 8-151, 8-152, 8-153, 8-154, 8-155, 9-150, 9-151, 9-152, 9-153, 9-154, 9-155, 10-150, 10-151, 10-152, 10-153, 10-154, 10-155, 11-150, 11-151, 11-152, 11-153, 11-154, 11-155, 12-150, 12-151, 12-152, 12-153, 12-154, 12-155, 13-150, 13-151, 13-152, 13-153, 13-154, 13-155, 14-150, 14-151, 14-152, 14-153, 14-154, 14-155, 15-150, 15-151, 15-152, 15-153, 15-154, 15-155, 16-150, 16-151, 16-152, 16-153, 16-154, 16-155, 17-150, 17-151, 17-152, 17-153, 17-154, 17-155, 18-150, 18-151, 18-152, 18-153, 18-154, 18-155, 19-150, 19-151, 19-152, 19-153, 19-154, 19-155, 20-150, 20-151, 20-152, 20-153, 20-154, 20-155, 21-150, 21-151, 21-152, 21-153, 21-154, 21-155, 22-150, 22-151, 22-152, 22-153, 22-154, 22-155, 23-150, 23-151, 23-152, 23-153, 23-154, 23-155, 24-150, 24-151, 24-152, 24-153, 24-154, 24-155, 25-151, 25-152, 25-153, 25-154, or 25-155 of SEQ ID NO: 1.

4. The chimeric protein according to claim 1, wherein the one or more substitutions are selected from the group consisting of N33T; K127D; K128Q; N129T; K133V; R134L; R137H; Q142M; K143T, K143L, or K143I; and combinations thereof.

5. A pharmaceutical composition comprising the chimeric protein according to claim 1 and a pharmaceutically-acceptable carrier.

6. The pharmaceutical composition according to claim 5 further comprising:

a hypophosphatemic agent, a phosphate binder, a vitamin D antagonist, an analgesic and/or an anti-inflammatory agent.

7. The chimeric protein according to claim 1, wherein the FGF1 portion is amino acid residues 25-150 of SEQ ID NO: 1.

8. The chimeric protein according to claim 1, wherein the chimeric protein comprises the amino acid sequence of SEQ ID NO: 321 or SEQ ID NO: 322.

9. The chimeric protein according to claim 1, wherein the one or more amino acid substitutions comprises a substitution at amino acid residue N33.

10. The chimeric protein according to claim 9, wherein the substitution is N33T.

11. The chimeric protein according to claim 1, wherein the one or more amino acid substitutions comprises a substitution at amino acid residue K127.

12. The chimeric protein according to claim 11, wherein the substitution is K127D.

13. The chimeric protein according to claim 1, wherein the one or more amino acid substitutions comprises a substitution at amino acid residue K128.

14. The chimeric protein according to claim 13, wherein the substitution is K128Q.

15. The chimeric protein according to claim 1, wherein the one or more amino acid substitutions comprises a substitution at amino acid residue N129.

16. The chimeric protein according to claim 15, wherein the substitution is N129T.

17. The chimeric protein according to claim 1, wherein the one or more amino acid substitutions comprises a substitution at amino acid residue K133.

18. The chimeric protein according to claim 17, wherein the substitution is K133V.

19. The chimeric protein according to claim 1, wherein the one or more amino acid substitutions comprises a substitution at amino acid residue R134.

20. The chimeric protein according to claim 19, wherein the substitution is R134L.

21. The chimeric protein according to claim 1, wherein the one or more amino acid substitutions comprises a substitution at amino acid residue R137.

22. The chimeric protein according to claim 21, wherein the substitution is R137H.

23. The chimeric protein according to claim 1, wherein the one or more amino acid substitutions comprises a substitution at amino acid residue Q142.

24. The chimeric protein according to claim 23, wherein the substitution is Q142M.

25. The chimeric protein according to claim 1, wherein the one or more amino acid substitutions comprises a substitution at amino acid residue K143.

26. The chimeric protein according to claim 25, wherein the substitution is K143T.

27. The chimeric protein according to claim 25, wherein the substitution is K143L.

28. The chimeric protein according to claim 25, wherein the substitution is K143I.

29. The chimeric protein of claim 1, wherein the one or more amino acid substitutions comprises substitutions at amino acid residues K127, K128, and K133.

30. The chimeric protein of claim 29, wherein the one or more amino acid substitutions are K127D, K128Q, and K133V.

* * * * *

SEQUENCE LISTING

```
<160> NUMBER OF SEQ ID NOS: 334

<210> SEQ ID NO 1
<211> LENGTH: 155
<212> TYPE: PRT
<213> ORGANISM: Homo sapiens

<400> SEQUENCE: 1

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 2
<211> LENGTH: 155
<212> TYPE: PRT
<213> ORGANISM: Papio Anubis

<400> SEQUENCE: 2

Met Ala Glu Gly Glu Ile Thr Thr Phe Thr Ala Leu Thr Glu Lys Phe
1               5                   10                  15

Asn Leu Pro Pro Ala Asn Tyr Lys Lys Pro Lys Leu Leu Tyr Cys Ser
            20                  25                  30
```

Asn Gly Gly His Phe Leu Arg Ile Leu Pro Asp Gly Thr Val Asp Gly
35 40 45

Thr Arg Asp Arg Ser Asp Gln His Ile Gln Leu Gln Leu Ser Ala Glu
50 55 60

Ser Val Gly Glu Val Tyr Ile Lys Ser Thr Glu Thr Gly Gln Tyr Leu
65 70 75 80

Ala Met Asp Thr Asp Gly Leu Leu Tyr Gly Ser Gln Thr Pro Asn Glu
85 90 95

Glu Cys Leu Phe Leu Glu Arg Leu Glu Glu Asn His Tyr Asn Thr Tyr
100 105 110

Ile Ser Lys Lys His Ala Glu Lys Asn Trp Phe Val Gly Leu Lys Lys
115 120 125

Asn Gly Ser Cys Lys Arg Gly Pro Arg Thr His Tyr Gly Gln Lys Ala
130 135 140

Ile Leu Phe Leu Pro Leu Pro Val Ser Ser Asp
145 150 155

<210> SEQ ID NO 3
<211> LENGTH: 155
<212> TYPE: PRT
<213> ORGANISM: Pongo abelii

<400> SEQUENCE: 3

Met Ala Glu Gly Glu Ile Thr Thr Phe Thr Ala Leu Thr Glu Lys Phe
1 5 10 15

Asn Leu Pro Pro Gly Asn Tyr Lys Lys Pro Lys Leu Leu Tyr Cys Ser
20 25 30

Asn Gly Gly His Phe Leu Arg Ile Leu Pro Asp Gly Thr Val Asp Gly
35 40 45

Thr Arg Asp Arg Ser Asp Gln His Ile Gln Leu Gln Leu Ser Ala Glu
50 55 60

Ser Val Gly Glu Val Tyr Ile Lys Ser Thr Glu Thr Gly Gln Tyr Leu
65 70 75 80

Ala Met Asp Thr Asp Gly Leu Leu Tyr Gly Ser Gln Thr Pro Asn Glu
85 90 95

Glu Cys Leu Phe Leu Glu Arg Leu Glu Glu Asn His Tyr Asn Thr Tyr
100 105 110

Ile Ser Lys Lys His Ala Glu Lys Asn Trp Phe Val Gly Leu Lys Lys
115 120 125

Asn Gly Ser Cys Lys Arg Gly Pro Arg Thr His Tyr Gly Gln Lys Ala
130 135 140

Ile Leu Phe Leu Pro Leu Pro Val Ser Ser Asp
145 150 155

<210> SEQ ID NO 4
<211> LENGTH: 155
<212> TYPE: PRT
<213> ORGANISM: Callithrix jacchus

<400> SEQUENCE: 4

Met Ala Glu Gly Glu Ile Thr Thr Phe Thr Ala Leu Thr Glu Lys Phe
1 5 10 15

Asp Leu Pro Pro Gly Asn Tyr Lys Lys Pro Lys Leu Leu Tyr Cys Ser
20 25 30

Asn Gly Gly His Phe Leu Arg Ile Leu Pro Asp Gly Thr Val Asp Gly
35 40 45

```
Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 5
<211> LENGTH: 155
<212> TYPE: PRT
<213> ORGANISM: Equus caballus

<400> SEQUENCE: 5

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 6
<211> LENGTH: 155
<212> TYPE: PRT
<213> ORGANISM: Pan troglodytes

<400> SEQUENCE: 6

Met Ala Glu Gly Glu Ile Thr Thr Phe Thr Ala Leu Thr Glu Lys Phe
1               5                   10                  15

Asn Leu Pro Ser Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60
```

```
Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 7
<211> LENGTH: 155
<212> TYPE: PRT
<213> ORGANISM: Loxodonta africana

<400> SEQUENCE: 7

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Gly Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 8
<211> LENGTH: 155
<212> TYPE: PRT
<213> ORGANISM: Canis lupus familiaris

<400> SEQUENCE: 8

Met Ala Glu Gly Glu Ile Thr Thr Phe Thr Ala Leu Thr Glu Lys Phe
1               5                   10                  15

Asn Leu Pro Pro Gly Asn Tyr Met Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80
```

```
Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 9
<211> LENGTH: 155
<212> TYPE: PRT
<213> ORGANISM: Ailuropoda melanoleuca

<400> SEQUENCE: 9

Met Ala Glu Gly Glu Ile Thr Thr Phe Thr Ala Leu Thr Glu Lys Phe
1               5                   10                  15

Asn Leu Pro Ala Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 10
<211> LENGTH: 155
<212> TYPE: PRT
<213> ORGANISM: Saimiri boliviensis boliviensis

<400> SEQUENCE: 10

Met Ala Glu Gly Glu Ile Thr Thr Phe Thr Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95
```

```
Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 11
<211> LENGTH: 155
<212> TYPE: PRT
<213> ORGANISM: Sus scrofa

<400> SEQUENCE: 11

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Ser Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 12
<211> LENGTH: 155
<212> TYPE: PRT
<213> ORGANISM: Otolemur garnettii

<400> SEQUENCE: 12

Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Gln Asp Arg Ser Asp Gln His Ile Gln Leu Gln Leu Ser Ala Glu
    50                  55                  60

Ser Val Gly Glu Val Tyr Ile Lys Ser Thr Gln Thr Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110
```

Val Ser Lys Lys His Ala Glu Lys Asn Trp Phe Val Gly Leu Lys Lys
115 120 125

Asn Gly Ser Cys Lys Arg Gly Pro Arg Thr His Tyr Gly Gln Lys Ala
130 135 140

Ile Leu Phe Leu Pro Leu Pro Val Ser Ser Asp
145 150 155

<210> SEQ ID NO 13
<211> LENGTH: 155
<212> TYPE: PRT
<213> ORGANISM: Rhinolophus ferrumequinum

<400> SEQUENCE: 13

Met Ala Glu Gly Glu Val Thr Thr Phe Thr Ala Leu Thr Glu Lys Phe
1 5 10 15

Asn Leu Pro Thr Gly Asn Tyr Lys Lys Pro Lys Leu Leu Tyr Cys Ser
20 25 30

Asn Gly Gly His Phe Leu Arg Ile Leu Pro Asp Gly Thr Val Asp Gly
35 40 45

Thr Arg Asp Lys Ser Asp Gln His Ile Gln Leu Gln Leu Ser Ala Glu
50 55 60

Ser Val Gly Glu Val Tyr Ile Lys Ser Thr Glu Ser Gly Gln Tyr Leu
65 70 75 80

Ala Met Asp Ser Asp Gly Leu Leu Tyr Gly Ser Gln Thr Pro Asn Glu
85 90 95

Glu Cys Leu Phe Leu Glu Arg Leu Glu Glu Asn His Tyr Asn Thr Tyr
100 105 110

Thr Ser Lys Lys His Ala Glu Lys Asn Trp Phe Val Gly Leu Lys Lys
115 120 125

Asn Gly Ser Cys Lys Arg Gly Pro Arg Thr His Tyr Gly Gln Lys Ala
130 135 140

Ile Leu Phe Leu Pro Leu Pro Val Ser Ser Asp
145 150 155

<210> SEQ ID NO 14
<211> LENGTH: 155
<212> TYPE: PRT
<213> ORGANISM: Sorex araneus

<400> SEQUENCE: 14

Met Ala Glu Gly Glu Ile Thr Thr Phe Gly Ala Leu Met Glu Lys Phe
1 5 10 15

Asn Leu Pro Pro Gly Asn Tyr Lys Lys Pro Lys Leu Leu Tyr Cys Ser
20 25 30

Asn Gly Gly His Phe Leu Arg Ile Leu Pro Asp Gly Thr Val Asp Gly
35 40 45

Thr Arg Asp Arg Ser Asp Gln His Ile Gln Leu Gln Leu Ser Ala Glu
50 55 60

Ser Val Gly Glu Val Tyr Ile Lys Ser Thr Glu Thr Gly His Tyr Leu
65 70 75 80

Ala Met Asp Thr Asp Gly Leu Leu Tyr Gly Ser Gln Thr Pro Asn Glu
85 90 95

Glu Cys Leu Phe Leu Glu Arg Leu Glu Glu Asn His Tyr Asn Thr Tyr
100 105 110

Thr Ser Lys Lys His Ala Glu Lys Asn Trp Phe Val Gly Leu Lys Lys
115 120 125

```
Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 15
<211> LENGTH: 155
<212> TYPE: PRT
<213> ORGANISM: Oryctolagus cuniculus

<400> SEQUENCE: 15

Met Ala Glu Gly Glu Val Thr Thr Phe Thr Ala Leu Thr Glu Lys Phe
1               5                   10                  15

Asn Leu Pro Ala Gly Asn Tyr Lys Leu Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 16
<211> LENGTH: 155
<212> TYPE: PRT
<213> ORGANISM: Cricetulus griseus

<400> SEQUENCE: 16

Met Ala Glu Gly Glu Ile Thr Thr Phe Ser Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Arg
65                  70                  75                  80

Asn Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140
```

-continued

```
Ile Leu Phe Leu Pro Leu Pro Val Ser Ser Asp
145                 150                 155


<210> SEQ ID NO 17
<211> LENGTH: 155
<212> TYPE: PRT
<213> ORGANISM: Sarcophilus harrisii

<400> SEQUENCE: 17

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Thr Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155


<210> SEQ ID NO 18
<211> LENGTH: 155
<212> TYPE: PRT
<213> ORGANISM: Mus musculus

<400> SEQUENCE: 18

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 19
<211> LENGTH: 154
<212> TYPE: PRT
<213> ORGANISM: Cavia porcellus

<400> SEQUENCE: 19

```
Met Ala Glu Gly Glu Ile Thr Thr Phe Ala Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Gly Val Gly Glu Val Tyr Ile Gln Ser Thr Glu Thr Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Val Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Asp
145                 150
```

<210> SEQ ID NO 20
<211> LENGTH: 155
<212> TYPE: PRT
<213> ORGANISM: Monodelphis domestica

<400> SEQUENCE: 20

```
Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Thr Glu
    50                  55                  60

Ser Val Gly Glu Val Tyr Ile Lys Ser Thr Glu Ser Gly Gln Tyr Leu
65                  70                  75                  80

Ala Met Asp Thr Asp Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Lys Gly Pro Arg Thr His Tyr Gly Gln Lys Ala
    130                 135                 140

Ile Leu Phe Leu Pro Leu Pro Val Ser Ser Glu
145                 150                 155
```

<210> SEQ ID NO 21

<211> LENGTH: 155
<212> TYPE: PRT
<213> ORGANISM: Desmodus rotundus

<400> SEQUENCE: 21

```
Met Ala Glu Gly Glu Val Thr Thr Phe Thr Ala Leu Thr Glu Lys Phe
1               5                   10                  15

Asn Leu Pro Leu Glu Ser Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Gly Ser Gly Gln Tyr Leu
65                  70                  75                  80

Ala Met Asp Ser Ala Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Asn Ser Asp
145                 150                 155
```

<210> SEQ ID NO 22
<211> LENGTH: 155
<212> TYPE: PRT
<213> ORGANISM: Bos taurus

<400> SEQUENCE: 22

```
Met Ala Glu Gly Glu Thr Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly Tyr Phe Leu Arg Ile Leu Pro Asp Gly Thr Val Asp Gly
        35                  40                  45

Thr Lys Asp Arg Ser Asp Gln His Ile Gln Leu Gln Leu Cys Ala Glu
    50                  55                  60

Ser Ile Gly Glu Val Tyr Ile Lys Ser Thr Glu Thr Gly Gln Phe Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys His Trp Phe Val Gly Leu Lys Lys
        115                 120                 125

Asn Gly Arg Ser Lys Leu Gly Pro Arg Thr His Phe Gly Gln Lys Ala
    130                 135                 140

Ile Leu Phe Leu Pro Leu Pro Val Ser Ser Asp
145                 150                 155
```

<210> SEQ ID NO 23
<211> LENGTH: 155
<212> TYPE: PRT
<213> ORGANISM: Ornithorhynchus anatinus

<400> SEQUENCE: 23

Met Ala Glu Gly Glu Ile Thr Thr Phe Thr Ala Leu Met Glu Lys Phe
1               5                   10                  15

Asp Leu Pro Leu Gly Asn Tyr Lys Lys Pro Arg Leu Leu Tyr Cys Ser
            20                  25                  30

Asn Gly Gly Tyr Phe Leu Arg Ile Gln Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly His Tyr Leu
65                  70                  75                  80

Ala Met Asp Thr Glu Gly Leu Leu Tyr Gly Ser Gln Ala Pro Ser Glu
                85                  90                  95

Asp Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ala Ser Asp
145                 150                 155

<210> SEQ ID NO 24
<211> LENGTH: 155
<212> TYPE: PRT
<213> ORGANISM: Taeniopygia guttata

<400> SEQUENCE: 24

Met Ala Glu Gly Glu Ile Thr Thr Phe Ser Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Val Val His Ile Gln Ser Thr Gln Ser Gly Gln Tyr Leu
65                  70                  75                  80

Ala Met Asp Thr Asn Gly Leu Leu Tyr Gly Ser Gln Leu Pro Pro Gly
                85                  90                  95

Glu Cys Leu Phe Leu Glu Arg Leu Glu Glu Asn His Tyr Asn Thr Tyr
            100                 105                 110

Val Ser Lys Met His Ala Asp Lys Asn Trp Phe Val Gly Leu Lys Lys
        115                 120                 125

Asn Gly Thr Ser Lys Leu Gly Pro Arg Thr His Tyr Gly Gln Lys Ala
    130                 135                 140

Ile Leu Phe Leu Pro Leu Pro Val Ala Ala Asp
145                 150                 155

<210> SEQ ID NO 25
<211> LENGTH: 155
<212> TYPE: PRT
<213> ORGANISM: Dasypus novemcinctus

<400> SEQUENCE: 25

Met Ala Glu Gly Glu Ile Thr Thr Phe Met Ala Leu Met Glu Lys Phe
1 5 10 15

Asn Leu Pro Leu Glu Asn Tyr Lys His Pro Arg Leu Leu Tyr Cys Arg
20 25 30

Asn Gly Gly His Phe Leu Arg Ile Leu Pro Asp Gly Thr Val Asp Gly
35 40 45

Thr Arg Asp Arg Ser Asp Gln His Ile Gln Leu Gln Leu Ser Ala Glu
50 55 60

Ser Val Gly Glu Val Tyr Ile Lys Ser Ala Glu Thr Gly Gln Tyr Leu
65 70 75 80

Ala Met Asp Thr Asp Gly Leu Leu Tyr Gly Ser Glu Thr Pro Ser Glu
85 90 95

Glu Cys Leu Phe Met Glu Lys Leu Glu Glu Asn Asn Tyr Asn Thr Tyr
100 105 110

Ile Ser Lys Lys His Ala Glu Lys Lys Trp Phe Val Gly Leu Lys Lys
115 120 125

Asp Gly Ser Ser Lys Arg Gly Pro Gln Thr His Tyr Gly Gln Lys Ala
130 135 140

Ile Leu Phe Leu Pro Leu Pro Val Ser Ser Asp
145 150 155

<210> SEQ ID NO 26
<211> LENGTH: 155
<212> TYPE: PRT
<213> ORGANISM: Xenopus Silurana tropicalis

<400> SEQUENCE: 26

Met Ala Glu Gly Asp Ile Thr Thr Phe Asn Pro Ile Ala Glu Ser Phe
1 5 10 15

Ser Leu Pro Ile Gly Asn Tyr Lys Lys Pro Lys Leu Leu Tyr Cys Asn
20 25 30

Asn Gly Gly Tyr Phe Leu Arg Ile Leu Pro Asp Gly Val Val Asp Gly
35 40 45

Thr Arg Asp Arg Asp Asp Leu Tyr Ile Thr Leu Lys Leu Ser Ala Gln
50 55 60

Ser Gln Gly Glu Val His Ile Lys Ser Thr Glu Thr Gly Ser Tyr Leu
65 70 75 80

Ala Met Asp Ser Ser Gly Gln Leu Tyr Gly Thr Leu Thr Pro Asn Glu
85 90 95

Glu Ser Leu Phe Leu Glu Thr Leu Glu Glu Asn His Tyr Asn Thr Tyr
100 105 110

Lys Ser Lys Lys Tyr Ala Glu Asn Asn Trp Phe Val Gly Ile Lys Lys
115 120 125

Asn Gly Ala Ser Lys Lys Gly Ser Arg Thr His Tyr Gly Gln Lys Ala
130 135 140

Ile Leu Phe Leu Pro Leu Pro Ala Ser Pro Asp
145 150 155

<210> SEQ ID NO 27
<211> LENGTH: 155
<212> TYPE: PRT
<213> ORGANISM: Heterocephalus glaber

<400> SEQUENCE: 27

Met Ala Glu Gly Glu Ile Thr Thr Phe Thr Ala Leu Thr Glu Lys Phe
1 5 10 15

-continued

```
Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
    50                  55                  60

Gly Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Ala Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 28
<211> LENGTH: 155
<212> TYPE: PRT
<213> ORGANISM: Pteropus alecto

<400> SEQUENCE: 28

Met Ala Glu Gly Glu Val Thr Thr Phe Thr Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asp Glu
                85                  90                  95

Asp Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 29
<211> LENGTH: 155
<212> TYPE: PRT
<213> ORGANISM: Tupaia chinensis

<400> SEQUENCE: 29

Met Ala Glu Gly Glu Ile Thr Thr Phe Ala Ala Leu Thr Glu Lys Phe
1               5                   10                  15

Asp Leu Pro Pro Gly Asn Tyr Lys Lys Pro Lys Leu Leu Tyr Cys Ser
            20                  25                  30
```

```
Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Thr Ala Glu
    50                  55                  60

Asn Val Gly Glu Val Tyr Ile Lys Ser Thr Glu Thr Gly Gln Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Ala Leu Lys Lys
        115                 120                 125

Asn Gly Ser Cys Lys Leu Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 30
<211> LENGTH: 155
<212> TYPE: PRT
<213> ORGANISM: Columba livia

<400> SEQUENCE: 30

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Gln Ser Gly Gln Tyr Leu
65                  70                  75                  80

Ala Met Asp Pro Thr Gly Leu Leu Tyr Gly Ser Gln Leu Leu Gly Glu
                85                  90                  95

Glu Cys Leu Phe Leu Glu Arg Ile Glu Glu Asn His Tyr Asn Thr Tyr
            100                 105                 110

Val Ser Lys Lys His Ala Asp Lys Asn Trp Phe Val Gly Leu Lys Lys
        115                 120                 125

Asn Gly Asn Ser Lys Leu Gly Pro Arg Thr His Tyr Gly Gln Lys Ala
    130                 135                 140

Ile Leu Phe Leu Pro Leu Pro Val Ser Ala Asp
145                 150                 155


<210> SEQ ID NO 31
<211> LENGTH: 155
<212> TYPE: PRT
<213> ORGANISM: Ovis aries

<400> SEQUENCE: 31

Met Ala Glu Gly Glu Thr Thr Thr Phe Arg Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly Tyr Phe Leu Arg Ile Leu Pro Asp Gly Arg Val Asp Gly
        35                  40                  45
```

-continued

```
Thr Lys Asp Arg Ser Asp Gln His Ile Gln Leu Gln Leu Tyr Ala Glu
    50                  55                  60

Ser Ile Gly Glu Val Tyr Ile Lys Ser Thr Glu Thr Gly Gln Phe Leu
65                  70                  75                  80

Ala Met Asp Thr Asn Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Ile Gly Leu Lys Lys
        115                 120                 125

Asn Gly Ser Ser Lys Leu Gly Pro Arg Thr His Phe Gly Gln Lys Ala
    130                 135                 140

Ile Leu Phe Leu Pro Leu Pro Val Ser Ser Asp
145                 150                 155


<210> SEQ ID NO 32
<211> LENGTH: 155
<212> TYPE: PRT
<213> ORGANISM: Gallus gallus

<400> SEQUENCE: 32

Met Ala Glu Gly Glu Ile Thr Thr Phe Thr Ala Leu Thr Glu Arg Phe
1               5                   10                  15

Gly Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His Ile Gln Leu Gln Leu Ser Ala Glu
    50                  55                  60

Asp Val Gly Glu Val Tyr Ile Lys Ser Thr Ala Ser Gly Gln Tyr Leu
65                  70                  75                  80

Ala Met Asp Thr Asn Gly Leu Leu Tyr Gly Ser Gln Leu Pro Gly Glu
                85                  90                  95

Glu Cys Leu Phe Leu Glu Arg Leu Glu Glu Asn His Tyr Asn Thr Tyr
            100                 105                 110

Ile Ser Lys Lys His Ala Asp Lys Asn Trp Phe Val Gly Leu Lys Lys
        115                 120                 125

Asn Gly Asn Ser Lys Leu Gly Pro Arg Thr His Tyr Gly Gln Lys Ala
    130                 135                 140

Ile Leu Phe Leu Pro Leu Pro Val Ser Ala Asp
145                 150                 155


<210> SEQ ID NO 33
<211> LENGTH: 98
<212> TYPE: PRT
<213> ORGANISM: Vicugna pacos

<400> SEQUENCE: 33

Gln Leu Gln Leu Ser Ala Glu Ser Val Gly Glu Val Tyr Ile Lys Ser
1               5                   10                  15

Thr Glu Thr Gly Gln Tyr Leu Ala Met Asp Thr Asp Gly Leu Leu His
            20                  25                  30

Gly Ser Gln Thr Pro Asn Glu Glu Cys Leu Phe Leu Glu Arg Leu Glu
        35                  40                  45

Glu Asn His Tyr Asn Thr Tyr Thr Ser Lys Lys His Ala Glu Lys Asn
    50                  55                  60
```

-continued

Trp Phe Val Gly Leu Lys Lys Asn Gly Ser Cys Lys Arg Gly Pro Arg
65 70 75 80

Thr His Tyr Gly Gln Lys Ala Ile Leu Phe Leu Pro Leu Pro Val Ser
85 90 95

Ser Asp

<210> SEQ ID NO 34
<211> LENGTH: 155
<212> TYPE: PRT
<213> ORGANISM: Anolis carolinensis

<400> SEQUENCE: 34

Met Ala Glu Gly Glu Ile Thr Thr Phe Thr Ala Leu Thr Glu Arg Phe
1 5 10 15

Ala Leu Pro Met Glu Asn Tyr Lys Lys Pro Lys Leu Leu Tyr Cys Ser
20 25 30

Asn Gly Gly His Phe Leu Arg Ile Leu Pro Asp Gly Lys Val Asp Gly
35 40 45

Thr Met Asp Arg Asn Asp Ser Tyr Ile Gln Leu Leu Leu Thr Ala Glu
50 55 60

Asp Val Gly Val Val Tyr Ile Lys Gly Thr Glu Thr Gly Gln Tyr Leu
65 70 75 80

Ala Met Asp Ala Asn Gly His Leu Tyr Gly Ser Gln Leu Pro Thr Glu
85 90 95

Glu Cys Leu Phe Val Glu Thr Leu Glu Glu Asn His Tyr Asn Thr Tyr
100 105 110

Thr Ser Lys Met His Gly Asp Lys Lys Trp Tyr Val Gly Leu Lys Lys
115 120 125

Asn Gly Lys Gly Lys Leu Gly Pro Arg Thr His Arg Gly Gln Lys Ala
130 135 140

Ile Leu Phe Leu Pro Leu Pro Val Ser Pro Asp
145 150 155

<210> SEQ ID NO 35
<211> LENGTH: 155
<212> TYPE: PRT
<213> ORGANISM: Otolemur garnettii

<400> SEQUENCE: 35

Met Ala Glu Gly Glu Ile Thr Thr Phe Thr Ala Leu Thr Glu Lys Phe
1 5 10 15

Asn Leu Pro Leu Gly Asn Tyr Lys Lys Pro Lys Leu Leu Tyr Cys Ser
20 25 30

Asn Gly Gly His Phe Leu Arg Ile Leu Pro Asp Gly Thr Val Asp Gly
35 40 45

Thr Gln Asp Arg Ser Asp Gln His Ile Gln Leu Gln Leu Ser Ala Glu
50 55 60

Ser Val Gly Glu Val Tyr Ile Lys Ser Thr Gln Thr Gly Gln Tyr Leu
65 70 75 80

Ala Met Asp Ser Asp Gly Leu Leu Tyr Gly Ser Gln Thr Pro Asn Glu
85 90 95

Glu Cys Leu Phe Leu Glu Arg Leu Glu Glu Asn His Tyr Asn Thr Tyr
100 105 110

Val Ser Lys Lys His Ala Glu Lys Asn Trp Phe Val Gly Leu Lys Lys
115 120 125

Asn Gly Ser Cys Lys Arg Gly Pro Arg Thr His Tyr Gly Gln Lys Ala

```
    130                 135                 140

Ile Leu Phe Leu Pro Leu Pro Val Ser Ser Asp
145                 150                 155


<210> SEQ ID NO 36
<211> LENGTH: 155
<212> TYPE: PRT
<213> ORGANISM: Felis catus

<400> SEQUENCE: 36

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 37
<211> LENGTH: 155
<212> TYPE: PRT
<213> ORGANISM: Pelodiscus sinensis

<400> SEQUENCE: 37

Met Ala Glu Gly Glu Ile Thr Thr Phe Thr Ala Leu Thr Glu Lys Phe
1               5                   10                  15

Asn Leu Pro Leu Gly Asn Tyr Lys Asn Pro Lys Leu Leu Tyr Cys Ser
            20                  25                  30

Asn Gly Gly Tyr Phe Leu Arg Ile His Pro Asp Gly Lys Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly Gln Phe Leu
65                  70                  75                  80

Ala Met Asp Ala Asn Gly Leu Leu Tyr Gly Ser Leu Ser Pro Ser Glu
                85                  90                  95

Glu Cys Leu Phe Leu Glu Arg Met Glu Glu Asn His Tyr Asn Thr Tyr
            100                 105                 110

Ile Ser Lys Lys His Ala Asp Lys Asn Trp Phe Val Gly Leu Lys Lys
        115                 120                 125

Asn Gly Ser Cys Lys Leu Gly Pro Arg Thr His Tyr Gly Gln Lys Ala
    130                 135                 140

Val Leu Phe Leu Pro Leu Pro Val Ser Ala Asp
```

```
145                 150                 155


<210> SEQ ID NO 38
<211> LENGTH: 155
<212> TYPE: PRT
<213> ORGANISM: Latimeria chalumnae

<400> SEQUENCE: 38

Met Ala Glu Asp Lys Ile Thr Thr Leu Lys Ala Leu Ala Glu Lys Phe
1               5                   10                  15

Asn Leu Pro Met Gly Asn Tyr Lys Lys Ala Lys Leu Leu Tyr Cys Ser
            20                  25                  30

Asn Gly Gly Tyr Phe Leu Arg Ile Pro Pro Asp Gly Lys Val Glu Gly
        35                  40                  45

Ile Arg Glu Arg Ser Asp Lys Tyr Ile Gln Leu Gln Met Asn Ala Glu
    50                  55                  60

Ser Leu Gly Met Val Ser Ile Lys Gly Val Glu Ala Gly Gln Tyr Leu
65                  70                  75                  80

Ala Met Asn Thr Asn Gly Leu Leu Tyr Gly Ser Gln Ser Leu Thr Glu
                85                  90                  95

Glu Cys Leu Phe Met Glu Lys Met Glu Glu Asn His Tyr Asn Thr Tyr
            100                 105                 110

Arg Ser Lys Thr His Ala Asp Lys Asn Trp Tyr Val Gly Ile Arg Lys
        115                 120                 125

Asn Gly Ser Ile Lys Pro Gly Pro Arg Thr His Ile Gly Gln Lys Ala
    130                 135                 140

Val Leu Phe Leu Pro Leu Pro Ala Ser Ser Asp
145                 150                 155


<210> SEQ ID NO 39
<211> LENGTH: 155
<212> TYPE: PRT
<213> ORGANISM: Tursiops truncatus

<400> SEQUENCE: 39

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ala Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 40
<211> LENGTH: 155
<212> TYPE: PRT
<213> ORGANISM: Mustela putorius furo

<400> SEQUENCE: 40

```
Met Ala Glu Gly Glu Ile Thr Thr Phe Thr Ala Leu Met Glu Lys Phe
1               5                   10                  15

Asn Leu Pro Ala Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 41
<211> LENGTH: 155
<212> TYPE: PRT
<213> ORGANISM: Nomascus leucogenys

<400> SEQUENCE: 41

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 42
<211> LENGTH: 155
<212> TYPE: PRT

<213> ORGANISM: Gorilla gorilla

<400> SEQUENCE: 42

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 43
<211> LENGTH: 155
<212> TYPE: PRT
<213> ORGANISM: Erinaceus europaeus

<400> SEQUENCE: 43

```
Met Ala Glu Gly Glu Ile Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 44
<211> LENGTH: 91
<212> TYPE: PRT
<213> ORGANISM: Procavia capensis

<400> SEQUENCE: 44

```
Met Ala Glu Gly Glu Ile Thr Thr Phe Thr Ala Leu Thr Glu Lys Phe
1               5                   10                  15

Asn Leu Pro Leu Glu Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Gly Thr Glu Thr Gly Gln Tyr Leu
65                  70                  75                  80

Ala Met Asp Thr Asp Gly Leu Leu Tyr Gly Ser
                85                  90


<210> SEQ ID NO 45
<211> LENGTH: 114
<212> TYPE: PRT
<213> ORGANISM: Dipodomys ordii

<400> SEQUENCE: 45

Met Ala Glu Gly Glu Ile Thr Thr Phe Thr Ala Leu Thr Glu Arg Phe
1               5                   10                  15

Gln Leu Gln Leu Ser Ala Glu Ser Val Gly Glu Val Tyr Ile Lys Ser
            20                  25                  30

Thr Glu Thr Gly Gln Tyr Leu Ala Met Asp Ala Asp Gly Leu Leu Tyr
        35                  40                  45

Gly Ser Gln Thr Pro Asp Glu Glu Cys Leu Phe Leu Glu Arg Leu Glu
    50                  55                  60

Glu Asn His Tyr Asn Thr Tyr Ile Ala Lys Lys His Ala Glu Lys Asn
65                  70                  75                  80

Trp Phe Val Gly Leu Lys Lys Asn Gly Ser Cys Lys Arg Gly Pro Arg
                85                  90                  95

Thr His Tyr Gly Gln Lys Ala Ile Leu Phe Leu Pro Leu Pro Val Ser
            100                 105                 110

Ser Asp


<210> SEQ ID NO 46
<211> LENGTH: 92
<212> TYPE: PRT
<213> ORGANISM: Petromyzon marinus

<400> SEQUENCE: 46

Met Glu Val Gly His Ile Gly Thr Leu Pro Val Val Pro Ala Gly Pro
1               5                   10                  15

Val Phe Pro Gly Ser Phe Lys Glu Pro Arg Arg Leu Tyr Cys Arg Ser
            20                  25                  30

Ala Gly His His Leu Gln Ile Leu Gly Asp Gly Thr Val Ser Gly Thr
        35                  40                  45

Gln Asp Glu Asn Glu Pro His Ala Val Leu Gln Leu Gln Ala Val Arg
    50                  55                  60

Arg Gly Val Val Thr Ile Arg Gly Leu Cys Ala Glu Arg Phe Leu Ala
65                  70                  75                  80

Met Ser Thr Glu Gly His Leu Tyr Gly Ala Val Arg
                85                  90


<210> SEQ ID NO 47
<211> LENGTH: 98
```

-continued

<212> TYPE: PRT
<213> ORGANISM: Echinops telfairi

<400> SEQUENCE: 47

Gln Leu Lys Leu Val Ala Glu Ser Val Gly Val Val Tyr Ile Lys Ser
1               5                   10                  15

Ile Lys Thr Gly Gln Tyr Leu Ala Met Asn Pro Asp Gly Leu Leu Tyr
            20                  25                  30

Gly Ser Glu Thr Pro Glu Glu Glu Cys Leu Phe Leu Glu Thr Leu Glu
        35                  40                  45

Glu Asn His Tyr Thr Thr Phe Lys Ser Lys Lys His Val Glu Lys Asn
    50                  55                  60

Trp Phe Val Gly Leu Arg Lys Asn Gly Arg Val Lys Ile Gly Pro Arg
65                  70                  75                  80

Thr His Gln Gly Gln Lys Ala Ile Leu Phe Leu Pro Leu Pro Val Ser
                85                  90                  95

Ser Asp

<210> SEQ ID NO 48
<211> LENGTH: 155
<212> TYPE: PRT
<213> ORGANISM: Macaca mulatta

<400> SEQUENCE: 48

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 49
<211> LENGTH: 155
<212> TYPE: PRT
<213> ORGANISM: Pteropus vampyrus

<400> SEQUENCE: 49

Met Ala Glu Gly Glu Val Thr Thr Phe Thr Ala Leu Thr Glu Arg Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Lys Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asp Glu
                85                  90                  95

Asp Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 50
<211> LENGTH: 155
<212> TYPE: PRT
<213> ORGANISM: Myotis lucifugus

<400> SEQUENCE: 50

Met Ala Glu Gly Glu Val Thr Thr Phe Thr Ala Leu Thr Glu Arg Phe
1               5                   10                  15

Asn Leu Pro Leu Glu Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Ser Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 51
<211> LENGTH: 155
<212> TYPE: PRT
<213> ORGANISM: Microcebus murinus

<400> SEQUENCE: 51

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Ser Thr Gln Thr Gly Arg Tyr Leu
65 70 75 80

Ala Met Asp Ala Asp Gly Leu Leu Tyr Gly Ser Gln Thr Pro Asn Glu
85 90 95

Glu Cys Leu Phe Leu Glu Arg Leu Glu Glu Asn His Tyr Asn Thr Tyr
100 105 110

Val Ser Lys Lys His Ala Glu Lys Asn Trp Phe Val Gly Leu Lys Lys
115 120 125

Asn Gly Ser Cys Lys Arg Gly Pro Arg Thr His Tyr Gly Gln Lys Ala
130 135 140

Ile Leu Phe Leu Pro Leu Pro Val Ser Ser Asp
145 150 155

<210> SEQ ID NO 52
<211> LENGTH: 144
<212> TYPE: PRT
<213> ORGANISM: Ochotona princeps

<400> SEQUENCE: 52

Met Ala Glu Gly Glu Val Thr Thr Phe Ser Ala Leu Thr Glu Lys Phe
1 5 10 15

Asn Leu Pro Gly Gly Asn Tyr Lys Leu Pro Lys Leu Leu Tyr Cys Ser
20 25 30

Asn Gly Gly His Phe Leu Arg Ile Leu Pro Asp Gly Thr Val Asp Gly
35 40 45

Thr Arg Asp Arg Ser Asp Leu His Glu Val Phe Ile Lys Ser Thr Glu
50 55 60

Thr Gly Gln Tyr Leu Ala Met Asp Thr Asp Gly Leu Leu Tyr Gly Ser
65 70 75 80

Gln Thr Pro Ser Glu Glu Cys Leu Phe Leu Glu Arg Leu Glu Glu Asn
85 90 95

His Tyr Asn Thr Tyr Thr Ser Lys Lys His Ala Glu Lys Asn Trp Phe
100 105 110

Val Gly Ile Lys Lys Asn Gly Ser Cys Lys Arg Gly Pro Arg Thr His
115 120 125

Tyr Gly Gln Lys Ala Ile Leu Phe Leu Pro Leu Pro Val Ser Ser Asp
130 135 140

<210> SEQ ID NO 53
<211> LENGTH: 155
<212> TYPE: PRT
<213> ORGANISM: Rattus norvegicus

<400> SEQUENCE: 53

Met Ala Glu Gly Glu Ile Thr Thr Phe Ala Ala Leu Thr Glu Arg Phe
1 5 10 15

Asn Leu Pro Leu Gly Asn Tyr Lys Lys Pro Lys Leu Leu Tyr Cys Ser
20 25 30

Asn Gly Gly His Phe Leu Arg Ile Leu Pro Asp Gly Thr Val Asp Gly
35 40 45

Thr Arg Asp Arg Ser Asp Gln His Ile Gln Leu Gln Leu Ser Ala Glu
50 55 60

Ser Ala Gly Glu Val Tyr Ile Lys Gly Thr Glu Thr Gly Gln Tyr Leu
65 70 75 80

Ala Met Asp Thr Glu Gly Leu Leu Tyr Gly Ser Gln Thr Pro Asn Glu
85 90 95

```
Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 54
<211> LENGTH: 155
<212> TYPE: PRT
<213> ORGANISM: Choloepus hoffmanni

<400> SEQUENCE: 54

Met Ala Glu Gly Glu Ile Thr Thr Phe Thr Ala Leu Met Glu Lys Phe
1               5                   10                  15

Asn Leu Pro Pro Gly Asn Tyr Met Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Leu His Ile Gln Leu Gln Leu Ser Ala Glu
    50                  55                  60

Ser Val Gly Glu Val Tyr Ile Lys Ser Ala Glu Thr Gly Gln Tyr Leu
65                  70                  75                  80

Ala Met Asp Thr Gly Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Ser Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 55
<211> LENGTH: 155
<212> TYPE: PRT
<213> ORGANISM: Ictidomys tridecemlineatus

<400> SEQUENCE: 55

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110
```

```
Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 56
<211> LENGTH: 155
<212> TYPE: PRT
<213> ORGANISM: Tarsius syrichta

<400> SEQUENCE: 56

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Val Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 57
<211> LENGTH: 155
<212> TYPE: PRT
<213> ORGANISM: Tupaia belangeri

<400> SEQUENCE: 57

Met Ala Glu Gly Glu Ile Thr Thr Phe Ala Ala Leu Thr Glu Lys Phe
1               5                   10                  15

Asp Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Thr Ala Glu
    50                  55                  60

Asn Val Gly Glu Val Tyr Ile Lys Ser Thr Glu Thr Gly Gln Tyr Leu
65                  70                  75                  80

Ala Met Asp Ala Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Ala Leu Lys Lys
        115                 120                 125
```

```
Asn Gly Ser Cys Lys Leu Gly Pro Arg Thr His Tyr Gly Gln Lys Ala
    130                 135                 140

Ile Leu Phe Leu Pro Leu Pro Val Ser Ser Asp
145                 150                 155


<210> SEQ ID NO 58
<211> LENGTH: 56
<212> TYPE: PRT
<213> ORGANISM: Meleagris gallopavo

<400> SEQUENCE: 58

Met Ala Glu Gly Glu Ile Thr Thr Phe Thr Ala Leu Thr Glu Arg Phe
1               5                   10                  15

Gly Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Ser Asp Gln His
    50                  55


<210> SEQ ID NO 59
<211> LENGTH: 155
<212> TYPE: PRT
<213> ORGANISM: Macropus eugenii

<400> SEQUENCE: 59

Met Ala Glu Gly Glu Ile Thr Thr Phe Thr Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Lys Val Asp Gly
        35                  40                  45

Thr Arg Asp Arg Asn Asp Gln His Ile Gln Leu Gln Leu Ser Ala Glu
    50                  55                  60

Ser Val Gly Glu Val Tyr Ile Lys Ser Thr Glu Ser Gly Gln Tyr Leu
65                  70                  75                  80

Ala Met Asp Thr Asn Gly Leu Leu Tyr Gly Ser Gln Thr Pro Ser Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Glu
145                 150                 155


<210> SEQ ID NO 60
<211> LENGTH: 147
<212> TYPE: PRT
<213> ORGANISM: Danio rerio

<400> SEQUENCE: 60

Met Thr Glu Ala Asp Ile Ala Val Lys Ser Ser Pro Arg Asp Tyr Lys
1               5                   10                  15

Lys Leu Thr Arg Leu Tyr Cys Met Asn Gly Gly Phe His Leu Gln Ile
            20                  25                  30
```

Leu Ala Asp Gly Thr Val Ala Gly Ala Ala Asp Glu Asn Thr Tyr Ser
            35                  40                  45

Ile Leu Arg Ile Lys Ala Thr Ser Pro Gly Val Val Ile Glu Gly
 50                  55                  60

Ser Glu Thr Gly Leu Tyr Leu Ser Met Asn Glu His Gly Lys Leu Tyr
 65                  70                  75                  80

Ala Ser Ser Leu Val Thr Asp Glu Ser Tyr Phe Leu Glu Lys Met Glu
                85                  90                  95

Glu Asn His Tyr Asn Thr Tyr Gln Ser Gln Lys His Gly Glu Asn Trp
            100                 105                 110

Tyr Val Gly Ile Lys Lys Asn Gly Lys Met Lys Arg Gly Pro Arg Thr
            115                 120                 125

His Ile Gly Gln Lys Ala Ile Phe Phe Leu Pro Arg Gln Val Glu Gln
            130                 135                 140

Glu Glu Asp
145

<210> SEQ ID NO 61
<211> LENGTH: 468
<212> TYPE: DNA
<213> ORGANISM: Homo sapiens

<400> SEQUENCE: 61
atggctgaag gggaaatcac caccttcaca gccctgaccg agaagtttaa tctgcctcca     60
gggaattaca agaagcccaa actcctctac tgtagcaacg ggggccactt cctgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatggg agctgcaaac gcggtcctcg gactcactat    420
ggccagaaag caatcttgtt tctccccctg ccagtctctt ctgattaa                 468

<210> SEQ ID NO 62
<211> LENGTH: 468
<212> TYPE: DNA
<213> ORGANISM: Olive Baboon

<400> SEQUENCE: 62
atggctgaag gggaaatcac cacgttcaca gccctgaccg agaagtttaa tctgcctcca     60
gcgaattaca agaagcccaa actgctctac tgtagcaacg ggggacactt cttgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctacatat ccaagaagca cgcagagaag    360
aattggtttg ttggcctcaa gaagaatgga agctgcaaac gtggtcctcg gactcactat    420
ggccagaaag caatcttgtt tcttcccctg ccagtctctt ctgattaa                 468

<210> SEQ ID NO 63
<211> LENGTH: 468
<212> TYPE: DNA
<213> ORGANISM: Sumatran orangutan

<400> SEQUENCE: 63

```
atggctgaag gggaaatcac caccttcaca gccctgaccg agaagtttaa tctgcctcca      60

gggaattaca agaagcccaa actcctctac tgtagcaacg ggggccactt cttgaggatc     120

cttccggatg gcacagtgga tgggacaagg gacaggagcg accagcacat tcagctgcag     180

ctcagtgcgg aaagcgtggg ggaggtgtat ataaagagta ccgagactgg ccagtacttg     240

gccatggaca ccgacgggct tttatacggc tcacagacac caaatgagga atgtttgttc     300

ctggaaaggc tggaggagaa ccattacaac acctatatat ccaagaagca tgcagagaag     360

aattggtttg ttggcctcaa gaagaatgga agctgcaaac gcggtcctcg gactcactat     420

ggccagaaag caatcttgtt tctccccctg ccagtctctt ccgattaa                  468
```

<210> SEQ ID NO 64
<211> LENGTH: 468
<212> TYPE: DNA
<213> ORGANISM: White-tufted-ear marmoset

<400> SEQUENCE: 64

```
atggctgaag gggaaatcac caccttcaca gccctgaccg agaagtttga tctgcctcca      60

gggaattaca agaagcccaa actcctctac tgtagcaatg ggggccactt cttgaggatc     120

cttccggatg gcacagtgga tgggacaagg gacaggagcg accagcacat tcagctgcag     180

ctcagtgcgg aaagcgtggg ggaggtgtat ataaagagta ccgagactgg ccagtacttg     240

gccatggaca ccgacgggct tttatacggc tcacagacac caaatgagga atgtttgttc     300

ctggagaggc tggaggagaa ccattacaac acctatatat ccaagaaaca tgcagagaag     360

aattggtttg tcggcctcaa gaagaatgga agctgtaaac gtggtcctcg gactcactat     420

ggtcagaaag cgatcttgtt tctccccctg ccagtttctt ctgattaa                  468
```

<210> SEQ ID NO 65
<211> LENGTH: 468
<212> TYPE: DNA
<213> ORGANISM: Horse

<400> SEQUENCE: 65

```
atggctgaag gagaaatcac aaccttcacg gccctgaccg agaagtttaa tctgcctcca      60

gggaattaca agaagcccaa actcctctac tgtagcaatg ggggccactt cctgaggatc     120

cttccagatg gcacagtgga tgggacaagg gacaggagcg accagcacat tcagctgcag     180

ctcagtgcgg aaagcgtggg ggaggtgtat ataaagagta ccgagactgg ccagtacttg     240

gccatggaca ccgacgggct gttgtacggc tcacagacac caaacgagga atgtttgttc     300

ctggaaaggc tggaggaaaa ccattacaac acctacacat ccaagaagca tgcagagaag     360

aactggttcg ttggtctcaa gaagaatggg agctgcaaac gcggtcctcg gactcactat     420

gggcagaaag caatcttgtt tcttcccctg cccgtctcct ctgactaa                  468
```

<210> SEQ ID NO 66
<211> LENGTH: 468
<212> TYPE: DNA
<213> ORGANISM: Chimpanzee

<400> SEQUENCE: 66

```
atggctgaag gggaaatcac caccttcaca gccctgaccg agaagtttaa tctgccttca      60

gggaattaca agaagcccaa actcctctac tgtagcaacg ggggccactt cctgaggatc     120

cttccggatg gcacagtgga tgggacaagg gacaggagcg accagcacat tcagctgcag     180
```

-continued

```
ctcagtgcgg aaagcgtggg ggaggtgtat ataaagagta ccgagactgg ccagtacttg    240

gccatggaca ccgacgggct tttatacggc tcacagacac caaatgagga atgtttgttc    300

ctggaacggc tggaggagaa ccattacaac acctatatat ccaagaagca tgcagagaag    360

aattggtttg ttggcctcaa gaagaatgga agctgcaaac gcggtcctcg gactcactat    420

ggccagaaag caatcttgtt tctccccctg ccagtctctt ccgattaa                 468
```

```
<210> SEQ ID NO 67
<211> LENGTH: 468
<212> TYPE: DNA
<213> ORGANISM: Elephant

<400> SEQUENCE: 67

atggccgaag ggaaatcac aactttcaca gccctgacag agaagttcaa cctgcctcca     60

gggaattaca agaagcccaa actcctctac tgtagcaatg gaggtcactt cttaaggatc    120

cttccagatg gcacagtgga tggcaccagg gacaggagtg accagcacat tcagctgcag    180

ctcagtgcgg aaagcgtggg ggaggtgtat ataaagggca ccgagactgg ccagtacttg    240

gccatggaca ccgacgggct tttatacggc tcacagacac caaatgagga atgtttgttc    300

ctggaaaggc tggaggaaaa ccattacaac acctacacat ccaagaagca cgcagagaag    360

aattggttcg ttggtctcaa gaagaatgga agctgcaaac gcggtcctcg gactcactat    420

ggccagaaag caatcttgtt tctccccctg ccagtctcct ctgattaa                 468
```

```
<210> SEQ ID NO 68
<211> LENGTH: 468
<212> TYPE: DNA
<213> ORGANISM: Dog

<400> SEQUENCE: 68

atggctgaag ggaaatcac aaccttcact gccctgacgg agaagtttaa tctgcctccg     60

gggaattaca tgaagcccaa actcctctac tgtagcaacg gggccactt cctgaggatc     120

cttccagatg gcacagtgga tgggacaagg gacaggagcg accagcacat tcagctgcag    180

ctcagcgcgg aaagcgtggg ggaggtgtat ataaagagca ccgagactgg ccagtacttg    240

gccatggaca ccgatgggct tctgtacggc tcacagacac cgaatgagga atgtttgttc    300

ctggaaaggc tggaggaaaa ccattacaac acctacacat ccaagaagca tgcagaaaaa    360

aattggtttg ttggtctcaa gaagaatgga agctgcaaac gcggtcctcg gactcactat    420

ggtcaaaaag caattttgtt tctccccctg ccagtgtcct ctgattaa                 468
```

```
<210> SEQ ID NO 69
<211> LENGTH: 468
<212> TYPE: DNA
<213> ORGANISM: Giant panda

<400> SEQUENCE: 69

atggctgaag ggagatcac aaccttcacc gccctgacgg agaagtttaa tctgcctgcg     60

gggaattaca agaagcccaa actcctctac tgtagcaacg gggccactt cctgaggatc     120

cttccagatg gcacagtgga cgggacgagg gacaggagcg accagcacat tcaactgcag    180

ctcagcgcgg aaagcgtagg ggaggtgtac ataaagagca ccgagaccgg ccagtacttg    240

gccatggaca ccgatgggct tctgtacggc tcacagacac caaatgagga atgtttgttc    300

ctggaaaggc tggaggaaaa ccattacaac acctacacat ccaagaagca cgcggagaag    360

aattggtttg ttggtctcaa gaagaatgga agctgcaaac gtggtcctcg gactcactat    420
```

ggccagaaag caattctgtt tctccccctg ccagtctcct ctgattaa 468

<210> SEQ ID NO 70
<211> LENGTH: 468
<212> TYPE: DNA
<213> ORGANISM: Bolivian squirrel monkey

<400> SEQUENCE: 70
atggctgaag gggaaatcac cacctttaca gccctgaccg agaagtttga tctgcctcca 60
gggaattaca agaagcccaa actcctctac tgtagcaacg gggccactt cttgaggatc 120 cttccggatg gcacagtgga tgggaccagg gacaggagcg atcttcacat tcagctgcag 180
ctcagtgcgg aaagcgtggg ggaggtgtat ataaagagta ccgagactgg ccagtacttg 240
gccatggaca ccgacgggct tttatacggc tcacagacac caaatgagga atgtttgttc 300
ctggaaaggc tggaggagaa ccattacaac acctatatat ccaagaaaca cgcagagaag 360
aattggtttg ttggcctcaa gaagaatgga agctgcaagc gcggtcctcg gactcactat 420
ggccagaaag caatcttgtt tctccccctg ccagtctctt ctgattaa 468

<210> SEQ ID NO 71
<211> LENGTH: 468
<212> TYPE: DNA
<213> ORGANISM: Pig

<400> SEQUENCE: 71
atggctgaag gcgaaatcac aaccttcacg gccctgaccg agaagtttaa tctgcctcca 60
ggaaattaca agaagcccaa gctcctctac tgcagcaacg gggccattt cctcaggatc 120 cttccagatg gcacagtgga tgggaccagg gacaggagcg accagcacat tcagctgcag 180
ctcagtgcgg aaagcgtggg ggaggtgtat ataaagagta cggagactgg ccagtacttg 240
gccatggaca ccagcgggct tttgtacggc tcacagacac ccagtgagga gtgtttgttc 300
ctggagaggc tggaggaaaa ccattacaat acctacacat ccaagaagca cgcagagaag 360
aactggttcg ttggcctcaa gaagaatgga agctgcaaac gcggtcctcg gactcactat 420
ggccagaaag ccatcctgtt tctccccctg ccagtatcct cggattaa 468

<210> SEQ ID NO 72
<211> LENGTH: 468
<212> TYPE: DNA
<213> ORGANISM: Small-eared galago

<400> SEQUENCE: 72
atggctgaag gggaaatcac aaccttcaca gccctcacag agaagtttaa tctgcctcta 60
ggaaattaca agaagcccaa gctcctctac tgtagcaacg gggtcactt tctgaggatc 120 ctgccggatg gcaccgtgga tgggacacaa gacaggagcg accagcacat tcagctgcag 180
ctcagtgcgg aaagcgtggg ggaggtgtat ataaagagta cccagactgg ccagtacttg 240
gccatggact ccgacgggct tttatacggc tcacaaacac caaatgagga atgcctgttc 300
ctggaacggc tggaggaaaa ccattacaac acctatgtgt ccaagaagca cgccgagaag 360
aattggtttg tcggtctcaa gaagaacgga agttgcaaac gtggtcctcg gactcactac 420
ggccagaaag caatcttgtt tctccccctg ccagtctcct ctgattaa 468

<210> SEQ ID NO 73
<211> LENGTH: 468
<212> TYPE: DNA

<213> ORGANISM: Greater horseshoe bat

<400> SEQUENCE: 73
ttaatcagag gagactggca gggggagaaa caggattgct ttctggccat agtgagtccg 60
aggaccgcgc ttgcagcttc cattcttctt gagcccaacg aaccaattct tttctgcgtg 120
cttcttggac gtgtaggtgt tgtaatggtt ttcctccagc ctttccagga acagacattc 180
ctcatttggt gtctgtgagc cgtacaaaag cccgtcggag tccatggcca agtactggcc 240
actctcggtg ctctttatat acacctcccc cacgctttcc gcactgagct gcagctgaat 300
gtgctggtca ctcttgtccc ttgtcccatc cactgtgcca tctggaagga tcctcaggaa 360
gtggcccccg ttgctgcagt agagaagttt gggtttcttg taattccctg taggcagatt 420
aaacttctca gtaagggctg tgaacgtggt gacttcccct tcggccat 468

<210> SEQ ID NO 74
<211> LENGTH: 468
<212> TYPE: DNA
<213> ORGANISM: European shrew

<400> SEQUENCE: 74
ctagtcggag gagacgggca gggggagaaa caagatcgct ttctggccgt agtgagtccg 60
gggaccacgc ttgcagcttc cgttcttctt cagaccaaca aaccaattct tctcggcatg 120
cttcttggag gtataggtgt tgtaatggtt ttcctccagc ctttccagaa acagacattc 180
ctcattcggt gtttgtgagc cgtataaaag cccgtcggtg tccatggcca agtaatggcc 240
agtctccgtg ctctttatat acacctcccc cacgctttcc gcactgagct gcagctgaat 300
gtgctggtcg ctgcggtccc tggtcccatc cactgtgccg tccgggagga tgcgcaggaa 360
gtggcccccg ttgctgcagt acaggagttt gggcttcttg tagttccctg gtggcaggtt 420
aaacttctcc atgagggccc caaaggtggt gatctccccc tcggccat 468

<210> SEQ ID NO 75
<211> LENGTH: 468
<212> TYPE: DNA
<213> ORGANISM: Rabbit

<400> SEQUENCE: 75
atggctgagg gggaggtcac caccttcaca gccctgaccg agaagttcaa cctgcctgca 60
gggaactaca agttgcccaa actcctctac tgcagcaacg gggccactt cctgaggatc 120 ctgccggacg gcactgtgga cggcacaagg gacaggagcg accagcacat tcagctgcag 180
ctgagtgcgg aaagcgtggg ggaggtgtat ataaagagta cggagaccgg ccagtacttg 240
gccatggaca ccgacggcct tttatacggc tcgcaaacgc ccagtgagga gtgtttgttc 300
ctggaacggc tggaggagaa ccactacaac acctacacgt ccaagaagca cgccgagaag 360
aactggttcg tggggctgaa gaaaaacggg agctgcaagc gcggtcctcg gactcactac 420
ggccagaaag ccatcttgtt cctccccctg ccggtctcct ccgactaa 468

<210> SEQ ID NO 76
<211> LENGTH: 468
<212> TYPE: DNA
<213> ORGANISM: Chinese hamster

<400> SEQUENCE: 76
atggctgaag gagaaatcac caccttctca gccctgacag agagatttaa tctgcctcca 60
ggaaactaca agaagcccaa actgctctac tgcagcaacg gggccactt cttgaggatc 120

```
cttccagatg gcacagtgga tgggacaagg gacaggagtg accagcacat tcagctgcag    180

ctgagtgcgg aaagcgcggg cgaagtgtat ataaagggta cagagacagg ccagtacagg    240

aacatggaca cggatggcct tttatacggc tcacagacac caaatgaaga atgcctgttc    300

ctggaaaggc tggaagaaaa ccattacaac acttatacat ccaagaagca cgcagagaag    360

aactggtttg tgggcctcaa gaaaaacggg agctgcaagc gtggtcctcg gactcactat    420

ggccagaaag caatcttgtt tctccccctg cctgtatctt ctgactag                 468
```

<210> SEQ ID NO 77
<211> LENGTH: 468
<212> TYPE: DNA
<213> ORGANISM: Tasmanian devil

<400> SEQUENCE: 77

```
atggccgaag gggagatcac aaccttcaca gccctgaccg aaagatttaa tctgccactg     60

gggaattaca agaagcccaa gcttctctac tgtagcaatg gggggccactt tttgaggatt    120

cttcctgatg gtaaagtgga tgggacaagg gacagaaatg atcaacacat tcaactgcaa    180

ctaagcgcgg aaagcgtggg tgaggtgtat ataaagagca ctgagtctgg ccagtatttg    240

gctatggaca ccgatggact tttatacggc tcacagacac ccactgaaga atgcttgttc    300

ctggagagat tggaggagaa tcattacaac acctacatat caaagaagca tgcggagaaa    360

aattggtttg tgggcctcaa gaaaaatgga agctgcaaaa gaggtcccag gactcactat    420

ggccagaaag ccatcctctt ccttcccctc cctgtgtcct ctgagtaa                 468
```

<210> SEQ ID NO 78
<211> LENGTH: 468
<212> TYPE: DNA
<213> ORGANISM: House mouse

<400> SEQUENCE: 78

```
atggctgaag gggagatcac aaccttcgca gccctgaccg agaggttcaa cctgcctcta     60

ggaaactaca aaaagcccaa actgctctac tgcagcaacg gggggccactt cttgaggatc    120

cttcctgatg gcaccgtgga tgggacaagg gacaggagcg accagcacat tcagctgcag    180

ctcagtgcgg aaagtgcggg cgaagtgtat ataaagggta cggagaccgg ccagtacttg    240

gccatggaca ccgaagggct tttatacggc tcgcagacac caaatgagga atgtctgttc    300

ctggaaaggc tggaagaaaa ccattataac acttacacct ccaagaagca tgcggagaag    360

aactggtttg tgggcctcaa gaagaacggg agctgtaagc gcggtcctcg gactcactat    420

ggccagaaag ccatcttgtt tctgcccctc ccggtgtctt ctgactag                 468
```

<210> SEQ ID NO 79
<211> LENGTH: 465
<212> TYPE: DNA
<213> ORGANISM: Domestic guinea pig

<400> SEQUENCE: 79

```
atggctgaag gagaaatcac aacttttgca gccctgactg agaagtttaa tctgcctcca     60

gggaattata agaagcccaa actgctctac tgcagcaatg gggggccactt cctgaggatc    120

cttccagacg gcacagtgga cggcacaaga gacaggagcg accagcacat tcagctgcag    180

ctcagtgcgg aaggcgtggg ggaggtgtat atacagagca ccgagaccgg ccagtacttg    240

gccatggaca ccgacgggct tttatacggc tcacagacac caagtgagga atgcttgttc    300
```

```
ctggaaaggc tggaggaaaa ccattacaac acctacacat ccaagaagca tgtggagaag    360

aattggtttg ttggcctcaa gaagaacgga agctgcaagc gtggtcctcg gactcactat    420

ggccagaaag caatcttgtt cctccccttg ccagtctctg attag                    465


<210> SEQ ID NO 80
<211> LENGTH: 468
<212> TYPE: DNA
<213> ORGANISM: Gray short-tailed opossum

<400> SEQUENCE: 80

atggccgaag gggagatcac aaccttcaca gccctgactg aaagatttaa cctgccactg     60

gggaattaca agaaacccaa gcttctctac tgtagcaatg ggggccattt cttgaggatc    120

cttcctgatg gcaaagtgga tgggacacgg gacagaaatg atcaacacat tcaactgcag    180

ctgagcacgg aaagtgtggg tgaggtgtat ataaagagca ctgagtctgg ccagtatttg    240

gctatggaca ccgatggact tttatatggc tcacagacac ccagtgaaga atgcttgttt    300

ctggagaggt tggaggagaa tcattacaac acctacacat cgaagaagca tgcagagaaa    360

aattggtttg ttggtctcaa gaagaatgga agctgcaaaa agggtcccag gactcactac    420

ggccagaaag ccatcctgtt ccttcccctc cctgtgtcct ctgagtaa                 468


<210> SEQ ID NO 81
<211> LENGTH: 468
<212> TYPE: DNA
<213> ORGANISM: Common vampire bat

<400> SEQUENCE: 81

atggctgaag ggaagtcac cacgttcaca gctctgactg agaagtttaa tctgcctctg      60

gagagttaca agaagcccaa acttctctac tgcagcaacg gtggccactt cctgaggatc    120

cttccagatg gtacagtgga tgggacaagg gacaagagcg accagcacat tcagctgcag    180

ctcagtgcgg aaagcgtggg ggaggtgtac ataaagagca ccgggagtgg ccagtacttg    240

gccatggact ccgccgggct tttgtatggc tcacagacac caaatgagga atgtttgttc    300

ctggaaaggc tggaggaaaa ccattacaac acctacacat ccaagaagca tgcagaaaag    360

aattggttcg tggggctcaa gaagaatgga agctgcaagc gtggcccccg gactcattat    420

ggccagaaag caatcttgtt tctccccctg ccagtcaact ctgattaa                 468


<210> SEQ ID NO 82
<211> LENGTH: 468
<212> TYPE: DNA
<213> ORGANISM: Cattle

<400> SEQUENCE: 82

atggctgaag gagaaaccac gaccttcacg gccctgactg agaagtttaa cctgcctcta     60

ggcaattaca agaagcccaa gctcctctac tgcagcaacg ggggctactt cctgagaatc    120

ctcccagatg gcacagtgga tgggacgaag gacaggagcg accagcacat tcagctgcag    180

ctctgtgcgg aaagcatagg ggaggtgtat attaagagta cggagactgg ccagttcttg    240

gccatggaca ccgacgggct tttgtacggc tcacagacac ccaatgagga atgtttgttc    300

ctggaaaggt tggaggaaaa ccattacaac acctacatat ccaagaagca tgcagagaag    360

cattggttcg ttggtctcaa gaagaacgga aggtctaaac tcggtcctcg gactcacttc    420

ggccagaaag ccatcttgtt tctccccctg ccagtctcct ctgattaa                 468
```

<210> SEQ ID NO 83
<211> LENGTH: 468
<212> TYPE: DNA
<213> ORGANISM: Platypus

<400> SEQUENCE: 83
atggcggagg gtgaaatcac cacgttcaca gccctgatgg agaagttcga cctacccctg 60
ggcaactaca aaaagcctag gctgctctac tgcagcaatg gcggctactt cctgcgcatc 120
cagccagacg gtaaagtgga cgggaccagg gatcggagcg atcagcacat tcaactgcag 180
ctaagcgcgg aaagcgtggg cgaggtgtat ataaagagca ccgagtctgg ccactatttg 240
gctatggaca ccgaaggact tttatatggc tcacaggcac ccagtgaaga ctgcttgttc 300
ctggagcggc tggaggagaa ccactataac acgtacgtgt ccaagaagca cgctgagaag 360
aattggtttg tcggtctcaa gaagaacggg agctgcaaac gaggtccccg gactcactac 420
ggccagaaag ccatcctctt cctcccgctc cccgtggcat ccgactag 468

<210> SEQ ID NO 84
<211> LENGTH: 468
<212> TYPE: DNA
<213> ORGANISM: Zebra finch

<400> SEQUENCE: 84
atggccgagg gggagatcac caccttcagc gccctgacgg agaagttcaa cctgcccccg 60
gggaactaca agaagcccaa actgctgtac tgcagcaacg gggggcattt cctgcgcatc 120
ctcccggacg gcaccgtgga tggcaccagg gaccgcagcg accagcacat tcagctccag 180
ctgagtgcag agagcgtggg ggtggtgcac atccagagca cccagtcggg gcagtacctg 240
gccatggaca ccaacgggct gctctacggc tcgcagctgc cacccggtga gtgtctgttc 300
ctggaaaggc tggaggagaa ccattacaac acctacgtct ccaaaatgca cgcggacaag 360
aactggtttg tggggctgaa gaagaacggg acaagcaagc tgggcccgcg gactcactac 420
ggccagaagg cgatcctgtt cctgccgctg cccgtggcgg ccgactga 468

<210> SEQ ID NO 85
<211> LENGTH: 468
<212> TYPE: DNA
<213> ORGANISM: Nine-banded armadillo

<400> SEQUENCE: 85
ttaatcagag gagactggca ggggaagaaa caagatagct ttctggccat agtgagtctg 60
aggaccacgt ttgctgcttc cgtccttctt gagaccaaca aaccatttct tctctgcatg 120
cttcttggat atgtaggtgt tgtaattgtt ttcttccagc ttttccatga acaagcattc 180
ctcacttggt gtctctgagc catataaaag cccgtcggtg tccatggcta agtactggcc 240
ggtctctgca ctctttatat acacctcccc cacgctttcc gcactgagct gcagctgaat 300
gtgttggtcg ctcctgtccc ttgtcccatc caccgtgcca tctggaagga tcctcaagaa 360
gtggcccccg tttctgcagt agaggagtct ggggtgcttg taattttcta ggggcaggtt 420
gaacttctcc atcagggcca tgaaggttgt gatctcccct tcagccat 468

<210> SEQ ID NO 86
<211> LENGTH: 468
<212> TYPE: DNA
<213> ORGANISM: Xenopus Silurana tropicalis

<400> SEQUENCE: 86

```
atggcagagg gagacatcac aacattcaac cccattgcag agtccttcag tcttccaatt     60

ggcaactaca agaaaccaaa acttctgtac tgtaataatg gagggtattt tttgcgcatc    120

ctcccagatg ggggttgtgga tggaacaaga gacagagatg acctttacat tacactgaag    180

ttaagcgcac aaagccaagg ggaggtgcat atcaaaagca cagagacagg gagttactta    240

gccatggact ccagtggaca gttgtatgga actctcacac caaatgaaga aagcctgttt    300

ctggagacat tagaagagaa tcactataac acatacaagt caaagaagta tgcagaaaat    360

aactggtttg tggggataaa gaagaacggg gcaagcaaaa agggatcaag gactcactat    420

ggacaaaaag ccatcctttt tctgccgctg ccagcatcac ctgactag                  468
```

<210> SEQ ID NO 87
<211> LENGTH: 465
<212> TYPE: DNA
<213> ORGANISM: Heterocephalus glaber

<400> SEQUENCE: 87

```
atggcggaag gcgaaattac cacctttacc gcgctgaccg aaaaatttaa cctgccgccg     60

ggcaactata aaaaaccgaa actgctgtat tgcagcaacg gcggccattt tctgcgcatt    120

ctgccggatg gcaaagtgga tggcacccgc gatcgcagcg atcagcatat tcagctgcag    180

ctgagcgcgg aaggcgtggg cgaagtgtat attaaaagca ccgaaaccgg ccagtatctg    240

gcgatggata ccgatggcct gctgtatggc agccagaccg cgagcgaaga atgcctgttt    300

ctggaacgcc tggaagaaaa ccattataac acctatatta gcaaaaaaca tgcggaaaaa    360

aactggtttg tgggcctgaa aaaaaacggc agctgcaaac gcggcccgcg cacccattat    420

ggccagaaag cgattctgtt tctgccgctg ccggtgagca gcgat                    465
```

<210> SEQ ID NO 88
<211> LENGTH: 465
<212> TYPE: DNA
<213> ORGANISM: Black flying fox

<400> SEQUENCE: 88

```
atggcggaag gcgaagtgac cacctttacc gcgctgaccg aacgctttaa cctgccgccg     60

ggcaactata aaaaaccgaa actgctgtat tgcagcaacg gcggccattt tctgcgcatt    120

ctgccggatg gcaccgtgga tggcacccgc gataaaagcg atcagcatat tcagctgcag    180

ctgagcgcgg aaagcgtggg cgaagtgtat attaaaagca ccgaaagcgg ccagtatctg    240

gcgatggata gcgatggcct gctgtatggc agccagaccc cggatgaaga ttgcctgttt    300

ctggaacgcc tggaagaaaa ccattataac acctatacca gcaaaaaaca tgcggaaaaa    360

aactggtttg tgggcctgaa aaaaaacggc agctgcaaac gcggcccgcg cacccattat    420

ggccagaaag cgattctgtt tctgccgctg ccggtgagca gcgat                    465
```

<210> SEQ ID NO 89
<211> LENGTH: 465
<212> TYPE: DNA
<213> ORGANISM: Chinese tree shrew

<400> SEQUENCE: 89

```
atggcggaag gcgaaattac cacctttgcg gcgctgaccg aaaaatttga tctgccgccg     60

ggcaactata aaaaaccgaa actgctgtat tgcagcaacg gcggccattt tctgcgcatt    120

ctgccggatg gcaccgtgga tggcacccgc gatcgcagcg atcagcatat tcagctgcag    180

ctgaccgcgg aaaacgtggg cgaagtgtat attaaaagca ccgaaaccgg ccagtatctg    240
```

gcgatggatg cggatggcct gctgtatggc agccagaccc cgaacgaaga atgcctgttt 300
ctggaacgcc tggaagaaaa ccattataac acctatatta gcaaaaaaca tgcggaaaaa 360
aactggtttg tggcgctgaa aaaaaacggc agctgcaaac tgggcccgcg cacccattat 420
ggccagaaag cgattctgtt tctgccgctg ccggtgagca gcgat 465

<210> SEQ ID NO 90
<211> LENGTH: 465
<212> TYPE: DNA
<213> ORGANISM: Rock pigeon

<400> SEQUENCE: 90
atggcggaag gcgaaattac cacctttacc gcgctgaccg aaaaatttaa cctgccgccg 60
ggcaactata aaaaaccgaa actgctgtat tgcagcaacg gcggccattt tctgcgcatt 120
ctgccggatg gcaaagtgga tggcacccgc gatcgcagcg atcagcatat tcagctgcag 180
ctgagcgcgg aaagcgtggg cgaagtgtat attaaaagca cccagagcgg ccagtatctg 240
gcgatggatc cgaccggcct gctgtatggc agccagctgc tgggcgaaga atgcctgttt 300
ctggaacgca ttgaagaaaa ccattataac acctatgtga gcaaaaaaca tgcggataaa 360
aactggtttg tgggcctgaa aaaaaacggc aacagcaaac tgggcccgcg cacccattat 420
ggccagaaag cgattctgtt tctgccgctg ccggtgagcg cggat 465

<210> SEQ ID NO 91
<211> LENGTH: 468
<212> TYPE: DNA
<213> ORGANISM: Sheep

<400> SEQUENCE: 91
atggctgaag gagaaaccac aaccttcagg gccctgactg agaagtttaa cctgcctcta 60
ggcaattaca agaagcccaa gctcctctat tgcagcaacg gggcctactt cctgagaatc 120
ctcccagatg gcagagtgga tgggacgaag gacaggagcg accagcacat tcagctgcag 180
ctctatgcgg aaagcatagg ggaggtgtat attaagagta cggagactgg ccagttcttg 240
gccatggaca ccaacgggct tttgtacggc tcacaaacac ccagtgagga atgtttgttc 300
ctggaaaggc tggaggaaaa ccattataac acctacatat ccaagaagca tgcagagaag 360
aattggttca ttggtctcaa gaagaacgga agctccaaac tcggtcctcg gactcacttc 420
ggccagaaag ccatcttgtt tctccccctg ccagtttcct ctgattaa 468

<210> SEQ ID NO 92
<211> LENGTH: 468
<212> TYPE: DNA
<213> ORGANISM: Chicken

<400> SEQUENCE: 92
atggccgagg gggagataac caccttcacc gccctgaccg agcgcttcgg cctgccgctg 60
ggcaactaca agaagcccaa actcctgtac tgcagcaacg gggggccactt cctacggatc 120 ctgccggacg gcaaggtgga cgggacgcgg gaccggagtg accagcacat tcagctgcag 180
ctcagcgcgg aagatgtggg cgaggtctat ataaagagca cagcgtcggg gcagtacctg 240
gcaatggaca ccaacgggct cctgtatggc tcgcagctac caggcgagga gtgcttgttc 300
cttgagaggc tcgaggagaa ccattacaac acatacatct ccaaaaagca cgcagacaag 360
aactggttcg tcgggctgaa gaaaaacggg aacagcaagc tggggccgcg gactcactat 420
gggcaaaagg cgatcctctt cctcccattg ccggtgtcgg ctgactga 468

<210> SEQ ID NO 93
<211> LENGTH: 297
<212> TYPE: DNA
<213> ORGANISM: Alpaca

<400> SEQUENCE: 93
cagctgcagc tcagtgcgga aagcgtgggg gaggtgtata taaagagtac cgagactggc 60
cagtacttgg ccatggacac cgacgggctt ttgcacggct cacagacacc aaatgaggaa 120
tgtttgttcc tggaaaggct ggaggagaac cattacaaca cctacacgtc caagaagcac 180
gccgaaaaga attggtttgt tggtctcaag aagaatggaa gctgcaaacg cggtcctcgg 240
actcactacg gccagaaggc gatcttgttt ctccccttgc cagtctcctc tgattaa 297

<210> SEQ ID NO 94
<211> LENGTH: 468
<212> TYPE: DNA
<213> ORGANISM: Anole lizard

<400> SEQUENCE: 94
atggctgaag gtgaaataac aacattcaca gccttgaccg agaggtttgc tctcccaatg 60
gagaattaca agaagcccaa actcctgtat tgcagcaatg gaggccactt cctgaggatc 120
cttccagatg gaaaagtgga tggcaccatg gaccggaatg acagctatat tcagttgctg 180
ttaacagcag aagatgtggg tgtggtatat ataaaaggca ctgagaccgg gcagtacttg 240
gccatggatg ccaatggaca tttatatggc tcgcagttgc caacagaaga gtgtttattt 300
gtggaaacgc tggaagaaaa ccattacaat acatatacct caaagatgca tggcgataag 360
aagtggtatg ttggcttgaa aaagaatggg aaaggcaaac tggggccacg gactcatcgc 420
ggccaaaagg caatactttt ccttccactg ccagtatcac ctgattag 468

<210> SEQ ID NO 95
<211> LENGTH: 468
<212> TYPE: DNA
<213> ORGANISM: Bushbaby

<400> SEQUENCE: 95
atggctgaag gggaaatcac aaccttcaca gccctcacag agaagtttaa tctgcctcta 60
ggaaattaca agaagcccaa gctcctctac tgtagcaacg gggtcactt tctgaggatc 120 ctgccggatg gcaccgtgga tgggacacaa gacaggagcg accagcacat tcagctgcag 180
ctcagtgcgg aaagcgtggg ggaggtgtat ataaagagta cccagactgg ccagtacttg 240
gccatggact ccgacgggct tttatacggc tcacaaacac caaatgagga atgcctgttc 300
ctggaacggc tggaggaaaa ccattacaac acctatgtgt ccaagaagca cgccgagaag 360
aattggtttg tcggtctcaa gaagaacgga agttgcaaac gtggtcctcg gactcactac 420
ggccagaaag caatcttgtt tctccccctg ccagtctcct ctgattaa 468

<210> SEQ ID NO 96
<211> LENGTH: 468
<212> TYPE: DNA
<213> ORGANISM: Cat

<400> SEQUENCE: 96
atggctgaag gggaaatcac aaccttcacg gccctgacgg agaagttcaa tctgcctcca 60
gggaattaca agaaacccaa actcctctac tgtagcaacg gggccactt cctgaggatc 120

```
cttccagatg gcacagtgga tgggacgagg gacaggagcg accagcacat tcagctgcag    180

ctcagtgcgg aaagcgtggg ggaggtgtat ataaagagta ccgagactgg ccagtacttg    240

gccatggaca ccgacgggct tttgtacggc tcacagacac caaatgagga atgcttgttc    300

ctggaaaggc tggaagaaaa ccattacaac acctacacat ccaagaagca cgcagaaaag    360

aattggtttg tgggtctcaa gaagaatgga agctgcaaac gcggtccccg gactcactat    420

ggccagaagg caattttgtt tctccccctg ccagtctcct ctgattaa                 468
```

<210> SEQ ID NO 97
<211> LENGTH: 468
<212> TYPE: DNA
<213> ORGANISM: Chinese softshell turtle

<400> SEQUENCE: 97

```
atggctgaag gggaaataac aacgttcacc gccctgaccg aaaaattcaa ccttcccctg     60

gggaattaca agaatcccaa actcttatat tgcagcaatg gaggctactt cttgaggata    120

catccagatg gcaaagtaga tgggacaagg gaccgaagtg accaacacat tcagctgcag    180

ctaagtgcgg aaagcgtggg tgaggtatat ataaagagca ctgagtctgg acagtttttg    240

gctatggacg ccaatggact tttatatgga tcactgtcac cgagtgagga atgcttattc    300

ttggaaagaa tggaagaaaa tcattataac acctacatct ccaagaagca tgcagacaag    360

aactggttcg ttggcttaaa gaagaatgga agctgcaaac tgggaccgcg gacgcactac    420

ggccaaaagg ccgtcctttt ccttccactg ccagtgtcag ctgattaa                 468
```

<210> SEQ ID NO 98
<211> LENGTH: 468
<212> TYPE: DNA
<213> ORGANISM: Coelacanth

<400> SEQUENCE: 98

```
atggctgaag acaaaataac aacactgaag gccttggctg aaaaatttaa ccttcctatg     60

ggaaattaca agaaagcaaa actcctctac tgcagcaacg gagggtattt cctgcgaata    120

cccccagacg ggaaagtgga aggaattaga gaacgaagcg acaagtacat tcagctgcaa    180

atgaatgcag aaagtttagg catggtgtct ataaagggtg tggaggcagg gcaataccta    240

gctatgaata caaatggact cctgtatgga tctcagtctc taactgaaga atgccttttc    300

atggaaaaga tggaagaaaa ccactacaac acatacaggt ctaagacaca tgcagataaa    360

aactggtatg ttggcattag aaagaacggt agcatcaaac caggaccaag gactcacatt    420

ggccaaaagg ctgttctttt tctccctctg cctgcctcga gtgattag                 468
```

<210> SEQ ID NO 99
<211> LENGTH: 468
<212> TYPE: DNA
<213> ORGANISM: Dolphin

<400> SEQUENCE: 99

```
atggctgaag gggaaatcac aaccttcaca gccctgaccg agaagtttaa tctgcctcca     60

gggaattaca agaagcccaa actcctctac tgtagcaacg gggggccactt cctgaggatc    120

cttccagatg gcacagtgga tgggacaagg gacaggagtg accagcacat tcagctgcag    180

ctcagtgcgg aaagcgtggg ggaggtgtat ataaagagta cggagactgg ccagtacttg    240

gccatggaca ccgacgggct tttgtacggc tcacagacac ccaatgagga atgtttgttc    300
```

-continued ctggaaaggt tggaggaaaa ccattacaac acctacgcat ccaagaagca tgcagaaaag 360
aattggttcg ttggtctcaa gaagaacgga agctgcaaac gcggtcctcg gactcactac 420
ggccagaaag caatcttgtt tctccccctg ccagtctcct ccgattaa 468

<210> SEQ ID NO 100
<211> LENGTH: 468
<212> TYPE: DNA
<213> ORGANISM: Ferret

<400> SEQUENCE: 100
atggctgaag ggaaatcac aaccttcaca gccctgatgg agaagtttaa tctgcctgcg 60
gggaattaca agaagcccaa actcctctac tgtagcaatg ggggccactt cctgaggatc 120
cttccagatg gcacagtgga cggcacaagg gacaggagcg accagcacat tcagctgcag 180
ctcagtgcgg aaagcgtggg ggaggtgtac ataaagagta ccgagactgg ccagtacttg 240
gccatggaca ccgatgggct tttgtacggc tcacaaacac caaatgagga atgtctgttc 300
ctggaaaggc tggaggaaaa ccattacaac acctacacat ccaagaagca cgctgagaag 360
aattggtttg taggtctcaa gaagaacgga agctgcaaac gcggtcctcg gactcactat 420
ggccagaaag caattctgtt tctccccctg ccagtctcct ctgattaa 468

<210> SEQ ID NO 101
<211> LENGTH: 468
<212> TYPE: DNA
<213> ORGANISM: Gibbon

<400> SEQUENCE: 101
atggccgaag ggaaatcac caccttcaca gccctgaccg agaagtttaa tctgcctcca 60
gggaattaca agaagcccaa actcctctac tgtagcaacg ggggccactt cttgaggatc 120
cttccggatg gcacagtgga tgggacaagg gacaggagcg accagcacat tcagctgcag 180
ctcagtgcgg aaagcgtggg ggaggtgtat ataaagagta ccgagactgg ccagtacttg 240
gccatggaca ccgacgggct tttatacggc tcacagacac caaatgagga atgtttgttc 300
ctggaaaggc tggaggagaa ccattacaac acctatatat ccaagaagca tgcagagaag 360
aattggtttg ttggcctcaa gaagaatgga agctgcaaac gcggtcctcg gactcactat 420
ggccagaaag caatcttgtt tctccccctg ccagtctctt ctgattaa 468

<210> SEQ ID NO 102
<211> LENGTH: 468
<212> TYPE: DNA
<213> ORGANISM: Gorilla

<400> SEQUENCE: 102
atggctgaag ggaaatcac caccttcaca gccctgaccg agaagtttaa tctgcctcca 60
gggaattaca agaagcccaa actcctctac tgtagcaatg ggggccactt cttgaggatc 120
cttccggatg gcacagtgga tgggacaagg gacaggagcg accagcacat tcagctgcag 180
ctcagtgcgg aaagcgtggg ggaggtgtat ataaagagta ccgagactgg ccagtacttg 240
gccatggaca ccgacgggct tttatacggc tcacagacac caaatgagga atgtttgttc 300
ctggaaaggc tggaggagaa ccattacaac acctatatat ccaagaagca tgcagagaag 360
aattggtttg ttggcctcaa gaagaatgga agctgcaaac gcggtcctcg gactcactat 420
ggccagaaag caatcttgtt tctccccctg ccagtctctt ccgattaa 468

<210> SEQ ID NO 103
<211> LENGTH: 468
<212> TYPE: DNA
<213> ORGANISM: Hedgehog

<400> SEQUENCE: 103
atggctgaag gagaaatcac caccttcacg gccctgactg agaagtttaa tctgccacta 60
gggaattaca agaagcccaa gctcctctac tgtagcaacg ggggccactt cctgaggatc 120
cttccagatg gcaccgtgga tgggacaagg gacaggagcg accagcatat tcagctgcag 180
ctcagtgcgg aaagcgtggg ggaggtgtat ataaagagta cggagactgg ccagtacttg 240
gccatggaca ccgacgggct tttatacggc tcacaaacac caaatgagga atgtctgttc 300
cttgaaaggc tggaagagaa ccattacaat acctacacat ccaagaagca tgccgagaag 360
aactggtttg ttggcctcaa gaagaatgga agctgcaagc gtggtcctcg gactcattat 420
ggccagaaag ctattttgtt tctccccctg ccagtttcct ctgattaa 468

<210> SEQ ID NO 104
<211> LENGTH: 273
<212> TYPE: DNA
<213> ORGANISM: Hyrax

<400> SEQUENCE: 104
atggctgaag gcgaaatcac aaccttcaca gccctgactg agaagtttaa cctgccacta 60
gagaattaca agaagcccaa actcctctac tgtagcaacg gaggccactt cctgaggatc 120
cttccggacg gcacagtgga tggcaccagg gacaggagtg accagcacat tcagctgcag 180
ctcagtgcgg aaagcgtggg ggaggtgtat ataaagggca ccgagactgg ccagtacttg 240
gccatggaca ccgacgggct tttatatggc tca 273

<210> SEQ ID NO 105
<211> LENGTH: 349
<212> TYPE: DNA
<213> ORGANISM: Kangaroo rat

<400> SEQUENCE: 105
atggctgaag gggaaatcac aaccttcaca gccctgacgg aaaggtttaa ttcagctgca 60
actgagtgcg gaaagcgtgg gggaggtcta tataaagagc accgagactg gccaatactt 120
ggccatggat gccgacgggc ttttatacgg ctcacagaca cctgatgaag aatgcttgtt 180
cctggagagg ctggaagaaa atcattataa cacctacata gccaagaaac atgctgaaaa 240
gaattggttt gtcggcctca aaaagaatgg aagctgcaag cgtggtcctc ggactcacta 300
tggccagaaa gcaatcctgt tcctcccctt gcctgtctcc tctgattag 349

<210> SEQ ID NO 106
<211> LENGTH: 276
<212> TYPE: DNA
<213> ORGANISM: Lamprey

<400> SEQUENCE: 106
atggaggtgg gccacatcgg cacgctgccc gtggtccccg cggggcccgt gttccccggc 60
agtttcaagg agccacggcg cctctactgc cgcagcgcgg gccaccacct ccagatcctg 120
ggggacggca ccgtgagtgg cacccaggac gagaacgagc cccacgccgt tctgcagctg 180
caggcggtgc gccgcggggt ggtgacgatc cgtgggctct gcgccgagag gttcctcgcc 240
atgagcacgg agggacacct gtacggggcg gtgagg 276

<210> SEQ ID NO 107
<211> LENGTH: 297
<212> TYPE: DNA
<213> ORGANISM: Lesser hedgehog tenrec

<400> SEQUENCE: 107
cagctgaagc tcgttgccga aagcgtgggg gtggtgtata taaagagcat caagaccggc 60
cagtacttgg ccatgaaccc cgacgggctt ttatacggct ccgagacccc agaggaagaa 120
tgcttgttcc tggaaacgct ggaggaaaac cactacacca ccttcaaatc taagaagcac 180
gtagagaaga attggttcgt tggtctccgg aagaatggaa gggtcaagat cgggcctcgg 240
actcaccaag gccagaaagc aatcttgttc ctgcccctcc cggtgtcctc tgattaa 297

<210> SEQ ID NO 108
<211> LENGTH: 468
<212> TYPE: DNA
<213> ORGANISM: Rhesus monkey

<400> SEQUENCE: 108
atggctgaag gggaaatcac cacgttcaca gccctgaccg agaagtttaa tctgcctcca 60
gggaattaca agaagcccaa actgctctac tgtagcaatg gggccactt cttgaggatc 120 cttccggatg gcacagtgga tgggacaagg gacaggagcg accagcacat tcagctgcag 180
ctcagtgcgg aaagcgtggg ggaggtgtat ataaagagta ccgagactgg ccagtacttg 240
gccatggaca ccgacgggct tttatacggc tcacagacac caaatgagga atgtttgttc 300
ctggaaaggc tggaggagaa ccattacaac acctatacat ccaagaagca cgcagagaag 360
aattggtttg ttggcctcaa gaagaatgga agctgcaaac gtggtcctcg gactcactat 420
ggccagaaag caatcttgtt tcttcccctg ccagtctctt ctgattaa 468

<210> SEQ ID NO 109
<211> LENGTH: 468
<212> TYPE: DNA
<213> ORGANISM: Megabat

<400> SEQUENCE: 109
atggccgagg gggaagtcac gacgttcacg gccctgaccg agaggtttaa cctgcctcca 60
gggaattaca agaagcccaa acttctctac tgcagcaacg gggccactt cctgaggatc 120 ctcccagatg gcacagtgga tgggacaagg gacaagagcg accagcacat tcagctgcag 180
ctcagtgcgg aaagtgtggg ggaggtgtat ataaagagca ccgagagtgg ccagtacttg 240
gccatggact ccgacgggct tttgtacggc tcacagacac cagatgagga ctgtttgttc 300
ctggaaaggc tggaggaaaa ccattacaac acctacacat ccaagaagca cgcagagaag 360
aattggtttg ttgggctcaa gaagaatgga agctgcaagc gcggtccccg gactcactac 420
ggccagaaag cgatcctgtt tctccccctg ccagtctcct ctgattag 468

<210> SEQ ID NO 110
<211> LENGTH: 468
<212> TYPE: DNA
<213> ORGANISM: Microbat

<400> SEQUENCE: 110
atggctgagg gggaagtcac cacattcacg gccctgaccg agaggttcaa tctgcctctg 60
gagaactaca agaagcccaa gcttctctac tgcagcaacg ggggccactt cctgcggatc 120
ctcccagacg gcaccgtgga cgggacgagg gacaggagcg accagcacat tcagctgcag 180
ctcagtgcgg aaagcgtggg ggaggtgtat ataaagagca ccgagagtgg ccagtacttg 240
gccatggact ccgacgggct tttgtacggc tcacaaacac ccaatgagga atgtttgttc 300
ctggaaaggc tggaggagaa ccactacaac acctacacgt ccaagaagca cgcagaaaag 360
aattggttcg ttgggctcaa gaagaacgga agctgcaagc gtggtcctcg gacgcattat 420
ggccagaaag caatcttgtt tctccccctg ccagtctcct ccgattaa 468

<210> SEQ ID NO 111
<211> LENGTH: 468
<212> TYPE: DNA
<213> ORGANISM: Mouse lemur

<400> SEQUENCE: 111
atggccgaag ggagatcac aaccttcacg gccctcaccg agaagtttaa cctgcctccg 60
gggaactaca agaagcccaa gctcctctac tgcagcaacg gcggccactt cctgcgcatc 120
cttcccgacg gcaccgtgga tggcacgaga gacaggagcg accagcacat tcagctgcag 180
ctcagtgcgg aaagcgcggg ggaggtgtat ataaagagca cccagactgg ccggtacttg 240
gccatggacg ccgacgggct tttatacggc tcacaaacac caaatgagga atgtttgttc 300
ctggaaaggc tggaggaaaa ccattacaac acctacgtat ccaagaagca cgcagagaag 360
aattggtttg ttggcctcaa gaagaatgga agttgcaaac gcggcccccg gactcactat 420
ggccagaaag caatcttgtt tctgcccctg ccagtctcct ctgattaa 468

<210> SEQ ID NO 112
<211> LENGTH: 436
<212> TYPE: DNA
<213> ORGANISM: Pika

<400> SEQUENCE: 112
atggccgagg gagaagtcac caccttctca gccctgacgg agaagttcaa tctgcctgga 60
ggaaactaca agttgcccaa gctcctttac tgtagcaacg gaggccactt cctgaggatc 120
cttccagatg gcacagtgga tgggaccagg gacaggagcg acctgcacag aggtgtttat 180
aaagagtacg gagactggcc agtacttggc tatggacacc gatggccttt tatatggctc 240
gcagacaccc agtgaggagt gtttgttcct ggagcggctg gaggagaacc actacaacac 300
ctacacatcc aagaagcatg ccgagaagaa ctggtttgtg ggcatcaaga agaatggaag 360
ctgcaagcgt ggtcctcgga ctcactacgg ccagaaagcc atcttgtttc tccctctgcc 420
agtctcttct gactaa 436

<210> SEQ ID NO 113
<211> LENGTH: 468
<212> TYPE: DNA
<213> ORGANISM: Rat

<400> SEQUENCE: 113
atggccgaag ggagatcac aacctttgca gccctgaccg agaggttcaa tctgcctcta 60
gggaactaca aaaaacccaa actgctctac tgcagcaacg ggggccactt cttgaggatt 120
cttcccgatg gcaccgtgga tgggaccagg gacaggagcg accagcacat tcagctgcag 180
ctcagtgcgg aaagcgcggg cgaagtgtat ataaagggta cagagactgg ccagtacttg 240
gccatggaca ccgaagggct tttatacggc tcgcagacac caaatgaaga atgcctattc 300
ctggaaaggc tagaagaaaa ccattataac acttacacat ccaagaagca cgcggagaag 360
aactggtttg tgggcctcaa gaagaacggg agttgtaagc gcggtcctcg gactcactac 420
ggccagaaag ccatcttgtt tctccccctc ccggtatctt ctgactaa 468

<210> SEQ ID NO 114
<211> LENGTH: 468
<212> TYPE: DNA
<213> ORGANISM: Sloth

<400> SEQUENCE: 114
atggctgaag gggaaatcac aaccttcaca gctctgatgg agaagtttaa cctgccacca 60
gggaattaca tgaagcccaa actcctctac tgtagcaacg ggggccactt cttgaggatc 120
cttccagacg gcacagtgga tgggacaagg gacaggagcg acctgcacat tcagctgcag 180
ctcagtgcgg aaagcgtggg ggaggtgtat ataaagagtg cggagaccgg ccagtactta 240
gccatggaca ccggcgggct tttatacggc tcacagacac caagtgagga atgcctgttc 300
ctagaaaggc tggaggaaaa ccattacaac acctacgtat ccaagaagca tgcggagaag 360
aactggttcg ttggcctaaa gaagaatgga agcagcaaac gcggccccg gactcactat 420 ggccagaaag ccatcttgtt tcttcccctg ccagtctcct ctgattaa 468

<210> SEQ ID NO 115
<211> LENGTH: 468
<212> TYPE: DNA
<213> ORGANISM: Squirrel

<400> SEQUENCE: 115
atggctgaag gggaaatcac aaccttcaca gccctgaccg agaagttcaa tctgcctcca 60
gggaactaca agaagcccaa actgctctac tgtagcaacg gaggccactt cttgaggatc 120
cttcctgatg gcacagtgga tgggacaaga gacaggagcg accaacacat tcagctgcag 180
ctcagtgcgg aaagcgtggg ggaggtgtat ataaagagta ccgagaccgg ccagtacttg 240
gccatggaca ccgacgggct tttatatggc tcacagaccc caaatgagga atgcttattc 300
ctggaaaggc tggaggaaaa ccattacaac acgtacacat ccaagaagca tgcagagaag 360
aattggtttg ttggcctcaa gaagaacgga agctgcaagc gcggtccccg gactcactat 420
ggccagaaag cgatcttgtt tctcccactg cctgtctcct ctgattag 468

<210> SEQ ID NO 116
<211> LENGTH: 468
<212> TYPE: DNA
<213> ORGANISM: Tarsier

<400> SEQUENCE: 116
atggccgaag gggaaatcac aaccttcaca gccctgaccg agaagttcaa cctgcccccg 60
gggaattaca agaagcccaa actcctctac tgcagcaacg ggggccactt cttgaggatc 120
cttccggatg gcactgtgga tggaacgagg gacaggagcg accagcacat tcagctgcag 180
ctcagcgcgg aaagcgtggg ggaggtgtat ataaagagta ccgagaccgg ccagtacttg 240
gccatggaca ccgacgggct tttgtacggc tcacagacac caaatgagga gtgtctgttc 300
ctggaaaggc tggaagagaa tcattacaat acctacgtgt ccaagaagca tgcggagaag 360
aattggtttg tcggcctcaa gaagaatgga agctgcaaac gcggtcctcg gactcactat 420
ggccagaaag caatcttgtt tctccccctg ccagtttcct ctgattaa 468

<210> SEQ ID NO 117
<211> LENGTH: 468

<212> TYPE: DNA
<213> ORGANISM: Tree shrew

<400> SEQUENCE: 117

```
atggctgaag gggaaatcac gaccttcgca gccctgaccg agaagtttga tctgcctcca      60
gggaattaca agaagcccaa acttctctac tgtagcaacg ggggccattt cttgaggatt     120
cttccagatg gcaccgtgga tgggacaaga gacaggagcg accagcacat tcagctgcag     180
ctcactgcgg aaaacgtggg ggaggtgtac ataaagagta cggagactgg ccagtacttg     240
gccatggacg ccgacgggct tttatatggc tcacagacac caaacgagga atgtttgttc     300
ctggaaaggc tggaggagaa ccattacaac acctacatat ccaagaagca cgcagagaag     360
aattggtttg ttgccctcaa gaagaacgga agctgcaaac tcggtcctcg gactcactat     420
ggccagaaag caatcttgtt tctcccccctg ccagtctcct ctgattaa                468
```

<210> SEQ ID NO 118
<211> LENGTH: 168
<212> TYPE: DNA
<213> ORGANISM: Turkey

<400> SEQUENCE: 118

```
atggccgagg gggagataac caccttcaca gccctgaccg agcgcttcgg cctgccgctg      60
ggcaactaca agaagcccaa actcctgtac tgcagcaacg ggggccactt cctacggatc     120
ctgccggacg gcaaggtgga cgggacgcgg gaccggagcg accagcac                  168
```

<210> SEQ ID NO 119
<211> LENGTH: 468
<212> TYPE: DNA
<213> ORGANISM: Wallaby

<400> SEQUENCE: 119

```
atggccgaag gggagatcac aaccttcaca gccctgaccg aaagatttaa cctgccactg      60
gggaattaca agaagcccaa gcttctctac tgtagcaatg ggggccactt tttgaggatc     120
cttcctgatg gcaaagtgga tgggacaagg gacagaaatg atcaacacat tcaactgcaa     180
ctaagcgcgg aaagcgtggg tgaggtgtat ataaagagca ctgagtctgg gcagtatttg     240
gccatggaca ccaatggact tttatatggc tcacagaccc ccagcgaaga atgcttattc     300
ctggagaggt tggaggagaa tcattacaac acctacatat caaagaagca tgcggagaaa     360
aattggtttg ttggcctcaa gaagaacgga agttgcaaaa gaggtcccag gactcactat     420
ggccagaaag ccatcctatt ccttcccctc cctgtgtcct ctgagtaa                 468
```

<210> SEQ ID NO 120
<211> LENGTH: 444
<212> TYPE: DNA
<213> ORGANISM: Zebrafish

<400> SEQUENCE: 120

```
atgaccgagg ccgatattgc ggtaaagtcc agcccgcgcg actataaaaa actgacgcgg      60
ctgtactgta tgaatggagg atttcacctt cagatcctgg cggacgggac agtggctgga     120
gcagcagacg aaaacacata cagcatactg cgcataaaag caacaagtcc aggagtggtg     180
gtgatcgaag gatcagaaac aggtctttac ctctcgatga atgaacatgg caagctgtac     240
gcttcatcat tagtgacgga tgaaagttat ttcctggaga agatggagga aaaccactac     300
aacacatatc agtctcaaaa gcacggtgaa aactggtacg tcggaataaa aaagaacggg     360
```

aaaatgaaac ggggcccaag aactcacatc ggacaaaagg ccattttctt tcttccacga 420
caggtggagc aggaagagga ctga 444

<210> SEQ ID NO 121
<211> LENGTH: 155
<212> TYPE: PRT
<213> ORGANISM: Homo sapiens

<400> SEQUENCE: 121

Met Ala Ala Gly Ser Ile Thr Thr Leu Pro Ala Leu Pro Glu Asp Gly
1 5 10 15

Gly Ser Gly Ala Phe Pro Pro Gly His Phe Lys Asp Pro Lys Arg Leu
20 25 30

Tyr Cys Lys Asn Gly Gly Phe Phe Leu Arg Ile His Pro Asp Gly Arg
35 40 45

Val Asp Gly Val Arg Glu Lys Ser Asp Pro His Ile Lys Leu Gln Leu
50 55 60

Gln Ala Glu Glu Arg Gly Val Val Ser Ile Lys Gly Val Cys Ala Asn
65 70 75 80

Arg Tyr Leu Ala Met Lys Glu Asp Gly Arg Leu Leu Ala Ser Lys Cys
85 90 95

Val Thr Asp Glu Cys Phe Phe Phe Glu Arg Leu Glu Ser Asn Asn Tyr
100 105 110

Asn Thr Tyr Arg Ser Arg Lys Tyr Thr Ser Trp Tyr Val Ala Leu Lys
115 120 125

Arg Thr Gly Gln Tyr Lys Leu Gly Ser Lys Thr Gly Pro Gly Gln Lys
130 135 140

Ala Ile Leu Phe Leu Pro Met Ser Ala Lys Ser
145 150 155

<210> SEQ ID NO 122
<211> LENGTH: 155
<212> TYPE: PRT
<213> ORGANISM: Gorilla gorilla

<400> SEQUENCE: 122

Met Ala Ala Gly Ser Ile Thr Thr Leu Pro Ala Leu Pro Glu Asp Gly
1 5 10 15

Gly Ser Gly Ala Phe Pro Pro Gly His Phe Lys Asp Pro Lys Arg Leu
20 25 30

Tyr Cys Lys Asn Gly Gly Phe Phe Leu Arg Ile His Pro Asp Gly Arg
35 40 45

Val Asp Gly Val Arg Glu Lys Ser Asp Pro His Ile Lys Leu Gln Leu
50 55 60

Gln Ala Glu Glu Arg Gly Val Val Ser Ile Lys Gly Val Cys Ala Asn
65 70 75 80

Arg Tyr Leu Ala Met Lys Glu Asp Gly Arg Leu Leu Ala Ser Lys Cys
85 90 95

Val Thr Asp Glu Cys Phe Phe Phe Glu Arg Leu Glu Ser Asn Asn Tyr
100 105 110

Asn Thr Tyr Arg Ser Arg Lys Tyr Thr Ser Trp Tyr Val Ala Leu Lys
115 120 125

Arg Thr Gly Gln Tyr Lys Leu Gly Ser Lys Thr Gly Pro Gly Gln Lys
130 135 140

Ala Ile Leu Phe Leu Pro Met Ser Ala Lys Ser
145 150 155

<210> SEQ ID NO 123
<211> LENGTH: 155
<212> TYPE: PRT
<213> ORGANISM: Pongo abelii

<400> SEQUENCE: 123

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 124
<211> LENGTH: 155
<212> TYPE: PRT
<213> ORGANISM: Macaca mulatta

<400> SEQUENCE: 124

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 125

<211> LENGTH: 155
<212> TYPE: PRT
<213> ORGANISM: Pan troglodytes

<400> SEQUENCE: 125

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 126
<211> LENGTH: 155
<212> TYPE: PRT
<213> ORGANISM: Pan paniscus

<400> SEQUENCE: 126

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 127
<211> LENGTH: 155
<212> TYPE: PRT
<213> ORGANISM: Saimiri boliviensis boliviensis -continued

<400> SEQUENCE: 127

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 128
<211> LENGTH: 155
<212> TYPE: PRT
<213> ORGANISM: Nomascus leucogenys

<400> SEQUENCE: 128

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 129
<211> LENGTH: 155
<212> TYPE: PRT
<213> ORGANISM: Equus caballus

<400> SEQUENCE: 129

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155


<210> SEQ ID NO 130
<211> LENGTH: 155
<212> TYPE: PRT
<213> ORGANISM: Bos taurus

<400> SEQUENCE: 130

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ala Ser Lys Ser
145                 150                 155


<210> SEQ ID NO 131
<211> LENGTH: 155
<212> TYPE: PRT
<213> ORGANISM: Papio anubis

<400> SEQUENCE: 131

Met Ala Ala Gly Ser Ile Thr Thr Leu Pro Ala Leu Pro Glu Asp Gly
1               5                   10                  15
```

Gly Ser Gly Ala Phe Pro Pro Gly His Phe Lys Asp Pro Lys Arg Leu
20 25 30

Tyr Cys Lys Asn Gly Gly Phe Phe Leu Arg Ile His Pro Asp Gly Arg
35 40 45

Val Asp Gly Val Arg Glu Lys Ser Asp Pro His Ile Lys Leu Gln Leu
50 55 60

Gln Ala Glu Glu Arg Gly Val Val Ser Ile Lys Gly Val Cys Ala Asn
65 70 75 80

Arg Tyr Leu Ala Met Lys Glu Asp Gly Arg Leu Leu Ala Ser Lys Cys
85 90 95

Val Thr Asp Glu Cys Phe Phe Phe Glu Arg Leu Glu Ser Asn Asn Tyr
100 105 110

Asn Thr Tyr Arg Ser Arg Lys Tyr Thr Ser Trp Tyr Val Ala Leu Lys
115 120 125

Arg Thr Gly Gln Tyr Lys Leu Gly Ser Lys Thr Gly Pro Gly Gln Lys
130 135 140

Ala Ile Leu Phe Leu Pro Met Ala Ser Lys Ser
145 150 155

<210> SEQ ID NO 132
<211> LENGTH: 155
<212> TYPE: PRT
<213> ORGANISM: Vicugna pacos

<400> SEQUENCE: 132

Met Ala Ala Gly Ser Ile Thr Thr Leu Pro Ala Leu Pro Glu Asp Gly
1 5 10 15

Gly Ser Gly Ala Phe Pro Pro Gly His Phe Lys Asp Pro Lys Arg Leu
20 25 30

Tyr Cys Lys Asn Gly Gly Phe Phe Leu Arg Ile His Pro Asp Gly Arg
35 40 45

Val Asp Gly Val Arg Glu Lys Ser Asp Pro His Ile Lys Leu Gln Leu
50 55 60

Gln Ala Glu Glu Arg Gly Val Val Ser Ile Lys Gly Val Cys Ala Asn
65 70 75 80

Arg Tyr Leu Ala Met Lys Glu Asp Gly Arg Leu Leu Ala Ser Lys Cys
85 90 95

Val Thr Asp Glu Cys Phe Phe Phe Glu Arg Leu Glu Ser Asn Asn Tyr
100 105 110

Asn Thr Tyr Arg Ser Arg Lys Tyr Ser Ser Trp Tyr Val Ala Leu Lys
115 120 125

Arg Thr Gly Gln Tyr Lys Leu Gly Pro Lys Thr Gly Pro Gly Gln Lys
130 135 140

Ala Ile Leu Phe Leu Pro Met Ser Ala Lys Ser
145 150 155

<210> SEQ ID NO 133
<211> LENGTH: 155
<212> TYPE: PRT
<213> ORGANISM: Ovis aries

<400> SEQUENCE: 133

Met Ala Ala Gly Ser Ile Thr Thr Leu Pro Ala Leu Pro Glu Asp Gly
1 5 10 15

Gly Ser Ser Ala Phe Pro Pro Gly His Phe Lys Asp Pro Lys Arg Leu
20 25 30

```
Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155


<210> SEQ ID NO 134
<211> LENGTH: 108
<212> TYPE: PRT
<213> ORGANISM: Capreolus capreolus

<400> SEQUENCE: 134

Arg Ile His Pro Asp Gly Arg Val Asp Gly Val Arg Glu Lys Ser Asp
1               5                   10                  15

Pro His Ile Lys Leu Gln Leu Gln Ala Glu Glu Arg Gly Val Val Ser
            20                  25                  30

Ile Lys Gly Val Cys Ala Asn Arg Tyr Leu Ala Met Lys Glu Asp Gly
        35                  40                  45

Arg Leu Leu Ala Ser Lys Cys Val Thr Asp Glu Cys Phe Phe Phe Glu
    50                  55                  60

Arg Leu Glu Ser Asn Asn Tyr Asn Thr Tyr Arg Ser Arg Lys Tyr Ser
65                  70                  75                  80

Ser Trp Tyr Val Ala Leu Lys Arg Thr Gly Gln Tyr Lys Leu Gly Pro
                85                  90                  95

Lys Thr Gly Pro Gly Gln Lys Ala Ile Leu Phe Leu
            100                 105


<210> SEQ ID NO 135
<211> LENGTH: 96
<212> TYPE: PRT
<213> ORGANISM: Loxodonta africana

<400> SEQUENCE: 135

Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
            20                  25                  30

Leu Ala Ser Arg Cys Val Thr Asp Glu Cys Phe Phe Phe Glu Arg Leu
        35                  40                  45

Glu Ser Asn Asn Tyr Asn Thr Tyr Arg Ser Arg Lys Tyr Thr Ser Trp
    50                  55                  60

Tyr Val Ala Leu Lys Arg Thr Gly Gln Tyr Lys Leu Gly Ser Lys Thr
65                  70                  75                  80

Gly Pro Gly Gln Lys Ala Ile Leu Phe Leu Pro Met Ser Ala Lys Ser
                85                  90                  95
```

<210> SEQ ID NO 136
<211> LENGTH: 120
<212> TYPE: PRT
<213> ORGANISM: Sus scrofa

<400> SEQUENCE: 136

```
Asn Gly Gly Phe Phe Leu Arg Ile His Pro Asp Gly Arg Val Asp Gly
1               5                   10                  15

Val Arg Glu Lys Ser Asp Pro His Ile Lys Leu Gln Leu Gln Ala Glu
            20                  25                  30

Glu Arg Gly Val Val Ser Ile Lys Gly Val Cys Ala Asn Arg Tyr Leu
        35                  40                  45

Ala Met Lys Glu Asp Gly Arg Leu Leu Ala Ser Lys Cys Val Thr Asp
    50                  55                  60

Glu Cys Phe Phe Phe Glu Arg Leu Glu Ser Asn Asn Tyr Asn Thr Tyr
65                  70                  75                  80

Arg Ser Arg Lys Tyr Ser Ser Trp Tyr Val Ala Leu Lys Arg Thr Gly
                85                  90                  95

Gln Tyr Lys Leu Gly Pro Lys Thr Gly Pro Gly Gln Lys Ala Ile Leu
            100                 105                 110

Phe Leu Pro Met Ser Ala Lys Ser
        115                 120
```

<210> SEQ ID NO 137
<211> LENGTH: 96
<212> TYPE: PRT
<213> ORGANISM: Ailuropoda melanoleuca

<400> SEQUENCE: 137

```
Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
            20                  25                  30

Leu Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Thr Gly Gln Tyr Lys Leu Gly Pro Lys Thr
65                  70                  75                  80

Gly Pro Gly Gln Lys Ala Ile Leu Phe Leu Pro Met Ser Ala Lys Ser
                85                  90                  95
```

<210> SEQ ID NO 138
<211> LENGTH: 155
<212> TYPE: PRT
<213> ORGANISM: Choloepus hoffmanni

<400> SEQUENCE: 138

```
Met Ala Ala Gly Ser Ile Thr Thr Leu Pro Ala Leu Pro Glu Asp Gly
1               5                   10                  15

Gly Ser Gly Ala Leu Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
```

-continued

```
65                  70                  75                  80

Arg Tyr Leu Ala Met Lys Glu Asp Gly Arg Leu Gln Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155


<210> SEQ ID NO 139
<211> LENGTH: 155
<212> TYPE: PRT
<213> ORGANISM: Bubalus bubalis

<400> SEQUENCE: 139

Met Ala Ala Gly Ser Ile Thr Thr Leu Pro Pro Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Ser Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155


<210> SEQ ID NO 140
<211> LENGTH: 155
<212> TYPE: PRT
<213> ORGANISM: Canis lupus familiaris

<400> SEQUENCE: 140

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Lys Gly Gly Phe Phe Leu Arg Ile His Pro Asp Gly Arg
        35                  40                  45

Val Asp Gly Val Arg Glu Lys Ser Asp Pro His Val Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
```

```
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Pro Lys Thr Gly Pro Gly Gln Lys
    130                 135                 140

Ala Ile Leu Phe Leu Pro Met Ser Ala Lys Ser
145                 150                 155


<210> SEQ ID NO 141
<211> LENGTH: 154
<212> TYPE: PRT
<213> ORGANISM: Rattus norvegicus

<400> SEQUENCE: 141

Met Ala Ala Gly Ser Ile Thr Ser Leu Pro Ala Leu Pro Glu Asp Gly
1               5                   10                  15

Gly Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
    130                 135                 140

Ile Leu Phe Leu Pro Met Ser Ala Lys Ser
145                 150


<210> SEQ ID NO 142
<211> LENGTH: 134
<212> TYPE: PRT
<213> ORGANISM: Heterocephalus glaber

<400> SEQUENCE: 142

Pro Pro Gly His Phe Lys Asp Pro Lys Arg Leu Tyr Cys Lys Asn Gly
1               5                   10                  15

Gly Phe Phe Leu Arg Ile His Pro Asp Gly Arg Val Asp Gly Val Arg
            20                  25                  30

Glu Lys Ser Asp Pro His Val Lys Leu Gln Leu Gln Ala Glu Glu Arg
        35                  40                  45

Gly Val Val Ser Ile Lys Gly Val Cys Ala Asn Arg Tyr Leu Ala Met
    50                  55                  60

Lys Glu Asp Gly Arg Leu Leu Ala Ser Lys Cys Val Thr Asp Glu Cys
65                  70                  75                  80

Phe Phe Phe Glu Arg Leu Glu Ser Asn Asn Tyr Asn Thr Tyr Arg Ser
                85                  90                  95

Arg Lys Tyr Ser Ser Trp Tyr Val Ala Leu Lys Arg Thr Gly Gln Tyr
```

```
            100                 105                 110

Lys Leu Gly Ser Lys Thr Gly Pro Gly Gln Lys Ala Ile Leu Phe Leu
        115                 120                 125

Pro Met Ser Ala Lys Ser
    130
```

<210> SEQ ID NO 143
<211> LENGTH: 155
<212> TYPE: PRT
<213> ORGANISM: Otolemur garnettii

<400> SEQUENCE: 143

```
Met Ala Ala Gly Ser Ile Thr Thr Leu Pro Ser Leu Pro Glu Asp Gly
1               5                   10                  15

Gly Ser Asp Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Leu
                85                  90                  95

Ile Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 144
<211> LENGTH: 154
<212> TYPE: PRT
<213> ORGANISM: Mus musculus

<400> SEQUENCE: 144

```
Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Val Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
        115                 120                 125

Thr Gly Gln Tyr Lys Leu Gly Ser Lys Thr Gly Pro Gly Gln Lys Ala
```

```
    130                 135                 140

Ile Leu Phe Leu Pro Met Ser Ala Lys Ser
145                 150


<210> SEQ ID NO 145
<211> LENGTH: 144
<212> TYPE: PRT
<213> ORGANISM: Ictidomys tridecemlineatus

<400> SEQUENCE: 145

Leu Pro Glu Asp Gly Gly Gly Gly Ala Phe Pro Pro Gly His Phe Lys
1               5                   10                  15

Asp Pro Lys Arg Leu Tyr Cys Lys Asn Gly Gly Phe Phe Leu Arg Ile
            20                  25                  30

His Pro Asp Gly Arg Val Asp Gly Val Arg Glu Lys Ser Asp Pro His
        35                  40                  45

Ile Lys Leu Gln Leu Gln Ala Glu Asp Arg Gly Val Val Ser Ile Lys
    50                  55                  60

Gly Val Cys Ala Asn Arg Tyr Leu Ala Met Lys Glu Asp Gly Arg Leu
65                  70                  75                  80

Leu Ala Ser Lys Cys Val Thr Asp Glu Cys Phe Phe Phe Glu Arg Leu
                85                  90                  95

Glu Ser Asn Asn Tyr Asn Thr Tyr Arg Ser Arg Lys Tyr Ser Ser Trp
            100                 105                 110

Tyr Val Ala Leu Lys Arg Thr Gly Gln Tyr Lys Leu Gly Ser Lys Thr
        115                 120                 125

Gly Pro Gly Gln Lys Ala Ile Leu Phe Leu Pro Met Ser Ala Lys Ser
    130                 135                 140


<210> SEQ ID NO 146
<211> LENGTH: 106
<212> TYPE: PRT
<213> ORGANISM: Felis catus

<400> SEQUENCE: 146

His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Ser Ser Trp Tyr Val Ala Leu Lys Arg Thr
            100                 105


<210> SEQ ID NO 147
<211> LENGTH: 96
<212> TYPE: PRT
<213> ORGANISM: Cavia porcellus

<400> SEQUENCE: 147

Val Lys Leu Gln Leu Gln Ala Glu Asp Arg Gly Val Val Ser Ile Lys
1               5                   10                  15
```

Gly Val Cys Ala Asn Arg Tyr Leu Ala Met Lys Glu Asp Gly Arg Leu
20 25 30

Leu Ala Ser Lys Cys Val Thr Asp Glu Cys Phe Phe Phe Glu Arg Leu
35 40 45

Glu Ser Asn Asn Tyr Asn Thr Tyr Arg Ser Arg Lys Tyr Ser Ser Trp
50 55 60

Tyr Val Ala Leu Lys Arg Thr Gly Gln Tyr Lys Leu Gly Ser Lys Thr
65 70 75 80

Gly Pro Gly Gln Lys Ala Ile Leu Phe Leu Pro Met Ser Ala Lys Ser
85 90 95

<210> SEQ ID NO 148
<211> LENGTH: 156
<212> TYPE: PRT
<213> ORGANISM: Sarcophilus harrisii

<400> SEQUENCE: 148

Met Ala Ala Gly Ser Ile Thr Thr Leu Pro Ala Leu Ala Gly Asp Gly
1 5 10 15

Ala Ser Gly Gly Ala Phe Pro Pro Gly His Phe Gln Asp Pro Lys Arg
20 25 30

Leu Tyr Cys Lys Asn Gly Gly Phe Phe Leu Arg Ile His Pro Asp Gly
35 40 45

His Val Asp Gly Ile Arg Glu Lys Ser Asp Pro His Ile Lys Leu Gln
50 55 60

Leu Gln Ala Glu Glu Arg Gly Val Val Ser Ile Lys Gly Val Cys Ala
65 70 75 80

Asn Arg Tyr Leu Ala Met Lys Glu Asp Gly Arg Leu Leu Ala Leu Lys
85 90 95

Cys Val Thr Glu Glu Cys Phe Phe Phe Glu Arg Leu Glu Ser Asn Asn
100 105 110

Tyr Asn Thr Tyr Arg Ser Arg Lys Tyr Ser Asn Trp Tyr Val Ala Leu
115 120 125

Lys Arg Thr Gly Gln Tyr Lys Leu Gly Ser Lys Thr Gly Pro Gly Gln
130 135 140

Lys Ala Ile Leu Phe Leu Pro Met Ser Ala Lys Ser
145 150 155

<210> SEQ ID NO 149
<211> LENGTH: 156
<212> TYPE: PRT
<213> ORGANISM: Monodelphis domestica

<400> SEQUENCE: 149

Met Ala Ala Gly Ser Ile Thr Thr Leu Pro Ala Leu Ser Gly Asp Gly
1 5 10 15

Gly Gly Gly Gly Ala Phe Pro Pro Gly His Phe Lys Asp Pro Lys Arg
20 25 30

Leu Tyr Cys Lys Asn Gly Gly Phe Phe Leu Arg Ile His Pro Asp Gly
35 40 45

Arg Val Asp Gly Ile Arg Glu Lys Ser Asp Pro Asn Ile Lys Leu Gln
50 55 60

Leu Gln Ala Glu Glu Arg Gly Val Val Ser Ile Lys Gly Val Cys Ala
65 70 75 80

Asn Arg Tyr Leu Ala Met Lys Glu Asp Gly Arg Leu Leu Ala Leu Lys
85 90 95

-continued

```
Tyr Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Leu Pro Met Ser Ala Lys Ser
145                 150                 155


<210> SEQ ID NO 150
<211> LENGTH: 155
<212> TYPE: PRT
<213> ORGANISM: Oryctolagus cuniculus

<400> SEQUENCE: 150

Met Ala Ala Glu Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155


<210> SEQ ID NO 151
<211> LENGTH: 125
<212> TYPE: PRT
<213> ORGANISM: Meleagris gallopavo

<400> SEQUENCE: 151

Arg Leu Tyr Cys Lys Asn Gly Gly Phe Phe Leu Arg Ile Asn Pro Asp
1               5                   10                  15

Gly Arg Val Asp Gly Val Arg Glu Lys Ser Asp Pro His Ile Lys Leu
            20                  25                  30

Gln Leu Gln Ala Glu Glu Arg Gly Val Val Ser Ile Lys Gly Val Ser
        35                  40                  45

Ala Asn Arg Phe Leu Ala Met Lys Glu Asp Gly Arg Leu Leu Ala Leu
    50                  55                  60

Lys Cys Ala Thr Glu Glu Cys Phe Phe Phe Glu Arg Leu Glu Ser Asn
65                  70                  75                  80

Asn Tyr Asn Thr Tyr Arg Ser Arg Lys Tyr Ser Asp Trp Tyr Val Ala
                85                  90                  95

Leu Lys Arg Thr Gly Gln Tyr Lys Pro Gly Pro Lys Thr Gly Pro Gly
            100                 105                 110
```

```
Gln Lys Ala Ile Leu Phe Leu Pro Met Ser Ala Lys Ser
        115                 120                 125
```

<210> SEQ ID NO 152
<211> LENGTH: 158
<212> TYPE: PRT
<213> ORGANISM: Gallus gallus

<400> SEQUENCE: 152

```
Met Ala Ala Gly Ala Ala Gly Ser Ile Thr Thr Leu Pro Ala Leu Pro
1               5                   10                  15

Asp Asp Gly Gly Gly Gly Ala Phe Pro Pro Gly His Phe Lys Asp Pro
            20                  25                  30

Lys Arg Leu Tyr Cys Lys Asn Gly Gly Phe Phe Leu Arg Ile Asn Pro
        35                  40                  45

Asp Gly Arg Val Asp Gly Val Arg Glu Lys Ser Asp Pro His Ile Lys
    50                  55                  60

Leu Gln Leu Gln Ala Glu Glu Arg Gly Val Val Ser Ile Lys Gly Val
65                  70                  75                  80

Ser Ala Asn Arg Phe Leu Ala Met Lys Glu Asp Gly Arg Leu Leu Ala
                85                  90                  95

Leu Lys Cys Ala Thr Glu Glu Cys Phe Phe Phe Glu Arg Leu Glu Ser
            100                 105                 110

Asn Asn Tyr Asn Thr Tyr Arg Ser Arg Lys Tyr Ser Asp Trp Tyr Val
        115                 120                 125

Ala Leu Lys Arg Thr Gly Gln Tyr Lys Pro Gly Pro Lys Thr Gly Pro
    130                 135                 140

Gly Gln Lys Ala Ile Leu Phe Leu Pro Met Ser Ala Lys Ser
145                 150                 155
```

<210> SEQ ID NO 153
<211> LENGTH: 153
<212> TYPE: PRT
<213> ORGANISM: Taeniopygia guttata

<400> SEQUENCE: 153

```
Met Ala Ala Ala Gly Gly Ile Ala Thr Leu Pro Asp Asp Gly Gly Ser
1               5                   10                  15

Gly Ala Phe Pro Pro Gly His Phe Lys Asp Pro Lys Arg Leu Tyr Cys
            20                  25                  30

Lys Asn Gly Gly Phe Phe Leu Arg Ile Asn Pro Asp Gly Lys Val Asp
        35                  40                  45

Gly Val Arg Glu Lys Ser Asp Pro His Ile Lys Leu Gln Leu Gln Ala
    50                  55                  60

Glu Glu Arg Gly Val Val Ser Ile Lys Gly Val Ser Ala Asn Arg Phe
65                  70                  75                  80

Leu Ala Met Lys Glu Asp Gly Arg Leu Leu Ala Leu Lys Tyr Ala Thr
                85                  90                  95

Glu Glu Cys Phe Phe Phe Glu Arg Leu Glu Ser Asn Asn Tyr Asn Thr
            100                 105                 110

Tyr Arg Ser Arg Lys Tyr Ser Asp Trp Tyr Val Ala Leu Lys Arg Thr
        115                 120                 125

Gly Gln Tyr Lys Pro Gly Pro Lys Thr Gly Pro Gly Gln Lys Ala Ile
    130                 135                 140

Leu Phe Leu Pro Met Ser Ala Lys Ser
145                 150
```

<210> SEQ ID NO 154
<211> LENGTH: 155
<212> TYPE: PRT
<213> ORGANISM: Cynops pyrrhogaster

<400> SEQUENCE: 154

```
Met Ala Ala Gly Ser Ile Thr Ser Leu Pro Ala Leu Pro Glu Asp Gly
1               5                   10                  15

Asn Gly Gly Thr Phe Thr Pro Gly Gly Phe Lys Glu Pro Lys Arg Leu
            20                  25                  30

Tyr Cys Lys Asn Gly Gly Phe Phe Leu Arg Ile Asn Ser Asp Gly Lys
        35                  40                  45

Val Asp Gly Ala Arg Glu Lys Ser Asp Ser Tyr Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Asp Asp Gly Arg Leu Met Ala Leu Lys Trp
                85                  90                  95

Ile Thr Asp Glu Cys Phe Phe Phe Glu Arg Leu Glu Ser Asn Asn Tyr
            100                 105                 110

Asn Thr Tyr Arg Ser Arg Lys Tyr Ser Asp Trp Tyr Val Ala Leu Lys
        115                 120                 125

Arg Thr Gly Gln Tyr Lys Asn Gly Ser Lys Thr Gly Ala Gly Gln Lys
    130                 135                 140

Ala Ile Leu Phe Leu Pro Met Ser Ala Lys Ser
145                 150                 155
```

<210> SEQ ID NO 155
<211> LENGTH: 155
<212> TYPE: PRT
<213> ORGANISM: Xenopus laevis

<400> SEQUENCE: 155

```
Met Ala Ala Gly Ser Ile Thr Thr Leu Pro Thr Glu Ser Glu Asp Gly
1               5                   10                  15

Gly Asn Thr Pro Phe Ser Pro Gly Ser Phe Lys Asp Pro Lys Arg Leu
            20                  25                  30

Tyr Cys Lys Asn Gly Gly Phe Phe Leu Arg Ile Asn Ser Asp Gly Arg
        35                  40                  45

Val Asp Gly Ser Arg Asp Lys Ser Asp Ser His Ile Lys Leu Gln Leu
    50                  55                  60

Gln Ala Val Glu Arg Gly Val Val Ser Ile Lys Gly Ile Thr Ala Asn
65                  70                  75                  80

Arg Tyr Leu Ala Met Lys Glu Asp Gly Arg Leu Thr Ser Leu Arg Cys
                85                  90                  95

Ile Thr Asp Glu Cys Phe Phe Phe Glu Arg Leu Glu Ala Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Asn Gly Ser Ser Thr Gly Pro Gly Gln Lys
    130                 135                 140

Ala Ile Leu Phe Leu Pro Met Ser Ala Lys Ser
145                 150                 155
```

<210> SEQ ID NO 156

<211> LENGTH: 156
<212> TYPE: PRT
<213> ORGANISM: Didelphis albiventris

<400> SEQUENCE: 156

Met Ala Ala Gly Ser Ile Thr Thr Leu Pro Ala Leu Ser Gly Asp Gly
1               5                   10                  15

Gly Gly Gly Gly Ala Phe Pro Pro Gly His Phe Lys Asp Pro Lys Arg
            20                  25                  30

Leu Tyr Cys Lys Asn Gly Gly Phe Phe Leu Arg Ile His Pro Asp Gly
        35                  40                  45

Arg Val Asp Gly Ile Arg Glu Lys Ser Asp Pro Asn Ile Lys Leu Gln
    50                  55                  60

Leu Gln Ala Glu Glu Arg Gly Val Val Ser Ile Lys Gly Val Cys Ala
65                  70                  75                  80

Asn Arg Tyr Leu Ala Met Lys Glu Asp Gly Arg Leu Leu Ala Leu Lys
                85                  90                  95

Tyr Val Thr Glu Glu Cys Phe Phe Phe Glu Arg Leu Glu Ser Asn Asn
            100                 105                 110

Tyr Asn Thr Tyr Arg Ser Arg Lys Tyr Ser Asn Trp Tyr Val Ala Leu
        115                 120                 125

Lys Arg Thr Gly Gln Tyr Lys Leu Gly Ser Lys Thr Gly Pro Gly Gln
    130                 135                 140

Lys Ala Ile Leu Phe Ser Pro Cys Leu Leu Arg Cys
145                 150                 155

<210> SEQ ID NO 157
<211> LENGTH: 96
<212> TYPE: PRT
<213> ORGANISM: Myotis lucifugus

<400> SEQUENCE: 157

Val Lys Leu Gln Leu Gln Ala Glu Glu Arg Gly Val Val Ser Ile Lys
1               5                   10                  15

Gly Val Cys Ala Asn Arg Tyr Leu Ala Met Lys Glu Asp Gly Arg Leu
            20                  25                  30

Gln Ala Ser Lys Cys Val Thr Asp Glu Cys Phe Phe Phe Glu Arg Leu
        35                  40                  45

Glu Ser Asn Asn Tyr Asn Thr Tyr Arg Ser Arg Lys Tyr Ser Ser Trp
    50                  55                  60

Tyr Val Ala Leu Lys Arg Asn Gly Gln Tyr Lys Leu Gly Pro Lys Thr
65                  70                  75                  80

Gly Pro Gly Gln Lys Ala Ile Leu Phe Leu Pro Met Ser Ala Lys Ser
                85                  90                  95

<210> SEQ ID NO 158
<211> LENGTH: 140
<212> TYPE: PRT
<213> ORGANISM: Anolis carolinensis

<400> SEQUENCE: 158

Ala Ala Ala Ala Ser Phe Pro Pro Gly Pro Phe Lys Asp Pro Lys Arg
1               5                   10                  15

Leu Tyr Cys Lys Asn Gly Gly Phe Phe Leu Arg Ile Asn Pro Asp Gly
            20                  25                  30

Gly Val Asp Gly Val Arg Glu Lys Ser Asp Pro Asn Ile Lys Leu Leu
        35                  40                  45

```
Leu Gln Ala Glu Glu Arg Gly Val Val Ser Ile Lys Gly Val Cys Ala
    50                  55                  60

Asn Arg Phe Leu Ala Met Asn Glu Asp Gly Arg Leu Leu Ala Leu Lys
65                  70                  75                  80

Tyr Val Thr Asp Glu Cys Phe Phe Phe Glu Arg Leu Glu Ser Asn Asn
                85                  90                  95

Tyr Asn Thr Tyr Arg Ser Arg Lys Tyr Arg Asp Trp Tyr Ile Ala Leu
            100                 105                 110

Lys Arg Thr Gly Gln Tyr Lys Leu Gly Pro Lys Thr Gly Arg Gly Gln
        115                 120                 125

Lys Ala Ile Leu Phe Leu Pro Met Ser Ala Lys Ser
    130                 135                 140


<210> SEQ ID NO 159
<211> LENGTH: 94
<212> TYPE: PRT
<213> ORGANISM: Dasypus novemcinctus

<400> SEQUENCE: 159

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro Asn Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Arg Glu Asp Gly Arg Leu Gln Ala Ser
                85                  90


<210> SEQ ID NO 160
<211> LENGTH: 189
<212> TYPE: PRT
<213> ORGANISM: Tupaia belangeri

<400> SEQUENCE: 160

Ala Gly Val Arg Ala Glu Arg Glu Glu Ala Pro Gly Ser Gly Asp Ser
1               5                   10                  15

Arg Gly Thr Asp Pro Ala Ala Arg Ser Leu Ile Arg Arg Pro Asp Ala
            20                  25                  30

Ala Ala Arg Glu Ala Leu Leu Gly Ala Arg Ser Arg Val Gln Gly Ser
        35                  40                  45

Ser Thr Ser Trp Pro Ala Ser Ser Arg Thr Gly Ile Lys Leu Pro Asp
    50                  55                  60

Asp Ser Gly Gln Gly Met Gly Gly Tyr Pro Leu Asp Arg Pro Ser Arg
65                  70                  75                  80

Ser Thr Gly Arg Gly Leu Gly Gly Ala Pro Asp Pro Ala Val Lys Leu
                85                  90                  95

Gln Leu Gln Ala Glu Glu Arg Gly Val Val Ser Ile Lys Gly Val Cys
            100                 105                 110

Ala Asn Arg Tyr Leu Ala Met Lys Glu Asp Gly Arg Leu Leu Ala Ser
        115                 120                 125

Lys Cys Val Thr Asp Glu Cys Phe Phe Phe Glu Arg Leu Glu Ser Asn
    130                 135                 140
```

```
Asn Tyr Asn Thr Tyr Arg Ser Arg Lys Tyr Ser Ser Trp Tyr Val Ala
145                 150                 155                 160

Leu Lys Arg Thr Gly Gln Tyr Lys Leu Gly Ser Lys Thr Gly Pro Gly
                165                 170                 175

Gln Lys Ala Ile Leu Phe Leu Pro Met Ser Ala Lys Ser
            180                 185


<210> SEQ ID NO 161
<211> LENGTH: 154
<212> TYPE: PRT
<213> ORGANISM: Xenopus silurana tropicalis

<400> SEQUENCE: 161

Met Ala Ala Gly Ser Ile Thr Thr Leu Pro Thr Glu Ser Glu Asp Gly
1               5                   10                  15

Asn Thr Pro Phe Pro Pro Gly Asn Phe Lys Asp Pro Lys Arg Leu Tyr
            20                  25                  30

Cys Lys Asn Gly Gly Tyr Phe Leu Arg Ile Asn Ser Asp Gly Arg Val
        35                  40                  45

Asp Gly Ser Arg Asp Lys Ser Asp Leu His Ile Lys Leu Gln Leu Gln
    50                  55                  60

Ala Val Glu Arg Gly Val Val Ser Ile Lys Gly Ile Thr Ala Asn Arg
65                  70                  75                  80

Tyr Leu Ala Met Lys Glu Asp Gly Arg Leu Thr Ser Leu Lys Cys Ile
                85                  90                  95

Thr Asp Glu Cys Phe Phe Tyr Glu Arg Leu Glu Ala Asn Asn Tyr Asn
            100                 105                 110

Thr Tyr Arg Ser Arg Lys Asn Asn Ser Trp Tyr Val Ala Leu Lys Arg
        115                 120                 125

Thr Gly Gln Tyr Lys Asn Gly Ser Thr Thr Gly Pro Gly Gln Lys Ala
    130                 135                 140

Ile Leu Phe Leu Pro Met Ser Ala Lys Ser
145                 150


<210> SEQ ID NO 162
<211> LENGTH: 155
<212> TYPE: PRT
<213> ORGANISM: Latimeria chalumnae

<400> SEQUENCE: 162

Met Ala Ala Gly Gly Ile Thr Thr Leu Pro Ala Val Pro Glu Asp Gly
1               5                   10                  15

Gly Ser Ser Thr Phe Pro Pro Gly Asn Phe Lys Glu Pro Lys Arg Leu
            20                  25                  30

Tyr Cys Lys Asn Gly Gly Tyr Phe Leu Arg Ile Asn Pro Asp Gly Arg
        35                  40                  45

Val Asp Gly Thr Arg Glu Lys Asn Asp Pro Tyr Ile Lys Leu Gln Leu
    50                  55                  60

Gln Ala Glu Ser Ile Gly Val Val Ser Ile Lys Gly Val Cys Ser Asn
65                  70                  75                  80

Arg Tyr Leu Ala Met Asn Glu Asp Cys Arg Leu Phe Gly Leu Lys Tyr
                85                  90                  95

Pro Thr Asp Glu Cys Phe Phe His Glu Arg Leu Glu Ser Asn Asn Tyr
            100                 105                 110

Asn Thr Tyr Arg Ser Lys Lys Tyr Ser Asp Trp Tyr Val Ala Leu Lys
        115                 120                 125
```

-continued

Arg Thr Gly Gln Tyr Lys Pro Gly Pro Lys Thr Gly Leu Gly Gln Lys
    130                 135                 140

Ala Ile Leu Phe Leu Pro Met Ser Ala Lys Ser
145                 150                 155

<210> SEQ ID NO 163
<211> LENGTH: 155
<212> TYPE: PRT
<213> ORGANISM: Tetraodon nigroviridis

<400> SEQUENCE: 163

Met Ala Thr Gly Gly Ile Thr Thr Leu Pro Ser Thr Pro Glu Asp Gly
1               5                   10                  15

Gly Ser Ser Gly Phe Pro Pro Gly Ser Phe Lys Asp Pro Lys Arg Leu
            20                  25                  30

Tyr Cys Lys Asn Gly Gly Phe Phe Leu Arg Ile Lys Ser Asp Gly Val
        35                  40                  45

Val Asp Gly Ile Arg Glu Lys Ser Asp Pro His Ile Lys Leu Gln Leu
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Thr Lys Arg
                85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Thr Met Phe Val Gly Leu Thr
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155

<210> SEQ ID NO 164
<211> LENGTH: 155
<212> TYPE: PRT
<213> ORGANISM: Gasterosteus aculeatus

<400> SEQUENCE: 164

Met Ala Thr Ala Gly Phe Ala Thr Leu Pro Ser Thr Pro Glu Asp Gly
1               5                   10                  15

Gly Ser Gly Gly Phe Thr Pro Gly Gly Phe Lys Asp Pro Lys Arg Leu
            20                  25                  30

Tyr Cys Lys Asn Gly Gly Phe Phe Leu Arg Ile Arg Ser Asp Gly Gly
        35                  40                  45

Val Asp Gly Ile Arg Glu Lys Ser Asp Ala His Ile Lys Leu Gln Ile
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Val Arg Arg
                85                  90                  95

Ala Thr Asp Glu Cys Tyr Phe Leu Glu Arg Leu Glu Ser Asn Asn Tyr
            100                 105                 110

Asn Thr Tyr Arg Ser Arg Lys Tyr Pro Gly Met Tyr Val Ala Leu Lys
        115                 120                 125

Arg Thr Gly Gln Tyr Lys Ser Gly Ser Lys Thr Gly Pro Gly Gln Lys
    130                 135                 140

```
Ala Ile Leu Phe Leu Pro Met Ser Ala Lys Cys
145                 150                 155


<210> SEQ ID NO 165
<211> LENGTH: 155
<212> TYPE: PRT
<213> ORGANISM: Takifugu rubripes

<400> SEQUENCE: 165

Met Ala Thr Gly Gly Ile Thr Thr Leu Pro Ser Thr Pro Glu Asp Gly
1               5                   10                  15

Gly Ser Gly Gly Phe Pro Pro Gly Ser Phe Lys Asp Pro Lys Arg Leu
            20                  25                  30

Tyr Cys Lys Asn Gly Gly Phe Phe Leu Arg Ile Arg Ser Asp Gly Ala
        35                  40                  45

Val Asp Gly Thr Arg Glu Lys Thr Asp Pro His Ile Lys Leu Gln Leu
    50                  55                  60

Gln Ala Thr Ser Val Gly Glu Val Val Ile Lys Gly Val Cys Ala Asn
65                  70                  75                  80

Arg Tyr Leu Ala Met Asn Arg Asp Gly Arg Leu Phe Gly Met Lys Arg
                85                  90                  95

Ala Thr Asp Glu Cys His Phe Leu Glu Arg Leu Glu Ser Asn Asn Tyr
            100                 105                 110

Asn Thr Tyr Arg Ser Arg Lys Tyr Pro Asn Met Phe Val Gly Leu Thr
        115                 120                 125

Arg Thr Gly Asn Tyr Lys Ser Gly Thr Lys Thr Gly Pro Cys Gln Lys
    130                 135                 140

Ala Ile Leu Phe Leu Pro Met Ser Ala Lys Tyr
145                 150                 155


<210> SEQ ID NO 166
<211> LENGTH: 155
<212> TYPE: PRT
<213> ORGANISM: Oncorhynchus mykiss

<400> SEQUENCE: 166

Met Ala Thr Gly Glu Ile Thr Thr Leu Pro Ala Thr Pro Glu Asp Gly
1               5                   10                  15

Gly Ser Gly Gly Phe Leu Pro Gly Asn Phe Lys Glu Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Asp Lys Asn Asp Pro His Asn Lys Leu Gln Leu
    50                  55                  60

Gln Ala Thr Ser Val Gly Glu Val Val Ile Lys Gly Val Ser Ala Asn
65                  70                  75                  80

Arg Tyr Leu Ala Met Asn Ala Asp Gly Arg Leu Phe Gly Pro Arg Arg
                85                  90                  95

Thr Thr Asp Glu Cys Tyr Phe Met Glu Arg Leu Glu Ser Asn Asn Tyr
            100                 105                 110

Asn Thr Tyr Arg Ser Arg Lys Tyr Pro Glu Met Tyr Val Ala Leu Lys
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Arg Arg
145                 150                 155
```

<210> SEQ ID NO 167
<211> LENGTH: 150
<212> TYPE: PRT
<213> ORGANISM: Salmo salar

<400> SEQUENCE: 167

```
Met Ala Thr Gly Glu Ile Thr Thr Leu Pro Ala Thr Pro Glu Asp Gly
1               5                   10                  15

Gly Ser Gly Gly Phe Pro Pro Gly Asn Phe Lys Asp Pro Lys Arg Leu
            20                  25                  30

Tyr Cys Lys Asn Gly Gly Tyr Phe Leu Arg Ile Asn Ser Asn Gly Ser
        35                  40                  45

Val Asp Gly Ile Arg Glu Lys Asn Asp Pro His Lys Gln Pro Gln Phe
    50                  55                  60

Val Arg Ala Trp Thr Leu Gln Gly Val Lys Arg Ser Thr Gly Met Leu
65                  70                  75                  80

Ala His Val Asp Ser Asn Ala Ser His Asn Cys Val Lys Val Ala Gly
                85                  90                  95

Cys Ser Leu Gly Glu Phe Gly Ser Met Ser Asn Arg Pro His Asn Arg
            100                 105                 110

Arg Pro Arg Val Ala Thr Pro Ala Gln Asp Leu His Ile Arg Leu Leu
        115                 120                 125

His Leu Arg Asp Arg Leu Lys Pro Ala Thr Arg Thr Ala Asp Lys Thr
    130                 135                 140

Glu Glu Tyr Phe Cys Leu
145                 150
```

<210> SEQ ID NO 168
<211> LENGTH: 154
<212> TYPE: PRT
<213> ORGANISM: Danio rerio

<400> SEQUENCE: 168

```
Met Ala Thr Gly Gly Ile Thr Thr Leu Pro Ala Ala Pro Asp Ala Glu
1               5                   10                  15

Asn Ser Ser Phe Pro Ala Gly Ser Phe Arg Asp Pro Lys Arg Leu Tyr
            20                  25                  30

Cys Lys Asn Gly Gly Phe Phe Leu Arg Ile Asn Ala Asp Gly Arg Val
        35                  40                  45

Asp Gly Ala Arg Asp Lys Ser Asp Pro His Ile Arg Leu Gln Leu Gln
    50                  55                  60

Ala Thr Ala Val Gly Glu Val Leu Ile Lys Gly Ile Cys Thr Asn Arg
65                  70                  75                  80

Phe Leu Ala Met Asn Ala Asp Gly Arg Leu Phe Gly Thr Lys Arg Thr
                85                  90                  95

Thr Asp Glu Cys Tyr Phe Leu Glu Arg Leu Glu Ser Asn Asn Tyr Asn
            100                 105                 110

Thr Tyr Arg Ser Arg Lys Tyr Pro Asp Trp Tyr Val Ala Leu Lys Arg
        115                 120                 125

Thr Gly Gln Tyr Lys Ser Gly Ser Lys Thr Ser Pro Gly Gln Lys Ala
    130                 135                 140

Ile Leu Phe Leu Pro Met Ser Ala Lys Cys
145                 150
```

<210> SEQ ID NO 169
<211> LENGTH: 155

<212> TYPE: PRT
<213> ORGANISM: Oreochromis niloticus

<400> SEQUENCE: 169

Met Ala Thr Gly Gly Ile Thr Thr Leu Pro Ala Thr Pro Glu Asp Gly
1               5                   10                  15

Gly Ser Ser Gly Phe Pro Pro Gly Asn Phe Lys Asp Pro Lys Arg Leu
            20                  25                  30

Tyr Cys Lys Asn Gly Gly Phe Phe Leu Arg Ile Lys Ser Asp Gly Gly
        35                  40                  45

Val Asp Gly Ile Arg Glu Lys Asn Asp Pro His Ile Lys Leu Gln Leu
    50                  55                  60

Gln Ala Thr Ser Val Gly Glu Val Val Ile Lys Gly Ile Cys Ala Asn
65                  70                  75                  80

Arg Tyr Leu Ala Met Asn Arg Asp Gly Arg Leu Phe Gly Ala Arg Arg
                85                  90                  95

Ala Thr Asp Glu Cys Tyr Phe Leu Glu Arg Leu Glu Ser Asn Asn Tyr
            100                 105                 110

Asn Thr Tyr Arg Ser Arg Lys Tyr Pro Asn Met Tyr Val Ala Leu Lys
        115                 120                 125

Arg Thr Gly Gln Tyr Lys Ser Gly Ser Lys Thr Gly Pro Gly Gln Lys
    130                 135                 140

Ala Ile Leu Phe Leu Pro Met Ser Ala Lys Cys
145                 150                 155

<210> SEQ ID NO 170
<211> LENGTH: 155
<212> TYPE: PRT
<213> ORGANISM: Oryzias latipes

<400> SEQUENCE: 170

Met Ala Thr Gly Glu Ile Thr Thr Leu Pro Ser Pro Ala Glu Asn Ser
1               5                   10                  15

Arg Ser Asp Gly Phe Pro Pro Gly Asn Tyr Lys Asp Pro Lys Arg Leu
            20                  25                  30

Tyr Cys Lys Asn Gly Gly Leu Phe Leu Arg Ile Lys Pro Asp Gly Gly
        35                  40                  45

Val Asp Gly Ile Arg Glu Lys Lys Asp Pro His Val Lys Leu Arg Leu
    50                  55                  60

Gln Ala Thr Ser Ala Gly Glu Val Val Ile Lys Gly Val Cys Ser Asn
65                  70                  75                  80

Arg Tyr Leu Ala Met His Gly Asp Gly Arg Leu Phe Gly Val Arg Gln
                85                  90                  95

Ala Thr Glu Glu Cys Tyr Phe Leu Glu Arg Leu Glu Ser Asn Asn Tyr
            100                 105                 110

Asn Thr Tyr Arg Ser Lys Lys Tyr Pro Asn Met Tyr Val Ala Leu Lys
        115                 120                 125

Arg Thr Gly Gln Tyr Lys Pro Gly Asn Lys Thr Gly Pro Gly Gln Lys
    130                 135                 140

Ala Ile Leu Phe Leu Pro Met Ser Ala Lys Tyr
145                 150                 155

<210> SEQ ID NO 171
<211> LENGTH: 468
<212> TYPE: DNA
<213> ORGANISM: Homo sapiens

<400> SEQUENCE: 171

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttacctgg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 172
<211> LENGTH: 468
<212> TYPE: DNA
<213> ORGANISM: Gorilla

<400> SEQUENCE: 172

```
atggcagccg ggagcatcac cacgctgccc gccttgcccg aggatggcgg cagcggcgcc      60
ttcccgcccg gccacttcaa ggaccccaag cggctgtact gcaaaaacgg gggcttcttc     120
ctgcgcatcc accccgacgg ccgagttgac ggggtccggg agaagagcga ccctcacatc     180
aagctacaac ttcaagcaga agagagagga gttgtgtcta tcaaaggagt gtgtgctaac     240
cgttaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 173
<211> LENGTH: 468
<212> TYPE: DNA
<213> ORGANISM: Sumatran orangutan

<400> SEQUENCE: 173

```
atggcagccg ggagcatcac cacgctgccc gccttgcccg aggatggcgg cagcggcgcc      60
ttcccgccgg gccacttcaa ggaccccaag cggctgtact gcaaaaacgg gggcttcttc     120
ctgcgcatcc accccgacgg ccgagttgac ggggtccgag agaagagcga ccctcacatc     180
aaactacaac ttcaagcaga agaaagagga gttgtgtcta tcaaaggagt gtgtgctaac     240
cgctaccttg ctatgaagga agatggaaga ttactggctt ctaaatgtgt tacggatgag     300
tgtttctttt ttgaacgatt ggaatctaat aactacaata cttaccggtc aaggaaatac     360
accagttggt atgtggcact gaaacgaact gggcagtata aacttggatc caaaacagga     420
cctgggcaga aagctatact ttttcttcca atgtctgcta agagctga                  468
```

<210> SEQ ID NO 174
<211> LENGTH: 468
<212> TYPE: DNA
<213> ORGANISM: Rhesus monkey

<400> SEQUENCE: 174

```
atggcagccg ggagcatcac cacgctgccc gccttgcccg aggatggcgg cagcggcgcc      60
ttcccgcctg gccacttcaa ggaccccaag cggctgtact gcaaaaacgg gggcttcttc     120
ctgcgcattc accccgacgg ccgagttgac ggggtccggg agaagagcga ccctcacatc     180
```

```
aaattacaac ttcaagcaga agagagagga gttgtgtcta tcaaaggagt gtgtgctaac    240

cgttaccttg ctatgaagga agatggaaga ttactggctt ctaaatgtgt tacagatgag    300

tgtttctttt ttgaacgatt ggaatctaat aactacaata cttaccggtc aaggaaatac    360

accagttggt atgtggcact gaaacgaact gggcaatata aacttggatc caaaacagga    420

cctgggcaga aagctatact ttttcttcca atgtctgcta agagctga                 468
```

<210> SEQ ID NO 175
<211> LENGTH: 468
<212> TYPE: DNA
<213> ORGANISM: Chimpanzee

<400> SEQUENCE: 175

```
atggcagccg ggagcatcac cacgctgccc gccttgcccg aggatggcgg cagcggcgcc     60

ttcccgcccg gccacttcaa ggaccccaag cggctgtact gcaaaaacgg gggcttcttc    120

ctgcgcatcc accccgacgg ccgagttgac ggggtccggg agaagagcga ccctcacatc    180

aagctacaac ttcaagcaga agagagagga gttgtgtcta tcaaaggagt gtgtgctaac    240

cgttaccttg ctatgaagga agatggaaga ttactggctt ctaaatgtgt tacggatgag    300

tgtttctttt ttgaacgatt ggaatctaat aactacaata cttaccggtc aaggaaatac    360

accagttggt atgtggcact gaaacgaact gggcagtata aacttggatc caaaacagga    420

cctgggcaga aagctatact ttttcttcca atgtctgcta agagctga                 468
```

<210> SEQ ID NO 176
<211> LENGTH: 468
<212> TYPE: DNA
<213> ORGANISM: Pygmy chimpanzee

<400> SEQUENCE: 176

```
atggcagccg ggagcatcac cacgctgccc gccttgcccg aggatggcgg cagcggcgcc     60

ttcccgcccg gccacttcaa ggaccccaag cggctgtact gcaaaaacgg gggcttcttc    120

ctgcgcatcc accccgacgg ccgagttgac ggggtccggg agaagagcga ccctcacatc    180

aagctacaac ttcaagcaga agagagagga gttgtgtcta tcaaaggagt gtgtgctaac    240

cgttaccttg ctatgaagga agatggaaga ttactggctt ctaaatgtgt tacggatgag    300

tgtttctttt ttgaacgatt ggaatctaat aactacaata cttaccggtc aaggaaatac    360

accagttggt atgtggcact gaaacgaact gggcagtata aacttggatc caaaacagga    420

cctgggcaga aagctatact ttttcttcca atgtctgcta agagctga                 468
```

<210> SEQ ID NO 177
<211> LENGTH: 468
<212> TYPE: DNA
<213> ORGANISM: Bolivian squirrel monkey

<400> SEQUENCE: 177

```
atggcagccg ggagcatcac cacgctgccc gccctgcccg aagacggcgg cagcggcgcc     60

ttcccgcccg gccacttcaa agaccccaag cggctgtact gcaaaaacgg gggcttcttc    120

ctgcgaatcc accccgacgg ccgagtggac ggggtccggg agaagagcga ccctcacatc    180

aaactacaac ttcaagcaga agagagagga gttgtatcta tcaaaggagt gtgtgctaac    240

cgttaccttg ctatgaagga agatggaaga ttactggctt ctaaatgtgt tacggacgag    300

tgtttctttt ttgaacgatt ggaatctaat aactacaata cttaccgatc aaggaaatac    360
```

accagttggt atgtggcact gaaacgaact gggcagtata aacttggatc caaaacagga 420
cctgggcaga aagctatact ttttcttcca atgtctgcta agagctga 468

<210> SEQ ID NO 178
<211> LENGTH: 468
<212> TYPE: DNA
<213> ORGANISM: Northern white-cheeked gibbon

<400> SEQUENCE: 178
atggcagccg ggagcatcac cacgctgccc gccttgccgg aggatggcgg cagcggcgcc 60
ttcccgcccg gccacttcaa ggaccccaag cggctgtact gcaaaaacgg gggtttcttc 120
ctgcgcatcc accccgacgg tcgagttgac ggggtccggg agaagagcga ccctcacatc 180
aaactacaac ttcaagcaga agagagagga gttgtgtcta tcaaaggagt gtgtgctaac 240
cgttaccttg ctatgaagga agatggaaga ttactggctt ctaaatgtgt tacggatgag 300
tgtttctttt ttgaacgatt ggaatctaat aactacaata cttaccggtc aaggaaatac 360
accagttggt atgtggcact gaaacgaact gggcagtata aacttggatc caaaacagga 420
cctgggcaga aagctatact ttttcttcca atgtctgcta agagctga 468

<210> SEQ ID NO 179
<211> LENGTH: 468
<212> TYPE: DNA
<213> ORGANISM: Horse

<400> SEQUENCE: 179
atggcagccg ggagcatcac cacgctgccc gccctgcccg aggacggcgg cagcggcgcc 60
ttcccgcccg gccacttcaa ggaccccaag cggctctact gcaaaaacgg gggcttcttc 120
ctgcgcatcc accccgacgg ccgagtggac ggggtccggg agaagagcga ccctcacatc 180
aaactacaac ttcaagcaga agagagaggg gttgtgtcta tcaaaggagt gtgtgcgaac 240
cgttatcttg ctatgaagga agatggaagg ttactggctt ctaaatgtgt tacggacgag 300
tgtttctttt ttgaacgatt ggaatctaat aactacaata cttaccggtc aaggaaatac 360
tccagttggt atgtggccct gaaacgaacg gggcagtata aacttggacc caaaacagga 420
cctggacaga aagctatact ttttcttcca atgtctgcta agagctga 468

<210> SEQ ID NO 180
<211> LENGTH: 468
<212> TYPE: DNA
<213> ORGANISM: Cattle

<400> SEQUENCE: 180
atggccgccg ggagcatcac cacgctgcca gccctgccgg aggacggcgg cagcggcgct 60
ttcccgccgg gccacttcaa ggaccccaag cggctgtact gcaagaacgg gggcttcttc 120
ctgcgcatcc accccgacgg ccgagtggac ggggtccgcg agaagagcga cccacacatc 180
aaactacaac ttcaagcaga agagagaggg gttgtgtcta tcaaaggagt gtgtgcaaac 240
cgttaccttg ctatgaaaga agatggaaga ttactagctt ctaaatgtgt tacagacgag 300
tgtttctttt ttgaacgatt ggagtctaat aactacaata cttaccggtc aaggaaatac 360
tccagttggt atgtggcact gaaacgaact gggcagtata aacttggacc caaaacagga 420
cctgggcaga aagctatact ttttcttcca atgtctgcta agagctga 468

<210> SEQ ID NO 181
<211> LENGTH: 468

<212> TYPE: DNA
<213> ORGANISM: Olive baboon

<400> SEQUENCE: 181
atggcagccg ggagcatcac cacgctgccc gccttgcccg aggatggcgg cagcggcgcc 60
ttcccgcccg gccacttcaa ggaccccaag cggctgtact gcaaaaacgg gggcttcttc 120
ctgcgcattc accccgacgg ccgagttgac ggggtccggg agaagagcga ccctcacatc 180
aaattacaac ttcaagcaga agagagagga gttgtgtcta tcaaaggagt gtgtgctaac 240
cgttaccttg ctatgaagga agatggaaga ttactggctt ctaaatgtgt tacggatgag 300
tgtttctttt ttgaacgatt ggaatctaat aactacaata cttaccggtc aaggaaatac 360
accagttggt atgtggcact gaaacgaact gggcagtata aacttggatc caaaacagga 420
cctgggcaga aagctatact tttcttccca atgtctgcta agagctga 468

<210> SEQ ID NO 182
<211> LENGTH: 468
<212> TYPE: DNA
<213> ORGANISM: Alpaca

<400> SEQUENCE: 182
atggcagctg ggagcatcac cacgctgccc gccctgccgg aggacggcgg cagcggcgcc 60
ttcccgcccg gccacttcaa ggaccccaag cggttgtact gcaaaaacgg gggcttcttc 120
ctgcgcatcc accccgacgg ccgagtggac ggggtccggg agaagagcga ccctcacatc 180
aaactacaac ttcaagcaga agagagaggg gtcgtgtcta tcaaaggagt gtgtgcaaac 240
cgttaccttg ctatgaagga agatggaaga ttactggctt ctaaatgtgt cacagacgag 300
tgtttctttt ttgaacgatt ggaatctaat aactacaata cttaccggtc aaggaaatac 360
tccagttggt atgtggcact gaaacgaact gggcagtaca aacttggacc caaaacagga 420
cctgggcaga aagctatact tttccttcca atgtctgcta agagctga 468

<210> SEQ ID NO 183
<211> LENGTH: 468
<212> TYPE: DNA
<213> ORGANISM: Sheep

<400> SEQUENCE: 183
atggccgccg ggagcatcac cacgctgcca gccctgccgg aggacggcgg cagcagcgct 60
ttcccgcccg gccactttaa ggaccccaag cggctgtact gcaagaacgg gggcttcttc 120
ctgcgcatcc accccgacgg ccgagtggac ggggtccgcg agaagagcga ccctcacatc 180
aaactacaac ttcaagcaga agagagaggg gttgtgtcta tcaaaggagt gtgtgcaaac 240
cgttaccttg ctatgaaaga agatggaaga ttactagctt ctaaatgtgt tacagacgag 300
tgtttctttt ttgaacgatt ggagtctaat aactacaata cttaccggtc aaggaaatac 360
tccagttggt atgtggcact gaaacgaact gggcagtata aacttggacc caaaacagga 420
cctgggcaga aagctatact tttcttcca atgtctgcta agagctga 468

<210> SEQ ID NO 184
<211> LENGTH: 325
<212> TYPE: DNA
<213> ORGANISM: Western roe deer

<400> SEQUENCE: 184
gcgcatccac cccgacggcc gagtggacgg ggtccgcgag aagagtgacc ctcacatcaa 60
actacaactt caagcagaag agagaggggt tgtgtctatc aaaggagtgt gtgcgaaccg 120
ttatcttgct atgaaagaag acggaagatt attggcttca aaatgtgtta cagacgaatg 180
tttctttttt gaacgattgg agtctaataa ctacaatact taccggtcaa ggaaatactc 240
cagttggtat gtggcactga aacgaactgg gcagtataaa cttggaccca aaacaggacc 300
tgggcagaaa gctatacttt ttctt 325

<210> SEQ ID NO 185
<211> LENGTH: 288
<212> TYPE: DNA
<213> ORGANISM: Elephant

<400> SEQUENCE: 185
gttaaactac agcttcaagc agaagagaga ggtgttgtgt ctatcaaagg agtgtgtgcc 60
aaccgttatc tggctatgaa ggaagatgga agattgctgg cttctagatg tgtgacagat 120
gaatgtttct tctttgaacg actggaatct aataactaca atacttaccg gtcaaggaaa 180
tacaccagtt ggtatgtggc actgaaacga acggggcagt ataaacttgg atccaaaaca 240
ggacctggac agaaagctat actttttctt cccatgtctg ctaagagc 288

<210> SEQ ID NO 186
<211> LENGTH: 361
<212> TYPE: DNA
<213> ORGANISM: Pig

<400> SEQUENCE: 186
gaacgggggc ttcttcctgc gcatccaccc cgacggccga gtggatgggg tccgggagaa 60
gagcgaccct cacatcaaac tacaacttca agcagaagag agaggggttg tgtctatcaa 120
aggagtgtgt gcaaaccgtt atcttgctat gaaggaagat ggaagattac tggcttctaa 180
atgtgttaca gacgagtgtt tctttttga acgactggaa tctaataact acaatactta 240
ccggtcgagg aaatactcca gttggtatgt ggcactgaaa cgaactgggc agtataaact 300
tggacccaaa acaggacctg ggcagaaagc tatacttttt cttccaatgt ctgctaagag 360
c 361

<210> SEQ ID NO 187
<211> LENGTH: 288
<212> TYPE: DNA
<213> ORGANISM: Panda

<400> SEQUENCE: 187
gtcaaactgc aacttcaagc ggaagagaga ggggttgtat ccatcaaagg agtatgtgca 60
aatcgctatc ttgccatgaa ggaagatgga agattactgg cttctaaatg tgttaccgat 120
gagtgtttct tttttgagcg actggaatct aataactaca atacttaccg gtcaaggaaa 180
tactccagtt ggtatgtggc actgaaacga actgggcagt ataaacttgg acccaaaaca 240
ggacctgggc agaaagctat actttttctt ccaatgtctg ctaagagc 288

<210> SEQ ID NO 188
<211> LENGTH: 468
<212> TYPE: DNA
<213> ORGANISM: Sloth

<400> SEQUENCE: 188
atggcagccg ggagcatcac cacgctgccc gccctgcccg aggacggagg cagcggcgcc 60
ttaccgcccg gccacttcaa agatcccaag cggctctact gcaaaaacgg gggcttcttc 120
ctgcgtatcc atcccgacgg cagagtggac ggggtccggg agaagagcga cccccacatc 180
aaactacaac ttcaagcaga agagagaggg gttgtgtcta tcaaaggtgt gtgtgcaaac 240
cgatatcttg ctatgaagga agatggaaga ttacaggctt ctaaatgtgt aacggacgag 300
tgtttctttt ttgaacgatt ggaatctaat aactacaata cgtaccgatc aaggaaatac 360
tccagttggt atgtggcact gaaacgaact gggcaatata aacttggacc caaaacagga 420
cctgggcaga aagccatact ttttcttcca atgtctgcta agagctga 468

<210> SEQ ID NO 189
<211> LENGTH: 468
<212> TYPE: DNA
<213> ORGANISM: Water buffalo

<400> SEQUENCE: 189
atggccgccg ggagcatcac cacgctgcca cccctgccgg aggacggcgg cagcggcgct 60
ttcccgcccg gccacttcaa ggaccccaag cggctgtact gcaagaacgg gggcttcttc 120
ctgcgcatcc accccgacgg ccgagtggac ggggtccgcg agaagagcga cccacacatc 180
aaactacaac ttcaagcaga agagagaggg gttgtgtcta tcaaaggagt gtgtgcaaac 240
cgttaccttg ctatgaaaga agatggaaga ttactagctt ccaaatgtgt tacagacgag 300
tgtttctttt ttgaacgatt ggagtctagt aactacaata cttaccggtc aaggaaatac 360
tccagttggt atgtggcact gaaacgaact gggcagtata aacttggacc caaaacagga 420
cctgggcaga aagctatact ttttcttcca atgtctgcta agagctga 468

<210> SEQ ID NO 190
<211> LENGTH: 468
<212> TYPE: DNA
<213> ORGANISM: Dog

<400> SEQUENCE: 190
atggcagccg ggagcatcac cacgctgccc gccctgccgg aggacggcgg cagcggcgcc 60
ttcccgcccg gccacttcaa ggaccccaag aggctgtact gcaaaaaagg gggcttcttc 120
ctgcggatcc accccgacgg ccgggtggac ggggtccggg agaagagcga tccccacgtc 180
aaattgcaac ttcaagcaga agagagaggc gttgtgtcca tcaaaggagt atgtgcaaat 240
cgctatcttg ctatgaagga agatggaaga ttactggctt ctaaatgtgt tactgacgag 300
tgcttctttt ttgaacgatt ggaatctaat aactacaata cttaccggtc aaggaaatac 360
tccagttggt atgtggcact gaaacgaact gggcagtata aacttggacc aaaaacagga 420
cctgggcaga aagctatact ttttcttcca atgtctgcta agagctga 468

<210> SEQ ID NO 191
<211> LENGTH: 465
<212> TYPE: DNA
<213> ORGANISM: Norway rat

<400> SEQUENCE: 191
atggctgccg gcagcatcac ttcgcttccc gcactgccgg aggacggcgg cggcgccttc 60
ccacccggcc acttcaagga tcccaagcgg ctctactgca agaacggcgg cttcttcctg 120
cgcatccatc cagacggccg cgtggacggc gtccgggaga agagcgaccc acacgtcaaa 180
ctacagctcc aagcagaaga gagaggagtt gtgtccatca agggagtgtg tgcgaaccgg 240
tacctggcta tgaaggaaga tggacggctg ctggcttcta agtgtgttac agaagagtgt 300

-continued ttcttctttg aacgcctgga gtccaataac tacaacactt accggtcacg gaaatactcc 360
agttggtatg tggcactgaa acgaactggg cagtataaac tcggatccaa aacggggcct 420
ggacagaagg ccatactgtt tcttccaatg tctgctaaga gctga 465

<210> SEQ ID NO 192
<211> LENGTH: 405
<212> TYPE: DNA
<213> ORGANISM: Naked mole-rat

<400> SEQUENCE: 192
ccacccggcc acttcaagga cccaaagcgg ctgtactgca aaaacggggg cttcttcctg 60
cgcatccacc ccgacggccg cgtggacggg gtccgggaga agagcgaccc tcacgtcaaa 120
ctacaacttc aagcagaaga gagaggagtt gtgtctatta agggagtgtg tgcgaaccgt 180
taccttgcta tgaaggaaga tggaagatta ctggcttcta aatgtgttac agatgagtgt 240
ttcttttttg aacgattgga atctaataac tacaatactt atcggtcaag gaaatactcc 300
agttggtatg tggcactgaa acgaactgga caatataaac ttggatccaa aacaggaccg 360
gggcagaaag ctatactttt tcttccaatg tctgctaaga gctga 405

<210> SEQ ID NO 193
<211> LENGTH: 468
<212> TYPE: DNA
<213> ORGANISM: Bushbaby

<400> SEQUENCE: 193
atggcagccg ggagcatcac cacgctgccc tccctgcccg aggacggcgg cagcgacgcc 60
tttccgcccg gccacttcaa ggaccccaag cgactgtact gcaaaaacgg gggcttcttc 120
ctgcgcatcc accccgacgg ccgagtggac ggggtccggg agaagagcga cccttacatc 180
aaactacaac ttcaagcaga agagagagga gttgtgtcta tcaaaggagt gtgtgcgaac 240
cgttaccttg ctatgaagga agacggaaga ttgctggctt ctaaattgat tacagacgag 300
tgcttctttt ttgaacgact ggaatctaat aactacaata cttaccggtc aagaaaatac 360
tccagttggt atgtggcact gaaacgaact ggacagtata aacttggatc caaaacagga 420
cctgggcaga aagctatact tttcttcca atgtctgcta agagctga 468

<210> SEQ ID NO 194
<211> LENGTH: 465
<212> TYPE: DNA
<213> ORGANISM: House mouse

<400> SEQUENCE: 194
atggctgcca gcggcatcac ctcgcttccc gcactgccgg aggacggcgg cgccgccttc 60
ccaccaggcc acttcaagga ccccaagcgg ctctactgca agaacggcgg cttcttcctg 120
cgcatccatc ccgacggccg cgtggatggc gtccgcgaga agagcgaccc acacgtcaaa 180
ctacaactcc aagcagaaga gagaggagtt gtgtctatca agggagtgtg tgccaaccgg 240
taccttgcta tgaaggaaga tggacggctg ctggcttcta agtgtgttac agaagagtgt 300
ttcttctttg aacgactgga atctaataac tacaatactt accggtcacg gaaatactcc 360
agttggtatg tggcactgaa acgaactggg cagtataaac tcggatccaa aacgggacct 420
ggacagaagg ccatactgtt tcttccaatg tctgctaaga gctga 465

<210> SEQ ID NO 195
<211> LENGTH: 432

<212> TYPE: DNA
<213> ORGANISM: Squirrel

<400> SEQUENCE: 195
ctgcccgagg acggcggcgg cggcgccttc ccgcccggcc actttaagga ccccaagcgg 60
ctctactgca aaaacggagg cttcttcctg cgcatccacc ccgacggccg agtggacggg 120
gtccgggaga agagcgaccc ccacatcaag ctccagcttc aagccgaaga ccgaggggtt 180
gtgtccatca agggagtgtg tgcaaaccga tacctggcca tgaaggagga cgggaggctc 240
ctggcttcta aatgtgttac ggacgagtgt ttcttttttg aacgactgga atcaaataac 300
tacaatactt accggtcaag gaaatactcc agttggtatg tggccctgaa acgaacaggg 360
cagtataaac ttggatccaa aacaggacct gggcagaaag ctatactttt tcttccaatg 420
tctgctaaga gc 432

<210> SEQ ID NO 196
<211> LENGTH: 318
<212> TYPE: DNA
<213> ORGANISM: Domestic cat

<400> SEQUENCE: 196
ccacttcaag gaccccaagc gtctgtactg caaaaacggg ggcttcttcc tgcgcatcca 60
ccccgacggc cgagtggatg ggtccggga gaagagcgac cctcacatca aactgcaact 120
tcaggcagaa gagagagggg ttgtgtccat caaaggagtc tgtgcaaacc gctatcttgc 180
catgaaggaa gatggaagat tactggcttc taaatgtgtt acggacgagt gtttcttttt 240
tgaacgattg gaatctaata actacaatac ttatcggtca aggaaatact ccagctggta 300
tgtggcactg aaacgaac 318

<210> SEQ ID NO 197
<211> LENGTH: 288
<212> TYPE: DNA
<213> ORGANISM: Guinea pig

<400> SEQUENCE: 197
gttaaactac aacttcaagc cgaagacaga ggagttgtgt ctatcaaggg agtctgtgcg 60
aaccgttacc ttgctatgaa ggaagacgga agattattgg cttccaaatg tgttacagat 120
gaatgtttct tttttgaacg actggaatct aataactaca acacttaccg gtcaaggaaa 180
tactccagtt ggtatgtggc actgaaacga actggacaat ataaacttgg gtccaaaaca 240
ggaccagggc agaaagccat actttttctt ccaatgtctg cgaagagc 288

<210> SEQ ID NO 198
<211> LENGTH: 471
<212> TYPE: DNA
<213> ORGANISM: Tasmanian devil

<400> SEQUENCE: 198
atggccgcgg gcagcatcac cacgttgccg gccctggccg gggatggagc cagcgggggc 60
gcctttcccc cgggccactt ccaggacccc aagcggctgt actgcaagaa cggaggcttc 120
ttcttgcgca tccatcccga cggtcacgtg gacggcatcc gcgagaagag cgatccgcac 180
attaaacttc agcttcaggc agaagagaga ggagtagtgt ctattaaagg agtttgtgcc 240
aaccgctatc ttgccatgaa agaggatggc agattactgg ctctgaaatg tgtgactgaa 300
gagtgtttct tctttgaacg tctagagtcc aacaattaca acacttatcg ctcaaggaaa 360

```
tactccaatt ggtatgtggc attgaaacgc acaggccagt ataagcttgg atccaagact    420

ggaccagggc agaaagccat ccttttcctt cccatgtctg ctaagagctg a             471


<210> SEQ ID NO 199
<211> LENGTH: 471
<212> TYPE: DNA
<213> ORGANISM: Gray short-tailed opossum

<400> SEQUENCE: 199

atggccgcag gcagcatcac cacgctgcca gccctgtccg gggacggagg cggcgggggc     60

gcctttcccc cgggccactt caaggacccc aagcggctgt actgcaagaa cggaggcttc    120

ttcctgcgca tccaccccga cggccgtgtg gacggcatcc gcgagaagag cgacccgaac    180

attaaactac aacttcaggc agaagagaga ggagtggtgt ctattaaagg agtatgtgcc    240

aatcgctatc ttgccatgaa ggaagatgga agattattgg ctttgaaata tgtgaccgaa    300

gagtgtttct ttttcgaacg cttggagtcc aacaactaca acacttatcg ctcgaggaaa    360

tattccaatt ggtacgtggc actgaaacga acggggcagt acaagcttgg atccaagact    420

ggcccggggc agaaagccat ccttttcctc cccatgtctg ctaagagctg a             471


<210> SEQ ID NO 200
<211> LENGTH: 468
<212> TYPE: DNA
<213> ORGANISM: Rabbit

<400> SEQUENCE: 200

atggcagccg agagcatcac cacgctgccc gccctgccgg aggatggagg cagcggcgcc     60

ttcccgcccg gccacttcaa ggaccccaag cggctgtact gcaaaaacgg gggtttcttc    120

ctgcgtatcc accccgacgg ccgcgtggac ggggtccggg agaagagcga cccacacatc    180

aaattacaac ttcaagcaga agagagagga gttgtatcca tcaaaggtgt gtgtgcaaac    240

cgttaccttg ctatgaagga agatggaaga ctgctggctt ctaaatgtgt tacagacgag    300

tgcttctttt ttgaacgact ggagtctaat aactacaata cttaccggtc aaggaaatat    360

tccagctggt atgtggcact gaaacgaact gggcagtata aacttggatc caaaacagga    420

cctgggcaga aggctatact tttcttccca atgtctgcta agagctga                 468


<210> SEQ ID NO 201
<211> LENGTH: 375
<212> TYPE: DNA
<213> ORGANISM: Turkey

<400> SEQUENCE: 201

cggctctact gtaagaacgg cggcttcttc ctgcgcatca atcccgacgg cagagtggac     60

ggcgtccgcg agaagagcga tccgcacatc aaactgcagc ttcaggcaga agaaagagga    120

gtggtatcaa tcaaaggtgt aagtgcaaac cgctttctgg ctatgaagga ggatggcaga    180

ttgctggcac tgaaatgtgc aacagaagaa tgtttctttt ttgagcgttt ggaatctaat    240

aattataaca cttaccggtc acggaagtac tctgattggt atgtggcact gaaaagaact    300

ggacagtaca agcccggacc aaaaactgga cctggacaga aagctatcct tttcttcca     360

atgtctgcta aaagc                                                     375


<210> SEQ ID NO 202
<211> LENGTH: 477
<212> TYPE: DNA
<213> ORGANISM: Gallus gallus
```

<400> SEQUENCE: 202
atggcggcgg gggcggcggg gagcatcacc acgctgccgg cgctgcccga cgacgggggc 60
ggcggcgctt ttccccccgg gcacttcaag gaccccaagc ggctctactg caagaacggc 120
ggcttcttcc tgcgcatcaa ccccgacggc agggtggacg gcgtccgcga gaagagcgat 180
ccgcacatca aactgcagct tcaagcagaa gaaagaggag tagtatcaat caaaggcgta 240
agtgcaaacc gctttctggc tatgaaggag gatggcagat tgctggcact gaaatgtgca 300
acagaggaat gtttcttttt cgagcgcttg gaatctaata actataacac ttaccggtca 360
cggaagtact ctgattggta tgtggcactg aaaaggactg gacagtacaa gcccggacca 420
aaaactggac ctggacagaa agctatcctt tttcttccaa tgtctgctaa aagctga 477

<210> SEQ ID NO 203
<211> LENGTH: 462
<212> TYPE: DNA
<213> ORGANISM: Zebra finch

<400> SEQUENCE: 203
atggcggcgg cggggggcat cgctacgctg cccgacgacg gcggcagcgg cgcctttccc 60
ccggggcact tcaaggaccc caagcgcctg tactgcaaga acggcggctt cttcctgcgc 120
atcaaccccg acgggaaggt ggacggcgtc cgcgagaaga gcgacccgca catcaagctg 180
cagcttcagg cggaggaacg aggagtggtg tccatcaaag gtgtcagtgc caatcgcttc 240
ctggccatga aagaggatgg cagattgctg gccttgaaat atgcaacaga agaatgtttc 300
ttttttgaac gtttggaatc caataactat aacacttacc ggtcacggaa atactcggat 360
tggtatgtgg cactgaaaag aactggacag tacaaacctg gaccaaaaac tggacctgga 420
cagaaagcta tccttttcct tcctatgtct gctaaaagct ga 462

<210> SEQ ID NO 204
<211> LENGTH: 468
<212> TYPE: DNA
<213> ORGANISM: Japanese firebelly newt

<400> SEQUENCE: 204
atggctgctg ggagcatcac cagtctccct gccctacccg aggacgggaa tggcggcacc 60
ttcacacccg gcggattcaa agagccgaag aggctgtact gcaagaacgg gggcttcttt 120
ctccggatca actccgacgg caaggtggac ggagcccggg agaagagcga ctcctacatt 180
aaactgcagc ttcaagcaga agagcgcggt gtggtgtcca tcaagggagt atgtgcaaac 240
cgctatctcg ctatgaagga tgatggcagg ctgatggcgc tgaaatggat aaccgatgaa 300
tgcttctttt tcgagcgact ggagtccaac aactataaca cgtatcgatc acggaaatat 360
tccgattggt atgtggcgct gaaaagaact gggcaataca aaaatggatc aaaaaccgga 420
gcaggacaga aagcaatcct tttctaccc atgtcggcca agagttga 468

<210> SEQ ID NO 205
<211> LENGTH: 468
<212> TYPE: DNA
<213> ORGANISM: African clawed frog

<400> SEQUENCE: 205
atggcggcag ggagcatcac aactctgcca actgaatccg aggatggggg aaacactcct 60
ttttcaccag ggagttttaa agaccccaag aggctctact gcaagaacgg gggcttcttc 120

-continued

```
ctcaggataa actcagacgg gagagtggac gggtcaaggg acaaaagtga ctcgcacata    180

aaattacagc tacaagctgt agagcgggga gtggtatcaa taaagggaat cactgcaaat    240

cgctaccttg ccatgaagga agatgggaga ttaacatcgc tgaggtgtat aacagatgaa    300

tgcttctttt ttgaacgact ggaagctaat aactacaaca cttaccggtc tcggaaatac    360

agcagctggt atgtggcact aaagcgaacc gggcagtaca aaaatggatc gagcactgga    420

ccgggacaaa aagctatttt atttctccca atgtccgcaa agagctga                 468
```

<210> SEQ ID NO 206
<211> LENGTH: 471
<212> TYPE: DNA
<213> ORGANISM: White-eared opossum

<400> SEQUENCE: 206

```
atggcagcag gcagcatcac cacattgccg gccctgtccg gggacggagg cggcggggga     60

gcctttcctc caggccactt caaggacccc aagcggctgt actgcaagaa cggaggcttc    120

ttcctgcgca tccaccccga cggccgcgtg gacggcatcc gcgagaagag cgacccgaac    180

attaaactac aacttcaggc agaagagaga ggagtagtgt ctattaaagg agtatgtgcc    240

aaccgatatc ttgccatgaa ggaggatggc agattattgg ctttgaaata tgtgaccgaa    300

gagtgtttct tttttgaacg tttggagtcc aacaactaca acacttatcg ctcaagaaaa    360

tattccaatt ggtatgtggc actgaaacga acggggcagt ataagcttgg atccaagact    420

ggcccggggc agaaagccat ccttttctcc ccatgtctgc taagatgctg a             471
```

<210> SEQ ID NO 207
<211> LENGTH: 288
<212> TYPE: DNA
<213> ORGANISM: Microbat

<400> SEQUENCE: 207

```
gtcaaactcc aacttcaagc agaagagaga ggggtcgtgt ctatcaaagg agtgtgtgcc     60

aaccgctatc tcgctatgaa ggaggacggc cggttacagg cttctaaatg tgttacggat    120

gagtgtttct tttttgaacg gttggaatcc aataactaca acacttaccg gtcaagaaag    180

tactccagtt ggtatgtggc attgaagcgg aatgggcagt ataaacttgg acccaaaaca    240

ggacctggcc agaaagccat actttttctt cccatgtctg ctaagagc                 288
```

<210> SEQ ID NO 208
<211> LENGTH: 420
<212> TYPE: DNA
<213> ORGANISM: Anole lizard

<400> SEQUENCE: 208

```
gcggcggcgg cctctttccc cccgggcccc ttcaaggacc ccaagcgcct ctactgcaag     60

aacgggggct tcttcctgcg gatcaacccc gacggcggcg tggacggcgt ccgagagaag    120

agcgacccca acatcaaatt gctgctccag gcagaggaga gaggtgtagt gtccatcaaa    180

ggtgtatgcg caaaccgttt cctggctatg aatgaagacg gtcgattgtt agcactgaaa    240

tacgtaacag atgaatgctt cttttttgaa cgcttggaat ctaataatta caatacttat    300

cggtctcgta aataccgtga ttggtacatt gcactgaaac gaactggtca gtacaaactt    360

ggaccaaaaa ctggacgagg ccagaaagct atccttttcc ttccaatgtc tgccaaaagt    420
```

<210> SEQ ID NO 209
<211> LENGTH: 282

-continued

<212> TYPE: DNA
<213> ORGANISM: Armadillo

<400> SEQUENCE: 209
atggcagccg ggagcatcac cacgctgccc gctctgcccg aggacggcgg cagcggcgcc 60
ttcccgccgg gccacttcaa ggaccccaag cggctgtact gcaaaaacgg gggcttcttc 120
ctgcgcatcc atcccgacgg ccgagtggac ggggtccggg agaagagcga ccctaacatc 180
aaactacaac ttcaagcaga agagagaggg gtcgtgtcta tcaaaggcgt gtgtgcgaac 240
cgttaccttg ctatgcggga agacggaaga ctccaggcgt ct 282

<210> SEQ ID NO 210
<211> LENGTH: 567
<212> TYPE: DNA
<213> ORGANISM: Tree shrew

<400> SEQUENCE: 210
gcgggggtta gagctgagag ggaggaggca ccggggagcg gtgacagccg ggggaccgat 60
cccgccgcgc gttcgctcat caggaggccg gatgctgcag cgcgagaggc gcttcttgga 120
gccaggagcc gggttcaggg cagctccacc tcctggccag cctcgtcacg aaccgggatc 180
aagttgccgg acgactcagg tcaaggaatg ggcggctatc ctctggaccg cccgagccgg 240
agcacagggc gagggctggg cggtgccccg gaccctgccg taaaactaca gcttcaagcg 300
gaagagagag gggtcgtgtc tatcaaagga gtgtgtgcaa accgttacct ggccatgaag 360
gaggatgggc gactgctggc ttctaaatgt gttacagatg agtgtttctt ttttgaacga 420
ctggaatcta ataactacaa tacttaccgg tcccgaaagt actccagctg gtatgtggca 480
ctgaaacgaa ctgggcagta taaacttgga tccaaaacag gacctgggca gaaagctata 540
ctttttcttc caatgtctgc taaaagc 567

<210> SEQ ID NO 211
<211> LENGTH: 465
<212> TYPE: DNA
<213> ORGANISM: Western clawed frog

<400> SEQUENCE: 211
atggcagcag gaagcatcac aaccctacca accgaatctg aggatggaaa cactcctttc 60
ccaccgggga actttaagga ccccaagagg ctctactgca agaatggggg ctacttcctc 120
aggattaact cagacgggag agtggacgga tcaagggata aaagtgactt acacataaaa 180
ttacagctac aagcagtaga gcggggagtg gtatcaataa agggaatcac tgcaaatcgc 240
taccttgcca tgaaggaaga tgggagatta acatcgctga agtgtataac agatgaatgc 300
ttcttttatg aacgattgga agctaataac tacaacactt accggtctcg gaaaaacaac 360
agctggtatg tggcactaaa gcgaactggg cagtataaaa atggatcgac cactggacca 420
ggacaaaaag ctattttgtt tctcccaatg tcagcaaaaa gctga 465

<210> SEQ ID NO 212
<211> LENGTH: 468
<212> TYPE: DNA
<213> ORGANISM: Coelacanth

<400> SEQUENCE: 212
atggctgcgg gaggaatcac taccctgccg gcggtacctg aggatggagg cagcagcacc 60
ttccctccag gaaacttcaa ggagcccaag agactttact gtaagaatgg aggctatttc 120
ttaaggataa accccgatgg aagagtggat ggaacaaggg agaaaaatga tccttatata 180
aaattacaac tgcaagctga atctatagga gtggtgtcga taaagggagt ttgttcaaac 240
cgttacctag cgatgaatga agactgtaga ctttttggat tgaaatatcc aacggatgaa 300
tgtttcttcc atgagaggct ggagtccaac aactacaata cttatcgttc aaagaagtat 360
tcggattggt atgtggcgct gaaacggact ggtcagtaca aacctgggcc aaaaactgga 420
ctgggacaaa aagcaatcct tttccttccg atgtctgcca agagttga 468

<210> SEQ ID NO 213
<211> LENGTH: 468
<212> TYPE: DNA
<213> ORGANISM: Spotted green pufferfish

<400> SEQUENCE: 213
atggccacgg gagggatcac gacgcttcca tccacacctg aagacggcgg cagcagcggc 60
tttcctcccg gcagcttcaa ggatcccaaa aggctctact gtaaaaacgg aggtttcttc 120
ctgaggatca agtccgacgg ggtcgtggac ggaatccggg agaagagtga cccccacata 180
aagcttcagc tccaggcgac ctctgtgggg gaggtggtca tcaagggggt gtgcgctaac 240
cgctatctgg ccatgaacag agatggacgg ctgttcggaa cgaaacgagc cacggacgaa 300
tgccatttct tagagcggct tgagagcaac aactacaaca cttaccgctc caggaagtac 360
ccaaccatgt ttgtgggact gacgcggacg ggccagtaca agtctgggag caaaactgga 420
ccgggccaaa aggccatcct tttcttccg atgtccgcca aatgctaa 468

<210> SEQ ID NO 214
<211> LENGTH: 468
<212> TYPE: DNA
<213> ORGANISM: Stickleback

<400> SEQUENCE: 214
atggccacgg caggcttcgc gacgcttccc tccacgcccg aagacggcgg cagcggcggc 60
ttcacccccg gggattcaa ggatcccaag aggctgtact gcaaaaacgg gggcttcttc 120
ttgaggatca ggtccgacgg aggtgtagat ggaatcaggg agaagagcga cgcccacata 180
aagctccaaa tccaggcgac gtcggtgggg gaggtggtca tcaaaggagt ctgtgccaac 240
cgctatctgg ccatgaacag agacggccgg ctgttcggag tgagacgggc gacggacgaa 300
tgctacttcc tggagcggct ggagagtaac aactacaaca cctaccgctc caggaagtac 360
cccggcatgt acgtggctct gaagcggacc ggccagtaca agtccgggag caaaaccgga 420
cccggtcaaa aggccattct gttcctcccc atgtcggcta agtgctaa 468

<210> SEQ ID NO 215
<211> LENGTH: 468
<212> TYPE: DNA
<213> ORGANISM: Fugu rubripes

<400> SEQUENCE: 215
atggccacgg gagggatcac aacacttcca tccacacctg aagacggcgg cagcggcggt 60
tttcctcccg ggagcttcaa ggatcccaaa aggctgtact gtaaaaacgg cggcttcttc 120
ctgaggatca ggtccgacgg ggccgtggac ggaacccggg agaagactga cccccacata 180
aagcttcagc tccaggcgac ctctgtgggg gaggtggtca tcaagggggt ttgtgctaat 240
cgttatctgg ccatgaacag agatggacga ctgtttggaa tgaaacgagc gacggatgaa 300
tgccacttct tagagcggct cgagagcaac aactacaaca cctaccgctc caggaagtac 360
cccaacatgt ttgtgggact gacgcgaact ggcaactaca agtctgggac taaaactgga 420
ccgggccaaa aggccatcct ctttcttccg atgtcggcca aatactaa 468

<210> SEQ ID NO 216
<211> LENGTH: 468
<212> TYPE: DNA
<213> ORGANISM: Rainbow trout

<400> SEQUENCE: 216
atggccacag gagaaatcac cactctaccc gccacacctg aagatggagg cagtggcggc 60
ttccttccag gaaactttaa ggagcccaag aggttgtact gtaaaaatgg aggctacttc 120
ttgaggataa actctaacgg aagcgtggac gggatcagag ataagaacga cccccacaat 180
aagcttcaac tccaggcgac ctcagtgggg gaagtagtaa tcaaaggggt ctcagccaac 240
cgctatctgg ccatgaatgc agatggaaga ctgtttggac cgagacggac aacagatgaa 300
tgctacttca tggagaggct ggagagtaac aactacaaca cctaccgctc tcgaaagtac 360
cctgaaatgt atgtggcact gaaaaggact ggccagtaca agtcaggatc caaaactgga 420
cccggccaaa aagccatcct cttcctcccc atgtcagcca gacgctga 468

<210> SEQ ID NO 217
<211> LENGTH: 453
<212> TYPE: DNA
<213> ORGANISM: Salmon

<400> SEQUENCE: 217
atggccacag gagaaatcac cactctaccc gccacacctg aagatggagg cagtggcggc 60
ttccctccag gaaactttaa ggatcccaag aggctgtact gtaaaaacgg gggctacttc 120
ttgagaataa actctaatgg aagcgtggac gggatccgag agaagaacga cccccacaaa 180
cagcctcaat ttgtcagggc atggactctt caaggtgtca aacgttccac agggatgctg 240
gcccatgttg actccaacgc ttcccacaat tgtgtcaagg tggctggatg ttctttggga 300
gaatttggca gtatgtccaa ccggcctcat aaccgcagac cacgtgtagc tacaccagcc 360
caggacctcc acatccggct tcttcatcta cgggatcgtc tgaaaccagc caccccgaaca 420 gctgataaaa ctgaggagta tttctgtctg taa 453

<210> SEQ ID NO 218
<211> LENGTH: 465
<212> TYPE: DNA
<213> ORGANISM: Zebrafish

<400> SEQUENCE: 218
atggccaccg gagggatcac cacactcccg gccgctccgg acgccgaaaa cagcagcttt 60
cccgcgggca gcttcaggga tcccaagcgc ctgtactgca aaaacggagg attcttcctg 120
cggatcaacg cggacggccg agtggacgga gcccgagaca agagcgaccc gcacattcgt 180
ctgcagctgc aggcgacggc agtgggtgaa gtactcatta aaggcatctg taccaaccgt 240
ttccttgcca tgaacgcaga cggacgactg ttcgggacga aaaggaccac agatgaatgt 300
tatttcctgg agcgcctgga gtccaacaac tacaacacat acagatcccg caagtatccc 360
gactggtacg tggctctgaa gagaaccggc cagtataaaa gcggctctaa aaccagcccg 420
ggacagaagg ccatcctgtt tctgcccatg tcggccaaat gctga 465

<210> SEQ ID NO 219

<211> LENGTH: 468
<212> TYPE: DNA
<213> ORGANISM: Nile tilapia

<400> SEQUENCE: 219
atggccacgg gaggaatcac aacacttccc gctacacctg aagacggcgg cagcagcggc 60
tttcctcctg ggaacttcaa ggaccctaaa aggctgtact gtaaaaatgg tggcttcttc 120
ttgaggataa aatctgatgg aggagtggat ggaatacgag agaaaaacga cccccacata 180
aagcttcaac tccaggcgac ctcagtggga gaagtggtca tcaaagggat ttgtgcaaac 240
cgatatctgg caatgaacag agatggacga ctgtttggag cgagaagagc aacagatgag 300
tgctacttct tagagcggct cgagagcaac aactacaaca cctaccgctc caggaagtac 360
ccaaacatgt acgtggcgct gaagcggact ggccagtaca agtctggaag caaaactgga 420
ccgggtcaaa aggcaattct ctttctccca atgtctgcta aatgctaa 468

<210> SEQ ID NO 220
<211> LENGTH: 468
<212> TYPE: DNA
<213> ORGANISM: Medaka

<400> SEQUENCE: 220
atggctacgg gagaaatcac aacacttccc tccccagctg aaaacagcag aagcgatggc 60
tttcctccag ggaactacaa ggatcctaag aggctctact gtaaaaatgg aggtttgttt 120
ttgaggatta aacctgatgg aggagtggat ggaatccggg aaaaaaaaga tccccacgtt 180
aagcttcgcc ttcaggctac ctcagcggga gaggtggtga tcaaaggagt ttgttcaaac 240
agatatctgg cgatgcatgg agatggacgt ctatttggag tgagacaagc aacagaggaa 300
tgctacttct tggagcgact agagagcaac aactataaca cctatcgctc taaaaagtac 360
ccaaacatgt acgtggcact gaagcggaca ggccagtaca aacctggaaa caaaactgga 420
ccaggtcaaa aggccattct ctttctgcct atgtctgcca agtactaa 468

<210> SEQ ID NO 221
<211> LENGTH: 206
<212> TYPE: PRT
<213> ORGANISM: Homo sapiens

<400> SEQUENCE: 221

Met Ser Gly Pro Gly Thr Ala Ala Val Ala Leu Leu Pro Ala Val Leu
1 5 10 15

Leu Ala Leu Leu Ala Pro Trp Ala Gly Arg Gly Gly Ala Ala Ala Pro
20 25 30

Thr Ala Pro Asn Gly Thr Leu Glu Ala Glu Leu Glu Arg Arg Trp Glu
35 40 45

Ser Leu Val Ala Leu Ser Leu Ala Arg Leu Pro Val Ala Ala Gln Pro
50 55 60

Lys Glu Ala Ala Val Gln Ser Gly Ala Gly Asp Tyr Leu Leu Gly Ile
65 70 75 80

Lys Arg Leu Arg Arg Leu Tyr Cys Asn Val Gly Ile Gly Phe His Leu
85 90 95

Gln Ala Leu Pro Asp Gly Arg Ile Gly Gly Ala His Ala Asp Thr Arg
100 105 110

Asp Ser Leu Leu Glu Leu Ser Pro Val Glu Arg Gly Val Val Ser Ile
115 120 125

Phe Gly Val Ala Ser Arg Phe Phe Val Ala Met Ser Ser Lys Gly Lys

```
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205


<210> SEQ ID NO 222
<211> LENGTH: 268
<212> TYPE: PRT
<213> ORGANISM: Homo sapiens

<400> SEQUENCE: 222

Met Ser Leu Ser Phe Leu Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ser Ala Ser Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
    130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Lys Pro Pro
225                 230                 235                 240

Ser Pro Ile Lys Pro Lys Ile Pro Leu Ser Ala Pro Arg Lys Asn Thr
                245                 250                 255

Asn Ser Val Lys Tyr Arg Leu Lys Phe Arg Phe Gly
            260                 265


<210> SEQ ID NO 223
<211> LENGTH: 208
<212> TYPE: PRT
<213> ORGANISM: Homo sapiens
```

<400> SEQUENCE: 223

Met Ala Leu Gly Gln Lys Leu Phe Ile Thr Met Ser Arg Gly Ala Gly
1               5                   10                  15

Arg Leu Gln Gly Thr Leu Trp Ala Leu Val Phe Leu Gly Ile Leu Val
            20                  25                  30

Gly Met Val Val Pro Ser Pro Ala Gly Thr Arg Ala Asn Asn Thr Leu
        35                  40                  45

Leu Asp Ser Arg Gly Trp Gly Thr Leu Leu Ser Arg Ser Arg Ala Gly
    50                  55                  60

Leu Ala Gly Glu Ile Ala Gly Val Asn Trp Glu Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
        115                 120                 125

Ser Leu Phe Gly Val Arg Ser Ala Leu Phe Val Ala Met Asn Ser Lys
    130                 135                 140

Gly Arg Leu Tyr Ala Thr Pro Ser Phe Gln Glu Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205

<210> SEQ ID NO 224
<211> LENGTH: 208
<212> TYPE: PRT
<213> ORGANISM: Homo sapiens

<400> SEQUENCE: 224

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

-continued

```
Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205


<210> SEQ ID NO 225
<211> LENGTH: 207
<212> TYPE: PRT
<213> ORGANISM: Homo sapiens

<400> SEQUENCE: 225

Met Ala Glu Val Gly Gly Val Phe Ala Ser Leu Asp Trp Asp Leu His
1               5                   10                  15

Gly Phe Ser Ser Ser Leu Gly Asn Val Pro Leu Ala Asp Ser Pro Gly
            20                  25                  30

Phe Leu Asn Glu Arg Leu Gly Gln Ile Glu Gly Lys Leu Gln Arg Gly
        35                  40                  45

Ser Pro Thr Asp Phe Ala His Leu Lys Gly Ile Leu Arg Arg Arg Gln
    50                  55                  60

Leu Tyr Cys Arg Thr Gly Phe His Leu Glu Ile Phe Pro Asn Gly Thr
65                  70                  75                  80

Val His Gly Thr Arg His Asp His Ser Arg Phe Gly Ile Leu Glu Phe
                85                  90                  95

Ile Ser Leu Ala Val Gly Leu Ile Ser Ile Arg Gly Val Asp Ser Gly
            100                 105                 110

Leu Tyr Leu Gly Met Asn Glu Arg Gly Glu Leu Tyr Gly Ser Lys Lys
        115                 120                 125

Leu Thr Arg Glu Cys Val Phe Arg Glu Gln Phe Glu Glu Asn Trp Tyr
    130                 135                 140

Asn Thr Tyr Ala Ser Thr Leu Tyr Lys His Ser Asp Ser Glu Arg Gln
145                 150                 155                 160

Tyr Tyr Val Ala Leu Asn Lys Asp Gly Ser Pro Arg Glu Gly Tyr Arg
                165                 170                 175

Thr Lys Arg His Gln Lys Phe Thr His Phe Leu Pro Arg Pro Val Asp
            180                 185                 190

Pro Ser Lys Leu Pro Ser Met Ser Arg Asp Leu Phe His Tyr Arg
        195                 200                 205


<210> SEQ ID NO 226
<211> LENGTH: 211
<212> TYPE: PRT
<213> ORGANISM: Homo sapiens

<400> SEQUENCE: 226

Met Ala Pro Leu Ala Glu Val Gly Gly Phe Leu Gly Gly Leu Glu Gly
1               5                   10                  15

Leu Gly Gln Gln Val Gly Ser His Phe Leu Leu Pro Pro Ala Gly Glu
            20                  25                  30

Arg Pro Pro Leu Leu Gly Glu Arg Arg Ser Ala Ala Glu Arg Ser Ala
        35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80
```

-continued

```
Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210
```

<210> SEQ ID NO 227
<211> LENGTH: 621
<212> TYPE: DNA
<213> ORGANISM: Homo sapiens

<400> SEQUENCE: 227

```
atgtcggggc ccgggacggc cgcggtagcg ctgctcccgg cggtcctgct ggccttgctg     60

gcgccctggg cgggccgagg gggcgccgcc gcacccactg cacccaacgg cacgctggag    120

gccgagctgg agcgccgctg ggagagcctg gtggcgctct cgttggcgcg cctgccggtg    180

gcagcgcagc ccaaggaggc ggccgtccag agcggcgccg gcgactacct gctgggcatc    240

aagcggctgc ggcggctcta ctgcaacgtg ggcatcggct tccacctcca ggcgctcccc    300

gacggccgca tcggcggcgc gcacgcggac acccgcgaca gcctgctgga gctctcgccc    360

gtggagcggg gcgtggtgag catcttcggc gtggccagcc ggttcttcgt ggccatgagc    420

agcaagggca agctctatgg ctcgcccttc ttcaccgatg agtgcacgtt caaggagatt    480

ctccttccca acaactacaa cgcctacgag tcctacaagt accccggcat gttcatcgcc    540

ctgagcaaga atgggaagac caagaagggg aaccgagtgt cgcccaccat gaaggtcacc    600

cacttcctcc ccaggctgtg a                                              621
```

<210> SEQ ID NO 228
<211> LENGTH: 807
<212> TYPE: DNA
<213> ORGANISM: Homo sapiens

<400> SEQUENCE: 228

```
atgagcttgt ccttcctcct cctcctcttc ttcagccacc tgatcctcag cgcctgggct     60

cacggggaga agcgtctcgc ccccaaaggg caacccggac ccgctgccac tgataggaac    120

cctagaggct ccagcagcag acagagcagc agtagcgcta tgtcttcctc ttctgcctcc    180

tcctccccg cagcttctct gggcagccaa ggaagtggct tggagcagag cagtttccag    240

tggagcccct cggggcgccg gaccggcagc ctctactgca gagtgggcat cggtttccat    300

ctgcagatct acccggatgg caaagtcaat ggatcccacg aagccaatat gttaagtgtt    360

ttggaaatat ttgctgtgtc tcaggggatt gtaggaatac gaggagtttt cagcaacaaa    420
```

-continued

```
tttttagcga tgtcaaaaaa aggaaaactc catgcaagtg ccaagttcac agatgactgc    480

aagttcaggg agcgttttca agaaaatagc tataatacct atgcctcagc aatacataga    540

actgaaaaaa cagggcggga gtggtatgtg gccctgaata aaagaggaaa agccaaacga    600

gggtgcagcc cccgggttaa accccagcat atctctaccc attttctgcc aagattcaag    660

cagtcggagc agccagaact ttctttcacg gttactgttc ctgaaaagaa aaagccacct    720

agccctatca agccaaagat tcccctttct gcacctcgga aaaataccaa ctcagtgaaa    780

tacagactca agtttcgctt tggataa                                        807
```

<210> SEQ ID NO 229
<211> LENGTH: 627
<212> TYPE: DNA
<213> ORGANISM: Homo sapiens

<400> SEQUENCE: 229

```
atggccctgg gacagaaact gttcatcact atgtcccggg gagcaggacg tctgcagggc     60

acgctgtggg ctctcgtctt cctaggcatc ctagtgggca tggtggtgcc ctcgcctgca    120

ggcacccgtg ccaacaacac gctgctggac tcgaggggct ggggcaccct gctgtccagg    180

tctcgcgcgg ggctagctgg agagattgcc ggggtgaact gggaaagtgg ctatttggtg    240

gggatcaagc ggcagcggag gctctactgc aacgtgggca tcggctttca cctccaggtg    300

ctccccgacg gccggatcag cgggacccac gaggagaacc cctacagcct gctggaaatt    360

tccactgtgg agcgaggcgt ggtgagtctc tttggagtga gaagtgccct cttcgttgcc    420

atgaacagta aaggaagatt gtacgcaacg cccagcttcc aagaagaatg caagttcaga    480

gaaaccctcc tgcccaacaa ttacaatgcc tacgagtcag acttgtacca agggacctac    540

attgccctga gcaaatacgg acgggtaaag cggggcagca aggtgtcccc gatcatgact    600

gtcactcatt tccttcccag gatctaa                                        627
```

<210> SEQ ID NO 230
<211> LENGTH: 627
<212> TYPE: DNA
<213> ORGANISM: Homo sapiens

<400> SEQUENCE: 230

```
atggctccct taggtgaagt tgggaactat ttcggtgtgc aggatgcggt accgtttggg     60

aatgtgcccg tgttgccggt ggacagcccg gttttgttaa gtgaccacct gggtcagtcc    120

gaagcagggg ggctccccag gggacccgca gtcacggact tggatcattt aaaggggatt    180

ctcaggcgga ggcagctata ctgcaggact ggatttcact tagaaatctt ccccaatggt    240

actatccagg gaaccaggaa agaccacagc cgatttggca ttctggaatt tatcagtata    300

gcagtgggcc tggtcagcat tcgaggcgtg gacagtggac tctacctcgg gatgaatgag    360

aagggggagc tgtatggatc agaaaaacta acccaagagt gtgtattcag agaacagttc    420

gaagaaaact ggtataatac gtactcatca aacctatata agcacgtgga cactggaagg    480

cgatactatg ttgcattaaa taaagatggg accccgagag aagggactag gactaaacgg    540

caccagaaat tcacacattt tttacctaga ccagtggacc ccgacaaagt acctgaactg    600

tataaggata ttctaagcca aagttga                                        627
```

<210> SEQ ID NO 231
<211> LENGTH: 624
<212> TYPE: DNA
<213> ORGANISM: Homo sapiens

<400> SEQUENCE: 231
atggcagagg tggggggcgt cttcgcctcc ttggactggg atctacacgg cttctcctcg 60
tctctgggga acgtgccctt agctgactcc ccaggtttcc tgaacgagcg cctgggccaa 120
atcgagggga agctgcagcg tggctcaccc acagacttcg cccacctgaa ggggatcctg 180
cggcgccgcc agctctactg ccgcaccggc ttccacctgg agatcttccc caacggcacg 240
gtgcacggga cccgccacga ccacagccgc ttcggaatcc tggagtttat cagcctggct 300
gtggggctga tcagcatccg ggagtggac tctggcctgt acctaggaat gaatgagcga 360
ggagaactct atgggtcgaa gaaactcaca cgtgaatgtg ttttccggga acagtttgaa 420
gaaaactggt acaacaccta tgcctcaacc ttgtacaaac attcggactc agagagacag 480
tattacgtgg ccctgaacaa agatggctca ccccgggagg gatacaggac taaacgacac 540
cagaaattca ctcacttttt acccaggcct gtagatcctt ctaagttgcc ctccatgtcc 600
agagacctct ttcactatag gtaa 624

<210> SEQ ID NO 232
<211> LENGTH: 636
<212> TYPE: DNA
<213> ORGANISM: Homo sapiens

<400> SEQUENCE: 232
atggctccct tagccgaagt cgggggcttt ctgggcggcc tggagggctt gggccagcag 60
gtgggttcgc atttcctgtt gcctcctgcc ggggagcggc cgccgctgct gggcgagcgc 120
aggagcgcgg cggagcggag cgcgcgcggc gggccggggg ctgcgcagct ggcgcacctg 180
cacggcatcc tgcgccgccg gcagctctat tgccgcaccg gcttccacct gcagatcctg 240
cccgacggca gcgtgcaggg cacccggcag gaccacagcc tcttcggtat cttggaattc 300
atcagtgtgg cagtgggact ggtcagtatt agaggtgtgg acagtggtct ctatcttgga 360
atgaatgaca aaggagaact ctatggatca gagaaactta cttccgaatg catctttagg 420
gagcagtttg aagagaactg gtataacacc tattcatcta acatatataa acatggagac 480
actggccgca ggtattttgt ggcacttaac aaagacggaa ctccaagaga tggcgccagg 540
tccaagaggc atcagaaatt tacacatttc ttacctagac cagtggatcc agaaagagtt 600
ccagaattgt acaaggacct actgatgtac acttga 636

<210> SEQ ID NO 233
<211> LENGTH: 251
<212> TYPE: PRT
<213> ORGANISM: Homo sapiens

<400> SEQUENCE: 233

Met Leu Gly Ala Arg Leu Arg Leu Trp Val Cys Ala Leu Cys Ser Val
1 5 10 15

Cys Ser Met Ser Val Leu Arg Ala Tyr Pro Asn Ala Ser Pro Leu Leu
20 25 30

Gly Ser Ser Trp Gly Gly Leu Ile His Leu Tyr Thr Ala Thr Ala Arg
35 40 45

Asn Ser Tyr His Leu Gln Ile His Lys Asn Gly His Val Asp Gly Ala
50 55 60

Pro His Gln Thr Ile Tyr Ser Ala Leu Met Ile Arg Ser Glu Asp Ala
65 70 75 80

Gly Phe Val Val Ile Thr Gly Val Met Ser Arg Arg Tyr Leu Cys Met

```
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250


<210> SEQ ID NO 234
<211> LENGTH: 251
<212> TYPE: PRT
<213> ORGANISM: Gorilla gorilla

<400> SEQUENCE: 234

Met Leu Gly Ala Arg Leu Arg Leu Trp Val Cys Ala Leu Cys Ser Val
1               5                   10                  15

Cys Ser Leu Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205
```

```
Glu Leu Pro Ser Ala Glu Asp Asn Ser Pro Met Ala Ser Asp Pro Leu
    210                 215                 220

Gly Val Val Arg Gly Gly Arg Val Asn Thr Tyr Ala Gly Gly Thr Gly
225                 230                 235                 240

Pro Glu Gly Cys Arg Pro Phe Pro Lys Phe Ile
                245                 250


<210> SEQ ID NO 235
<211> LENGTH: 251
<212> TYPE: PRT
<213> ORGANISM: Nomascus leucogenys

<400> SEQUENCE: 235

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Gln His Gln Thr Leu Glu Asn Gly Tyr Asp Val Tyr His
        115                 120                 125

Ser Pro Gln His His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Leu His Phe Asn Thr Pro Thr Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Leu Ser Ser Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Pro Lys Phe Ile
                245                 250


<210> SEQ ID NO 236
<211> LENGTH: 251
<212> TYPE: PRT
<213> ORGANISM: Macaca mulatta

<400> SEQUENCE: 236

Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
            20                  25                  30
```

```
Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Arg His Trp Thr Leu Glu Asn Gly Tyr Asp Val Tyr His
        115                 120                 125

Ser Pro Gln His His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Arg Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
    210                 215                 220

Gly Val Val Arg Gly Gly Arg Val Asn Thr His Ala Gly Gly Thr Gly
225                 230                 235                 240

Pro Glu Ala Cys Arg Pro Phe Pro Lys Phe Ile
                245                 250


<210> SEQ ID NO 237
<211> LENGTH: 251
<212> TYPE: PRT
<213> ORGANISM: Macaca fascicularis

<400> SEQUENCE: 237

Met Leu Gly Ala Arg Leu Arg Leu Trp Val Cys Ala Leu Cys Ser Val
1               5                   10                  15

Cys Ser Met Ser Val Ile Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Arg His Trp Thr Leu Glu Asn Gly Tyr Asp Val Tyr His
        115                 120                 125

Ser Pro Gln His His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160
```

```
Arg Asn Glu Ile Pro Leu Ile His Phe Asn Thr Pro Arg Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Val Ala Ser Asp Pro Leu
    210                 215                 220

Gly Val Val Arg Ala Gly Arg Val Asn Thr His Ala Gly Gly Thr Gly
225                 230                 235                 240

Pro Glu Ala Cys Arg Pro Phe Pro Lys Phe Ile
                245                 250


<210> SEQ ID NO 238
<211> LENGTH: 251
<212> TYPE: PRT
<213> ORGANISM: Pan troglodytes

<400> SEQUENCE: 238

Met Leu Gly Ala Arg Leu Arg Leu Trp Val Cys Ala Leu Cys Ser Val
1               5                   10                  15

Cys Ser Val Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Gln His Gln Thr Leu Glu Asn Gly Tyr Asp Val Tyr Tyr
        115                 120                 125

Ser Pro Gln Tyr His Phe Leu Val Ser Leu Gly Arg Ala Lys Arg Ala
    130                 135                 140

Phe Leu Pro Ser Met Asn Pro Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Pro Lys Phe Ile
                245                 250


<210> SEQ ID NO 239
<211> LENGTH: 251
<212> TYPE: PRT
```

<213> ORGANISM: Callithrix jacchus

<400> SEQUENCE: 239

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Ala Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Leu Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn
            100                 105                 110

Cys Arg Phe Arg Pro Gln Arg Leu Glu Asn Gly Tyr Asp Val Tyr Gln
        115                 120                 125

Ser Pro Gln His His Phe Leu Val Ser Leu Gly Arg Ala Lys Arg Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Lys Pro Arg Arg
                165                 170                 175

His Thr Arg Ser Ala Glu Asp Asp Pro Glu Leu Asp Pro Leu Asn Val
            180                 185                 190

Leu Lys Ser Arg Val Arg Met Thr Pro Ala Pro Ala Ser Cys Ser Gln
        195                 200                 205

Glu Leu Leu Ser Ala Glu Asp Asn Ser Pro Val Gly Ser Asp Pro Leu
    210                 215                 220

Gly Met Val Arg Gly Gly Arg Val Asn Ser His Ala Glu Gly Thr Gly
225                 230                 235                 240

Pro Glu Gly Cys Ser Pro Phe Pro Lys Leu Ile
                245                 250

<210> SEQ ID NO 240
<211> LENGTH: 251
<212> TYPE: PRT
<213> ORGANISM: Loxodonta Africana

<400> SEQUENCE: 240

Met Leu Gly Ala Arg Leu Arg Leu Trp Val Cys Thr Leu Cys Ser Ala
1               5                   10                  15

Cys Ser Met Cys Ser Val Arg Ala Tyr Pro Asn Ala Ser Pro Leu Leu
            20                  25                  30

His Ser Ser Trp Gly Gly Leu Thr His Leu Tyr Thr Ala Thr Ala Arg
        35                  40                  45

Asn Ser Tyr His Leu Gln Ile His Lys Asp Gly His Val Asp Gly Thr
    50                  55                  60

Pro Asp Gln Thr Ile Tyr Ser Ala Leu Ile Ile Arg Ser Glu Glu Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asn Pro Glu Asn

```
            100                 105                 110

Cys Arg Phe Lys His Trp Thr Leu Glu Asn Gly Tyr Asp Val Tyr His
        115                 120                 125

Ser Pro Gln His His Phe Leu Val Ser Leu Gly Arg Val Lys Lys Ala
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile Tyr Phe Asn Thr Pro Lys Pro Arg Arg
                165                 170                 175

His Thr Arg Ser Ala Glu Asp Asp Ser Glu Arg Asp Pro Leu Asn Val
            180                 185                 190

Leu Lys Pro Arg Pro Arg Met Thr Pro Ala Pro Ala Ser Cys Ser Gln
        195                 200                 205

Glu Leu Leu Ser Ala Glu Asp Asn Ser Val Val Ala Asn Asp Pro Leu
    210                 215                 220

Gly Val Val Arg Ser Asn Arg Val Asn Thr His Ala Gly Gly Ile Gly
225                 230                 235                 240

Val Glu Arg Cys Arg Pro Phe Pro Lys Phe Ile
                245                 250


<210> SEQ ID NO 241
<211> LENGTH: 250
<212> TYPE: PRT
<213> ORGANISM: Erinaceus telfairi

<400> SEQUENCE: 241

Met Leu Gly Ala His Leu Arg Leu Trp Val Cys Ala Leu Cys Ser Val
1               5                   10                  15

Ser Ala Met Tyr His Val Arg Ala Tyr Pro Asn Ala Ser Pro Leu Leu
            20                  25                  30

Gly Thr Ser Trp Ala Gly Leu Thr His Leu Tyr Thr Ala Thr Ala Arg
        35                  40                  45

Asn Ser Phe His Leu Gln Ile His Lys Asp Gly His Val Asp Gly Thr
    50                  55                  60

Pro His Gln Thr Ile Tyr Ser Ala Leu Met Ile Arg Ser Glu Asp Ser
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Thr Ala Asp Ser
            100                 105                 110

Cys Arg Phe Arg Gln Arg Thr Leu Glu Asn Gly Tyr Asp Val Tyr His
        115                 120                 125

Ser Pro Gln His His Phe Leu Ile Ser Leu Gly Arg Ala Lys Arg Val
    130                 135                 140

Phe Leu Pro Gly Met Asn Pro Pro Pro Tyr Ser Gln Phe Leu Ser Arg
145                 150                 155                 160

Arg Asn Glu Ile Pro Leu Ile His Phe Asn Thr Pro Arg Pro Arg Arg
                165                 170                 175

His Thr Arg Ser Ala Glu Glu Glu Val Glu Gln Asp Pro Leu Asn Val
            180                 185                 190

Leu Lys Pro Arg Pro Arg Met Thr Pro Ala Pro Ala Ser Cys Ser Gln
        195                 200                 205

Glu Leu Pro Ser Ala Glu Asp Asn Ser Ala Leu Ala Ser Asp Pro Leu
    210                 215                 220
```

```
Gly Val Val Arg Gly Lys Lys Leu Asn Thr His Ala Val Gly Met Gly
225                 230                 235                 240

Ala Glu Arg Cys Arg Pro Phe Pro Lys Phe
                245                 250
```

<210> SEQ ID NO 242
<211> LENGTH: 235
<212> TYPE: PRT
<213> ORGANISM: Erinaceus europaeus

<400> SEQUENCE: 242

```
Met Leu Gly Ala His Leu Gly Leu Val Val Cys Ala Leu Val Ser Arg
1               5                   10                  15

Ala Tyr Pro Asn Ala Ser Pro Leu Leu Gly Phe Ser Trp Gly Gly Leu
            20                  25                  30

Thr His Leu Tyr Thr Ala Thr Ala Arg Asn Ser Tyr His Leu Gln Ile
        35                  40                  45

His Lys Asp Gly His Val Asp Gly Ser Pro Gln Gln Thr Ile Tyr Ala
    50                  55                  60

Gly Phe Val Met Ile Thr Gly Val Met Ser Arg Arg Tyr Leu Cys Met
65                  70                  75                  80

Asp Phe Arg Ser Asn Ile Phe Gly Ser His His Phe Ala Pro Glu Ser
                85                  90                  95

Cys Arg Phe Arg His Arg Thr Leu Glu Asn Gly Tyr Asp Val Tyr His
            100                 105                 110

Ser Pro Gln His His Phe Leu Val Ser Leu Gly Arg Ala Lys Arg Ala
        115                 120                 125

Phe Leu Pro Gly Thr Asn Pro Pro Pro Tyr Ser Gln Phe Leu Ser Arg
    130                 135                 140

Arg Asn Glu Val Pro Leu Ile His Phe Asn Thr Pro Arg Pro Arg Arg
145                 150                 155                 160

His Thr Arg Ser Ala Glu Asp Asn Ser Glu Leu Asp Pro Leu Asn Val
                165                 170                 175

Leu Lys Pro Arg Pro Arg Met Thr Pro Ala Pro Ala Ser Cys Ser Gln
            180                 185                 190

Glu Leu Pro Ser Ala Glu Asp Asn Ser Met Val Ala Ser Asp Pro Leu
        195                 200                 205

Gly Val Val Arg Ala Asn Arg Val Asn Thr His Ala Gly Gly Leu Gly
    210                 215                 220

Val Asp Lys Cys Arg Pro Phe Pro Lys Phe Ile
225                 230                 235
```

<210> SEQ ID NO 243
<211> LENGTH: 252
<212> TYPE: PRT
<213> ORGANISM: Otolemur garnettii

<400> SEQUENCE: 243

```
Met Leu Gly Thr Cys Leu Arg Leu Trp Val Cys Ala Leu Cys Ser Val
1               5                   10                  15

Cys Ser Val Ser Ile Val Arg Ala Tyr Pro Asn Ala Ser Pro Leu Leu
            20                  25                  30

Ser Ser Ser Trp Gly Gly Leu Thr His Leu Tyr Thr Ala Ser Ala Arg
        35                  40                  45

Asn Ser Tyr His Leu Gln Ile His Lys Asp Gly His Val Asp Gly Thr
    50                  55                  60
```

Pro His Gln Thr Ile Tyr Ser Ala Leu Met Ile Arg Ser Glu Asp Ala
65 70 75 80

Gly Phe Val Val Ile Thr Gly Val Met Ser Arg Arg Tyr Leu Cys Met
85 90 95

Asp Phe Lys Gly Asn Ile Phe Gly Ser His Ser Phe His Pro Glu Ser
100 105 110

Cys Arg Phe Arg His Arg Thr Leu Glu Asn Gly Tyr Asp Val Tyr Leu
115 120 125

Ser Pro Gln His His Phe Leu Val Ser Leu Gly Arg Ser Lys Arg Pro
130 135 140

Phe Leu Pro Gly Met Asn Pro Pro Pro Phe Ser Gln Phe Leu Ser Arg
145 150 155 160

Arg Asn Asp Ile Pro Leu Ile His Phe Asn Thr Pro Arg Pro Arg Arg
165 170 175

His Thr Arg Ser Ala Glu Asp Asn Asp Ser Glu Leu Asp Pro Leu Asn
180 185 190

Val Leu Lys Pro Arg Pro Arg Ala Thr Pro Gly Pro Ala Ser Cys Ser
195 200 205

Gln Glu Leu Pro Ser Ala Glu Asp Asn Ser Leu Val Ala Ser Asp Pro
210 215 220

Leu Gly Val Val Arg Gly Asn Arg Val Asn Ala His Ala Gly Arg Ala
225 230 235 240

Gly Leu Asp Arg Cys Arg Pro Phe Pro Arg Tyr Phe
245 250

<210> SEQ ID NO 244
<211> LENGTH: 252
<212> TYPE: PRT
<213> ORGANISM: Oryctolagus cuniculus

<400> SEQUENCE: 244

Met Leu Gly Ala Arg Leu Leu Arg Leu Leu Val Cys Ala Leu Gly Ser
1 5 10 15

Val Cys Ser Trp Cys Val Val Arg Ala Tyr Pro Asp Thr Ser Pro Leu
20 25 30

Leu Ser Ser Ser Trp Ala Gly Leu Thr His Leu Tyr Thr Ala Thr Ala
35 40 45

Arg Asn Ser Tyr His Leu Gln Ile His Lys Asp Gly Gln Val Asp Gly
50 55 60

Thr Pro His Gln Thr Ile Tyr Ser Ala Leu Met Ile Arg Ser Glu Asp
65 70 75 80

Ala Gly Phe Val Val Ile Thr Gly Val Met Ser Arg Arg Tyr Leu Cys
85 90 95

Met Asp Phe Arg Gly Asn Ile Phe Gly Ser His Tyr Phe Asp Pro Gln
100 105 110

Asn Cys Arg Phe Arg His Arg Thr Leu Glu Asn Gly Tyr Asp Val Tyr
115 120 125

His Ser Pro Glu His His Phe Leu Val Ser Leu Gly Arg Ala Lys Arg
130 135 140

Pro Phe Leu Pro Gly Met Asn Pro Pro Pro Tyr Ser Gln Phe Leu Ser
145 150 155 160

Arg Arg Asn Glu Ile Pro Leu Ile His Phe Asn Thr Pro Arg Pro Arg
165 170 175

Arg His Thr Arg Ser Ala Glu Asp Ala Trp Glu Gln Asp Pro Leu Asn
180 185 190

Val Leu Lys Pro Arg Phe Arg Leu Thr Pro Ala Pro Ala Ser Cys Ser
195 200 205

Gln Glu Ala Pro Ser Ala Glu Asp Asn Gly Leu Val Ala Ser Asp Pro
210 215 220

Phe Gly Val Leu Arg Gly Asn Arg Val Asn Met His Gly Asp Arg Met
225 230 235 240

Gly Pro Glu Arg Cys His His Phe Pro Lys Phe Ile
245 250

<210> SEQ ID NO 245
<211> LENGTH: 246
<212> TYPE: PRT
<213> ORGANISM: Equus caballus

<400> SEQUENCE: 245

Met Ser Gly Pro Cys Leu Gly Leu Leu Val Tyr Val Leu Cys Ser Ala
1 5 10 15

Val Lys Ala Tyr Pro Asn Ala Ser Pro Leu Leu Asp Ser Ser Trp Gly
20 25 30

Ser Leu Thr His Leu Tyr Thr Ala Thr Ala Arg Asn Ser Tyr His Leu
35 40 45

Gln Ile His Lys Asp Gly His Val Asp Gly Thr Pro His Gln Thr Ile
50 55 60

Tyr Ser Ala Leu Met Ile Arg Ser Glu Asp Ala Gly Phe Val Val Ile
65 70 75 80

Thr Gly Val Met Ser Arg Arg Tyr Leu Cys Met Asp Phe Arg Gly Asn
85 90 95

Ile Phe Gly Ser His His Phe Ser Pro Glu Ser Cys Ser Phe Arg Gln
100 105 110

Arg Thr Leu Glu Asn Gly Tyr Asp Val Tyr His Ser Pro Gln His Arg
115 120 125

Phe Leu Val Ser Leu Gly Arg Ala Lys Arg Ala Phe Leu Pro Gly Thr
130 135 140

Asn Pro Pro Pro Tyr Ser Gln Phe Leu Ser Arg Arg Asn Glu Ile Pro
145 150 155 160

Leu Val His Phe Asn Thr Pro Arg Pro Arg Arg His Thr Arg Ser Ala
165 170 175

Glu Asp Asn Ser Glu Arg Asp Pro Leu Asn Val Leu Lys Pro Arg Pro
180 185 190

Arg Met Thr Pro Ala Pro Ala Ser Cys Ser Gln Glu Leu Pro Ser Ala
195 200 205

Glu Asp Asn Ser Val Leu Ala Ser Asp Pro Leu Gly Val Val Arg Gly
210 215 220

Asn Arg Val Asn Thr His Ala Gly Gly Ala Gly Val Glu Arg Cys Arg
225 230 235 240

Pro Phe Pro Lys Phe Phe
245

<210> SEQ ID NO 246
<211> LENGTH: 245
<212> TYPE: PRT
<213> ORGANISM: Ailuropoda melanoleuca

<400> SEQUENCE: 246

Met Ser Gly Thr Arg Leu Gly Leu Leu Val Ser Val Leu Cys Trp Val
1 5 10 15

```
Gly Arg Ala Tyr Pro Asn Thr Ser Pro Leu Leu Gly Ser Ser Trp Gly
            20                  25                  30

Gly Leu Thr His Leu Tyr Thr Ala Ser Ala Arg Asn Ser Tyr His Leu
        35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Leu Arg Gly Asn
                85                  90                  95

Ile Phe Gly Ser His Leu Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Gln Ala Lys Arg Thr Phe Leu Pro Gly Thr
    130                 135                 140

Asn Pro Pro Pro Tyr Ser Gln Phe Leu Ser Arg Arg Asn Glu Ile Pro
145                 150                 155                 160

Leu Ile His Phe Asn Thr Pro Arg Pro Arg Arg His Thr Arg Ser Ala
                165                 170                 175

Glu Asp Thr Glu Arg Asp Pro Leu Asn Val Leu Lys Pro Arg Pro Arg
            180                 185                 190

Met Thr Pro Ala Pro Ala Ser Cys Ser Gln Glu Leu Pro Ser Ala Glu
        195                 200                 205

Asp Asn Ser Val Val Ala Ser Asp Pro Leu Gly Val Leu Arg Gly Asn
    210                 215                 220

Arg Val Asn Ala His Ala Gly Gly Met Gly Val Asp Arg Cys Arg Pro
225                 230                 235                 240

Phe Pro Lys Phe Ile
                245


<210> SEQ ID NO 247
<211> LENGTH: 250
<212> TYPE: PRT
<213> ORGANISM: Ochotona princeps

<400> SEQUENCE: 247

Met Leu Gly Gly Leu Gly Leu Trp Val Cys Val Leu Gly Ser Val Cys
1               5                   10                  15

Ser Trp Arg Gly Val Arg Ala Tyr Pro Asp Thr Ser Pro Leu Leu Gly
            20                  25                  30

Ser Ser Trp Thr Gly Leu Thr His Leu Tyr Thr Ala Thr Ala Arg Asn
        35                  40                  45

Ser Phe His Leu Gln Ile His Lys Asp Gly His Val Asp Gly Thr Pro
    50                  55                  60

Gln Gln Thr Ile Tyr Ser Ala Leu Met Ile Arg Ser Glu Asp Ala Gly
65                  70                  75                  80

Phe Val Val Ile Thr Gly Val Met Ser Arg Arg Tyr Leu Cys Met Asp
                85                  90                  95

Phe Arg Gly Asn Ile Phe Gly Ser His Tyr Phe Glu Pro Gln Asn Cys
            100                 105                 110

Arg Phe Gln Gln Arg Thr Leu Glu Asn Gly Tyr Asp Ile Tyr His Ser
        115                 120                 125

Pro Gln His Asp Phe Leu Val Ser Leu Gly Arg Ala Lys Arg Pro Phe
```

```
    130                 135                 140

Leu Pro Gly Met Asn Pro Pro Pro Tyr Ser Gln Phe Leu Ser Arg Arg
145                 150                 155                 160

Asn Glu Ile Pro Leu Ile Leu Phe Asn Thr Pro Arg Pro Arg Arg His
                165                 170                 175

Thr Arg Ser Ala Glu Glu Gly Trp Glu Arg Asp Pro Leu Asn Val Leu
            180                 185                 190

Lys Ser Arg Pro Arg Met Thr Pro Ala Pro Ala Ser Cys Ser Arg Glu
        195                 200                 205

Ala Pro Ser Ala Glu Asp Asp Gly Leu Leu Ala Ser Asp Pro Met Gly
    210                 215                 220

Val Leu Arg Gly His Arg Val Asp Val His Gly Gly Gly Thr Gly Arg
225                 230                 235                 240

Asp Arg Cys Arg Pro Phe Pro Arg Phe Ile
                245                 250


<210> SEQ ID NO 248
<211> LENGTH: 245
<212> TYPE: PRT
<213> ORGANISM: Bos Taurus

<400> SEQUENCE: 248

Met Leu Gly Ala Arg Leu Gly Leu Trp Val Cys Thr Leu Ser Cys Val
1               5                   10                  15

Val Gln Ala Tyr Pro Asn Ser Ser Pro Leu Leu Gly Ser Ser Trp Gly
            20                  25                  30

Gly Leu Thr His Leu Tyr Thr Ala Thr Ala Arg Asn Ser Tyr His Leu
        35                  40                  45

Gln Ile His Gly Asp Gly His Val Asp Gly Ser Pro Gln Gln Thr Val
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Thr Gly Asn
                85                  90                  95

Ile Phe Gly Ser His His Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Arg Ala Lys Arg Ala Phe Leu Pro Gly Thr
    130                 135                 140

Asn Pro Pro Pro Tyr Ala Gln Phe Leu Ser Arg Arg Asn Glu Ile Pro
145                 150                 155                 160

Leu Pro His Phe Ala Ala Thr Ala Arg Pro Arg Arg His Thr Arg Ser
                165                 170                 175

Ala His Asp Ser Gly Asp Pro Leu Ser Val Leu Lys Pro Arg Ala Arg
            180                 185                 190

Ala Thr Pro Val Pro Ala Ala Cys Ser Gln Glu Leu Pro Ser Ala Glu
        195                 200                 205

Asp Ser Gly Pro Ala Ala Ser Asp Pro Leu Gly Val Leu Arg Gly His
    210                 215                 220

Arg Leu Asp Val Arg Ala Gly Ser Ala Gly Ala Glu Arg Cys Arg Pro
225                 230                 235                 240

Phe Pro Gly Phe Ala
                245
```

<210> SEQ ID NO 249
<211> LENGTH: 244
<212> TYPE: PRT
<213> ORGANISM: Sus scrofa

<400> SEQUENCE: 249

Met Leu Gly Ala Arg Leu Gly Leu Trp Val Cys Thr Leu Cys Cys Ala
1 5 10 15

Ala Arg Ala Tyr Pro Asp Thr Ser Pro Leu Leu Ser Ser Gly Trp Gly
20 25 30

Gly Leu Thr His Leu Tyr Thr Ala Thr Ala Arg Asn Ser Tyr His Leu
35 40 45

Gln Ile His Lys Asp Gly His Val Asp Gly Ser Pro Gln Gln Thr Ile
50 55 60

Tyr Ser Ala Leu Met Ile Arg Ser Glu Asp Ala Gly Phe Val Val Ile
65 70 75 80

Thr Gly Val Met Ser Arg Arg Tyr Leu Cys Met Asp Leu Arg Gly Asn
85 90 95

Ile Phe Gly Ser Leu His Phe Ser Pro Glu Ser Cys Arg Phe Arg Gln
100 105 110

Arg Thr Leu Glu Asn Gly Tyr Asp Val Tyr His Ser Pro His Tyr Arg
115 120 125

Phe Leu Val Ser Leu Gly Arg Ala Lys Arg Ala Phe Leu Pro Gly Thr
130 135 140

Asn Pro Pro Pro Tyr Ala Gln Phe Leu Ser Arg Arg Asn Glu Ile Pro
145 150 155 160

Leu Leu His Phe Ala Thr Ala Arg Pro Arg Arg His Thr Arg Ser Ala
165 170 175

His Asp Gly Gly Asp Pro Leu Ser Val Leu Lys Pro Arg Ala Arg Ala
180 185 190

Thr Pro Ala Pro Val Ser Cys Ser Arg Glu Leu Pro Ser Ala Glu Asp
195 200 205

Gly Gly Pro Ala Ala Ser Asp Pro Leu Gly Val Leu Arg Gly Gln Arg
210 215 220

Leu Asp Ala Arg Ala Gly Val Gly Gly Ala Glu Arg Cys Arg Pro Phe
225 230 235 240

Pro Ser Phe Ala

<210> SEQ ID NO 250
<211> LENGTH: 312
<212> TYPE: PRT
<213> ORGANISM: Canis lupus familiaris

<400> SEQUENCE: 250

Met Trp Thr Val Glu Phe Phe Leu Phe Asp Val Thr Gly Pro Pro Phe
1 5 10 15

Lys Ser Leu Arg Glu Lys Arg Arg Glu Ser Ser Leu Gly Leu Ser Arg
20 25 30

Lys Ile Pro Thr Lys Lys Arg Arg Lys Arg Pro Val Arg His Ser Arg
35 40 45

Gly Ile Lys Glu Ala Val Ser Gly Phe Lys Leu Gln Pro Ala Ile Gln
50 55 60

Arg Ala Val Met Ser Gly Thr Arg Leu Gly Phe Leu Val Ser Val Leu
65 70 75 80

Cys Trp Val Val Arg Ala Tyr Ser Asn Thr Ser Pro Leu Leu Gly Ser

```
                85                  90                  95

Ser Trp Gly Ser Leu Thr His Leu Tyr Thr Ala Thr Ala Arg Asn Ser
            100                 105                 110

Tyr His Leu Gln Ile His Lys Asp Gly His Val Asp Gly Thr Pro His
        115                 120                 125

Gln Thr Ile Tyr Ser Ala Leu Met Ile Arg Ser Glu Asp Ala Gly Phe
    130                 135                 140

Val Val Ile Thr Gly Val Met Ser Arg Arg Tyr Leu Cys Met Asp Phe
145                 150                 155                 160

Arg Gly Asn Ile Phe Gly Ser His Leu Phe Ser Pro Glu Ser Cys Arg
                165                 170                 175

Phe Arg Gln Arg Thr Leu Glu Asn Gly Tyr Asp Val Tyr His Ser Pro
            180                 185                 190

Gln His Arg Phe Leu Val Ser Leu Gly Gln Ala Lys Arg Ala Phe Leu
        195                 200                 205

Pro Gly Thr Asn Pro Pro Pro Tyr Ser Gln Phe Leu Ser Arg Arg Asn
    210                 215                 220

Glu Ile Pro Leu Val His Phe His Thr Pro Arg Pro Arg Arg His Thr
225                 230                 235                 240

Arg Ser Ala Glu Ala Pro Glu Arg Asp Pro Leu Asn Val Leu Lys Pro
                245                 250                 255

Arg Pro Arg Leu Ala Pro Ala Pro Ala Ser Cys Ser Gln Glu Leu Pro
            260                 265                 270

Ser Ala Glu Asp Pro Gly Ala Pro Ala Ser Asp Pro Leu Gly Val Leu
        275                 280                 285

Arg Gly His Arg Ala Asn Ala Arg Ala Gly Gly Val Gly Val Asp Arg
    290                 295                 300

Cys Arg Ala Phe Pro Thr Pro Ile
305                 310


<210> SEQ ID NO 251
<211> LENGTH: 243
<212> TYPE: PRT
<213> ORGANISM: Cavia porcellus

<400> SEQUENCE: 251

Met Leu Gly Thr Cys Leu Gly Leu Leu Ala Cys Thr Val Ser Leu Val
1               5                   10                  15

Gly Ala Tyr Pro Asp Ala Ser Pro Leu Leu Thr Ser Ser Trp Gly Gly
            20                  25                  30

Leu Ile His Leu Tyr Thr Ala Thr Ala Arg Asn Ser Tyr His Leu Gln
        35                  40                  45

Ile His Lys Asp Gly His Ile Asp Gly Ala Pro Tyr Pro Thr Ile Tyr
    50                  55                  60

Ser Ala Leu Met Ile Arg Ser Glu Asp Ala Gly Phe Val Val Ile Thr
65                  70                  75                  80

Gly Val Thr Ser Arg Arg Phe Leu Cys Met Asp Phe Arg Gly Asn Ile
                85                  90                  95

Phe Gly Ser His His Phe Asn Pro Gln Asp Cys Arg Phe Gln His Arg
            100                 105                 110

Thr Leu Glu Asn Gly Tyr Asp Val Tyr Leu Ser Pro Glu His His Phe
        115                 120                 125

Leu Ile Ser Leu Gly Arg Thr Lys Lys Phe Phe Leu Pro Gly Thr Asn
    130                 135                 140
```

```
Pro Pro Pro Tyr Ser Gln Phe Leu Ser Arg Arg Asn Glu Leu Pro Leu
145                 150                 155                 160

Ala Arg Phe Val Thr Pro Gly Pro Arg Arg His Thr Arg Ser Ala Glu
                165                 170                 175

Glu Asp Gln Gly Arg Asp Pro Leu Ser Val Leu Lys Leu Arg Pro Arg
            180                 185                 190

Ala Thr Pro Ala Pro Ala Ser Cys Ser Gln Glu Leu Pro Ser Ala Glu
        195                 200                 205

Asp Ala Ala Gln Ala Ser Asp Pro Leu Gly Val Leu Arg Gly Ala Arg
    210                 215                 220

Val His Ala His Gly Gly Pro Arg Pro Ala Arg Cys Arg Pro Gly Pro
225                 230                 235                 240

Gly Ala Lys


<210> SEQ ID NO 252
<211> LENGTH: 251
<212> TYPE: PRT
<213> ORGANISM: Cricetulus griseus

<400> SEQUENCE: 252

Met Leu Gly Thr Cys Leu Arg Leu Leu Val Gly Val Leu Cys Ser Ala
1               5                   10                  15

Cys Ser Leu Gly Thr Val Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Asn Ser Tyr His Leu Gln Ile His Lys Asp Gly Arg Val Asp Gly Thr
    50                  55                  60

Pro His Gln Thr Ile Tyr Ser Ala Leu Met Ile Arg Ser Glu Asp Ala
65                  70                  75                  80

Gly Phe Val Ile Ile Thr Gly Ala Val Thr Arg Arg Phe Leu Cys Met
                85                  90                  95

Asp Leu Arg Gly Asn Ile Phe Gly Ser His His Phe Ser Pro Glu Asn
            100                 105                 110

Cys Arg Phe Arg Gln Arg Thr Leu Glu Asn Gly Tyr Asp Val Tyr Leu
        115                 120                 125

Ser Pro Gln His His Tyr Leu Val Ser Leu Gly Arg Ala Lys Arg Pro
    130                 135                 140

Phe Glu Pro Gly Thr Asn Pro Pro Pro Phe Ser Gln Phe Leu Ala Arg
145                 150                 155                 160

Arg Asn Glu Val Pro Leu Leu Arg Phe His Thr Ala Arg Pro Arg Arg
                165                 170                 175

His Thr Arg Ser Ala Glu Asp Pro Pro Glu Trp Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Asp Leu Ala Ala Ser Asp Pro Leu
    210                 215                 220

Gly Val Leu Arg Arg Gly Arg Gly Asp Ala Arg Gly Gly Ala Gly Gly
225                 230                 235                 240

Val Asp Arg Cys Arg Pro Phe Pro Arg Phe Ala
                245                 250


<210> SEQ ID NO 253
<211> LENGTH: 180
```

<212> TYPE: PRT
<213> ORGANISM: Tupaia belangeri

<400> SEQUENCE: 253

```
Ala Leu Leu Ile Arg Pro Glu Glu Ala Gly Phe Ala Val Ile Thr Gly
1               5                   10                  15

Val Met Ser Arg Arg Tyr Leu Cys Met Asp Phe Arg Gly Asn Ile Phe
            20                  25                  30

Gly Ser His Leu Phe Ser Pro Glu Ser Cys Arg Phe Arg Gln Arg Ala
        35                  40                  45

Leu Glu Asn Gly Tyr Asp Val Tyr His His Pro Gln His His Phe Leu
    50                  55                  60

Val Ser Leu Gly Arg Pro Lys Arg Ala Phe Val Pro Gly Thr Asn Pro
65                  70                  75                  80

Pro Pro Tyr Ser Gln Phe Leu Ala Arg Lys Asn Glu Ile Pro Leu Ile
                85                  90                  95

His Phe Asn Thr Pro Lys Pro Arg Arg His Thr Arg Ser Ala Glu Asp
            100                 105                 110

Asn Ser Gly Arg Asp Pro Leu Asn Val Leu Lys Pro Arg Pro Arg Met
        115                 120                 125

Thr Pro Ala Pro Ala Ser Cys Ser Gln Glu Leu Pro Ser Ala Glu Asp
    130                 135                 140

Asn Ser Val Val Ala Ser Asp Pro Leu Gly Val Leu Arg Gly Asn Arg
145                 150                 155                 160

Val Asn Thr His Ala Gly Gly Trp Gly Val Asp Arg Cys Arg Pro Phe
                165                 170                 175

Pro Arg Phe Ile
            180
```

<210> SEQ ID NO 254
<211> LENGTH: 251
<212> TYPE: PRT
<213> ORGANISM: Rattus norvegicus

<400> SEQUENCE: 254

```
Met Leu Gly Ala Cys Leu Arg Leu Leu Val Gly Ala Leu Cys Thr Val
1               5                   10                  15

Cys Ser Leu Gly Thr Ala Arg Ala Tyr Ser Asp Thr Ser Pro Leu Leu
            20                  25                  30

Gly Ser Asn Trp Gly Ser Leu Thr His Leu Tyr Thr Ala Thr Ala Arg
        35                  40                  45

Asn Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Ile Gly Ala Met Thr Arg Arg Phe Leu Cys Met
                85                  90                  95

Asp Leu Arg Gly Asn Ile Phe Gly Ser Tyr His Phe Ser Pro Glu Asn
            100                 105                 110

Cys Arg Phe Arg Gln Trp Thr Leu Glu Asn Gly Tyr Asp Val Tyr Leu
        115                 120                 125

Ser Pro Lys His His Tyr Leu Val Ser Leu Gly Arg Ser Lys Arg Ile
    130                 135                 140

Phe Gln Pro Gly Thr Asn Pro Pro Pro Phe Ser Gln Phe Leu Ala Arg
145                 150                 155                 160
```

-continued

```
Arg Asn Glu Val Pro Leu Leu His Phe Tyr Thr Ala Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Ile Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Arg Gly Ala Gly Gly
225                 230                 235                 240

Thr Asp Arg Cys Arg Pro Phe Pro Arg Phe Val
                245                 250


<210> SEQ ID NO 255
<211> LENGTH: 251
<212> TYPE: PRT
<213> ORGANISM: Mus musculus

<400> SEQUENCE: 255

Met Leu Gly Thr Cys Leu Arg Leu Leu Val Gly Ala Leu Cys Thr Val
1               5                   10                  15

Cys Ser Leu Gly Thr Ala Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Thr Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Thr Gly Ala Met Thr Arg Arg Phe Leu Cys Met
                85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
    130                 135                 140

Phe Gln Pro Gly Thr Asn Pro Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250


<210> SEQ ID NO 256
<211> LENGTH: 248
<212> TYPE: PRT
<213> ORGANISM: Pteropus vampyrus
```

<400> SEQUENCE: 256

Met Pro Arg Gly Ser Leu Gly Leu Leu Val Cys Ile Leu Cys Cys Arg
1 5 10 15

Ala Tyr Pro Asp Ala Ser Pro Leu Leu Ser Ser Ser Leu Gly Gly Leu
20 25 30

Ile His Leu Tyr Thr Ala Thr Ala Arg Asn Gly Tyr His Leu Gln Ile
35 40 45

His Lys Asp Gly His Val Asp Gly Thr Pro His Gln Thr Ile Tyr Ser
50 55 60

Ala Leu Met Ile Arg Ser Glu Asp Ser Gly Phe Val Val Ile Ile Gly
65 70 75 80

Val Met Ser Arg Arg Tyr Leu Cys Met Asp Phe Lys Gly Asn Ile Phe
85 90 95

Gly Ser His His Phe Ser Pro Glu Ser Cys Lys Phe Arg Gln Arg Thr
100 105 110

Leu Glu Asn Gly Tyr Asp Val Tyr His Ser Pro Gln His His Phe Phe
115 120 125

Val Ser Leu Gly Arg Ala Lys Arg Ala Phe Leu Pro Gly Thr Asn Pro
130 135 140

Pro Pro Tyr Ser Gln Phe Leu Ser Arg Arg Asn Glu Ile Pro Leu Phe
145 150 155 160

Gln Phe Asn Thr Pro Arg Pro Arg Arg His Thr Arg Ser Val Glu Asp
165 170 175

Tyr Lys Asp Tyr Asp Leu Asp Pro Asp Pro Leu Lys Val Leu Arg Pro
180 185 190

Arg Pro Arg Trp Val Pro Ala Leu Pro Ser Cys Ser Gln Glu Leu Pro
195 200 205

Ser Ala Glu Asp Asn Ser Val Val Ala Asn Asp Pro Leu Gly Val Leu
210 215 220

Arg Pro Ser Arg Val Asn Ile Tyr Arg Glu Arg Met Gly Lys Gly Arg
225 230 235 240

Cys Arg Pro His Pro Glu Phe Val
245

<210> SEQ ID NO 257
<211> LENGTH: 248
<212> TYPE: PRT
<213> ORGANISM: Myotis lucifugus

<400> SEQUENCE: 257

Met Pro Gly Ala Arg Leu Gly Leu Leu Val Cys Val Leu Ala Leu Arg
1 5 10 15

Cys Val Val Arg Ala Tyr Pro Asn Ala Ser Pro Leu Leu Gly Ser Ser
20 25 30

Trp Gly Gly Leu Thr His Leu Tyr Thr Ala Ser Ala Arg Asn Ser Tyr
35 40 45

His Leu Gln Ile His Lys Asp Gly His Val Asp Gly Thr Pro His Gln
50 55 60

Thr Ile Tyr Ser Ala Leu Met Ile Arg Ser Glu Asp Ala Gly Phe Val
65 70 75 80

Val Ile Thr Gly Val Met Ser Arg Arg Tyr Leu Cys Met Asp Phe Arg
85 90 95

Gly Asn Ile Phe Gly Ser Leu Phe Phe Ser Pro Ser Asn Phe Ser Phe
100 105 110

```
Leu Glu Trp Lys Lys Glu Ser Gly Met Asp His Trp Ile Ser Arg Gln
        115                 120                 125

Thr His Phe Leu Val Ser Pro Gly Pro Ser Gln Glu Gly Leu Pro Ala
    130                 135                 140

Gly His Asn Pro Pro Pro Tyr Ser Gln Phe Leu Ser Arg Asn Glu Ile
145                 150                 155                 160

Pro Leu Phe His Phe Asn Thr Pro Ala Pro Arg Arg His Thr Arg Ser
                165                 170                 175

Ala Glu Glu Asn Ser Ala Ala Asp Pro Leu Val Val Leu Lys Pro Val
            180                 185                 190

Pro Arg Leu Thr Pro Pro Pro Ala Ser Cys Ser Arg Glu Leu Ser Ser
        195                 200                 205

Ala Glu Asp Asn Ser Val Ala Ala His Asp Pro Leu Gly Val Leu Arg
    210                 215                 220

Ser Ser Asn Arg Val Asn Ser His Ala Pro Pro Pro Gly Pro Pro Arg
225                 230                 235                 240

Thr Arg Gln Gly Met Leu Leu Val
                245


<210> SEQ ID NO 258
<211> LENGTH: 245
<212> TYPE: PRT
<213> ORGANISM: Sarcophilus harrisii

<400> SEQUENCE: 258

Met Ser Gly Gly Cys Leu Arg Leu Leu Phe Cys Ala Leu Cys Ser Leu
1               5                   10                  15

Arg Ala Ile Gln Ala Phe Pro Asn Ala Ser Pro Leu Leu Ser Leu Gly
            20                  25                  30

Trp Gly Gly Leu Thr His Leu Tyr Thr Ala Thr Ala Arg Asn Ser Tyr
        35                  40                  45

His Leu Gln Ile His Lys Asp Gly His Val Asp Gly Ser Pro His Gln
    50                  55                  60

Thr Ile Tyr Ser Ala Leu Met Ile Arg Ser Glu Asp Ala Gly Leu Val
65                  70                  75                  80

Ile Ile Thr Gly Val Met Ser Arg Arg Tyr Leu Cys Met Asp Ile Arg
                85                  90                  95

Gly Asn Ile Phe Gly Ser His Phe Phe Ser Pro Asp Asn Cys Arg Phe
            100                 105                 110

Lys His Arg Thr Leu Glu Asn Gly Tyr Asp Ile Tyr His Ser Pro Gln
        115                 120                 125

Asn Asn Phe Leu Ile Ser Leu Gly Lys Ala Lys Arg Ala Phe Leu Pro
    130                 135                 140

Gly Met Asn Pro Pro Pro Tyr Ser Gln Phe Leu Ser Arg Arg Asn Glu
145                 150                 155                 160

Ile Pro Ile Ile His Phe Asn Thr Pro Glu Pro His Arg His Thr Arg
                165                 170                 175

Ser Ala Glu Asn Ser Pro Asp Leu Asp Pro Met Asn Val Leu Lys Leu
            180                 185                 190

Arg Pro Arg Ile Thr Pro Cys Ser Gln Glu Leu His Ser Ala Glu Glu
        195                 200                 205

Asn Ser Val Val Asp Asp Asp Pro Leu Glu Val Leu Arg Asn Ser Asn
    210                 215                 220

Arg Leu Lys Pro Tyr Pro Gly Arg Met Ser Leu Glu Arg Cys Leu His
```

```
225                 230                 235                 240

Val Pro Lys Ala Ala
                245


<210> SEQ ID NO 259
<211> LENGTH: 191
<212> TYPE: PRT
<213> ORGANISM: Monodelphis domestica

<400> SEQUENCE: 259

Met Ala Asn Cys Arg Glu Lys Glu Leu Glu Met Tyr Ile Cys Ala Leu
1               5                   10                  15

Met Ile Arg Ser Glu Asp Ala Gly Leu Val Ile Ile Thr Gly Val Met
            20                  25                  30

Ser Arg Arg Tyr Leu Cys Met Asp Ile Arg Gly Asn Ile Phe Gly Ser
        35                  40                  45

His Phe Phe Asn Pro Asp Asn Cys Lys Phe Lys His Arg Thr Leu Glu
    50                  55                  60

Asn Gly Tyr Asp Ile Tyr His Ser Pro Gln Asn Asn Phe Leu Ile Ser
65                  70                  75                  80

Leu Gly Lys Ala Lys Arg Ala Phe Leu Pro Gly Met Asn Pro Pro Pro
                85                  90                  95

Tyr Ser Gln Phe Leu Ser Arg Lys Asn Glu Ile Pro Ile Ile His Phe
            100                 105                 110

Asn Thr Pro Glu Pro His Arg His Thr Arg Ser Ala Glu Asn Ser Pro
        115                 120                 125

Asp Leu Asp Pro Met Asn Val Leu Lys Pro Arg Pro Arg Met Thr Pro
    130                 135                 140

Cys Ser Gln Glu Leu Tyr Ser Ala Glu Glu Asn Ser Val Val Asp Asp
145                 150                 155                 160

Asp Pro Leu Glu Val Leu Arg Asn Ser Asn Arg Leu Lys Pro Phe Pro
                165                 170                 175

Gly Arg Leu Gly Leu Glu Arg Cys His His Val Pro Lys Thr Asp
            180                 185                 190


<210> SEQ ID NO 260
<211> LENGTH: 180
<212> TYPE: PRT
<213> ORGANISM: Dasypus novemcinctus

<400> SEQUENCE: 260

Ala Leu Met Ile Ser Ser Glu Asp Ala Gly Phe Val Val Ile Thr Gly
1               5                   10                  15

Val Met Ser Arg Arg Tyr Leu Cys Met Asp Phe Arg Gly Asn Ile Phe
            20                  25                  30

Gly Ser His Asp Phe Thr Pro Asp Ser Cys Arg Phe Arg Gln Arg Thr
        35                  40                  45

Leu Glu Asn Gly Tyr Asp Val Tyr His Ser Pro Gln His His Phe Leu
    50                  55                  60

Val Ser Leu Gly Arg Ala Lys Arg Ala Phe Gln Pro Gly Ser Asn Pro
65                  70                  75                  80

Pro Pro Tyr Ser Gln Phe Leu Ser Arg Arg Asn Glu Ile Pro Leu Met
                85                  90                  95

Arg Phe Ser Thr Pro Arg Pro Arg Arg His Thr Arg Ser Ala Gln Asp
            100                 105                 110

His Ala Asp Pro Asp Pro Leu Arg Val Leu Lys Pro Arg Leu Arg Leu
```

```
        115                 120                 125

Thr Pro Ala Pro Ala Ser Cys Ser Gln Glu Leu Pro Ser Asp Glu Asp
    130                 135                 140

Asp Gly Ala Val Ala Ser Asp Pro Leu Arg Val Val Leu Gly Arg Arg
145                 150                 155                 160

Pro His Ala Arg Ala Ala Gly Ala Gly Gly Glu Arg Cys Arg Pro Gly
                165                 170                 175

Pro Gln Leu Ser
            180


<210> SEQ ID NO 261
<211> LENGTH: 177
<212> TYPE: PRT
<213> ORGANISM: Macropus eugenii

<400> SEQUENCE: 261

Ala Leu Met Ile Arg Ser Glu Asp Ala Gly Leu Val Ile Ile Ser Gly
1               5                   10                  15

Val Met Ser Arg Arg Tyr Leu Cys Met Asp Leu Arg Gly Asn Ile Phe
            20                  25                  30

Gly Ser His Phe Phe Ser Pro Asp Asn Cys Arg Phe Lys His Arg Thr
        35                  40                  45

Leu Glu Asn Gly Tyr Asp Ile Tyr His Ser Pro Gln Asn Asn Leu Leu
    50                  55                  60

Ile Ser Leu Gly Lys Ala Lys Arg Ala Phe Leu Pro Gly Met Asn Pro
65                  70                  75                  80

Pro Pro Tyr Ser Gln Phe Leu Ser Arg Arg Asn Glu Ile Pro Ile Ile
                85                  90                  95

His Phe Asn Thr Pro Glu Pro Arg Arg His Thr Arg Ser Ala Glu Asn
            100                 105                 110

Ser Pro Asp Leu Asp Pro Met Asn Val Leu Lys Pro Arg Pro Arg Val
        115                 120                 125

Thr Pro Cys Ser Gln Glu Leu Arg Ser Ala Glu Glu Asn Ser Val Val
    130                 135                 140

Asp Asp Asp Pro Leu Glu Val Leu Arg Asn Ser Asn Arg Leu Lys Pro
145                 150                 155                 160

Tyr Pro Gly Arg Met Ser Leu Glu Arg Cys Leu Gln Val Pro Lys Ala
                165                 170                 175

Ala


<210> SEQ ID NO 262
<211> LENGTH: 256
<212> TYPE: PRT
<213> ORGANISM: Taeniopygia guttata

<400> SEQUENCE: 262

Met Glu Trp Arg Ala Thr Leu Gln Gly Ile Pro Cys Ser Ser Leu Leu
1               5                   10                  15

Leu Leu Leu Cys Ser Leu Lys Ala Ser Leu Ala Phe Pro Asn Ser Ser
            20                  25                  30

Pro Leu Leu Ser Pro Ser Trp Gly Asn Gly Asp Arg Leu Met His Leu
        35                  40                  45

Tyr Thr Asp Thr Glu Arg Ser Ser Phe His Leu Gln Ile Asn Ala Asp
    50                  55                  60

Gly Tyr Ile Asp Gly Ala Pro His Gln Thr Ile Tyr Ser Ala Leu Met
65                  70                  75                  80
```

```
Ile Lys Ser Glu Gly Ala Gly Ser Val Ile Ile Thr Gly Val Lys Ser
                85                  90                  95

Gly Arg Tyr Leu Cys Met Asp Met Lys Gly Asn Ile Phe Gly Ser His
            100                 105                 110

Tyr Phe Ser Gln Glu Asp Cys Met Phe Asn His Arg Thr Leu Glu Asn
        115                 120                 125

Gly Tyr Asp Val Tyr Gln Ser Pro Lys His His Phe Leu Val Ser Leu
    130                 135                 140

Gly Arg Val Lys Gln Val Phe Ser Pro Gly Met Asn Pro Pro Pro Tyr
145                 150                 155                 160

Ser Gln Phe Leu Ser Arg Lys Asn Glu Ile Pro Leu Phe Arg Phe Asn
                165                 170                 175

Thr Pro Glu Pro His Arg His Thr Arg Ser Ala Asp Val Asp Pro Val
            180                 185                 190

Asp Pro His Gln Ile Leu Val Pro Gln Arg Lys Thr Pro Val Phe Gly
        195                 200                 205

Ser Leu Gln Gln Gln Pro Ala Asp Phe Pro His Met Pro Arg Glu Pro
    210                 215                 220

Met Arg Ile Asn Gln Asn Asp Val Val Asn Pro Asp Asp Pro His Ala
225                 230                 235                 240

Met Met Glu Ala Arg Arg Tyr Pro Ser Pro Arg Phe Tyr Ile Thr Arg
                245                 250                 255


<210> SEQ ID NO 263
<211> LENGTH: 254
<212> TYPE: PRT
<213> ORGANISM: Gallus gallus

<400> SEQUENCE: 263

Met Pro His Thr Ser Pro Cys Ser Cys Leu Glu Tyr Met Leu Leu Val
1               5                   10                  15

Leu Cys Ile Leu Lys Ala Ala Val Ala Phe Pro Asn Ser Ser Pro Leu
            20                  25                  30

Leu Asn Pro Ser Trp Gly Asn Gly Asp Gln Leu Met His Leu Tyr Thr
        35                  40                  45

Ser Thr Glu Arg Asn Ser Phe His Leu Gln Ile Asn Ala Asp Gly His
    50                  55                  60

Ile Asn Gly Val Pro His Gln Thr Ile Tyr Ser Ala Leu Met Ile Lys
65                  70                  75                  80

Ser Glu Gly Ala Gly Cys Val Ile Ile Thr Gly Val Lys Ser Gly Arg
                85                  90                  95

Tyr Leu Cys Met Asp Met Lys Gly Asp Ile Phe Gly Ser Tyr Tyr Phe
            100                 105                 110

Ser Gln Glu Asp Cys Val Phe Asn Gln Arg Thr Leu Glu Asn Gly Tyr
        115                 120                 125

Asp Val Tyr Gln Ser Pro Lys His Asn Phe Leu Val Ser Leu Gly Arg
    130                 135                 140

Thr Lys Gln Val Phe Phe Pro Gly Met Asn Pro Pro Pro Tyr Ser Gln
145                 150                 155                 160

Phe Leu Ser Arg Arg Asn Glu Ile Pro Leu Phe Arg Phe Asn Thr Pro
                165                 170                 175

Glu Pro His Arg Asn Thr Arg Ser Ala Asp Val Asp Pro Leu Asp Pro
            180                 185                 190

His Gln Ile Leu Val Pro Gln Arg Lys Val Ser Ala Leu Gly Ser Gln
```

-continued

```
        195                 200                 205

Leu Gln Leu Gln Met Asp Phe Ser His Val Pro Arg Glu Pro Met Arg
    210                 215                 220

Val Asn Gln Asn Asp Val Val Asn Pro Asp Asp Pro His Ala Met Met
225                 230                 235                 240

Asp Ala Arg Arg Tyr Ala Ser Pro Arg Phe Tyr Ile Thr Arg
                245                 250


<210> SEQ ID NO 264
<211> LENGTH: 254
<212> TYPE: PRT
<213> ORGANISM: Meleagris gallopavo

<400> SEQUENCE: 264

Met Pro His Thr Ser Pro Cys Ser Cys Leu Glu Tyr Met Leu Leu Val
1               5                   10                  15

Leu Cys Ile Leu Lys Ala Ala Val Ser Phe Pro Asn Ser Ser Pro Leu
            20                  25                  30

Leu Asn Pro Ser Trp Gly Asn Gly Asp Gln Leu Met His Leu Tyr Thr
        35                  40                  45

Ser Thr Glu Arg Asn Ser Phe His Leu Gln Ile Asn Ala Asp Gly His
    50                  55                  60

Ile Ser Gly Val Pro Tyr Gln Thr Ile Tyr Ser Ala Leu Met Ile Lys
65                  70                  75                  80

Ser Glu Gly Ala Gly Ser Val Ile Ile Thr Gly Val Lys Ser Gly Arg
                85                  90                  95

Tyr Leu Cys Met Asp Met Lys Gly Asp Ile Phe Gly Ser His Tyr Phe
            100                 105                 110

Ser Gln Glu Asp Cys Val Phe Asn Gln Arg Thr Leu Glu Asn Gly Tyr
        115                 120                 125

Asp Val Tyr Gln Ser Pro Lys His Asn Phe Leu Val Ser Leu Gly Arg
    130                 135                 140

Thr Lys Gln Val Phe Phe Pro Gly Met Asn Pro Pro Pro Tyr Ser Gln
145                 150                 155                 160

Phe Leu Ser Arg Arg Asn Glu Ile Pro Leu Phe Arg Phe Asn Thr Pro
                165                 170                 175

Glu Pro His Arg Asn Thr Arg Ser Ala Asp Val Asp Pro Met Asp Pro
            180                 185                 190

His Gln Ile Leu Val Pro Gln Arg Lys Val Ser Ala Ile Glu Ser Gln
        195                 200                 205

Leu Gln Leu Gln Met Asp Phe Ser His Val Pro Arg Glu Pro Met Arg
    210                 215                 220

Val Asn Gln Asn Asp Val Val Asn Pro Asp Asp Pro His Ala Met Met
225                 230                 235                 240

Asp Ala Arg Arg Tyr Ala Ser Pro Arg Phe Tyr Ile Thr Arg
                245                 250


<210> SEQ ID NO 265
<211> LENGTH: 242
<212> TYPE: PRT
<213> ORGANISM: Anolis carolinensis

<400> SEQUENCE: 265

Met Val Gln Ala Thr Leu Tyr Ser Phe Leu Lys Tyr Met Leu Leu Ala
1               5                   10                  15

Thr Cys Ser Trp Lys Ala Ile Ala Ala Phe Pro Asn Ala Ser Pro Leu
```

```
            20                  25                  30

Leu Ser Leu Asn Trp Gly Asn Ser Asp Ser Leu Leu His Leu Tyr Thr
        35                  40                  45

Ser Thr Ala Arg Asn Ser Phe His Leu Gln Ile His Ser Asn Gly Tyr
    50                  55                  60

Val Asp Gly Ser Pro Tyr Gln Thr Ile Tyr Ser Ala Leu Met Ile Lys
65                  70                  75                  80

Ser Glu Val Ala Gly Tyr Val Ile Ile Asn Gly Val Lys Ser Gly Arg
                85                  90                  95

Phe Leu Cys Met Asp Met Asn Gly Asn Ile Phe Gly Ser His Phe Phe
            100                 105                 110

Ser Tyr Glu Asp Cys Thr Phe Lys His Trp Val Leu Glu Asn Gly Tyr
        115                 120                 125

Asp Val Tyr Gln Ser Pro Lys Tyr Asn Tyr Leu Val Ser Leu Gly Lys
    130                 135                 140

Ala Lys Gln Pro Leu Phe Pro Asn Met Asn Pro Pro Pro Tyr Ser Gln
145                 150                 155                 160

Phe Leu Ser Arg Arg Asn Glu Ile Pro Leu Val Gln Phe Asn Thr Pro
                165                 170                 175

Lys Pro His Arg His Thr Arg Ser Ala Asn Ala Asp Pro Cys Gly Ser
            180                 185                 190

Ile Ile Ser Ser Gly Asn Ile Ala Lys Glu Asn Leu Gln Leu Gln Pro
        195                 200                 205

Leu Met Tyr Asn Thr Lys Met Asn Ser Asn Ser Glu Asp Glu Asp Pro
    210                 215                 220

Asn Ser Ala Ile Ile Asn Arg Arg Phe Leu Ser Pro Arg Thr Asp Val
225                 230                 235                 240

Arg Ser


<210> SEQ ID NO 266
<211> LENGTH: 249
<212> TYPE: PRT
<213> ORGANISM: Latimeria chalumnae

<400> SEQUENCE: 266

Leu Glu Ser Ala Leu Leu Ala Phe Ser Met Ala Ile Phe Tyr Ser Phe
1               5                   10                  15

Lys Ala Val Ser Ser Phe Pro Asn Ser Ser Pro Leu Leu Asn Pro Val
            20                  25                  30

Trp Gly Asn Thr Asp Asn Leu Ile His Leu Tyr Thr Ala Ser Glu Thr
        35                  40                  45

Asn Ser Phe His Leu Gln Ile Asn Ser Asp Gly His Val Asp Gly Thr
    50                  55                  60

Pro His Gln Thr Ala Tyr Ser Ala Leu Leu Ile Lys Ser Glu Glu Ala
65                  70                  75                  80

Gly Ser Val Val Ile Leu Gly Val Lys Ser Gly Arg Tyr Leu Cys Met
                85                  90                  95

Asp Ile Lys Gly Asn Ile Ile Gly Leu His His Phe Ser Lys Glu Asp
            100                 105                 110

Cys Thr Phe Lys Gln Glu Gly Leu Glu Asn Gly Phe Asp Val Leu Arg
        115                 120                 125

Ser Pro Lys His Asn Ile Leu Val Ser Leu Asp Lys Thr Lys Arg Ser
    130                 135                 140

Tyr Ile Pro Gly Met Asn Leu Pro Pro Tyr Ser Gln Phe Leu Ser Arg
```

```
145                 150                 155                 160

Gln Asn Glu Val Ala Leu Ile Asn Phe Ile Asn Thr Pro Asp Ile His
                165                 170                 175

Arg His Ser Arg Asn Val Asp Val Asp Pro Ser Asp Pro His Gly Met
            180                 185                 190

Ile Ile Gln Pro Asp Val Gly Val Ser Phe Arg Lys Ser Ser Ser Leu
        195                 200                 205

Phe Ser Asp Leu Pro Arg Asp Ser Met Arg Thr Ser His Asn Gly Met
    210                 215                 220

Asp Met Val Asp Pro Ala Asp Pro His Gly Met Leu Asp Ser Arg Arg
225                 230                 235                 240

Arg Pro Ser Pro Arg Phe Phe Ala Arg
                245


<210> SEQ ID NO 267
<211> LENGTH: 254
<212> TYPE: PRT
<213> ORGANISM: Xenopus silurana tropicalis

<400> SEQUENCE: 267

Met Thr Lys Gln Gln Thr Arg Leu Gly Leu Val Leu Thr Val Leu Ala
1               5                   10                  15

Ser Ile Lys Val Ile Ser Ala Phe Pro Asn Ser Ser Pro Ile Ile Ser
            20                  25                  30

Gly Gly Trp Gly Val Pro Asp Arg Leu Met His Leu Tyr Thr Ala Ser
        35                  40                  45

Asp Trp Asn Ser Phe His Leu Gln Ile Asn His Asp Gly Ser Ile Asp
    50                  55                  60

Gly Thr Pro Thr Gln Thr Ile Tyr Ser Ala Ile Met Ile Lys Ser Glu
65                  70                  75                  80

Ser Ala Gly His Val Val Ile Thr Gly Val Lys Thr Asn Arg Tyr Leu
                85                  90                  95

Cys Met Asp Lys Ser Gly Asn Ile Phe Gly Tyr His Asp Phe Asn His
            100                 105                 110

Asp Asp Cys Val Phe Lys His Glu Thr Leu Glu Asn Asn Phe Asp Val
        115                 120                 125

Tyr His Ser Pro Lys His Asn Phe Val Ile Ser Leu Lys Glu Pro Lys
    130                 135                 140

His His Phe Arg Leu Gly Met Asp Leu Pro Pro Tyr Ser Gln Phe Leu
145                 150                 155                 160

Ser Leu Glu Asn Glu Ile Pro Ile Thr Arg Phe Asn Ala Pro Glu Pro
                165                 170                 175

Glu Met Arg Ile Pro Glu Gly Asn Phe Ala Asp Pro Ser Asp Ile Ile
            180                 185                 190

Lys Asn Pro Arg Asn Trp Asp Phe Ser Gln Ser Ile His Asn Pro Phe
        195                 200                 205

Gln Asp Val Trp Leu Pro Phe Pro Ser Gly Ser Leu Pro Ile Ile Arg
    210                 215                 220

Ala Ser Leu Pro Ile Ile His Asn Asn Val Ile Asn Thr Asp Asp Pro
225                 230                 235                 240

Glu Glu Ile Val Lys Met Lys Arg Tyr Arg Tyr Phe Lys Arg
                245                 250


<210> SEQ ID NO 268
<211> LENGTH: 199
```

<212> TYPE: PRT
<213> ORGANISM: Felis catus

<400> SEQUENCE: 268

Met Ser Gly Thr Arg Leu Gly Leu Leu Val Ser Val Leu Cys Trp Val
1 5 10 15

Val Arg Ala Tyr Pro Asn Thr Ser Pro Leu Leu Gly Ser Ser Trp Gly
20 25 30

Gly Leu Thr His Leu Tyr Thr Ala Thr Ala Arg Asn Ser Tyr His Leu
35 40 45

Gln Ile His Lys Asp Gly His Val Asp Gly Thr Pro His Gln Thr Ile
50 55 60

Tyr Ser Ala Leu Met Ile Arg Ser Glu Asp Ala Gly Phe Val Val Ile
65 70 75 80

Thr Gly Val Met Ser Gln Arg Tyr Leu Cys Met Asp Phe Arg Gly Asn
85 90 95

Ile Phe Gly Ser His Leu Phe Ser Pro Glu Ser Cys Arg Phe Arg Gln
100 105 110

Arg Thr Leu Glu Asn Gly Tyr Asp Val Tyr His Ser Pro Gln His Arg
115 120 125

Phe Leu Val Ser Leu Gly Pro Ala Lys Arg Ala Phe Leu Pro Gly Thr
130 135 140

Asn Arg Met Thr Pro Ala Pro Ala Ser Cys Ser Gln Glu Leu Pro Ser
145 150 155 160

Ala Glu Asp Ser Gly Val Val Ala Ser Asp Pro Leu Gly Val Leu Arg
165 170 175

Gly Asn Arg Val Asn Ala His Ala Gly Gly Met Gly Val Glu Arg Cys
180 185 190

Arg Pro Phe Pro Lys Phe Asn
195

<210> SEQ ID NO 269
<211> LENGTH: 250
<212> TYPE: PRT
<213> ORGANISM: Pelodiscus sinensis

<400> SEQUENCE: 269

Met Ser Gln Pro Ser Gln Cys Ser Cys Leu Asn Phe Met Leu Phe Val
1 5 10 15

Leu Cys Ser Phe Lys Ala Ile Ala Ala Phe Pro Phe Phe Ser Ser Leu
20 25 30

Leu Asn Pro Ser Trp Gly Glu Thr Asp Ser Leu Ile His Leu Tyr Thr
35 40 45

Ala Thr Glu Lys Asn Ser Phe His Leu Gln Ile Asn Pro Asp Gly Tyr
50 55 60

Val Asp Gly Thr Pro His Gln Thr Ile Tyr Ser Ala Leu Met Ile Lys
65 70 75 80

Ser Glu Asp Ala Gly Tyr Val Val Ile Ser Gly Val Lys Ser Gly Arg
85 90 95

Tyr Leu Cys Met Asp Ile Lys Gly Asn Ile Phe Gly Ser His Tyr Phe
100 105 110

Ser Gln Glu Asp Cys Met Phe Lys His Arg Thr Leu Glu Asn Gly Tyr
115 120 125

Asp Val Tyr Gln Ser Pro Lys His Asn Phe Leu Val Ser Leu Gly Arg
130 135 140

```
Asn Lys Gln Ala Phe Phe Pro Gly Met Asn Leu Pro Pro Tyr Ser Gln
145                 150                 155                 160

Phe Leu Pro Arg Arg Asn Glu Ile Pro Leu Ile Arg Phe Asn Thr Pro
                165                 170                 175

Glu Pro His Arg His Thr Arg Asn Ala Asp Val Asp Pro Leu Gln Ile
            180                 185                 190

Leu Ile Pro Arg Gly Glu Ala Phe Asp Thr Gly Pro Gln Arg Leu Gln
        195                 200                 205

Thr His Phe Asp His Leu Pro Arg Glu Pro Met Arg Ile Asn Pro Asn
    210                 215                 220

Asp Val Val Ser Pro Asp Asp Pro Leu Ala Met Met Asp Val Arg Arg
225                 230                 235                 240

Asn Ala Ser Pro Arg Leu Tyr Ile Thr Arg
                245                 250


<210> SEQ ID NO 270
<211> LENGTH: 245
<212> TYPE: PRT
<213> ORGANISM: Mustela putorius furo

<400> SEQUENCE: 270

Met Ser Val Thr Arg Leu Gly Leu Leu Val Ser Val Leu Cys Trp Val
1               5                   10                  15

Val Arg Ala Tyr Pro Asn Ala Ser Pro Leu Leu Gly Ser Ser Trp Gly
            20                  25                  30

Gly Leu Thr His Leu Tyr Thr Ala Thr Ala Arg Asn Ser Tyr His Leu
        35                  40                  45

Gln Ile His Lys Asp Gly His Val Asp Gly Thr Pro His Gln Thr Ile
    50                  55                  60

Tyr Ser Ala Leu Met Ile Arg Ser Glu Asp Ala Gly Phe Val Val Ile
65                  70                  75                  80

Thr Gly Val Met Ser Arg Arg Tyr Leu Cys Met Asp Phe Arg Gly Asn
                85                  90                  95

Ile Phe Gly Ser His Leu Phe Ser Pro Glu Ser Cys Arg Phe Arg Gln
            100                 105                 110

Arg Thr Leu Glu Asn Gly Tyr Asp Val Tyr His Ser Pro Gln His Arg
        115                 120                 125

Phe Leu Val Ser Leu Gly Gln Ala Lys Arg Ala Phe Leu Pro Gly Thr
    130                 135                 140

Asn Pro Pro Pro Tyr Ser Gln Phe Leu Ser Arg Arg Asn Glu Ile Pro
145                 150                 155                 160

Leu Ile His Phe Asn Thr Pro Arg Pro Arg Arg His Thr Arg Ser Ala
                165                 170                 175

Glu Asp Met Glu His Asp Pro Leu Asn Val Leu Lys Pro Arg Pro Arg
            180                 185                 190

Met Thr Pro Ala Pro Ala Ser Cys Ser Gln Glu Leu Pro Ser Ala Glu
        195                 200                 205

Asp Asn Ser Val Val Ala Ser Asp Pro Leu Gly Val Leu Arg Gly Asn
    210                 215                 220

Arg Val Asn Val His Ala Gly Gly Met Gly Val Asp Arg Cys Arg Pro
225                 230                 235                 240

Leu Pro Lys Phe Ile
                245


<210> SEQ ID NO 271
```

<211> LENGTH: 206
<212> TYPE: PRT
<213> ORGANISM: Microcebus murinus

<400> SEQUENCE: 271

Met Leu Gly Ala Cys Leu Arg Leu Trp Val Cys Ala Leu Cys Ser Val
1 5 10 15

Cys Gly Val Ser Val Val Arg Ala Tyr Pro Asn Ala Ser Pro Leu Leu
20 25 30

Ala Ser Ser Trp Gly Gly Leu Ile His Leu Tyr Thr Ala Thr Ala Arg
35 40 45

Asn Ser Tyr His Leu Gln Ile His Lys Asp Gly His Val Asp Gly Thr
50 55 60

Pro His Gln Thr Ile Tyr Ser Ala Leu Met Ile Arg Ser Glu Asp Ala
65 70 75 80

Gly Phe Val Val Ile Thr Gly Val Met Ser Arg Arg Tyr Leu Cys Met
85 90 95

Asp Phe Arg Gly Asn Ile Phe Gly Ser His Val Phe Ser Ala Glu Ser
100 105 110

Cys Arg Phe Arg Gln Arg Thr Leu Glu Asn Gly Phe Asp Val Tyr Gln
115 120 125

Ser Pro Gln His His Phe Leu Val Ser Leu Gly Arg Ala Lys Gly Ala
130 135 140

Phe Pro Ala Gly Ala Lys Pro Pro Pro Phe Pro Gln Phe Leu Pro Arg
145 150 155 160

Gly Asn Glu Ala Pro Gly Arg Lys Thr Arg Gly Pro Glu Glu Lys Gly
165 170 175

Ala Pro His Pro Leu Arg Gly Val Glu Ser Gly Gly Arg Lys Gly Gly
180 185 190

Ala Pro Pro Leu Cys Leu Glu Arg Leu Ser Arg Ala Arg Glu
195 200 205

<210> SEQ ID NO 272
<211> LENGTH: 193
<212> TYPE: PRT
<213> ORGANISM: Pongo abelii

<400> SEQUENCE: 272

Met Arg Asn Glu Ser Leu Pro Cys Leu Val Phe Ser Ile Gly Ala Leu
1 5 10 15

Met Ile Arg Ser Glu Asp Ala Gly Phe Val Val Ile Thr Gly Val Met
20 25 30

Ser Arg Arg Tyr Leu Cys Met Asp Phe Arg Gly Asn Ile Phe Gly Ser
35 40 45

His Tyr Phe Asn Pro Glu Asn Cys Arg Phe Gln His Gln Thr Leu Glu
50 55 60

Asn Gly Tyr Asp Val Tyr His Ser Pro Gln His His Phe Leu Val Ser
65 70 75 80

Leu Gly Arg Val Lys Arg Ala Phe Leu Pro Gly Met Pro Pro Pro Tyr
85 90 95

Ser Gln Phe Leu Ser Arg Arg Asn Glu Ile Pro Leu Ile His Phe Asn
100 105 110

Thr Pro Val Pro Arg Arg His Thr Arg Ser Ala Glu Asp Asp Thr Glu
115 120 125

Arg Asp Pro Leu Lys Val Leu Lys Pro Arg Ala Arg Met Thr Pro Ala
130 135 140

```
Pro Ala Ser Cys Ser Gln Glu Leu Pro Ser Ser Glu Asp Asn Ser Pro
145                 150                 155                 160

Met Ala Ser Asp Pro Leu Gly Val Val Arg Gly Gly Arg Val Asn Thr
                165                 170                 175

His Ala Gly Gly Thr Gly Pro Glu Gly Cys Arg Pro Phe Pro Lys Phe
            180                 185                 190

Ile


<210> SEQ ID NO 273
<211> LENGTH: 188
<212> TYPE: PRT
<213> ORGANISM: Sorex araneus

<400> SEQUENCE: 273

Met Trp Gly Leu Arg Leu Gly Leu Leu Val Gly Leu Leu Gly Cys Val
1               5                   10                  15

Asp Arg Ala Ser Pro Met Leu Ala Ser Ser Trp Gly Gly Leu Thr His
            20                  25                  30

Leu Tyr Thr Ala Thr Ala Arg Asn Ser Tyr His Leu Gln Ile His Lys
        35                  40                  45

Asp Gly Leu Val Asp Gly Ser Pro Gln Gln Thr Val Tyr His His Phe
    50                  55                  60

Ser Pro Glu Ser Cys Arg Phe Gln Gln Arg Thr Leu Glu Asn Gly Tyr
65                  70                  75                  80

Asp Val Tyr Gln Ser Pro Gln His Arg Phe Leu Val Ser Leu Gly Arg
                85                  90                  95

Pro Lys Arg Ala Phe Gln Pro Gly Ala Asn Pro Pro Pro Tyr Ala Gln
            100                 105                 110

Phe Leu Ala Arg Arg Asn Glu Val Pro Leu Ala Arg Phe His Thr Pro
        115                 120                 125

Ala Pro Arg Arg His Thr Arg Ser Ala His Asp Asn Gly Asp Ala Asp
    130                 135                 140

Pro Leu Asn Val Leu Ala Pro Arg Ala Ala Ala Ala Ala Ser Cys Ser
145                 150                 155                 160

His Glu Leu Pro Ser Ala Glu Asp Asn Ser Val Val Ala Ser Asp Pro
                165                 170                 175

Leu Gly Val Ile Arg Ser Asn Arg Phe Arg Thr His
            180                 185


<210> SEQ ID NO 274
<211> LENGTH: 263
<212> TYPE: PRT
<213> ORGANISM: Tetraodon nigroviridis

<400> SEQUENCE: 274

Met Asp Val Asn Arg Arg Ile Gly Val Lys Asp Ala Leu Leu Ala Leu
1               5                   10                  15

Leu Leu Ala Leu Leu Gln Gly Cys Pro Leu Gly Glu Thr Ala Pro Asn
            20                  25                  30

Ala Ser Pro Leu Val Gly Ser Asn Trp Gly Asn Pro Arg Arg Tyr Val
        35                  40                  45

His Leu Gln Thr Ser Thr Asp Met Ser Asn Phe Tyr Leu Glu Ile Arg
    50                  55                  60

Leu Asp Gly Thr Val Arg Lys Ser Thr Ala Arg Thr Ser Tyr Ser Val
65                  70                  75                  80
```

```
Ile Leu Leu Lys Ala Asp Thr Arg Glu Arg Ile Ala Ile Leu Gly Val
                85                  90                  95

Lys Ser Asn Arg Tyr Leu Cys Met Asp Leu Glu Gly Ser Pro Phe Ser
            100                 105                 110

Ser Pro Thr Cys Ile Arg Asp Asp Cys Leu Phe Asn His Ser Leu Leu
        115                 120                 125

Glu Asn Asn Arg Asp Val Tyr Tyr Ser Ser Arg Thr Gly Ile Leu Phe
    130                 135                 140

Asn Leu Glu Gly Ser Arg Gln Val Phe Val Val Gly Gln Asn Val Pro
145                 150                 155                 160

Gln Thr Ser Leu Phe Leu Pro Arg Thr Asn Thr Val Pro Leu Glu Arg
                165                 170                 175

Leu Leu Leu His Arg Asp Lys Arg Asn Gln Val Val Asp Pro Ser Asp
            180                 185                 190

Pro His Arg Val Ala Val Gly Arg Ala Glu Glu Gly Ser Asp Ser Arg
        195                 200                 205

Ala Leu Gln Glu Asp Asp Ala Asp Leu Glu Val Glu Thr Glu Val Glu
    210                 215                 220

Val Gly Asp Asp Gly Arg Asn Ala Ser Arg Glu Arg Leu Gln Ala Pro
225                 230                 235                 240

Ser Asp His Asp Pro Trp Gly Val Phe Ser Ser Asn Pro Gly Ser Pro
                245                 250                 255

Arg Ser Ser Gly Thr Val Gly
            260


<210> SEQ ID NO 275
<211> LENGTH: 255
<212> TYPE: PRT
<213> ORGANISM: Oreochromis niloticus

<400> SEQUENCE: 275

Met Asp Val Asn Arg Arg Met Gly Met Arg Asp Thr Val Leu Ala Leu
1               5                   10                  15

Phe Leu Ala Val Leu Gln Gly Phe Pro Leu Gly Asp Thr Val Pro Asn
            20                  25                  30

Pro Ser Pro Leu Ala Gly Ser Asn Trp Gly Asn Pro Arg Arg Tyr Val
        35                  40                  45

His Leu Gln Thr Ser Thr Asp Leu Asn Asn Phe Tyr Leu Glu Ile Arg
    50                  55                  60

Leu Asp Gly Ser Val Arg Lys Thr Thr Ser Arg Ser Thr Tyr Ser Val
65                  70                  75                  80

Ile Leu Leu Lys Ser Glu Ala Arg Asp Arg Val Ala Ile Leu Gly Val
                85                  90                  95

Lys Ser Ser Arg Tyr Leu Cys Met Asp Leu Glu Gly Asn Pro Phe Ser
            100                 105                 110

Ser Pro Val Cys Leu Arg Asp Asp Cys Leu Phe Asn His Lys Leu Leu
        115                 120                 125

Glu Asn Asn Arg Asp Val Tyr Tyr Ser Ser Arg Thr Gly Ile Leu Phe
    130                 135                 140

Asn Leu Glu Gly Ser Arg Gln Val Tyr Ser Val Gly Gln Asn Leu Pro
145                 150                 155                 160

Gln Thr Ser Leu Phe Leu Pro Arg Lys Asn Thr Val Pro Leu Glu Arg
                165                 170                 175

Leu Leu Leu His Arg Glu Lys Arg Asn Arg Gly Gln Thr Glu Glu Gly
            180                 185                 190
```

```
Ser Asp Ser Arg Ala Val Pro Glu Glu Leu Glu Glu Arg Glu Val Glu
        195                 200                 205

Met Glu Thr Glu Ile Glu Thr Glu Val Gly Asp Asp Gly Arg Asn Val
    210                 215                 220

Ser Arg Glu Lys Leu Ala Ala Pro Ser Ser His Asp Pro Trp Asn Val
225                 230                 235                 240

His Phe Ser Asn Pro Ala Ser Pro Arg Ser Thr Gly Thr Val Gly
                245                 250                 255


<210> SEQ ID NO 276
<211> LENGTH: 258
<212> TYPE: PRT
<213> ORGANISM: Danio rerio

<400> SEQUENCE: 276

Met Arg Cys Ala Leu Ser Asn Leu His Met Leu His Ser Ser Val Leu
1               5                   10                  15

Ala Leu Trp Phe Thr Ala Leu Gln Gly Leu Arg Pro Ala Asp Ala Ala
            20                  25                  30

Pro Asn Pro Ser Pro Leu Leu Gly Ser Asn Trp Gly Asn Pro Arg Arg
        35                  40                  45

Tyr Ile His Leu Gln Thr Thr Ser Asp Leu Asn Asn Tyr Tyr Leu Glu
    50                  55                  60

Ile Ser Pro Ser Gly His Val Arg Lys Thr Thr Asn Arg Gly Ser Tyr
65                  70                  75                  80

Ser Val Ile Leu Leu Lys Thr Glu Ser Arg Asp Arg Leu Ala Ile Phe
                85                  90                  95

Gly Val Lys Ser Asn Arg Phe Leu Cys Met Asp Thr Gly Gly Thr Leu
            100                 105                 110

Phe Thr Ser Thr Ile Cys Asn Lys Glu Asp Cys Leu Phe His His Lys
        115                 120                 125

Leu Leu Glu Asn His Arg Asp Val Tyr Tyr Ser Thr Lys His Ser Ile
    130                 135                 140

Leu Leu Asn Leu Asp Gly Asp Lys Gln Ala Phe Ile Ala Gly Gln Asn
145                 150                 155                 160

Leu Pro Gln Ser Ser Leu Phe Leu Ser Glu Lys Asn Thr Val Pro Leu
                165                 170                 175

Glu Arg Leu Gln His Arg Glu Arg Arg Asn Arg Gln Val Asn Pro Thr
            180                 185                 190

Asp Pro Leu Asn Ala Leu Arg Tyr Ala Glu Glu Ser Asp Ser Arg Ala
        195                 200                 205

Ala Gln Glu Asp Asp Gly Asp Met Asp Phe Glu Pro Ser Glu Gly Gln
    210                 215                 220

Asn Ile Ser Arg Glu Thr Leu Val Ser Pro Ser Asp Asp Asp Pro Trp
225                 230                 235                 240

Asp Leu Leu His Asp Thr Ser Pro Gly Ser Pro Arg Ile Ala Ala Ile
                245                 250                 255

Val Gly


<210> SEQ ID NO 277
<211> LENGTH: 756
<212> TYPE: DNA
<213> ORGANISM: Homo sapiens

<400> SEQUENCE: 277
```

-continued

```
atgttggggg cccgcctcag gctctgggtc tgtgccttgt gcagcgtctg cagcatgagc      60

gtcctcagag cctatcccaa tgcctcccca ctgctcggct ccagctgggg tggcctgatc     120

cacctgtaca cagccacagc caggaacagc taccacctgc agatccacaa gaatggccat     180

gtggatggcg caccccatca gaccatctac agtgccctga tgatcagatc agaggatgct     240

ggctttgtgg tgattacagg tgtgatgagc agaagatacc tctgcatgga tttcagaggc     300

aacattttg gatcacacta tttcgacccg gagaactgca ggttccaaca ccagacgctg      360

gaaaacgggt acgacgtcta ccactctcct cagtatcact tcctggtcag tctgggccgg     420

gcgaagagag ccttcctgcc aggcatgaac ccaccccgt actcccagtt cctgtcccgg      480

aggaacgaga tcccctaat tcacttcaac acccccatac cacggcggca cacccggagc      540

gccgaggacg actcggagcg ggaccccctg aacgtgctga agccccgggc ccggatgacc     600

ccggccccgg cctcctgttc acaggagctc ccgagcgccg aggacaacag cccgatggcc     660

agtgacccat taggggtggt caggggcggt cgagtgaaca cgcacgctgg gggaacgggc     720

ccggaaggct gccgcccctt cgccaagttc atctag                               756
```

<210> SEQ ID NO 278
<211> LENGTH: 756
<212> TYPE: DNA
<213> ORGANISM: Gorilla

<400> SEQUENCE: 278

```
atgttggggg cccgcctcag gctctgggtc tgtgccttgt gcagcgtctg cagcttgagc      60

gtcctcagag cctatcccaa tgcctcccca ctgctcggct ccagctgggg tggcctgatc     120

cacctgtaca cagccacagc caggaacagc taccacctgc agatccacaa gaatggccat     180

gtggatggcg caccccatca gaccatctac agtgccctga tgatcagatc agaggatgct     240

ggctttgtgg tgattacagg tgtgatgagc agaagatacc tctgcatgga tttcagaggc     300

aacattttg gatcacacta tttcgacccg gagaactgca ggttccaaca ccagacgctg      360

gaaaacgggt acgacgtcta ccactctcct cagtatcact tcctggtcag tctgggccgg     420

gcgaagagag ccttcctgcc aggcatgaac ccaccccgt actcccagtt cctgtcccgg      480

aggaacgaga tcccctcat tcacttcaac acccccatac cacggcggca cacccggagc      540

gccgaggacg actcggagcg ggaccccctg aacgtgctga agccccgggc ccggatgacc     600

ccggccccgg cctcctgttc acaggagctc ccgagcgccg aggacaacag cccgatggcc     660

agtgacccat taggggtggt caggggcggt cgagtgaaca cgtacgctgg gggaacgggc     720

ccggaaggct gccgcccctt ccccaagttc atctag                               756
```

<210> SEQ ID NO 279
<211> LENGTH: 756
<212> TYPE: DNA
<213> ORGANISM: Northern white-cheeked gibbon

<400> SEQUENCE: 279

```
atgttggggg cccgcctcag gctctgggtc tgtgccttgt gcagcgtctg cagcatgagc      60

gtcctcagag cctatcccaa tgcctcccca ctgctcggct ccagctgggg tggcctgatc     120

cacctgtaca cagccacagc caggaacagc taccacctgc agatccacaa gaatggccat     180

gtggatggcg caccccatca gaccatctac agtgccctga tgatcagatc agaggatgct     240

ggctttgtgg tgattacagg tgtgatgagc agaagatacc tctgcatgga tttcagaggc     300

aacattttg gatcacacta tttcaacccg gagaactgca ggttccaaca ccagacgctg      360
```

```
gaaaacgggt acgacgtcta ccactctcct cagcatcact tcctggtcag tctgggccgg    420

gccaagagag ccttcctgcc gggcatgaac ccaccccgt actcccagtt cctgtcccgg    480

aggaacgaga tcccccctact tcacttcaac acccccacac cacggcggca cacccggagc    540

gccgaggacg actcggagcg ggaccccctg aacgtgctga aaccccgggc ccggatgacc    600

ccggccccgg cctcctgctc acaggagctc ctgagctccg aggacaacag cccgatggcc    660

agcgacccat taggggtggt caggggcggt cgagtgaaca cgcacgctgg gggaacgggc    720

ccggaaggct gccgcccctt ccccaagttc atctag                              756
```

<210> SEQ ID NO 280
<211> LENGTH: 756
<212> TYPE: DNA
<213> ORGANISM: Rhesus monkey

<400> SEQUENCE: 280

```
atgttggggg cccgcctcag gctctgggtc tgtgccttgt gcagcgtctg cagcatgagc     60

gtcatcagag cctatcccaa tgcctcccca ttgctcggct ccagctgggg tggcctgatc    120

cacctgtaca cagccacagc caggaacagc taccacctgc agatccacaa gaatggccac    180

gtggatggcg caccccatca gaccatctac agtgccctga tgatcagatc agaggatgct    240

ggctttgtgg tgattacagg tgtgatgagc agaagatacc tctgcatgga tttcagaggc    300

aacatttttg gatcacacta tttcaacccg gagaactgca ggttccgaca ctggacgctg    360

gagaacggct acgacgtcta ccactctcct cagcatcact ttctggtcag tctgggccgg    420

gcgaagaggg ccttcctgcc aggcatgaac ccacccccct actcccagtt cctgtcccgg    480

aggaacgaga tcccccctcat ccacttcaac acccccagac cacggcggca cacccggagc    540

gccgaggacg actcggagcg ggaccccctg aacgtgctga agccccgggc ccggatgacc    600

ccggccccgg cctcctgctc acaggagctc ccgagcgccg aggacaacag cccggtggcc    660

agcgacccgt taggggtggt caggggcggt cgggtgaaca cgcacgctgg gggaacgggc    720

ccggaagcct gccgcccctt ccccaagttc atctag                              756
```

<210> SEQ ID NO 281
<211> LENGTH: 756
<212> TYPE: DNA
<213> ORGANISM: Crab-eating macaque

<400> SEQUENCE: 281

```
atgttggggg cccgcctcag gctctgggtc tgtgccttgt gcagcgtctg cagcatgagc     60

gtcatcagag cctatcccaa tgcctcccca ttgctcggct ccagctgggg tggcctgatc    120

cacctgtaca cagccacagc caggaacagc taccacctgc agatccacaa gaatggccac    180

gtggatggcg caccccatca gaccatctac agtgccctga tgatcagatc agaggatgct    240

ggctttgtgg tgattacagg tgtgatgagc agaagatacc tctgcatgga tttcagaggc    300

aacatttttg gatcacacta tttcaacccg gagaactgca ggttccgaca ctggacgctg    360

gagaacggct acgacgtcta ccactctcct cagcatcact ttctggtcag tctgggccgg    420

gcgaagaggg ccttcctgcc aggcatgaac ccacccccct actcccagtt cctgtcccgg    480

aggaacgaga tcccccctcat ccacttcaac acccccagac cacggcggca cacccggagc    540

gccgaggacg actcggagcg ggaccccctg aacgtgctga agccccgggc ccggatgacc    600

ccggccccgg cctcctgctc acaggagctc ccgagcgccg aggacaacag cccggtggcc    660
```

agcgacccgt taggggtggt caggggcggt cgggtgaaca cgcacgctgg gggaacgggc 720
ccggaagcct gccgcccctt ccccaagttc atctag 756

<210> SEQ ID NO 282
<211> LENGTH: 756
<212> TYPE: DNA
<213> ORGANISM: Chimpanzee

<400> SEQUENCE: 282
atgttggggg cccgcctcag gctctgggtc tgtgccttgt gcagtgtctg cagcgtgagc 60
gtcctcagag cctaccccaa tgcctcccca ctgctcggct ccagctgggg tggcctgatc 120
cacctgtaca cagccacagc caggaacagc taccacctgc agatccacaa gaatggccat 180
gtggatggcg caccccatca gaccatctac agtgccctga tgatcagatc agaggatgct 240
ggctttgtgg tgattacagg tgtgatgagc agaagatacc tctgcatgga tttcagaggc 300
aacatttttg gatcacacta tttcaacccg gagaactgca ggttccaaca ccagacgctg 360
gaaaacgggt acgacgtcta ctactctcct cagtatcact tcctggtcag tctgggccgg 420
gcgaagagag ccttcctgcc aagcatgaac ccaccccgt actcccagtt cctgtcccgg 480
aggaacgaga tcccccctaat tcacttcaac acccccatac cacggcggca cacccggagc 540
gccgaggacg actcggagcg ggacccccctg aacgtgctga agccccgggc ccggatgacc 600
ccggccccgg cctcctgttc acaggagctc ccgagcgccg aggacaacag cccgatggcc 660
agtgacccat taggggtggt caggggcggt cgagtgaaca cgcacgctgg gggaacgggc 720
ccggaaggct gccgcccctt ccccaagttc atctag 756

<210> SEQ ID NO 283
<211> LENGTH: 756
<212> TYPE: DNA
<213> ORGANISM: White-tufted-ear marmoset

<400> SEQUENCE: 283
atgttggggg cccgcctcag gctctgggtc tgtgccttgt gcagcgtctg cagcatgagc 60
gtcctcagag cctatcccaa tgcctcccca ctgcttgcct ccagctgggg tggcctgatc 120
cacctgtaca cagccacagc caggaacagc taccacctgc agatccacaa gaatggccat 180
gtggatggcg caccccatca gaccatctac agtgccctgc tgatcagatc agaggatgct 240
ggctttgtgg tgattacagg tgtgatgagc agaagatacc tctgcatgga tttcagaggc 300
aacatttttg gatcacacta tttcaacccg gagaactgca ggttccgacc ccagaggctg 360
gagaacgggt acgacgtcta ccagtctcct cagcatcact tcctggtcag tctgggccgg 420
gcgaagaggg ccttcctgcc aggcatgaac ccaccccgt actcccagtt cctgtcccgg 480
aggaacgaga tcccccctcat tcacttcaac acccccaaac cgcggcggca cacccggagc 540
gccgaggacg acccggagct agacccccctg aacgtgctga agtcccgggt ccggatgacc 600
ccggccccgg cctcctgctc gcaggagctc ctgagcgccg aggacaacag cccggtgggc 660
agcgacccct tagggatggt ccggggtggt cgggtgaaca gccacgctga gggaacaggc 720
ccagaaggct gcagcccctt ccccaagctc atctag 756

<210> SEQ ID NO 284
<211> LENGTH: 756
<212> TYPE: DNA
<213> ORGANISM: Elephant

<400> SEQUENCE: 284
atgttggggg cccgcctcag gctctgggtc tgcaccctgt gcagtgcctg cagcatgtgc 60
agtgtcagag cctatcccaa tgcctccccg ctgctccact ccagctgggg tggcctgacc 120
cacctgtaca cagccaccgc caggaacagc taccacctgc agatccacaa ggacggccat 180
gtggatggta cgccggacca gaccatctac agtgccctga taatcagatc agaggaggcc 240
ggcttcgtgg tgattacagg ggtgatgagt aggagatacc tctgtatgga tttcagaggc 300
aacatttttg gatcgcatta cttcaaccca gagaactgca ggttcaaaca ctggacgctg 360
gaaaatggat atgacgtcta tcactctcct cagcatcatt tcctggtcag tctgggtcgc 420
gtgaagaagg ccttcctgcc aggcatgaac ccaccacctt actctcagtt cctgtcccgg 480
aggaatgaga tccccttgat ttacttcaac acccccaagc cccggcggca cacccggagt 540
gccgaggatg actctgaacg ggacccactg aatgtgctga agccccggcc ccgtatgaca 600
cctgctccag cttcttgctc ccaggaactc ctgagtgctg aagacaacag cgtggtggcc 660
aatgaccctt taggagtggt cagaagcaat agggtcaaca cacatgctgg tgggataggt 720
gtggaaaggt gccgcccctt ccccaagttc atctag 756

<210> SEQ ID NO 285
<211> LENGTH: 750
<212> TYPE: DNA
<213> ORGANISM: Lesser hedgehog tenrec

<400> SEQUENCE: 285
atgttggggg cccacctcag actctgggtc tgtgccttgt gcagtgtgag cgccatgtac 60
cacgtcagag cctaccccaa cgcctccccg ctcctgggta ccagctgggc tggcctgacc 120
cacctgtaca cggcgacagc caggaacagc ttccacctgc agatccacaa ggatggccac 180
gtggacggca ccccccacca gaccatctac agtgccctga tgatccgatc agaggactct 240
ggcttcgtgg tgatcacagg ggtgatgagc aggagatacc tgtgtatgga tttcagaggc 300
aacatttttg gatcgcacta cttcactgcg gacagctgca ggttcagaca gcggacgctg 360
gagaacggct atgacgtcta ccactctcct cagcatcatt tcctgatcag cctgggccgg 420
gccaagaggg tcttcctgcc cggcatgaac ccgccgcctt actcccagtt cctgtcccga 480
aggaatgaga tcccccctgat tcacttcaac acccccaggc cccggcggca cacacggagt 540
gccgaggagg aagtggagca ggatccgctg aacgtgctga agcccaggcc ccggatgacg 600
ccggctccag cctcctgctc ccaggagctg cccagtgccg aagacaacag cgccctggcc 660
agcgacccgc tgggagtggt cagaggcaaa aagctcaaca cccatgctgt gggcatgggc 720
gcggaaagat gccgcccctt tcccaagttc 750

<210> SEQ ID NO 286
<211> LENGTH: 710
<212> TYPE: DNA
<213> ORGANISM: Hedgehog

<400> SEQUENCE: 286
atgttggggg cccacctggg tctggtggtc tgcgccctgg tcagcagagc ctatcccaat 60
gcctcgccac tgctgggctt cagctggggg ggcctgacac atctgtacac ggccacagcc 120
aggaacagct accacctgca gatccacaag gacggccacg tggacggctc gcctcagcag 180
accatctaca tgctggtttc gtgatgatca caggcgtgat gagtaggcgc tacctctgca 240
tggacttcag gagcaacatc tttggatcgc atcacttcgc ccctgagagc tgcaggttca 300
gacatcggac actggaaaac ggctatgacg tctaccactc cccccagcac catttcctgg 360
tcagcctggg ccgggccaag cgggccttcc tgccgggcac caaccccca ccatactccc 420 agtttttgtc ccggaggaac gaggttcccc tcatccactt caacaccccc aggcccaggc 480
gtcacacccg cagcgccgag gacaactcag agctggatcc cctgaacgtg ctgaagccca 540
ggccccgcat gacccccgcc ccagcctcct gctcccagga gcttccgagc gctgaggaca 600
acagcatggt ggccagtgac ccactgggtg tggtcagagc caacagagtg aacacacacg 660
cagggggcct gggtgtggac aagtgccgcc ccttccccaa gtttatctag 710

<210> SEQ ID NO 287
<211> LENGTH: 759
<212> TYPE: DNA
<213> ORGANISM: Bushbaby

<400> SEQUENCE: 287
atgctgggga cctgcctcag gctctgggtc tgtgccctgt gcagtgtttg cagcgtgagc 60
attgtcagag cctatcccaa cgcctcccca ctgctcagct ccagctgggg tggcctgacc 120
cacctgtaca cggcctcggc cagaaacagc taccacctgc agatccacaa ggatggccat 180
gtggacggca caccccacca gaccatctac agcgccctaa tgatcaggtc agaggatgct 240
ggcttcgtgg tgattacagg cgtgatgagc agaagatacc tctgtatgga tttcaaaggc 300
aacatttttg gatcacactc cttccacccc gagagctgca ggttcagaca ccggactctg 360
gagaacggct atgacgtcta cctctcgccg cagcatcact tcttggtcag cctgggccgc 420
tccaagaggc ccttcctgcc gggcatgaac ccgccccct tctcccagtt cctgtcgcgg 480
aggaacgaca tcccgctcat tcacttcaac accccccgcc cgcggagaca cacccgcagc 540
gccgaggaca acgactcgga gctcgacccc ctgaacgtgc tgaagccgcg gccccgggcc 600
accccgggcc ccgcctcctg ctcgcaggag ctccccagcg ccgaggacaa cagcctggtg 660
gccagcgacc ctttaggggt ggtccggggc aacagggtga acgctcacgc cgggagggcc 720
ggcctggaca ggtgccgccc cttccccagg tatttctag 759

<210> SEQ ID NO 288
<211> LENGTH: 759
<212> TYPE: DNA
<213> ORGANISM: Rabbit

<400> SEQUENCE: 288
atgttagggg cccggctcct ccggctcttg gtctgtgccc tgggcagtgt gtgcagctgg 60
tgtgtggtcc gagcctaccc tgacacctcc ccgctgctca gctccagctg ggctggcctg 120
acccacctgt acacggccac cgccagaaac agctaccacc tgcagatcca caaggacggc 180
caagtggatg gcacacctca tcagaccatc tacagtgccc tgatgatcag atcggaggat 240
gctggcttcg tggtgataac aggtgtcatg agcaggaggt acctctgtat ggatttcaga 300
ggcaacattt ttggatcgca ttacttcgac ccccagaact gcaggttcag acacaggacg 360
ctggaaaacg ggtacgacgt ctaccactct ccggagcatc acttcctggt cagcctgggc 420
cgggccaaga ggcccttcct gccaggcatg aacccgccac cctattccca gttcctgtcc 480
cggaggaacg agatccccct gatccacttc aacacgccga ggccgcgaag gcacacccgg 540
agcgccgagg acgcctggga gcaggacccg ctgaacgtgc tgaagcccag gttccggctg 600
accccggccc cagcctcctg ctcacaggag gccccaagtg ctgaagacaa tggcctggtg 660
gccagcgacc ccttcggagt gctccggggc aatagggtga acatgcacgg ggacaggatg 720
ggcccggaaa ggtgccacca tttccccaag ttcatctag 759

<210> SEQ ID NO 289
<211> LENGTH: 741
<212> TYPE: DNA
<213> ORGANISM: Horse

<400> SEQUENCE: 289
atgtcagggc cctgccttgg gctcctggtc tacgtcctgt gctccgcagt gaaagcctat 60
cccaacgcct ccccgctgct agactccagc tggggcagcc tgacccacct gtacacggcc 120
acagccagga acagctacca cctgcagatc cacaaggatg gccacgtgga tggcacaccc 180
catcagacca tctacagtgc cctgatgatc agatcagagg atgctggctt tgtggtgata 240
acaggtgtga tgagcaggag atacctctgc atggacttca gaggaaacat ttttggatca 300
catcacttca gccccgagag ctgcagcttc cgacagcgga cgctggagaa cggctacgac 360
gtgtaccact cgccgcagca tcgcttcctc gtcagcctgg gccgcgccaa gagggccttc 420
ctgcccggca cgaacccccc gccctactcg cagttcctgt cccggaggaa cgagatcccc 480
ctggtccact tcaacacccc gcggccgcgg cggcacacgc gcagcgccga ggacaactcg 540
gagcgcgacc cgctgaacgt gctgaagccc cggccccgca tgacccccgc gccggcctcc 600
tgctcccagg agctcccgag cgccgaggac aacagcgtgc tggccagcga ccccttaggg 660
gtggtccgtg gcaacagggt gaacacgcac gcgggggcg cgggcgtgga gcgctgccgc 720
cccttcccca agttcttcta g 741

<210> SEQ ID NO 290
<211> LENGTH: 738
<212> TYPE: DNA
<213> ORGANISM: Giant panda

<400> SEQUENCE: 290
atgtcaggga cccgccttgg gctgctggtc tctgtcctgt gctgggtagg cagagcctat 60
cccaacacct ccccactgct cggctccagc tggggtggcc tgacccacct gtacacagcc 120
agcgccagga acagctacca cctgcagatc cacaaggacg gccatgtgga tggcacaccc 180
catcagacca tctacagtgc cctgatgatc aggtcagagg atgccggctt tgtggtgata 240
acaggtgtga tgagtaggcg atacctctgt atggacctca gaggcaacat ctttggatcc 300
cacctcttca gcccggagag ctgcaggttc cgacagcgga cgctggaaaa cggctacgac 360
gtgtaccact cgccgcagca ccgcttcctc gtcagcctgg gccaggccaa gaggaccttc 420
ctgccgggga ccaacccgcc gccctactcc cagttcctgt cccggaggaa cgagatcccc 480
ctcatccact tcaacacccc caggccaagg cggcacacgc gcagcgccga ggacacggag 540
cgcgacccgt tgaacgtgct gaagcccagg ccccgcatga cccccgcccc ggcctcctgc 600
tcccaggagc tcccgagcgc cgaggacaac agtgtggtgg ccagcgaccc gttaggggtg 660
ctcagaggca accgggtgaa cgcgcacgcc gggggatgg gcgtggacag gtgccgcccc 720
ttccccaagt tcatctag 738

<210> SEQ ID NO 291
<211> LENGTH: 753
<212> TYPE: DNA
<213> ORGANISM: Pika

<400> SEQUENCE: 291

-continued

```
atgctggggg ggctggggct gtgggtctgt gtcctgggca gtgtgtgcag ctggcgtggg      60

gtccgtgcct atcccgacac ctccccgctg ctcggctcca gctggactgg cctgacccac     120

ctgtacacgg ccaccgccag gaacagcttc cacctgcaga tccacaagga tggccatgtg     180

gatggcacac cccagcagac catctatagt gccctgatga tcagatcaga ggatgccggc     240

ttcgtggtga taacaggtgt catgagcagg aggtacctct gtatggattt cagaggcaac     300

atcttcggat cgcattactt cgagccacag aactgcaggt tccagcagag gacgctggag     360

aacggctacg acatctacca ctctccgcag cacgacttcc tggtcagcct aggtcgggcc     420

aagaggccgt tcctgccagg catgaacccg ccaccctact cccagttcct gtctcggagg     480

aacgagattc cgctgatcct cttcaacacg cccaggcctc ggaggcacac ccgcagcgcg     540

gaggagggct gggagcggga ccctctgaat gtgctgaagt ccaggccccg aatgaccccg     600

gccccagcct cctgctcgcg ggaggccccc agtgccgaag acgacggcct gctggccagt     660

gaccccatgg gagtgctcag aggccatagg gtggatgtgc acgggggtgg gacgggtagg     720

gacaggtgcc gcccgttccc caggttcatc tag                                  753
```

<210> SEQ ID NO 292
<211> LENGTH: 738
<212> TYPE: DNA
<213> ORGANISM: Cattle

<400> SEQUENCE: 292

```
atgctggggg cccgcctggg gctctgggtc tgcaccctga gctgtgtggt ccaagcctat      60

cccaacagct ccccgctgct gggctccagc tggggcggcc tgacccacct gtacacggcc     120

acggccagga acagctacca cctgcagatc cacggagacg ggcacgtaga tggctccccg     180

cagcagactg tctacagcgc cctgatgatc aggtcggagg atgccggctt cgtggtgata     240

acaggtgtga tgagcaggcg gtacctctgc atggacttca caggcaacat tttggatcc      300

catcacttca gtccggagag ctgccggttc cggcagcgga cactggagaa cggctacgac     360

gtgtaccact cgccgcagca ccgcttcctc gtcagcctgg gccgggccaa gcgcgccttc     420

ctgccgggca ccaacccgcc cccatacgcg cagttcctgt cgcgcaggaa cgagatcccg     480

ctgccgcact tcgccgccac cgcgcggccc cggcgccaca cgcgcagcgc acacgacagc     540

ggggacccgc tcagcgtgct caagccgcgc gcccgcgcca cgcccgtgcc cgccgcctgc     600

tcccaggagc tgcccagcgc cgaggactcc ggccctgccg ccagcgaccc gctcggggtg     660

ctccgcggac accgcctgga cgtgcgcgcc ggctccgcgg gcgccgagcg ctgccggccc     720

ttccccggct tcgcctag                                                   738
```

<210> SEQ ID NO 293
<211> LENGTH: 735
<212> TYPE: DNA
<213> ORGANISM: Pig

<400> SEQUENCE: 293

```
atgctggggg cccgcctcgg gctctgggtc tgcaccctgt gctgtgcggc cagagcctat      60

cccgacacct ccccgctgct gagctctggc tggggcggcc tgacccacct gtacacggcc     120

acggccagga acagctacca cctgcagatc cacaaggatg gccacgtgga tggctcaccc     180

caacagacca tctacagtgc cctaatgatc aggtcggagg acgcaggctt cgtggtcata     240

acaggcgtga tgagcaggag atacctctgc atggacttaa ggggcaacat tttggatcg      300

ctgcacttca gccccgagag ctgcaggttc cggcagcgga cgctggagaa cggctacgac     360
```

```
gtgtaccact cgccgcacta ccgcttcctc gtcagcctgg gccgggccaa gcgggccttc    420

ctgccgggta ccaacccgcc cccgtacgcg cagttcttgt cgcgcaggaa cgagatcccg    480

ctgctgcact tcgccaccgc gcggccccgg cgccacacgc gcagcgcgca cgacggcggg    540

gacccgctga gcgtcctgaa gccgcgcgcg cgcgccacgc ccgcgcccgt ctcctgctcc    600

cgcgagctgc ccagcgccga ggacggcggc cccgcggcca gcgacccgct cggggtgctc    660

cggggccagc ggctggacgc gcgcgctggg gtggggggcg ccgagcgctg ccggcccttc    720

cccagcttcg cctag                                                     735
```

<210> SEQ ID NO 294
<211> LENGTH: 939
<212> TYPE: DNA
<213> ORGANISM: Dog

<400> SEQUENCE: 294

```
atgtggacag tggagttttt cctgtttgat gtcacagggc caccctttaa aagtctgagg     60

gaaaaaagga gggaatctag cctgggactt tcacgcaaga tacccacaaa gaagaggaga    120

aaaaggcctg tgaggcacag ccggggaatc aaggaggcag tgtcaggttt caaactccag    180

ccagccattc agagagctgt gatgtctggc acccgccttg gattcctggt ctctgtcctg    240

tgctgggtag tcagagccta ttccaacacc tccccgctgc tcggctccag ctggggtagc    300

ctaacccacc tgtatacggc cacagccagg aacagctacc acctgcagat ccacaaggac    360

ggccatgtgg atggcacacc tcatcagacc atctacagtg ccttgatgat ccggtcagag    420

gatgccggct ttgtggtgat aacaggtgtg atgagtagga ggtacctctg tatggacttc    480

agaggcaaca tctttggatc acacctcttc agcccggaga gctgccggtt ccgacagcgg    540

acgctggaga acggctacga cgtgtaccac tccccgcagc accgcttcct cgtcagcctg    600

ggccaggcca agagggcctt cctgcccggc accaacccgc cgccctactc gcagttcctg    660

tcccggagga acgagatccc cctcgtgcac ttccacacgc ccaggccgcg gcggcacacg    720

cgcagcgccg aggccccgga gcgcgacccg ctgaacgtgc tgaagcccag gccgcgcttg    780

gcccccgccc cggcctcctg ctcgcaggag ctcccgagcg ccgaggaccc cggcgcgccg    840

gccagcgacc cgctcggggt gctcaggggc cacagggcca acgcgcgcgc cggcggggtg    900

ggcgtggaca ggtgccgcgc cttccccacg cccatctag                           939
```

<210> SEQ ID NO 295
<211> LENGTH: 732
<212> TYPE: DNA
<213> ORGANISM: Domestic guinea pig

<400> SEQUENCE: 295

```
atgctgggga cctgccttgg gctcctggcc tgcaccgtga gcttagtagg agcctatcct     60

gatgcctccc cattgctcac ctccagctgg ggtggcctga tccatctgta cacggccaca    120

gccagaaaca gctaccatct gcagatccac aaagatggcc acatagatgg tgcaccctat    180

ccgaccatct acagtgccct gatgatcaga tcagaagatg ctgggttcgt cgtgataaca    240

ggggtcacaa gcaggagatt cctctgcatg gatttcagag gcaacatttt tggatctcac    300

cacttcaatc cccaagactg ccgattccaa caccgcacgc tggaaaacgg ttacgacgtc    360

tacctctctc ccgagcacca ctttctgatc agcctgggca ggaccaagaa gttcttcctg    420

ccgggcacca acccaccgcc ctactcccag ttcctgtcgc gcaggaacga gctgcccctg    480
```

gcccgcttcg tcacgcccgg gccgcggcga cacacgcgca gcgcggagga ggaccagggc 540
cgcgacccgc tgagcgtgct caagcttcgg ccccgcgcca cgcccgcgcc cgcctcgtgc 600
tcgcaggagc tgcccagcgc ggaggacgcg gcccaggcca gcgaccccct gggcgtgctg 660
cggggcgcca gggtgcacgc gcacggcggg ccgcgccccg cgaggtgccg cccgggaccc 720
ggggccaagt aa 732

<210> SEQ ID NO 296
<211> LENGTH: 756
<212> TYPE: DNA
<213> ORGANISM: Chinese hamster

<400> SEQUENCE: 296
atgctgggga cctgcctcag actcctggtg ggtgttctgt gtagtgcctg cagcctgggc 60
actgttagag cctatcctga cacctcccca ctgctcggct ccaattgggg cagcctgacc 120
cacctgtaca cagctacagc caggaacagt tatcacctac agatccacaa ggatggccgt 180
gtagatggca caccccatca gaccatctac agtgccctga tgattagatc agaggatgct 240
ggcttcgtga tcataacagg agctgtgact agaaggttcc tttgtatgga tctcaggggc 300
aacatttttg gatcgcatca cttcagcccg gagaactgca ggttccgcca gcggactctg 360
gagaatggct atgacgtcta cctgtcgcca cagcatcact acctggtgag cctgggccgc 420
gccaagcgcc ccttcgagcc cggcaccaac ccgcctccct tctcgcagtt cctggcgcgc 480
aggaacgagg tcccgctgct gcgcttccat accgcacggc cacggcgcca cacgcgcagc 540
gccgaggacc ctcccgagtg ggacccactg aacgtgctca agccgcggcc ccgtgccacg 600
cccgtgcccg tgtcctgctc gcgggagctg ccgagcgccg aggaaggtga cctcgcggcc 660
agtgacccac tgggcgtcct gcgcagaggc cgcggggatg ctcgcggggg cgcaggaggc 720
gtggaccggt gccgtccctt tcccagattc gcctag 756

<210> SEQ ID NO 297
<211> LENGTH: 543
<212> TYPE: DNA
<213> ORGANISM: Tree shrew

<400> SEQUENCE: 297
gccctgctga tcaggccgga ggaggctggc ttcgcggtga tcacgggcgt gatgagcagg 60
agatacctct gcatggattt caggggcaac attttcggat cacacctctt cagcccggag 120
agctgcaggt tccggcagcg cgccctggag aacggctacg acgtctacca ccacccgcag 180
caccacttcc tggtcagcct gggccggccc aagagggcct tcgtgccagg cacgaacccg 240 ccccccctact cccagttcct ggcccggaag aacgagatcc cgctcatcca cttcaacacc 300
ccgaagccgc ggcggcacac ccgcagcgca gaggacaact cggggcgcga cccgctgaac 360
gtgctgaagc cccggccgcg catgaccccg gcgcccgcct cctgctcgca ggagctcccg 420
agtgccgagg acaacagcgt ggtggccagc gaccccctgg gagtgctcag gggcaacagg 480
gtgaacacgc acgcgggggg ctggggcgtg gaccgctgcc gccccttccc caggtttatc 540
tag 543

<210> SEQ ID NO 298
<211> LENGTH: 756
<212> TYPE: DNA
<213> ORGANISM: Norway rat

<400> SEQUENCE: 298
atgctggggg cctgcctcag actcctggtg ggcgctctgt gcaccgtctg cagcttgggc 60
actgctagag cctattcaga cacttcccca ctgcttggct ccaactgggg gagcctgacc 120
cacctgtaca cagctacagc caggaacagc tatcacctac agatccatag ggatggccat 180
gtagacggaa caccccatca gactatctac agtgccctga tgatcacatc agaggatgct 240
ggctccgtag tgataatagg ggccatgacc agaaggttcc tttgtatgga tctccgcggc 300
aacatttttg gatcgtatca cttcagcccg gagaactgca gattccgcca gtggacgcta 360
gagaacggct acgacgtcta cctgtcaccg aagcatcact acctggtgag cttgggccgc 420
tccaagcgca tcttccagcc cggtaccaac ccgccgccct tctcgcagtt cctggcgcgc 480
aggaacgagg tcccgctgct gcacttctac accgcgcgcc cacggcgcca cacgcgcagc 540
gccgaggacc cgcccgagcg cgacccgctg aatgtgctca agccgcggcc ccgcgctact 600
cccataccgg tatcctgctc gcgagagcta ccgagtgcag aggaaggtgg ccccgcggcc 660
agcgaccccc tgggagtgct gcgcagaggc cgcggggatg ctcgccgggg cgcgggaggc 720
acggatcggt gtcgcccctt tcccaggttc gtctag 756

<210> SEQ ID NO 299
<211> LENGTH: 756
<212> TYPE: DNA
<213> ORGANISM: House mouse

<400> SEQUENCE: 299
atgctaggga cctgccttag actcctggtg ggcgcgctct gcactgtctg cagcttgggc 60
actgctagag cctatccaga cacttcccca ttgcttggct ccaactgggg aagcctgacc 120
cacctgtaca cggctacagc caggaccagc tatcacctac agatccatag ggatggtcat 180
gtagatggca ccccccatca gaccatctac agtgccctga tgattacatc agaggacgcc 240
ggctctgtgg tgataacagg agccatgact cgaaggttcc tttgtatgga tctccacggc 300
aacatttttg gatcgcttca cttcagccca gagaattgca agttccgcca gtggacgctg 360
gagaatggct atgacgtcta cttgtcgcag aagcatcact acctggtgag cctgggccgc 420
gccaagcgca tcttccagcc gggcaccaac ccgccgccct tctcccagtt cctggcgcgc 480
aggaacgagg tcccgctgct gcacttctac actgttcgcc cacggcgcca cacgcgcagc 540
gccgaggacc cacccgagcg cgacccactg aacgtgctca agccgcggcc ccgcgccacg 600
cctgtgcctg tatcctgctc tcgcgagctg ccgagcgcag aggaaggtgg ccccgcagcc 660
agcgatcctc tgggggtgct gcgcagaggc cgtggagatg ctcgcggggg cgcgggaggc 720
gcggataggt gtcgcccctt tcccaggttc gtctag 756

<210> SEQ ID NO 300
<211> LENGTH: 747
<212> TYPE: DNA
<213> ORGANISM: Megabat

<400> SEQUENCE: 300
atgccgaggg gcagcctagg gctcctggtc tgcatcctgt gctgcagagc ctatcccgat 60
gcctctccgc tgcttagctc cagcttgggg ggcctgatcc acctctacac agccacagcc 120
aggaacggct accacctgca gatccacaag gatggccatg tggatggcac accccatcag 180
accatctaca gtgccctgat gataagatca gaggacagtg gctttgtggt gataataggt 240
gtgatgagta gaagatacct ctgcatggac ttcaaaggca acatttttgg atcacatcac 300
ttcagccccg agagctgcaa gttccgccag cgaacgctgg agaatggcta cgacgtgtat 360
cactcgcccc agcatcactt cttcgtcagc ctgggccgag ctaagagggc cttcctgccg 420
ggcacgaacc ccccacctta ctcccagttc ctgtcccgaa ggaatgagat ccccctgttc 480
cagttcaaca ccccgcggcc gcggcggcac acgcgcagcg tggaggacta caaagactac 540
gatttggacc ccgacccgct gaaagttctg aggccccgtc cccggtgggt ccccgccctg 600
ccctcctgct cccaggagct cccgagtgcc gaggacaaca gcgtggtagc caacgacccg 660
ttaggggtgc tcaggcccag cagggtaaac atataccgtg agagaatggg caaggggagg 720
tgccgtcccc accctgagtt tgtctag 747

<210> SEQ ID NO 301
<211> LENGTH: 744
<212> TYPE: DNA
<213> ORGANISM: Microbat

<400> SEQUENCE: 301
atgccagggg cccgccttgg gttgctggtc tgcgtcctgg ccctgcgctg tgtggtcaga 60
gcctatccca acgcctcccc actgctcggc tccagctggg gtggcctgac ccacctgtac 120
acggcctcag ccaggaacag ctaccacctg cagatccaca aggacggcca tgtggacggc 180
acaccccatc agaccatcta cagtgccctg atgatcagat cagaggacgc tggctttgtg 240
gtgataactg gagtgatgag taggagatac ctctgcatgg actttagagg caacattttt 300
ggatcccttt ttttcagtcc aagtaatttc agtttccttg aatggaaaaa ggaaagtggg 360
atggaccatt ggataagcag acagacgcac ttcctcgtca gccctgggcc gagccaagag 420
ggccttcctg ccgggcacaa cccgccgccc tactcgcagt tcctgtcgcg aaacgagatc 480
ccgctcttcc acttcaacac gcccgcgccg cgccggcaca cgcgcagcgc cgaggagaac 540
tcggcggccg acccgctggt cgtgctgaag cccgtgccgc gcctgacgcc cccgcccgcc 600
tcctgctccc gggagctgag cagcgccgag gacaacagcg tggcggccca cgacccgctc 660
ggggtgctgc ggagcagcaa cagggtgaac tcgcacgcgc cgcccccagg tccacctagg 720
acccgccaag gaatgcttct cgta 744

<210> SEQ ID NO 302
<211> LENGTH: 738
<212> TYPE: DNA
<213> ORGANISM: Tasmanian devil

<400> SEQUENCE: 302
atgtcagggg gttgcctcag gctcctattc tgtgccctgt gcagcttaag ggccatccaa 60
gccttcccca atgcttcccc cctgctcagc cttggctggg ggggtctgac tcacctctat 120
acggccacag ccaggaacag ctaccacctg cagatccaca aagatggcca cgtggatggg 180
tctcctcatc aaaccatcta tagtgccttg atgatcagat cagaggatgc tgggctagtc 240
ataataactg gtgtgatgag caggagatat ctctgtatgg acattagggg caacatcttc 300
ggatcgcatt tcttcagccc agacaactgc aggttcaaac accggacatt agaaaatggg 360
tatgacatct atcactctcc ccagaacaac ttcctgatca gccttggcaa ggcaaagagg 420
gccttcctac cagggatgaa cccacctcct tactcccaat tcctgtctcg gagaaatgaa 480
atccccataa tacacttcaa tacacctgaa ccccaccggc ataccaggag tgctgagaac 540
agtcctgact tggacccaat gaatgtgctg aaactccgac caaggataac tccctgctcc 600
caggaacttc acagtgctga agagaacagt gtagtggatg atgacccttt ggaagtactc 660
agaaatagca atagattgaa gccctatcct ggcaggatga gtttggaaag atgcctccat 720
gtccccaagg cagcttaa 738

<210> SEQ ID NO 303
<211> LENGTH: 576
<212> TYPE: DNA
<213> ORGANISM: Gray short-tailed opossum

<400> SEQUENCE: 303
atggcaaatt gtagagaaaa ggagctggag atgtacattt gtgccttgat gatcagatca 60
gaggatgctg ggctagtcat aataactggt gtgatgagca ggagatatct ctgtatggac 120
atcaggggca acatctttgg ttcgcatttc ttcaacccgg acaactgcaa gttcaagcac 180
cggacactag aaaatgggta tgacatctat cattctcccc agaacaactt cctgatcagc 240
cttggcaagg caaagagggc ctttctgcca ggcatgaatc cacctccgta ctctcaattc 300
ctgtctcgga agaatgagat ccccataatc cacttcaaca cacctgaacc ccaccggcac 360
accaggagtg ctgaaaacag tcctgacttg gacccaatga atgtgctgaa accccgacca 420
aggatgactc cctgctctca ggaactctac agtgctgaag agaacagtgt agtggatgat 480
gaccctttgg aagtacttag aaatagcaat cgactgaagc ccttccctgg taggctgggt 540
ttagaaaggt gccaccatgt tcccaagact gattaa 576

<210> SEQ ID NO 304
<211> LENGTH: 543
<212> TYPE: DNA
<213> ORGANISM: Armadillo

<400> SEQUENCE: 304
gccctgatga tcagctctga agatgctggc tttgtggtga taacaggtgt gatgagcagg 60
aggtacctct gtatggattt cagaggcaac atttttggat cgcacgactt caccccggac 120
agctgcaggt tccgccagcg cacgctggag aacggctacg acgtctacca ctcgccgcag 180
caccacttcc tcgtcagcct ggggcgggcc aagcgggcct tccagccggg ctccaacccg 240
ccgccctact cccagttcct gtcccgcagg aacgagatcc cgctgatgcg cttcagcacc 300
ccgcggccgc ggcggcacac gcgcagcgcc caggaccacg cggaccccga cccgctgagg 360
gtgctcaagc cccggctccg gctgaccccg gcccccgcct cctgctccca ggagctgccg 420
agcgacgagg acgacggcgc ggtggccagc gaccccctgc gcgtggtcct cggccgccgg 480
ccccacgcgc gggccgcggg cgcgggcggg gagcggtgcc gccccggccc gcagctcagc 540
tag 543

<210> SEQ ID NO 305
<211> LENGTH: 534
<212> TYPE: DNA
<213> ORGANISM: Wallaby

<400> SEQUENCE: 305
gccttgatga tcagatcaga ggacgctggg ctagtcataa taagtggtgt gatgagcagg 60
aggtatctct gtatggacct cagaggcaac atcttcggat cgcatttctt cagcccagac 120
aactgcaggt tcaaacaccg gacactagaa aatgggtatg acatctatca ctctccacag 180
aacaacctcc tgatcagcct tggcaaggca aaaagggcct tcctgccagg catgaaccca 240
cctccttact cccagttcct atctcggagg aatgagatcc ccataatcca cttcaataca 300

```
cctgaacccc gccggcacac caggagcgca gagaacagtc ctgacttgga cccaatgaat    360

gtgctgaaac cccgaccaag ggtgactccc tgctcccagg aactccgcag tgctgaagag    420

aacagtgtag tagatgatga ccctttggaa gtactcagaa atagtaatcg cctgaagccc    480

taccctggta gaatgagttt ggaaagatgc ctccaagtcc ccaaagctgc ttaa          534
```

<210> SEQ ID NO 306
<211> LENGTH: 771
<212> TYPE: DNA
<213> ORGANISM: Zebra finch

<400> SEQUENCE: 306

```
atggagtgga gagccactct ccagggcatt ccctgcagct ccctgctcct gctgctctgc     60

agcctaaagg cttcccttgc ctttcccaac tcctctccac tgctgagtcc cagctggggc    120

aatggagatc gcctgatgca cctctacacc gacaccgaga ggagcagctt ccacctccag    180

atcaacgctg atggctacat cgatggcgct cctcaccaaa ccatctacag tgccctaatg    240

atcaagtctg agggtgctgg ctcagtaata atcacaggtg tgaagagtgg acgctacctg    300

tgtatggaca tgaaaggaaa tatatttggc tcgcattact tcagccaaga ggactgcatg    360

ttcaaccaca ggacgctgga aaatgggtac gatgtgtacc aatcccccaa acaccacttc    420

ttggtgagct taggcagagt taaacaagtc ttctcccctg gtatgaatcc accaccatac    480

tcccagtttc tgtccaggaa gaatgagatc cctctgttcc gattcaacac ccccgagccc    540

cacaggcaca ccaggagtgc agatgttgat cccgtagatc ctcaccagat cctggtcccg    600

cagaggaaga ccccagtgtt tggctccctg cagcagcagc cagcagactt tccccacatg    660

cccagggagc ccatgaggat caaccagaac gacgtggtga accccgatga tccccacgca    720

atgatggagg ccaggaggta cccaagcccc cgcttctaca tcacgagata a             771
```

<210> SEQ ID NO 307
<211> LENGTH: 765
<212> TYPE: DNA
<213> ORGANISM: Chicken

<400> SEQUENCE: 307

```
atgccacaca ccagtccctg cagctgcctg gagtacatgc tgcttgtgct ctgtatcctg     60

aaggctgcag tcgccttccc caactcctct ccgctgctga atcccagctg gggaatgga    120

gatcagctga tgcacttgta cacttctaca gagaggaaca gcttccatct ccaaatcaat    180

gctgatggac acatcaatgg tgttcctcac caaaccattt acagtgcctt aatgatcaag    240

tctgagggtg ctggctgtgt aataatcaca ggtgtgaaga gtggacgcta cctatgcatg    300

gacatgaaag gagacatttt tggatcgtat tatttcagcc aagaggactg tgtgttcaac    360

caaaggacac tggaaaatgg atatgatgtg taccaatctc ccaagcacaa ttttctggtt    420

agcttgggca gaactaagca agttttcttc cctggtatga atccaccacc atactcccag    480

tttttgtcca ggagaaacga aatccctttg tttcgattca acacacctga accccacaga    540

aacactagaa gtgcagatgt cgatccactg gatcctcacc aaatcctggt cccacagaga    600

aaggtctctg cattagggtc tcagctgcag ctgcaaatgg acttttccca tgtgcccaga    660

gaacccatga gagtcaatca gaatgatgtg gtcaatccag atgacccaca tgctatgatg    720

gatgctagga ggtatgctag tcctcgcttt tacattacaa gataa                    765
```

<210> SEQ ID NO 308
<211> LENGTH: 765

<212> TYPE: DNA
<213> ORGANISM: Turkey

<400> SEQUENCE: 308
atgccgcaca ccagtccctg cagctgcctg gagtacatgc tgcttgtgct ctgtatcctg 60
aaggctgcag tcagcttccc caactcctct ccactgctga atcccagctg gggaacggga 120
gatcagctga tgcacttgta tacttctaca gagaggaaca gcttccatct tcaaatcaat 180
gctgatggcc acatcagtgg tgttccttac caaaccattt acagtgccct aatgatcaag 240
tctgagggtg ctggcagcgt tataatcaca ggtgtgaaga gtggacgcta cctatgcatg 300
gacatgaaag gagacatttt tggatcgcat tatttcagcc aagaggactg cgtgttcaac 360
caaagaacac tggaaaatgg atatgatgtg tatcaatctc ccaagcacaa ttttctggtt 420
agcttaggca gaactaagca agttttcttc cctggtatga atccaccacc gtactcccag 480
tttttgtcca ggagaaacga aatcccgttg tttcgattca acacacctga accccacaga 540
aacactagaa gtgcagatgt tgatccaatg gatcctcacc agatcctggt cccacagaga 600
aaggtctctg caatagagtc tcagctgcaa ctgcaaatgg acttttccca tgtgcccaga 660
gaacccatga gagtcaatca gaacgatgtg gtcaacccag atgacccaca cgctatgatg 720
gatgccagga gatatgctag tcctcgcttt tacattacaa gataa 765

<210> SEQ ID NO 309
<211> LENGTH: 729
<212> TYPE: DNA
<213> ORGANISM: Green anole

<400> SEQUENCE: 309
atggtccagg ctactctata cagcttcctc aaatatatgc tgcttgcaac atgtagctgg 60
aaagcaattg ctgctttccc caacgcatca cctttgctca gcctcaactg ggaaattca 120 gacagcctgc tacacttgta cacttccaca gcaagaaaca gcttccacct gcaaatccac 180
tccaatggct acgtggatgg aagtccgtat caaacaattt acagtgcctt gatgatcaaa 240
tctgaagttg ctggttatgt tataataaat ggtgtgaaaa gtggacgttt tctttgtatg 300
gatatgaatg ggaacatctt tggatcgcat ttcttcagtt atgaggactg cactttcaaa 360
cactgggtcc tggaaaatgg ttatgatgtt tatcagtctc ccaaatacaa ctaccttgtc 420
agcttaggaa aagcaaagca accattgttc cccaatatga atccaccacc ttactcccag 480
ttcttgtcca ggagaaatga aattccttta gtccagttca acacaccgaa acctcacaga 540
cataccagaa gtgccaacgc ggatccctgc ggcagcatca tatcatcagg aaatattgcg 600
aaagaaaacc tacagttaca gccactaatg tataacacta aaatgaattc aaacagtgaa 660
gatgaagacc caaacagtgc aataatcaat agaagatttt tgagtcctag aacagatgtc 720
aggagctga 729

<210> SEQ ID NO 310
<211> LENGTH: 750
<212> TYPE: DNA
<213> ORGANISM: Coelacanth

<400> SEQUENCE: 310
ctagagtccg ctcttcttgc gttttctatg gctatattct atagctttaa agctgtgagc 60
tcttttccaa attcttcgcc actgcttaac ccagtctggg gaaacactga caacctgata 120
cacctgtata cagcttctga gacgaacagc ttccacttgc agatcaactc cgatggacat 180

```
gtggatggta ctccacacca aaccgcttac agtgcactgc tgatcaagtc cgaggaggct    240

ggttctgtag ttatcctggg ggtgaagagt ggacgttacc tctgtatgga tatcaagggc    300

aatattattg gactgcatca cttcagcaag gaagactgta cattcaaaca agagggcttg    360

gaaaatggat ttgatgtgct gcgctcacct aagcacaaca ttttggtcag ccttgacaag    420

actaaacgct cctacatccc gggtatgaac ctgccacctt actcacagtt tttatcccga    480

cagaatgaag tagctctgat caacttcatt aacacacctg acatacacag acatagtcga    540

aatgttgatg ttgatccttc agacccccat gggatgataa ttcagcctga tgtgggtgtt    600

tcatttcgta agtcttcatc tctgttttca gatctgccca gagactccat gagaactagc    660

cataatggta tggatatggt tgatcctgct gacccacatg gaatgttaga ttccaggaga    720

agaccaagtc caaggttctt tgcaagatag                                     750
```

<210> SEQ ID NO 311
<211> LENGTH: 765
<212> TYPE: DNA
<213> ORGANISM: Western clawed frog

<400> SEQUENCE: 311

```
atgaccaagc agcaaactag actaggactg gtgctcactg ttcttgccag tataaaggtt     60

atatctgcct tccccaactc ttctccaata atcagtggcg gctgggggt ccctgacaga    120

ctgatgcacc tatatacggc cagtgactgg aacagcttcc acctacagat caaccatgat    180

ggaagcattg atggaacccc tacccaaacc atttacagtg caataatgat caaatcagaa    240

tccgctgggc acgtggttat tactggggtg aagactaatc ggtacctgtg catggataaa    300

agtgggaaca tttttggata tcacgacttc aaccacgacg actgcgtttt taagcacgag    360

actctggaga acaactttga cgtttaccat tctccaaaac acaactttgt gatcagcctc    420

aaggagccca agcatcattt ccgcctcggc atggacctgc cccttactc ccaattcctg    480

tccttggaga atgaaatccc cataaccaga ttcaatgctc cagagccgga aatgagaatc    540

ccagagggca actttgctga ccccagcgac atcataaaga accccaggaa ctgggacttt    600

tcgcagtcta ttcataatcc atttcaggat gtgtggttgc cgttccccag cggttcatta    660

ccaatcatta gagcttcctt gccaattatt cataacaatg tgattaatac agatgaccct    720

gaagaaattg taaaaatgaa gagatacaga tatttcaaga ggtag                    765
```

<210> SEQ ID NO 312
<211> LENGTH: 600
<212> TYPE: DNA
<213> ORGANISM: Cat

<400> SEQUENCE: 312

```
atgtcaggga cccgccttgg gctcctggtc tctgtcctgt gctgggtagt cagagcctat     60

cctaacacct ccccgctgct gggctccagc tggggtggcc tgacccacct gtacacggcc    120

acagccagga acagctacca cctgcagata cacaaggacg gccatgtgga tggcacaccc    180

catcagacca tctacagtgc cctgatgatc agatcggagg atgccggctt tgtggtgata    240

acaggtgtga tgagtcagag gtacctctgt atggacttca gaggcaatat cttcggatcg    300

cacctcttca gccccgagag ctgcaggttc cgacagcgga cgctggaaaa cggctacgac    360

gtgtaccact ccccgcagca ccgcttccta gtcagcctgg gcccggccaa gagggccttc    420

ctgccgggca ccaaccgcat gacccccgcg ccggcctcct gctcccagga gctcccaagc    480

gccgaggaca gcggcgtggt ggccagcgac ccgttagggg tgctcagggg caacagggtg    540
```

aacgcgcacg ccggggggat gggcgtggag aggtgccgcc ccttccccaa gttcaactag 600

<210> SEQ ID NO 313
<211> LENGTH: 750
<212> TYPE: DNA
<213> ORGANISM: Chinese softshell turtle

<400> SEQUENCE: 313
atgtcacagc ccagccagtg cagctgcctg aacttcatgc tgttcgtgct atgtagcttc 60
aaagctattg ctgcctttcc cttcttctct tcactgctga atcccagctg gggggaaacg 120
gatagtttga tacacctgta cacagctact gagaagaaca gcttccatct gcagatcaac 180
cctgatggtt atgttgacgg cacacctcac caaaccattt acagtgctct aatgatcaaa 240
tctgaggatg ctggctatgt ggtgataagt ggtgtaaaga gtgggcgcta cctatgtatg 300
gacattaaag gaaatatctt tggatcgcat tacttcagtc aagaggactg catgtttaaa 360
cacagaacac tggaaaatgg atatgatgtg taccagtctc ccaagcacaa cttcctggtc 420
agcctgggca ggaataaaca agctttcttc cctggtatga atctgccacc atactcccag 480
tttttgccca ggagaaatga aatccctctg atccgattca acacacccga accccacagg 540
cacactagga atgcagatgt tgatcccctc cagattttga tccctcgggg agaggctttt 600
gacacaggac ctcagaggtt gcagactcac tttgatcacc tgcctagaga acccatgaga 660
atcaatccaa atgatgtagt cagcccggat gacccactcg ccatgatgga tgtcagaagg 720
aatgcaagtc cacgccttta cattacaaga 750

<210> SEQ ID NO 314
<211> LENGTH: 738
<212> TYPE: DNA
<213> ORGANISM: Ferret

<400> SEQUENCE: 314
atgtcagtga cccgtcttgg gctcctggtc tctgtcctgt gctgggtagt cagagcctat 60
cccaacgcct ccccgctgct cggctccagc tggggtggcc tgacccacct gtacacggcc 120
actgccagga acagctacca cctgcagatc cacaaggatg gccatgtgga tggcacaccc 180
caccagacca tctacagcgc cctgatgatc agatcagagg atgccggctt tgtggtgatc 240
acaggtgtga tgagcaggcg gtacctgtgt atggacttcc gaggcaacat ctttggatcc 300
cacctcttca gccccgagag ctgcaggttc cgacagcgga cactggaaaa cggctacgac 360
gtgtaccact ccccgcagca ccgcttcctc gtcagcctgg gccaagccaa gagggccttc 420
ctgccgggca ccaacccgcc gccctactcc cagtttctgt cccggaggaa tgagatcccc 480
ctcatccact tcaacacccc caggccgcgg cgtcacacgc gcagcgccga ggacatggag 540
cacgacccgt tgaacgtgct gaagccccgg ccccgcatga ccccggcccc ggcctcctgc 600
tcccaggagc tcccgagcgc cgaggacaac agtgtggtgg ccagcgaccc gttaggggtg 660
ctcagaggca accgggtgaa cgtgcacgcg ggggggatgg gcgtggacag gtgccgcccc 720
ctccccaagt tcatctag 738

<210> SEQ ID NO 315
<211> LENGTH: 618
<212> TYPE: DNA
<213> ORGANISM: Mouse lemur

<400> SEQUENCE: 315

-continued

```
atgctggggg cctgcctcag gctctgggtc tgtgccctgt gcagtgtctg cggcgtgagc     60

gtcgtcagag cctatcccaa cgcctccccg ctgctcgcct ccagctgggg tggcctgatc    120

cacctgtaca cggccacggc caggaacagc taccacctgc agatccacaa ggacggccat    180

gtggacggca caccccacca gaccatctac agtgccttga tgatcaggtc agaggatgct    240

ggctttgtgg tgatcacagg tgtgatgagc agaagatacc tctgcatgga tttcagaggc    300

aacatttttg gatcacatgt cttcagcgcg gagagctgca ggttcagaca gcggacgctg    360

gagaacggct tcgacgtgta ccagtcccct cagcaccact tcctggtcag cctgggccgc    420

gccaaagggg cctttccggc cggggcgaaa ccgcccccct tcccccagtt cctgccgcgg    480

gggaacgagg ctcccgggcg caaaacgcgg gggcccgagg aaaaaggggc cccacaccct    540

ctccgcgggg tggaaagcgg gggccggaaa ggcggggccc cgcctctctg tttggagagg    600

ctctccagag cccgagag                                                  618
```

<210> SEQ ID NO 316
<211> LENGTH: 579
<212> TYPE: DNA
<213> ORGANISM: Orangutan

<400> SEQUENCE: 316

```
atgcgcaatg agtctttgcc ctgcctggtt ttctccatag gtgccctgat gatcagatca     60

gaggatgctg gctttgtggt gattacaggt gtgatgagca gaagatacct ctgcatggat    120

ttcagaggca acatttttgg atcacactat ttcaacccgg agaactgcag gttccaacac    180

cagacgctgg aaaacgggta tgacgtctac cactctcctc agcatcactt cctggtcagt    240

ctgggccggg tgaagagagc cttcctgcca ggcatgccac ccccgtactc ccagttcctg    300

tcccggagga acgagatccc cctaattcac ttcaacaccc ccgtaccacg gcggcacacc    360

cggagcgccg aggatgacac ggagcgggac cccctgaaag tgctgaagcc ccgggcccgg    420

atgaccccgg ccccggcctc ctgctcacag gagctcccga gctccgagga caacagcccg    480

atggccagcg acccattagg ggtggtcagg ggcggtcgag tgaacacgca cgctggggga    540

acgggcccgg aaggctgccg ccccttcccc aagttcatc                           579
```

<210> SEQ ID NO 317
<211> LENGTH: 564
<212> TYPE: DNA
<213> ORGANISM: Shrew

<400> SEQUENCE: 317

```
atgtggggac tccgcctggg tctcttggtc ggcctcctgg gctgcgtgga cagagcctcc     60

ccgatgctgg cgtccagctg gggcggcctg acgcacctgt acacggccac ggccaggaac    120

agctaccacc tccagatcca caaggacggc ctggtcgacg gctccccgca gcagaccgtc    180

taccaccatt tcagcccgga gagctgccgc ttccagcagc gcacgctgga gaacggctac    240

gacgtgtacc agtccccgca gcaccgcttc ctcgtgagcc tgggccggcc caagcgcgcc    300

ttccagccgg gcgccaaccc gccgccctac gcgcagttcc tggcgcgccg caacgaggtg    360

cccctggcgc gcttccacac gcccgcgccg cgccgccaca cgcgcagcgc gcacgacaac    420

ggcgacgccg acccgctcaa cgtgctggcg cctcgggccg ccgccgccgc ctcctgctcg    480

cacgagctgc ccagcgccga ggacaacagc gtggtggcca gcgacccgct gggcgtcatc    540

cgcagcaacc gcttccgcac gcac                                           564
```

-continued

<210> SEQ ID NO 318
<211> LENGTH: 792
<212> TYPE: DNA
<213> ORGANISM: Tetraodon

<400> SEQUENCE: 318
atggacgtaa acagaaggat cggggtgaag gacgccttgc tggcgctcct gctcgccctt 60
ctccagggat gccccctggg ggaaacggct cccaacgcgt caccgctggt cggttccaac 120
tgggggaacc cgaggaggta cgttcacctt cagacatcca cagacatgag caacttctac 180
ttggagatca gactggatgg aaccgtgcgc aaaagcacag cccggacttc atacagtgtg 240
attttactga aagccgacac gagggagcgc atcgccatcc tgggcgtcaa gagcaaccgt 300
tacctgtgta tggacctcga ggggagccca tttagctctc ccacctgcat cagggacgac 360
tgcttgttca accacagtct tctggagaac aaccgggacg tctactactc cagccggacc 420
ggcattctct tcaaccttga gggctcccgc caggtgttcg tggtgggcca gaacgtcccg 480
cagacctccc tcttcctgcc caggacgaac acggtgccgc tggagcgact ccttctgcac 540
agggacaagc ggaaccaggt ggtggacccc tctgacccgc accgcgtcgc cgtgggtcgc 600
gccgaggagg gctcggactc ccgggccttg caggaggacg acgccgacct ggaggtggag 660
acagaggttg aggtcgggga cgacggacgc aacgcgtccc gggagcggct gcaggctccg 720
tccgatcacg acccctgggg cgtgttctcc tccaaccccg ggagcccccg cagcagcggc 780
acggtgggct ga 792

<210> SEQ ID NO 319
<211> LENGTH: 768
<212> TYPE: DNA
<213> ORGANISM: Tilapia

<400> SEQUENCE: 319
atggacgtca acaggcgaat ggggatgaga gacaccgtgc tggcgctctt tctcgctgtc 60
ttgcagggat ttcctctcgg ggatacggtc ccgaacccat cacctctggc tggatccaac 120
tgggggaacc caaggagata cgtccacctg cagacatcca cagacctcaa taacttctac 180
ttggagatca gattagatgg gagtgtgcgc aaaactacgt ccaggagcac ctatagtgtg 240
attctactga aatctgaagc aagagatcgc gtcgccatcc tcggcgtcaa aagcagccgt 300
tacctatgca tggacctgga gggcaacccg ttcagctctc ctgtctgcct tcgggatgac 360
tgtctgttca accacaagct cctggagaac aaccgggacg tgtactactc cagccggaca 420
ggcatcttgt tcaacctgga gggctcccga caggtgtact cggtgggcca gaacctgccg 480
cagacctccc tcttcttgcc caggaaaaac accgtaccac tggagcgcct cctgctgcac 540
agggagaaga gaaaccgggg gcagacagaa gagggttcgg actcccgggc cgtgccggag 600
gagctggagg aaagggaggt ggaaatggag acggaaatag aaacagaggt cggggatgac 660
ggacgcaacg tgtcccggga gaaactcgcg gctccatcca gccacgaccc ctggaacgtg 720
cacttctcca acccggccag cccccggagc accgggacag tgggctga 768

<210> SEQ ID NO 320
<211> LENGTH: 777
<212> TYPE: DNA
<213> ORGANISM: Zebrafish

<400> SEQUENCE: 320
atgcgttgcg cactttccaa cctgcacatg ctgcattcat ccgtcctcgc gctgtggttc 60

```
acggctctcc agggactcag acctgcagat gcggccccca atccttctcc gctgctgggc    120
tccaactggg ggaacccgcg gagatacatc caccttcaga ccacttcaga cttaaacaac    180
tactacctgg agatcagccc gagtggacac gtgcgcaaaa ctacaaatcg ggctcatac    240
agtgtaatct tattgaaaac agaaagcaga gaccgtctgg cgatatttgg agtgaaaagt    300
aaccggtttt tgtgcatgga tacaggagga acccttttca catctacgat ctgcaataag    360
gaagactgtc ttttccacca caaactgttg gaaaaccatc gtgatgtgta ttactccact    420
aaacacagca tactgcttaa tctggacggg gacaaacagg cgtttatagc gggacaaaac    480
ctccctcagt cgtctctctt cttgtcggag aagaacacgg ttccgctgga gcgcctgcag    540
catcgggagc gcaggaaccg gcaggtgaac ccaacagacc cgctgaacgc gctccggtac    600
gcggaggagt ctgattccag agccgcgcag gaggatgatg gagacatgga ttttgagccc    660
tcagaaggtc aaaacatctc tagagaaacc cttgtttccc cttccgatga tgatccatgg    720
gatcttctgc acgacacgag ccctggaagt cctcggattg cagcaattgt cggataa       777
```

<210> SEQ ID NO 321
<211> LENGTH: 241
<212> TYPE: PRT
<213> ORGANISM: Artificial
<220> FEATURE:
<223> OTHER INFORMATION: Chimeric protein

<400> SEQUENCE: 321

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Asp Gln
        115                 120                 125

Asn Gly Ser Cys Val Arg Gly Pro Arg Thr His Tyr Gly Gln Lys Ala
    130                 135                 140

Ile Leu Phe Leu Pro Leu Arg Asn Glu Ile Pro Leu Ile His Phe Asn
145                 150                 155                 160

Thr Pro Ile Pro Arg Gln His Thr Gln Ser Ala Glu Asp Asp Ser Glu
                165                 170                 175

Arg Asp Pro Leu Asn Val Leu Lys Pro Arg Ala Arg Met Thr Pro Ala
            180                 185                 190

Pro Ala Ser Cys Ser Gln Glu Leu Pro Ser Ala Glu Asp Asn Ser Pro
        195                 200                 205

Met Ala Ser Asp Pro Leu Gly Val Val Arg Gly Gly Arg Val Asn Thr
    210                 215                 220

His Ala Gly Gly Thr Gly Pro Glu Gly Cys Arg Pro Phe Ala Lys Phe
225                 230                 235                 240
```

Ile

<210> SEQ ID NO 322
<211> LENGTH: 217
<212> TYPE: PRT
<213> ORGANISM: Artificial
<220> FEATURE:
<223> OTHER INFORMATION: Chimeric protein

<400> SEQUENCE: 322

```
Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Asp Gln Asn Gly Ser Cys Val Arg Gly Pro
            100                 105                 110

Arg Thr His Tyr Gly Gln Lys Ala Ile Leu Phe Leu Pro Leu Arg Asn
        115                 120                 125

Glu Ile Pro Leu Ile His Phe Asn Thr Pro Ile Pro Arg Gln His Thr
    130                 135                 140

Gln Ser Ala Glu Asp Asp Ser Glu Arg Asp Pro Leu Asn Val Leu Lys
145                 150                 155                 160

Pro Arg Ala Arg Met Thr Pro Ala Pro Ala Ser Cys Ser Gln Glu Leu
                165                 170                 175

Pro Ser Ala Glu Asp Asn Ser Pro Met Ala Ser Asp Pro Leu Gly Val
            180                 185                 190

Val Arg Gly Gly Arg Val Asn Thr His Ala Gly Gly Thr Gly Pro Glu
        195                 200                 205

Gly Cys Arg Pro Phe Ala Lys Phe Ile
    210                 215
```

<210> SEQ ID NO 323
<211> LENGTH: 242
<212> TYPE: PRT
<213> ORGANISM: Artificial
<220> FEATURE:
<223> OTHER INFORMATION: Chimeric protein

<400> SEQUENCE: 323

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80
```

```
Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Asp
        115                 120                 125

Gln Thr Gly Gln Tyr Val Leu Gly Ser Lys Thr Gly Pro Gly Gln Lys
    130                 135                 140

Ala Ile Leu Phe Leu Pro Met Arg Asn Glu Ile Pro Leu Ile His Phe
145                 150                 155                 160

Asn Thr Pro Ile Pro Arg Gln His Thr Gln Ser Ala Glu Asp Asp Ser
                165                 170                 175

Glu Arg Asp Pro Leu Asn Val Leu Lys Pro Arg Ala Arg Met Thr Pro
            180                 185                 190

Ala Pro Ala Ser Cys Ser Gln Glu Leu Pro Ser Ala Glu Asp Asn Ser
        195                 200                 205

Pro Met Ala Ser Asp Pro Leu Gly Val Val Arg Gly Gly Arg Val Asn
    210                 215                 220

Thr His Ala Gly Gly Thr Gly Pro Glu Gly Cys Arg Pro Phe Ala Lys
225                 230                 235                 240

Phe Ile


<210> SEQ ID NO 324
<211> LENGTH: 218
<212> TYPE: PRT
<213> ORGANISM: Artificial
<220> FEATURE:
<223> OTHER INFORMATION: Chimeric protein

<400> SEQUENCE: 324

His Phe Lys Asp Pro Lys Arg Leu Tyr Cys Lys Asn Gly Gly Phe Phe
1               5                   10                  15

Leu Arg Ile His Pro Asp Gly Arg Val Asp Gly Val Arg Glu Lys Ser
            20                  25                  30

Asp Pro His Ile Lys Leu Gln Leu Gln Ala Glu Glu Arg Gly Val Val
        35                  40                  45

Ser Ile Lys Gly Val Cys Ala Asn Arg Tyr Leu Ala Met Lys Glu Asp
    50                  55                  60

Gly Arg Leu Leu Ala Ser Lys Cys Val Thr Asp Glu Cys Phe Phe Phe
65                  70                  75                  80

Glu Arg Leu Glu Ser Asn Asn Tyr Asn Thr Tyr Arg Ser Arg Lys Tyr
                85                  90                  95

Thr Ser Trp Tyr Val Ala Leu Asp Gln Thr Gly Gln Tyr Val Leu Gly
            100                 105                 110

Ser Lys Thr Gly Pro Gly Gln Lys Ala Ile Leu Phe Leu Pro Met Arg
        115                 120                 125

Asn Glu Ile Pro Leu Ile His Phe Asn Thr Pro Ile Pro Arg Gln His
    130                 135                 140

Thr Gln Ser Ala Glu Asp Asp Ser Glu Arg Asp Pro Leu Asn Val Leu
145                 150                 155                 160

Lys Pro Arg Ala Arg Met Thr Pro Ala Pro Ala Ser Cys Ser Gln Glu
                165                 170                 175

Leu Pro Ser Ala Glu Asp Asn Ser Pro Met Ala Ser Asp Pro Leu Gly
            180                 185                 190

Val Val Arg Gly Gly Arg Val Asn Thr His Ala Gly Gly Thr Gly Pro
```

-continued

```
        195                 200                 205

Glu Gly Cys Arg Pro Phe Ala Lys Phe Ile
    210                 215
```

<210> SEQ ID NO 325
<211> LENGTH: 723
<212> TYPE: DNA
<213> ORGANISM: Artificial
<220> FEATURE:
<223> OTHER INFORMATION: Nucleic acid sequence encoding chimeric protein

<400> SEQUENCE: 325

```
atggctgaag ggaaatcac caccttcaca gccctgaccg agaagtttaa tctgcctcca     60
gggaattaca agaagcccaa actcctctac tgtagcaacg gggccactt cctgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcga tcagaatggg agctgcgttc gcggtcctcg gactcactat    420
ggccagaaag caatcttgtt tctccccctg aggaacgaga tcccccctaat tcacttcaac    480
acccccatac cacggcagca cacccagagc gccgaggacg actcggagcg ggacccccctg    540
aacgtgctga agccccgggc ccggatgacc ccggccccgg cctcctgttc acaggagctc    600
ccgagcgccg aggacaacag cccgatggcc agtgacccat taggggtggt caggggcggt    660
cgagtgaaca cgcacgctgg gggaacgggc ccggaaggct gccgcccctt cgccaagttc    720
atc                                                                  723
```

<210> SEQ ID NO 326
<211> LENGTH: 651
<212> TYPE: DNA
<213> ORGANISM: Artificial
<220> FEATURE:
<223> OTHER INFORMATION: Nucleic acid sequence encoding chimeric protein

<400> SEQUENCE: 326

```
aagcccaaac tcctctactg tagcaacggg ggccacttcc tgaggatcct tccggatggc     60
acagtggatg ggacaaggga caggagcgac cagcacattc agctgcagct cagtgcggaa    120
agcgtggggg aggtgtatat aaagagtacc gagactggcc agtacttggc catggacacc    180
gacgggcttt tatacggctc acagacacca aatgaggaat gtttgttcct ggaaaggctg    240
gaggagaacc attacaacac ctatatatcc aagaagcatg cagagaagaa ttggtttgtt    300
ggcctcgatc agaatgggag ctgcgttcgc ggtcctcgga ctcactatgg ccagaaagca    360
atcttgtttc tccccctgag gaacgagatc cccctaattc acttcaacac ccccatacca    420
cggcagcaca cccagagcgc cgaggacgac tcggagcggg acccccctgaa cgtgctgaag    480
ccccgggccc ggatgacccc ggccccggcc tcctgttcac aggagctccc gagcgccgag    540
gacaacagcc cgatggccag tgacccatta ggggtggtca ggggcggtcg agtgaacacg    600
cacgctgggg gaacgggccc ggaaggctgc cgccccttcg ccaagttcat c             651
```

<210> SEQ ID NO 327
<211> LENGTH: 726
<212> TYPE: DNA
<213> ORGANISM: Artificial
<220> FEATURE:

<223> OTHER INFORMATION: Nucleic acid sequence encoding chimeric protein

<400> SEQUENCE: 327
atggcagccg ggagcatcac cacgctgccc gccttgcccg aggatggcgg cagcggcgcc 60
ttcccgcccg gccacttcaa ggaccccaag cggctgtact gcaaaaacgg gggcttcttc 120
ctgcgcatcc accccgacgg ccgagttgac ggggtccggg agaagagcga ccctcacatc 180
aagctacaac ttcaagcaga agagagagga gttgtgtcta tcaaaggagt gtgtgctaac 240
cgttacctgg ctatgaagga agatggaaga ttactggctt ctaaatgtgt tacggatgag 300
tgtttctttt ttgaacgatt ggaatctaat aactacaata cttaccggtc aaggaaatac 360
accagttggt atgtggcact ggatcagact gggcagtatg ttcttggatc caaaacagga 420
cctgggcaga aagctatact tttcttccca atgaggaacg agatccccct aattcacttc 480
aacaccccca taccacggca gcacacccag agcgccgagg acgactcgga gcgggacccc 540
ctgaacgtgc tgaagccccg ggcccggatg accccggccc cggcctcctg ttcacaggag 600
ctcccgagcg ccgaggacaa cagcccgatg gccagtgacc cattaggggt ggtcaggggc 660
ggtcgagtga acacgcacgc tggggaacg ggcccggaag gctgccgccc cttcgccaag 720
ttcatc 726

<210> SEQ ID NO 328
<211> LENGTH: 654
<212> TYPE: DNA
<213> ORGANISM: Artificial
<220> FEATURE:
<223> OTHER INFORMATION: Nucleic acid sequence encoding chimeric protein

<400> SEQUENCE: 328
cacttcaagg accccaagcg gctgtactgc aaaaacgggg gcttcttcct gcgcatccac 60
cccgacggcc gagttgacgg ggtccgggag aagagcgacc ctcacatcaa gctacaactt 120
caagcagaag agagaggagt tgtgtctatc aaaggagtgt gtgctaaccg ttacctggct 180
atgaaggaag atggaagatt actggcttct aaatgtgtta cggatgagtg tttctttttt 240
gaacgattgg aatctaataa ctacaatact taccggtcaa ggaaatacac cagttggtat 300
gtggcactgg atcagactgg gcagtatgtt cttggatcca aaacaggacc tgggcagaaa 360
gctatacttt ttcttccaat gaggaacgag atccccctaa ttcacttcaa cacccccata 420
ccacggcagc acacccagag cgccgaggac gactcggagc gggacccct gaacgtgctg 480 aagccccggg cccggatgac cccggccccg gcctcctgtt cacaggagct cccgagcgcc 540
gaggacaaca gcccgatggc cagtgaccca ttaggggtgg tcaggggcgg tcgagtgaac 600
acgcacgctg gggaacggg cccggaaggc tgccgcccct tcgccaagtt catc 654

<210> SEQ ID NO 329
<211> LENGTH: 1012
<212> TYPE: PRT
<213> ORGANISM: Homo sapiens

<400> SEQUENCE: 329

Met Pro Ala Ser Ala Pro Pro Arg Arg Pro Arg Pro Pro Pro Pro Ser
1 5 10 15

Leu Ser Leu Leu Leu Val Leu Leu Gly Leu Gly Gly Arg Arg Leu Arg
20 25 30

Ala Glu Pro Gly Asp Gly Ala Gln Thr Trp Ala Arg Phe Ser Arg Pro
35 40 45

-continued

```
Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
    130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
```

```
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685

Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
    850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895
```

-continued

```
Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
    930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile  Phe Tyr Tyr Ser Lys  Lys Gly Arg
        995                 1000                1005

Arg Ser  Tyr Lys
    1010


<210> SEQ ID NO 330
<211> LENGTH: 3039
<212> TYPE: DNA
<213> ORGANISM: Homo sapiens

<400> SEQUENCE: 330

atgcccgcca gcgccccgcc gcgccgcccg cggccgccgc cgccgtcgct gtcgctgctg      60

ctggtgctgc tgggcctggg cggccgccgc ctgcgtgcgg agccgggcga cggcgcgcag     120

acctgggccc gtttctcgcg gcctcctgcc cccgaggccg cgggcctctt ccagggcacc     180

ttccccgacg gcttcctctg ggccgtgggc agcgccgcct accagaccga gggcggctgg     240

cagcagcacg gcaagggtgc gtccatctgg gatacgttca cccaccaccc cctggcaccc     300

ccgggagact cccggaacgc cagtctgccg ttgggcgccc cgtcgccgct gcagcccgcc     360

accggggacg tagccagcga cagctacaac aacgtcttcc gcgacacgga ggcgctgcgc     420

gagctcgggg tcactcacta ccgcttctcc atctcgtggg cgcgagtgct ccccaatggc     480

agcgcgggcg tccccaaccg cgaggggctg cgctactacc ggcgcctgct ggagcggctg     540

cgggagctgg gcgtgcagcc cgtggtcacc ctgtaccact gggacctgcc ccagcgcctg     600

caggacgcct acggcggctg ggccaaccgc gccctggccg accacttcag ggattacgcg     660

gagctctgct tccgccactt cggcggtcag gtcaagtact ggatcaccat cgacaacccc     720

tacgtggtgg cctggcacgg ctacgccacc gggcgcctgg cccccggcat ccggggcagc     780

ccgcggctcg ggtacctggt ggcgcacaac ctcctcctgg ctcatgccaa agtctggcat     840

ctctacaata cttctttccg tcccactcag ggaggtcagg tgtccattgc cctaagctct     900

cactggatca atcctcgaag aatgaccgac cacagcatca aagaatgtca aaaatctctg     960

gactttgtac taggttggtt tgccaaaccc gtatttattg atggtgacta tcccgagagc    1020

atgaagaata accttttcatc tattctgcct gattttactg aatctgagaa aaagttcatc    1080

aaaggaactg ctgacttttt tgctctttgc tttggaccca ccttgagttt tcaacttttg    1140

gaccctcaca tgaagttccg ccaattggaa tctcccaacc tgaggcaact gctttcctgg    1200

attgaccttg aatttaacca tcctcaaata tttattgtgg aaaatggctg gtttgtctca    1260

gggaccacca agagagatga tgccaaatat atgtattacc tcaaaaagtt catcatggaa    1320

accttaaaag ccatcaagct ggatggggtg gatgtcatcg ggtataccgc atggtccctc    1380
```

```
atggatggtt tcgagtggca cagaggttac agcatcaggc gtggactctt ctatgttgac   1440

tttctaagcc aggacaagat gttgttgcca aagtcttcag ccttgttcta ccaaaagctg   1500

atagagaaaa atggcttccc tcctttacct gaaaatcagc ccctagaagg gacatttccc   1560

tgtgactttg cttggggagt tgttgacaac tacattcaag tagataccac tctgtctcag   1620

tttaccgacc tgaatgttta cctgtgggat gtccaccaca gtaaaaggct tattaaagtg   1680

gatggggttg tgaccaagaa gaggaaatcc tactgtgttg actttgctgc catccagccc   1740

cagatcgctt tactccagga aatgcacgtt acacattttc gcttctccct ggactgggcc   1800

ctgattctcc ctctgggtaa ccagtcccag gtgaaccaca ccatcctgca gtactatcgc   1860

tgcatggcca gcgagcttgt ccgtgtcaac atcaccccag tggtggccct gtggcagcct   1920

atggccccga accaaggact gccgcgcctc ctggccaggc agggcgcctg ggagaacccc   1980

tacactgccc tggcctttgc agagtatgcc cgactgtgct ttcaagagct cggccatcac   2040

gtcaagcttt ggataacgat gaatgagccg tatacaagga atatgacata cagtgctggc   2100

cacaaccttc tgaaggccca tgccctggct tggcatgtgt acaatgaaaa gtttaggcat   2160

gctcagaatg ggaaaatatc catagccttg caggctgatt ggatagaacc tgcctgccct   2220

ttctcccaaa aggacaaaga ggtggctgag agagttttgg aatttgacat tggctggctg   2280

gctgagccca ttttcggctc tggagattat ccatgggtga tgagggactg gctgaaccaa   2340

agaaacaatt ttcttcttcc ttatttcact gaagatgaaa aaaagctaat ccagggtacc   2400

tttgactttt tggctttaag ccattatacc accatccttg tagactcaga aaaagaagat   2460

ccaataaaat acaatgatta cctagaagtg caagaaatga ccgacatcac gtggctcaac   2520

tcccccagtc aggtggcggt agtgccctgg gggttgcgca aagtgctgaa ctggctgaag   2580

ttcaagtacg gagacctccc catgtacata atatccaatg gaatcgatga cgggctgcat   2640

gctgaggacg accagctgag ggtgtattat atgcagaatt acataaacga agctctcaaa   2700

gcccacatac tggatggtat caatctttgc ggatactttg cttattcgtt taacgaccgc   2760

acagctccga ggtttggcct ctatcgttat gctgcagatc agtttgagcc caaggcatcc   2820

atgaaacatt acaggaaaat tattgacagc aatggtttcc cgggcccaga aactctggaa   2880

agattttgtc cagaagaatt caccgtgtgt actgagtgca gtttttttca cacccgaaag   2940

tctttactgg ctttcatagc ttttctattt tttgcttcta ttatttctct ctcccttata   3000

ttttactact cgaagaaagg cagaagaagt tacaaatag                          3039
```

<210> SEQ ID NO 331
<211> LENGTH: 1014
<212> TYPE: PRT
<213> ORGANISM: Mus musculus

<400> SEQUENCE: 331

```
Met Leu Ala Arg Ala Pro Pro Arg Arg Pro Pro Arg Leu Val Leu Leu
1               5                   10                  15

Arg Leu Leu Leu Leu His Leu Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
    50                  55                  60

Asp Gly Phe Leu Trp Ala Val Gly Ser Ala Ala Tyr Gln Thr Glu Gly
65                  70                  75                  80
```

-continued

```
Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

Ser Gly Ala Pro Ser Pro Pro Leu Ser Ser Thr Gly Asp Val Ala Ser
        115                 120                 125

Asp Ser Tyr Asn Asn Val Tyr Arg Asp Thr Glu Gly Leu Arg Glu Leu
    130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
        195                 200                 205

Trp Ala Asn Arg Ala Leu Ala Asp His Phe Arg Asp Tyr Ala Glu Leu
    210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
            260                 265                 270

Leu Leu Leu Ala His Ala Lys Val Trp His Leu Tyr Asn Thr Ser Phe
        275                 280                 285

Arg Pro Thr Gln Gly Gly Arg Val Ser Ile Ala Leu Ser Ser His Trp
    290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
            340                 345                 350

Asp Phe Thr Glu Ser Glu Lys Arg Leu Ile Arg Gly Thr Ala Asp Phe
        355                 360                 365

Phe Ala Leu Ser Phe Gly Pro Thr Leu Ser Phe Gln Leu Leu Asp Pro
    370                 375                 380

Asn Met Lys Phe Arg Gln Leu Glu Ser Pro Asn Leu Arg Gln Leu Leu
385                 390                 395                 400

Ser Trp Ile Asp Leu Glu Tyr Asn His Pro Pro Ile Phe Ile Val Glu
                405                 410                 415

Asn Gly Trp Phe Val Ser Gly Thr Thr Lys Arg Asp Asp Ala Lys Tyr
            420                 425                 430

Met Tyr Tyr Leu Lys Lys Phe Ile Met Glu Thr Leu Lys Ala Ile Arg
        435                 440                 445

Leu Asp Gly Val Asp Val Ile Gly Tyr Thr Ala Trp Ser Leu Met Asp
    450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asp Asn Gly Phe Pro Pro Leu Pro
```

```
            500                 505                 510

Glu Asn Gln Pro Leu Glu Gly Thr Phe Pro Cys Asp Phe Ala Trp Gly
        515                 520                 525

Val Val Asp Asn Tyr Val Gln Val Asp Thr Thr Leu Ser Gln Phe Thr
    530                 535                 540

Asp Pro Asn Val Tyr Leu Trp Asp Val His His Ser Lys Arg Leu Ile
545                 550                 555                 560

Lys Val Asp Gly Val Val Ala Lys Lys Arg Lys Pro Tyr Cys Val Asp
                565                 570                 575

Phe Ser Ala Ile Arg Pro Gln Ile Thr Leu Leu Arg Glu Met Arg Val
            580                 585                 590

Thr His Phe Arg Phe Ser Leu Asp Trp Ala Leu Ile Leu Pro Leu Gly
        595                 600                 605

Asn Gln Thr Gln Val Asn His Thr Val Leu His Phe Tyr Arg Cys Met
    610                 615                 620

Ile Ser Glu Leu Val His Ala Asn Ile Thr Pro Val Val Ala Leu Trp
625                 630                 635                 640

Gln Pro Ala Ala Pro His Gln Gly Leu Pro His Ala Leu Ala Lys His
                645                 650                 655

Gly Ala Trp Glu Asn Pro His Thr Ala Leu Ala Phe Ala Asp Tyr Ala
            660                 665                 670

Asn Leu Cys Phe Lys Glu Leu Gly His Trp Val Asn Leu Trp Ile Thr
        675                 680                 685

Met Asn Glu Pro Asn Thr Arg Asn Met Thr Tyr Arg Ala Gly His His
    690                 695                 700

Leu Leu Arg Ala His Ala Leu Ala Trp His Leu Tyr Asp Asp Lys Phe
705                 710                 715                 720

Arg Ala Ala Gln Lys Gly Lys Ile Ser Ile Ala Leu Gln Ala Asp Trp
                725                 730                 735

Ile Glu Pro Ala Cys Pro Phe Ser Gln Asn Asp Lys Glu Val Ala Glu
            740                 745                 750

Arg Val Leu Glu Phe Asp Ile Gly Trp Leu Ala Glu Pro Ile Phe Gly
        755                 760                 765

Ser Gly Asp Tyr Pro Arg Val Met Arg Asp Trp Leu Asn Gln Lys Asn
    770                 775                 780

Asn Phe Leu Leu Pro Tyr Phe Thr Glu Asp Glu Lys Lys Leu Val Arg
785                 790                 795                 800

Gly Ser Phe Asp Phe Leu Ala Val Ser His Tyr Thr Thr Ile Leu Val
                805                 810                 815

Asp Trp Glu Lys Glu Asp Pro Met Lys Tyr Asn Asp Tyr Leu Glu Val
            820                 825                 830

Gln Glu Met Thr Asp Ile Thr Trp Leu Asn Ser Pro Ser Gln Val Ala
        835                 840                 845

Val Val Pro Trp Gly Leu Arg Lys Val Leu Asn Trp Leu Arg Phe Lys
    850                 855                 860

Tyr Gly Asp Leu Pro Met Tyr Val Thr Ala Asn Gly Ile Asp Asp Asp
865                 870                 875                 880

Pro His Ala Glu Gln Asp Ser Leu Arg Ile Tyr Tyr Ile Lys Asn Tyr
                885                 890                 895

Val Asn Glu Ala Leu Lys Ala Tyr Val Leu Asp Asp Ile Asn Leu Cys
            900                 905                 910

Gly Tyr Phe Ala Tyr Ser Leu Ser Asp Arg Ser Ala Pro Lys Ser Gly
        915                 920                 925
```

```
Phe Tyr Arg Tyr Ala Ala Asn Gln Phe Glu Pro Lys Pro Ser Met Lys
    930                 935                 940

His Tyr Arg Lys Ile Ile Asp Ser Asn Gly Phe Leu Gly Ser Gly Thr
945                 950                 955                 960

Leu Gly Arg Phe Cys Pro Glu Glu Tyr Thr Val Cys Thr Glu Cys Gly
                965                 970                 975

Phe Phe Gln Thr Arg Lys Ser Leu Leu Val Phe Ile Ser Phe Leu Val
            980                 985                 990

Phe Thr Phe Ile Ile Ser Leu Ala  Leu Ile Phe His Tyr  Ser Lys Lys
        995                 1000                1005

Gly Gln  Arg Ser Tyr Lys
    1010


<210> SEQ ID NO 332
<211> LENGTH: 3045
<212> TYPE: DNA
<213> ORGANISM: Mouse

<400> SEQUENCE: 332

atgctagccc gcgcccctcc tcgccgcccg ccgcggctgg tgctgctccg tttgctgttg     60

ctgcatctgc tgctgctcgc cctgcgcgcc cgctgcctga gcgctgagcc gggtcagggc    120

gcgcagacct gggctcgctt cgcgcgcgct cctgccccag aggccgctgg cctcctccac    180

gacaccttcc ccgacggttt cctctgggcg gtaggcagcg ccgcctatca gaccgagggc    240

ggctggcgac agcacggcaa aggcgcgtcc atctgggaca ctttcaccca tcactctggg    300

gcggccccgt ccgactcccc gatcgtcgtg gcgccgtcgg gtgccccgtc gcctcccctg    360

tcctccactg gagatgtggc cagcgatagt tacaacaacg tctaccgcga cacagagggg    420

ctgcgcgaac tgggggtcac ccactaccgc ttctccatat cgtgggcgcg ggtgctcccc    480

aatggcaccg cgggcactcc caaccgcgag ggctgcgcgct actaccggcg gctgctggag   540

cggctgcggg agctgggcgt gcagccggtg gttaccctgt accattggga cctgccacag    600

cgcctgcagg acacctatgg cggatgggcc aatcgcgccc tggccgacca tttcagggat    660

tatgccgagc tctgcttccg ccacttcggt ggtcaggtca agtactggat caccattgac    720

aacccctacg tggtggcctg gcacgggtat gccaccgggc gcctggcccc gggcgtgagg    780

ggcagctcca ggctcgggta cctggttgcc cacaacctac ttttggctca tgccaaagtc    840

tggcatctct acaacacctc tttccgcccc acacagggag gccgggtgtc tatcgcctta    900

agctcccatt ggatcaatcc tcgaagaatg actgactata atatcagaga atgccagaag    960

tctcttgact ttgtgctagg ctggtttgcc aaacccatat ttattgatgg cgactaccca   1020

gagagtatga agaacaacct ctcgtctctt ctgcctgatt ttactgaatc tgagaagagg   1080

ctcatcagag gaactgctga cttttttgct ctctccttcg gaccaacctt gagctttcag   1140

ctattggacc ctaacatgaa gttccgccaa ttggagtctc ccaacctgag gcagcttctg   1200

tcttggatag atctggaata taaccaccct ccaatattta ttgtggaaaa tggctggttt   1260

gtctcgggaa ccaccaaaag ggatgatgcc aaatatatgt attatctcaa gaagttcata   1320

atggaaacct taaaagcaat cagactggat ggggtcgacg tcattgggta caccgcgtgg   1380

tcgctcatgg acggtttcga gtggcatagg ggctacagca tccggcgagg actcttctac   1440

gttgactttc tgagtcagga caaggagctg ttgccaaagt cttcggcctt gttctaccaa   1500

aagctgatag aggacaatgg ctttcctcct ttacctgaaa accagcccct tgaagggaca   1560
```

```
tttccctgtg actttgcttg gggagttgtt gacaactacg ttcaagtgga cactactctc   1620

tctcagttta ctgacccgaa tgtctatctg tgggatgtgc atcacagtaa gaggcttatt   1680

aaagtagacg gggttgtagc caagaagaga aaaccttact gtgttgattt ctctgccatc   1740

cggcctcaga taaccttact tcgagaaatg cgggtcaccc actttcgctt ctccctggac   1800

tgggccctga tcttgcctct gggtaaccag acccaagtga accacacggt tctgcacttc   1860

taccgctgca tgatcagcga gctggtgcac gccaacatca ctccagtggt ggccctgtgg   1920

cagccagcag ccccgcacca aggcctgcca catgcccttg caaaacatgg ggcctgggag   1980

aacccgcaca ctgctctggc gtttgcagac tacgcaaacc tgtgttttaa agagttgggt   2040

cactgggtca atctctggat caccatgaac gagccaaaca cacggaacat gacctatcgt   2100

gccgggcacc acctcctgag agcccatgcc ttggcttggc atctgtacga tgacaagttt   2160

agggcggctc agaaaggcaa aatatccatc gccttgcagg ctgactggat agaaccggcc   2220

tgccctttct ctcaaaatga caaagaagtg gccgagagag ttttggaatt tgatataggc   2280

tggctggcag agcctatttt tggttccgga gattatccac gtgtgatgag ggactggctg   2340

aaccaaaaaa acaattttct tttgccctat ttcaccgaag atgaaaaaaa gctagtccgg   2400

ggttcctttg acttcctggc ggtgagtcat tacaccacca ttctggtaga ctgggaaaag   2460

gaggatccga tgaaatacaa cgattacttg gaggtacagg agatgactga catcacatgg   2520

ctcaactctc ccagtcaggt ggcagtggtg ccttgggggc tgcgcaaagt gctcaactgg   2580

ctaaggttca agtacggaga cctcccgatg tatgtgacag ccaatggaat cgatgatgac   2640

ccccacgccg agcaagactc actgaggatc tattatatta agaattatgt gaatgaggct   2700

ctgaaagcct acgtgttgga cgacatcaac ctttgtggct actttgcgta ttcacttagt   2760

gatcgctcag ctcccaagtc tggcttttat cgatatgctg cgaatcagtt tgagcccaaa   2820

ccatctatga aacattacag gaaaattatt gacagcaatg gcttcctggg ttctggaaca   2880

ctgggaaggt tttgtccaga agaatacact gtgtgcaccg aatgtggatt ttttcaaacc   2940

cggaagtctt tgctggtctt catctcgttt cttgttttta cttttattat ttctcttgct   3000

ctcatttttc actactccaa gaaaggccag agaagttata agtaa                   3045
```

<210> SEQ ID NO 333
<211> LENGTH: 216
<212> TYPE: PRT
<213> ORGANISM: Homo sapiens

<400> SEQUENCE: 333

```
Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110
```

```
Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215


<210> SEQ ID NO 334
<211> LENGTH: 209
<212> TYPE: PRT
<213> ORGANISM: Homo sapiens

<400> SEQUENCE: 334

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

UNITED STATES PATENT AND TRADEMARK OFFICE
CERTIFICATE OF CORRECTION

| | | |
|---|---|---|
| PATENT NO. | : 10,364,278 B2 | Page 1 of 1 |
| APPLICATION NO. | : 15/598420 | |
| DATED | : July 30, 2019 | |
| INVENTOR(S) | : Mohammadi et al. | |

It is certified that error appears in the above-identified patent and that said Letters Patent is hereby corrected as shown below:

In the Specification

Column 1 at Lines 11-15, delete "This invention was made with government support under grant numbers DE13686, DK077276, AG019712, DK091392, and DK067158 awarded by the U.S. National Institutes of Health. The government has certain rights in this invention." and insert in its place --This invention was made with government support under DE13686 awarded by National Institutes of Health. The government has certain rights in the invention.--

Signed and Sealed this
Thirty-first Day of March, 2020

Andrei Iancu
*Director of the United States Patent and Trademark Office*